(12) United States Patent
Lapierre et al.

(10) Patent No.: US 11,247,988 B2
(45) Date of Patent: Feb. 15, 2022

(54) RAD51 INHIBITORS

(71) Applicant: Cyteir Therapeutics, Inc., Lexington, MA (US)

(72) Inventors: Jean-Marc Lapierre, Pelham, NH (US); Casey Cameron McComas, Phoenixville, PA (US); Joseph Vacca, Telford, PA (US)

(73) Assignee: Cyteir Therapeutics, Inc., Lexington, MA (US)

( * ) Notice: Subject to any disclaimer, the term of this patent is extended or adjusted under 35 U.S.C. 154(b) by 0 days.

(21) Appl. No.: 16/816,393

(22) Filed: Mar. 12, 2020

(65) Prior Publication Data

US 2020/0291014 A1    Sep. 17, 2020

Related U.S. Application Data

(60) Provisional application No. 62/816,998, filed on Mar. 12, 2019.

(51) Int. Cl.
| | | |
|---|---|---|
| C07D 417/14 | (2006.01) | |
| C07D 417/12 | (2006.01) | |
| C07D 471/04 | (2006.01) | |
| C07D 277/30 | (2006.01) | |

(52) U.S. Cl.
CPC ......... *C07D 417/14* (2013.01); *C07D 277/30* (2013.01); *C07D 417/12* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 5,837,832 | A | 11/1998 | Chee et al. |
| 10,336,746 | B1 | 6/2019 | Castro et al. |
| 10,590,122 | B2 | 3/2020 | Castro et al. |
| 2020/0129484 | A1 | 4/2020 | Castro et al. |
| 2020/0216437 | A1 | 7/2020 | Castro et al. |

FOREIGN PATENT DOCUMENTS

| | | |
|---|---|---|
| EP | 0834575 B1 | 11/2001 |
| EP | 0834576 B1 | 1/2002 |
| WO | WO 96/31622 A1 | 10/1996 |
| WO | WO 97/10365 A1 | 3/1997 |
| WO | WO 98/30883 A2 | 7/1998 |
| WO | WO 2012/113774 A1 | 8/2012 |
| WO | WO 2013/178362 A1 | 12/2013 |
| WO | WO 2016/094897 A1 | 6/2016 |
| WO | WO 2016/140971 A1 | 9/2016 |
| WO | WO 2016/196955 A1 | 12/2016 |
| WO | WO 2019/014315 A1 | 1/2019 |

OTHER PUBLICATIONS

Borchert, G.M. et al. (2011) "Repression of human activation induced cytidine deaminase by miR-93 and miR-155" *BMC Cancer*, 11:347, 9 pages.
Chaudhuri, J. et al. (2004) "Class-Switch Recombination: Interplay of Transcription, DNA Deamination and DNA Repair" *Nature Reviews, Immunology*, 4:541-552.
Chaudhuri, J. et al. (2004) "Replication protein A interacts with AID to promote deamination of somatic hypermutation targets" *Nature*, 430:992-998.
Chaudhuri, J. et al. (2007) "Evolution of the Immunoglobulin Heavy Chain Class Switch Recombination Mechanism" *Advances in Immunology*, 94:157-214.
Crouch, E.E. et al. (2007) "Regulation of AID expression in the immune response" *The Journal of Experimental Medicine*, 204(5):1145-1156.
Engels, K. et al. (2008) "Expression of Activation-induced Cytidine Deaminase in Malignant Lymphomas Infiltrating the Bone Marrow" *Appl Immunohistochem Mol Morphol*, 16(6):521-529.
Feldhahn, N. et al. (2007) "Activation-induced cytidine deaminase acts as a mutator in BCR-ABL1-transformed acute lymphoblastic leukemia cells" *J Exp Med*, 204:1157-1166.
Greeve, J. et al. (May 1, 2003) "Expression of activation-induced cytidine deaminase in human B-cell non-Hodgkin lymphomas" *Blood*, 101(9):3574-3580.
Gruber, T.A. et al. (2010) "Activation-Induced Cytidine Deaminase Accelerates Clonal Evolution in BCR-ABL1-Driven B-Cell Lineage Acute Lymphoblastic Leukemia" *Cancer Res*, 70:7411-7420.
Hancer, V.S. et al. (2011) "Activation-induced cytidine deaminase mRNA levels in chronic lymphocytic leukemia" *Leuk Lymphoma*, 52(1):79-84.
Hardianti, M.S. et al. (2004) "Activation-induced cytidine deaminase expression in follicular lymphoma: association between AID expression and ongoing mutation in FL" *Leukemia* 18:826-831.

(Continued)

*Primary Examiner* — Samantha L Shterengarts
(74) *Attorney, Agent, or Firm* — Cooley LLP; Matthew Pavao; Chen Chen

(57) ABSTRACT

This application is directed to inhibitors of RAD51 represented by the following structural formula,

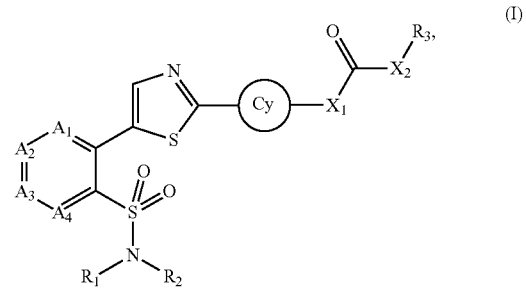

and methods for their use, such as to treat cancer, autoimmune diseases, immune deficiencies, or neurodegenerative diseases.

33 Claims, No Drawings

(56) References Cited

OTHER PUBLICATIONS

Heintel, D. et al. (2004) "High expression of activation-induced cytidine deaminase (AID) mRNA is associated with unmutated $IGV_H$ gene status and unfavourable cytogenetic aberrations in patients with chronic lymphocytic leukaemia" *Leukemia*, 18:756-762.

Hockley, S. L. et al. (2010) "Higher expression levels of activation-induced cytidine deaminase distinguish hairy cell leukemia from hairy cell leukemia-variant and splenic marginal zone lymphoma" *Leukemia*, 24:1084-1086.

Houllenberghs, H. et al. (May 2017) "Suspected Lynch syndrome associated MSH6 variants: A functional assay to determine their pathogenicity" *PLOS Genetics*, 13(5):e1006765, 18 pages.

Klemm, L. et al. (2009) "The B Cell Mutator AID Promotes B Lymphoid Blast Crisis and Drug Resistance in Chronic Myeloid Leukemia" *Cancer Cell*, 16:232-245.

Komori, J. et al. (2008) "Activation-Induced Cytidine Deaminase Links Bile Duct Inflammation to Human Cholangiocarcinoma" *Hepatology*, 47(3):888-896.

Kotani, A. et al. (2007) "Activation-induced cytidine deaminase (AID) promotes B cell lymphomagenesis in Emu-cmyc transgenic mice" *PNAS*, 104(5):1616-1620.

Kovalchuk, A.L. et al. (2007) "AID-deficient Bcl-xL transgenic mice develop delayed atypical plasma cell tumors with unusual Ig/Myc chromosomal rearrangements" *Journal of Experimental Medicine*, 204(12):2989-3001.

Kumari, S. et al. (2008) "DNA Damage: Detection Strategies" *EXCLI Journal*, 7:44-62.

Küppers, R. et al. (2001) "Mechanisms of chromosomal translocations in B cell lymphomas" *Oncogene*, 20:5580-5594.

Leuenberger, M. et al. (2010) "AID protein expression in chronic lymphocytic leukemia/small lymphocytic lymphoma is associated with poor prognosis and complex genetic alterations" *Modern Pathology*, 23:177-186.

Liu, M. et al. (2008) "Two levels of protection for the B cell genome during somatic hypermutation" *Nature*, 451:841-845, including "Methods", 1 page.

Liu, M. et al. (2009) "Balancing AID and DNA repair during somatic hypermutation" *Trends in Immunology*, 30(4):173-181.

Longerich, S. et al. (2006) "AID in somatic hypermutation and class switch recombination" *Curr Opin Immunol*, 18:164-176.

Manis, J.P. et al. (2002) "Mechanism and control of classswitch recombination" *Trends Immunol*, 23(1):31-39.

Mao, X. et al. (2001) "A case of adult T-cell leukaemia/lymphoma characterized by multiplex-fluorescence in situ hybridization, comparative genomic hybridization, fluorescence in situ hybridization and cytogenetics" *Br J Dermatol*, 145:117-122.

Marusawa, H. (2008) "Aberrant AID expression and human cancer development" *Int J Biochem Cell Biol*, 40:1399-1402.

Marusawa, H. et al. (2011) "Role of Activation-Induced Cytidine Deaminase in Inflammation-Associated Cancer Development" *Advances in Immunology*, 111:109-141.

Mills, K.D. et al. (2003) "The role of DNA breaks in genomic instability and tumorigenesis" *Immunological Reviews*, 194:77-95.

Motalleb, G. et al. (2012) "Methods for DNA Strand Breaks Detection" *Research Journal of Applied Sciences, Engineering and Technology*, 4(13):1888-1894.

Muramatsu, M. et al. (1999) "Specific Expression of Activation-induced Cytidine Deaminase (AID), a Novel Member of the RNA-editing Deaminase Family in Germinal Center B Cells" *The Journal of Biological Chemistry*, 274(26):18470-18476.

Muto, T. et al. (2006) "Negative regulation of activation-induced cytidine deaminase in B cells" *PNAS*, 103(8):2752-2757.

Nakamura, M. et al. (2011) "High levels of activation-induced cytidine deaminase expression in adult T-cell leukaemia/lymphoma" *Br J Dermatol*, 165(2):437-439.

NCBI Gene ID: 10930 (Aug. 18, 2020) "APOBEC2 apolipoprotein B mRNA editing enzyme catalytic subunit 2 [ *Homo sapiens* (human) ]" National Center for Biotechnology Information, U.S. National Library of Medicine [online]. Retrieved from: https://www.ncbi.nlm.nih.gov/gene/?term=10930, 6 printed pages.

NCBI Gene ID: 140564 (Aug. 18, 2020) "APOBEC3D apolipoprotein B mRNA editing enzyme catalytic subunit 3D [ *Homo sapiens* (human) ]" National Center for Biotechnology Information, U.S. National Library of Medicine [online]. Retrieved from: https://www.ncbi.nlm.nih.gov/gene/?term=140564, 10 printed pages.

NCBI Gene ID: 164668 (Aug. 18, 2020) "APOBEC3H apolipoprotein B mRNA editing enzyme catalytic subunit 3H [ *Homo sapiens* (human) ]" National Center for Biotechnology Information, U.S. National Library of Medicine [online]. Retrieved from: https://www.ncbi.nlm.nih.gov/gene/?term=164668, 8 printed pages.

NCBI Gene ID: 200315 (Aug. 30, 2020) "APOBEC3A apolipoprotein B mRNA editing enzyme catalytic subunit 3A [ *Homo sapiens* (human) ]" National Center for Biotechnology Information, U.S. National Library of Medicine [online]. Retrieved from: https://www.ncbi.nlm.nih.gov/gene/?term=200315, 10 printed pages.

NCBI Gene ID: 200316 (Aug. 18, 2020) "APOBEC3F apolipoprotein B mRNA editing enzyme catalytic subunit 3F [ *Homo sapiens* (human) ]" National Center for Biotechnology Information, U.S. National Library of Medicine [online]. Retrieved from: https://www.ncbi.nlm.nih.gov/gene/?term=200316, 7 printed pages.

NCBI Gene ID: 23626 (Aug. 18, 2020) "SPO11 initiator of meiotic double standard breaks [*Homo sapiens* (human)]" National Center for Biotechnology Information, U.S. National Library of Medicine [online]. Retrieved from: https://www.ncbi.nlm.nih.gov/gene?cmd=Retrieve&dopt=full_report&list_uids=23626; 11 printed pages.

NCBI Gene ID: 27350 (Aug. 22, 2020) "APOBEC3C apolipoprotein B mRNA editing enzyme catalytic subunit 3C [ *Homo sapiens* (human) ]" National Center for Biotechnology Information, U.S. National Library of Medicine [online]. Retrieved from: https://www.ncbi.nlm.nih.gov/gene/?term=27350, 6 printed pages.

NCBI Gene ID: 339 (Aug. 18, 2020) "APOBEC1 apolipoproteinB mRNA editing enzyme catalytic subunit 1 [*Homo sapiens* (human)]" National Center for Biotechnology Information, U.S. National Library of Medicine [online]. Retrieved from: https://www.ncbi.nlm.nih.gov/gene/?term=339; retrieved on Aug. 31, 2020, 9 printed pages.

NCBI Gene ID: 403314 (Aug. 22, 2020) "APOBEC4 apolipoprotein B mRNA editing enzyme catalytic polypeptide like 4 [ *Homo sapiens* (human) ]" National Center for Biotechnology Information, U.S. National Library of Medicine [online]. Retrieved from: https://www.ncbi.nlm.nih.gov/gene/?term=403314, 7 printed pages.

NCBI Gene ID: 57379 (Aug. 18, 2020) "AICDA activation induced cytidine deaminase [*Homo sapiens* (human)]" National Center for Biotechnology Information, U.S. National Library of Medicine [online]. Retrieved from: https://www.ncbi.nlm.nih.gov/gene/57379; retrieved on Aug. 21, 2020, 12 printed pages.

NCBI Gene ID: 5896 (Aug. 22, 2020) "RAG1 recombination activating 1 [*Homo sapiens* (human)]" National Center for Biotechnology Information, U.S. National Library of Medicine [online]. Retrieved from: https://www.ncbi.nlm.nih.gov/gene/5896; 7 printed pages.

NCBI Gene ID: 5897 (Aug. 22, 2020) "RAG2 recombination activating 2 [*Homo sapiens* (human)]" National Center for Biotechnology Information, U.S. National Library of Medicine [online]. Retrieved from: https://www.ncbi.nlm.nih.gov/gene/?term=5897; 6 printed pages.

NCBI Gene ID: 60489 (Aug. 22, 2020) "APOBEC3G apolipoprotein B mRNA editing enzyme catalytic subunit 3G [ *Homo sapiens* (human) ]" National Center for Biotechnology Information, U.S. National Library of Medicine [online]. Retrieved from: https://www.ncbi.nlm.nih.gov/gene/?term=60489, 8 printed pages.

NCBI Gene ID: 7150 (Aug. 30, 2020) "TOP1 DNA topoisomerase I [ *Homo sapiens* (human) ]" National Center for Biotechnology Information, U.S. National Library of Medicine [online]. Retrieved from: https://www.ncbi.nlm.nih.gov/gene/?term=7150, 7 printed pages.

NCBI Gene ID: 7153 (Aug. 18, 2020) "TOP2A DNA topoisomerase II alpha [ *Homo sapiens* (human) ]" National Center for Biotechnology Information, U.S. National Library of Medicine [online]. Retrieved from: https://www.ncbi.nlm.nih.gov/gene/?term=7153, 8 printed pages.

(56) References Cited

OTHER PUBLICATIONS

NCBI Gene ID: 7155 (Aug. 18, 2020) "TOP2B DNA topoisomerase II beta [ *Homo sapiens* (human) ]" National Center for Biotechnology Information, U.S. National Library of Medicine [online]. Retrieved from: https://www.ncbi.nlm.nih.gov/gene/?term=7155, 11 printed pages.

NCBI Gene ID: 9582 (Aug. 22, 2020) "APOBEC3B apolipoprotein B mRNA editing enzyme catalytic subunit 3B [ *Homo sapiens* (human) ]" National Center for Biotechnology Information, U.S. National Library of Medicine [online]. Retrieved from: https://www.ncbi.nlm.nih.gov/gene/?term=9582, 8 printed pages.

Okazaki, I. (2003) "Constitutive Expression of AID Leads to Tumorigenesis" *The Journal of Experimental Medicine*, 197(9):1173-1181.

Palacios, F. et al. (2010) "High expression of AID and active class switch recombination might account for a more aggressive disease in unmutated CLL patients: link with an activated microenvironment in CLL disease" *Blood*, 115(22):4488-4496.

Pasqualucci, L. et al. (2008) "AID is required for germinal center-derived lymphomagenesis" *Nature Genetics*, 40(1):108-112.

Pérez-Durán, P. et al. (2007) "Oncogenic events triggered by AID, the adverse effect of antibody diversification" *Carcinogenesis*, 28(12):2427-2433.

Qui, Y. et al. (2012) "Immunoglobulin G expression and its colocalization with complement proteins in papillary thyroid cancer" *Modern Pathology*, 25:36-45.

Reina-San-Martin, B. et al. (2004) "ATM Is Required for Efficient Recombination between Immunoglobulin Switch Regions" *The Journal of Experimental Medicine*, 200(9):1103-1110.

Robbiani, D.F. (2009) "AID Produces DNA Double-Strand Breaks in Non-Ig Genes and Mature B Cell Lymphomas with Reciprocal Chromosome Translocations" *Molecular Cell*, 36:631-641.

Shen, H.M. et al. (2008) "Expression of AID transgene is regulated in activated B cells but not in resting B cells and kidney" *Molecular Immunology*, 45:1883-1892.

Shikata, H. et al. (2012) "Role of activation-induced cytidine deaminase in the progression of follicular lymphoma" *Cancer Sci*, 103(3):415-421.

Volpi, E.V. et al. (2008) "FISH glossary: an overview of the fluorescence in situ hybridization technique" *BioTechniques*, 45(4):385-409.

White, C.A. et al. (2011) "AID dysregulation in lupus-prone MRL/Fas$^{lpr/lpr}$ mice increases class switch DNA recombination and promotes interchromosomal c-Myc/IgH loci translocations: Modulation by HoxC4" *Autoimmunity*, 44(8):585-598.

Xu, X. et al. (2009) "Increased Expression of Activation-Induced Cytidine Deaminase is Associated with Anti-CCP and Rheumatoid Factor in Rheumatoid Arthritis" *Scand J Immunol*, 70:309-316.

Yoshikawa, K. et al. (2002) "AID Enzyme-Induced Hypermutation in an Actively Transcribed Gene in Fibroblasts" *Science*, 296(5575):2033-2036.

Zhang, L. et al. (2012) "Expression of immunoglobulin G in esophageal squamous cell carcinomas and its association with tumor grade and Ki67" *Human Pathology*, 43:423-434.

U.S. Appl. No. 17/363,099, filed Jun. 30, 2021, by Castro et al.

RAD51 INHIBITORS

RELATED APPLICATION

This application claims priority to, and the benefit of U.S. Provisional Application No. 62/816,998, filed on Mar. 12, 2019, the entire contents of which are incorporated by reference.

BACKGROUND

RAD51 is a member of the RAD51 family which promotes the repair of DNA double strand breaks (DSB). RAD51 protein is highly conserved in most eukaryotes, from yeast to humans. The human RAD51 is a 339-amino acid protein that plays a major role in DNA replication and repair by homologous recombination (HR). RAD51 catalyzes strand transfer between a broken sequence and undamaged homologous template to allow re-synthesis of the damaged region.

Studies have demonstrated sensitization to certain DNA damaging therapies associated with defects in proteins that promote HR DNA repair. This sensitization is particularly dramatic for DNA cross-linking chemotherapeutic drugs and ionizing radiation. It has been shown that HR can be partially inhibited in order to sensitize cells to DNA damaging therapies. For example, inhibition of XRCC3 (a RAD51 paralog protein) using a synthetic peptide sensitized Chinese Hamster Ovary (CHO) cells to cisplatin and inhibited the formation of sub-nuclear RAD51 foci in response to DNA damage. Researchers have inhibited the expression of the RAD51 protein itself or blocked its function by overexpressing a dominant negative BRC peptide fragment derived from BRCA2. In view of the connection between increased sensitivity to DNA damaging therapies and defects in HR DNA repair-related proteins, there is a need for compounds that inhibit RAD51. The present application addresses the need.

SUMMARY

The present application relates to a compound of Formula I:

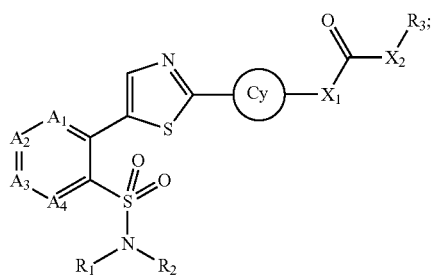

or a pharmaceutically acceptable salt or solvate thereof, wherein the definition of each variable is provided herein below.

The present application also relates to a pharmaceutical composition comprising a compound disclosed herein or a pharmaceutically acceptable salt or solvate thereof and a pharmaceutically acceptable carrier or diluent.

The present application further relates to a method of treating a disease or disorder in which RAD51 plays a role, for example, cancer, an autoimmune disease, an immune deficiency, or a neurodegenerative disease. The method comprises administering to a subject in need thereof an effective amount of a compound disclosed herein or a pharmaceutically acceptable salt or solvate thereof or a pharmaceutical composition disclosed herein.

The present application further relates to use of a compound disclosed herein, or a pharmaceutically acceptable salt or solvate thereof, or a pharmaceutical composition disclosed herein, in the manufacture of a medicament for the treatment of a disease or disorder in which RAD51 plays a role, for example, a cancer, an autoimmune disease, an immune deficiency, or a neurodegenerative disease.

The present application further relates to a compound disclosed herein, or a pharmaceutically acceptable salt or solvate thereof, or a pharmaceutical composition disclosed herein, for use in treating a disease or disorder in which RAD51 plays a role, for example, a cancer, an autoimmune disease, an immune deficiency, or a neurodegenerative disease.

The present application further relates to use of a compound disclosed herein, or a pharmaceutically acceptable salt or solvate thereof, or a pharmaceutical composition disclosed herein, in treating a disease or disorder in which RAD51 plays a role, for example, a cancer, an autoimmune disease, an immune deficiency, or a neurodegenerative disease.

The present application provides compounds and compositions with an improved efficacy and safety profile relative to known RAD51 inhibitors. The present application also provides agents with novel mechanisms of action toward RAD51 in the treatment of various types of diseases. Ultimately the present application provides a novel therapeutic strategy for the treatment of diseases and disorders associated with RAD51.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

DETAILED DESCRIPTION

Compounds of the Application

In one aspect, the present application relates to a compound of Formula I:

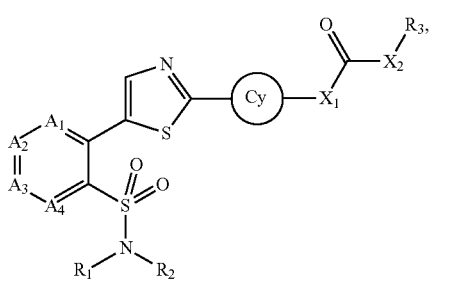

or a pharmaceutically acceptable salt or solvate thereof, wherein:

the thiazolyl ring

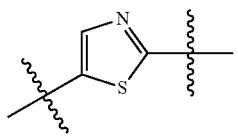 [SMILES: *c1cnc(*)s1]

is optionally substituted with F or Cl;

the ring Cy is $C_3$-$C_7$ cycloalkyl, bridged $C_6$-$C_{12}$ cycloalkyl, or saturated heterocyclyl comprising one or two 3- to 7-membered rings and 1-3 heteroatoms selected from N, O, and S, wherein the cycloalkyl or heterocyclyl moiety is optionally substituted with one or more groups selected from halogen, OH, CN, $NH_2$, $C_1$-$C_4$ alkyl, $C_1$-$C_4$ haloalkyl, $C_1$-$C_4$ alkoxy, and $C_1$-$C_4$ haloalkoxy;

$X_1$ is $NR_8$ or O, or, when $X_1$ is bonded to a nitrogen atom in the ring Cy, $X_1$ is absent;

$X_2$ is $NR_8$ or O;

$R_1$ is H or $C_1$-$C_6$ alkyl optionally substituted with halogen, OH, $C_1$-$C_6$ alkoxy, or $C_6$-$C_{10}$ aryloxy;

$R_2$ is H or $C_1$-$C_6$ alkyl optionally substituted with halogen, OH, $C_1$-$C_6$ alkoxy, or $C_6$-$C_{10}$ aryloxy;

or $R_1$ and $R_2$, together with the nitrogen atom to which they are attached, form a heterocyclyl comprising one or two 3- to 7-membered rings and 1-3 heteroatoms selected from N, O, and S;

$R_3$ is $C_1$-$C_6$ alkyl optionally substituted with one or more groups selected from halogen, OH, and CN, phenyl, $CH_2$-phenyl, $C_3$-$C_7$ cycloalkyl, $CH_2$—($C_3$-$C_7$) cycloalkyl, heterocyclyl, or $CH_2$-heterocyclyl, wherein the heterocyclyl comprises one or two 3- to 7-membered rings and 1-3 heteroatoms selected from N, O, and S, wherein the cycloalkyl, phenyl, or heterocyclyl moiety is optionally substituted with one or more groups selected from halogen, OH, CN, $C_1$-$C_4$ alkyl, $C_1$-$C_4$ haloalkyl, $C_1$-$C_4$ alkoxy, and $C_1$-$C_4$ haloalkoxy;

$A_1$, $A_2$, $A_3$, and $A_4$ are each independently N or $C(R_4)$;

each $R_4$ is independently H, halogen, CN, OH, $N(R_6')_2$, $C_1$-$C_6$ alkoxy, $C(=O)N(R_6)_2$, $C(=O)OR_6$, $C(=O)R_6$, Q-T, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$;

each Q is independently $C_1$-$C_4$ alkylene or O—($C_1$-$C_4$) alkylene wherein the oxygen atom is bonded to the ring

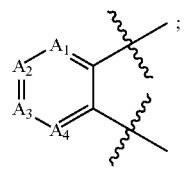

each T is independently $C_1$-$C_4$ alkoxy, OH, $N(R_6)_2$, $N(R_5)C(=O)R_6$, $N(R_5)C(=O)OR_6$, $C(=O)N(R_6)_2$, $C(=O)OR_6$, $C(=O)R_6$, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$;

each $R_5$ is independently H or $C_1$-$C_4$ alkyl;

each $R_6'$ is independently H, $C_1$-$C_6$ alkyl optionally substituted with one or more $R_7$, $C_1$-$C_6$ haloalkyl, $C_3$-$C_7$ cycloalkyl, heterocyclyl comprising one or two 3- to 7-membered rings and 1-3 heteroatoms selected from N, O, and S, $C_6$-$C_{10}$ aryl, or heteroaryl comprising one or two 5- or 6-membered rings and 1-3 heteroatoms selected from N, O, and S, wherein the cycloalkyl, heterocyclyl, aryl, or heteroaryl moiety is optionally substituted with one or more $R_9$, wherein at least one $R_6'$ is not H;

or two $R_6'$ together with the atoms to which they are attached form a 3- to 10-membered heterocyclyl comprising 1-3 heteroatoms selected from N, O, and S, wherein the heterocyclyl is optionally substituted with one or more $R_9$;

each $R_6$ is independently H, $C_1$-$C_6$ alkyl optionally substituted with one or more $R_7$, $C_1$-$C_6$ haloalkyl, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$;

or two $R_6$ together with the atoms to which they are attached form a 3- to 10-membered heterocyclyl comprising 1-3 heteroatoms selected from N, O, and S, wherein the heterocyclyl is optionally substituted with one or more $R_9$;

each $R_7$ is independently $N(R_8)_2$, $OR_8$, $C_6$-$C_{10}$ aryl, or heteroaryl comprising one or two 5- or 6-membered rings and 1-3 heteroatoms selected from N, O, and S;

each $R_8$ is independently H or $C_1$-$C_6$ alkyl; and each $R_9$ is independently oxo, halogen, OH, CN, $NH_2$, $N(C_1$-$C_4$ alkyl$)_2$, $C_1$-$C_6$ alkyl, $N(C_1$-$C_4$ alkyl$)_2$, $C_1$-$C_6$ haloalkyl, $C_1$-$C_6$ alkoxy, or $C_1$-$C_6$ haloalkoxy, wherein the $C_1$-$C_6$ alkyl is optionally substituted with one or more oxo, OH, O($C_1$-$C_4$ alkyl), CN, $NH_2$, $NH(C_1$-$C_4$ alkyl), or $N(C_1$-$C_4$ alkyl$)_2$.

In one aspect, the present application relates to a compound of Formula I:

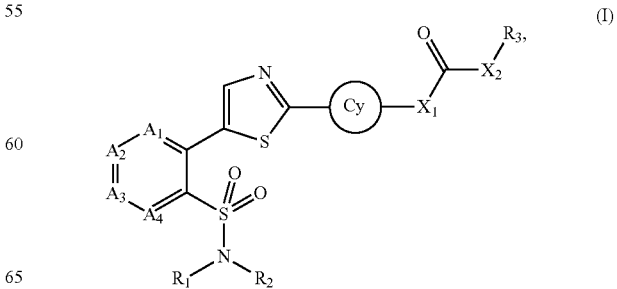

or a pharmaceutically acceptable salt or solvate thereof, wherein:

the thiazolyl ring

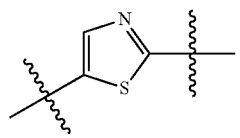 [SMILES: *c1cnc(*)s1]

is optionally substituted with F or Cl;

the ring Cy is $C_3$-$C_7$ cycloalkyl, bridged $C_6$-$C_{12}$ cycloalkyl, or saturated heterocyclyl comprising one or two 3- to 7-membered rings and 1-3 heteroatoms selected from N, O, and S, wherein the cycloalkyl or heterocyclyl moiety is optionally substituted with one or more groups selected from halogen, OH, CN, $NH_2$, $C_1$-$C_4$ alkyl, $C_1$-$C_4$ haloalkyl, $C_1$-$C_4$ alkoxy, and $C_1$-$C_4$ haloalkoxy;

$X_1$ is $NR_8$ or O, or, when $X_1$ is bonded to a nitrogen atom in the ring Cy, $X_1$ is absent;

$X_2$ is $NR_8$ or O;

$R_1$ is H or $C_1$-$C_6$ alkyl optionally substituted with halogen, OH, $C_1$-$C_6$ alkoxy, or $C_6$-$C_{10}$ aryloxy;

$R_2$ is H or $C_1$-$C_6$ alkyl optionally substituted with halogen, OH, $C_1$-$C_6$ alkoxy, or $C_6$-$C_{10}$ aryloxy;

or $R_1$ and $R_2$, together with the nitrogen atom to which they are attached, form a 3-7 membered heterocyclic ring comprising 1 or 2 heteroatoms selected from N, O, and S;

$R_3$ is $C_1$-$C_6$ alkyl optionally substituted with one or more groups selected from halogen, OH, and CN, phenyl, $CH_2$-phenyl, $C_3$-$C_7$ cycloalkyl, $CH_2$—($C_3$-$C_7$) cycloalkyl, heterocyclyl, or $CH_2$-heterocyclyl, wherein the heterocyclyl comprises one 3- to 7-membered ring and 1 or 2 heteroatoms selected from N, O, and S, wherein the cycloalkyl, phenyl, or heterocyclyl moiety is optionally substituted with one or more groups selected from halogen, OH, CN, $C_1$-$C_4$ alkyl, $C_1$-$C_4$ haloalkyl, $C_1$-$C_4$ alkoxy, and $C_1$-$C_4$ haloalkoxy;

$A_1$, $A_2$, $A_3$, and $A_4$ are each independently N or $C(R_4)$;

each $R_4$ is independently H, halogen, CN, OH, $N(R_6')_2$, $C_1$-$C_4$ alkoxy, $C(=O)N(R_6)_2$, $C(=O)OR_6$, $C(=O)R_6$, Q-T, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$;

each Q is independently $C_1$-$C_4$ alkylene or O—($C_1$-$C_4$) alkylene wherein the oxygen atom is bonded to the ring

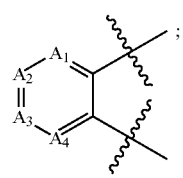

each T is independently $C_1$-$C_4$ alkoxy, $NH_2$, $NH(C_1$-$C_4$ alkyl), $N(C_1$-$C_4$ alkyl)$_2$, $N(R_5)C(=O)R_6$, $N(R_5)C(=O)OR_6$, $C(=O)N(R_6)_2$, $C(=O)OR_6$, or $C(=O)R_6$;

each $R_5$ is independently H or $C_1$-$C_4$ alkyl;

each $R_6'$ is independently H, $C_1$-$C_6$ alkyl optionally substituted with one or more $R_7$, $C_1$-$C_6$ haloalkyl, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$, wherein at least one $R_6'$ is not H;

each $R_6$ is independently H, $C_1$-$C_6$ alkyl optionally substituted with one or more $R_7$, $C_1$-$C_6$ haloalkyl, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$;

each $R_7$ is independently $N(R_8)_2$ or $OR_8$;

each $R_8$ is independently H or $C_1$-$C_6$ alkyl; and each $R_9$ is independently OH, CN, $NH_2$, $N(C_1$-$C_4$ alkyl)$_2$, $C_1$-$C_6$ alkyl optionally substituted with one or more groups selected from OH, CN, $NH_2$, and $N(C_1$-$C_4$ alkyl)$_2$, $C_1$-$C_6$ haloalkyl, $C_1$-$C_6$ alkoxy, or $C_1$-$C_6$ haloalkoxy.

In some embodiments, the compound of Formula I is of Formula Ia or Ib:

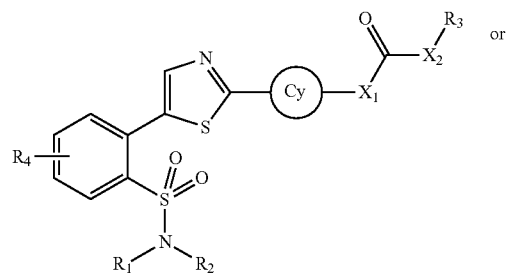

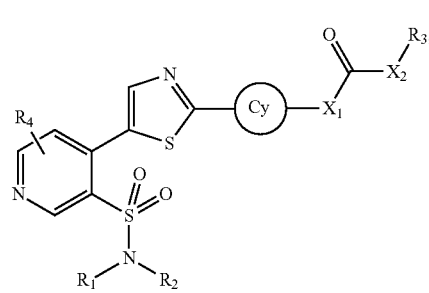

or a pharmaceutically acceptable salt or solvate thereof.

In some embodiments, the compound of Formula I is of Formula Ic:

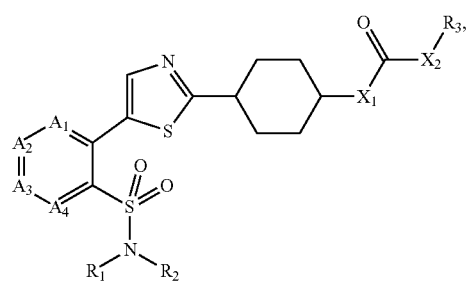

or a pharmaceutically acceptable salt or solvate thereof.

In some embodiments, the compound of Formula I is of Formula Id, Ie, If, or Ig:

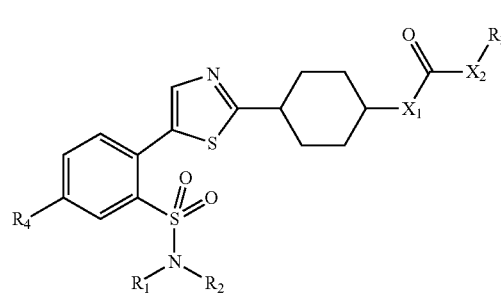
(Id)

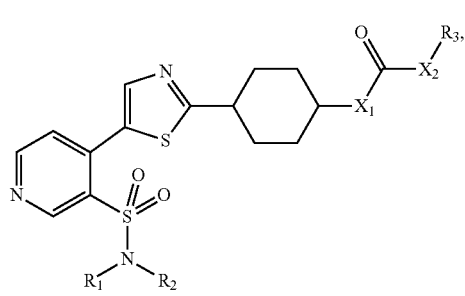
(Ie)

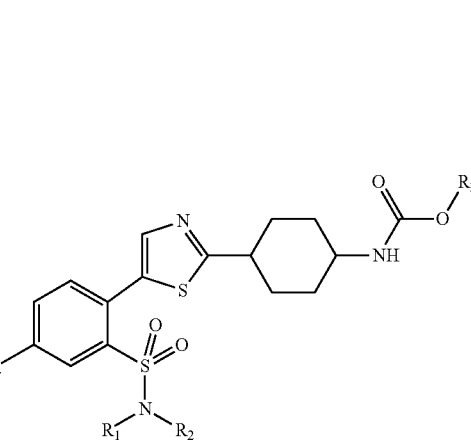
(If)

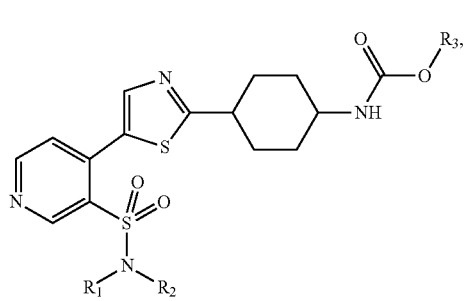
(Ig)

or a pharmaceutically acceptable salt or solvate thereof.

In some embodiments, the compound of Formula I is of Formula IIa or IIb:

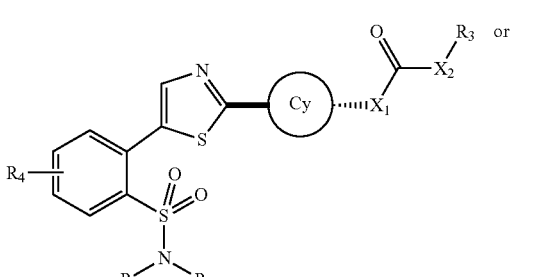
(IIa) or

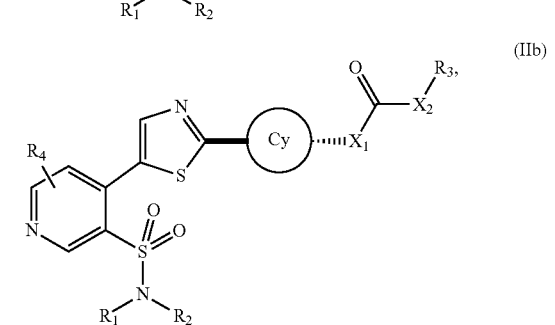
(IIb)

or a pharmaceutically acceptable salt or solvate thereof.

In some embodiments, the compound of Formula I is of Formula IIc:

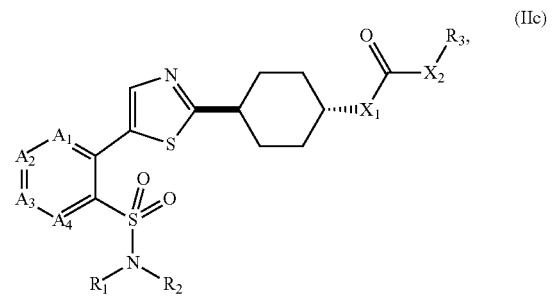
(IIc)

or a pharmaceutically acceptable salt or solvate thereof.

In some embodiments, the compound of Formula I is of Formula IId, IIe, IIf, or IIg:

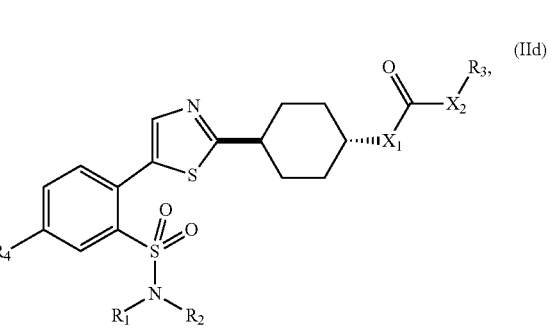
(IId)

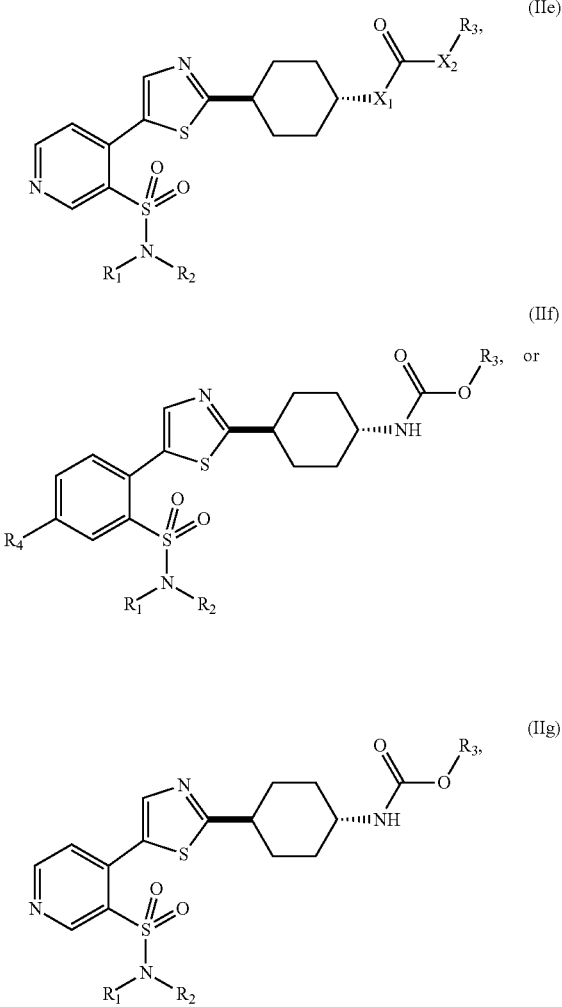

or a pharmaceutically acceptable salt or solvate thereof.

For a compound of any of Formula I, Ia, Ib, Ic, Id, Ie, If, Ig, IIa, IIb, IIc, IId, IIe, IIf, or IIg, where applicable:

(A1) In some embodiments, the thiazolyl ring

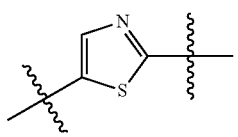

is unsubstituted.

(A2) In some embodiments, the thiazolyl ring

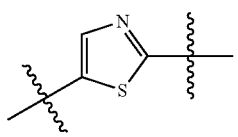

is substituted with F.

(A3) In some embodiments, the thiazolyl ring

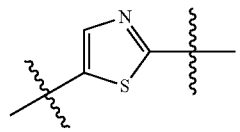 [SMILES: *c1cnc(*)s1]

is substituted with Cl.

(B1) In some embodiments, the ring Cy is $C_3$-$C_7$ cycloalkyl selected from cyclopropyl, cyclobutyl, cyclopentyl, cyclohexyl, and cycloheptyl, each of which is optionally substituted with one or more groups selected from halogen (e.g., F, Cl, Br, or I), OH, CN, $NH_2$, $C_1$-$C_4$ alkyl (e.g., methyl, ethyl, n-propyl, i-propyl, n-butyl, i-butyl, s-butyl, or t-butyl), $C_1$-$C_4$ haloalkyl (e.g., methyl, ethyl, n-propyl, i-propyl, n-butyl, i-butyl, s-butyl, or t-butyl, each of which is substituted with one or more halogen (e.g., F, Cl, Br, or I)), $C_1$-$C_4$ alkoxy (e.g., methoxy, ethoxy, propoxy, or butoxy), and $C_1$-$C_4$ haloalkoxy (e.g., methoxy, ethoxy, propoxy, or butoxy, each of which is substituted with one or more halogen (e.g., F, Cl, Br, or I)). In some embodiments, the ring Cy is cyclohexyl, optionally substituted as described herein.

(B2) In some embodiments, the ring Cy is bridged $C_6$-$C_{12}$ cycloalkyl selected from bicyclo[2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, bornenyl, norbornyl, norbornenyl, 6,6-dimethylbicyclo[3.1.1]heptyl, and adamantyl, each of which is optionally substituted with one or more groups selected from halogen (e.g., F, Cl, Br, or I), OH, CN, $NH_2$, $C_1$-$C_4$ alkyl (e.g., methyl, ethyl, n-propyl, i-propyl, n-butyl, i-butyl, s-butyl, or t-butyl), $C_1$-$C_4$ haloalkyl (e.g., methyl, ethyl, n-propyl, i-propyl, n-butyl, i-butyl, s-butyl, or t-butyl, each of which is substituted with one or more halogen (e.g., F, Cl, Br, or I)), $C_1$-$C_4$ alkoxy (e.g., methoxy, ethoxy, propoxy, or butoxy), and $C_1$-$C_4$ haloalkoxy (e.g., methoxy, ethoxy, propoxy, or butoxy, each of which is substituted with one or more halogen (e.g., F, Cl, Br, or I)).

(B3) In some embodiments, the ring Cy is saturated heterocyclyl selected from aziridinyl, oxiranyl, thiiranyl, diaziridinyl, oxaziridinyl, dioxiranyl, azetidinyl, oxetanyl, thietanyl, diazetidinyl, dioxetanyl, dithietanyl, pyrrolidinyl, tetrahydrofuranyl, tetrahydrothiophenyl, imidazolidinyl, pyrazolidinyl, oxazolidinyl, isoxazolidinyl, thiazolidinyl, isothiazolidinyl, dioxolanyl, dithiolany, piperidinyl, tetrahydropyranyl, thianyl, piperazinyl, morpholinyl, thiomorpholinyl, dioxanyl, dithianyl, hexahydro-1,3,5-triazinyl, trioxanyl, trithianyl, azepanyl, oxepanyl, thiepanyl, diazepanyl, diazaspiro[4.4]nonyl, diazaspiro[3.5]nonyl, hexahydropyridazinyl, hexahydropyrimidinyl, tetrahydrothiopyranyl, thiomorpholinyl, tropanyl, valerolactamyl, azanorbornyl, quinuclidinyl, isoquinuclidinyl, azabicyclo[2.2.1]heptanyl, 2-azabicyclo[3.2.1]octanyl, azabicyclo[3.2.1]octanyl, azabicyclo[3.2.2]nonanyl, azabicyclo[3.3.0]nonanyl, azabicyclo[3.3.1]nonanyl, diazabicyclo[2.2.1]heptanyl, diazabicyclo[3.2.1]octanyl, octahydropyrrolo[3,4-b]pyrrolyl, and octahydropyrrolo[3,4-c]pyrrolyl, each of which is optionally substituted with one or more groups selected from halogen (e.g., F, Cl, Br, or I), OH, CN, $NH_2$, $C_1$-$C_4$ alkyl (e.g., methyl, ethyl, n-propyl, i-propyl, n-butyl, i-butyl, s-butyl, or t-butyl), $C_1$-$C_4$ haloalkyl (e.g., methyl, ethyl, n-propyl, i-propyl, n-butyl, i-butyl, s-butyl, or t-butyl, each of which is substituted with one or more halogen (e.g., F, Cl, Br, or I)), $C_1$-$C_4$ alkoxy (e.g., methoxy, ethoxy, propoxy, or butoxy), and $C_1$-$C_4$ haloalkoxy (e.g., methoxy, ethoxy, propoxy, or butoxy, each of which is substituted with one or more halogen (e.g., F, Cl, Br, or I)).

(C1) In some embodiments, $X_1$ is $NR_8$ and $X_2$ is $NR_8$. In a further embodiment, each $R_8$ is H. In another further embodiment, one $R_8$ is H, and the other $R_8$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched)). In another further embodiment, each $R_8$ is independently $C_1$-$C_6$ alkyl (e.g., methyl, ethyl, n-propyl, i-propyl, n-butyl, i-butyl, s-butyl, t-butyl, pentyl (straight or branched), or hexyl (straight or branched)).

(C2) In some embodiments, $X_1$ is $NR_8$ and $X_2$ is O. In a further embodiment, $R_8$ is H. In another further embodiment, $R_8$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched)).

(C3) In some embodiments, $X_1$ is O and $X_2$ is $NR_8$. In a further embodiment, $R_8$ is H. In another further embodiment, $R_8$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched)).

(C4) In some embodiments, $X_1$ is O and $X_2$ is O.

(C5) In some embodiments, $X_1$ is absent and $X_2$ is $NR_8$. In a further embodiment, $R_8$ is H. In another further embodiment, $R_8$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched)).

(C6) In some embodiments, $X_1$ is absent and $X_2$ is O.

(D1) In some embodiments, $R_1$ is H.

(D2) In some embodiments, $R_1$ is $C_1$-$C_6$ alkyl selected from methyl, ethyl, n-propyl, propyl, n-butyl, i-butyl, s-butyl, t-butyl, pentyl (straight or branched), and hexyl (straight or branched), each of which is optionally substituted with one or more groups selected from halogen (e.g., F, Cl, Br, or I), OH, $C_1$-$C_6$ alkoxy (e.g., methoxy, ethoxy, propoxy, butoxy, pentoxy, or hexyloxy), and $C_6$-$C_{10}$ aryloxy (e.g., phenoxy). In some embodiments, $R_1$ is $C_1$-$C_4$ alkyl selected from methyl, ethyl, n-propyl, i-propyl, n-butyl, i-butyl, s-butyl, and t-butyl, each of which is optionally substituted with one or more groups selected from halogen (e.g., F, Cl, Br, or I), OH, $C_1$-$C_6$ alkoxy (e.g., methoxy, ethoxy, propoxy, butoxy, pentoxy, or hexyloxy), and $C_6$-$C_{10}$ aryloxy (e.g., phenoxy). In some embodiments, $R_1$ is $C_1$-$C_4$ alkyl selected from methyl, ethyl, n-propyl, i-propyl, n-butyl, i-butyl, s-butyl, and t-butyl, each of which is optionally substituted with one or more groups selected from halogen (e.g., F, Cl, Br, or I) and OH. In some embodiments, $R_1$ is unsubstituted $C_1$-$C_6$ alkyl. In some embodiments, $R_1$ is unsubstituted $C_1$-$C_4$ alkyl.

(E1) In some embodiments, $R_2$ is H.

(E2) In some embodiments, $R_2$ is $C_1$-$C_6$ alkyl selected from methyl, ethyl, n-propyl, i-propyl, n-butyl, i-butyl, s-butyl, t-butyl, pentyl (straight or branched), and hexyl (straight or branched), each of which is optionally substituted with one or more groups selected from halogen (e.g., F, Cl, Br, or I), OH, $C_1$-$C_6$ alkoxy (e.g., methoxy, ethoxy, propoxy, butoxy, pentoxy, or hexyloxy), and $C_6$-$C_{10}$ aryloxy (e.g., phenoxy). In some embodiments, $R_2$ is $C_1$-$C_4$ alkyl selected from methyl, ethyl, n-propyl, i-propyl, n-butyl, i-butyl, s-butyl, and t-butyl, each of which is optionally substituted with one or more groups selected from halogen (e.g., F, Cl, Br, or I), OH, $C_1$-$C_6$ alkoxy (e.g., methoxy, ethoxy, propoxy, butoxy, pentoxy, or hexyloxy), and $C_6$-$C_{10}$ aryloxy (e.g., phenoxy). In some embodiments, $R_2$ is $C_1$-$C_4$ alkyl selected from methyl, ethyl, n-propyl, i-propyl, n-butyl, i-butyl, s-butyl, and t-butyl, each of which is optionally substituted with one or more groups selected from halogen (e.g., F, Cl, Br, or I) and OH. In some embodiments, $R_2$ is unsubstituted $C_1$-$C_6$ alkyl. In some embodiments, $R_2$ is unsubstituted $C_1$-$C_4$ alkyl.

(DE) In some embodiments, $R_1$ and $R_2$, together with the nitrogen atom to which they are attached, form heterocyclic ring selected from aziridinyl, oxiranyl, thiiranyl, diaziridinyl, oxaziridinyl, dioxiranyl, azetidinyl, oxetanyl, thietanyl, diazetidinyl, dioxetanyl, dithietanyl, pyrrolidinyl, tetrahydrofuranyl, tetrahydrothiophenyl, imidazolidinyl, pyrazolidinyl, oxazolidinyl, isoxazolidinyl, thiazolidinyl, isothiazolidinyl, dioxolanyl, dithiolany, piperidinyl, tetrahydropyranyl, thianyl, piperazinyl, morpholinyl, thiomorpholinyl, dioxanyl, dithianyl, hexahydro-1,3,5-triazinyl, trioxanyl, trithianyl, azepanyl, oxepanyl, thiepanyl, diazepanyl, hexahydropyridazinyl, hexahydropyrimidinyl, tetrahydrothiopyranyl, and thiomorpholinyl. In some embodiments, $R_1$ and $R_2$, together with the nitrogen atom to which they are attached, form azetidinyl or pyrrolidinyl.

(F1) In some embodiments, $R_3$ is $C_1$-$C_6$ alkyl selected from methyl, ethyl, n-propyl, propyl, n-butyl, i-butyl, s-butyl, t-butyl, pentyl (straight or branched), and hexyl (straight or branched), each of which is optionally substituted with one or more groups selected from halogen (e.g., F, Cl, Br, or I), OH, and CN. In some embodiments, $R_3$ is $C_1$-$C_4$ alkyl selected from methyl, ethyl, n-propyl, i-propyl, n-butyl, i-butyl, s-butyl, and t-butyl, each of which is optionally substituted with one or more groups selected from halogen (e.g., F, Cl, Br, or I), OH, and CN. In some embodiments, $R_3$ is unsubstituted $C_1$-$C_6$ alkyl. In some embodiments, $R_3$ is unsubstituted $C_1$-$C_4$ alkyl. In some embodiments, $R_3$ is unsubstituted methyl. In some embodiments, $R_3$ is unsubstituted i-propyl. In some embodiments, $R_3$ is unsubstituted t-butyl.

(F2) In some embodiments, $R_3$ is phenyl or $CH_2$-phenyl, wherein the phenyl moiety is optionally substituted with one or more groups selected from halogen (e.g., F, Cl, Br, or I), OH, CN, $C_1$-$C_4$ alkyl (e.g., methyl, ethyl, n-propyl, i-propyl, n-butyl, i-butyl, s-butyl, or t-butyl), $C_1$-$C_4$ haloalkyl (e.g., methyl, ethyl, n-propyl, i-propyl, n-butyl, i-butyl, s-butyl, or t-butyl, each of which is substituted with one or more halogen (e.g., F, Cl, Br, or I)), $C_1$-$C_4$ alkoxy (e.g., methoxy, ethoxy, propoxy, or butoxy), and $C_1$-$C_4$ haloalkoxy (e.g., methoxy, ethoxy, propoxy, or butoxy, each of which is substituted with one or more halogen (e.g., F, Cl, Br, or I)).

(F3) In some embodiments, $R_3$ is $C_3$-$C_7$ cycloalkyl or $CH_2$—($C_3$-$C_7$) cycloalkyl, wherein the cycloalkyl moiety is selected from cyclopropyl, cyclobutyl, cyclopentyl, cyclohexyl, and cycloheptyl, each of which is optionally substituted with one or more groups selected from halogen (e.g., F, Cl, Br, or I), OH, CN, $C_1$-$C_4$ alkyl (e.g., methyl, ethyl, n-propyl, i-propyl, n-butyl, i-butyl, s-butyl, or t-butyl), $C_1$-$C_4$ haloalkyl (e.g., methyl, ethyl, n-propyl, i-propyl, n-butyl, i-butyl, s-butyl, or t-butyl, each of which is substituted with one or more halogen (e.g., F, Cl, Br, or I)), $C_1$-$C_4$ alkoxy (e.g., methoxy, ethoxy, propoxy, or butoxy), and $C_1$-$C_4$ haloalkoxy (e.g., methoxy, ethoxy, propoxy, or butoxy, each of which is substituted with one or more halogen (e.g., F, Cl, Br, or I)). In some embodiments, $R_3$ is cyclopropyl or cyclobutyl, or $CH_2$-cyclopropyl or $CH_2$-cyclobutyl, each of which is optionally substituted as described herein. In some embodiments, $R_3$ is cyclopropyl optionally substituted as described herein.

(F4) In some embodiments, $R_3$ is heterocyclyl or $CH_2$-heterocyclyl, wherein the heterocyclyl moiety is selected from aziridinyl, oxiranyl, thiiranyl, diaziridinyl, oxaziridinyl, dioxiranyl, azetidinyl, oxetanyl, thietanyl, diazetidinyl, dioxetanyl, dithietanyl, pyrrolidinyl, tetrahydrofuranyl, tetrahydrothiophenyl, imidazolidinyl, pyrazolidinyl, oxazolidinyl, isoxazolidinyl, thiazolidinyl, isothiazolidinyl, dioxolanyl, dithiolany, piperidinyl, tetrahydropyranyl, thianyl, piperazinyl, morpholinyl, thiomorpholinyl, dioxanyl, dithianyl, hexahydro-1,3,5-triazinyl, trioxanyl, trithianyl, azepanyl, oxepanyl, thiepanyl, diazepanyl, hexahydropyridazinyl, hexahydropyrimidinyl, tetrahydrothiopyranyl, and thiomorpholinyl, each of which is optionally substituted with one or more groups selected from halogen (e.g., F, Cl, Br, or I), OH, CN, $C_1$-$C_4$ alkyl (e.g., methyl, ethyl, n-propyl, i-propyl, n-butyl, i-butyl, s-butyl, or t-butyl), $C_1$-$C_4$ haloalkyl (e.g., methyl, ethyl, n-propyl, i-propyl, n-butyl, i-butyl, s-butyl, or t-butyl, each of which is substituted with one or more halogen (e.g., F, Cl, Br, or I)), $C_1$-$C_4$ alkoxy (e.g., methoxy, ethoxy, propoxy, or butoxy), and $C_1$-$C_4$ haloalkoxy (e.g., methoxy, ethoxy, propoxy, or butoxy, each of which is substituted with one or more halogen (e.g., F, Cl, Br, or I)). In some embodiments, $R_3$ is unsubstituted oxetanyl.

(G1) In some embodiments, $A_1$, $A_2$, $A_3$, and $A_4$ are each $C(R_4)$.

(G2) In some embodiments, one, two, or three of $A_1$, $A_2$, $A_3$, and $A_4$ are N, and the remaining of $A_1$, $A_2$, $A_3$, and $A_4$ are $C(R_4)$.

(G3) In some embodiments, one of $A_1$, $A_2$, $A_3$, and $A_4$ is N, and the remaining of $A_1$, $A_2$, $A_3$, and $A_4$ are $C(R_4)$.

(G3a) In some embodiments, $A_1$ is N, and $A_2$, $A_3$, and $A_4$ are $C(R_4)$.

(G3b) In some embodiments, $A_2$ is N, and $A_1$, $A_3$, and $A_4$ are $C(R_4)$.

(G3c) In some embodiments, $A_3$ is N, and $A_1$, $A_2$, and $A_4$ are $C(R_4)$.

(G3d) In some embodiments, $A_4$ is N, and $A_1$, $A_2$, and $A_3$ are $C(R_4)$.

(G4) In some embodiments, two of $A_1$, $A_2$, $A_3$, and $A_4$ are N, and the remaining of $A_1$, $A_2$, $A_3$, and $A_4$ are $C(R_4)$.

(G4a) In some embodiments, $A_1$ and $A_2$ are N, and $A_3$ and $A_4$ are $C(R_4)$.

(G4b) In some embodiments, $A_1$ and $A_3$ are N, and $A_2$ and $A_4$ are $C(R_4)$.

(G4c) In some embodiments, $A_1$ and $A_4$ are N, and $A_2$ and $A_3$ are $C(R_4)$.

(G4d) In some embodiments, $A_2$ and $A_3$ are N, and $A_1$ and $A_4$ are $C(R_4)$.

(G4e) In some embodiments, $A_2$ and $A_4$ are N, and $A_1$ and $A_3$ are $C(R_4)$.

(G4f) In some embodiments, $A_3$ and $A_4$ are N, and $A_1$ and $A_2$ are $C(R_4)$.

(G5) In some embodiments, three of $A_1$, $A_2$, $A_3$, and $A_4$ are N, and the remaining of $A_1$, $A_2$, $A_3$, and $A_4$ is $C(R_4)$.

(G5a) In some embodiments, $A_2$, $A_3$, and $A_4$ are N, and $A_1$ is $C(R_4)$.

(G5b) In some embodiments, $A_1$, $A_3$, and $A_4$ are N, and $A_2$ is $C(R_4)$.

(G5c) In some embodiments, $A_1$, $A_2$, and $A_4$ are N, and $A_3$ is $C(R_4)$.

(G5d) In some embodiments, $A_1$, $A_2$, and $A_3$ are N, and $A_4$ is $C(R_4)$.

(G6) In some embodiments, $A_1$, $A_2$, $A_3$, and $A_4$ are each N.

(G7) In some embodiments, at most two of $A_1$, $A_2$, $A_3$, and $A_4$ are N.

(H1) In some embodiments, each $R_4$ is H.

(H2) In some embodiments, at least one $R_4$ is halogen, CN, OH, $N(R_6')_2$, $C_1$-$C_6$ alkoxy, $C(=O)N(R_6)_2$, $C(=O)OR_6$, $C(=O)R_6$, Q-T, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$.

(H2a) In some embodiments, at least one $R_4$ is halogen (e.g., F, Cl, Br, or I), CN, OH, $N(R_6')_2$, $C_1$-$C_6$ alkoxy (e.g., methoxy, ethoxy, propoxy, butoxy, pentoxy, or hexoxy), $C(=O)N(R_6)_2$, $C(=O)OR_6$, $C(=O)R_6$, or Q-T.

(H2b) In some embodiments, at least one $R_4$ is CN, OH, $N(R_6')_2$, $C_1$-$C_6$ alkoxy (e.g., methoxy, ethoxy, propoxy, butoxy, pentoxy, or hexoxy), $C(=O)N(R_6)_2$, $C(=O)OR_6$, $C(=O)R_6$, or Q-T.

(H2c) In some embodiments, at least one $R_4$ is $C(=O)N(R_6)_2$, $C(=O)OR_6$, $C(=O)R_6$, or Q-T.

(H2d) In some embodiments, at least one $R_4$ is Q-T.

(H2e) In some embodiments, at least one $R_4$ is $N(R_6')_2$, and one of $R_6'$ is H, and the other $R_6'$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched), each of which is optionally substituted with one or more $R_7$), $C_1$-$C_6$ haloalkyl (e.g., methyl, ethyl, n-propyl, propyl, n-butyl, i-butyl, s-butyl, t-butyl, pentyl (straight or branched), or hexyl (straight or branched), each of which is substituted with one or more halogen (e.g., F, Cl, Br, or I)), $C_3$-$C_7$ cycloalkyl (e.g., cyclopropyl, cyclobutyl, cyclopentyl, cyclohexyl, or cycloheptyl), heterocyclyl comprising one or two 3- to 7-membered rings and 1-3 heteroatoms selected from N, O, and S (e.g., aziridinyl, oxiranyl, thiiranyl, diaziridinyl, oxaziridinyl, dioxiranyl, azetidinyl, oxetanyl, thietanyl, diazetidinyl, dioxetanyl, dithietanyl, pyrrolidinyl, tetrahydrofuranyl, tetrahydrothiophenyl, imidazolidinyl, pyrazolidinyl, oxazolidinyl, isoxazolidinyl, thiazolidinyl, isothiazolidinyl, dioxolanyl, dithiolany, piperidinyl, tetrahydropyranyl, thianyl, piperazinyl, morpholinyl, thiomorpholinyl, dioxanyl, dithianyl, hexahydro-1,3,5-triazinyl, trioxanyl, trithianyl, azepanyl, oxepanyl, thiepanyl, diazepanyl, hexahydropyridazinyl, hexahydropyrimidinyl, tetrahydrothiopyranyl, or thiomorpholinyl), $C_6$-$C_{10}$ aryl (e.g., phenyl), or heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl), wherein the cycloalkyl, heterocyclyl, aryl, or heteroaryl moiety is optionally substituted with one or more $R_9$.

(H2e-1) In some embodiments, at least one $R_4$ is $N(R_6')_2$, and one of $R_6'$ is H, and the other $R_6'$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched), each of which is optionally substituted with one or more $R_7$), or $C_1$-$C_6$ haloalkyl (e.g., methyl, ethyl, n-propyl, i-propyl, n-butyl, i-butyl, s-butyl, t-butyl, pentyl (straight or branched), or hexyl (straight or branched), each of which is substituted with one or more halogen (e.g., F, Cl, Br, or I)).

(H2e-2) In some embodiments, at least one $R_4$ is $N(R_6')_2$, and one of $R_6'$ is H, and the other $R_6'$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched), each of which is optionally substituted with one or more $R_7$).

(H2e-3) In some embodiments, at least one $R_4$ is $N(R_6')_2$, and one of $R_6'$ is H, and the other $R_6'$ is $C_1$-$C_6$ haloalkyl (e.g., methyl, ethyl, n-propyl, i-propyl, n-butyl, i-butyl, s-butyl, t-butyl, pentyl (straight or branched), or hexyl (straight or branched), each of which is substituted with one or more halogen (e.g., F, Cl, Br, or I)).

(H2e-4) In some embodiments, at least one $R_4$ is $N(R_6')_2$, and one of $R_6'$ is H, and the other $R_6'$ is $C_3$-$C_7$ cycloalkyl (e.g., cyclopropyl, cyclobutyl, cyclopentyl, cyclohexyl, or cycloheptyl), wherein the cycloalkyl moiety is optionally substituted with one or more $R_9$.

(H2e-5) In some embodiments, at least one $R_4$ is $N(R_6')_2$, and one of $R_6'$ is H, and the other $R_6'$ is heterocyclyl comprising one or two 3- to 7-membered rings and 1-3 heteroatoms selected from N, O, and S (e.g., aziridinyl, oxiranyl, thiiranyl, diaziridinyl, oxaziridinyl, dioxiranyl, azetidinyl, oxetanyl, thietanyl, diazetidinyl, dioxetanyl, dithietanyl, pyrrolidinyl, tetrahydrofuranyl, tetrahydrothiophenyl, imidazolidinyl, pyrazolidinyl, oxazolidinyl, isoxazolidinyl, thiazolidinyl, isothiazolidinyl, dioxolanyl, dithiolany, piperidinyl, tetrahydropyranyl, thianyl, piperazinyl, morpholinyl, thiomorpholinyl, dioxanyl, dithianyl, hexahydro-1,3,5-triazinyl, trioxanyl, trithianyl, azepanyl, oxepanyl, thiepanyl, diazepanyl, hexahydropyridazinyl, hexahydropyrimidinyl, tetrahydrothiopyranyl, or thiomorpholinyl), wherein the heterocyclyl moiety is optionally substituted with one or more $R_9$. In some embodiments, at least one $R_4$ is $N(R_6')_2$, and one of $R_6'$ is H, and the other $R_6'$ is heterocyclyl comprising one 4- to 6-membered ring and 1-3 heteroatoms selected from N, O, and S, as described herein, wherein the heterocyclyl moiety is optionally substituted with one or more $R_9$. In some embodiments, at least one $R_4$ is $N(R_6')_2$, and one of $R_6'$ is H, and the other $R_6'$ is heterocyclyl comprising one 4- to 5-membered ring and 1-3 heteroatoms selected from N, O, and S, as described herein, wherein the heterocyclyl moiety is optionally substituted with one or more $R_9$. In some embodiments, at least one $R_4$ is $N(R_6')_2$, and one of $R_6'$ is H, and the other $R_6'$ is heterocyclyl comprising one 4-membered ring and 1-2 heteroatoms selected from N, O, and S, as described herein, wherein the heterocyclyl moiety is optionally substituted with one or more $R_9$. In some embodiments, at least one $R_4$ is $N(R_6')_2$, and one of $R_6'$ is H, and the other $R_6'$ is heterocyclyl comprising one 4-membered ring and 1 heteroatom selected from N, O, and S, as described herein, wherein the heterocyclyl moiety is optionally substituted with one or more $R_9$.

(H2e-6) In some embodiments, at least one $R_4$ is $N(R_6')_2$, and one of $R_6'$ is H, and the other $R_6'$ is $C_6$-$C_{10}$ aryl (e.g., phenyl), wherein the aryl moiety is optionally substituted with one or more $R_9$.

(H2e-7) In some embodiments, at least one $R_4$ is $N(R_6')_2$, and one of $R_6'$ is H, and the other $R_6'$ is heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl), wherein the heteroaryl moiety is optionally substituted with one or more $R_9$. In some embodiments, at least one $R_4$ is $N(R_6')_2$, and one of $R_6'$ is H, and the other $R_6'$ is heteroaryl comprising one 5- or 6-membered ring and 1-3 heteroatoms selected from N, O, and S, as described herein, wherein the heteroaryl moiety is optionally substituted with one or more $R_9$. In some embodiments, at least one $R_4$ is $N(R_6')_2$, and one of $R_6'$ is H, and the other $R_6'$ is heteroaryl comprising one 5-membered ring and 1-3 heteroatoms selected from N, O, and S, as described herein, wherein the heteroaryl moiety is optionally substituted with one or more $R_9$. In some embodiments, at least one $R_4$ is $N(R_6')_2$, and one of $R_6'$ is H, and the other $R_6'$ is heteroaryl comprising one 6-membered ring and 1-3 heteroatoms selected from N, O, and S, as described herein, wherein the heteroaryl moiety is optionally substituted with one or more $R_9$.

(H2e-8) In some embodiments, at least one $R_4$ is $N(R_6')_2$, and the two $R_6'$ are each independently $C_1$-$C_6$ alkyl (e.g., methyl, ethyl, n-propyl, i-propyl, n-butyl, i-butyl, s-butyl, t-butyl, pentyl (straight or branched), or hexyl (straight or branched), each of which is optionally substituted with one or more $R_7$), or $C_1$-$C_6$ haloalkyl (e.g., methyl, ethyl, n-propyl, i-propyl, n-butyl, i-butyl, s-butyl, t-butyl, pentyl (straight or branched), or hexyl (straight or branched), each of which is substituted with one or more halogen (e.g., F, Cl, Br, or I)).

(H2e-9) In some embodiments, at least one $R_4$ is $N(R_6')_2$, and the two $R_6'$ together with the atoms to which they are attached form a 3- to 10-membered heterocyclyl comprising 1-3 heteroatoms selected from N, O, and S (e.g., aziridinyl, oxiranyl, thiiranyl, diaziridinyl, oxaziridinyl, dioxiranyl, azetidinyl, oxetanyl, thietanyl, diazetidinyl, dioxetanyl, dithietanyl, pyrrolidinyl, tetrahydrofuranyl, tetrahydrothiophenyl, imidazolidinyl, pyrazolidinyl, oxazolidinyl, isoxazolidinyl, thiazolidinyl, isothiazolidinyl, dioxolanyl, dithiolany, piperidinyl, tetrahydropyranyl, thianyl, piperazinyl, morpholinyl, thiomorpholinyl, dioxanyl, dithianyl, hexahydro-1,3,5-triazinyl, trioxanyl, trithianyl, azepanyl, oxepanyl, thiepanyl, diazepanyl, hexahydropyridazinyl, hexahydropyrimidinyl, tetrahydrothiopyranyl, or thiomorpholinyl), wherein the heterocyclyl is optionally substituted with one or more $R_9$. In some embodiments, at least one $R_4$ is $N(R_6')_2$, and the two $R_6'$ together with the atoms to which they are attached form a 3- to 6-membered heterocyclyl comprising 1-3 heteroatoms selected from N, O, and S, as described herein, and is optionally substituted with one or more $R_9$. In some embodiments, at least one $R_4$ is $N(R_6')_2$, and the two $R_6'$ together with the atoms to which they are attached form a 4- to 6-membered heterocyclyl comprising 1-3 heteroatoms selected from N, O, and S, as described herein, and is optionally substituted with one or more $R_9$. In some embodiments, at least one $R_4$ is $N(R_6')_2$, and the two $R_6'$ together with the atoms to which they are attached form azetidinyl, piperidinyl, morpholinyl, or thiomorpholino, each of which is optionally substituted with one or more $R_9$.

(H2e-10) In some embodiments, at least one $R_4$ is $N(R_6')_2$, and one of $R_6'$ is $C_1$-$C_6$ alkyl or $C_1$-$C_6$ haloalkyl, as described herein, and the other $R_6'$ is cycloalkyl, heterocyclyl comprising one or two 3- to 7-membered rings and 1-3 heteroatoms selected from N, O, and S, $C_6$-$C_{10}$ aryl, or heteroaryl comprising one or two 5- or 6-membered rings and 1-3 heteroatoms selected from N, O, and S, as described herein, wherein the cycloalkyl, heterocyclyl, aryl, or heteroaryl moiety is optionally substituted with one or more $R_9$.

(H2f) In some embodiments, at least one $R_4$ is $C_6$-$C_{10}$ aryl (e.g., phenyl) or heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl), wherein the aryl or heteroaryl moiety is optionally substituted with one or more $R_9$.

(H2f-1) In some embodiments, at least one $R_4$ is $C_6$-$C_{10}$ aryl (e.g., phenyl), wherein the aryl moiety is optionally substituted with one or more $R_9$.

(H2f-2) In some embodiments, at least one $R_4$ is heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl), wherein the heteroaryl moiety is optionally substituted with one or more $R_9$. In some embodiments, at least one $R_4$ is heteroaryl comprising one 5- or 6-membered ring and 1-3 heteroatoms selected from N, O, and S, as described herein, wherein the heteroaryl moiety is optionally substituted with one or more $R_9$. In some embodiments, at least one $R_4$ is heteroaryl comprising one 5-membered ring and 1-3 heteroatoms selected from N, O, and S, as described herein, wherein the heteroaryl moiety is optionally substituted with one or more $R_9$. In some embodiments, at least one $R_4$ is heteroaryl comprising one 6-membered ring and 1-3 heteroatoms selected from N, O, and S, as described herein, wherein the heteroaryl moiety is optionally substituted with one or more $R_9$.

(H3) In some embodiments, only one $R_4$ is halogen, CN, OH, $N(R_6')_2$, $C_1$-$C_6$ alkoxy, $C(=O)N(R_6)_2$, $C(=O)OR_6$, $C(=O)R_6$, Q-T, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$.

(H3a) In some embodiments, only one $R_4$ is halogen (e.g., F, Cl, Br, or I), CN, OH, $N(R_6')_2$, $C_1$-$C_6$ alkoxy (e.g., methoxy, ethoxy, propoxy, butoxy, pentoxy, or hexoxy), $C(=O)N(R_6)_2$, $C(=O)OR_6$, $C(=O)R_6$, or Q-T.

(H3b) In some embodiments, only one $R_4$ is CN, OH, $N(R_6')_2$, $C_1$-$C_6$ alkoxy (e.g., methoxy, ethoxy, propoxy, butoxy, pentoxy, or hexoxy), $C(=O)N(R_6)_2$, $C(=O)OR_6$, $C(=O)R_6$, or Q-T.

(H3c) In some embodiments, only one $R_4$ is $C(=O)N(R_6)_2$, $C(=O)OR_6$, $C(=O)R_6$, or Q-T.

(H3d) In some embodiments, only one $R_4$ is Q-T.

(H3e) In some embodiments, only one $R_4$ is $N(R_6')_2$, and one of $R_6'$ is H, and the other $R_6'$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched), each of which is optionally substituted with one or more $R_7$), $C_1$-$C_6$ haloalkyl (e.g., methyl, ethyl, n-propyl, propyl, n-butyl, i-butyl, s-butyl, t-butyl, pentyl (straight or branched), or hexyl (straight or branched), each of which is substituted with one or more halogen (e.g., F, Cl, Br, or I)), $C_3$-$C_7$ cycloalkyl, heterocyclyl comprising one or two 3- to 7-membered rings and 1-3 heteroatoms selected from N, O, and S (e.g., aziridinyl, oxiranyl, thiiranyl, diaziridinyl, oxaziridinyl, dioxiranyl, azetidinyl, oxetanyl, thietanyl, diazetidinyl, dioxetanyl, dithietanyl, pyrrolidinyl, tetrahydrofuranyl, tetrahydrothiophenyl, imidazolidinyl, pyrazolidinyl, oxazolidinyl, isoxazolidinyl, thiazolidinyl, isothiazolidinyl, dioxolanyl, dithiolany, piperidinyl, tetrahydropyranyl, thianyl, piperazinyl, morpholinyl, thiomorpholinyl, dioxanyl, dithianyl, hexahydro-1,3,5-triazinyl, trioxanyl, trithianyl, azepanyl, oxepanyl, thiepanyl, diazepanyl, hexahydropyridazinyl, hexahydropyrimidinyl, tetrahydrothiopyranyl, or thiomorpholinyl), $C_6$-$C_{10}$ aryl (e.g., phenyl), or heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl), wherein the cycloalkyl, heterocyclyl, aryl, or heteroaryl moiety is optionally substituted with one or more $R_9$.

(H3e-1) In some embodiments, only one $R_4$ is $N(R_6')_2$, and one of $R_6'$ is H, and the other $R_6'$ is $C_1$-$C_6$ alkyl (e.g., methyl, ethyl, n-propyl, i-propyl, n-butyl, i-butyl, s-butyl, butyl, pentyl (straight or branched), or hexyl (straight or branched), each of which is optionally substituted with one or more $R_7$), or $C_1$-$C_6$ haloalkyl (e.g., methyl, ethyl, n-propyl, i-propyl, n-butyl, i-butyl, s-butyl, t-butyl, pentyl (straight or branched), or hexyl (straight or branched), each of which is substituted with one or more halogen (e.g., F, Cl, Br, or I)).

(H3e-2) In some embodiments, only one $R_4$ is $N(R_6')_2$, and one of $R_6'$ is H, and the other $R_6'$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched), each of which is optionally substituted with one or more $R_7$).

(H3e-3) In some embodiments, only one $R_4$ is $N(R_6')_2$, and one of $R_6'$ is H, and the other $R_6'$ is $C_1$-$C_6$ haloalkyl (e.g., methyl, ethyl, n-propyl, i-propyl, n-butyl, i-butyl, s-butyl, butyl, pentyl (straight or branched), or hexyl (straight or branched), each of which is substituted with one or more halogen (e.g., F, Cl, Br, or I)).

(H3e-4) In some embodiments, only one $R_4$ is $N(R_6')_2$, and one of $R_6'$ is H, and the other $R_6'$ is $C_3$-$C_7$ cycloalkyl (e.g., cyclopropyl, cyclobutyl, cyclopentyl, cyclohexyl, or cycloheptyl), wherein the cycloalkyl moiety is optionally substituted with one or more $R_9$.

(H3e-5) In some embodiments, only one $R_4$ is $N(R_6')_2$, and one of $R_6'$ is H, and the other $R_6'$ is heterocyclyl comprising one or two 3- to 7-membered rings and 1-3 heteroatoms selected from N, O, and S (e.g., aziridinyl, oxiranyl, thiiranyl, diaziridinyl, oxaziridinyl, dioxiranyl, azetidinyl, oxetanyl, thietanyl, diazetidinyl, dioxetanyl, dithietanyl, pyrrolidinyl, tetrahydrofuranyl, tetrahydrothiophenyl, imidazolidinyl, pyrazolidinyl, oxazolidinyl, isoxazolidinyl, thiazolidinyl, isothiazolidinyl, dioxolanyl, dithiolany, piperidinyl, tetrahydropyranyl, thianyl, piperazinyl, morpholinyl, thiomorpholinyl, dioxanyl, dithianyl, hexahydro-1,3,5-triazinyl, trioxanyl, trithianyl, azepanyl, oxepanyl, thiepanyl, diazepanyl, hexahydropyridazinyl, hexahydropyrimidinyl, tetrahydrothiopyranyl, or thiomorpholinyl), wherein the heterocyclyl moiety is optionally substituted with one or more $R_9$. In some embodiments, only one $R_4$ is $N(R_6')_2$, and one of $R_6'$ is H, and the other $R_6'$ is heterocyclyl comprising one 4- to 6-membered ring and 1-3 heteroatoms selected from N, O, and S, as described herein, wherein the heterocyclyl moiety is optionally substituted with one or more $R_9$. In some embodiments, only one $R_4$ is $N(R_6')_2$, and one of $R_6'$ is H, and the other $R_6'$ is heterocyclyl comprising one 4- to 5-membered ring and 1-3 heteroatoms selected from N, O, and S, as described herein, wherein the heterocyclyl moiety is optionally substituted with one or more $R_9$. In some embodiments, only one $R_4$ is $N(R_6')_2$, and one of $R_6'$ is H, and the other $R_6'$ is heterocyclyl comprising one 4-membered ring and 1-2 heteroatoms selected from N, O, and S, as described herein, wherein the heterocyclyl moiety is optionally substituted with one or more $R_9$. In some embodiments, only one $R_4$ is $N(R_6')_2$, and one of $R_6'$ is H, and the other $R_6'$ is heterocyclyl comprising one 4-membered ring and 1 heteroatom selected from N, O, and S, as described herein, wherein the heterocyclyl moiety is optionally substituted with one or more $R_9$.

(H3e-6) In some embodiments, only one $R_4$ is $N(R_6')_2$, and one of $R_6'$ is H, and the other $R_6'$ is $C_6$-$C_{10}$ aryl (e.g., phenyl), wherein the aryl moiety is optionally substituted with one or more $R_9$.

(H3e-7) In some embodiments, only one $R_4$ is $N(R_6')_2$, and one of $R_6'$ is H, and the other $R_6'$ is heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl), wherein the heteroaryl moiety is optionally substituted with one or more $R_9$. In some embodiments, only one $R_4$ is $N(R_6')_2$, and one of $R_6'$ is H, and the other $R_6'$ is heteroaryl comprising one 5- or 6-membered ring and 1-3 heteroatoms selected from N, O, and S, as described herein, wherein the heteroaryl moiety is optionally substituted with one or more $R_9$. In some embodiments, only one $R_4$ is $N(R_6')_2$, and one of $R_6'$ is H, and the other $R_6'$ is heteroaryl comprising one 5-membered ring and 1-3 heteroatoms selected from N, O, and S, as described herein, wherein the heteroaryl moiety is optionally substituted with one or more $R_9$. In some embodiments, only one $R_4$ is $N(R_6')_2$, and one of $R_6'$ is H, and the other $R_6'$ is heteroaryl comprising one 6-membered ring and 1-3 heteroatoms selected from N, O, and S, as described herein, wherein the heteroaryl moiety is optionally substituted with one or more $R_9$.

(H3e-8) In some embodiments, only one $R_4$ is $N(R_6')_2$, and the two $R_6'$ are each independently $C_1$-$C_6$ alkyl (e.g., methyl, ethyl, n-propyl, i-propyl, n-butyl, i-butyl, s-butyl, t-butyl, pentyl (straight or branched), or hexyl (straight or branched), each of which is optionally substituted with one or more $R_7$), or $C_1$-$C_6$ haloalkyl (e.g., methyl, ethyl, n-propyl, i-propyl, n-butyl, i-butyl, s-butyl, t-butyl, pentyl (straight or branched), or hexyl (straight or branched), each of which is substituted with one or more halogen (e.g., F, Cl, Br, or I)).

(H3e-9) In some embodiments, only one $R_4$ is $N(R_6')_2$, and the two $R_6'$ together with the atoms to which they are attached form a 3- to 10-membered heterocyclyl comprising 1-3 heteroatoms selected from N, O, and S (e.g., aziridinyl, oxiranyl, thiiranyl, diaziridinyl, oxaziridinyl, dioxiranyl, azetidinyl, oxetanyl, thietanyl, diazetidinyl, dioxetanyl, dithietanyl, pyrrolidinyl, tetrahydrofuranyl, tetrahydrothiophenyl, imidazolidinyl, pyrazolidinyl, oxazolidinyl, isoxazolidinyl, thiazolidinyl, isothiazolidinyl, dioxolanyl, dithiolany, piperidinyl, tetrahydropyranyl, thianyl, piperazinyl, morpholinyl, thiomorpholinyl, dioxanyl, dithianyl, hexahydro-1,3,5-triazinyl, trioxanyl, trithianyl, azepanyl, oxepanyl, thiepanyl, diazepanyl, hexahydropyridazinyl, hexahydropyrimidinyl, tetrahydrothiopyranyl, or thiomorpholinyl), wherein the heterocyclyl is optionally substituted with one or more $R_9$. In some embodiments, only one $R_4$ is $N(R_6')_2$, and the two $R_6'$ together with the atoms to which they are attached form a 3- to 6-membered heterocyclyl comprising 1-3 heteroatoms selected from N, O, and S, as described herein, and is optionally substituted with one or more $R_9$. In some embodiments, only one $R_4$ is $N(R_6')_2$, and the two $R_6'$ together with the atoms to which they are attached form a 4- to 6-membered heterocyclyl comprising 1-3 heteroatoms selected from N, O, and S, as described herein, and is optionally substituted with one or more $R_9$. In some embodiments, only one $R_4$ is $N(R_6')_2$, and the two $R_6'$ together with the atoms to which they are attached form azetidinyl, piperidinyl, morpholinyl, or thiomorpholino, each of which is optionally substituted with one or more $R_9$.

(H3e-10) In some embodiments, only one $R_4$ is $N(R_6')_2$, and one of $R_6'$ is $C_1$-$C_6$ alkyl or $C_1$-$C_6$ haloalkyl, as described herein, and the other $R_6'$ is cycloalkyl, heterocyclyl comprising one or two 3- to 7-membered rings and 1-3 heteroatoms selected from N, O, and S, $C_6$-$C_{10}$ aryl, or heteroaryl comprising one or two 5- or 6-membered rings and 1-3 heteroatoms selected from N, O, and S, as described herein, wherein the cycloalkyl, heterocyclyl, aryl, or heteroaryl moiety is optionally substituted with one or more $R_9$.

(H3f) In some embodiments, only one $R_4$ is $C_6$-$C_{10}$ aryl (e.g., phenyl) or heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl), wherein the aryl or heteroaryl moiety is optionally substituted with one or more $R_9$.

(H3f-1) In some embodiments, only one $R_4$ is $C_6$-$C_{10}$ aryl (e.g., phenyl), wherein the aryl moiety is optionally substituted with one or more $R_9$.

(H3f-2) In some embodiments, only one $R_4$ is heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl), wherein the heteroaryl moiety is optionally substituted with one or more $R_9$. In some embodiments, only one $R_4$ is heteroaryl comprising one 5- or 6-membered ring and 1-3 heteroatoms selected from N, O, and S, as described herein, wherein the heteroaryl moiety is optionally substituted with one or more $R_9$. In some embodiments, only one $R_4$ is heteroaryl comprising one 5-membered ring and 1-3 heteroatoms selected from N, O, and S, as described herein, wherein the heteroaryl moiety is optionally substituted with one or more $R_9$. In some embodiments, only one $R_4$ is heteroaryl comprising one 6-membered ring and 1-3 heteroatoms selected from N, O, and S, as described herein, wherein the heteroaryl moiety is optionally substituted with one or more $R_9$.

(H3g) In some embodiments, at least one $R_4$ is $C_1$-$C_6$ alkoxy (e.g., methoxy, ethoxy, propoxy, butoxy, pentoxy, or hexoxy).

(H3g-1) In some embodiments, only one $R_4$ is $C_1$-$C_6$ alkoxy (e.g., methoxy, ethoxy, propoxy, butoxy, pentoxy, or hexoxy).

(I1) In some embodiments, at least one Q is $C_1$-$C_4$ alkylene (e.g., methylene, ethylene, propylene, or butylene).

(I2) In some embodiments, at least one Q is O—($C_1$-$C_4$) alkylene (e.g., O-methylene, O-ethylene, O-propylene, or O-butylene).

(J1) In some embodiments, at least one T is $C_1$-$C_4$ alkoxy (e.g., methoxy, ethoxy, propoxy, or butoxy), OH, $N(R_6)_2$, $N(R_5)C(=O)R_6$, $N(R_5)C(=O)OR_6$, $C(=O)N(R_6)_2$, $C(=O)OR_6$, $C(=O)R_6$, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$.

(J2) In some embodiments, at least one T is $C_1$-$C_4$ alkoxy (e.g., methoxy, ethoxy, propoxy, or butoxy).

(J3) In some embodiments, at least one T is $NH_2$, $NH(R_6)$, or $N(R_6)_2$.

(J3-1) In some embodiments, at least one T is $NH_2$, $NH(R_6)$, or $N(R_6)_2$, wherein $R_6$ is $C_1$-$C_4$ alkyl moiety is selected from methyl, ethyl, n-propyl, i-propyl, n-butyl, i-butyl, s-butyl, and t-butyl.

(J4) In some embodiments, at least one T is $N(R_5)C(=O)R_6$ or $N(R_5)C(=O)OR_6$.

(J5) In some embodiments, at least one T is $C(=O)N(R_6)_2$, $C(=O)OR_6$, or $C(=O)R_6$.

(J6) In some embodiments, at least one T is OH.

(J7) In some embodiments, at least one T is $C_6$-$C_{10}$ aryl or heteroaryl comprising one or two 5- or 6-membered rings and 1-3 heteroatoms selected from N, O, and S, wherein the aryl or heteroaryl moiety is optionally substituted with one or more $R_9$.

(J7-1) In some embodiments, at least one T is $C_6$-$C_{10}$ aryl (e.g., phenyl), optionally substituted with one or more $R_9$.

(J7-2) In some embodiments, at least one T is heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl), optionally substituted with one or more $R_9$. In some embodiments, at least one T is heteroaryl comprising one 5- or 6-membered ring and 1-3 heteroatoms selected from N, O, and S, as described herein, wherein the heteroaryl moiety is optionally substituted with one or more $R_9$. In some embodiments, at least one T is heteroaryl comprising one 5-membered ring and 1-3 heteroatoms selected from N, O, and S, as described herein, wherein the heteroaryl moiety is optionally substituted with one or more $R_9$. In some embodiments, at least one T is heteroaryl comprising one 6-membered ring and 1-3 heteroatoms selected from N, O, and S, as described herein, wherein the heteroaryl moiety is optionally substituted with one or more $R_9$.

(K1) In some embodiments, each $R_5$ is H.

(K2) In some embodiments, at least one $R_5$ is $C_1$-$C_4$ alkyl (e.g., methyl, ethyl, n-propyl, i-propyl, n-butyl, i-butyl, s-butyl, or t-butyl).

(L1) In some embodiments, each $R_6$ is H.

(L2) In some embodiments, at least one $R_6$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched), each of which is optionally substituted with one or more $R_7$), $C_1$-$C_6$ haloalkyl (e.g., methyl, ethyl, n-propyl, i-propyl, n-butyl, i-butyl, s-butyl, t-butyl, pentyl (straight or branched), or hexyl (straight or branched), each of which is substituted with one or more halogen (e.g., F, Cl, Br, or I)), $C_6$-$C_{10}$ aryl (e.g., phenyl), or heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl), wherein the aryl or heteroaryl moiety is optionally substituted with one or more $R_9$.

(L2a) In some embodiments, at least one $R_6$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched), each of which is optionally substituted with one or more $R_7$), or $C_1$-$C_6$ haloalkyl (e.g., methyl, ethyl, n-propyl, i-propyl, n-butyl, i-butyl, s-butyl, t-butyl, pentyl (straight or branched), or hexyl (straight or branched), each of which is substituted with one or more halogen (e.g., F, Cl, Br, or I)).

(L2b) In some embodiments, at least one $R_6$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched), each of which is optionally substituted with one or more $R_7$).

(L2c) In some embodiments, at least one $R_6$ is $C_6$-$C_{10}$ aryl (e.g., phenyl), wherein the aryl moiety is optionally substituted with one or more $R_9$.

(L2d) In some embodiments, at least one $R_6$ is heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl), wherein the heteroaryl moiety is optionally substituted with one or more $R_9$. In some embodiments, at least one $R_6$ is heteroaryl comprising one 5- or 6-membered ring and 1-3 heteroatoms selected from N, O, and S, as described herein, wherein the heteroaryl moiety is optionally substituted with one or more $R_9$. In some embodiments, at least one $R_6$ is heteroaryl comprising one 5-membered ring and 1-3 heteroatoms selected from N, O, and S, as described herein, wherein the heteroaryl moiety is optionally substituted with one or more $R_9$. In some embodiments, at least one $R_6$ is heteroaryl comprising one 6-membered ring and 1-3 heteroatoms selected from N, O, and S, as described herein, wherein the heteroaryl moiety is optionally substituted with one or more $R_9$.

(L2e) In some embodiments, two $R_6$ together with the atoms to which they are attached form a 3- to 10-membered heterocyclyl comprising 1-3 heteroatoms selected from N, O, and S (e.g., aziridinyl, oxiranyl, thiiranyl, diaziridinyl, oxaziridinyl, dioxiranyl, azetidinyl, oxetanyl, thietanyl, diazetidinyl, dioxetanyl, dithietanyl, pyrrolidinyl, tetrahydrofuranyl, tetrahydrothiophenyl, imidazolidinyl, pyrazolidinyl, oxazolidinyl, isoxazolidinyl, thiazolidinyl, isothiazolidinyl, dioxolanyl, dithiolany, piperidinyl, tetrahydropyranyl, thianyl, piperazinyl, morpholinyl, thiomorpholinyl, dioxanyl, dithianyl, hexahydro-1,3,5-triazinyl, trioxanyl, trithianyl, azepanyl, oxepanyl, thiepanyl, diazepanyl, hexahydropyridazinyl, hexahydropyrimidinyl, tetrahydrothiopyranyl, or thiomorpholinyl), wherein the heterocyclyl is optionally substituted with one or more $R_9$. In some embodiments, two $R_6$ together with the atoms to which they are attached form a 3- to 6-membered heterocyclyl comprising 1-3 heteroatoms selected from N, O, and S, as described herein, and is optionally substituted with one or more $R_9$. In some embodiments, two $R_6$ together with the atoms to which they are attached form a 4- to 6-membered heterocyclyl comprising 1-3 heteroatoms selected from N, O, and S, as described herein, and is optionally substituted with one or more $R_9$.

(M1a) In some embodiments, each $R_7$ is independently $N(R_8)_2$, and each $R_8$ is H.

(M1b) In some embodiments, each $R_7$ is independently $N(R_8)_2$, and one $R_8$ is H, and the other $R_8$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched)).

(M1c) In some embodiments, each $R_7$ is independently $N(R_8)_2$, and each $R_8$ is independently $C_1$-$C_6$ alkyl (e.g., methyl, ethyl, n-propyl, i-propyl, n-butyl, i-butyl, s-butyl, t-butyl, pentyl (straight or branched), or hexyl (straight or branched)).

(M2a) In some embodiments, each $R_7$ is independently $OR_8$, and $R_8$ is H.

(M2b) In some embodiments, each $R_7$ is independently $OR_8$, and $R_8$ is $C_1$-$C_6$ alkyl (e.g., methyl, ethyl, n-propyl, i-propyl, n-butyl, i-butyl, s-butyl, t-butyl, pentyl (straight or branched), or hexyl (straight or branched)).

(M2c) In some embodiments, each $R_7$ is independently $C_6$-$C_{10}$ aryl (e.g., phenyl) or heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl).

(M2c-1) In some embodiments, each $R_7$ is independently $C_6$-$C_{10}$ aryl (e.g., phenyl).

(M2c-2) In some embodiments, each $R_7$ is independently heteroaryl comprising one or two 5- or 6-membered rings and 1-3 heteroatoms selected from N, O, and S (e.g., pyridinyl, pyrazinyl, pyrimidinyl, pyridazinyl, pyrrolyl, pyrazolyl, imidazolyl, thiazolyl, oxazolyl, isooxazolyl, isothiazolyl, thiadiazolyl, oxadiazolyl, thiophenyl, furanyl, isoquinolinyl, indolyl, pyrazolopyridinyl, indazolyl, benzofuranyl, benzoxazolyl, benzothiazolyl, or benzotriazolyl).

(N1) In some embodiments, each $R_9$ is independently oxo, halogen (e.g., F, Cl, Br, or I), OH, CN, $NH_2$, $N(C_1$-$C_4$ alkyl$)_2$ (e.g., dimethylamino, methylethylamino, diethylamino, methylpropylamino, ethylpropylamino, dipropylamino, methylbutylamino, ethylbutylamino, propylbutylamino, or dibutyamino), $C_1$-$C_6$ alkyl (e.g., methyl, ethyl, n-propyl, i-propyl, n-butyl, i-butyl, s-butyl, t-butyl, pentyl (straight or branched), or hexyl (straight or branched)), $C_1$-$C_6$ haloalkyl (e.g., methyl, ethyl, n-propyl, i-propyl, n-butyl, i-butyl, s-butyl, t-butyl, pentyl (straight or branched), or hexyl (straight or branched), each of which is substituted with one or more halogen (e.g., F, Cl, Br, or I)), $C_1$-$C_6$ alkoxy (e.g., methoxy, ethoxy, propoxy, butoxy, pentoxy, or hexyloxy), or $C_1$-$C_6$ haloalkoxy (e.g., methoxy, ethoxy, propoxy, butoxy, pentoxy, or hexyloxy, each of which is substituted with one or more halogen (e.g., F, Cl, Br, or I)), wherein the $C_1$-$C_6$ alkyl is optionally substituted with one or more groups selected from oxo, OH, O($C_1$-$C_4$ alkyl), CN, $NH_2$, and $N(C_1$-$C_4$ alkyl$)_2$ (e.g., dimethylamino, methylethylamino, diethylamino, methylpropylamino, ethylpropylamino, dipropylamino, methylbutylamino, ethylbutylamino, propylbutylamino, or dibutyamino).

(N2) In some embodiments, each $R_9$ is independently OH, CN, $NH_2$, $N(C_1$-$C_4$ alkyl$)_2$ (e.g., dimethylamino, methylethylamino, diethylamino, methylpropylamino, ethylpropylamino, dipropylamino, methylbutylamino, ethylbutylamino, propylbutylamino, or dibutyamino), $C_1$-$C_6$ alkyl (e.g., methyl, ethyl, n-propyl, i-propyl, n-butyl, i-butyl, s-butyl, t-butyl, pentyl (straight or branched), or hexyl (straight or branched)), $C_1$-$C_6$ haloalkyl (e.g., methyl, ethyl, n-propyl, i-propyl, n-butyl, i-butyl, s-butyl, t-butyl, pentyl (straight or branched), or hexyl (straight or branched)), each of which is substituted with one or more halogen (e.g., F, Cl, Br, or I)), $C_1$-$C_6$ alkoxy (e.g., methoxy, ethoxy, propoxy, butoxy, pentoxy, or hexyloxy), or $C_1$-$C_6$ haloalkoxy (e.g., methoxy, ethoxy, propoxy, butoxy, pentoxy, or hexyloxy, each of which is substituted with one or more halogen (e.g., F, Cl, Br, or I)), wherein the $C_1$-$C_6$ alkyl is optionally substituted with one or more groups selected from OH, CN, $NH_2$, and $N(C_1$-$C_4$ alkyl$)_2$ (e.g., dimethylamino, methylethylamino, diethylamino, methylpropylamino, ethylpropylamino, dipropylamino, methylbutylamino, ethylbutylamino, propylbutylamino, or dibutyamino).

For a compound of any of Formula I, Ia, Ib, Ic, Id, Ie, If, Ig, IIa, IIb, IIc, IId, IIe, IIf, or IIg, where applicable, each of the substituent groups illustrated herein for any of Cy, $X_1$, $X_2$, $A_1$, $A_2$, $A_3$, $A_4$, $R_1$, $R_2$, $R_3$, $R_4$, $R_5$, $R_6$, $R_6'$, $R_7$, $R_8$, $R_9$, Q, and T, can be combined with any of the substituent groups illustrated herein for one or more of the remainder of Cy, $X_1$, $X_2$, $A_1$, $A_2$, $A_3$, $A_4$, $R_1$, $R_2$, $R_3$, $R_4$, $R_5$, $R_6$, $R_6'$, $R_7$, $R_8$, $R_9$, Q, and T.

For example:

(O1) The thiazolyl ring

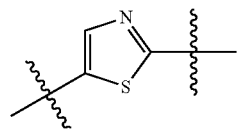 [SMILES: *c1cnc(*)s1]

is as illustrated in any of (A1)-(A3), and the Cy ring is as illustrated in (B1).

(O2) The thiazolyl ring

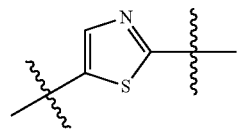 [SMILES: *c1cnc(*)s1]

is as illustrated in any of (A1)-(A3), and the Cy ring is as illustrated in (B2).

(O3) The thiazolyl ring

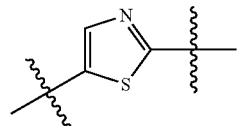 [SMILES: *c1cnc(*)s1]

is as illustrated in any of (A1)-(A3), and the Cy ring is as illustrated in (B3).

(P1) The thiazolyl ring

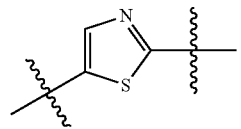 [SMILES: *c1cnc(*)s1]

is as illustrated in any of (A1)-(A3), and $A_1$, $A_2$, $A_3$, and $A_4$ are each as illustrated in (G1).

(P2) The thiazolyl ring

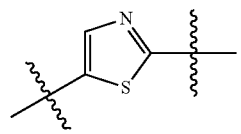

is as illustrated in any of (A1)-(A3), and $A_1$, $A_2$, $A_3$, and $A_4$ are each as illustrated in (G2).

(P3) The thiazolyl ring

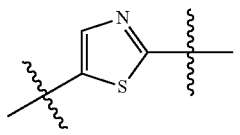

is as illustrated in any of (A1)-(A3), and $A_1$, $A_2$, $A_3$, and $A_4$ are each as illustrated in any of (G3)-(G3d).

(P4) The thiazolyl ring

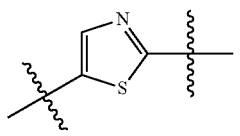

is as illustrated in any of (A1)-(A3), and $A_1$, $A_2$, $A_3$, and $A_4$ are each as illustrated in any of (G4)-(G4f).

(P5) The thiazolyl ring

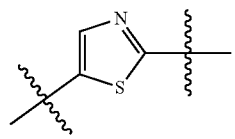 [SMILES: *c1cnc(*)s1]

is as illustrated in any of (A1)-(A3), and $A_1$, $A_2$, $A_3$, and $A_4$ are each as illustrated in any of (G5)-(G5d).

(P6) The thiazolyl ring

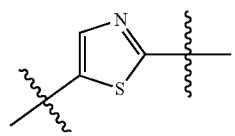 [SMILES: *c1cnc(*)s1]

is as illustrated in any of (A1)-(A3), and $A_1$, $A_2$, $A_3$, and $A_4$ are each as illustrated in any of (G6).

(P7) The thiazolyl ring

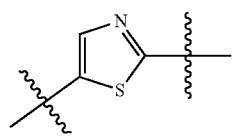 [SMILES: *c1cnc(*)s1]

is as illustrated in any of (A1)-(A3), and $A_1$, $A_2$, $A_3$, and $A_4$ are each as illustrated in any of (G7).

(Q1a) The Cy ring is as illustrated in (B1), and $A_1$, $A_2$, $A_3$, and $A_4$ are each as illustrated in (G1).

(Q1b) The Cy ring is as illustrated in (B1), and $A_1$, $A_2$, $A_3$, and $A_4$ are each as illustrated in (G2).

(Q1c) The Cy ring is as illustrated in (B1), and $A_1$, $A_2$, $A_3$, and $A_4$ are each as illustrated in any of (G3)-(G3d).

(Q1d) The Cy ring is as illustrated in (B1), and $A_1$, $A_2$, $A_3$, and $A_4$ are each as illustrated in any of (G4)-(G4f).

(Q1e) The Cy ring is as illustrated in (B1), and $A_1$, $A_2$, $A_3$, and $A_4$ are each as illustrated in any of (G5)-(G5d).

(Q1f) The Cy ring is as illustrated in (B1), and $A_1$, $A_2$, $A_3$, and $A_4$ are each as illustrated in any of (G6).

(Q1g) The Cy ring is as illustrated in (B1), and $A_1$, $A_2$, $A_3$, and $A_4$ are each as illustrated in any of (G7).

(Q2a) The Cy ring is as illustrated in (B2), and $A_1$, $A_2$, $A_3$, and $A_4$ are each as illustrated in (G1).

(Q2b) The Cy ring is as illustrated in (B2), and $A_1$, $A_2$, $A_3$, and $A_4$ are each as illustrated in (G2).

(Q2c) The Cy ring is as illustrated in (B2), and $A_1$, $A_2$, $A_3$, and $A_4$ are each as illustrated in any of (G3)-(G3d).

(Q2d) The Cy ring is as illustrated in (B2), and $A_1$, $A_2$, $A_3$, and $A_4$ are each as illustrated in any of (G4)-(G4f).

(Q2e) The Cy ring is as illustrated in (B2), and $A_1$, $A_2$, $A_3$, and $A_4$ are each as illustrated in any of (G5)-(G5d).

(Q2f) The Cy ring is as illustrated in (B2), and $A_1$, $A_2$, $A_3$, and $A_4$ are each as illustrated in any of (G6).

(Q2g) The Cy ring is as illustrated in (B2), and $A_1$, $A_2$, $A_3$, and $A_4$ are each as illustrated in any of (G7).

(Q3a) The Cy ring is as illustrated in (B3), and $A_1$, $A_2$, $A_3$, and $A_4$ are each as illustrated in (G1).

(Q3b) The Cy ring is as illustrated in (B3), and $A_1$, $A_2$, $A_3$, and $A_4$ are each as illustrated in (G2).

(Q3c) The Cy ring is as illustrated in (B3), and $A_1$, $A_2$, $A_3$, and $A_4$ are each as illustrated in any of (G3)-(G3d).

(Q3d) The Cy ring is as illustrated in (B3), and $A_1$, $A_2$, $A_3$, and $A_4$ are each as illustrated in any of (G4)-(G4f).

(Q3e) The Cy ring is as illustrated in (B3), and $A_1$, $A_2$, $A_3$, and $A_4$ are each as illustrated in any of (G5)-(G5d).

(Q3f) The Cy ring is as illustrated in (B3), and $A_1$, $A_2$, $A_3$, and $A_4$ are each as illustrated in any of (G6).

(Q3g) The Cy ring is as illustrated in (B3), and $A_1$, $A_2$, $A_3$, and $A_4$ are each as illustrated in any of (G7).

(Q4a) The thiazolyl ring

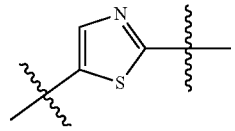 [SMILES: *c1cnc(*)s1]

and the Cy ring are illustrated as in any of (O1)-(O3), and $A_1$, $A_2$, $A_3$, and $A_4$ are each as illustrated in (G1).

(Q4b) The thiazolyl ring

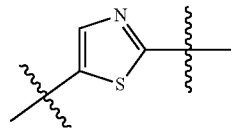 [SMILES: *c1cnc(*)s1]

and the Cy ring are illustrated as in any of (O1)-(O3), and $A_1$, $A_2$, $A_3$, and $A_4$ are each as illustrated in (G2).

(Q4c) The thiazolyl ring

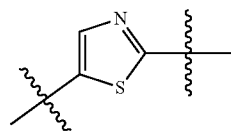 [SMILES: *c1cnc(*)s1]

and the Cy ring are illustrated as in any of (O1)-(O3), and $A_1$, $A_2$, $A_3$, and $A_4$ are each as illustrated in any of (G3)-(G3d).

(Q4d) The thiazolyl ring

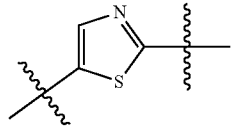 [SMILES: *c1cnc(*)s1]

and the Cy ring are illustrated as in any of (O1)-(O3), and $A_1$, $A_2$, $A_3$, and $A_4$ are each as illustrated in any of (G4)-(G4f).

(Q4e) The thiazolyl ring

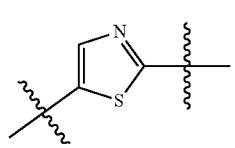 [SMILES: *c1cnc(*)s1]

and the Cy ring are illustrated as in any of (O1)-(O3), and $A_1$, $A_2$, $A_3$, and $A_4$ are each as illustrated in any of (G5)-(G5d).

(Q4f) The thiazolyl ring

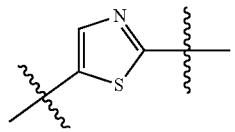 [SMILES: *c1cnc(*)s1]

and the Cy ring are illustrated as in any of (O1)-(O3), and $A_1$, $A_2$, $A_3$, and $A_4$ are each as illustrated in any of (G6).

(Q4g) The thiazolyl ring

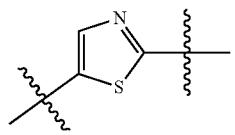 [SMILES: *c1cnc(*)s1]

and the Cy ring are illustrated as in any of (O1)-(O3), and $A_1$, $A_2$, $A_3$, and $A_4$ are each as illustrated in any of (G7).

(R1) The thiazolyl ring

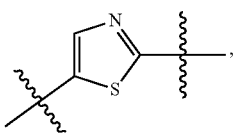 [SMILES: *c1cnc(*)s1]

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H1).

(R2) The thiazolyl ring

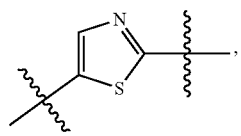 [SMILES: *c1cnc(*)s1]

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H2).

(R3) The thiazolyl ring

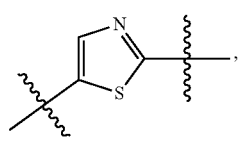 [SMILES: *c1cnc(*)s1]

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H2a).

($R_4$) The thiazolyl ring

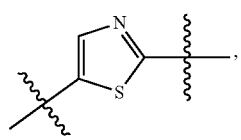 [SMILES: *c1cnc(*)s1]

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H2b).

(R5) The thiazolyl ring

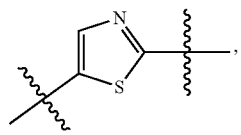

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H2c).

($R_6$) The thiazolyl ring

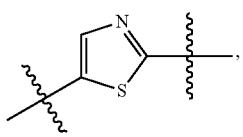 [SMILES: *c1cnc(*)s1]

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H2d).

(R7) The thiazolyl ring

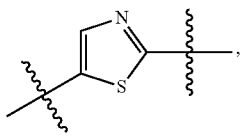

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in any of (H2e)-(H2e-10).

(R8) The thiazolyl ring

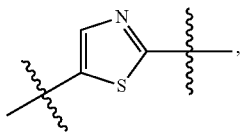

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H2f)-(H2f-2).

(R9) The thiazolyl ring

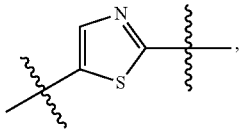

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H3).

(R10) The thiazolyl ring

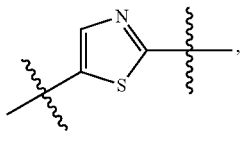

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H3a).

(R11) The thiazolyl ring

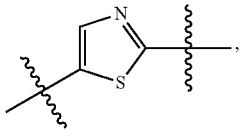

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H3b).

(R12) The thiazolyl ring

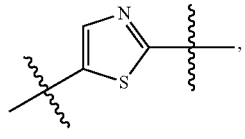

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H3c).

(R13) The thiazolyl ring

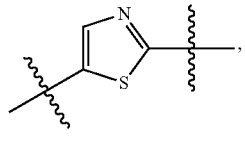

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H3d).

(R14) The thiazolyl ring

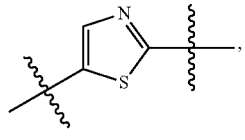

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in any of (H3e)-(H3e-10).

(R15) The thiazolyl ring

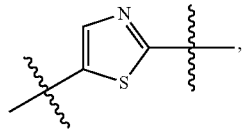 [SMILES: *c1cnc(*)s1]

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H3f-1)-(H3f-2).

(R16) The thiazolyl ring

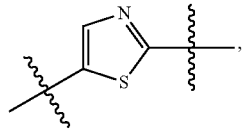 [SMILES: *c1cnc(*)s1]

the Cy ring, and/or $A_1$, $A_2$, $A_3$, and $A_4$ are each as illustrated, as applicable, in any or (A1)-(A3), (B1)-(B3), (G1)-(G7), and (O1)-(Q4g), $R_4$ is as illustrated in (H3g)-(H3g-1).

Non-limiting illustrative compounds of the application are listed in Table 1.

TABLE 1

| Cmpd No. | Structure | Chemical Name |
|---|---|---|
| 1 | 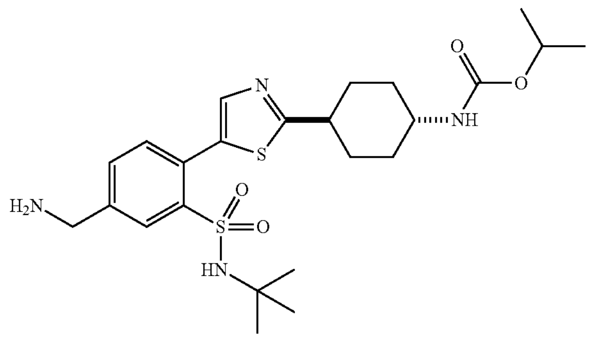 | isopropyl (trans-4-(5-(4-(aminomethyl)-2-(N-(tert-butyl)sulfamoyl)phenyl)thiazol-2-yl)cyclohexyl)carbamate |
| 2 | 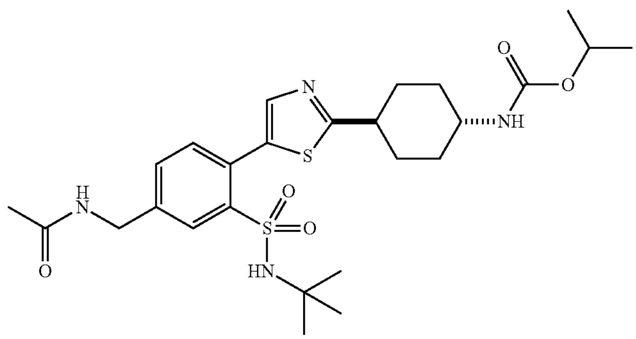 | isopropyl (trans-4-(5-(4-(acetamidomethyl)-2-(N-(tert-butyl)sulfamoyl)phenyl)thiazol-2-yl)cyclohexyl)carbamate |
| 3 | 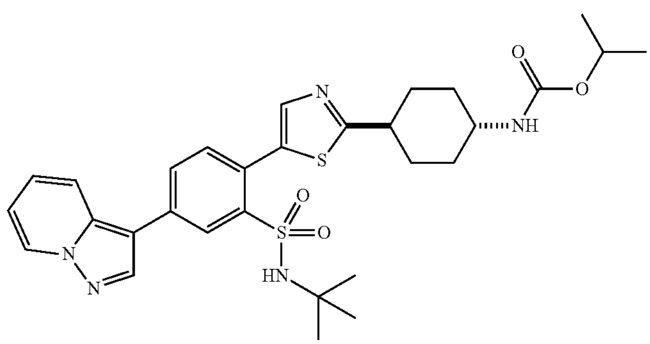 | isopropyl (trans-4-(5-(2-(N-(tert-butyl)sulfamoyl)-4-(pyrazolo[1,5-a]pyridin-3-yl)phenyl)thiazol-2-yl)cyclohexyl)carbamate |
| 4 | 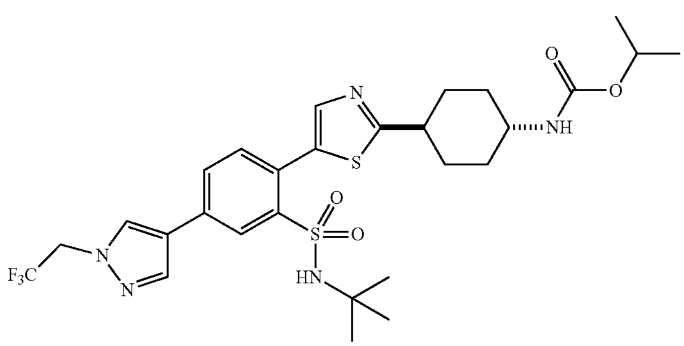 | isopropyl (trans-4-(5-(2-(N-(tert-butyl)sulfamoyl)-4-(1-(2,2,2-trifluoroethyl)-1H-pyrazol-4-yl)phenyl)thiazol-2-yl)cyclohexyl)carbamate |

TABLE 1-continued

| Cmpd No. | Structure | Chemical Name |
|---|---|---|
| 5 | 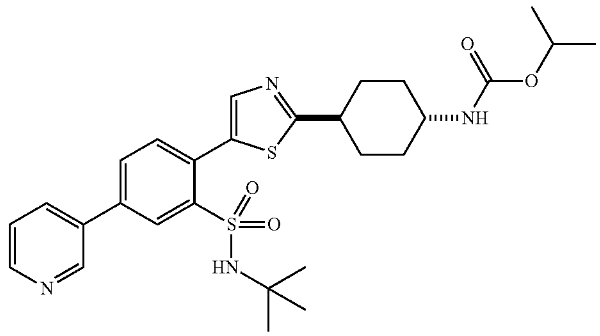 | isopropyl (trans-4-(5-(2-(N-(tert-butyl)sulfamoyl)-4-(pyridin-3-yl)phenyl)thiazol-2-yl)cyclohexyl)carbamate |
| 6 | 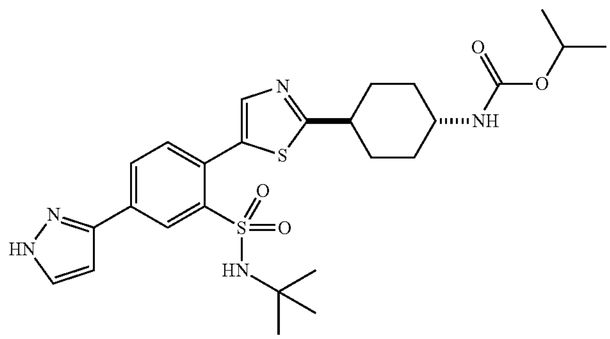 | isopropyl (trans-4-(5-(2-(N-(tert-butyl)sulfamoyl)-4-(1H-pyrazol-3-yl)phenyl)thiazol-2-yl)cyclohexyl)carbamate |
| 7 | 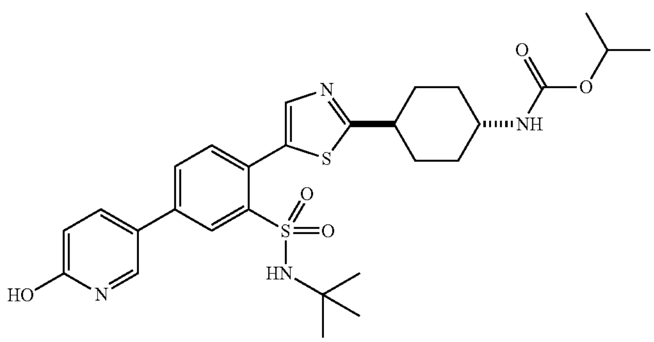 | isopropyl (trans-4-(5-(2-(N-(tert-butyl)sulfamoyl)-4-(6-hydroxy-pyridin-3-yl)phenyl)thiazol-2-yl)cyclohexyl)carbamate |
| 8 | 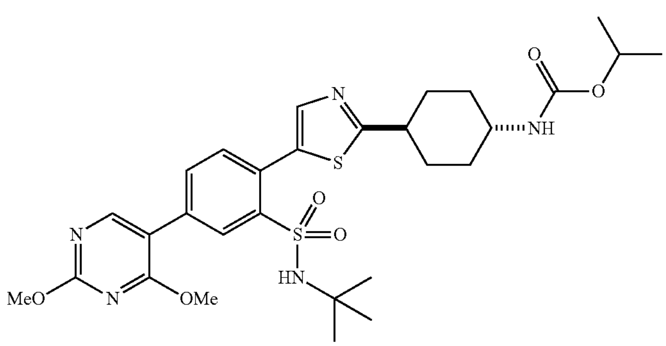 | isopropyl (trans-4-(5-(2-(N-(tert-butyl)sulfamoyl)-4-(2,4-dimethoxy pyrimidin-5-yl)phenyl)thiazol-2-yl)cyclohexyl)carbamate |

TABLE 1-continued

| Cmpd No. | Structure | Chemical Name |
|---|---|---|
| 9 | 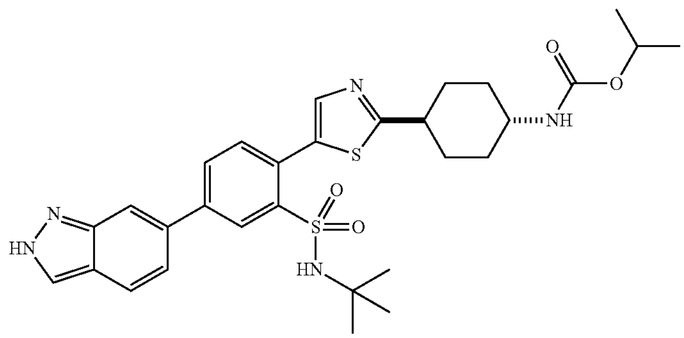 | isopropyl (trans-4-(5-(2-(N-(tert-butyl)sulfamoyl)-4-(2H-indazol-6-yl)phenyl)thiazol-2-yl)cyclohexyl)carbamate |
| 10 | 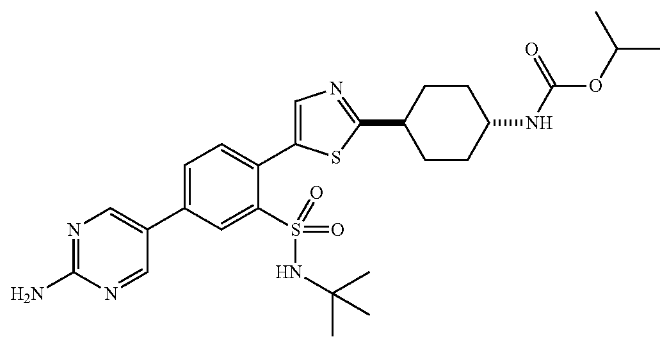 | isopropyl (trans-4-(5-(4-(2-aminopyrimidin-5-yl)-2-(N-(tert-butyl)sulfamoyl) phenyl)thiazol-2-yl)cyclohexyl)carbamate |
| 11 | 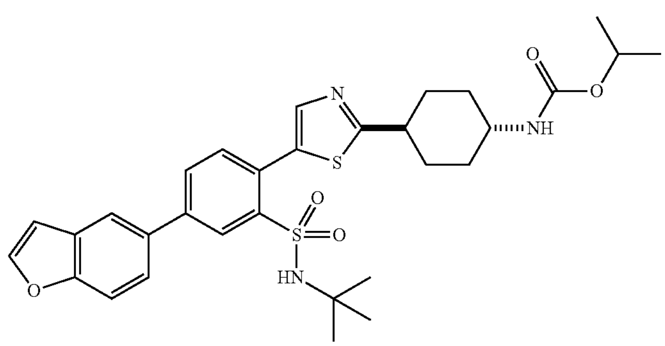 | isopropyl (trans-4-(5-(4-(benzofuran-5-yl)-2-(N-(tert-butyl) sulfamoyl)phenyl)thiazol-2-yl)cyclohexyl)carbamate |
| 12 | 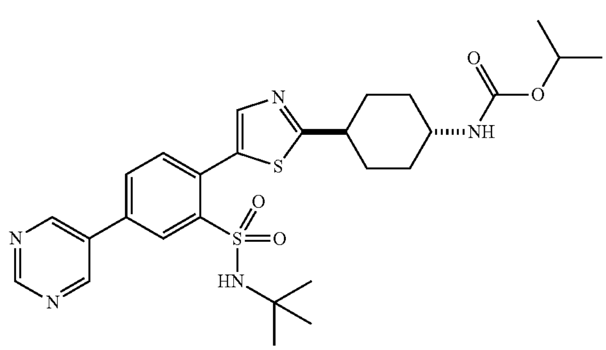 | isopropyl (trans-4-(5-(2-(N-(tert-butyl)sulfamoyl)-4-(pyrimidin-5-yl)phenyl)thiazol-2-yl)cyclohexyl)carbamate |

TABLE 1-continued

| Cmpd No. | Structure | Chemical Name |
|---|---|---|
| 13 | 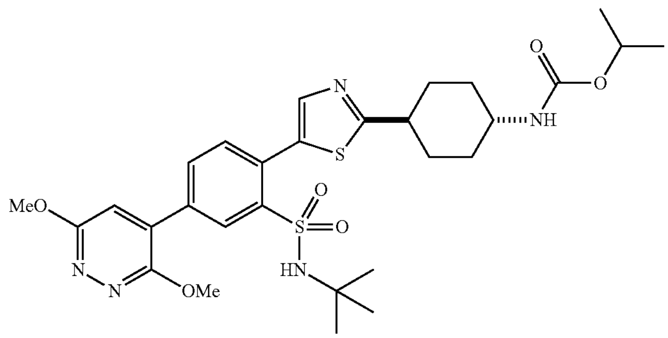 | isopropyl (trans-4-(5-(2-(N-(tert-butyl)sulfamoyl)-4-(3,6-dimethoxypyridazin-4-yl)phenyl)thiazol-2-yl)cyclohexyl)carbamate |
| 14 | 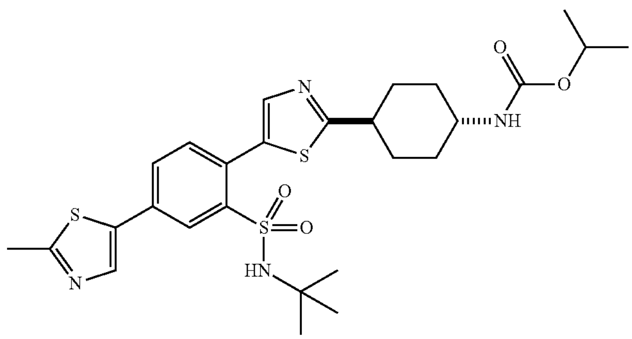 | isopropyl (trans-4-(5-(2-(N-(tert-butyl)sulfamoyl)-4-(2-methylthiazol-5-yl)phenyl)thiazol-2-yl)cyclohexyl)carbamate |
| 15 | 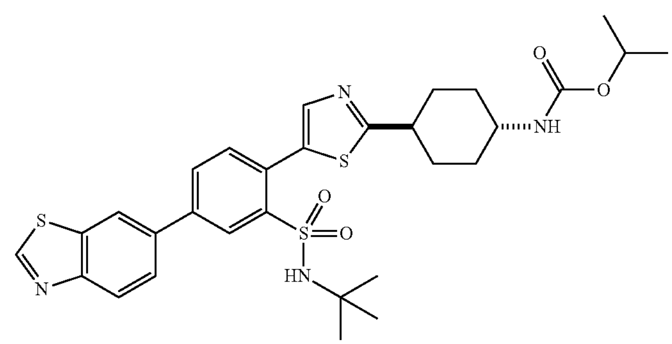 | isopropyl (trans-4-(5-(4-(benzo[d]thiazol-6-yl)-2-(N-(tert-butyl)sulfamoyl)phenyl)thiazol-2-yl)cyclohexyl)carbamate |
| 16 | 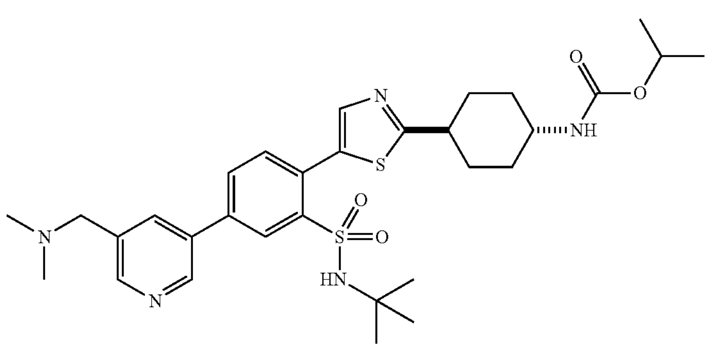 | isopropyl (trans-4-(5-(2-(N-(tert-butyl)sulfamoyl)-4-(5-((dimethylamino)methyl)pyridin-3-yl)phenyl)thiazol-2-yl)cyclohexyl)carbamate |

TABLE 1-continued

| Cmpd No. | Structure | Chemical Name |
|---|---|---|
| 17 | 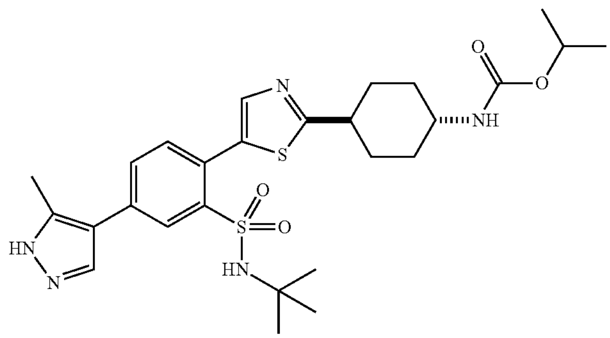 | isopropyl (trans-4-(5-(2-(N-(tert-butyl)sulfamoyl)-4-(5-methyl-1H-pyrazol-4-yl)phenyl)thiazol-2-yl)cyclohexyl)carbamate |
| 18 | 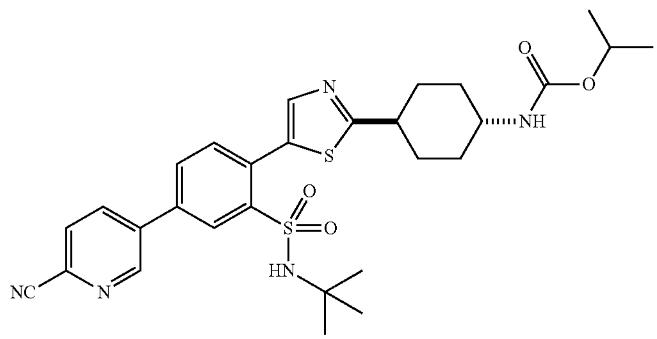 | isopropyl (trans-4-(5-(2-(N-(tert-butyl)sulfamoyl)-4-(6-cyano-pyridin-3-yl)phenyl)thiazol-2-yl)cyclohexyl)carbamate |
| 19 | 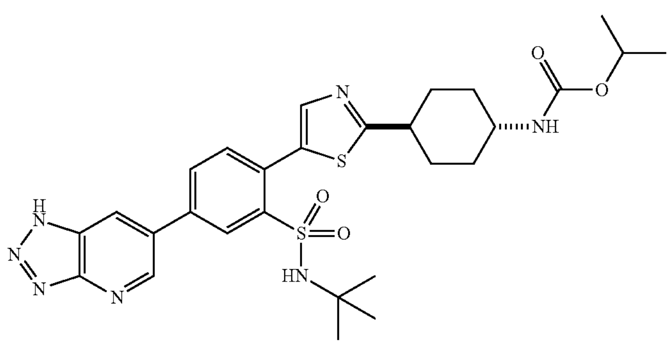 | isopropyl (trans-4-(5-(4-(1H-benzo[d][1,2,3]triazol-6-yl)-2-(N-(tert-butyl)sulfamoyl)phenyl)thiazol-2-yl)cyclohexyl)carbamate |
| 20 | 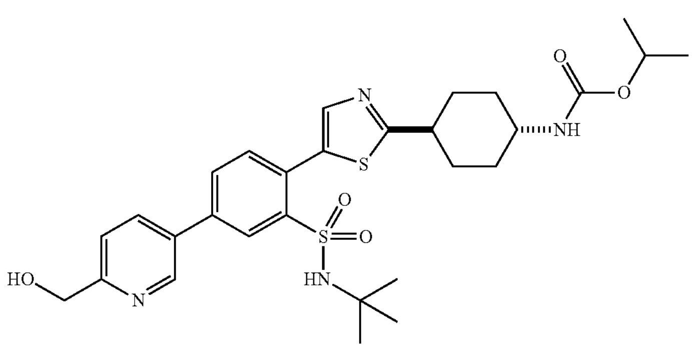 | isopropyl (trans-4-(5-(2-(N-(tert-butyl)sulfamoyl)-4-(6-(hydroxymethyl)pyridin-3-yl)phenyl)thiazol-2-yl)cyclohexyl)carbamate |

TABLE 1-continued

| Cmpd No. | Structure | Chemical Name |
|---|---|---|
| 21 | 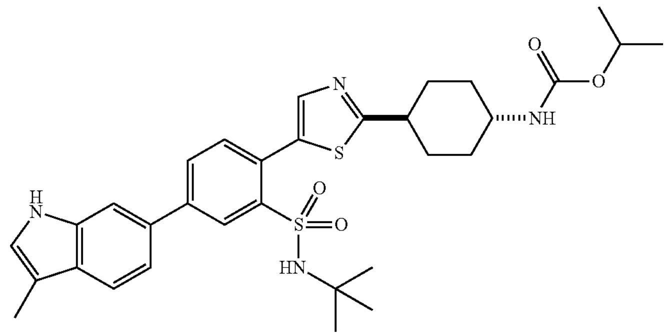 | isopropyl (trans-4-(5-(2-(N-(tert-butyl)sulfamoyl)-4-(3-methyl-1H-indol-6-yl)phenyl)thiazol-2-yl)cyclohexyl)carbamate |
| 22 | 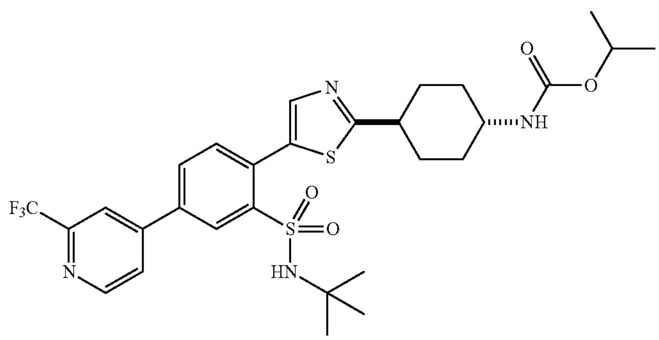 | isopropyl (trans-4-(5-(2-(N-(tert-butyl)sulfamoyl)-4-(2-(trifluoromethyl)pyridin-4-yl)phenyl)thiazol-2-yl)cyclohexyl)carbamate |
| 23 | 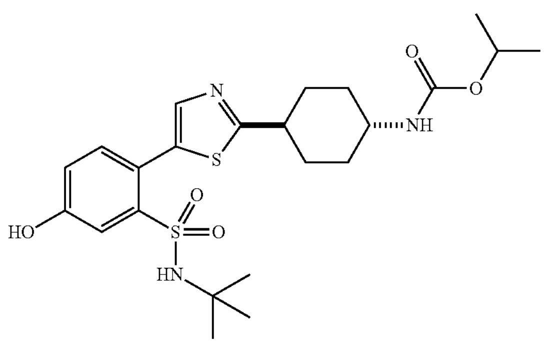 | isopropyl (trans-4-(5-(2-(N-(tert-butyl)sulfamoyl)-4-hydroxyphenyl)thiazol-2-yl)cyclohexyl)carbamate |
| 24 | 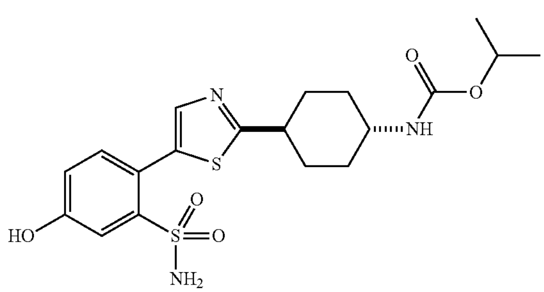 | isopropyl (trans-4-(5-(4-hydroxy-2-sulfamoylphenyl)thiazol-2-yl)cyclohexyl)carbamate |

TABLE 1-continued

| Cmpd No. | Structure | Chemical Name |
|---|---|---|
| 25 | 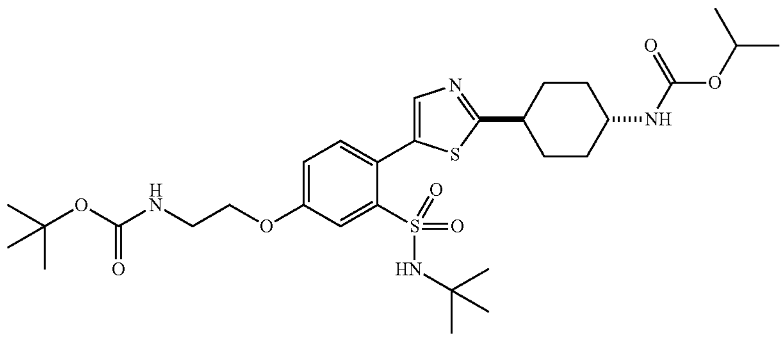 | isopropyl N-[trans-4-[5-[4-[2-(tert-butoxycarbonylamino)ethoxy]-2-(tert-butylsulfamoyl)phenyl]thiazol-2-yl]cyclohexyl]carbamate |
| 26 | 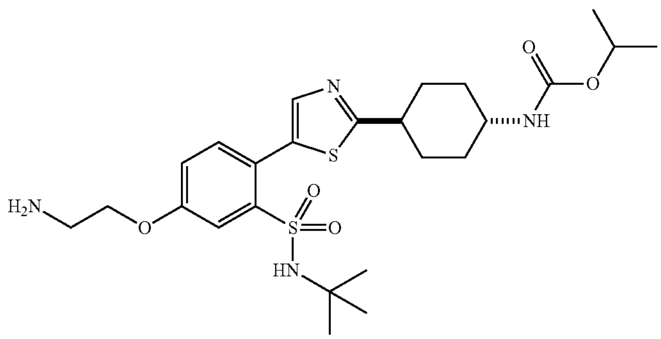 | isopropyl (trans-4-(5-(4-(2-aminoethoxy)-2-(N-(tert-butyl)sulfamoyl)phenyl)thiazol-2-yl)cyclohexyl)carbamate |
| 27 | 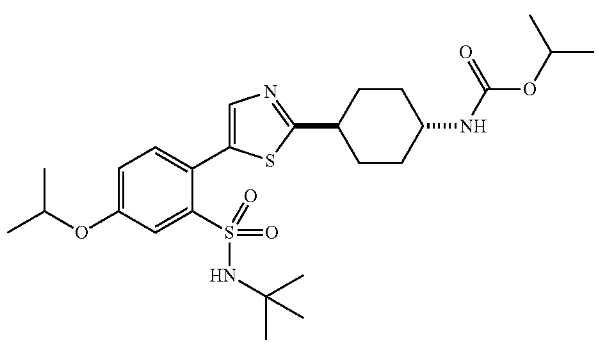 | isopropyl (trans-4-(5-(2-(N-(tert-butyl)sulfamoyl)-4-isopropoxy-phenyl)thiazol-2-yl)cyclohexyl)carbamate |
| 28 | 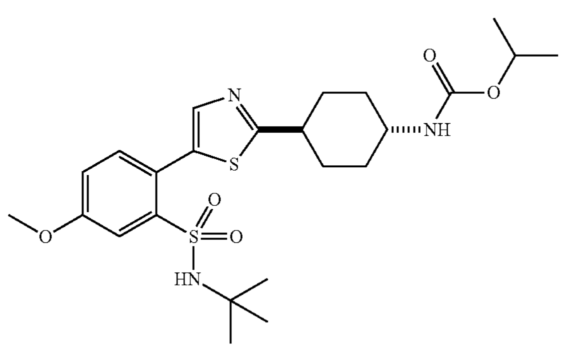 | isopropyl (trans-4-(5-(2-(N-(tert-butyl)sulfamoyl)-4-methoxy-phenyl)thiazol-2-yl)cyclohexyl)carbamate |

TABLE 1-continued

| Cmpd No. | Structure | Chemical Name |
|---|---|---|
| 29 | 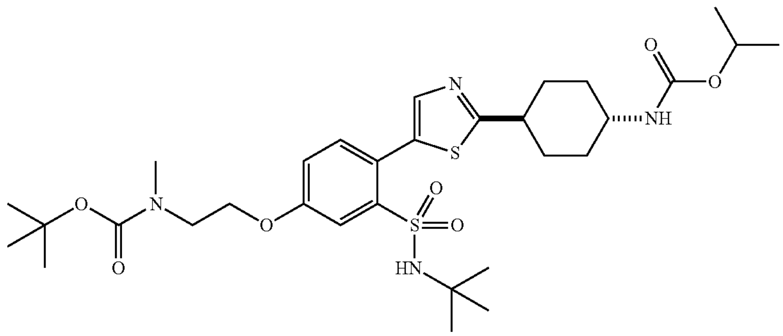 | tert-butyl (2-(3-(N-(tert-butyl)sulfamoyl)-4-(2-(trans-4-((iso-propoxycarbonyl)amino)cyclohexyl)thiazol-5-yl)phenoxy)ethyl)methyl)carbamate |
| 30 | 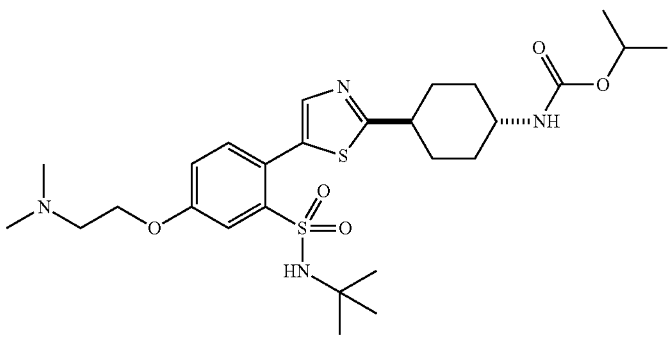 | isopropyl (trans-4-(5-(2-(N-(tert-butyl)sulfamoyl)-4-(2-(dimethylamino)ethoxy)phenyl)thiazol-2-yl)cyclohexyl)carbamate |
| 31 | 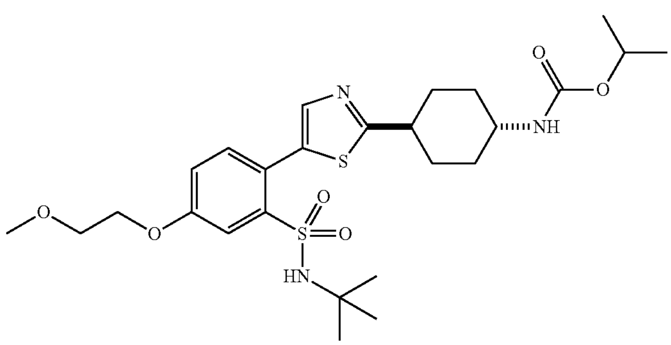 | isopropyl (trans-4-(5-(2-(N-(tert-butyl)sulfamoyl)-4-(2-methoxyethoxy)phenyl)thiazol-2-yl)cyclohexyl)carbamate |
| 32 | 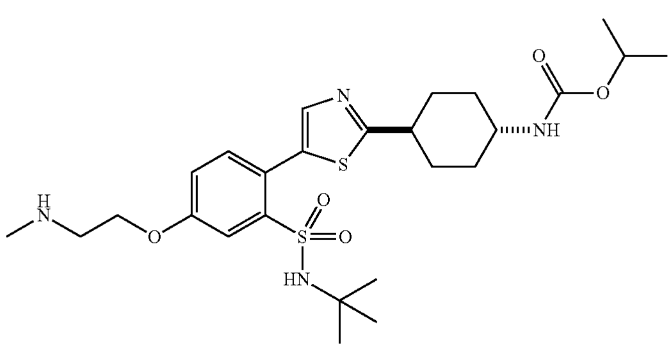 | isopropyl (trans-4-(5-(2-(N-(tert-butyl)sulfamoyl)-4-(2-(methylamino)ethoxy)phenyl)thiazol-2-yl)cyclohexyl)carbamate |

TABLE 1-continued

| Cmpd No. | Structure | Chemical Name |
|---|---|---|
| 33 | 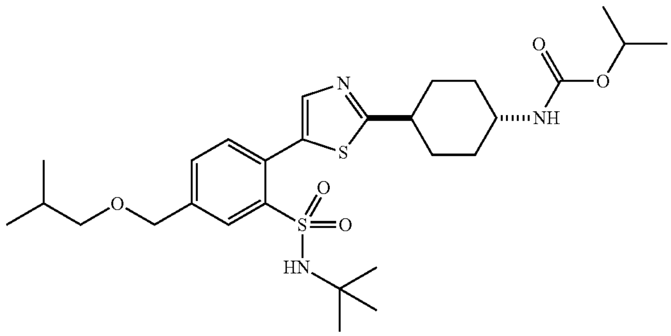 | isopropyl (trans-4-(5-(2-(N-(tert-butyl)sulfamoyl)-4-(isobutoxymethyl)phenyl)thiazol-2-yl)cyclohexyl)carbamate |
| 34 | 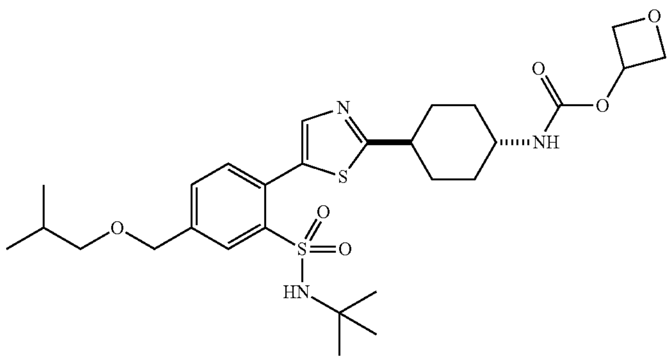 | oxetan-3-yl (trans-4-(5-(2-(N-(tert-butyl)sulfamoyl)-4-isobutoxymethyl)phenyl)thiazol-2-yl)cyclohexyl)carbamate |
| 35 | 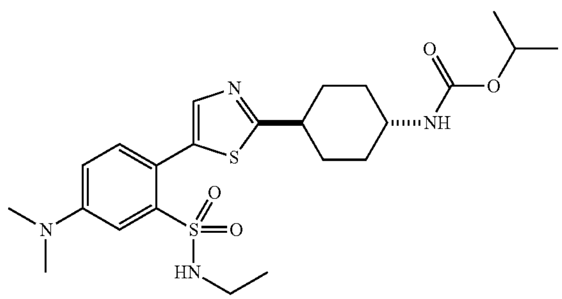 | isopropyl (trans-4-(5-(4-(dimethylamino)-2-(N-ethylsulfamoyl)phenyl)thiazol-2-yl)cyclohexyl)carbamate |
| 36 | 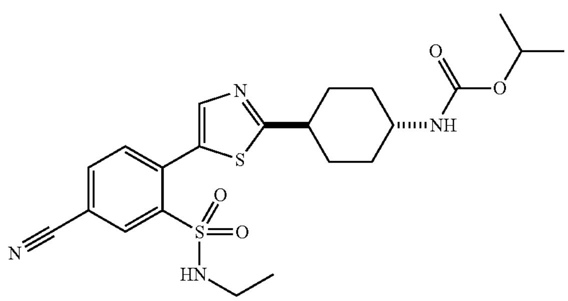 | isopropyl (trans-4-(5-(4-cyano-2-(N-ethylsulfamoyl)phenyl)thiazol-2-yl)cyclohexyl)carbamate |
| 37 | 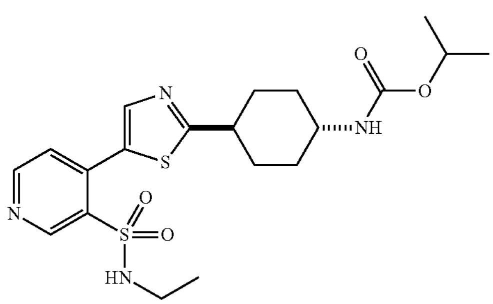 | isopropyl (trans-4-(5-(3-(N-ethylsulfamoyl)pyridin-4-yl)thiazol-2-yl)cyclohexyl)carbamate |

TABLE 1-continued

| Cmpd No. | Structure | Chemical Name |
| --- | --- | --- |
| 38 | 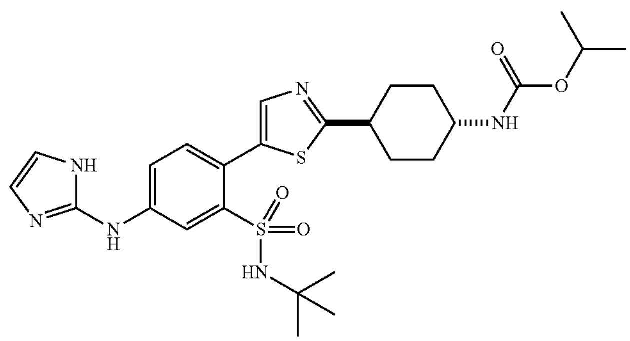 | isopropyl (trans-4-(5-(4-((1H-imidazol-2-yl)amino)-2-(N-(tert-butyl)sulfamoyl)phenyl)thiazol-2-yl)cyclohexyl)carbamate |
| 39 | 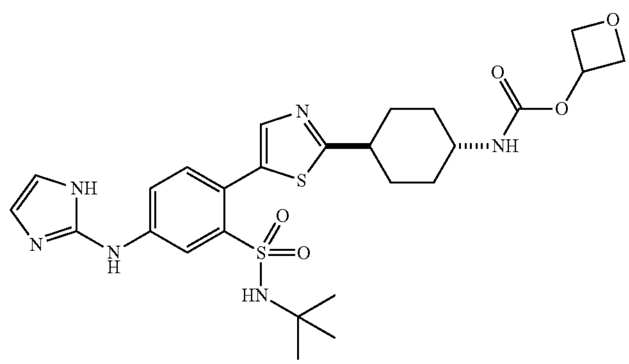 | oxetan-3-yl (trans-4-(5-(4-((1H-imidazol-2-yl)amino)-2-(N-(tert-butyl)sulfamoyl)phenyl)thiazol-2-yl)cyclohexyl)carbamate |
| 40 | 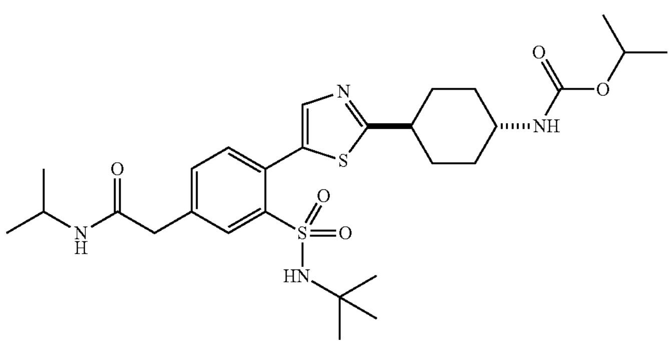 | isopropyl (trans-4-(5-(2-(N-(tert-butyl)sulfamoyl)-4-(2-(isopropylamino)-2-oxoethyl)phenyl)thiazol-2-yl)cyclohexyl)carbamate |
| 41 | 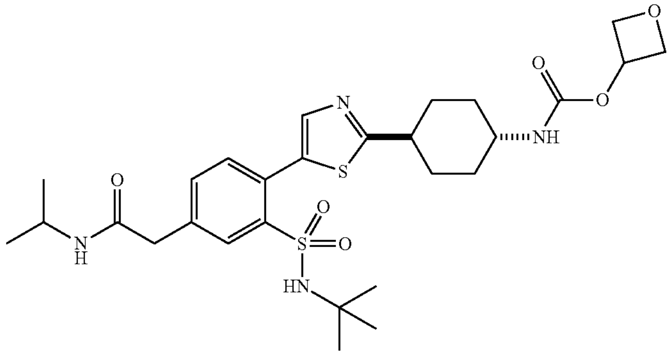 | oxetan-3-yl (trans-4-(5-(2-(N-(tert-butyl)sulfamoyl)-4-(2-(isopropylamino)-2-oxoethyl)phenyl)thiazol-2-yl)cyclohexyl)carbamate |

TABLE 1-continued

| Cmpd No. | Structure | Chemical Name |
|---|---|---|
| 42 | 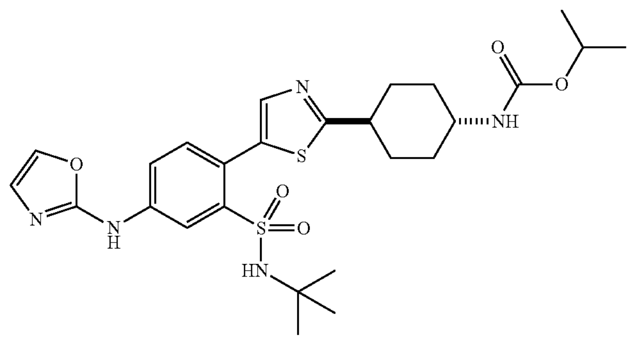 | isopropyl (trans-4-(5-(2-(N-(tert-butyl)sulfamoyl)-4-(oxazol-2-ylamino)phenyl)thiazol-2-yl)cyclohexyl)carbamate |
| 43 | 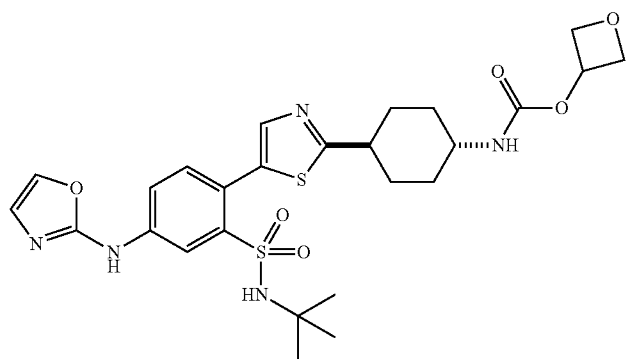 | oxetan-3-yl (trans-4-(5-(2-(N-(tert-butyl)sulfamoyl)-4-(oxazol-2-ylamino)phenyl)thiazol-2-yl)cyclohexyl)carbamate |
| 44 | 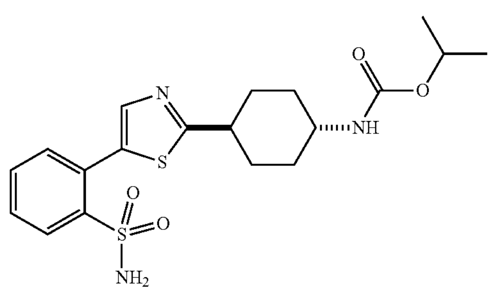 | isopropyl (trans-4-(5-(2-sulfamoylphenyl)thiazol-2-yl)cyclohexyl)carbamate |
| 45 | 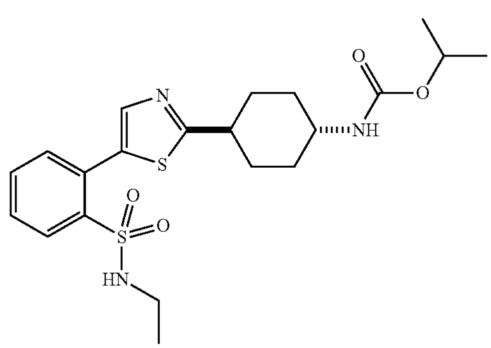 | isopropyl (trans-4-(5-(2-(N-ethylsulfamoyl)phenyl)thiazol-2-yl)cyclohexyl)carbamate |

TABLE 1-continued

| Cmpd No. | Structure | Chemical Name |
|---|---|---|
| 46 | 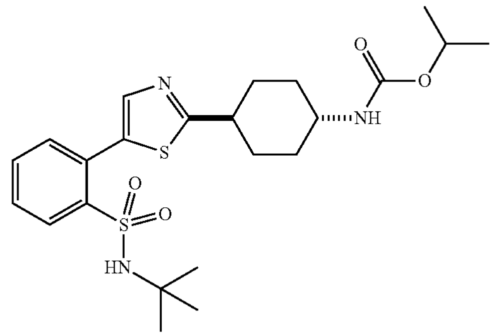 | isopropyl (trans-4-(5-(2-(N-(tert-butyl)sulfamoyl)phenyl)thiazol-2-yl)cyclohexyl)carbamate |
| 47 | 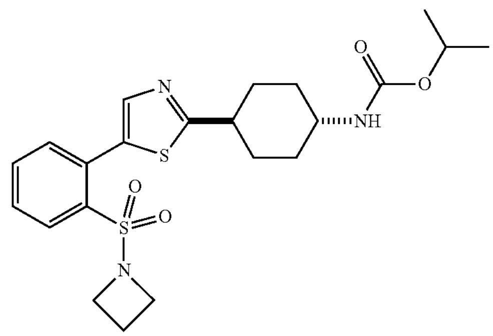 | isopropyl (trans-4-(5-(2-(azetidin-1-ylsulfonyl)phenyl)thiazol-2-yl)cyclohexyl)carbamate |
| 48 | 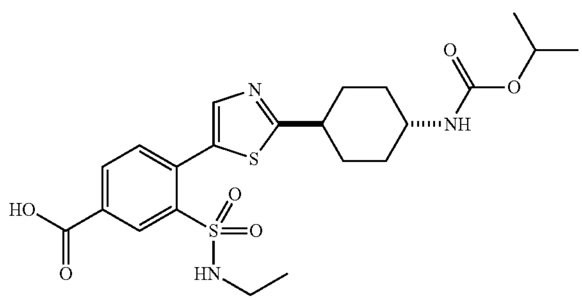 | 3-(N-ethylsulfamoyl)-4-(2-(trans-4-((isopropoxycarbonyl)amino)cyclohexyl)thiazol-5-yl)benzoic acid |
| 49 | 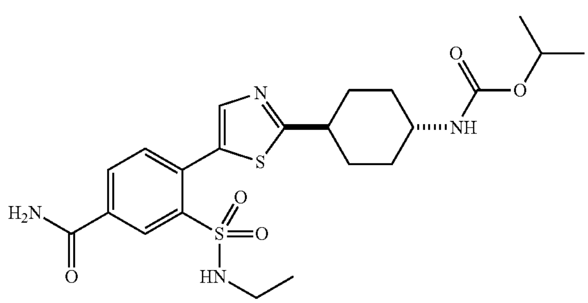 | isopropyl (trans-4-(5-(4-carbamoyl-2-(N-ethylsulfamoyl)phenyl)thiazol-2-yl)cyclohexyl)carbamate |
| 50 | 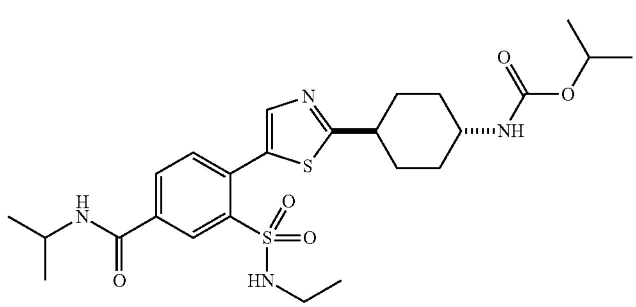 | isopropyl (trans-4-(5-(2-(N-ethylsulfamoyl)-4-(isopropylcarbamoyl)phenyl)thiazol-2-yl)cyclohexyl)carbamate |

TABLE 1-continued

| Cmpd No. | Structure | Chemical Name |
|---|---|---|
| 51 | 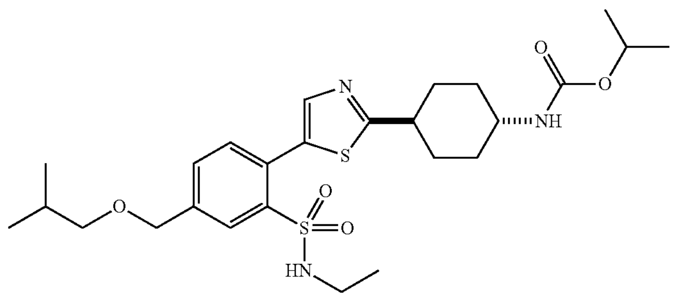 | isopropyl (trans-4-(5-(2-(N-ethylsulfamoyl)-4-(isobutoxymethyl)phenyl)thiazol-2-yl)cyclohexyl)carbamate |
| 52 | 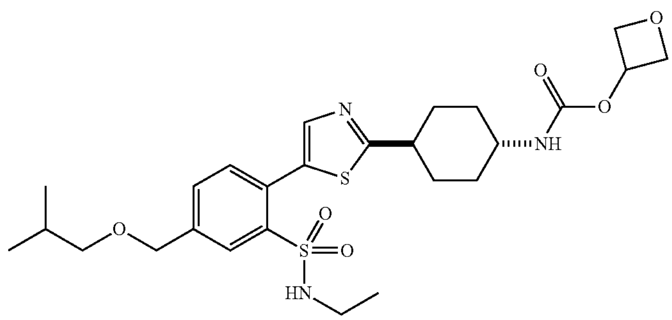 | oxetan-3-yl (trans-4-(5-(2-(N-ethylsulfamoyl)-4-isobutoxymethyl)phenyl)thiazol-2-yl)cyclohexyl)carbamate |
| 53 | 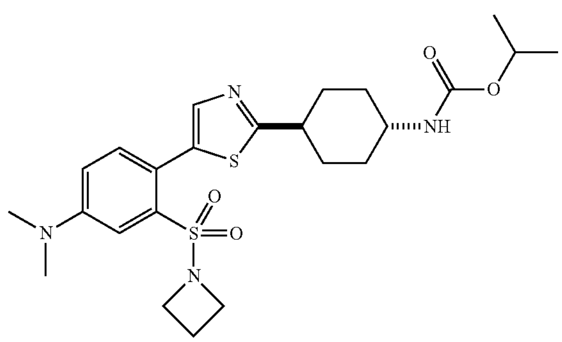 | isopropyl (trans-4-(5-(2-(azetidin-1-ylsulfonyl)-4-(dimethylamino)phenyl)thiazol-2-yl)cyclohexyl)carbamate |
| 54 | 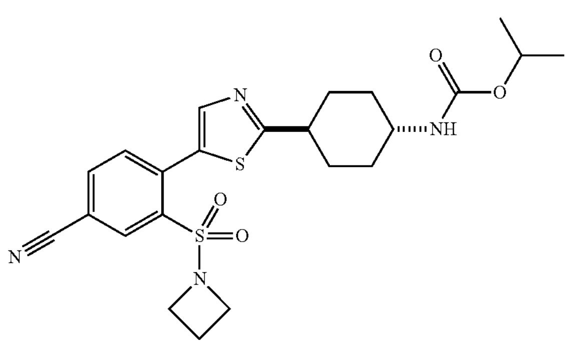 | isopropyl (trans-4-(5-(2-(azetidin-1-ylsulfonyl)-4-cyanophenyl)thiazol-2-yl)cyclohexyl)carbamate |

TABLE 1-continued

| Cmpd No. | Structure | Chemical Name |
|---|---|---|
| 55 | 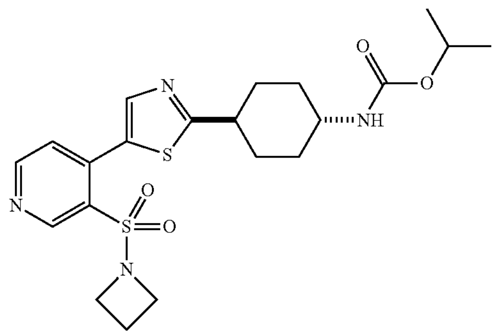 | isopropyl (trans-4-(5-(3-(azetidin-1-ylsulfonyl)pyridin-4-yl)thiazol-2-yl)cyclohexyl)carbamate |
| 56 | 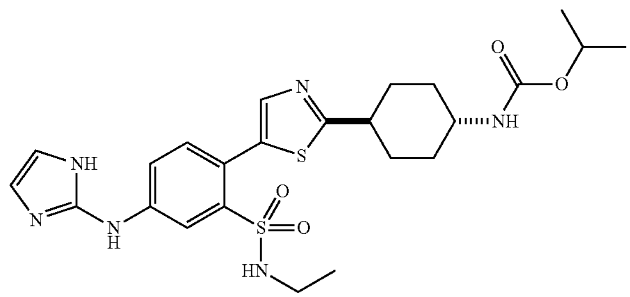 | isopropyl (trans-4-(5-(4-((1H-imidazol-2-yl)amino)-2-(N-ethylsulfamoyl)phenyl)thiazol-2-yl)cyclohexyl)carbamate |
| 57 | 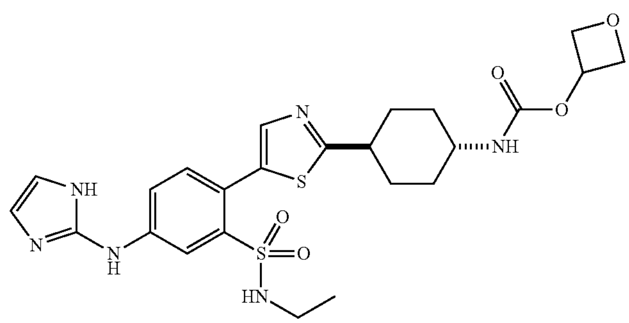 | oxetan-3-yl (trans-4-(5-(4-((1H-imidazol-2-yl)amino)-2-(N-ethylsulfamoyl)phenyl)thiazol-2-yl)cyclohexyl)carbamate |
| 58 | 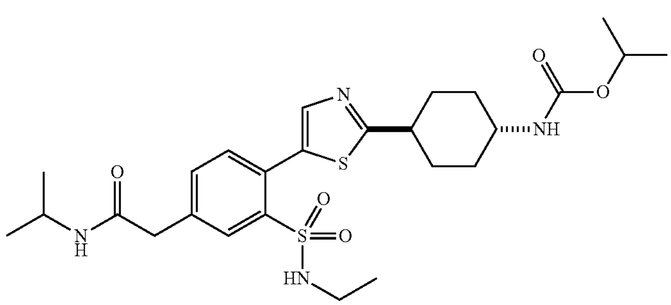 | isopropyl (trans-4-(5-(2-(N-ethylsulfamoyl)-4-(2-(isopropylamino)-2-oxoethyl)phenyl)thiazol-2-yl)cyclohexyl)carbamate |
| 59 | 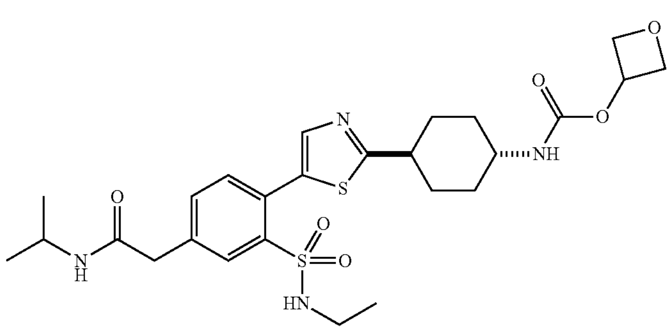 | oxetan-3-yl (trans-4-(5-(2-(N-ethylsulfamoyl)-4-(2-(isopropylamino)-2-oxoethyl)phenyl)thiazol-2-yl)cyclohexyl)carbamate |

TABLE 1-continued

| Cmpd No. | Structure | Chemical Name |
| --- | --- | --- |
| 60 | 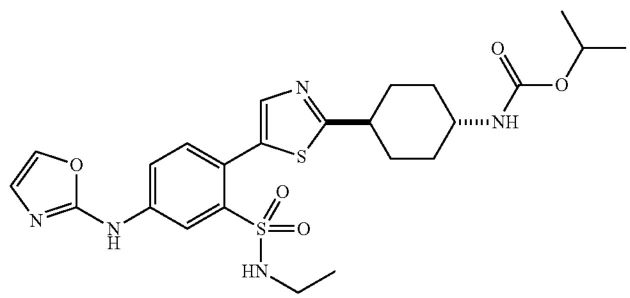 | isopropyl (trans-4-(5-(2-(N-ethylsulfamoyl)-4-(oxazol-2-ylamino)phenyl)thiazol-2-yl)cyclohexyl)carbamate |
| 61 | 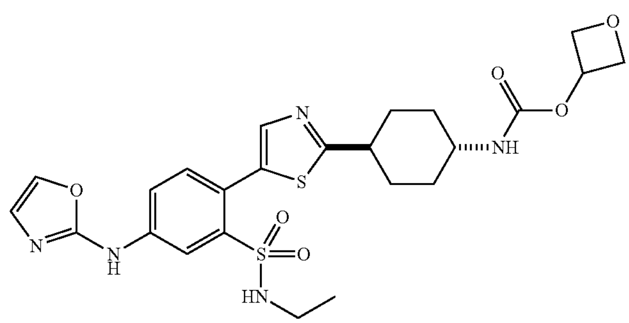 | oxetan-3-yl (trans-4-(5-(2-(N-ethylsulfamoyl)-4-(oxazol-2-ylamino)phenyl)thiazol-2-yl)cyclohexyl)carbamate |
| 62 | 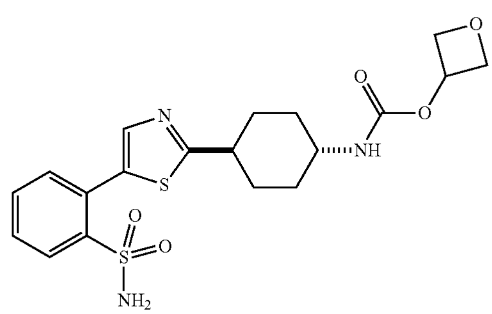 | oxetan-3-yl (trans-4-(5-(2-sulfamoylphenyl)thiazol-2-yl)cyclohexyl)carbamate |
| 63 | 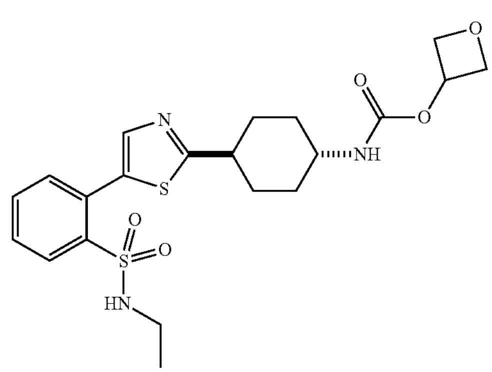 | oxetan-3-yl (trans-4-(4-(2-(N-ethylsulfamoyl)phenyl)thiazol-2-yl)cyclohexyl)carbamate |

TABLE 1-continued

| Cmpd No. | Structure | Chemical Name |
|---|---|---|
| 64 | 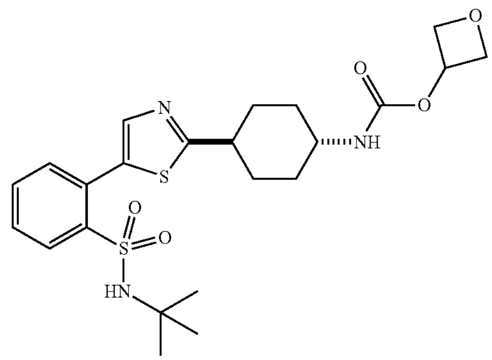 | oxetan-3-yl (trans-4-(5-(2-(N-(tert-butyl)sulfamoyl)phenyl)thiazol-2-yl)cyclohexyl)carbamate |
| 65 | 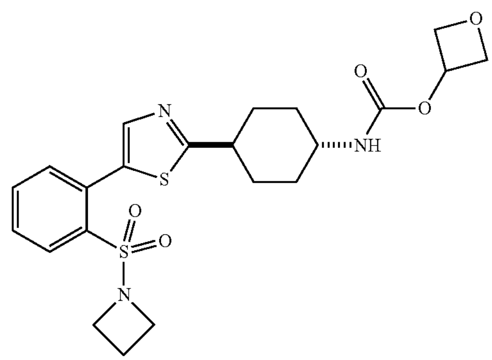 | oxetan-3-yl (trans-4-(5-(2-(azetidin-1-ylsulfonyl)phenyl)thiazol-2-yl)cyclohexyl)carbamate |
| 66 | 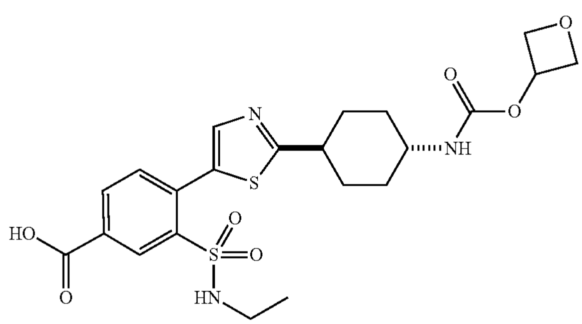 | 3-(N-ethylsulfamoyl)-4-(2-(trans-4-(((oxetan-3-yloxy)carbonyl)amino)cyclohexyl)thiazol-5-yl)benzoic acid |
| 67 | 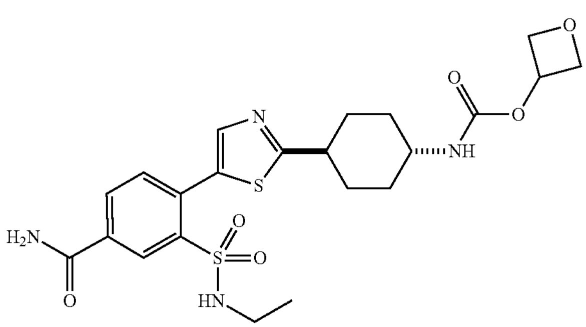 | oxetan-3-yl (trans-4-(5-(4-carbamoyl-2-(N-ethylsulfamoyl)phenyl)thiazol-2-yl)cyclohexyl)carbamate |

TABLE 1-continued

| Cmpd No. | Structure | Chemical Name |
|---|---|---|
| 68 | 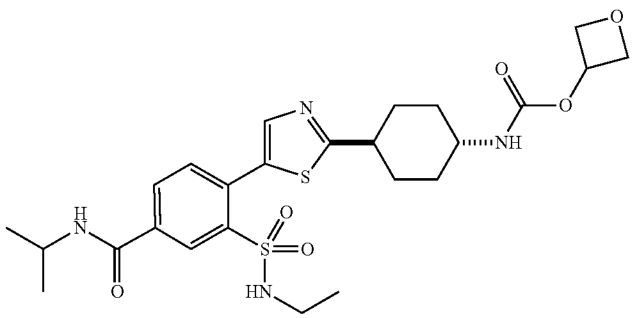 | oxetan-3-yl (trans-4-(5-(2-(N-ethylsulfamoyl)-4-(isopropylcarbamoyl)phenyl)thiazol-2-yl)cyclohexyl)carbamate |
| 69 | 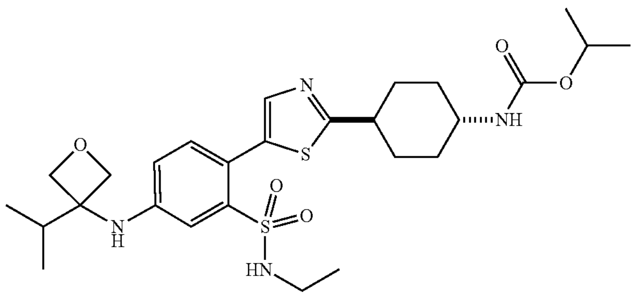 | isopropyl (trans-N-(4-(5-(2-(ethylsulfamoyl)-4-((3-isopropyl-oxetan-3-yl)amino)phenyl)thiazol-2-yl)cyclohexyl))carbamate |
| 70 | 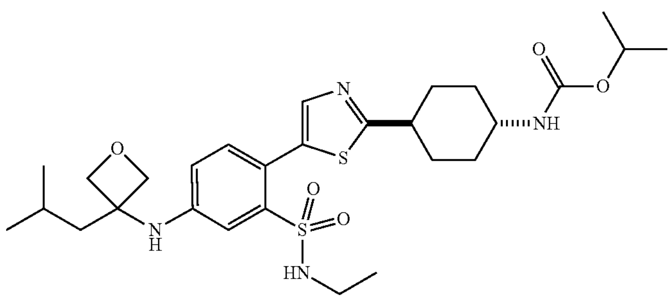 | isopropyl trans-N-[4-[5-[2-(ethylsulfamoyl)-4-[(3-isobutyloxetan-3-yl)amino]phenyl]thiazol-2-yl]cyclohexyl]carbamate |
| 71 | 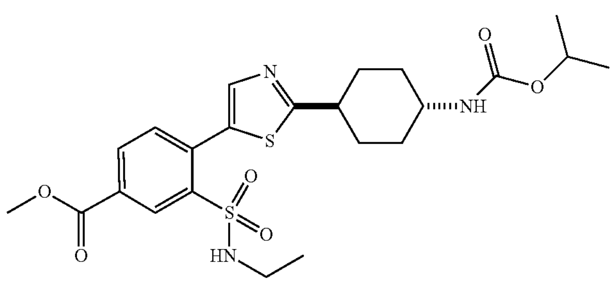 | methyl trans-3-(ethylsulfamoyl)-4-[2-[4-(isopropoxycarbonyl-amino)cyclohexyl]thiazol-5-yl]benzoate |
| 72 | 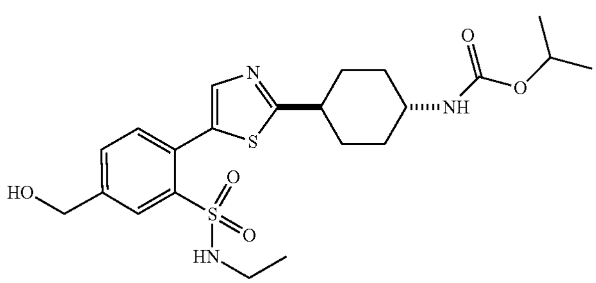 | isopropyl trans-N-[4-[5-[2-(ethylsulfamoyl)-4-(hydroxy-methyl)phenyl]thiazol-2-yl]cyclohexyl]carbamate |

TABLE 1-continued

| Cmpd No. | Structure | Chemical Name |
|---|---|---|
| 73 | 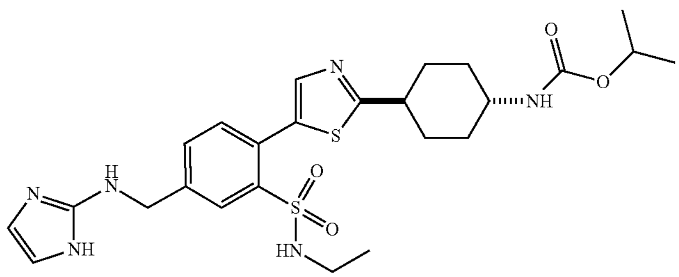 | isopropyl trans-N-[4-[5-[2-(ethylsulfamoyl)-4-[(1H-imidazol-2-ylamino)methyl]phenyl]thiazol-2-yl]cyclohexyl]carbamate |
| 74 | 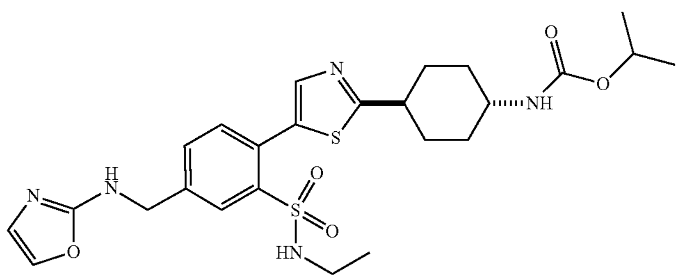 | isopropyl trans-N-[4-[5-[2-(ethylsulfamoyl)-4-[(oxazol-2-ylamino) methyl]phenyl]thiazol-2-yl]cyclohexyl]carbamate |
| 75 | 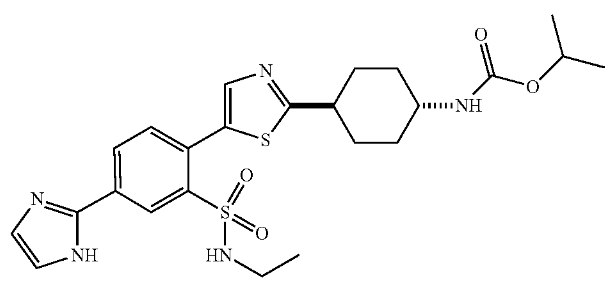 | isopropyl trans-N-[4-[5-[2-(ethylsulfamoyl)-4-(1H-imidazol-2-yl)phenyl]thiazol-2-yl]cyclohexyl]carbamate |
| 76 | 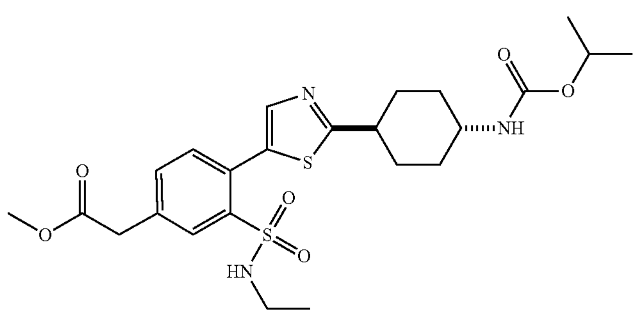 | methyl trans-2-[3-(ethylsulfamoyl)-4-[2-[4-(isopropoxycarbonylamino) cyclohexyl]thiazol-5-yl]phenyl]acetate |
| 77 | 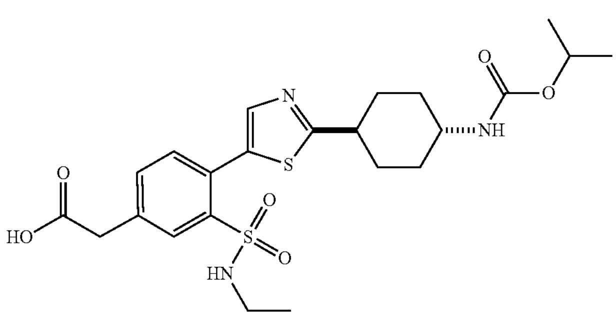 | trans-2-[3-(ethylsulfamoyl)-4-[2-[4-(isopropoxycarbonyl-amino)cyclohexyl]thiazol-5-yl]phenyl]acetic acid |

TABLE 1-continued

| Cmpd No. | Structure | Chemical Name |
|---|---|---|
| 78 | 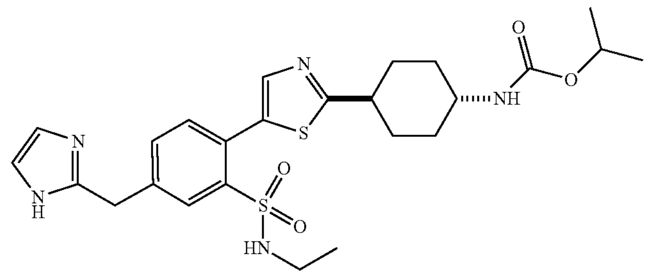 | isopropyl trans-N-[4-[5-[2-(ethylsulfamoyl)-4-(1H-imidazol-2-ylmethyl)phenyl]thiazol-2-yl]cyclohexyl]carbamate |
| 79 | 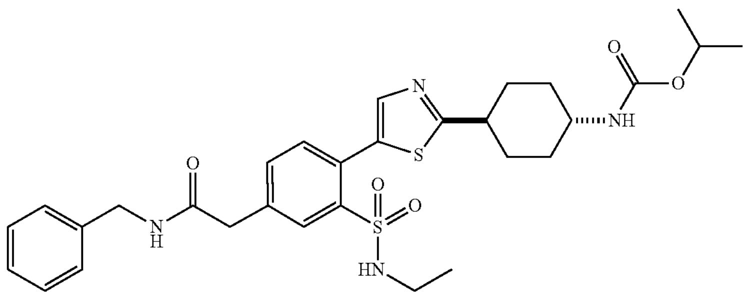 | isopropyl trans-N-[4-[5-[4-[2-(benzylamino)-2-oxo-ethyl]-2-(ethyl-sulfamoyl)phenyl]thiazol-2-yl]cyclohexyl]carbamate |
| 80 | 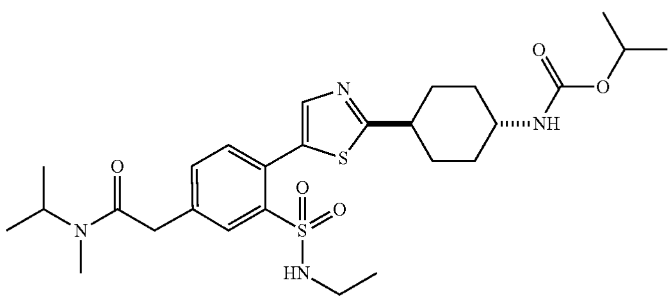 | isopropyl trans-N-[4-[5-[4-[2-(isopropyl(methyl)amino)-2-oxo-ethyl]-2-(ethyl-sulfamoyl)phenyl]thiazol-2-yl]cyclohexyl]carbamate |
| 81 | 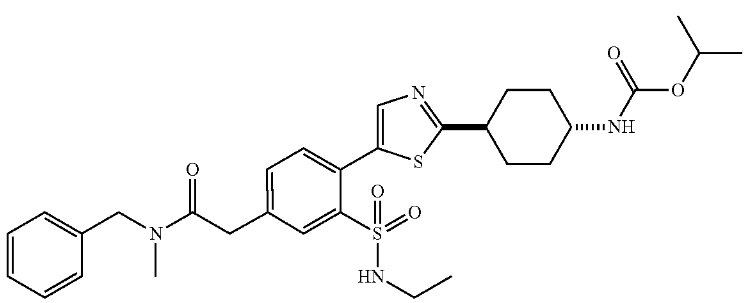 | isopropyl trans-N-[4-[5-[4-[2-(benzyl(methyl)amino)-2-oxo-ethyl]-2-(ethyl-sulfamoyl)phenyl]thiazol-2-yl]cyclohexyl]carbamate |
| 82 | 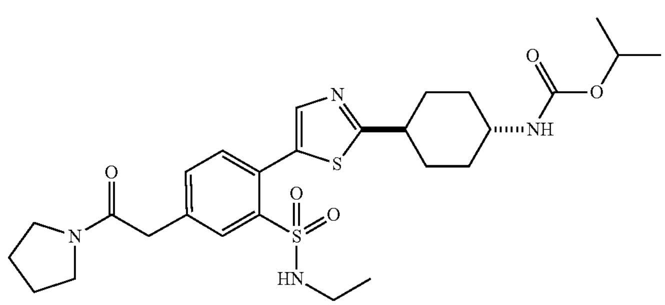 | isopropyl trans-N-[4-[5-[4-[2-oxo-2-(pyrrolidin-1-yl)ethyl]-2-(ethyl-sulfamoyl)phenyl]thiazol-2-yl]cyclohexyl]carbamate |

TABLE 1-continued

| Cmpd No. | Structure | Chemical Name |
|---|---|---|
| 83 | 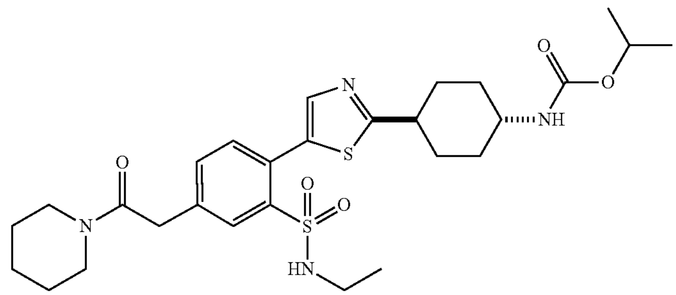 | isopropyl trans-N-[4-[5-[4-[2-oxo-2-(piperidin-1-yl)ethyl]-2-(ethyl-sulfamoyl)phenyl]thiazol-2-yl]cyclohexyl]carbamate |
| 84 | 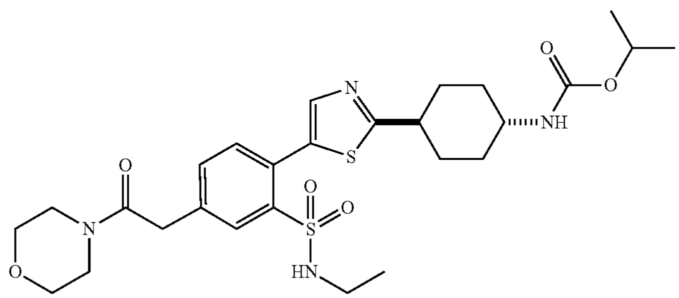 | isopropyl trans-N-[4-[5-[4-[2-oxo-2-(morpholin-4-yl)ethyl]-2-(ethyl-sulfamoyl)phenyl]thiazol-2-yl]cyclohexyl]carbamate |
| 85 | 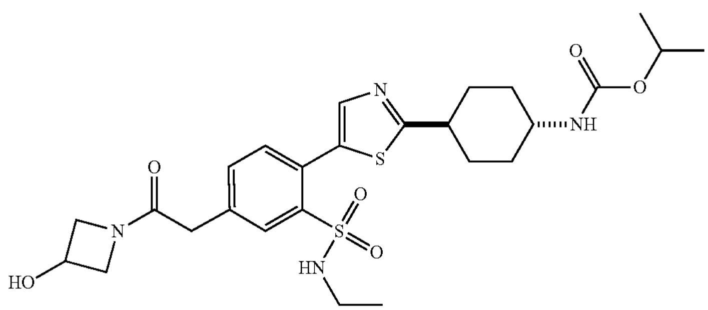 | isopropyl trans-N-[4-[5-[4-[2-oxo-2-(3-hydroxyazetidin-1-yl)ethyl]-2-(ethyl-sulfamoyl)phenyl]thiazol-2-yl]cyclohexyl]carbamate |
| 86 | 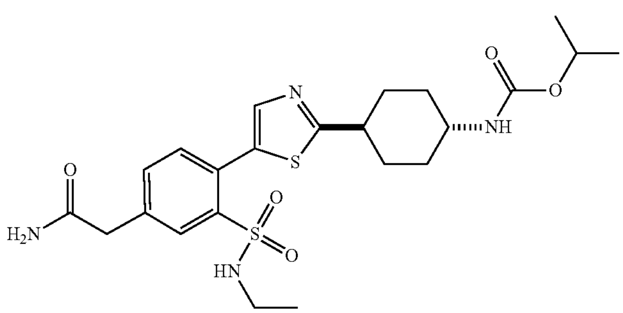 | isopropyl trans-N-[4-[5-[4-[2-amino-2-oxo-ethyl]-2-(ethyl-sulfamoyl)phenyl]thiazol-2-yl]cyclohexyl]carbamate |
| 87 | 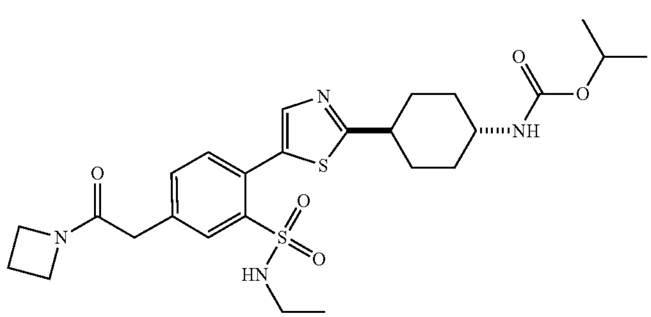 | isopropyl trans-N-[4-[5-[4-[2-oxo-2-(azetidin-1-yl)ethyl]-2-(ethyl-sulfamoyl)phenyl]thiazol-2-yl]cyclohexyl]carbamate |

TABLE 1-continued

| Cmpd No. | Structure | Chemical Name |
|---|---|---|
| 88 | 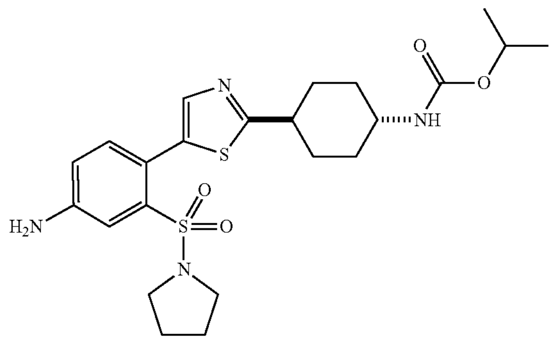 | isopropyl trans-N-[4-[5-(4-amino-2-pyrrolidin-1-ylsulfonyl-phenyl)thiazol-2-yl]cyclohexyl]carbamate |
| 89 | 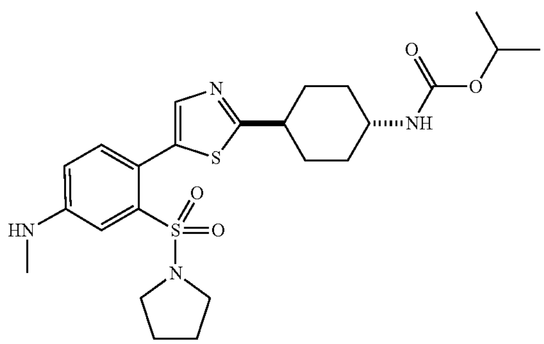 | isopropyl trans-N-[4-[5-(4-(methylamino)-2-pyrrolidin-1-ylsulfonyl-phenyl)thiazol-2-yl]cyclohexyl]carbamate |
| 90 | 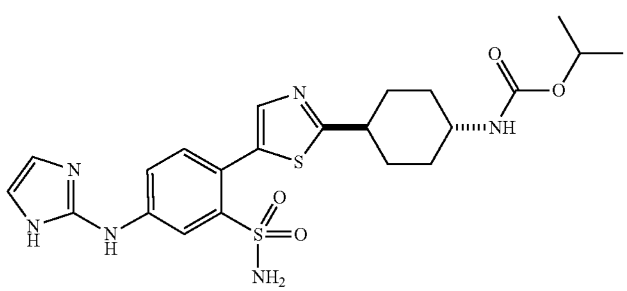 | isopropyl trans-N-[4-[5-[4-(1H-imidazol-2-ylamino)-2-sulfamoyl-phenyl]thiazol-2-yl]cyclohexyl]carbamate |
| 91 | 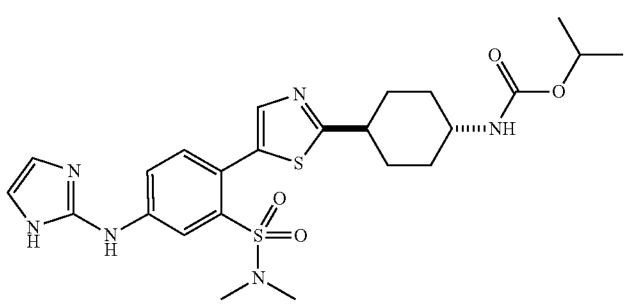 | isopropyl trans-N-[4-[5-[2-(dimethylsulfamoyl)-4-(1H-imidazol-2-ylamino)phenyl]thiaol-2-yl]cyclohexyl]carbamate |

TABLE 1-continued

| Cmpd No. | Structure | Chemical Name |
|---|---|---|
| 92 | 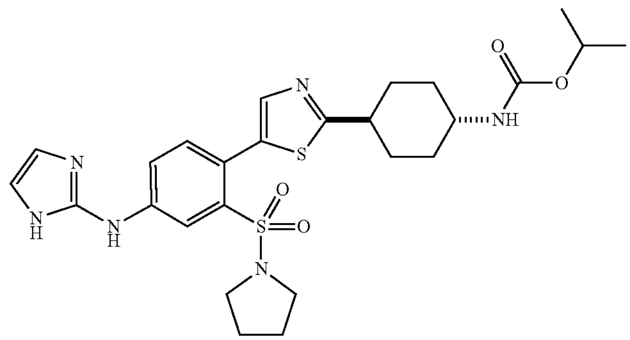 | isopropyl trans-N-[4-[5-[4-(1H-imidazol-2-ylamino)-2-pyrrolidin-1-ylsulfonyl-phenyl]thiaol-2-yl]cyclohexyl]carbamate |
| 93 | 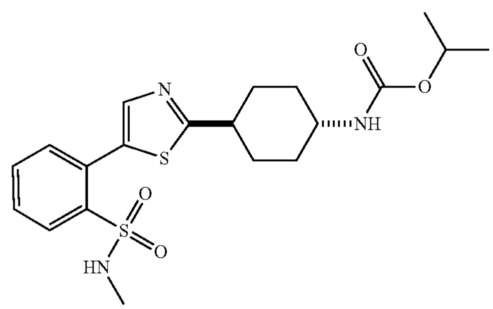 | isopropyl trans-N-[4-[5-(2-methylsulfamoylphenyl)thiazol-2-yl]cyclohexyl]carbamate |
| 94 | 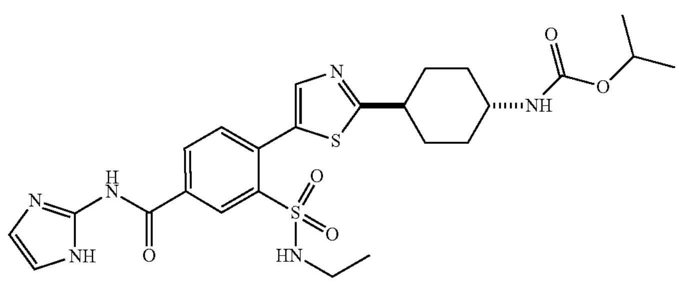 | isopropyl trans-N-[4-[5-[2-(ethylsulfamoyl)-4-(1H-imidazol-2-ylcarbamoyl)phenyl]thiazol-2-yl]cyclohexyl]carbamate |
| 95 | 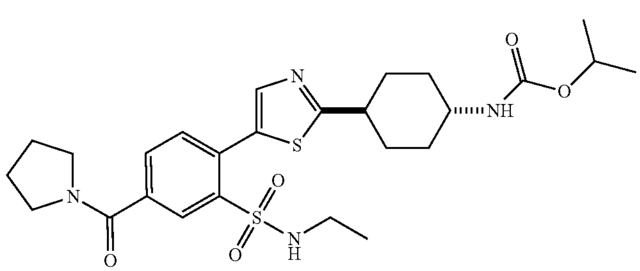 | isopropyl trans-N-[4-[5-[4-pyrrolidin-1-ylcarbonyl-2-(ethylsulfamoyl)phenyl] thiazol-2-yl]cyclohexyl]carbamate |
| 96 | 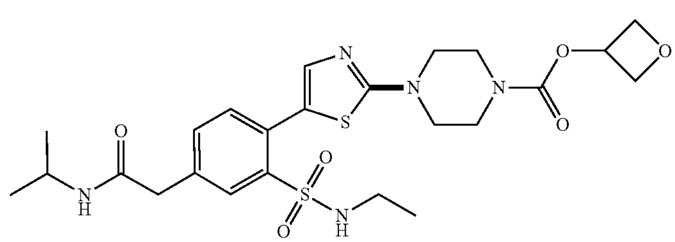 | oxetan-3-yl 4-(5-(2-(N-ethylsulfamoyl)-4-(2-(isopropylamino)-2-oxoethyl)phenyl)thiazol-2-yl)piperazine-1-carboxylate |

TABLE 1-continued

| Cmpd No. | Structure | Chemical Name |
|---|---|---|
| 97 | 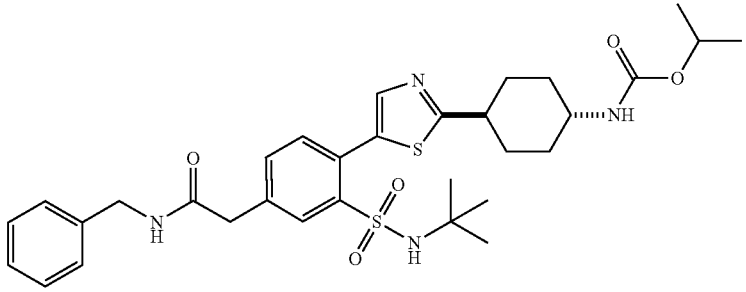 | isopropyl trans-N-[4-[5-[4-[2-(benzylamino)-2-oxo-ethyl]-2-(tert-butylsulfamoyl)phenyl]thiazol-2-yl]cyclohexyl]carbamate |
| 98 | 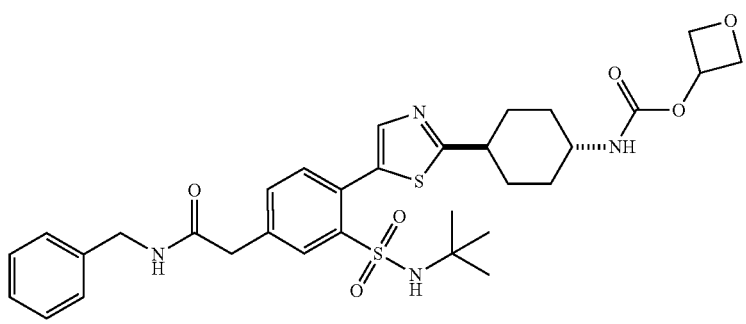 | oxetan-3-yl trans-N-[4-[5-[4-[2-(benzylamino)-2-oxo-ethyl]-2-(tert-butylsulfamoyl)phenyl]thiazol-2-yl]cyclohexyl]carbamate |
| 99 | 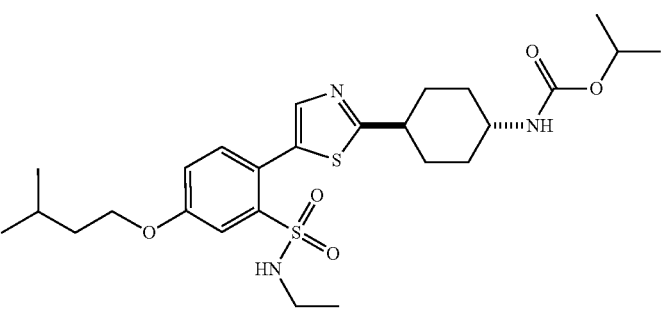 | isopropyl trans-N-[4-[5-[2-(ethylsulfamoyl)-4-isopentyloxy-phenyl]thiazol-2-yl]cyclohexyl]carbamate |
| 100 | 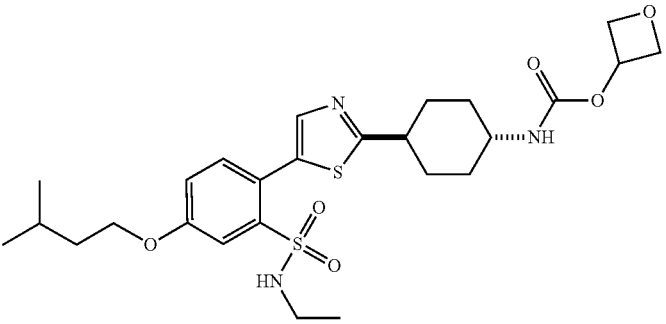 | oxetan-3-yl trans-N-[4-[5-[2-(ethylsulfamoyl)-4-isopentyloxy-phenyl]thiazol-2-yl]cyclohexyl]carbamate |
| 101 | 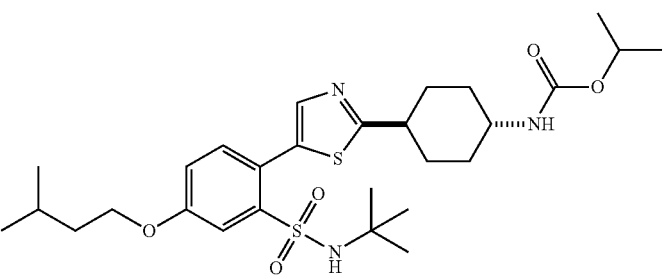 | isopropyl trans-N-[4-[5-[2-(tert-butylsulfamoyl)-4-isopentyloxy-phenyl]thiazol-2-yl]cyclohexyl]carbamate |

TABLE 1-continued

| Cmpd No. | Structure | Chemical Name |
|---|---|---|
| 102 | 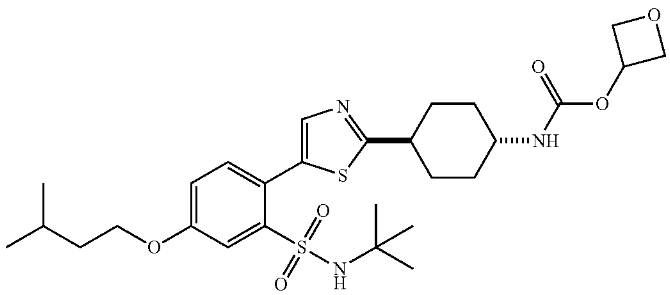 | oxetan-3-yl trans-N-[4-[5-[2-(tert-butylsulfamoyl)-4-isopentyloxy-phenyl]thiazol-2-yl]cyclohexyl]carbamate |
| 103 | 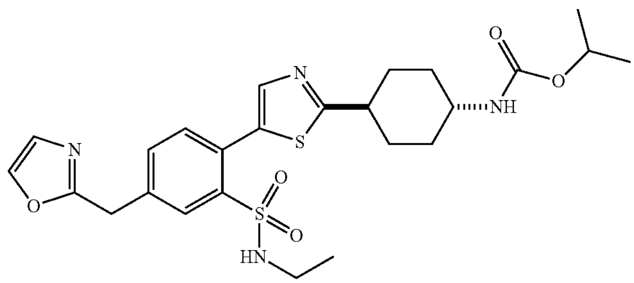 | isopropyl trans-N-[4-[5-[2-(ethylsulfamoyl)-4-(oxazol-2-ylmethyl)phenyl]thiazol-2-yl]cyclohexyl]carbamate |
| 104 | 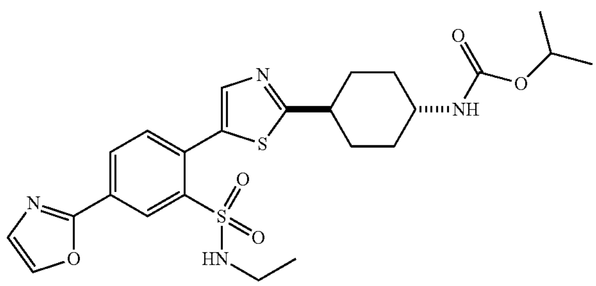 | isopropyl trans-N-[4-[5-[2-(ethylsulfamoyl)-4-oxazol-2-yl-phenyl]thiazol-2-yl]cyclohexyl]carbamate |
| 105 | 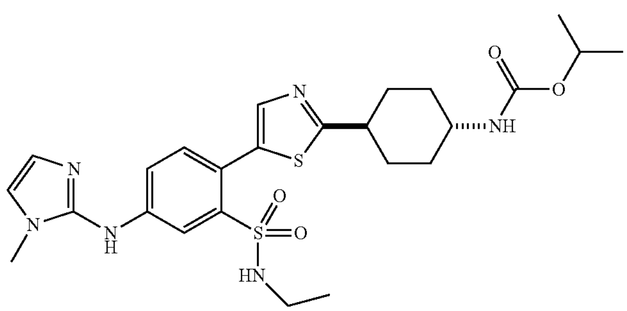 | isopropyl trans-N-[4-[5-[2-(ethylsulfamoyl)-4-[(1-methylimidazol-2-yl)amino]phenyl]thiazol-2-yl]cyclohexyl]carbamate |
| 106 | 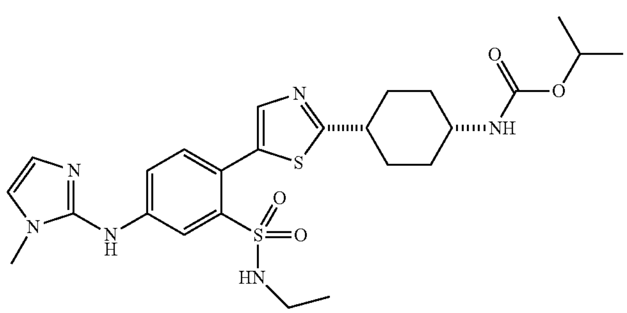 | isopropyl cis-N-[4-[5-[2-(ethylsulfamoyl)-4-[(1-methylimidazol-2-yl)amino]phenyl] thiazol-2-yl]cyclohexyl]carbamate |

TABLE 1-continued

| Cmpd No. | Structure | Chemical Name |
|---|---|---|
| 107 | 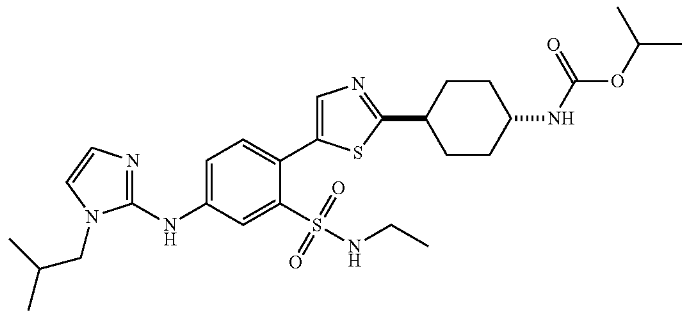 | isopropyl trans-N-[4-[5-[2-(ethylsulfamoyl)-4-[(1-isobutyl-imidazol-2-yl)amino]phenyl]thiazol-2-yl]cyclohexyl]carbamate |
| 108 | 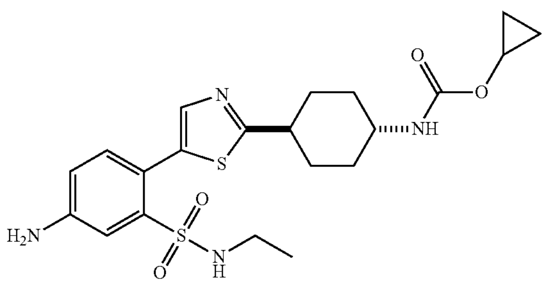 | cyclopropyl trans-N-[4-[5-[4-amino-2-(ethylsulfamoyl)phenyl]thiazol-2-yl]cyclohexyl]carbamate |
| 109 | 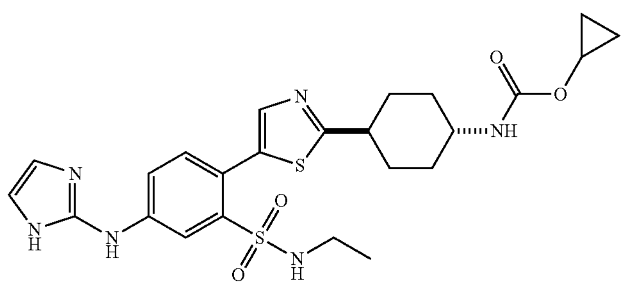 | cyclopropyl trans-N-[4-[5-[2-(ethylsulfamoyl)-4-(1H-imidazol-2-ylamino)phenyl]thiazol-2-yl]cyclohexyl]carbamate |
| 110 | 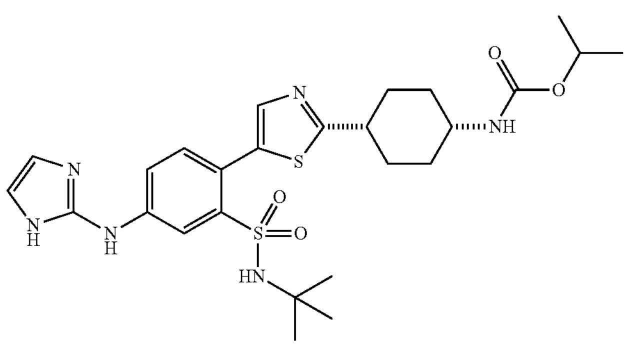 | isopropyl cis-N-[4-[5-[2-(tert-butylsulfamoyl)-4-(1H-imidazol-2-ylamino)phenyl]thiazol-2-yl]cyclohexyl]carbamate |
| 111 | 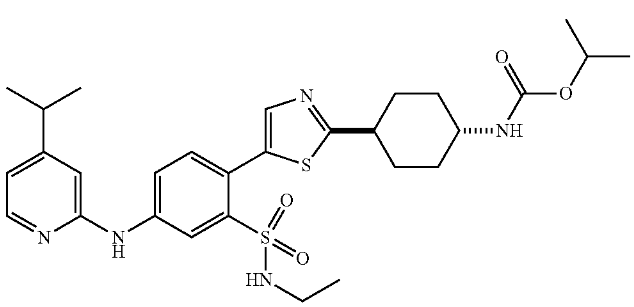 | isopropyl trans-N-[4-[5-[2-(ethylsulfamoyl)-4-[(4-isopropyl-2-pyridyl)amino]phenyl]thiazol-2-yl]cyclohexyl]carbamate |

TABLE 1-continued

| Cmpd No. | Structure | Chemical Name |
|---|---|---|
| 112 | 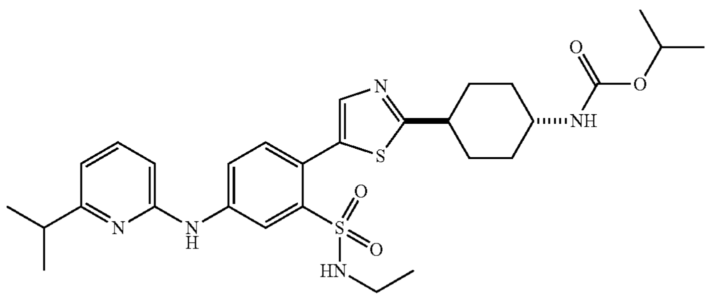 | isopropyl trans-N-[4-[5-[2-(ethylsulfamoyl)-4-[(6-isopropyl-2-pyridyl)amino]phenyl]thiazol-2-yl]cyclohexyl]carbamate |
| 113 | 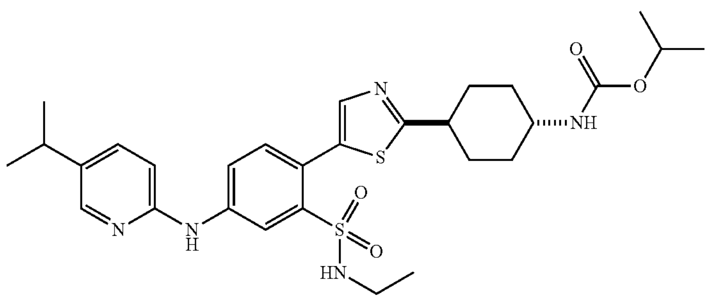 | isopropyl trans-N-[4-[5-[2-(ethylsulfamoyl)-4-[(5-isopropyl-2-pyridyl)amino]phenyl]thiazol-2-yl]cyclohexyl]carbamate |
| 114 | 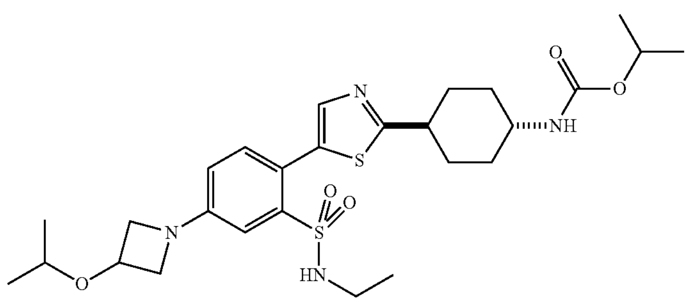 | isopropyl trans-N-[4-[5-[2-(ethylsulfamoyl)-4-[3-isopropoxyazetidin-1-yl]phenyl]thiazol-2-yl]cyclohexyl]carbamate |
| 115 | 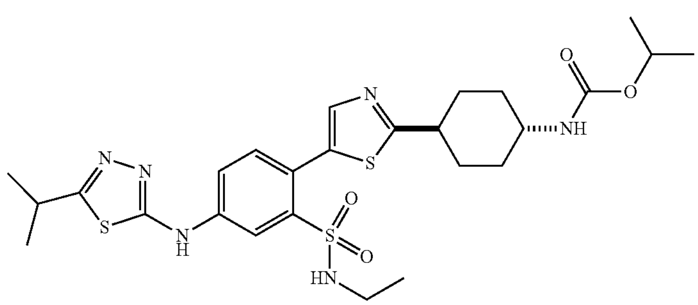 | isopropyl trans-N-[4-[5-[2-(ethylsulfamoyl)-4-[(5-isopropyl-1,3,4-thiadiazol-2-y)amino]phenyl]thiazol-2-yl]cyclohexyl]carbamate |
| 116 | 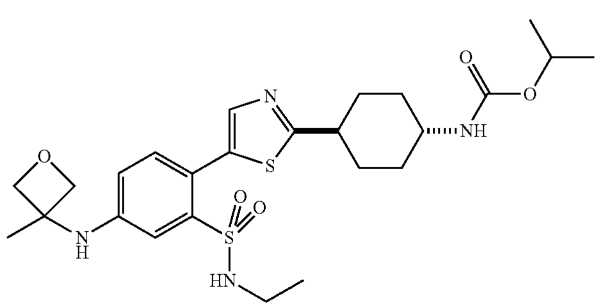 | isopropyl trans-N-[4-[5-[2-(ethylsulfamoyl)-4-[(3-methyloxetan-3-yl)amino]phenyl]thiazol-2-yl]cyclohexyl]carbamate |

TABLE 1-continued

| Cmpd No. | Structure | Chemical Name |
|---|---|---|
| 117 | 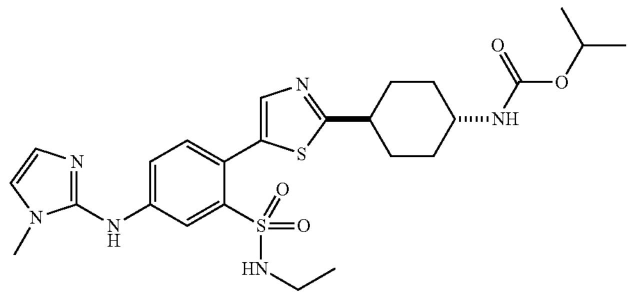 | isopropyl trans-N-[4-[5-[2-(ethylsulfamoyl)-4-[methyl(1-methyl-1H-imidazol-2-yl)amino]phenyl]thiazol-2-yl]cyclohexyl]carbamate |
| 118 | 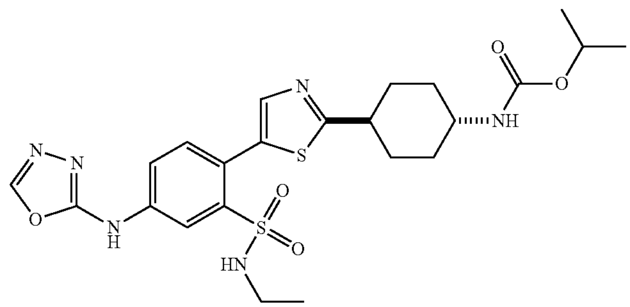 | isopropyl trans-N-[4-[5-[2-(ethylsulfamoyl)-4-[(1,3,4-oxadiazool-2-yl)amino]phenyl]thiazol-2-yl]cyclohexyl]carbamate |
| 119 | 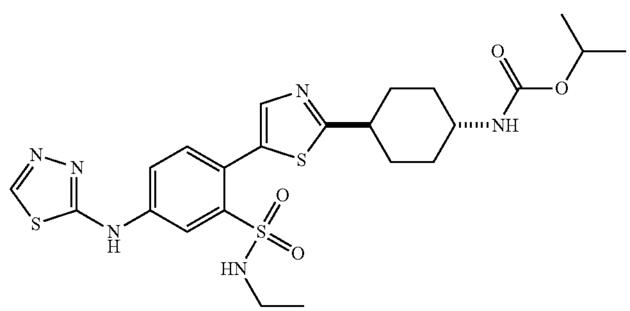 | isopropyl trans-N-[4-[5-[2-(ethylsulfamoyl)-4-[(1,3,4-thiadiazol-2-yl)amino]phenyl]thiazol-2-yl]cyclohexyl]carbamate |
| 120 | 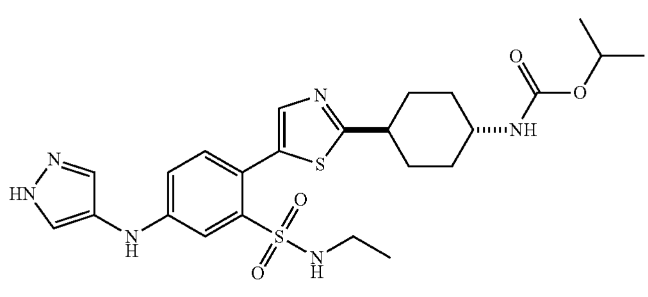 | isopropyl trans-N-[4-[5-[2-(ethylsulfamoyl)-4-[(1H-pyrazol-4-yl)amino]phenyl]thiazol-2-yl]cyclohexyl]carbamate |
| 121 | 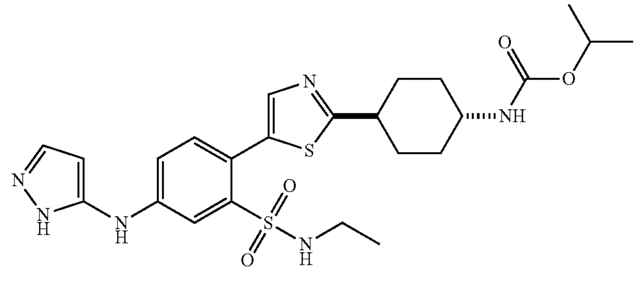 | isopropyl trans-N-[4-[5-[2-(ethylsulfamoyl)-4-[(1H-pyrazol-5-yl)amino]phenyl]thiazol-2-yl]cyclohexyl]carbamate |

TABLE 1-continued

| Cmpd No. | Structure | Chemical Name |
|---|---|---|
| 122 | 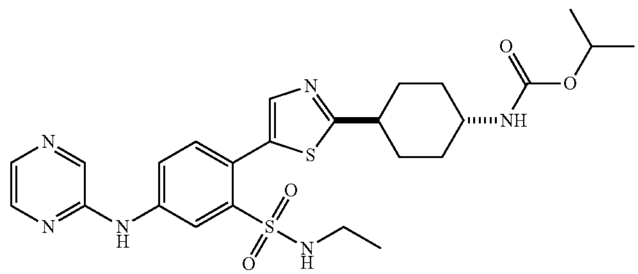 | isopropyl trans-N-[4-[5-[2-(ethylsulfamoyl)-4-[(pyrazin-2-yl)amino]phenyl]thiazol-2-yl]cyclohexyl]carbamate |
| 123 | 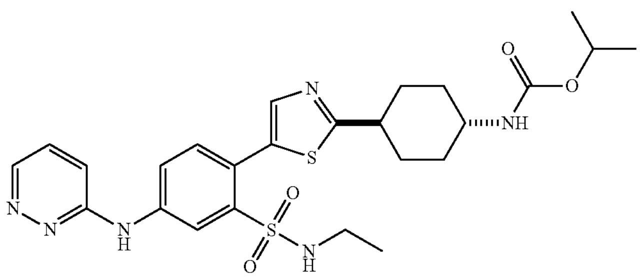 | isopropyl trans-N-[4-[5-[2-(ethylsulfamoyl)-4-[(pyridazin-3-yl)amino]phenyl]thiazol-2-yl]cyclohexyl]carbamate |
| 124 | 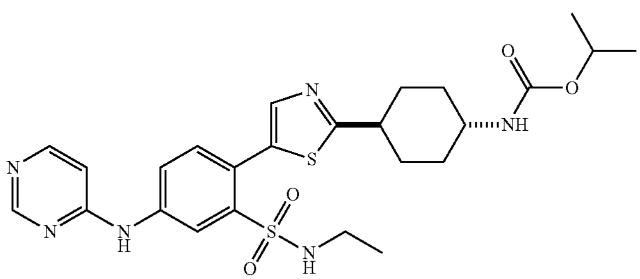 | isopropyl trans-N-[4-[5-[2-(ethylsulfamoyl)-4-[(pyrimidin-4-yl)amino]phenyl]thiazol-2-yl]cyclohexyl]carbamate |
| 125 | 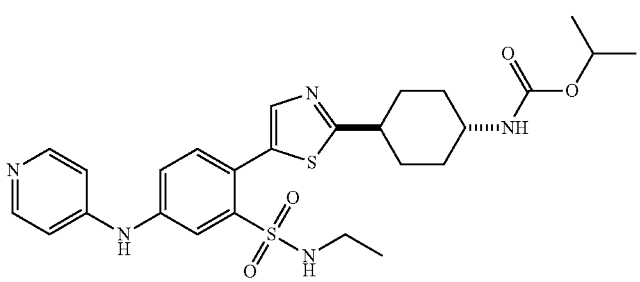 | isopropyl trans-N-[4-[5-[2-(ethylsulfamoyl)-4-[(pyridin-4-yl)amino]phenyl]thiazol-2-yl]cyclohexyl]carbamate |
| 126 | 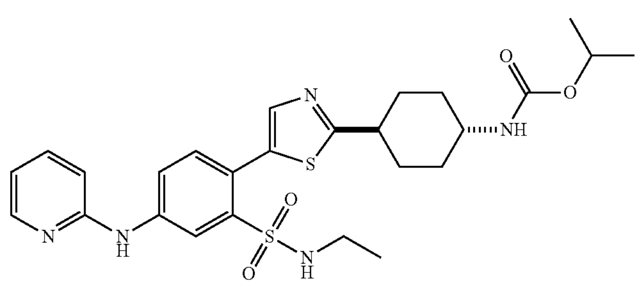 | isopropyl trans-N-[4-[5-[2-(ethylsulfamoyl)-4-[(pyridin-2-yl)amino]phenyl]thiazol-2-yl]cyclohexyl]carbamate |

TABLE 1-continued

| Cmpd No. | Structure | Chemical Name |
|---|---|---|
| 127 | 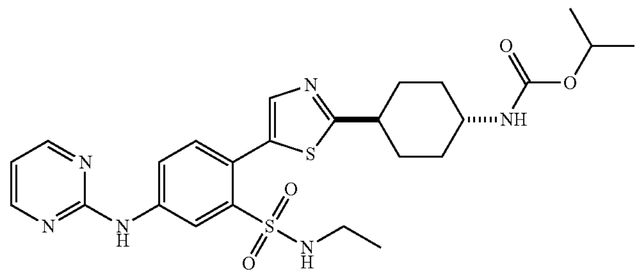 | isopropyl trans-N-[4-[5-[2-(ethylsulfamoyl)-4-[(pyrimidin-2-yl)amino]phenyl]thiazol-2-yl]cyclohexyl]carbamate |
| 128 | 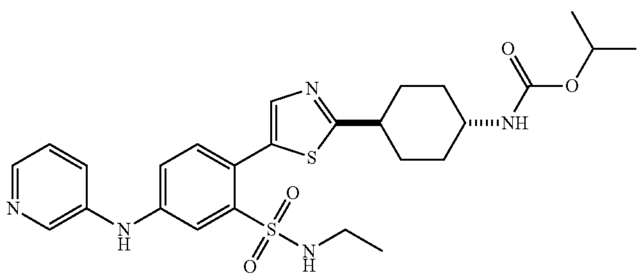 | isopropyl trans-N-[4-[5-[2-(ethylsulfamoyl)-4-[(pyridin-3-yl)amino]phenyl]thiazol-2-yl]cyclohexyl]carbamate |
| 129 | 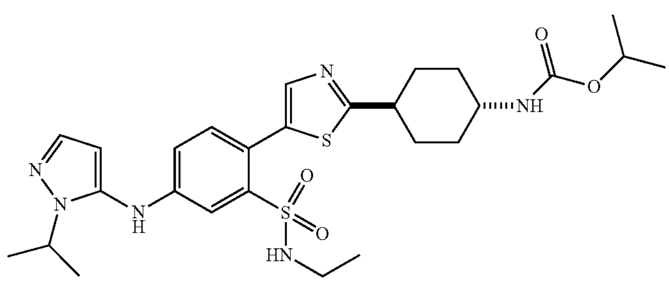 | isopropyl trans-N-[4-[5-[2-(ethylsulfamoyl)-4-[(1-isopropyl-1H-pyrazol-5-yl)amino]phenyl]thiazol-2-yl]cyclohexyl]carbamate |
| 130 | 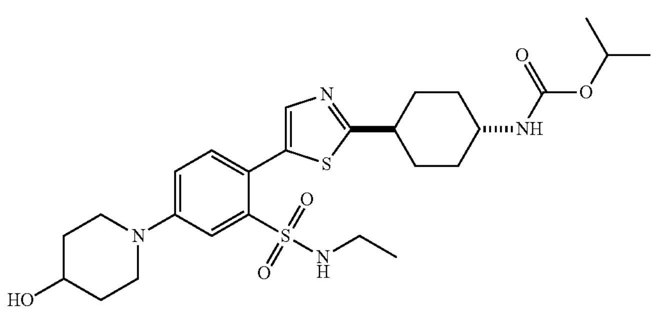 | isopropyl trans-N-[4-[5-[2-(ethylsulfamoyl)-4-[4-hydroxypiperidin-1-yl]phenyl]thiazol-2-yl]cyclohexyl]carbamate |
| 131 | 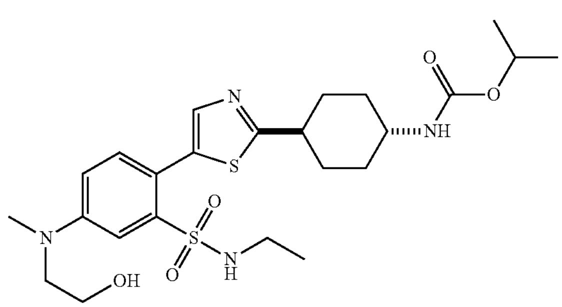 | isopropyl trans-N-[4-[5-[2-(ethylsulfamoyl)-4-[(2-hydroxyethyl)(methyl))amino]phenyl]thiaol-2-yl]cyclohexyl]carbamate |

TABLE 1-continued

| Cmpd No. | Structure | Chemical Name |
|---|---|---|
| 132 | 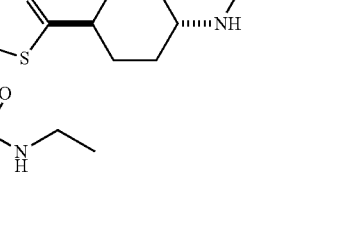 | isopropyl trans-N-[4-[5-[2-(ethylsulfamoyl)-4-[(2-methoxyethyl)(methyl))amino]phenyl]thiazol-2-yl]cyclohexyl]carbamate |
| 133 | 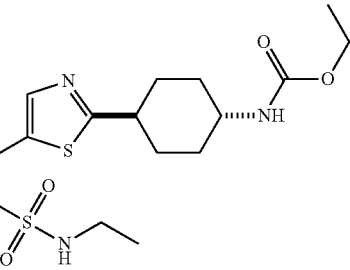 | isopropyl trans-N-[4-[5-[2-(ethylsulfamoyl)-4-[1,1-dioxidothiomorpholino]phenyl]thiazol-2-yl]cyclohexyl]carbamate |
| 134 | 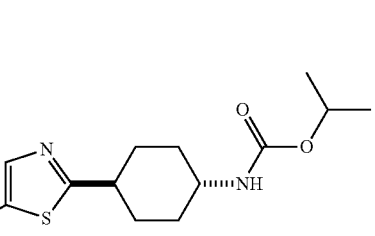 | isopropyl trans-N-[4-[5-[2-(ethylsulfamoyl)-4-[morpholino]phenyl]thiazol-2-yl]cyclohexyl]carbamate |
| 135 | 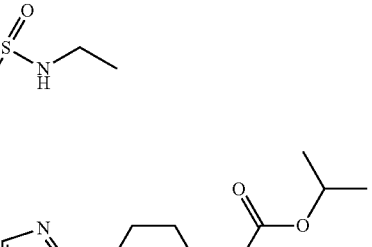 | isopropyl trans-N-[4-[5-[2-(ethylsulfamoyl)-4-[piperidin-1-yl]phenyl]thiazol-2-yl]cyclohexyl]carbamate |
| 136 | 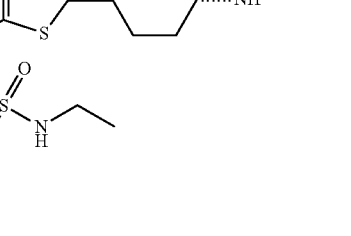 | isopropyl trans-N-[4-[5-[2-(ethylsulfamoyl)-4-[(2-isopropylpyrimidin-4-yl)amino]phenyl]thiazol-2-yl]cyclohexyl]carbamate |

TABLE 1-continued

| Cmpd No. | Structure | Chemical Name |
|---|---|---|
| 137 | 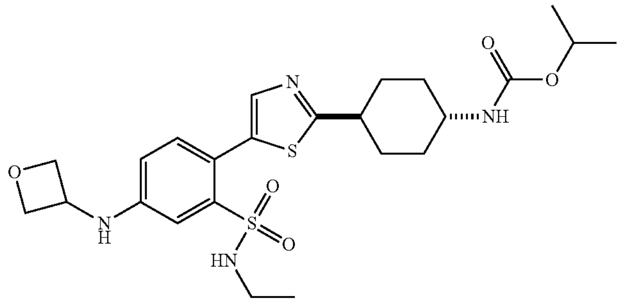 | isopropyl trans-N-[4-[5-[2-(ethylsulfamoyl)-4-[(oxetan-3-yl)amino]phenyl]thiazol-2-yl]cyclohexyl]carbamate |
| 138 | 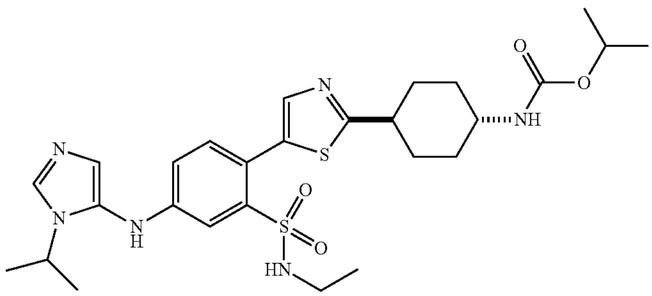 | isopropyl trans-N-[4-[5-[2-(ethylsulfamoyl)-4-[(3-isopropylimidazol-4-yl)amino]phenyl]thiazol-2-yl]cyclohexyl]carbamate |
| 139 | 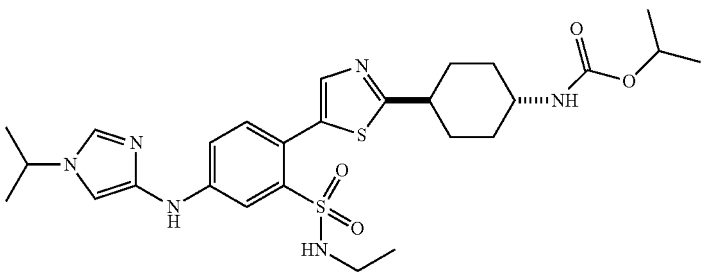 | isopropyl trans-N-[4-[5-[2-(ethylsulfamoyl)-4-[(1-isopropyl-1H-imidazol-4-yl)amino]phenyl]thiazol-2-yl]cyclohexyl]carbamate |
| 140 | 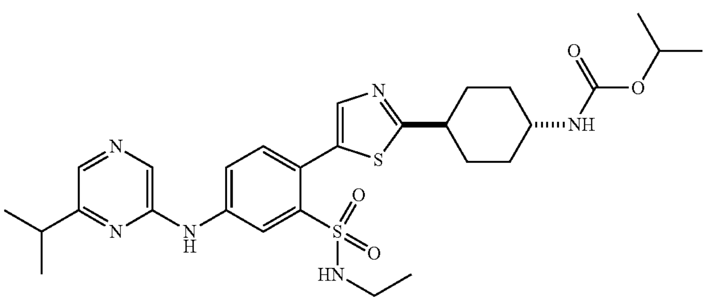 | isopropyl trans-N-[4-[5-[2-(ethylsulfamoyl)-4-[(6-isopropylpyrazin-2-yl)amino]phenyl]thiazol-2-yl]cyclohexyl]carbamate |
| 141 | 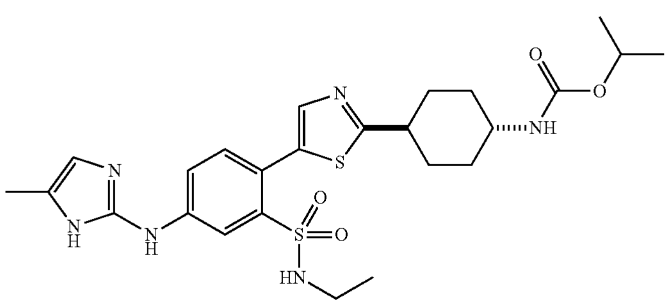 | isopropyl trans-N-[4-[5-[2-(ethylsulfamoyl)-4-[(5-methyl-1H-imidazol-2-yl)amino]phenyl]thiazol-2-yl]cyclohexyl]carbamate |

TABLE 1-continued

| Cmpd No. | Structure | Chemical Name |
|---|---|---|
| 142 | 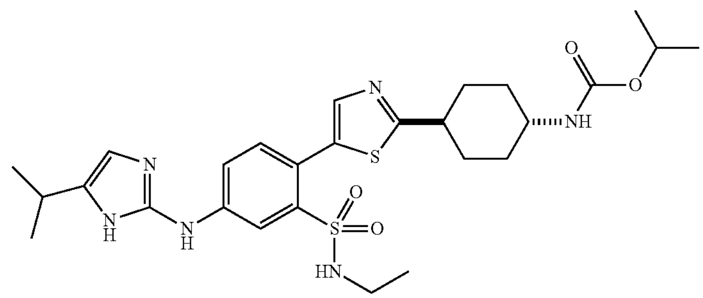 | isopropyl trans-N-[4-[5-[2-(ethylsulfamoyl)-4-[(5-isopropyl-1H-imidazol-2-yl)amino]phenyl]thiazol-2-yl]cyclohexyl]carbamate |
| 143 | 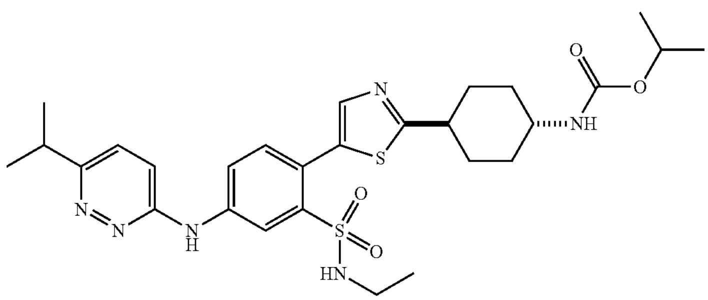 | isopropyl trans-N-[4-[5-[2-(ethylsulfamoyl)-4-[(6-isopropylpyridazin-3-yl)amino]phenyl]thiazol-2-yl]cyclohexyl]carbamate |
| 144 | 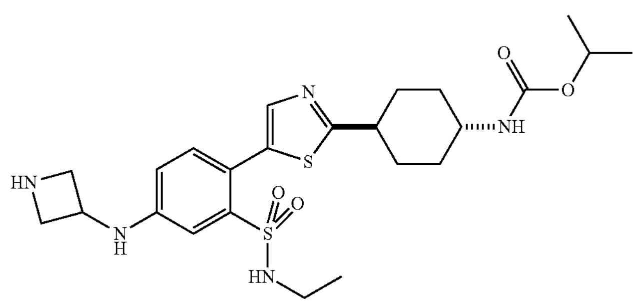 | isopropyl trans-N-[4-[5-[4-(azetidin-3-ylamino)-2-(ethyl-sulfamoyl)phenyl]thiazol-2-yl]cyclohexyl]carbamate |
| 145 | 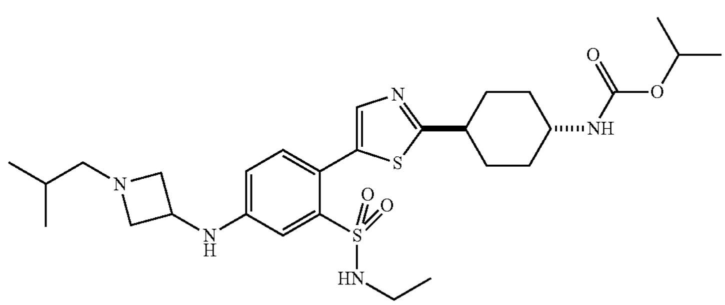 | isopropyl trans-N-[4-[5-[2-(ethylsulfamoyl)-4-[(1-isobutyl-azetidin-3-yl)amino]phenyl]thiazol-2-yl]cyclohexyl]carbamate |
| 146 | 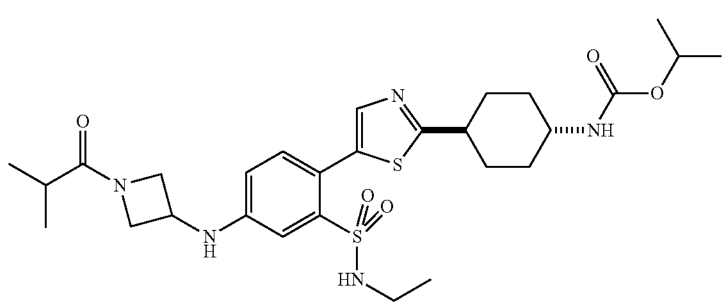 | isopropyl trans-N-[4-[5-[2-(ethylsulfamoyl)-4-[[1-(2-methylpropanoyl)azetidin-3-yl]amino]phenyl]thiazol-2-yl]cyclohexyl]carbamate |

TABLE 1-continued

| Cmpd No. | Structure | Chemical Name |
|---|---|---|
| 147 | 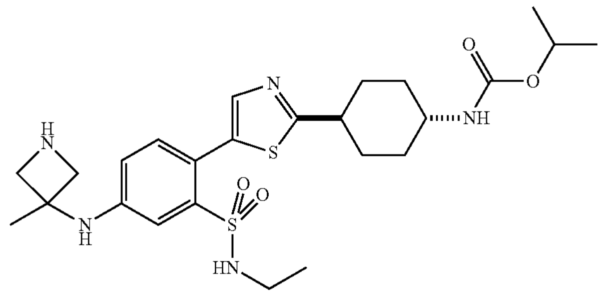 | isopropyl trans-N-[4-[5-[2-(ethylsulfamoyl)-4-[(3-methylazetidin-3-yl)amino]phenyl]thiazol-2-yl]cyclohexyl]carbamate |
| 148 | 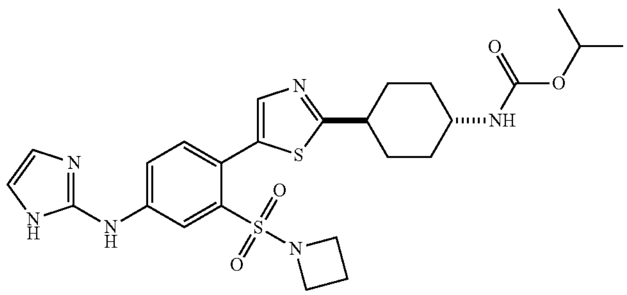 | isopropyl trans-N-[4-[5-[2-(azetidin-1-ylsulfonyl)-4-(1H-imidazol-2-ylamino)phenyl]thiazol-2-yl]cyclohexyl]carbamate |
| 149 | 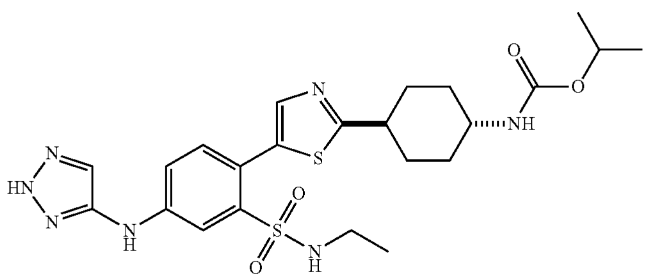 | isopropyl trans-N-[4-[5-[2-(ethylsulfamoyl)-4-(2H-triazol-4-ylamino)phenyl]thiazol-2-yl]cyclohexyl]carbamate |
| 150 | 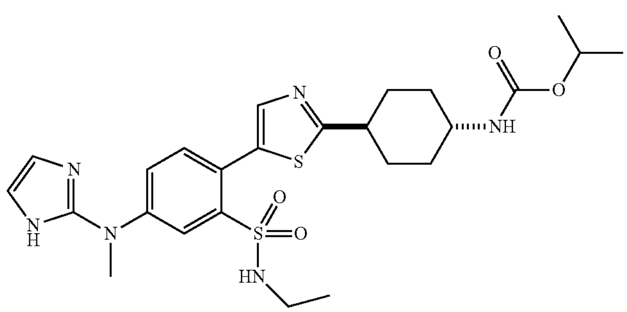 | isopropyl trans-N-[4-[5-[2-(ethylsulfamoyl)-4-[1H-imidazol-2-yl(methyl)amino]phenyl]thiazol-2-yl]cyclohexyl]carbamate |
| 151 | 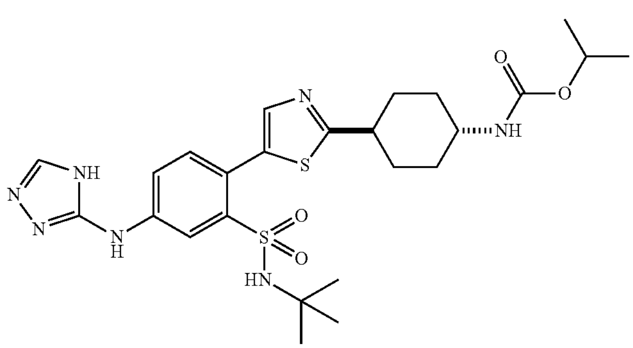 | isopropyl trans-N-[4-[5-[2-(tert-butylsulfamoyl)-4-(4H-1,2,4-triazol-3-ylamino)phenyl]thiazol-2-yl]cyclohexyl]carbamate |

TABLE 1-continued

| Cmpd No. | Structure | Chemical Name |
|---|---|---|
| 152 | 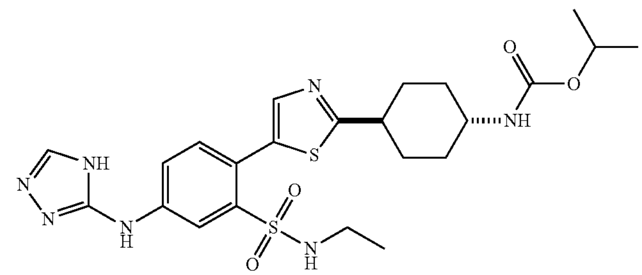 | isopropyl trans-N-[4-[5-[2-(ethylsulfamoyl)-4-(4H-1,2,4-triazl-3-ylamino)phenyl]thiazol-2-yl]cyclohexyl]carbamate |
| 153 | 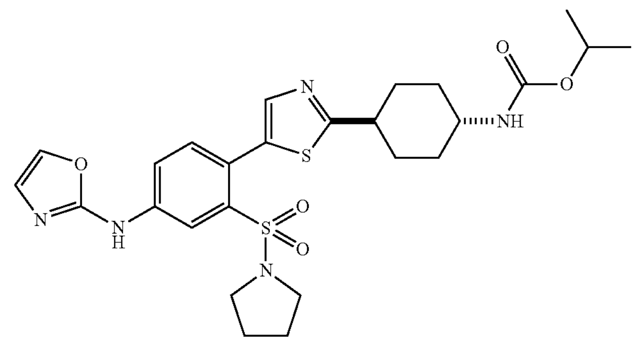 | isopropyl trans-[4-[5-[4-(oxazol-2-ylamino)-2-pyrrolidin-1-ylsulfonyl-phenyl]thiazol-2-yl]cyclohexyl]carbamate |
| 154 | 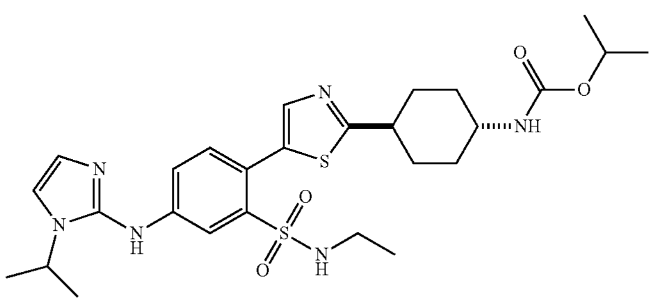 | isopropyl trans-N-[4-[5-[2-(ethylsulfamoyl)-4[(1-isopropylimidazol-2-yl)amino]phenyl]thiazol-2-yl]cyclohexyl]carbamate |
| 155 | 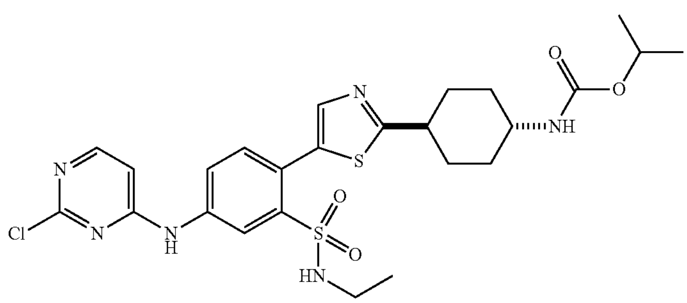 | isopropyl trans-N-[4-[5-[4-[(2-chloropyrimidin-4-yl)amino]-2-(ethylsulfamoyl)phenyl]thiazol-2-yl]cyclohexyl]carbamate |
| 156 | 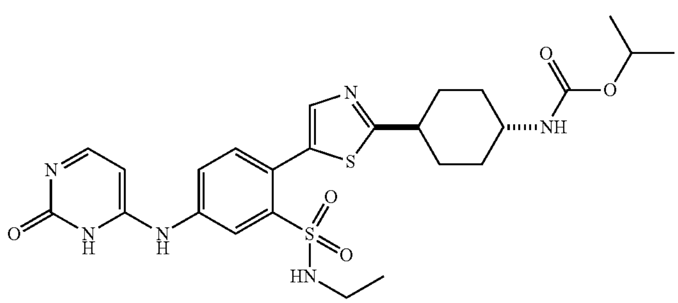 | isopropyl trans-N-[4-[5-[2-(ethylsulfamoyl)-4-[(2-hydroxypyrimidin-4-yl)amino]phenyl]thiazol-2-yl]cyclohexyl]carbamate |

TABLE 1-continued

| Cmpd No. | Structure | Chemical Name |
|---|---|---|
| 157 | 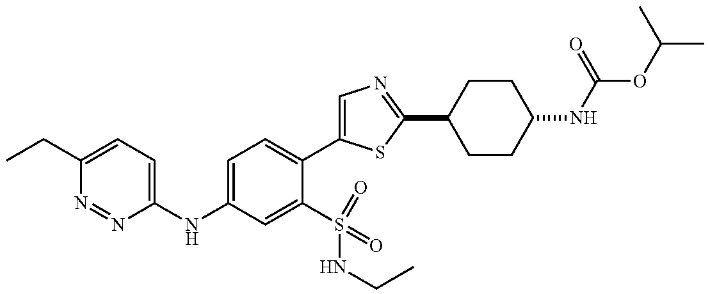 | isopropyl trans-N-[4-[5-[4-[(6-ethylpyridazin-3-yl)amino]-2-(ethylsulfamoyl)phenyl]thiazol-2-yl]cyclohexyl]carbamate |
| 158 | 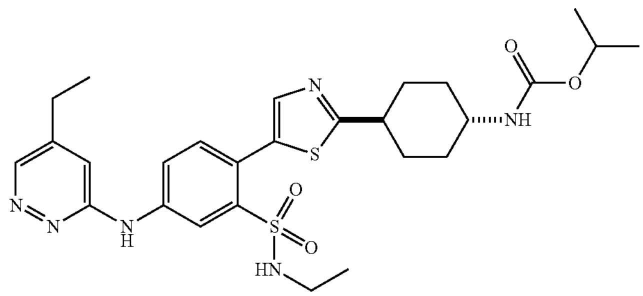 | isopropyl trans-N-[4-[5-[4-[(5-ethylpyridazin-3-yl)amino]-2-(ethylsulfamoyl)phenyl]thiazol-2-yl]cyclohexyl]carbamate |
| 159 | 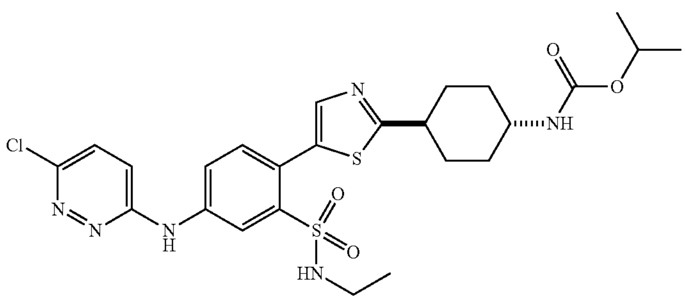 | isopropyl trans-N-[4-[5-[4-[(6-chloropyridazin-3-yl)amino]-2-(ethylsulfamoyl)phenyl]thiazol-2-yl]cyclohexyl]carbamate |
| 160 | 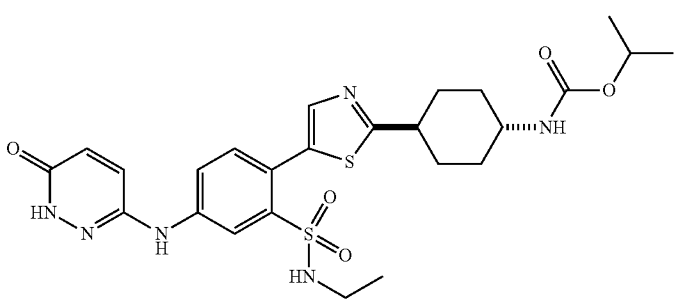 | isopropyl trans-N-[4-[5-[2-(ethylsulfamoyl)-4-[(6-oxo-1H-pyridazin-3-yl)amino]phenyl]thiazol-2-yl]cyclohexyl]carbamate |
| 161 | 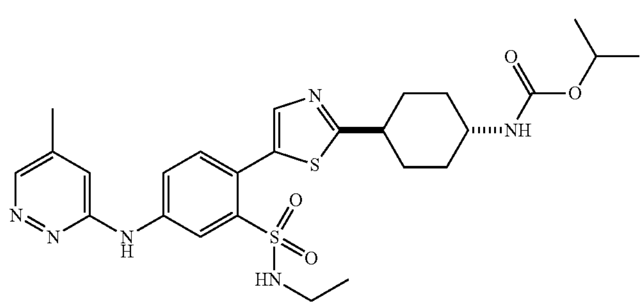 | isopropyl trans-N-[4-[5-[2-(ethylsulfamoyl)-4-[(5-methylpyridazin-3-yl)amino]phenyl]thiazol-2-yl]cyclohexyl]carbamate |

TABLE 1-continued

| Cmpd No. | Structure | Chemical Name |
|---|---|---|
| 162 | 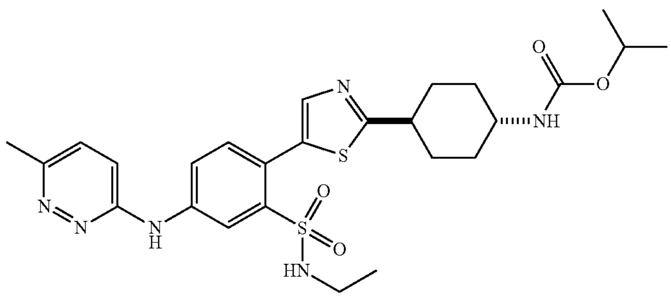 | isopropyl trans-N-[4-[5-[2-(ethylsulfamoyl)-4-[(6-methylpyridazin-3-yl)amino]phenyl]thiazol-2-yl]cyclohexyl]carbamate |
| 163 | 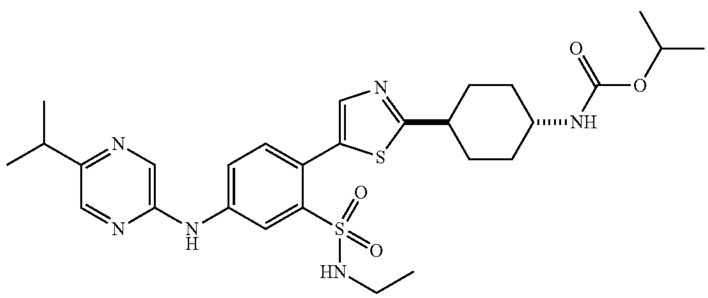 | isopropyl trans-N-[4-[5-[2-(ethylsulfamoyl)-4-[(5-isopropylpyrazin-2-yl)amino]phenyl]thiazol-2-yl]cyclohexyl]carbamate |
| 164 | 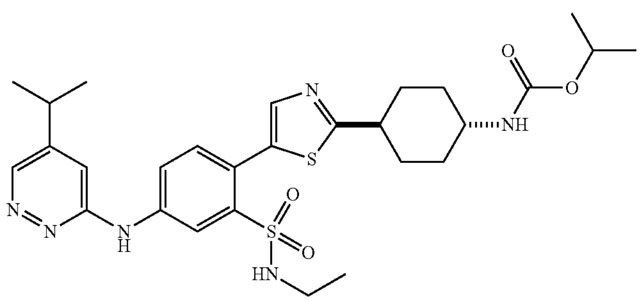 | isopropyl trans-N-[4-[5-[2-(ethylsulfamoyl)-4-[(5-isopropylpyridazin-3-yl)amino]phenyl]thiazol-2-yl]cyclohexyl]carbamate |
| 165 | 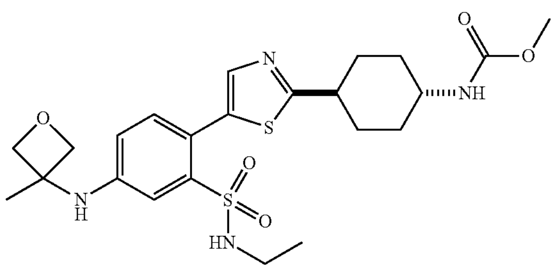 | methyl trans-N-[4-[5-[2-(ethylsulfamoyl)-4-[(3-methyloxetan-3-yl)amino]phenyl]thiazol-2-yl]cyclohexyl]carbamate |
| 166 | 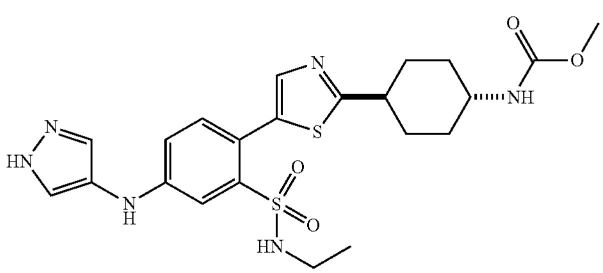 | methyl trans-N-[4-[5-[2-(ethylsulfamoyl)-4-[(1H-pyrazol-4-yl)amino]phenyl]thiazol-2-yl]cyclohexyl]carbamate |

TABLE 1-continued

| Cmpd No. | Structure | Chemical Name |
|---|---|---|
| 167 | 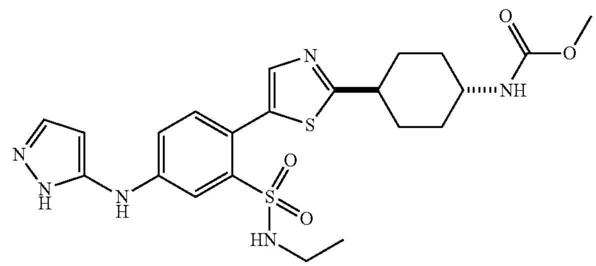 | methyl trans-N-[4-[5-[2-(ethylsulfamoyl)-4-[(1H-pyrazol-5-yl)amino]phenyl]thiazol-2-yl]cyclohexyl]carbamate |
| 168 | 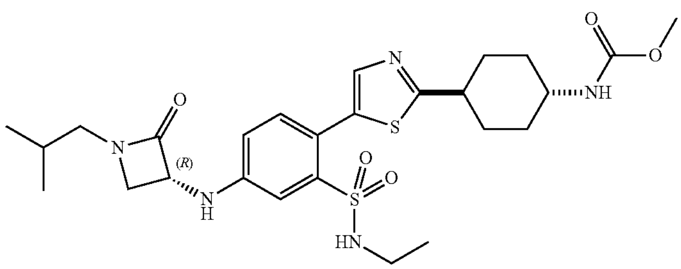 | isopropyl trans-N-[4-[5-[2-(ethylsulfamoyl)-4-[[(3R)-1-isobutyl-2-oxo-azetidin-3-yl]amino]phenyl]thiazol-2-yl]cyclohexyl]carbamate |
| 169 | 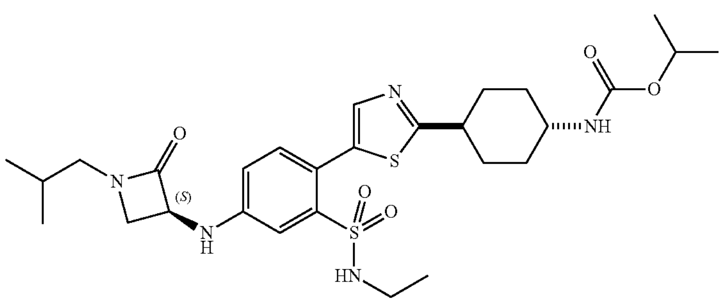 | isopropyl trans-N-[4-[5-[2-(ethylsulfamoyl)-4-[[(3S)-1-isobutyl-2-oxo-azetidin-3-yl]amino]phenyl]thiazol-2-yl]cyclohexyl]carbamate |
| 170 | 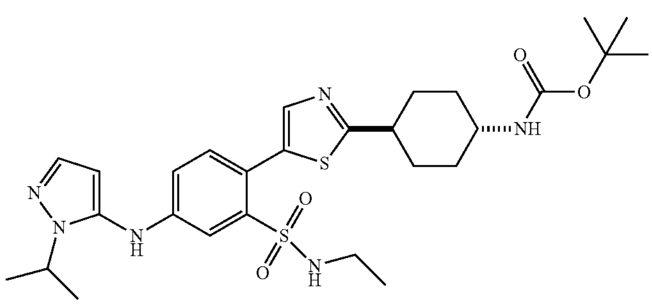 | tert-butyl trans-N-[4-[5-[2-(ethylsulfamoyl)-4-[(2-isopropylpyrazol-3-yl)amino]phenyl]thiazol-2-yl]cyclohexyl]carbamate |
| 171 | 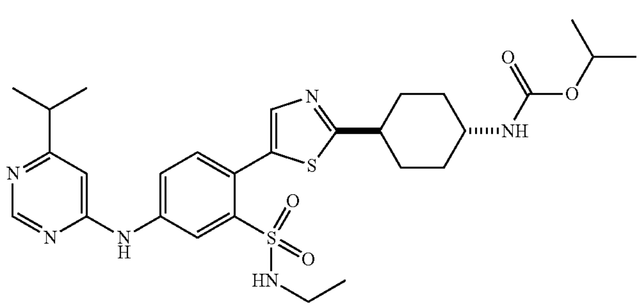 | isopropyl trans-N-[4-[5-[2-(ethylsulfamoyl)-4-[(6-isopropylpyrimidin-4-yl)amino]phenyl]thiazol-2-yl]cyclohexyl]carbamate |

TABLE 1-continued

| Cmpd No. | Structure | Chemical Name |
|---|---|---|
| 172 | 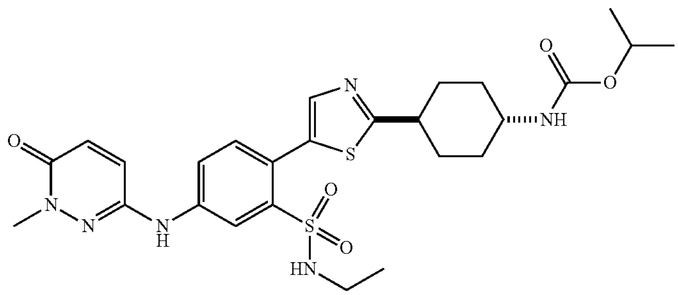 | isopropyl trans-N-[4-[5-[2-(ethylsulfamoyl)-4-[(1-methyl-6-oxo-pyridazin-3-yl)amino]phenyl]thiazol-2-yl]cyclohexyl]carbamate |
| 173 | 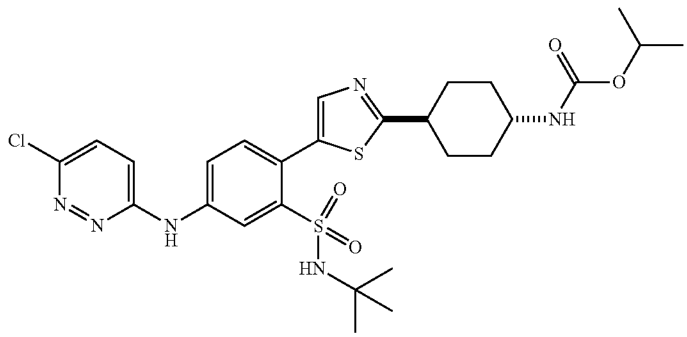 | isopropyl trans-N-[4-[5-[2-(tert-butylsulfamoyl)-4-[(6-chloropyridazin-3-yl)amino]phenyl]thiazol-2-yl]cyclohexyl]carbamate |
| 174 | 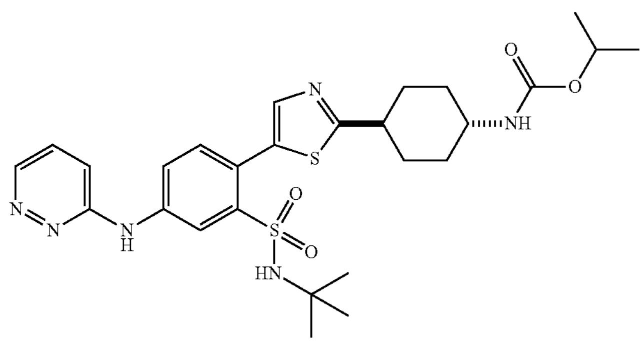 | isopropyl trans-N-[4-[5-[2-(tert-butylsulfamoyl)-4-(pyridazin-3-ylamino)phenyl]thiazol-2-yl]cyclohexyl]carbamate |

In some embodiments, a compound of the present application (e.g., a compound of any of the formulae or any individual compounds disclosed herein) is a pharmaceutically acceptable salt. In another embodiment, a compound of the present application (e.g., a compound of any of the formulae or any individual compounds disclosed herein) is a solvate. In another embodiment, a compound of the present application (e.g., a compound of any of the formulae or any individual compounds disclosed herein) is a hydrate.

The compounds of the present application may form salts which are also within the scope of this application. Reference to a compound of the Formula herein is understood to include reference to salts thereof, unless otherwise indicated.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

"Solvate" means solvent addition forms that contain either stoichiometric or non stoichiometric amounts of solvent. Some compounds or salts have a tendency to trap a fixed molar ratio of solvent molecules in the crystalline solid state, thus forming a solvate. If the solvent is water, the solvate formed is a hydrate; and if the solvent is alcohol, the solvate formed is an alcoholate. Hydrates are formed by the combination of one or more molecules of water with one molecule of the substance in which the water retains its molecular state as $H_2O$.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof.

The term "geometric isomer" refers to cyclic compounds having at least two substituents, wherein the two substituents are both on the same side of the ring (cis) or wherein the substituents are each on opposite sides of the ring (trans). When a disclosed compound is named or depicted by structure without indicating stereochemistry, it is understood that the name or the structure encompasses one or more of the possible stereoisomers, or geometric isomers, or a mixture of the encompassed stereoisomers or geometric isomers. When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geometric isomers in the mixture.

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

In some embodiments of the application, the compounds of the application are diastereomers. In some embodiments, the compounds are the syn diastereomer. In other embodiments, the compounds are the anti diastereomer.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diastereomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

It is also possible that the compounds of the application may exist in different tautomeric forms, and all such forms are embraced within the scope of the application. "Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-imine.

The application also comprehends isotopically-labeled compounds, which are identical to those recited in the each of the formulae described herein, but for the fact that one or more atoms are replaced by an atom having an atomic mass or mass number different from the atomic mass or mass number most commonly found in nature. Examples of isotopes that can be incorporated into compounds of the application include isotopes of hydrogen, carbon, nitrogen, fluorine, such as $^3$H, $^{11}$C, $^{14}$C, $^2$H and $^{18}$F.

Compounds of the application that contain the aforementioned isotopes and/or other isotopes of other atoms are within the scope of the present application. Isotopically-labeled compounds of the present application, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are useful for their ease of preparation and detectability. $^{11}$C and $^{18}$F isotopes are useful in PET (positron emission tomography). PET is useful in brain imaging. Further, substitution with heavier isotopes such as deuterium, i.e., $^2$H, can afford certain therapeutic advantages resulting from greater metabolic stability, for example, increased in vivo half-life or reduced dosage requirements and, hence, may be preferred in some circumstances. Isotopically labeled compounds of the application, can generally be prepared by carrying out the procedures disclosed in the Schemes and/or in the Examples described herein, by substituting a readily available isotopically labeled reagent for a non-isotopically labeled reagent. In some embodiments, the compounds of the application are not isotopically labelled.

Methods for Preparing the Compounds

The compounds of the present application may be made by a variety of methods, including standard chemistry. Suitable synthetic routes are depicted in the Schemes given below.

The compounds of Formula I may be prepared by methods known in the art of organic synthesis as set forth in part by the following synthetic schemes. In the scheme described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, N.Y. 1999). These groups are removed at a convenient stage of the compound synthesis using methods that are readily apparent to those skilled in the art. The selection processes, as well as the reaction conditions and order of their execution, shall be consistent with the preparation of the compounds of the present application.

Those skilled in the art will recognize if a stereocenter exists in the compounds of Formula I. Accordingly, the present application includes both possible stereoisomers (unless specified in the synthesis) and includes not only racemic compound but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-lnterscience, 1994).

The compounds described herein may be made from commercially available starting materials or synthesized using known organic, inorganic, and/or enzymatic processes. The compounds of the present application can be prepared in a number of ways well known to those skilled in the art of organic synthesis. By way of example, the compounds of the present application can be synthesized using the methods described below, together with synthetic methods known in the art of synthetic organic chemistry, or variations thereon as appreciated by those skilled in the art. Preferred methods include but are not limited to those methods described below. The compounds of the present application (i.e., a compound of Formula I) can be synthesized by following the steps outlined in General Schemes and/or General Methods below. Starting materials are either commercially available or made by known procedures in the reported literature or as illustrated.

General Scheme 1: Synthesis of Compounds VII where Cy is connected to the thiazole via a carbon-carbon bond

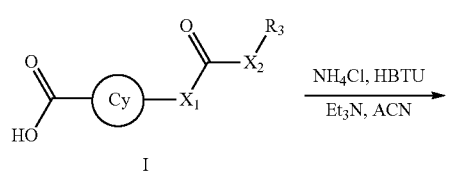

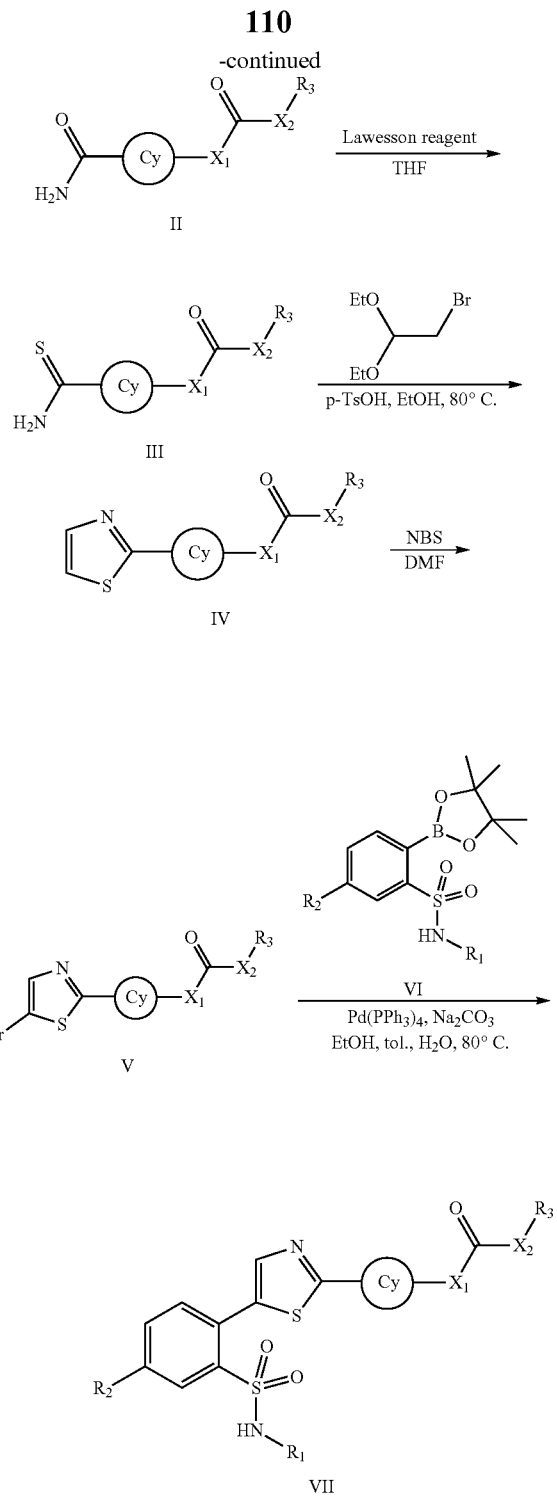

A carboxylic acid I is converted to the amide II using HBTU and ammonium chloride. The resulting amide is reacted with Lawesson's reagent in THF to provide the thioamide III. Cyclization with 2-bromo-1,1-diethoxyethane under acidic conditions gives the thiazole IV which is then brominated using N-bromosuccinimide. The bromothiazole V is then reacted under Suzuki coupling conditions with the boronate VI to give the Rad51 inhibitor VII or an intermediate which is further transformed using conventional chemistry protocols.

General Scheme 2: Synthesis of Compounds XI where Cy is connected to the thiazole via a carbon-nitrogen bond

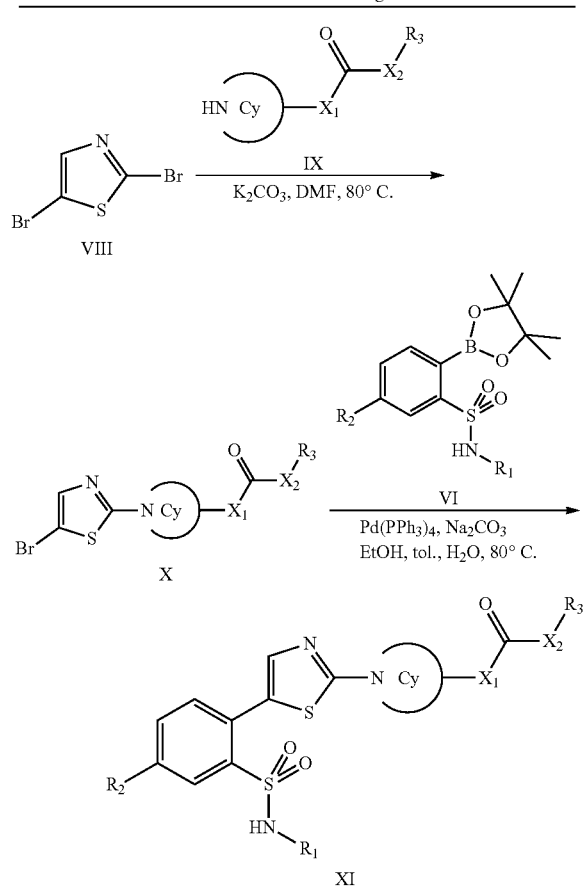

2,5-dibromothiazole (VIII) is reacted with a cycloalkylamine or heterocyclic amine (IX) in DMF to give the bromothiazole X. A Suzuki coupling with the boronate VI provides the Rad51 inhibitor XI or an intermediate which is further transformed using conventional chemistry protocols.

The following General Methods further illustrate the preparation of the compounds of the present application. Although certain reagents/materials and conditions are described in the General Methods, it is understood that equivalent reagents/materials and conditions may also be used.

| General Method | Reaction Name |
| --- | --- |
| A | Amide coupling reaction |
| B | Borate formation |
| C | Suzuki Reaction A |
| D | Suzuki Reaction B |
| E | Deprotection of tert-butylsulfonamide |
| F | Buchwald Reaction |
| G | Sulfamide formation |
| H | Reductive amination |
| I | Deprotection of SEM group |
| J | Hydrolysis reaction |
| K | Substitution Reaction |
| L | Sandmeyer reaction |

General Method A

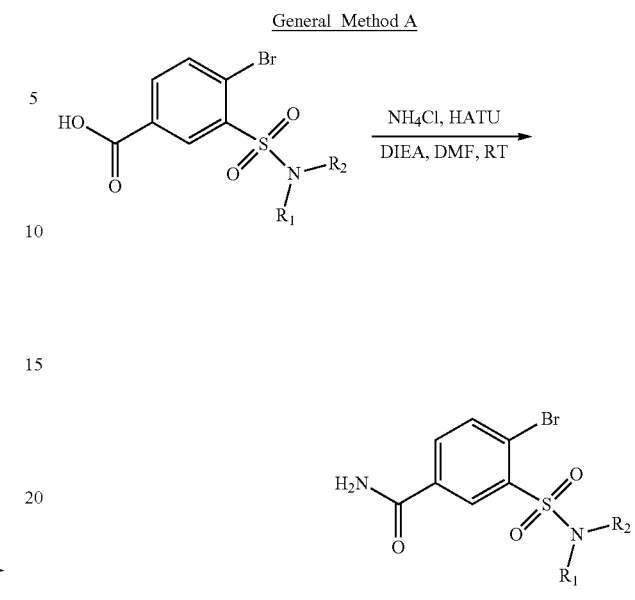

To a solution of carboxylic acid (1.0 eq.) and DIEA (15.0 eq.) in DMF may be added $NH_4Cl$ (10.0 eq.) and HATU (1.3 eq.). The mixture may be stirred at 25° C. for 12 h, then poured into $H_2O$ and extracted with EtOAc (3×). The combined organic layers may be washed with brine, dried over $Na_2SO_4$, filtered, and concentrated to yield the amide product.

General Method B

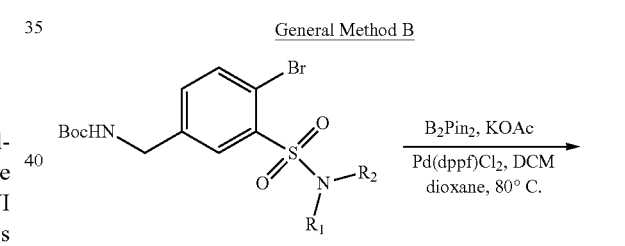

A mixture of Boc-protected amine (1.0 eq.), $B_2Pin_2$ (3.0 eq.), KOAc (3.0 eq.) and $Pd(dppf)Cl_2 \cdot CH_2Cl_2$ (0.1 eq.) in dioxane may be degassed and purged with $N_2$ (3×) and stirred at 80° C. for 12 h. The reaction mixture may be concentrated and the residue may be purified by prep-TLC ($SiO_2$, Petroleum ether/Ethyl acetate=3/1) to yield the borate product.

General Method C

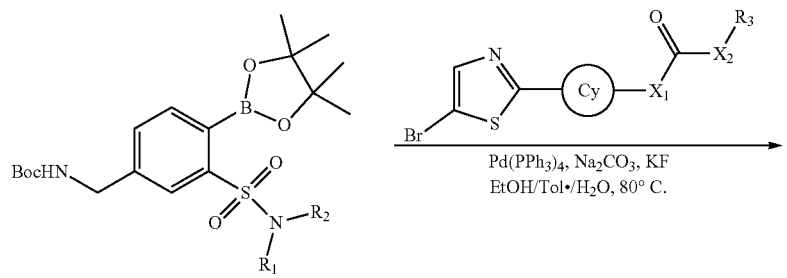

A mixture of borate (1.0 eq.), thiazole (1.2 eq.), Na$_2$CO$_3$ (3.0 eq.), Pd(PPh$_3$)$_4$ (0.1 eq.) and KF (3.0 eq.) in EtOH/H$_2$O/Tol. may be degassed and purged with N$_2$ (3×) and then stirred at 80° C. for 12 h. The reaction mixture may be concentrated and the residue may be purified by prep-TLC (SiO$_2$, Petroleum ether/Ethyl acetate=2/1) to yield the Suzuki Reaction A product.

General Method D

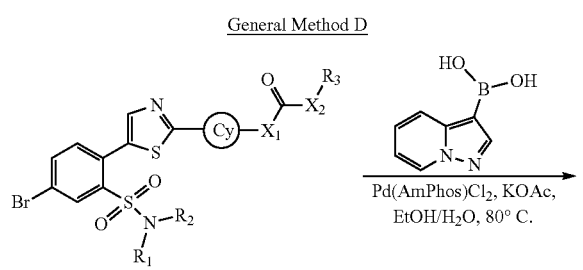

A mixture of brominated thiazole moiety (1.0 eq.), 3-(4,4,5,5-tetramethyl-1,3,2-dioxaborolan-2-yl)pyrazolo[1,5-a]pyridine (1.2 eq.), KOAc (3.0 eq.) and Pd(AmPhos)Cl$_2$ (0.1 eq.) in 1:0.25 EtOH/H$_2$O may be degassed and purged with N$_2$ (3×), and then stirred at 80° C. for 12 h. The reaction mixture may be concentrated and the residue may be purified by prep-HPLC (column: Welch Ultimate AQ-C18 150*30 mm*5 um; mobile phase: [water(0.1% TFA)-ACN]; B %: 50%-80%, 12 min) to yield the Suzuki Reaction B product.

General Method E

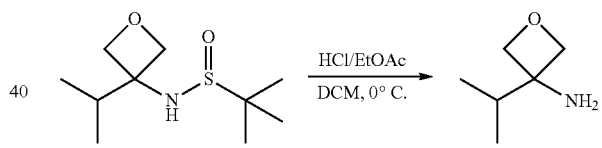

To a solution of N-(3-isopropyloxetan-3-yl)-2-methylpropane-2-sulfinamide (1 eq.) in DCM may be added HCl/EtOAc (4 M, 4.4 eq.). The mixture may be stirred at 0° C. for 5 min, then the reaction mixture may be diluted with MTBE then the solid may be formed. The residue may be concentrated under reduced pressure to remove solvent at 0° C. Then the residue may be triturated with MTBE:Petroleum ether=1:1 and filtered, the filter cake may be collected to yield 3-isopropyloxetan-3-amine which may be used into the next step without further purification.

General Method F

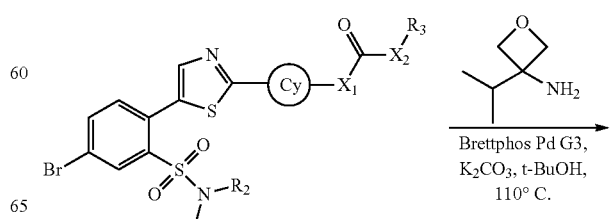

115

-continued

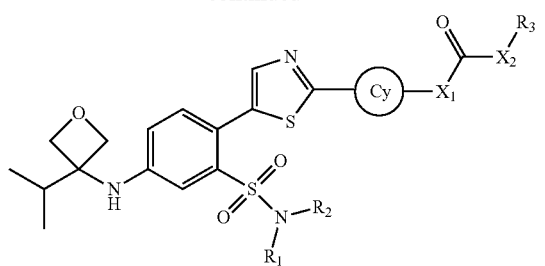

A mixture of 3-isopropyloxetan-3-amine (2 eq.), brominated thiazole moiety (1 eq.), K₂CO₃ (3 eq.) and BrettPhos Pd G3 (0.1 eq.) in t-BuOH may be stirred at 110° C. for 12 h under Ar atmosphere. The reaction mixture may be concentrated under reduced pressure, then the residue may be purified by prep-TLC (SiO₂, petroleum ether:ethyl acetate=2:1) and purified by prep-HPLC (column: YMC-Actus Triart C18 100*30 mm*5 um; mobile phase: [water (0.1% TFA)-ACN]; B %: 25%-60%, 10 min) to yield the Buchwald Reaction product.

General Method G

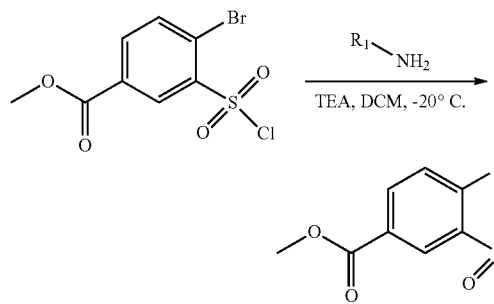

To a solution of TEA (3 eq.) in DCM may be added alkylamine (1.1 eq.) at −20° C. Then the methyl 4-bromo-3-chlorosulfonyl-benzoate (1.0 eq.) may be added batchwise. The mixture may be stirred at −20° C. for 5 min, then the reaction mixture may be quenched with HCl (1M, pH=2) and extracted with DCM, the organic layers may be dried over Na₂SO₄, filtered and concentrated under reduced pressure to yield the sulfamide formation product.

General Method H

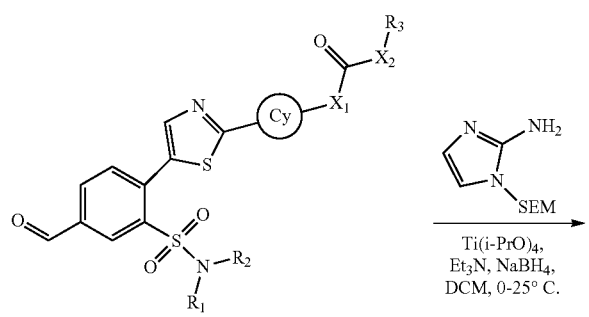

116

-continued

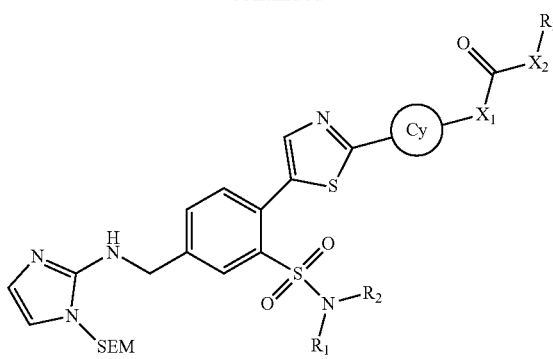

To a mixture of 1-(2-trimethylsilylethoxymethyl)imidazol-2-amine (1.5 eq.) and formyl-phenyl-thiazol moiety (1 eq.) in DCM may be added Ti(i-PrO)₄ (2 eq.) and Et₃N (0.1 eq.), then the mixture may be stirred at 25° C. for 16 h under N₂ atmosphere. The mixture may be added NaBH₄ (1.5 eq.) at 0° C., and stirred at 25° C. for 2 h. The reaction mixture may be quenched with H₂O at 25° C. and concentrated under reduced pressure. The residue may be purified by prep-TLC (SiO₂, petroleum ether:ethyl acetate=0:1) to yield the reductive amination product.

General Method I

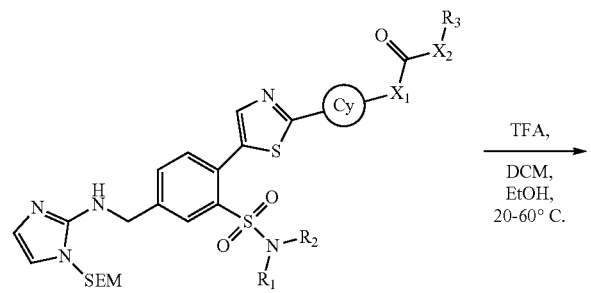

A mixture of SEM protected conjugated imidazole (1 eq.) in TFA and DCM may be stirred at 20° C. for 1 h. The reaction mixture may be concentrated under reduced pressure to remove DCM at 25° C. The residue may be diluted with EtOH and stirred at 60° C. for 3 h. The mixture may be concentrated under reduced pressure. The residue may be purified by prep-HPLC (TFA condition). (column: Welch Ultimate AQ-C18 150*30 mm*5 um; mobile phase: [water (0.1% TFA)-ACN]; B %: 18%-48%, 12 min) to yield the deprotection of SEM group product.

General Method J

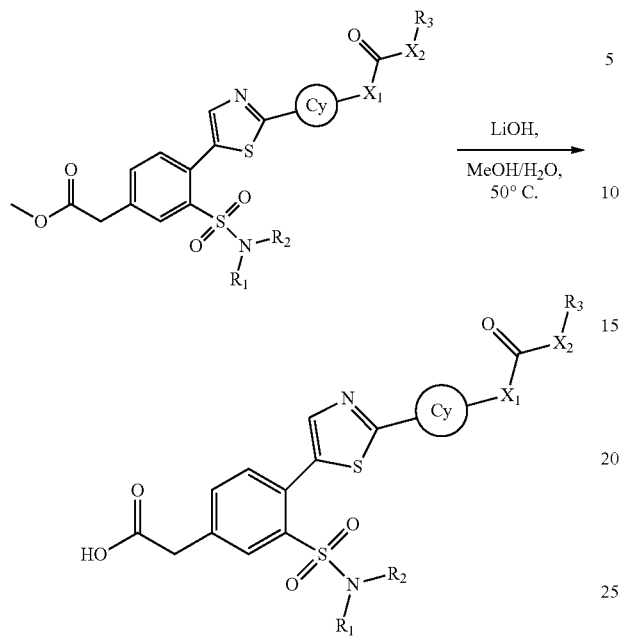

To a solution of ester (1 eq.) in 2:1 MeOH:H$_2$O, may be added LiOH (3 eq.). The mixture may be stirred at 50° C. for 2 h. The mixture may be concentrated under reduced pressure. The residue may be adjusted pH=2 with HCl (6M) and extracted with EtOAc (2×). The combined organic layers may be dried over Na$_2$SO$_4$, filtered and concentrated under reduced pressure to yield the hydrolysis reaction product.

General Method K

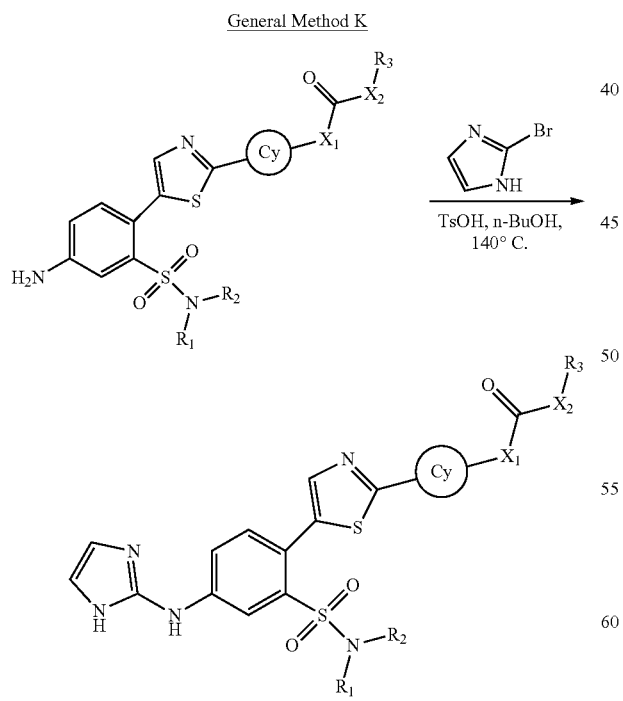

To a solution of amine (1 eq.) in n-BuOH may be added TsOH (3 eq.) and 2-bromo-1H-imidazole (5 eq.). The mixture may be stirred at 140° C. for 12 h. The reaction mixture may be concentrated under reduced pressure and purified by prep-HPLC (column: Waters Xbridge BEH C18 100*30 mm*10 um; mobile phase: [water(0.1% TFA)-ACN]; B %: 30%-90%, 10 min) to yield the substitution reaction product.

General Method L

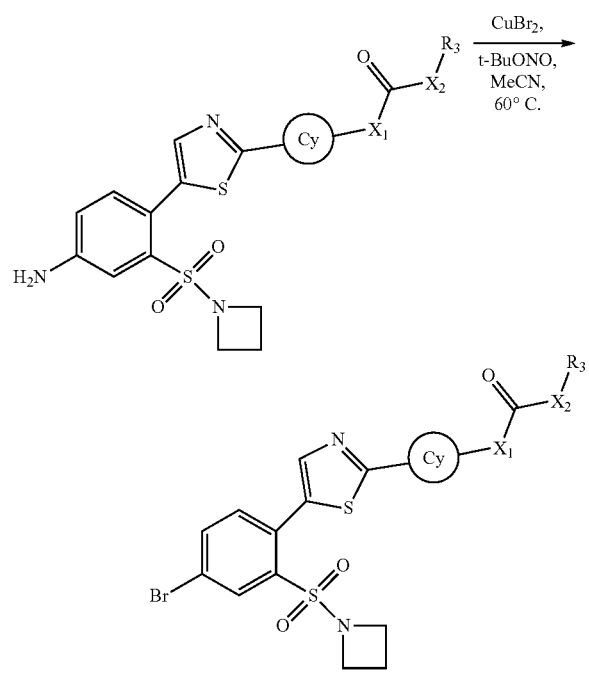

To a solution of amine (1 eq.) in MeCN may be added CuBr$_2$ (0.4 eq.) and tert-butyl nitrite (1.5 eq.). The mixture may be stirred at 60° C. for 1 h and concentrated. The residue may be diluted with H$_2$O and extracted with EtOAc (3×). The combined organic layers may be dried over Na$_2$SO$_4$, filtered and concentrated under reduced pressure to give a residue. The residue may be purified by prep-TLC (SiO$_2$, petroleum ether:ethyl acetate=1:2) to yield the Sandmeyer reaction product.

Definitions

The articles "a" and "an" are used in this application to refer to one or more than one (i.e., at least one) of the grammatical object of the article. By way of example, "an element" means one element or more than one element.

The term "and/or" is used in this application to mean either "and" or "or" unless indicated otherwise.

The term "halo" or "halogen" as used herein includes fluoro, chloro, bromo, and iodo.

The term "alkyl," as used herein, refers to saturated, straight or branched-chain hydrocarbon radicals containing, In some embodiments, between one and six carbon atoms. Examples of C$_1$-C$_8$ alkyl radicals include, but are not limited to, methyl, ethyl, propyl, isopropyl, n-butyl, tert-butyl, neopentyl, n-hexyl, n-heptyl, and n-octyl radicals. Examples of C$_1$-C$_6$ alkyl radicals include, but are not limited to, methyl, ethyl, propyl, isopropyl, n-butyl, tert-butyl, neopentyl, and n-hexyl radicals.

The term "alkoxy" means an alkyl radical attached through an oxygen linking atom, represented by —O-alkyl. For example, "(C$_1$-C$_4$) alkoxy" includes methoxy, ethoxy, propoxy, and butoxy.

The terms "haloalkyl" and "haloalkoxy" means alkyl or alkoxy, as the case may be, substituted with one or more halogen atoms.

An "alkylene group" is a saturated aliphatic branched or straight-chain divalent hydrocarbon radical. Unless otherwise specified, an alkylene group typically has 1-6 carbon atoms, e.g., ($C_1$-$C_6$) alkylene.

The term "cycloalkyl" means a monocyclic saturated hydrocarbon ring system. For example, $C_3$-$C_7$ cycloalkyl includes cyclopropyl, cyclobutyl, cyclopentyl, and cyclohexyl, cycloheptyl.

A bridged cycloalkyl means a bicyclic hydrocarbon ring system in which the two rings share at least three adjacent ring carbon atoms. For example, a bridged cycloalkyl has 6-12 ring carbon atoms. Examples include, but are not limited to, bicyclo[2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, bomenyl, norbomyl, norbomenyl, 6,6-dimethylbicyclo[3.1.1]heptyl, and adamantyl.

The terms "heterocyclyl", "heterocyclic ring", and "heterocyclic group", are used interchangeably herein, and means saturated or unsaturated non-aromatic 4-10 membered ring radical containing from 1 to 4 ring heteroatoms, which may be the same or different, selected from N, O, or S. It can be monocyclic, bicyclic or tricyclic (e.g., a fused or bridged bicyclic or tricyclic ring). Examples of include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl. A heterocyclic ring optionally contains one or more double bonds and/or is optionally fused with one or more aromatic rings (for example, tetrahydronaphthyridine, indolinone, dihydropyrrolotriazole, imidazopyrimidine, quinolinone, dioxaspirodecane). Examples of 3-7 membered monocyclic heterocyclic ring include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl.

A bridged heterocyclyl means a bicyclic ring system containing from 1 to 4 ring heteroatoms in which the two rings share at least three adjacent ring atoms. For example, a bridged heterocyclyl has 6-12 ring atoms. Examples include, but are not limited to, azanorbornyl, quinuclidinyl, isoquinuclidinyl, tropanyl, azabicyclo[3.2.1]octanyl, azabicyclo[2.2.1]heptanyl, 2-azabicyclo[3.2.1]octanyl, azabicyclo[3.2.1]octanyl, azabicyclo[3.2.2]nonanyl, azabicyclo[3.3.0]nonanyl, and azabicyclo [3.3.1]nonanyl.

The terms "heteroaryl", "heteroaromatic", "heteroaryl ring", "heteroaryl group", "heteroaromatic ring", and "heteroaromatic group", are used interchangeably herein. "Heteroaryl", when used alone or as part of a larger moiety as in "heteroaralkyl" or "heteroarylalkoxy", refers to aromatic ring groups having five to ten ring atoms selected from carbon and at least one (typically 1 to 4, more typically 1 or 2) heteroatoms (e.g., oxygen, nitrogen, or sulfur). "Heteroaryl" includes monocyclic rings and polycyclic rings in which a monocyclic heteroaromatic ring is fused to one or more other aromatic or heteroaromatic rings. "Heteroaryl" includes monocyclic and bicyclic ring systems.

"Monocyclic 5-6 membered heteroaromatic ring (or heteroaryl)" means a monocyclic heteroaromatic ring having five or six ring atoms selected from carbon and at least one (typically 1 to 3, more typically 1 or 2) heteroatoms (e.g., oxygen, nitrogen, or sulfur). Examples of monocyclic 5-6 membered heteroaromatic ring groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl).

If a group is described as being "substituted," a non-hydrogen substituent replaces a hydrogen atom on a carbon or nitrogen. Thus, for example, a substituted alkyl is an alkyl wherein at least one non-hydrogen substituent is in the place of a hydrogen atom on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent can be identical or different (unless otherwise stated). As used herein, many moieties (e.g., alkyl, cycloalkyl, or a heterocyclic ring) are referred to as being either "substituted" or "optionally substituted". It will be appreciated that the phrase "optionally substituted" is used interchangeably with the phrase "substituted or unsubstituted." When a moiety is modified by one of these terms, unless otherwise noted, it denotes that any portion of the moiety that is known to one skilled in the art as being available for substitution can be substituted, which includes one or more substituents. If more than one substituent is present, then each substituent is independently selected. Such means for substitution are well-known in the art and/or taught by the instant application. The optional substituents can be any substituents that are suitable to attach to the moiety. A person of ordinary skill in the art will recognize that the compounds and definitions provided do not include impermissible substituent patterns (e.g., methyl substituted with 5 different groups, and the like). Such impermissible substitution patterns are clearly recognized by a person of ordinary skill in the art. When a group is described as being optionally substituted by "one or more" substituents, it denotes that the group is optionally substituted by one, two, three, four, five or six substituents. In some embodiments, a group is optionally substituted by 1-3 substituents. In some embodiments, a group is optionally substituted by 1-2 substituents. In some embodiments, a group is optionally substituted by one substituent.

Suitable substituents are those which do not have a significant adverse effect on the ability of the compound to inhibit RAD51. Where suitable substituents are not specifically enumerated, exemplary substituents include, but are not limited to, halo, CN, alkyl, alkoxy, halomethyl, halomethoxy, ($C_1$-$C_5$)alkyl, halo($C_1$-$C_5$)alkyl, ($C_1$-$C_5$) alkoxy, $NO_2$, $OR^{c'}$, $NR^{a'}R^{b'}$, $S(O)_iR^{a'}$, $NR^{a'}S(O)_iR^{b'}$, $S(O)_iNR^{a'}R^{b'}$, $C(=O)OR^{a'}$, $OC(=O)OR^{a'}$, $C(=S)OR^{a'}$, $O(C=S)R^{a'}$, $C(=O)NR^{a'}R^{b'}$, $NR^{a'}C(=O)R^{b'}$, $C(=S)$ NR$^{a'}$R$^{b'}$, NR$^{a'}$C(=S)R$^{b'}$, NR$^{a'}$(C=O)OR$^{b'}$, O(C=O)NR$^{a'}$R$^{b'}$, NR$^{a'}$(C=S)OR$^{b'}$, O(C=S)NR$^{a'}$R$^{b'}$, NR$^{a'}$(C=O)NR$^{a'}$R$^{b'}$, NR$^{a'}$(C=S)NR$^{a'}$R$^{b'}$, C(=S)R$^{a'}$, C(=O)R$^{a'}$, (C$_3$-C$_6$) cycloalkyl, monocyclic heteroaryl, and phenyl, wherein the (C$_3$-C$_6$) cycloalkyl, monocyclic heteroaryl, and phenyl substituents are optionally and independently substituted, for example, with CH$_3$, halomethyl, halo, methoxy, or halomethoxy. Each R$^{a'}$ and each R$^{b'}$ are independently H or (C$_1$-C$_6$) alkyl, wherein the (C$_1$-C$_6$) alkyl group represented by R$^{a'}$ or R$^{b'}$ is optionally substituted, for example, with hydroxyl or (C$_1$-C$_3$) alkoxy; R$^{c'}$ is H, halo(C$_1$-C$_6$) alkyl, or (C$_1$-C$_6$) alkyl, wherein the (C$_1$-C$_6$) alkyl group represented by R$^c$ is optionally substituted, for example with hydroxyl or (C$_1$-C$_3$) alkoxy; and i is 0, 1, or 2. =O is also a suitable substituent for alkyl, cycloalkyl, and a heterocyclic ring.

Suitable substituents may also include: —F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, NHC(O)NH-heterocycloalkyl, —NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NHheterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, C(NH)NH—C$_3$-C$_{12}$-cycloalkyl, —C(NH)NH-aryl, —C(NH)NH-heteroaryl, —C(NH)NHheterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" or "therapeutically effective amount" when used in connection with a compound or pharmaceutical composition is an amount effective for treating or preventing a disease in a subject as described herein.

The term "treating" with regard to a subject, refers to improving at least one symptom of the subject's disorder. Treating includes curing, improving, or at least partially ameliorating the disorder.

The compounds of the present application, or a pharmaceutically acceptable salt or solvate thereof, can also be used to prevent a disease, condition or disorder. As used herein, "preventing" or "prevent" describes reducing or eliminating the onset of the symptoms or complications of the disease, condition or disorder.

The term "disorder" is used in this application to mean, and is used interchangeably with, the terms disease, condition, or illness, unless otherwise indicated.

As used herein, the term diseases or disorders in which RAD51 plays a role means any disease or other deleterious condition in which RAD51 is known to play a role. Accordingly, another embodiment of the present application relates to treating or lessening the severity of one or more diseases in which RAD51 is known to play a role.

Pharmaceutical Compositions

The compounds disclosed therein are RAD51 inhibitors. The pharmaceutical composition of the present application comprises one or more RAD51 inhibitors, or a pharmaceutically acceptable salt or solvate thereof, and a pharmaceutically acceptable carrier or diluent.

A "pharmaceutical composition" is a formulation containing the compound of the present application in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or a pharmaceutically acceptable salt or solvate thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In some embodiments, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable carrier" and "pharmaceutically acceptable diluent" refer to a substance that aids the formulation and/or administration of an active agent to and/or absorption by a subject and can be included in the compositions of the present application without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The term "carrier", as used in this application, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-$20^{th}$ edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Pharmaceutical compositions of the application are formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the application can be administered to a subject in many of the well-known methods currently used for chemotherapeutic treatment. For example, for treatment of cancers, a compound of the application may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compound (i.e., a compound of Formula (I)) of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compound into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compound is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound is formulated into ointments, salves, gels, or creams as generally known in the art.

The active compound can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by and directly dependent on the unique characteristics of the active compound and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. An effective amount of a pharmaceutical agent is that which provides an objectively identifiable improvement as noted by the clinician or other qualified observer. For example, regression of a tumor in a subject may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The dosage regimen utilizing the compound is selected in accordance with a variety of factors including type, species, age, weight, sex and medical condition of the patient; the severity of the condition to be treated; the route of administration; the renal and hepatic function of the patient; and the particular compound or pharmaceutically acceptable salt or solvate thereof employed. An ordinarily skilled physician or veterinarian can readily determine and prescribe the effective amount of the drug required to prevent, counter or arrest the progress of the condition.

Techniques for formulation and administration of the disclosed compound of the application can be found in *Remington: the Science and Practice of Pharmacy*, 19$^{th}$ edition, Mack Publishing Co., Easton, Pa. (1995). In an embodiment, the compound described herein, and the pharmaceutically acceptable salts or solvates thereof, are used in pharmaceutical preparations in combination with a pharmaceutically acceptable carrier or diluent. Suitable pharmaceutically acceptable carriers include inert solid fillers or diluents and sterile aqueous or organic solutions. The compound or pharmaceutically acceptable salts or solvates thereof will be present in such pharmaceutical compositions in amounts sufficient to provide the desired dosage amount in the range described herein.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present application the skilled artisan can identify and employ other components and methodology useful for practicing the present application.

Methods of Using the Compounds

The present application provides a method of treating a subject with a disease or disorder which can be ameliorated by inhibition of RAD51, by administering to the subject an effective amount of one or more disclosed compounds, or a pharmaceutically acceptable salt or solvate thereof, or the corresponding pharmaceutical composition. Diseases which can be ameliorated by inhibition of RAD51 include treating cancer, autoimmune disease, immune deficiency, or neurodegenerative disease.

The present application further relates to a method of treating a disease or disorder in which RAD51 plays a role, for example, cancer, an autoimmune disease, an immune deficiency, or a neurodegenerative disease. The method comprises administering to a subject in need thereof an effective amount of a compound disclosed herein or a pharmaceutically acceptable salt or solvate thereof or a pharmaceutical composition disclosed herein.

In one aspect, described herein is a method of treating cancer, autoimmune disease, immune deficiency, or neurodegenerative disease, the method comprising administering a therapeutically effective dose of a composition as described herein, e.g., a composition comprising a compound of the present application, to a subject in need of treatment for cancer, autoimmune disease, immune deficiency, or neurodegenerative disease.

In some embodiments, described herein is a method of treating cancer comprising administering a therapeutically effective dose of a composition as described herein, e.g., a composition comprising a compound of the present application, to a subject in need of treatment for cancer.

In some embodiments, described herein is a method of treating autoimmune disease comprising administering a therapeutically effective dose of a composition as described herein, e.g., a composition comprising a compound of the present application, to a subject in need of treatment for autoimmune disease.

In some embodiments, described herein is a method of treating immune deficiency comprising administering a therapeutically effective dose of a composition as described herein, e.g., a composition comprising a compound of the present application, to a subject in need of treatment for immune deficiency.

In some embodiments, described herein is a method of treating neurodegenerative disease comprising administering a therapeutically effective dose of a composition as described herein, e.g., a composition comprising a compound of the present application, to a subject in need of treatment for neurodegenerative disease.

The present application further relates to use of a compound disclosed herein, or a pharmaceutically acceptable salt or solvate thereof, or a pharmaceutical composition disclosed herein, in the manufacture of a medicament for the treatment of a disease or disorder in which RAD51 plays a role, for example, a cancer, an autoimmune disease, an immune deficiency, or a neurodegenerative disease.

The present application provides use of a compound disclosed herein, or a pharmaceutically acceptable salt or solvate thereof, or a pharmaceutical composition disclosed herein, in the manufacture of a medicament for the treatment of a disease or disorder which can be ameliorated by inhibition of RAD51.

In one aspect, described herein is use of a compound disclosed herein, or a pharmaceutically acceptable salt or solvate thereof, or a pharmaceutical composition disclosed herein, in the manufacture of a medicament for the treatment of a cancer, autoimmune disease, immune deficiency, or neurodegenerative disease.

In one aspect, described herein is use of a compound disclosed herein, or a pharmaceutically acceptable salt or solvate thereof, or a pharmaceutical composition disclosed herein, in the manufacture of a medicament for the treatment of a cancer.

In one aspect, described herein is use of a compound disclosed herein, or a pharmaceutically acceptable salt or solvate thereof, or a pharmaceutical composition disclosed herein, in the manufacture of a medicament for the treatment of an autoimmune disease.

In one aspect, described herein is use of a compound disclosed herein, or a pharmaceutically acceptable salt or solvate thereof, or a pharmaceutical composition disclosed herein, in the manufacture of a medicament for the treatment of an immune deficiency.

In one aspect, described herein is use of a compound disclosed herein, or a pharmaceutically acceptable salt or solvate thereof, or a pharmaceutical composition disclosed herein, in the manufacture of a medicament for the treatment of a neurodegenerative disease.

The present application further relates to a compound disclosed herein, or a pharmaceutically acceptable salt or solvate thereof, or a pharmaceutical composition disclosed herein, for use in treating a disease or disorder in which RAD51 plays a role, for example, a cancer, an autoimmune disease, an immune deficiency, or a neurodegenerative disease.

The present application provides a compound disclosed herein, or a pharmaceutically acceptable salt or solvate thereof, or a pharmaceutical composition disclosed herein, for use in treating a disease or disorder which can be ameliorated by inhibition of RAD51.

In one aspect, described herein is a compound disclosed herein, or a pharmaceutically acceptable salt or solvate thereof, or a pharmaceutical composition disclosed herein, for use in treating a cancer, autoimmune disease, immune deficiency, or neurodegenerative disease.

In one aspect, described herein is a compound disclosed herein, or a pharmaceutically acceptable salt or solvate thereof, or a pharmaceutical composition disclosed herein, for use in treating a cancer.

In one aspect, described herein is a compound disclosed herein, or a pharmaceutically acceptable salt or solvate thereof, or a pharmaceutical composition disclosed herein, for use in treating an autoimmune disease.

In one aspect, described herein is a compound disclosed herein, or a pharmaceutically acceptable salt or solvate thereof, or a pharmaceutical composition disclosed herein, for use in treating an immune deficiency.

In one aspect, described herein is a compound disclosed herein, or a pharmaceutically acceptable salt or solvate thereof, or a pharmaceutical composition disclosed herein, for use in treating a neurodegenerative disease.

The present application further relates to use of a compound disclosed herein, or a pharmaceutically acceptable salt or solvate thereof, or a pharmaceutical composition disclosed herein, in treating a disease or disorder in which RAD51 plays a role, for example, a cancer, an autoimmune disease, an immune deficiency, or a neurodegenerative disease.

The present application provides use of a compound disclosed herein, or a pharmaceutically acceptable salt or solvate thereof, or a pharmaceutical composition disclosed herein, in treating a disease or disorder which can be ameliorated by inhibition of RAD51.

In one aspect, described herein is use of a compound disclosed herein, or a pharmaceutically acceptable salt or solvate thereof, or a pharmaceutical composition disclosed herein, in treating a cancer, autoimmune disease, immune deficiency, or neurodegenerative disease.

In one aspect, described herein is use of a compound disclosed herein, or a pharmaceutically acceptable salt or solvate thereof, or a pharmaceutical composition disclosed herein, in treating a cancer.

In one aspect, described herein is use of a compound disclosed herein, or a pharmaceutically acceptable salt or solvate thereof, or a pharmaceutical composition disclosed herein, in treating an autoimmune disease.

In one aspect, described herein is use of a compound disclosed herein, or a pharmaceutically acceptable salt or solvate thereof, or a pharmaceutical composition disclosed herein, in treating an immune deficiency.

In one aspect, described herein is use of a compound disclosed herein, or a pharmaceutically acceptable salt or solvate thereof, or a pharmaceutical composition disclosed herein, in treating a neurodegenerative disease.

In some embodiments, the subject can be a subject determined to have an increased level of DNA damage occurring in one or more cell types relative to a reference level. As used herein, "DNA damage" refers to breaks, nicks, and mutations of the DNA present in a cell. In some embodiments, the DNA damage can comprise one or more of single-strand breaks (e.g., "nicks"), double strand breaks (DSBs), and mutations. In some embodiments, the DNA damage can be one or more DSBs. As used herein, "mutation" refers to a change or difference in the genetic material of a cell as compared to a reference wildtype cell, e.g., a deletion, an insertion, a SNP, a gene rearrangement, and/or the introduction of an exogenous gene or sequence.

In some embodiments, the subject can be determined to have an increased level of DNA damage if the subject is determined to have an increased level and/or activity of a DNA damage process or DNA editing enzyme. As used herein, "DNA damage process" refers to any activity or process in a cell which causes one or more types of DNA damage to occur.

In some embodiments, an increased level of DNA damage can be an increased level of mutations, e.g., by determining the overall mutation status in all or a portion of the genome of a cell. An overall mutation status at least 2% greater, e.g., 2% greater or more, 3% greater or more, 5% greater or more, 10% greater or more, or 20% greater or more than the overall mutation status in a reference cell can be indicative of an increased, elevated, and/or significant level of a DNA editing enzyme activity. In some embodiments, the level of hyper mutations can be determined. In some embodiments, the overall mutation status in the whole genome or a portion thereof can be determined using FISH, whole genome sequencing, high throughput sequencing, exome sequencing, hybridization, and/or PCR. In some embodiments the activity of a DNA editing enzyme can be measured by determining the level of hypermutations in the specific target genes including, but not limited to IGH, BCL6, MYC, BCL1 1A, CD93, PIM1 and/or PAX5. In some embodiments the DNA editing enzyme is AID. In some embodiments, a level of mutation in specific target genes including IGH, BCL6, MYC, BCL1 1A, CD93, PIM1 and/or PAX5 which is at least 2% greater, e.g., 2% greater or more, 3% greater or more, 5% greater or more, 10% greater or more, or 20% greater or more than the level of mutation in IGH, BCL6, MYC, BCL1 1A, CD93, PIM1 and/or PAX5 in a reference cell can be indicative of an increased, elevated, and/or significant level of AID activity.

In some embodiments, an increased level of DNA damage can be an increased level of double strand breaks (DSBs). The level of DSBs can be determined, by way of non-limiting example, by karyotyping, by γ-H2AX foci formation, and/or by using FISH analysis to detect DNA double strand breaks, e.g., DNA breakage detection fish (DBD-FISH) (Volpi and Bridger, BioTechniques, Vol. 45, No. 4, October 2008, pp. 385-409).

In some embodiments, an increased level of DNA damage can be an increased level of single strand breaks. The level of single-strand breaks in DNA can be determined, by way of non-limiting example, by COMET assays, FISH, or the use of single-strand break-specific probes. Detection of DNA breaks, both single and double-stranded is known in the art and described further, at, e.g., Kumari et al., EXCLI Journal 2009 7:44-62 and Motalleb et al., Research Journal of Applied Sciences, Engineering and Technology 2012 4: 1888-1894; each of which is incorporated by reference herein in its entirety.

In some embodiments, an increased level of activity of a DNA damage process can comprise an increased level and/or activity of a DNA editing enzyme. In some embodiments, the technology described herein is directed to treating cells having an active DNA editing enzyme with a compound of the present application. In some embodiments, the technology described herein is directed to treating cells having an increased level and/or activity of a DNA editing enzyme with a compound of the present application. As used herein, "DNA editing enzyme" refers to an enzyme which normally catalyzes the mutation, exchange or excision of DNA segments, particularly enzymes which can generate or promote the generation of point mutations, DNA single strand breaks, DNA double-strand breaks or protein-DNA adducts. A DNA editing enzyme, as referred to herein, is not necessarily site-specific in its action. Similarly, it is not necessarily cell specific. In some embodiments, the cell is a B cell expressing a detectable amount of such an enzyme.

Non-limiting examples of DNA editing enzymes include, but are not limited to Recombination Activating Gene 1 (RAG1; NCBI Gene ID: 5896), Recombination Activating Gene 1 (RAG2; NCBI Gene ID: 5897), Sporulation-specific protein 11 (SPO1 1; NCBI Gene ID: 23626), APOBEC family members a Type 1 Topoisomerase; a Type 2 Topoisomerase; and/or AID. In some embodiments, the DNA editing enzyme can be AID.

In some embodiments, the DNA editing enzyme can be a member of the APOBEC (apolipoprotein B mRNA editing enzyme, catalytic polypeptide-like) family. As used herein "APOBEC family" refers to a family of cytidine deaminase enzymes having an N-terminal zinc-dependent cytidine deaminase catalytic domain comprising and a C-terminal pseudocatalytic domain. Non-limiting examples of APOBEC family members include AID, APOBEC 1 (e.g., NCBI Gene ID: 339), APOBEC2 (e.g., NCBI Gene ID: 10930), APOBEC3A (e.g., NCBI Gene ID: 200315), APOBEC3B (e.g., NCBI Gene ID: 9582), APOBEC3C (e.g., NCBI Gene ID: 27350), APOBEC3E (e.g., NCBI Gene ID: 140564), APOBEC3F (e.g., NCBI Gene ID:200316), APOBEC3G (e.g., NCBI Gene ID: 60489), APOBEC3H (e.g., NCBI Gene ID: 164668), and APOBEC4 (e.g., NCBI Gene ID: 403314).

In some embodiments, the DNA editing enzyme can be a Type 1 topoisomerase. In some embodiments, the DNA editing enzyme can be a Type 2 topoisomerase. Topoisomerases generate breaks in DNA to help uncoil or relax the strand. Type II topoisomerases hydrolyze ATP to generate DSB cuts, while Type I topoisomerases generate single-stranded breaks. Non-limiting examples of Type II topoisomerases can include topoisomerase II (e.g., NCBI Gene ID: 7153 and 7155). Non-limiting examples of Type I topoisomerases can include topoisomerase I (e.g., NCBI Gene ID: 7150).

Embodiments of the technology described herein are based on the discovery that the compounds described herein can inhibit DNA repair mechanisms, e.g., homologous recombination repair. Activation-induced cytidine deaminase (AID, or AICDA, also known as ARP2, CDA2 or HIGM2), a DNA-editing enzyme that is a member of the apolipoprotein B mRNA editing enzymes, catalytic polypeptide-like (APOBEC), will cause widespread genomic breaks and cell death in cells with diminished homologous recombination ability (e.g., cells with diminished DNA double strand break repair abilities). Accordingly, provided herein is a method of causing cell death comprising detecting increased expression of a DNA-editing enzyme (e.g., AID) in a cell and thereafter contacting the cell with a compound of the present application; thereby resulting in cell death. Accordingly, provided herein is a method of causing cell death comprising increasing expression of a DNA-editing enzyme (e.g., AID) in a cell and thereafter contacting the cell with a compound of the present application; thereby resulting in cell death. Accordingly, provided herein is a method of causing cell death comprising administering to a cell a therapeutically effective amount of a DNA editing enzyme (e.g., AID) and thereafter contacting the cell with a compound of the present application; thereby resulting in cell death.

AID, encoded by the AICDA gene (NCBI Gene ID: 57379), is required for proper B-cell function and is most prominently expressed in centroblast B-cells. The protein is involved in somatic hypermutation, gene conversion, and class-switch recombination of immunoglobulin genes. AID is normally expressed almost exclusively in antigen-activated germinal center B-cells, where it initiates immunoglobulin isotype class switching (Manis et al., 2002, Trends Immunol, 23, 31-39; Chaudhuri and Alt, Nat Rev Immunol, 2004, 4, 541-552; Longerich et al., Curr Opin Immunol, 2006, 18, 164-174; Chaudhuri et al., Adv Immunol 2007, 94, 157-214). AID is required for somatic hypermutation and immunoglobulin class switching in activated B cells. AID expression is regulated by CD40 ligand, B-cell receptor, IL4R, or Toll-like receptor stimulation (Crouch et al., J Exp Med 2007 204: 1145-1156; Muramatsu et al., J Biol Chem 1999 274: 18470-6). After activation, AID is transiently upregulated, induces point mutations or DNA double strand breaks in a sequence nonspecific manner within immunoglobulin genes, and is then downregulated (Longerich et al., Curr Opin Immunol, 2006, 18, 164-176; Chaudhuri et al., Adv Immunol 2007, 94, 157-214). Overall, AID is active in only a tiny population of normal cells (antigen-activated B-cells) at any given time. The genomic rearrangements and mutations controlled by AID lead to the development of antigen-recognition diversity, receptor editing and lymphoid effector function required for functional adaptive immunity (Mills, et al., Immunol Rev 2003 194:77-95). It has been reported that AID has off-target point mutation activities (Liu, M. et al., Nature 2008, 451, 841-845; Liu and Schatz, Trends Immunol. 2009, 30, 173-181; Perez-Duran et al., Carcinogenesis. 2007, 28(12):2427-33). Robbiani et al. has reported off-target activities of AID in B-cells, especially c-myc/IgH translocations (Robbiani et al., Mol Cell 2009, 36(4):631-41). AID expression accelerates the rate of tumor development in Bcl6 transgenic mice (Pasqualucci et al., 2008, Nat. Genet. 40, 108-112). However, deregulated AID does not necessarily cause malignancy or translocation-associated cancer on its own in B cells (Muto et al., 2006, Proc. Natl. Acad. Sci. USA 103, 2752-2757; Okazaki et al., 2003, J. Exp. Med. 197, 1173-1181; Shen et al., 2008, Mol. Immunol. 45, 1883-1892). In addition, despite its role in promoting c-myc/IgH translocation, AID is not required for the development of plasmacytosis or plasmacytoma in IL-6 transgenic or pristane-treated mice, respectively (Kovalchuk et al., 2007, J. Exp. Med. 204, 2989-3001; Ramiro et al., 2004, J. Exp. Med. 200, 1103-1110). However, most human B cell lymphoma-associated translocations do not involve c-myc, and many do not involve Ig genes (Kuppers, 2005, Oncogene 20, 5580-5594).

Overexpression of AID has been reported in chronic lymphocytic leukemia (CLL) (Hancer et al., Leuk Lymphoma. 2011 January; 52(1):79-84; Heintel et al., Leukemia. 2004 April; 18(4):756-62). Further, AID expression has been shown to be correlated with blast crisis B lineage leukemia and therapy resistance in myeloid leukemia and to be associated with generally poor prognosis in chronic B lymphocytic leukemia (Mao et al., Br J Dermatol 2001, 145: 117-122; Chaudhuri et al., Nature 2004, 430:992-8). Further expression of AID in tumor cells from a variety of cancers has been reported including but not limited to lung, breast, gastric, colon, intestinal, liver cancer and choriangiocarcinoma (Greeve et al., Blood 2003, 1010, 3574-3580; Feldhahn et al., J Exp Med 2007, 204, 1157-1166; Kotani et al., PNAS USA 2007, 104, 1616-1620; Engels et al., 2008, Appl Immunohistochem Mol Morphol 16, 521-529; Klemm et al., 2009, Cancer Cell 6, 232-245; Palacios et al., 2010, Blood 115(22), 4488-4496; Leuenberger et al., 2009, Mod Pathol 32, 177-186; Gruber et al., 2010, Cancer Res 70, 7411-7420; inflammatory cancer (Marusawa 2008, Int J Biochem Cell Biol.40, 399-402); follicular lymphoma (Hardianti et al., 2004, Leukemia 18, 826-831; Shikata et al., 2012, Cancer Sci. 103(3):415-21); thyroid cancer (Qiu et al., 2012, Mod Pathol 25(1), 36-45); breast cancer (Borchert et al., 2011, BMC Cancer 11:347); Marusawa, et al., 2011, Adv Immunol 111: 109-41; Zhang et al., 2012, Hum Pathol 43(3):423-34; Komori et al., 2008, Hepatology 47(3):888-896; Hockley 2010, Leukemia 24(5): 1084-6; adult T-cell leukemia (Nakamura et al., 2011, Br J Dermatol. 165(2):437-9). All of the references in the foregoing paragraph are incorporated by reference herein in their entireties.

Elevated levels of AID have been reported in arthritis (Xu et al., Scand. J. Immunol. 2009, 296, 2033-6) and in the MRL/Fas(lpr/lpr) mouse lupus model (White et al., 2011, Autoimmunity 44(8), 585-98). All of the references in the foregoing paragraph are incorporated by reference herein in their entireties.

When DSB repair is inhibited, the extent of the DSBs generated by AID is much higher than previously suspected and the extent of genomic damage is so severe as to result in cell death. Accordingly, In some embodiments of the technology described herein, there is provided a method of treatment comprising; (a) selecting a subject having cells that express elevated levels of activation-induced cytidine deaminase (AID); and (b) administering a therapeutically effective amount of an inhibitor of double strand break repair (e.g., a compound of the present application) to the subject; wherein an elevated level of AID is a level of AID that is higher than the level of AID in cells of the same type from a healthy individual. In some embodiments, the cells expressing elevated levels of AID are B cells. In some embodiments, the B cell expressing elevated levels of AID is a cancerous B cells or a B cell associated with autoimmune disease. In some embodiments, the subject can be a human subject.

Methods provided herein treat cancers, autoimmune disorders, immune deficiencies, or neurodegenerative disorders by inhibiting DNA double strand break repair. This inhibition proves lethal to cells expressing AID, as AID generates widespread genomic breaks, and the treatment with a double strand break repair inhibitor prevents the repair of these lesions which are being generated by the cell itself. This results in cell death in the subject which is specific to the cells expressing AID, e.g., cancerous B cells and/or autoimmune cells. Accordingly, as described herein, In some embodiments there is a provided a treatment paradigm that selectively induces self-destruction of certain diseased cells, while reducing the unintended side effects in healthy tissues.

In some embodiments, an increased level and/or activity of a DNA editing enzyme can be an increased level of DNA editing enzyme mRNA. mRNA levels can be assessed using, e.g., biochemical and molecular biology techniques such as Northern blotting or other hybridization assays, nuclease protection assay, reverse transcription (quantitative RT-PCR) techniques, RNA-Seq, high throughput sequencing and the like. Such assays are well known to those in the art. In some embodiments, nuclear "run-on" (or "run-off) transcription assays are used (see e.g., Methods in Molecular Biology, Volume: 49, Sep. 27, 1995, Page Range: 229-238). Arrays can also be used; arrays, and methods of analyzing mRNA using such arrays have been described previously, e.g., in EP0834575, EP0834576, WO96/31622, U.S. Pat. No. 5,837,832 or WO98/30883. WO97/10365 provides methods for monitoring of expression levels of a multiplicity of genes using high density oligonucleotide arrays.

In some embodiments, a subject can be determined to have an increased level of DNA damage occurring in one or more cell types relative to a reference level if the subject has been exposed to an agent that is known to cause such DNA damage. Non-limiting examples of such agents can include a viral infection with a DNA integrating virus (e.g., adeno-associated virus, retrovirus, human T-lymphotropic virus, HIV-1, oncovirus, hepatitis virus, hepatitis B virus); DNA damaging chemicals (e.g., acetaldehyde, polycyclic aromatic hydrocarbons, benzenes, nitrosamines, tobacco smoke, aflatoxin, and the like); DNA damaging chemotherapeutic agents (e.g., bleomycin, mitomycin, nitrogen mustards (e.g., mechlorethamine, cyclophosphamide, melphalan, chlorambucil, ifosfamide and busulfan), nitrosoureas (e.g., N-Nitroso-N-methylurea (MNU), carmustine (BCNU), lomustine (CCNU) and semustine (MeCCNU), fotemustine and streptozotocin), tetrazines (e.g., dacarbazine, mitozolomide and temozolomide),aziridines (e.g., thiotepa, mytomycin and diaziquone (AZQ)), cisplatins (e.g., cisplatin, carboplatin and oxaliplatin) procarbazine and hexamethylmelamine); and ionizing or ultraviolet radiation. Exposure to such agents can be the result of an accident, infection and/or environmental exposure or the result of a therapeutic administration of such agents.

In some embodiments, the increased level of DNA damage can be occurring in a cell type affected by the cancer, autoimmune disease, immunodeficiency, and/or neurodegenerative disease. In some embodiments, the subject is determined to have an increased level of DNA damage occurring in a cell selected from the group consisting of: a cancer cell; an immune system cell; or a nervous system cell.

In some embodiments, the DNA editing enzyme can be AID. In some embodiments, the level of AID can be the level of AID in a blood cell. In some embodiments, the level of AID can be the level of AID in a B cell.

In some embodiments, an increased level of AID can be a detectable level of AID, e.g., as described below herein.

In some embodiments, the subject can be a human subject.

In some embodiments, methods provided herein treat cancers and/or autoimmune disorders by inhibiting DNA double strand break repair. This inhibition proves lethal to cells expressing AID, as AID generates widespread genomic breaks, and the treatment with a double strand break repair inhibitor prevents the repair of these lesions which are being generated by the cell itself. This results in cell death in the subject which is specific to the cells expressing AID, e.g., cancerous B cells and/or autoimmune cells. Accordingly, as described herein, In some embodiments there is a provided a treatment paradigm that selectively induces self-destruction of certain diseased cells, while reducing the unintended side effects in healthy tissues.

In some embodiments, methods of detecting cancers in patients with increased levels of DNA damage or increased levels of DNA editing enzymes are disclosed in WO2016/094897, incorporated herein by reference.

In some embodiments, the cancer to be treated is a type with high expression of a DNA editing enzyme. In some embodiments, the cancer to be treated is a B-cell neoplasm.

Another embodiment is a method of treating a cancer by administering to the subject an effective amount of one or more disclosed compounds, or a pharmaceutically acceptable salt or solvate thereof, or the corresponding pharmaceutical composition. In one aspect, the cancer is selected from the group consisting of lymphoma, leukemia, and a plasma cell neoplasm. In another aspect, the cancer selected from the group consisting of carcinoma and sarcoma.

In some embodiments, the cancer to be treated is a lymphoma. Lymphomas which can be treated by the disclosed methods include Non-Hodgkin's lymphoma; Burkitt's lymphoma; small lymphocytic lymphoma; lymphoplasmacytic lymphoma; MALT lymphoma; follicular lymphoma; diffuse large B-cell lymphoma; mantle cell lymphoma; and T-cell lymphoma.

Lymphoma is a malignancy in the lymphatic cells of the immune system (e.g., B cells, T cells, or natural killer (NK) cells). Lymphomas often originate in the lymph nodes and present as solid tumors. They can metastasize to other organs such as the brain, bone, or skin. Extranodal sites are often located in the abdomen. Lymphomas are closely related to the lymphoid leukemia and in some cases a particular form of cancer is categorized as both a lymphoma and a leukemia.

Leukemias which can be treated by the disclosed methods include acute lymphoblastic leukemia (ALL); Burkitt's leukemia; B-cell leukemia; B-cell acute lymphoblastic leukemia; chronic lymphocytic leukemia (CLL); acute myelogenous leukemia (AML); chronic myelogenous leukemia (CML); and T-cell acute lymphoblastic leukemia (T-ALL).

In some embodiments, the cancer to be treated is B-cell neoplasms, B-cell leukemia, B-cell acute lymphoblastic leukemia, chronic lymphocytic leukemia, chronic myelogenous leukemia, Burkitt's leukemia, acute myelogenous leukemia and/or T-ALL. The maturation of B cells most typically ceases or substantially decreases when the foreign antigen has been neutralized. Occasionally, however, proliferation of a particular B cell will continue unabated; such proliferation can result in a cancer referred to as "B-cell lymphoma" or a "B-cell leukemia." In some embodiments the cancer to be treated is chronic lymphocytic leukemia (CLL) or chronic myelogenous leukemia (CML).

In some embodiments, the cancer to be treated is a plasma cell neoplasm. Examples for plasma cell neoplasms include multiple myeloma; plasma cell myeloma; plasma cell leukemia and plasmacytoma.

Carcinomas which can be treated by the disclosed methods include colon cancer; liver cancer; gastric cancer; intestinal cancer; esophageal cancer; breast cancer; ovarian cancer; head and neck cancer; lung cancer; and thyroid cancer.

Sarcomas which can be treated by the disclosed methods include soft tissue sarcoma and bone sarcoma.

Any cancer characterized by high levels of DNA damage and/or DNA editing enzyme expression can be treated with a compound as described herein, e.g., a compound of the present application. For example, sarcomas, epithelial cell cancer (carcinomas), colon cancer, gastric cancer, intestinal cancer, liver cancer, hepatocellular cancer, breast cancer, thyroid cancer, esophageal cancer, lung cancer, brain cancer, head and neck cancer, melanoma, renal cancer, prostate cancer, hemangioma, rhabdomyosarcoma, chondrosarcoma, osteosarcoma, fibrosarcoma and cholangiocarcinoma may be characterized by high levels of a DNA editing enzyme expression, e.g., AID. In some embodiments the cancer to be treated is colon cancer, liver cancer, gastric cancer, intestinal cancer, breast cancer, lung cancer, thyroid cancer and/or cholangiocarcinoma.

In some embodiments, cancers that can be treated by the disclosed methods include cancer of the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; sarcomas; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, for the disclosed method, the cancer is characterized by mutations in the mutS homologues (e.g., MSH2, MSH3, and MSH6), mutL homologues (e.g., MLH1), or mismatch repair endonuclease PMS2. Mutations are changes in the genetic code. They include point mutations and frameshift mutations. In a point mutation, one nucleotide is swapped out for another. Therefore, the mutation occurs at a single point or location within the DNA strand. Frameshift mutations are due to either insertions or deletions of nucleotides. This causes the entire DNA strand to elongate or to shrink in size. Thus, frameshift mutations may alter all of the codons that occur after the deletion or insertion. The mutations referred to herein include, but are not limited to, insertions, deletions, duplications, inversions, or other recognized point mutations. It has now been found that RAD51 inhibitors are particularly effective in treating cancers with mutations in MSH (e.g., MSH6), MLH, or PMS2.

MutS Homolog 2 (MSH2) is a protein that in humans is encoded by the MSH2 gene, which is located on chromosome 2. MSH2 is a tumor suppressor gene and more specifically a caretaker gene that codes for a DNA mismatch repair (MMR) protein, MSH2, which forms a heterodimer with MSH6 to make the human MutSa mismatch repair complex. It also dimerizes with MSH3 to form the MutSI3 DNA repair complex. MSH2 is involved in many different forms of DNA repair, including transcription-coupled repair, homologous recombination, and base excision repair. Examples of the mutations in MSH2 include, but are not limited to, g.47630253_47630254del, g.47702411_47702421del, g.47709913_47709915inv, g.47635629_47635634del, g.47637227_47637236dup, g.47639550_47639561del, g.(?_47630206)_(47710367_?)del, g.(?_47630206)_(47643569_47656880)del, g.47630263_47643568del, g.(?_47630206)_(47657081_47672686)del, g.47630263_47657080del, g.(?_47630206)_(47672797_47690169)del, g.47630263_47672796del, g.(?_47630206)_(47672797_47690169)del, g.(?_47630206)_(47693948_47698103)del, g.47630263_47693947del, g.(?_47630206)_(47698202_47702163)del, g.(?_47630206)_(47630542_47635539)del, g.(?_47630206)_(47708011_47709917)del, g.(?_47630206)_(47635695_47637232)del, g.(?_47630206)_(47635695_47637232)del, g.(?_47630206)_(47637512_47639552)del, g.(?_47630206)_(47639700_47641407)del, g.(?_47630206)_(47641558_47643434)del, g.47618487_47650860delins(155), g.47628578_47638433del, g.47595033_47662777del, g.47583175_47667707de, g.47625602_47636880del, g.47554933_47699909del, g.47629508_47649552del, g.47629375_47651274del, g.(?_47630206)_(47630542_47635539)del, g.(?_47630206)_(47635695_47637232)del, g.47643509_47643510del, g.47643529_47643530dup, g.47656746_47657199dup, g.47656661_47663325del, g.(47643569_47656880)_(47710367_?)del, g.(47643569_47656880)_(47710367_?)del, g.47656881_47657080del, g.(47643569_47656880)_(47657081_47672686)del, g.(47643569_47656880)_(47657081_47672686)del, g.(47643569_47656880)_(47657081_47672686)del, g.(47643569_47656880)_(47657081_47672686)dup, g.(47643569_47656880)_(47657081_47672686)dup, g.(47643569_47656880)_(47672797_47690169)del, g.(47643569_47656880)_(47693948_47698103)del, g.47656881_47693947del, g.(47643569_47656880)_(47702410_47703505)del, g.47656881_47656882ins(173), g.47656901_47656902insA, g.47656903del, g.47656912del, g.47630440del, g.47656923del, g.47656931_47656932dup, g.47656943del, g.47656943_47656949delinsCCCAGA, g.47656948dup, g.47656996dup, g.47657000_47657001dup, g.47630449del, g.47657007dup, g.47657008del, g.47657020_47657023dup, g.47657025_47657026del, g.47657026dup, g.47657030_47657031del, g.47657047_47657050del, g.47657053del, g.47657053_47657057del, g.47657064del, g.47657073dup, g.47657312_47676594del, g.47668611_47674615del, g.47672116_47675123del, g.47666463_47677632del, g.47666403_47677572del, g.(47657081_47672686)_(47710367_?)del, g.(47657081_47672686)_(47710367_?)inv, g.47671507_47675022delinsCATTCTCTTTGAAAA, g.47657278_47676557del, g.47672687_47672796del, g.(47657081_47672686)_(47672797_47690169)del, g.(47657081_47672686)_(47672797_47690169)del, g.(47657081_47672686)_(47693948_47698103)del, g.(47657081_47672686)_(47698202_47702163)del, g.(47657081_47672686)_(47708011_47709917)del, g.47672691dup, g.47672697dup, g.47672721_47672744delins47672748_47672771inv, g.47672728_47672729del, g.47672731dup, g.47672750_47672751insGG, g.47672755_47672758del, g.47672762_47672763del, g.47630466_47630494del, g.47686194_47697740del, g.(47672797_47690169)_(47710367_?)del, g.(47672797_47690169)_(47690294_47693796)del, g.(47672797_47690169)_(47693948_47698103)del, g.47690170_47693947del, g.(47672797_47690169)_(47693948_47698103)del, g.(47672797_47690169)_(47693948_47698103)dup, g.(47672797_47690169)_(47705659_47707834)del, g.47690173del, g.47690191del, g.47690216_47690217dup, g.47690227del, g.47690227dup, g.47690228_47690232del, g.47690230_47690231del, g.47690240del, g.47690240_47690243del, g.47630475del, g.47630475_47630476del, g.47690259_47690260delinsCT, g.47690277dup, g.47690280del, g.47690283dup, g.(47690294_47693796)_(47702410_47703505)del, g.47630484_47630485insG, g.47693838_47693839del, g.47693862del, g.47693864del, g.47693873del, g.47693880dup, g.47693913del, g.47693924_47693925dup, g.47630493del, g.47697730_47706125del, g.(47693948_47698103)_(47710367_?)del, g.(47693948_47698103)_(47698202_47702163)del, g.(47693948_47698103)_(47705659_47707834)del, g.47698107del, g.47698109del, g.47698109_47698110insA, g.47630496del, g.47698118del, g.47698125del, g.47698129dup, g.47698138_47698139del, g.47698142_47698146del, g.47698144dup, g.47698147_47698148del, g.47698147_47698148dup, g.47698147_47698148insT, g.47698159del, g.47698162del, g.47698506_47703472del, g.47701803_47708848del, g.(47698202_47702163)_(47710367_?)del, g.(47698202_47702163)_(47702410_47703505)del, g.(47698202_47702163)_(47703711_47705410)del, g.(47698202_47702163)_(47705659_47707834)del, g.47702164del, g.47702175_47702176insA, g.47702183_47702186del, g.47702185_47702186insCT, g.47702190_47702192del, g.47702191dup, g.47702192_47702193del, g.47702213del, g.47702231del, g.47702242dup, g.47702257del, g.47702262_47702263dup, g.46630516_47630517dup, g.47630517del, g.47630517dup, g.47702289_47702290inv, g.47702293_47702296del, g.47702301dup, g.47702315del, g.47702315del, g.47702328_47702329del, g.46630522dup, g.47702339del, g.47702371_47702374dup, g.47702384_47702385del, g.47702386_47702389del, g.47702388del, g.47702388_47702389del, g.47702390del, g.47702390_47702391del, g.47702400_47702401del, g.47703506_47703710del, g.47703506_47708010del, g.47703510del, g.47703515del, g.47703521_47703522del, g.47703535_47703536del, g.47703546_47703547del, g.47703548_47703611dup, g.47630534del, g.47703571dup, g.47703574_47703581del, g.47703585dup, g.47630350del, g.47632107_47668733del, g.47703613del, g.(47630542_47635539)_(47643569_47656880)del, g.(47630542_47635539)_(47643569_47656880)inv, g.(47630542_47635539)_(47657081_47672686)del, g.47635540_47657080del, g.(47630542_47635539)_(47672797_47690169)del, g.(47630542_47635539)_(47690294_47693796)del, g.(47630542_47635539)_(47705659_47707834)del, g.47635540_47635694del, g.(47630542_47635539)_(47635695_47637232)del, g.(47630542_47635539)_(47635695_47637232)del, g.(47630542_47635539)_(47637512_47639552)del, g.47703635dup, g.47703641dup, g.47635542_47635549del, g.47703660_47703663del, g.47703667dup, g.47630351dup, g.47703704del, g.47703826_47707938del, g.(47703711_47705410)_(47705659_47707834)del, g.47705428_47705431del, g.47705437_47705438insA, g.47635551_47635552del, g.47705440_47705441del, g.47705461del, g.47705490del, g.47705494del, g.47705495del, g.47635557_47635558del, g.47705505del, g.47705535dup, g.47705547del, g.47705560_47705561dup, g.47705561dup, g.47705562dup, g.47705588del, g.47705608_47705609del, g.47705618dup, g.47705627dup, g.47635571_47635601delins(217), g.(47705659_47707834)_(47710367_?)del, g.(47705659_47707834)_(47708011_047709917)del, g.47707842_47707843del, g.47707861del, g.47707861_47707874dup, g.47707878_47707884del, g.47707878_47707884del, g.47707883del, g.47707895_47707905del, g.47707897del, g.47707901_47707902del, g.47707905_47707906del, g.47707921del, g.47635583dup, g.47635583_47635584del, g.47707969_47707973del, g.47707996_47707997ins(115), g.47708009_47708010del, g.(47708011_47709917)_(47710367_?)del, g.47635591_47635592del, g.47635597_47635618dup, g.47635606_47635607del, g.47630359dup, g.47635672del, g.47635675_47635678del, g.47630364dup, g.47635680dup, g.47636862_47639040del, g.47636781_47638831del, g.47636753_47638155del, g.47636552_47638597del, g.(47635695_47637232)_(47643569_47656880)del, g.(47635695_47637232)_(47643569_47656880)del, g.(47635695_47637232)_(47657081_47672686)del, g.(47635695_47637232)_(47672797_47690169)del, g.(47635695_47637232)_(47698202_47702163)del, g.(47635695_47637232)_(47637512_47639552)del, g.(47635695_47637232)_(47641558_47643434)del, g.47637234del, g.47637246_47637247del, g.47637253_47637254del, g.47637254_47637255del, g.47637254_47637255del, g.47637265del, g.47637274del, g.47637282del, g.47637320del, g.47637372_47637375del, g.47637377_47637449dup, g.47637379del, g.47637384del, g.47637394_47637395del, g.47637396_47637397del, g.47637417del, g.47637427_47637435del, g.47637437_47637439del, g.47637453del, g.47637458dup, g.47637479_47637482dup, g.47637482dup, g.47637504_47637505del, g.47637508_47637511del, g.47638050_47653430del, g.47638302_47648462del, g.47638478_47648643del, g.(47637512_47639552)_(47710367_?)del, g.(47637512_47639552)_(47643569_47656880)del, g.47639553_47643568del, g.(47637512_47639552)_(47657081_47672686)del, g.(47637512_47639552)_(47657081_47672686)del, g.(47637512_47639552)_(47672797_47690169)del, g.(47637512_47639552)_(47639700_47641407)del, g.(47637512_47639552)_(47641558_47643434)del, g.47639557_47639561del, g.47639582_47639586delinsTAAT, g.47639583_47639584del, g.47639594del, g.47639594dup, g.47639598del, g.47639603_47639604del, g.47639611_47639612del, g.47639612del, g.47639618_47639621del, g.47639624_47639628delinsTTA, g.47630401dup, g.47639632dup, g.47639638_47639641dup, g.47639638_47639641dup, g.47639639del, g.47639639del, g.47639642dup, g.47630403_47630404insC, g.47639653del, g.47639666del, g.47639666_47639669del, g.47639668del, g.47639670_47639673delinsTT, g.47639674_47639675dup, g.47639695_47639696del, g.47639707_47642985del, g.47641402_47642007del, g.(47639700_47641407)_(47643569_47656880)del, g.47641408_47643568del, g.(47639700_47641407)_(47657081_47672686)del, g.(47639700_47641407)_(47672797_47690169)del, g.(47639700_47641407)_(47641558_47643434)del, g.(47639700_47641407)_(47641558_47643434)del, g.47641410del, g.47641425_47641426del, g.47641426_47641429del, g.47630412del, g.47641451del, g.47641454dup, g.47641455dup, g.47641469del, g.47641478del, g.47641488_47641491del, g.47641496_47641497del, g.47641503del, g.47641513_47641514dup, g.47641530_47641537dup, g.47642509_47655432del, g.(47641558_47643434)_(47643569_47656880)del, g.(47641558_47643434)_(47693948_47698103)del, g.47630424_47630433del, g.47643450dup, g.47643462_47643463del, g.47643462_47643463ins(4), g.47643464_47643465insNC_000022.10: 3578816935788352, g.47643465dup.

MutS Homolog 3 (MSH3) is a human homologue of the bacterial mismatch repair protein MutS that participates in the mismatch repair (MMR) system. MSH3 typically forms the heterodimer MutSβ with MSH2 in order to correct long insertion/deletion loops and base-base mispairs in microsatellites during DNA synthesis. Deficient capacity for MMR is found in approximately 15% of colorectal cancers, and somatic mutations in the MSH3 gene can be found in nearly 50% of MMR-deficient colorectal cancers. Examples of the mutations in MSH3 include, but are not limited to, g.79970809del.

MSH6 encodes MutS homologue 6 (MSH6), a member of the Mutator S (MutS) family of proteins that are involved in DNA mismatch repair (MMR). The MSH6 protein forms a heterodimer with MutS homologue 2 (MSH2) in both human and yeast. Human MSH2/6 recognizes single base-base mismatches and short insertion/deletion loops. Upon recognition of a mismatch, MSH2/6 complex binds and exchanges ADP for ATP, resulting in a conformational change to the complex that precedes base pair dissolution, base excision, and repair.

MSH6 mutations include frameshift and/or nonsense mutations and can result in non-functional MSH6 and loss of protein expression. Examples include a frameshift mutation at MSH6 amino acid residue 290 and a compounding missense T1189I.

Inactivating MSH6 mutations can be detected in cancers by routine diagnostics methods. These methods include, but are not limited to, obtaining cancer cells and other diagnostic indicators such as peripheral blood mononuclear cells (PBMCs), PBMC subpopulations, circulating blasts (CD34+ cells), circulating tumor cells and circulating exosomescancer cells by biopsy and blood tests and by obtaining lymphatic or other bodily fluids. It is then determined from the cancer cells or other diagnostic indicators whether the cancer exhibits an inactivating MSH6 mutation is by methodology known in the art, for example, direct DNA sequencing and multiplex ligation dependent probe amplification, RNA sequencing (RNA-Seq), microarray, quantitative PCR, or NanoString™ gene expression panels, or MSH6 protein by immunohistochemistry, flow cytometry, immunocytochemistry or Western blot. Methods for identifying inactivating MSH6 mutations are disclosed in Houlleberghs H, Goverde A, Lusseveld J, Dekker M, Bruno M J, et al. (2017) Suspected Lynch syndrome associated MSH6 variants: A functional assay to determine their pathogenicity. PLOS Genetics 13(5): e1006765. https://doi.org/10.1371/j our-nal.pgen.1006765.

Examples of the mutations in MSH6 include, but are not limited to, g.48032846_48032849del, g.48032846_48032849del, g.48032846_48032849del, g.48033337_48033342del, g.48033420_48033422del, g.(?_48010221)_(48034092)del, g.(?_48010221)_(48018263_48023032)del, g.47998510_48020183del, g.48007276_48020272del, g.48026207del, g.48026223del, g.48026223del, g.48026257_48026261del, g.48026261_48026265del, g.48026312_48026313del, g.48026398del, g.48026543_48026544dup, g.48026693dup, g.48026702del, g.48026712del, g.48026718dup, g.48026736_48026737delinsAG, g.48026736_48026737delinsG, g.48026750_48026751del, g.48026754_48026757del, g.48026756_48026759del, g.48026759_48026760del, g.48026906del, g.48026928_48026931del, g.48026941dup, g.48026991del, g.48027023_48027024del, g.48027079del, g.48027079_48027082dup, g.48027167_48027168del, g.48027172_48027173dup, g.48027178_48027185del, g.48027184_48027185del, g.48027272_48027275del, g.48027470_48027471del, g.48027501_48027502del, g.48027501_48027502delTG, g.48027657dup, g.48027691_48027694del, g.48027733_48027736dup, g.48027794_48027796delinsC, g.48027841_48027842del, g.48027887del, g.48027890dup, g.48027973_48027980del, g.48028067del, g.48028098del, g.48028106del, g.48028175_48028176del, g.48028241_48028242del, g.48028241_48028242delTT, g.48028272_48028284dup, g.48028277_48028278del, g.48030558_48030559del, g.48030126_48032394del, g.48030568del, g.48030581_48030584del, g.48030584_48030585dup, g.48030607del, g.48030645_48030646insT, g.48030647del, g.48030647dup, g.48030649dup, g.48030654_48030660del, g.48030659dup, g.48030697_48030698del, g.48030698del, g.48030706del, g.48030710dup, g.48030727_48030728insC, g.48030765_48030829del, c.3438+797_3438+798insTATins1839_3439–428, Tins1839_3439–428, g.48032123_48032124del, g.48032126_48032129del, g.48032129_48032132dup, (48034092_?)del, g.48032835dup, g.48033374_48033402dup, g.48033421_48033433del, g.48033453_48033454insA, g.48033495_48033496del, g.48033610_48033613dup, g.48033636_48033639dup, g.48033707dup, g.48033721_48033724dup, g.48033728_48033746dup, (48033742_48033743)ins(32), g.48033748_48033751del, g.48033773_48033774insATCA, g.48033773_48033776dup, g.48033887_48033910inv, (48032167_48032756)del, (48023203_48025749)del, g.48025773dup, g.48025860_48025861insT, g.48025967dup, c.3438+797_3438+798insTAg.48032121_48032122del, g.48032124dup, g.48032129_48032130insA, g.(48032167_48032756)_ g.48032809_48032812del, g.48032846_48032849del, g.48033395_48033398del, g.48033425_48033428dup, g.48033494_48033523del, g.48033593dup, g.48033629_48033635del, g.48033676_48033682del, g.48033709_48033716dup, g.48033727_48033730dup, g.(48033742_48033743)_ g.48033746dup, g.48033758_48033768del, g.48033785_48033789dup, g.(48018263_48023032)_ g.(48018263_48023032)_ g.48023097_48023098del, g.48025832del, g.48025884_48025885del, MutL homolog 1, colon cancer, nonpolyposis type 2 (*E. coli*) is a protein that in humans is encoded by the MLH1 gene located on Chromosome 3. It is a gene commonly associated with hereditary nonpolyposis colorectal cancer.

Examples of the mutations in MSH6 include, but are not limited to, g.37089113_37089115del, g.37089175del, g.37090379_37090393del, g.37038201_37038202del, g.37042531_37042542del, g.37053339_37053355del, g.37053354del, g.37053590_37053591insT, g.37034841_37092337del, g.(?_37034841)_(37092337_?)del, g.(?_37034841)_(37061955_37067127)del, g.(?_37034841)_(37035155_37038109)del, g.(?_37034841)_(37035155_37038109)del, g.(?_37034841)_(37070424_37081676)del, g.(?_37034841)_(37083823_37089009)del, g.37034841_37083822del, g.(?_37034841)_(37038201_37042445)del, g.(?_37034841)_(37042545_37045891)del, g.37034841_37042544del, g.(?_37034841)_(37042545_37045891)del, g.(?_37034841)_(37042545_37045891)del, g.(?_37034841)_(37045966_37048481)del, g.(?_37034841)_(37050397_37053310)del, g.(?_37034841)_(37059091_37061800)del, g.37034658_37038806del, g.36961079_37138741del, g.37061923del, g.37061927del, g.37061933del, g.37061939del, g.37061942dup, g.37035140_37035141del, g.37070417del, g.37070417_37070418insT, g.37070419dup, g.37070422_37070423insT, g.37080355_37083368del, g.(37070424_37081676)_ (37092337_?)del, g.(37070424_37081676)_ (37081786_37083758)del, g.(37070424_37081676)_ (37083823_37089009)del, g.37038148_37038151del, g.37038149del, g.37038149dup, g.37081690_37081691del, g.37081691_37081692del, g.37081706_37081708del, g.37081710_37081711del, g.37035053_37035066del, g.37038154del, g.37038154_37038157del, g.37081738_37081739del, g.37081740del, g.37081753dup, g.37081757_37081761dup, g.37081782_37081783insAAGT, g.37081787_37081793delinsATTT, g.(37081786_37083758)_(37083823_37089009)del, g.(37081786_37083758)_(37089175_37090007)del, g.37083759del, g.37083780dup, g.37083781_37083784del, g.37083781_37083784delCTCA, g.37083808_37083809del, g.37083816del, g.37086069_37089606del, g.37084092_37089247del, g.37084590_37089786del, g.(37083823_37089009)_(37092337_?)del, g.(37083823_37089009)_(37089175_37090007)del, g.37089010_37089174del, g.(37083823_37089009)_(37090509_37091976)del, g.37089023del, g.37089026_37089027del, g.37089027del, g.37089036del, g.37089036dup, g.37038168dup, g.37089042del, g.37089047del, g.37089050_37089053del, g.37089056_37089057del, g.37089061_37089062del, g.37089078_37089096del, g.37089090dup, g.37089099dup, g.37089107_37089110dup, g.37089109_37089110del, g.37089130_37089132del, g.37089130_37089132delAAG, g.37089131delinsTTCTT, g.37089133del, g.37089133delG, g.37089144del, g.37089155del, g.37089155_37089161del, g.37089158_37089161del, g.37089162_37089166del, g.37089171del, g.(37089175_37090007)_(37090101_37090394)del, g.37035056_37035072del, g.37090013del, g.37090015dup, g.37038183_37038184del, g.37090024_37090037dup, g.37090025_37090053dup, g.37090027dup, g.37038184del, g.37090031_37090032insT, g.37090041del, g.37090057del, g.37090064_37090067del, g.37038188del, g.37090082del, g.37090086_37090087del, g.37090087_37090088del, g.37090097_37090101delinsC, g.37090099del, g.37038191dup, g.(37090101_37090394)_(37092337_?)del, g.37035057_37035073del, g.37090405dup, g.37090411_37090415del, g.37090414del, g.37038194del, g.37038198del, g.37090472_37090478del, g.37039445_37059613dup, g.37039760_37052440del, g.37090481_37090482del, g.37090483_37090484del, g.37090483_37092045del, g.37040732_37043185delinsACATAGTA, g.37042445_37042446del, g.(37038201_37042445)_(37042545_37045891)del, g.(37038201_37042445)_(37048555_37050304)del, g.(37038201_37042445)_(37050397_37053310)del, g.(37038201_37042445)_(37053591_37055922)del, g.37090497_37090498del, g.37090497_37090498delTC, g.37090504_37090507del, g.(37090509_37091976)_(37092337_?)del, g.(37090509_37091976)_(37092337_?)dup, g.37091977_37091978del, g.37091978_37091987del, g.37042448_37042451del, g.37091984_37091990del, g.37042451_37042453del, g.37092020_37092021del, g.37092022_37092068dup, g.37092027_37092028del, g.37092027_37092028dup, g.37092030dup, g.37092052_37092055del, g.37092054_37092055del, g.37092068_37092071dup, g.37092091dup, g.37092094_37092097delins(30), g.37092096_37092106del, g.37092097del, g.37092125_37092126delAA, g.37092125_37092126del, g.37092139_37092142dup, g.37092142dup, g.37035060dup, g.37042469_37042470del, g.37042470del, g.37042482dup, g.37042485del, g.37042499del, g.37042546dup, g.37044472_37046589del, g.37045648_37049941del, g.37045095_37054651del, g.37045072_37046861del, g.(37042545_37045891)_(37045966_37048481)del, g.(37042545_37045891)_(37092337_?)del, g.(37042545_37045891)_(37048555_37050304)del, g.(37042545_37045891)_(37050397_37053310)del, g.37045892_37050396del, g.37035069del, g.37045926del, g.37045931del, g.37045939_37045940dup, g.37045957_37045958del, g.37045963del, g.37035075del, g.37048067_37049287del, g.(37045966_37048481)_(37048555_37050304)del, g.(37045966_37048481)_(37050397_37053310)del, g.37048483del, g.37048483_37048503delinsT, g.37048486_37048487delinsGTT, g.37048489del, g.37048490del, g.37035076_37035077insCCCA, g.37035077_37035078dup, g.37048505_37048508del, g.37048521del, g.37048529dup, g.37035082dup, g.37049873_37052281del, g.37049839_37052249del, g.37049800_37052209del, g.37049640_37050445del, g.37050305_37050396del, g.(37048555_37050304)_(37050397_37053310)del, g.37050305_37050396del, g.37050319_37050320del, g.37050339del, g.37050348del, g.37050353_37050354del, g.37050354dup, g.37050364del, g.37050375_37050376insGA, g.37035090del, g.37050382_37050383delinsAT, g.37050382_37050383delinsCT, g.37050390_37050396del, g.37052950_37060990del, g.(37050397_37053310)_(37067499_37070274)dup, g.(37050397_37053310)_(37053591_37055922)del, g.(37050397_37053310)_(37056036_37058996)del, g.37053353del, g.37053510_37053511del, g.37035099del, g.37053545_37053546insT, g.37053562del, g.37053578del, g.37053578dup, g.37053585del, g.37053586_37053589del, g.37053591del, g.37053590_37053591delinsAT, g.37055920_37055921del, g.37055914_37055938del, g.(37053591_37055922)_(37070424_37081676)del, g.(37053591_37055922)_(37083823_37089009)del, g.(37053591_37055922)_(37059091_37061800)del, g.37035105del, g.37055928dup, g.37035106_37035116del, g.37055938del, g.37035108del, g.37055972_37055975del, g.37055976_37055979del, g.37035111del, g.37055990dup, g.37035114del, g.37035116del, g.37056036del, g.37056037dup, g.37058993_37059001del, g.(37056036_37058996)_(37070424_37081676)del, g.(37056036_37058996)_(37059091_37061800)del, g.37058997_37059000del, g.37059014_37059017del, g.37059017_37059021del, g.37059027_37059030dup, g.37035122del, g.37059062_37059063insT, g.37059065_37059066del, g.37059066del, g.37059066dup, g.37059072_37059073del, g.37059072_37059073dup, g.37059090_37059093del, g.37061595_37061913del, g.37061308_37066756del, g.37061207_37063077del, g.(37059091_37061800)_(37092337_?)del, g.(37059091_37061800)_(37061955_37067127)del, g.37061801_37061954del, g.(37059091_37061800)_(37083823_37089009)del, g.37061803dup, g.37061804del, g.37061817del, g.37061837_37061838dup, g.37061844del, g.37061851dup, g.37061855dup, g.37061870del, g.37061904_37061906del, g.37061910del, g.37035047del, g. [37049179_37051317delinsTG; 37051667_37054327delinsCA].

Human PMS2 related genes are located at bands 7p12, 7p13, 7q11, and 7q22. Exons 1 through 5 of these homologues share high degree of identity to human PMS2. The product of this gene is involved in DNA mismatch repair. The protein forms a heterodimer with MLH1 and this complex interacts with MSH2 bound to mismatched bases. Defects in this gene are associated with hereditary nonpolyposis colorectal cancer, with Turcot syndrome, and are a cause of supratentorial primitive neuroectodermal tumors.

Examples of the mutations in PMS2 include, but are not limited to, g.(?_6012870)_(6048737_?)del, g.6012870_6048737del, g.(6027252_6029430)_(6048737_?)del, g.(6045663_6048627)_(6048737_?)del, g.6029554del, g.6029499dup, g.6029495_6029496del, g.6029462_6029463delinsTAAA, g.5992485_6028601del, g.(6018328_6022454)_(6027252_6029430)del, g.(6013174_6017218)_(6027252_6029430)del, g.6027226_6027227ins(20), g.6027175del, g.6027090dup, g.6036705_6044207delinsCG, g.6026666dup, g.6026628del, g.6043671del, g.6026565dup, g.6026565dupT, g.6018315_6018316del, g.6018306_6018310del, g.6018306_6018310delAGTTA, g.6043633_6043634dup, g.6018256_6018259del, g.6015623_6017501del, g.6016429_6017479del, g.6017300_6017303del, g.6045579_6045674delinsATTT, g.(6043690_6045522)_(6045663_6048627)del, g.(?_6012870)_(6042268_6043320)del, g.(6035265_6036956)_(6042268_6043320)del, g.6038283_6039384del, g.6038901del, g.6038851dup, g.(6035265_6036956)_(6037055_6038738)del, g.6037019_6037024delinsCTTCACACACA, g.6036980del, g.6036958dup, g.6035323_6035324insJN866832.1, g.(6022623_6026389)_(6035265_6036956)del, g.(6031689_6035164)_(6035265_6036956)del, g.6035204_6035207del, g.6035205_6035206del, g.(?_6012870)_(6031689_6035164)del, g.(6027252_6029430)_(6031689_6035164)del, g.(6029587_6031603)_(6031689_6035164)del, g.6028725_6029882del, g.(?_6012870)_(6029587_6031603)del.

The present application provides a method of treating patients with Lynch syndrome to reduce the likelihood of developing or treating cancers derived from Lynch syndrome patients, by administering to the subject an effective amount of one or more disclosed compounds, or a pharmaceutically acceptable salt or solvate thereof, or the corresponding pharmaceutical composition.

Lynch syndrome is a hereditary disorder caused by a mutation in a mismatch repair gene in which affected individuals have a higher than normal chance of developing colorectal cancer, endometrial cancer, and various other types of aggressive cancers, often at a young age—also called hereditary nonpolyposis colon cancer (HNPCC).

The mutations of specific mismatch repair (MMR) genes including but not limited to MLH1, MSH2, MSH6, PMS2, and EPCAM-TACSTD1 deletions are responsible for Lynch syndrome. These genes work in repairing mistakes made when DNA is copied in preparation for cell division. The defects in the genes disallow repair of DNA mistakes and as cells divide, errors stack and uncontrollable cell growth may result in cancer.

Those with Lynch syndrome carry up to an 85% risk of contracting colon cancer as well as a higher than average risk for endometrial cancer, stomach cancer, pancreatic cancer, kidney/ureter tract cancer, hepatobiliary tract cancer, gastric tract cancer, prostate cancer, ovarian cancer, gallbladder duct cancer, brain cancer, small intestine cancer, breast cancer, and skin cancer.

In some embodiments for the disclosed method, the method is a method of treating cancer derived from Lynch syndrome, selected from the group consisting of colon cancer, endometrial cancer, stomach cancer, pancreatic cancer, kidney/ureter tract cancer, hepatobiliary tract cancer, gastric tract cancer, prostate cancer, ovarian cancer, gallbladder duct cancer, brain cancer, small intestine cancer, breast cancer, and skin cancer.

In some embodiments, the method is a method of treating autoimmune disease. Exemplary autoimmune diseases include lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosus; discoid lupus; subacute cutaneous lupus erythematosus; cutaneous lupus erythematosus including chilblain lupus erythematosus; chronic arthritis; Sjogren's syndrome; inflammatory chronic rhinosinusitis; colitis; celiac disease; inflammatory bowel disease; Barrett's esophagus; inflammatory gastritis; autoimmune nephritis; autoimmune vasculitis; autoimmune hepatitis; autoimmune carditis; autoimmune encephalitis; autoimmune diabetes; autoimmune diabetes nephritis; psoriasis; Graft-versus-host disease (GvHD); and autoimmune mediated hematological disease.

In one aspect of this embodiment, the method is a method of treating immune deficiency selected from the group consisting of Autoimmune Lymphoproliferative Syndrome (ALPS), Autoimmune polyglandular syndrome type 1 (APS-1), BENTA Disease, Caspase Eight Deficiency State (CEDS), Chronic Granulomatous Disease (CGD), Common Variable Immunodeficiency (CVID), Congenital Neutropenia Syndromes, CTLA4 Deficiency, DOCK8 Deficiency, GATA2 Deficiency, Glycosylation Disorders With Immunodeficiency, hyper-immunoglobulin E syndrome (HIES), Hyper-Immunoglobulin M (Hyper-IgM) Syndromes, Leukocyte adhesion deficiency (LAD), LRBA deficiency, PI3 Kinase disease, PLCG2-associated antibody deficiency and immune dysregulation (PLAID), severe combined immunodeficiency (SCID), STAT3 gain-of-function disease, Warts, Hypogammaglobulinemia, Infections, and Myelokathexis Syndrome (WHIMS), X-Linked Agammaglobulinemia (XLA), X-Linked Lymphoproliferative Disease (XLP), and XMEN Disease.

As used herein, the term "immune deficiency" refers to a condition in which a portion or some portions of cell components constituting an immune system are defective or dysfunction, so that a normal immune mechanism is damaged. In other words, "immune deficiency" means a condition under which: congenital immunity and/or acquired immunity are suppressed and/or decreased. In some embodiments, the immune-deficiency subject is an immunocompromised subject. Non-limiting examples of immune deficiencies can include AIDS, hypogammaglobulinemia, agammaglobulinemia, granulocyte deficiency, chronic granulomatous disease, asplenia, SCID, complement deficiency, and/or sickle cell anemia.

In another aspect of this embodiment, the method is a method of treating a neurodegenerative disorder selected from the group consisting of multiple sclerosis, Parkinson's disease (PD), Alzheimer's disease (AD), Dentatorubropallidoluysian atrophy (DRPLA), Huntington's Disease (HD), Spinocerebellar ataxia Type 1 (SCA1), Spinocerebellar ataxia Type 2 (SCA2), Spinocerebellar ataxia Type 3 (SCA3), Spinocerebellar ataxia 6 (SCA6), Spinocerebellar ataxia Type 7 (SCAT), Spinocerebellar ataxia Type 8 (SCAB), Spinocerebellar ataxia Type 12 (SCA12), Spinocerebellar ataxia Type 17 (SCA17), Spinobulbar Muscular Ataxia/Kennedy Disease (SBMA), Fargile X syndrome (FRAXA), Fragile XE mental retardation (FRAXE), and Myotonic dystrophy (DM).

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In some embodiments, the methods disclosed herein further comprise co-administering an effective amount of a DNA repair inhibitor, a DNA damage response (DDR) inhibitor, a DNA damaging agent or an immunomodulatory agent to the subject being treated for cancer, in addition to an effective amount of a disclosed RAD51 inhibitor.

The term "DNA repair inhibitor" refers to any agent that targets components/processes which a cell uses to repair mutations or changes in DNA and restore the DNA to its original state and prevents the repair of DNA. Examples of DNA repair inhibitors include: RPA inhibitors, APE1 inhibitors, DNA ligase inhibitors, DNA polymerase inhibitors, Parp inhibitors etc.

The term "DNA damage response inhibitor" refers to any agent that targets components/processes involved in detecting DNA lesions, signaling the presence of DNA damage, and/or promote the repair of DNA damage. Examples of DNA damage response inhibitors include checkpoint inhibitors, ATM and ATR inhibitiors, DNA-PK inhibitors, etc.

The term "DNA damaging agent" refers to any agent that directly or indirectly damages DNA. The DNA damaging agents is selected from the group consisting of: exposure to a DNA damaging chemical; exposure to a chemotherapeutic agent; exposure to a radiochemotherapy, and exposure to ionizing or ultraviolet radiation. Specific examples of DNA-damaging chemotherapeutic agents include alkylating agents, nitrosoureas, anti-metabolites, plant alkaloids, plant extracts and radioisotopes. Specific examples of the chemotherapeutic agents also include DNA-damaging drugs, for example, 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochlorine (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracycline such as doxorubicin (adriamycin; ADR), daunorubicin (Cerubicine), idarubicin (Idamycin) and epirubicin (Ellence), anthracyclin analogs such as mitoxantrone, actinimycin D, non-intercalating topoisomerase inhibitors such as epipodophyllotoxins (etoposide or VP16, teniposide or VM-26), podophylotoxin, bleomycin (Bleo), pepleomycin, compounds that form adducts with nucleic acid including platinum derivatives, e.g., cisplatin (CDDP), trans analog of cisplatin, carboplatin, iproplatin, tetraplatin and oxaliplatin, as well as camptothecin, topotecan, irinotecan (CPT-11), and SN-38. Specific examples of nucleic acid damaging treatments include radiation e.g., ultraviolet (UV), infrared (IR), or .alpha.-, .beta.-, or .gamma.-radiation, as well as environmental shock, e.g., hyperthermia.

"Immunomodulatory agent" means an agent that modulates an immune response to an antigen but is not the antigen or derived from the antigen. "Modulate", as used herein, refers to inducing, enhancing, suppressing, directing, or redirecting an immune response. Such agents include immunostimulatory agents, such as adjuvants, that stimulate (or boost) an immune response to an antigen but is not an antigen or derived from an antigen. There are several distinct types of immunomodulatory agents, which include, but are not limited to, Toll-like Receptor (TLR) agonists and Toll-like Receptor (TLR) antagonists. Such agents also include immunosuppressants. The immunomodulatory agent is selected from the group consisting of immune checkpoint modulators, Toll-like receptor (TLR) agonists, cell-based therapies, cytokines and cancer vaccines.

In some embodiments, the subject is determined to have an increased level and/or activity of a DNA damage process or DNA editing enzyme. In one aspect of this embodiment, the DNA editing enzyme is selected from the group consisting of activation induced cytidine deaminase (AID or AICDA), APOBEC2, APOBEC3A, APOBEC3C, APOBEC3D, APOBEC3F, APOBEC3G, APOBEC3H, APOBEC4, a Type 1 Topoisomerase, a Type 2 Topoisomerase, Recombination Activating Gene 1 (RAG 1), and Recombination Activating Gene 2 (RAG2).

In some embodiments, blood cells obtained from the subject have been determined to have a detectable level of activation-induced cytidine deaminase (AID).

In some embodiments, B cells obtained from the subject have been determined to have a detectable level of activation-induced cytidine deaminase (AID).

In some embodiments, the detectable level of activation-induced cytidine deaminase (AID) is statistically significantly higher than the level of AID expressed in unactivated B-cells or normal non-immune cells from a healthy subject.

The precise amount of compound administered to provide an "effective amount" to the subject will depend on the mode of administration, the type, and severity of the disease, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the application being used by following, for example, dosages reported in the literature and recommended in the *Physician's Desk Reference* (57th ed., 2003).

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

In addition, the disclosed RAD51 inhibitors can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g., the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a RAD51 mediated disease using the disclosed RAD51 inhibitors for guidance.

The compounds or the corresponding pharmaceutical compositions taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the application is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

EXAMPLES

| Abbreviations | |
|---|---|
| Ac | acetyl |
| ACN | acetonitrile |
| aq | aqueous |
| Bn | benzyl |
| Boc | tert-butoxycarbonyl |
| br. | Broad |
| CAN | cerium ammonium nitrate |
| d | doublet (when in reference to an $^1$H NMR spectra) |
| DCM | dichloromethane |
| DIEA (DIPEA) | diisopropylethylamine |
| DMA | dimethylacetamide |
| DMAP | 4-dimethylaminopyridine |
| DMF | N,N-dimethylformamide |
| DMSO | dimethylsulfoxide |
| dppf | 1,1'-bis(diphenylphosphino) ferrocene |
| eq | equivalent |
| EtOAc | ethyl acetate |
| h | hour |
| HBTU | N,N,N',N',-tetramethyl-O-(1H-benzotriazol-1-yl)uronium hexafluorophosphate |
| HPLC | high performance liquid chromatography |
| LC-MS | liquid chromatography coupled to mass spectrometry |
| m | multiplet (when in reference to an $^1$H NMR spectra) |
| MS ESI | mass spectra, electrospray ionization |
| NBS | N-bromosuccinimide |
| NMR | nuclear magnetic resonance |
| prep | preparative |
| Py | pyridine |
| s | singlet (when in reference to an $^1$H NMR spectra) |
| sat | saturated |
| SFC | supercritical fluid chromatography |
| t | triplet (when in reference to an $^1$H NMR spectra) |
| TEA | triethylamine |
| TFA | trifluoroacetic acid |
| THF | tetrahydrofuran |
| TLC | thin layer chromatography |
| Tol | toluene |

Example 1

Preparation of isopropyl (trans-4-(5-(4-(aminomethyl)-2-(N-(tert-butyl)sulfamoyl)phenyl)thiazol-2-yl)cyclohexyl)carbamate (Compound 1)

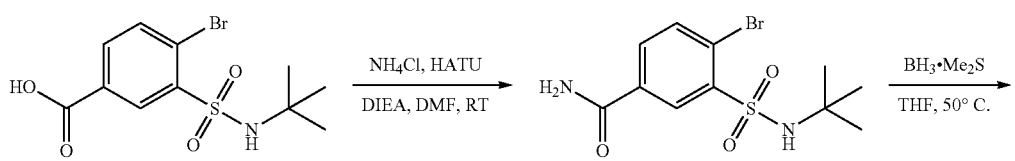

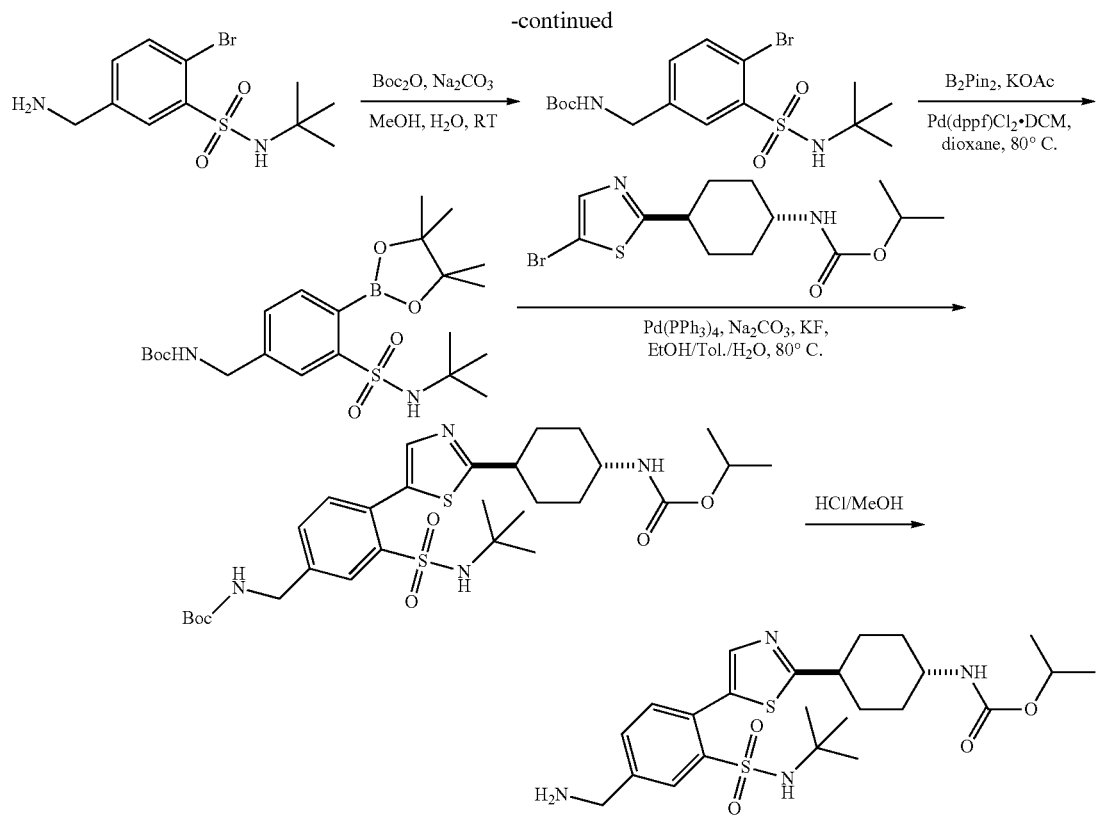

a) Synthesis of 4-bromo-3-(tert-butylsulfamoyl)benzamide (General Method A)

b) Synthesis of 5-(aminomethyl)-2-bromo-N-tert-butyl-benzene sulfonamide

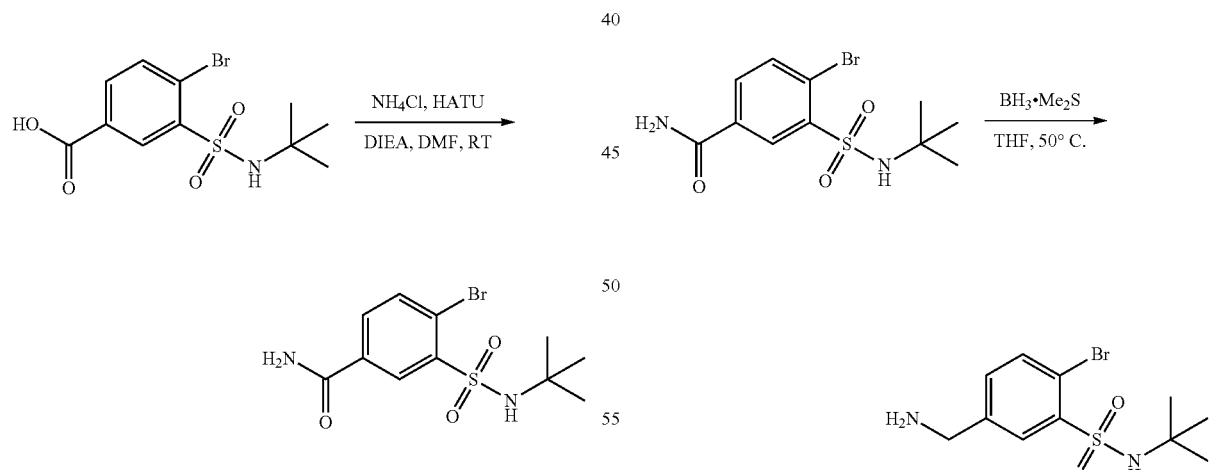

To a solution of 4-bromo-3-(tert-butylsulfamoyl)benzoic acid (1.9 g, 5.65 mmol, 1.0 eq.) and DIEA (84.77 mmol, 14.77 mL, 15.0 eq.) in DMF (50 mL) was added NH$_4$Cl (3.02 g, 56.51 mmol, 10.0 eq.) and HATU (2.79 g, 7.35 mmol, 1.3 eq.). The mixture was stirred at 25° C. for 12 h, then poured into H$_2$O (200 mL) and extracted with EtOAc (30 mL×3). The combined organic layers were washed with brine (100 mL), dried over Na$_2$SO$_4$, filtered and concentrated to give 4-bromo-3-(tert-butylsulfamoyl)benzamide (2.2 g, crude) as a yellow gum. [M+H]=335.0/337.0.

To a solution of 4-bromo-3-(tert-butylsulfamoyl)benzamide (1 g, 2.98 mmol, 1.0 eq.) in THF (30 mL) was added BH$_3$·Me$_2$S (10 M in THF, 1.49 mL, 5 eq.). The mixture was stirred at 50° C. for 2 h. The reaction mixture was quenched by 1N HCl (2 mL) at 0° C., stirred at 50° C. for 1 hr, then concentrated under reduced pressure to give 5-(aminomethyl)-2-bromo-N-tert-butyl-benzenesulfonamide (1.5 g, crude, HCl salt) as a white solid. [M+H]=321.1/323.1.

c) Synthesis of tert-butyl N-[[4-bromo-3-(tert-butylsulfamoyl)phenyl]methyl]carbamate d) Synthesis of tert-butyl N-[[3-(tert-butylsulfamoyl)-4-(4,4,5,5-tetramethyl-1,3,2-dioxaborolan-2-yl)phenyl]methyl]carbamate (General Method B)

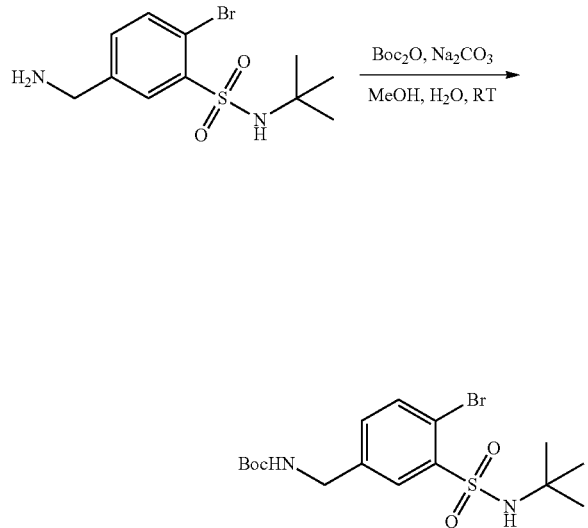

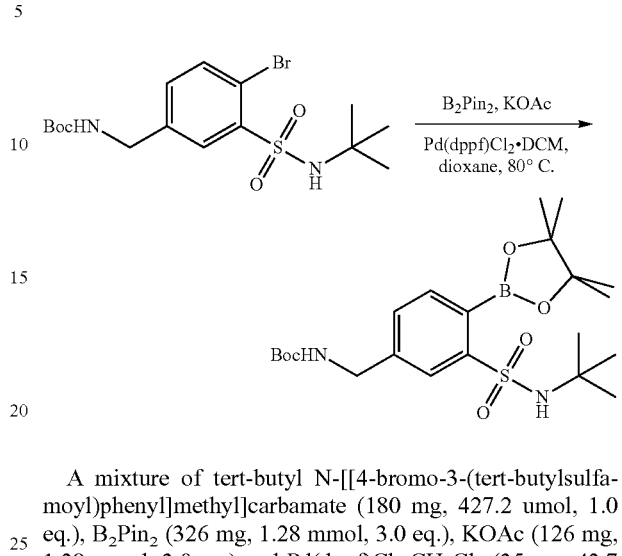

To a solution of 5-(aminomethyl)-2-bromo-N-tert-butylbenzenesulfonamide (HCl salt, 1.5 g, 4.67 mmol, 1.0 eq.) and Boc$_2$O (1.22 g, 5.60 mmol, 1.2 eq.) in MeOH (10 mL) and H$_2$O (10 mL) was added Na$_2$CO$_3$ (990 mg, 9.34 mmol, 2.0 eq.). The mixture was stirred at 25° C. for 12 h under N$_2$ atmosphere and then concentrated. The residue was purified by prep-HPLC to give tert-butyl N-[[4-bromo-3-(tert-butylsulfamoyl)phenyl]methyl]carbamate (190 mg, 451 umol, 10% yield) as a white solid. $^1$H NMR (400 MHz, CDCl$_3$) δ=7.99 (d, J=1.3 Hz, 1H), 7.59 (d, J=8.2 Hz, 1H), 7.27-7.22 (m, 1H), 4.25 (br d, J=5.7 Hz, 2H), 1.38 (s, 9H), 1.14 (s, 9H). [M+Na]=443.1/445.1.

A mixture of tert-butyl N-[[4-bromo-3-(tert-butylsulfamoyl)phenyl]methyl]carbamate (180 mg, 427.2 umol, 1.0 eq.), B$_2$Pin$_2$ (326 mg, 1.28 mmol, 3.0 eq.), KOAc (126 mg, 1.28 mmol, 3.0 eq.) and Pd(dppf)Cl$_2$.CH$_2$Cl$_2$ (35 mg, 42.7 umol, 0.1 eq.) in dioxane (5 mL) was degassed and purged with N$_2$ for 3 times and stirred at 80° C. for 12 h. The reaction mixture was concentrated and the residue was purified by prep-TLC (SiO$_2$, Petroleum ether/Ethyl acetate=3/1) to give tert-butyl N-[[3-(tert-butylsulfamoyl)-4-(4,4,5,5-tetramethyl-1,3,2-dioxaborolan-2-yl)phenyl]methyl]carbamate (20 mg, 42.7 umol, 10% yield) as a yellow gum. ESI [M+H]=469.2.

e) Synthesis of isopropyl N-[trans-4-[5-[4-[(tert-butoxycarbonylamino)methyl]-2-(tert-butylsulfamoyl)phenyl]thiazol-2-yl]cyclohexyl]carbamate (General Method C)

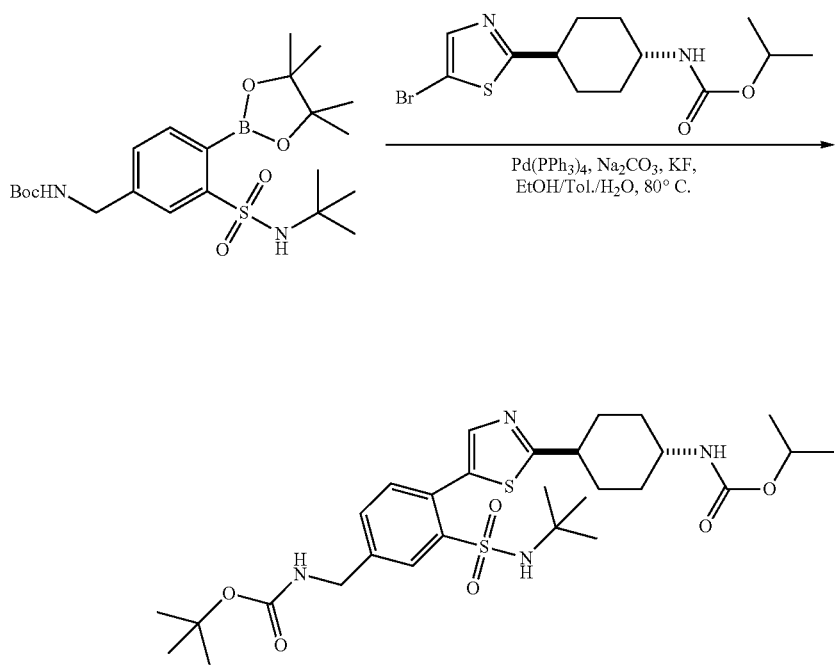

A mixture of tert-butyl N-[[3-(tert-butylsulfamoyl)-4-(4,4,5,5-tetramethyl-1,3,2-dioxaborolan-2-yl)phenyl]methyl]carbamate (20 mg, 42.7 umol, 1.0 eq.), isopropyl (trans-4-(5-bromothiazol-2-yl)cyclohexyl)carbamate (18 mg, 51.2 umol, 1.2 eq.), Na$_2$CO$_3$ (14 mg, 128 umol, 3.0 eq.), Pd(PPh$_3$)$_4$ (4.9 mg, 4.3 umol, 0.1 eq.) and KF (7.4 mg, 128 umol, 3.0 uL, 3.0 eq.) in EtOH (1 mL)/H$_2$O (0.3 mL)/Tol. (1 mL) was degassed and purged with N$_2$ for 3 times and then stirred at 80° C. for 12 h. The reaction mixture was concentrated and the residue was purified by prep-TLC (SiO$_2$, Petroleum ether/Ethyl acetate=2/1) to give isopropyl N-[trans-4-[5-[4-[(tert-butoxycarbonylamino)methyl]-2-(tert-butylsulfamoyl)phenyl]thiazol-2-yl]cyclohexyl]carbamate (20 mg, crude) as a yellow gum. ESI [M+H]=609.3.

f) Synthesis of isopropyl (trans-4-(5-(4-(aminomethyl)-2-(N-(tert-butyl)sulfamoyl)phenyl)thiazol-2-yl)cyclohexyl)carbamate (Compound 1)

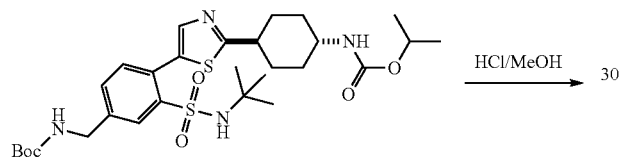

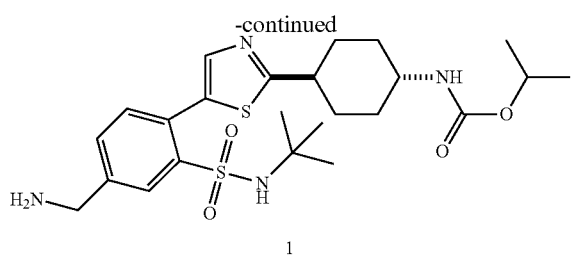

A solution of isopropyl N-[trans-4-[5-[4-[(tert-butoxycarbonylamino)methyl]-2-(tert-butylsulfamoyl)phenyl]thiazol-2-yl]cyclohexyl]carbamate (20 mg, crude) in HCl/MeOH (4 M, 1 mL) was stirred at 25° C. for 30 mins. The reaction mixture was concentrated and the residue was purified by prep-HPLC (column: Nano-Micro UniSil 5-100 C18 ULTRA 100*250 mm 5 um; mobile phase: [water(0.1% TFA)-ACN]; B %: 30%-60%,10 min) to give isopropyl (trans-4-(5-(4-(aminomethyl)-2-(N-(tert-butyl)sulfamoyl)phenyl)thiazol-2-yl)cyclohexyl)carbamate (1.03 mg, 1.47 umol, 89% purity, TFA salt) as a pale yellow solid. $^1$H NMR (400 MHz, methanol-d$_4$) δ=8.32 (d, J=1.7 Hz, 1H), 7.81 (s, 1H), 7.75-7.70 (m, 1H), 7.60 (d, J=7.8 Hz, 1H), 4.86-4.82 (m, 1H), 4.28 (s, 2H), 3.52-3.43 (m, 1H), 3.11-3.00 (m, 1H), 2.26 (br d, J=13.7 Hz, 2H), 2.09 (br d, J=11.1 Hz, 2H), 1.79-1.68 (m, 2H), 1.50-1.37 (m, 2H), 1.25 (br d, J=6.1 Hz, 6H), 1.09 (s, 9H). ESI [M+H]=509.2.

Example 2

Preparation of isopropyl (trans-4-(5-(4-(acetamidomethyl)-2-(N-(tert-butyl)sulfamoyl)phenyl)thiazol-2-yl)cyclohexyl)carbamate (Compound 2)

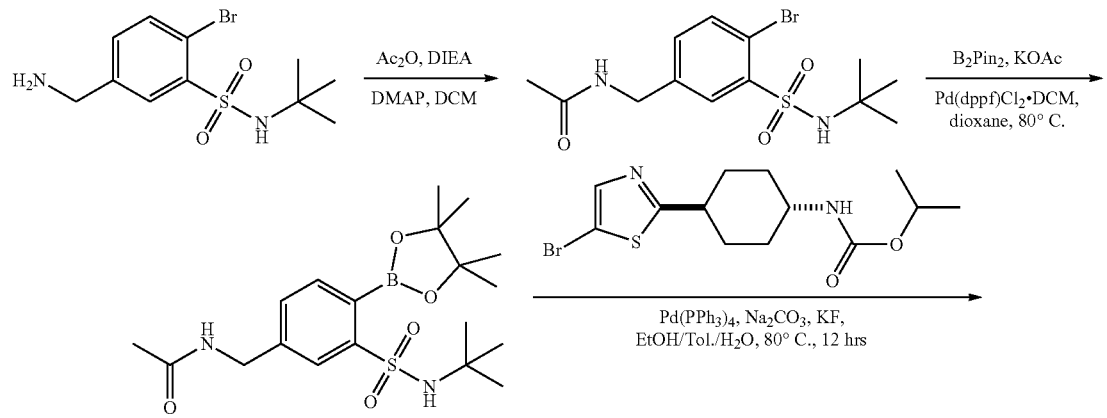

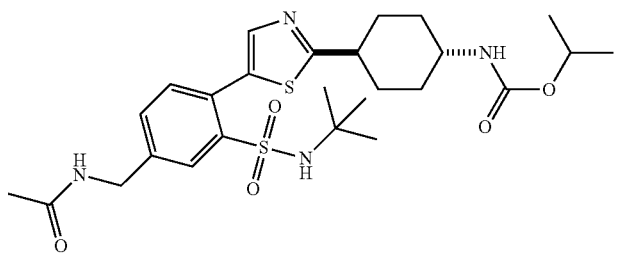

a) Synthesis of N-[[4-bromo-3-(tert-butylsulfamoyl)phenyl]methyl]acetamide

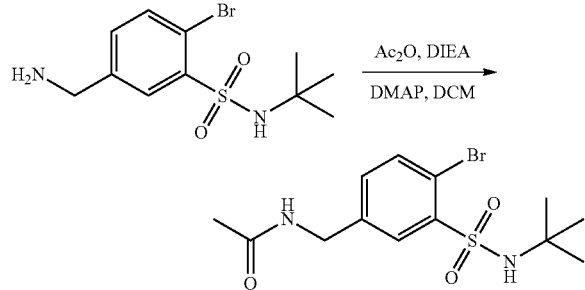

To a solution of 5-(aminomethyl)-2-bromo-N-tert-butyl-benzenesulfonamide (0.4 g, 1.25 mmol, 1.0 eq.) in DCM (5 mL) were added DIEA (6.25 mmol, 1.1 mL, 5.0 eq.), DMAP (15.2 mg, 125 umol, 0.1 eq.) and Ac₂O (153 mg, 1.5 mmol, 1.2 eq.). The mixture was stirred at 25° C. for 1 hr, then poured into H₂O (20 mL) and extracted with EtOAc (20 mL×3). The combined organic layers were dried over Na₂SO₄, filtered and concentrated to give N-[[4-bromo-3-(tert-butylsulfamoyl)phenyl]methyl]acetamide (320 mg, crude) as a yellow oil. ESI [M+H]=363.1/365.1 b) Synthesis of N-[[3-(tert-butylsulfamoyl)-4-(4,4,5,5-tetramethyl-1,3,2-dioxaborolan-2-yl)phenyl]methyl]acetamide

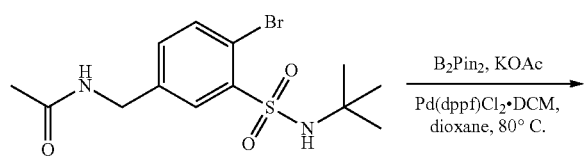

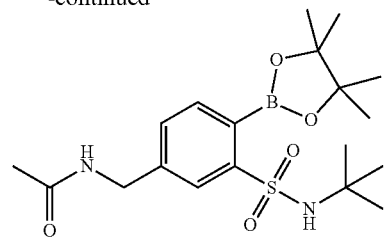

A mixture of N-[[4-bromo-3-(tert-butylsulfamoyl)phenyl]methyl]acetamide (0.3 g, 826 umol, 1.0 eq.), B₂Pin₂ (629 mg, 2.5 mmol, 3.0 eq.), KOAc (243 mg, 2.5 mmol, 3 eq.) and Pd(dppf)Cl₂·CH₂Cl₂ (67.5 mg, 82.6 umol, 0.1 eq.) in dioxane (5 mL) was degassed and purged with N₂ for 3 times and then stirred at 80° C. for 12 h. The reaction mixture was concentrated and the residue was purified by column chromatography (SiO₂, Petroleum ether/Ethyl acetate=10/1 to 0:1) to give N-[[3-(tert-butylsulfamoyl)-4-(4,4,5,5-tetramethyl-1,3,2-dioxaborolan-2-yl)phenyl]methyl]acetamide (70 mg, 171 umol, 21% yield) as a yellow gum. ESI [M+H]=411.3.

c) Synthesis of isopropyl (trans-4-(5-(4-(acetamidomethyl)-2-(N-(tert-butyl)sulfamoyl)phenyl)thiazol-2-yl)cyclohexyl)carbamate (Compound 2)

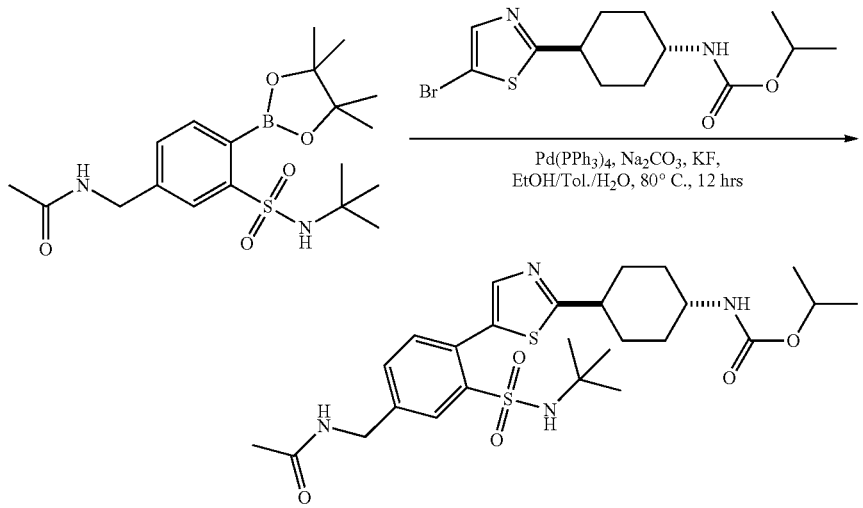

A mixture of N-[[3-(tert-butylsulfamoyl)-4-(4,4,5,5-tetramethyl-1,3,2-dioxaborolan-2-yl)phenyl]methyl]acetamide (66 mg, 161 umol, 0.93 eq.), isopropyl N-[trans-4-(5-bromothiazol-2-yl)cyclohexyl]carbamate (60 mg, 173 umol, 1.0 eq.), Na₂CO₃ (54.9 mg, 518 umol, 3.0 eq.), KF (30.1 mg, 518 umol, 3.0 eq.) and Pd(PPh₃)₄ (19.9 mg, 17.3 umol, 0.1 eq.) in H₂O (0.3 mL)/EtOH (1.0 mL)/Tol. (1.0 mL) was degassed and purged with N₂ for 3 times. The mixture was stirred at 80° C. for 12 h under N₂ atmosphere and then concentrated. The residue was purified by prep-TLC (SiO₂, Petroleum ether/Ethyl acetate=1/1) to give isopropyl (trans-4-(5-(4-(acetamidomethyl)-2-(N-(tert-butyl)sulfamoyl)phenyl)thiazol-2-yl)cyclohexyl)carbamate (16.99 mg, 30.85 umol, 18% yield, 100% purity) as a white solid. ¹H NMR (400 MHz, methanol-d₄) δ=8.10 (d, J=1.6 Hz, 1H), 7.81 (s, 1H), 7.57 (dd, J=1.6, 7.9 Hz, 1H), 7.47 (d, J=7.8 Hz, 1H), 4.88-4.81 (m, 1H), 4.48 (s, 2H), 3.52-3.43 (m, 1H), 3.07 (br t, J=12.2 Hz, 1H), 2.26 (br d, J=12.1 Hz, 2H), 2.10 (br d, J=9.9 Hz, 2H), 2.04 (s, 3H), 1.80-1.66 (m, 2H), 1.50-1.38 (m, 2H), 1.24 (d, J=6.1 Hz, 6H), 1.11 (s, 9H). ESI [M+H]=551.2.

Example 3

Preparation of isopropyl (trans-4-(5-(2-(N-(tert-butyl)sulfamoyl)-4-(pyrazolo[1,5-a]pyridin-3-yl)phenyl)thiazol-2-yl)cyclohexyl)carbamate (Compound 3)

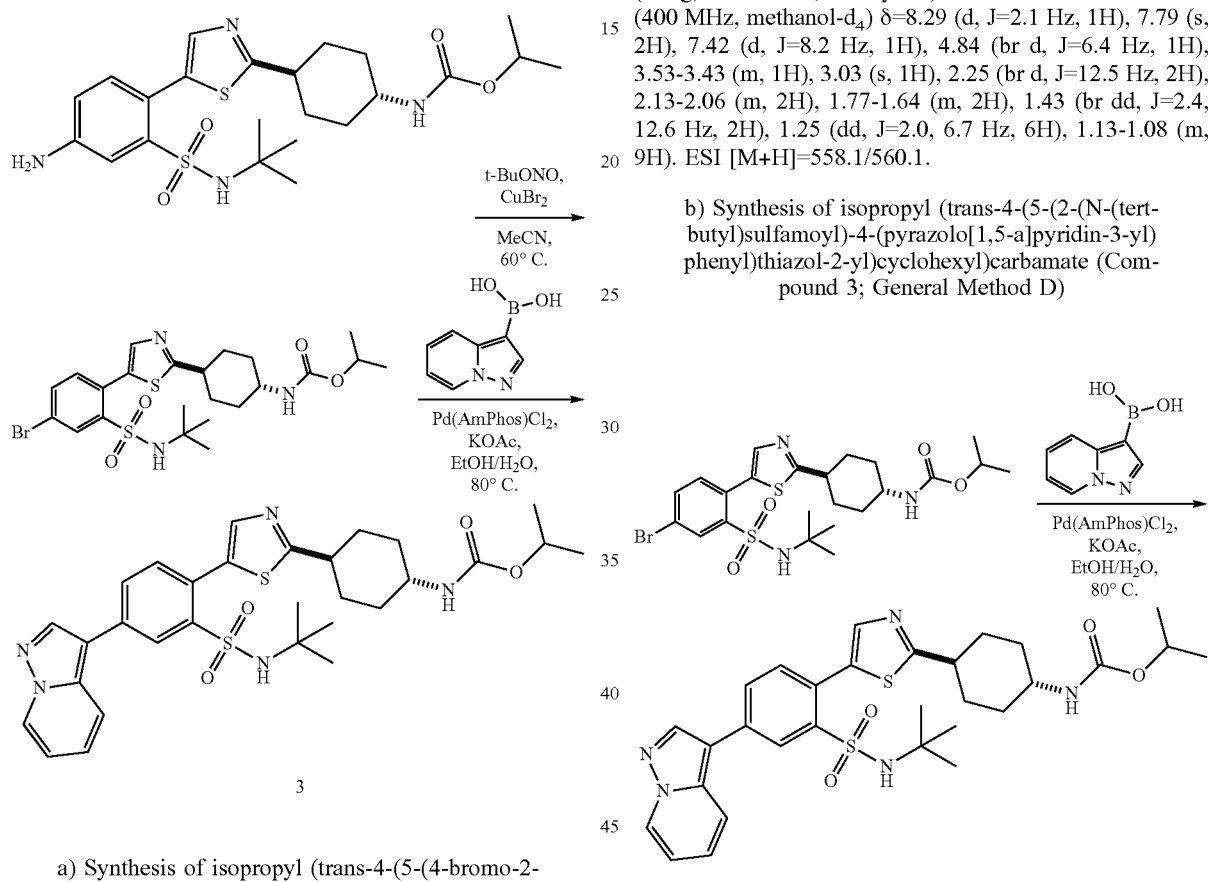

a) Synthesis of isopropyl (trans-4-(5-(4-bromo-2-(N-(tert-butyl)sulfamoyl)phenyl)thiazol-2-yl)cyclohexyl)carbamate

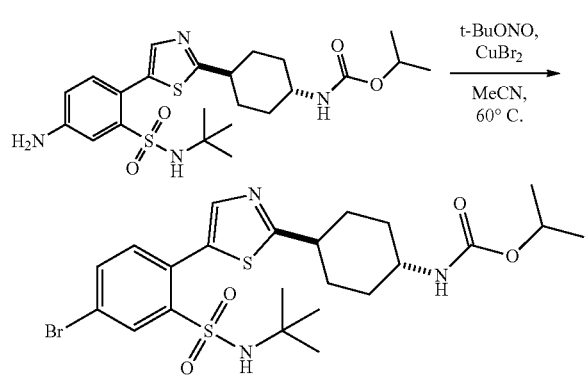

To a solution of tert-butyl nitrite (2.2 g, 21.2 mmol, 1.5 eq.) in MeCN (20 mL) was added CuBr$_2$ (3.16 g, 14.2 mmol, 1.0 eq.) and isopropyl (trans-4-(5-(4-amino-2-(N-(tert-butyl)sulfamoyl)phenyl)thiazol-2-yl)cyclohexyl)carbamate (7.0 g, 14.2 mmol, 1.0 eq.). The mixture was stirred at 60° C. for 1 hr, then poured into 1N NaHCO$_3$ solution (100 mL) at 25° C. and extracted with EtOAc (50 mL×3). The combined organic layers dried over Na$_2$SO$_4$, filtered and concentrated. The residue was purified by column chromatography (SiO$_2$, Petroleum ether/Ethyl acetate=10:1 to 5:1 to 0:1) to give isopropyl (trans-4-(5-(4-bromo-2-(N-(tert-butyl)sulfamoyl)phenyl)thiazol-2-yl) cyclohexyl)carbamate (4.2 g, 7.52 mmol, 53% yield) as a white solid. $^1$H NMR (400 MHz, methanol-d$_4$) δ=8.29 (d, J=2.1 Hz, 1H), 7.79 (s, 2H), 7.42 (d, J=8.2 Hz, 1H), 4.84 (br d, J=6.4 Hz, 1H), 3.53-3.43 (m, 1H), 3.03 (s, 1H), 2.25 (br d, J=12.5 Hz, 2H), 2.13-2.06 (m, 2H), 1.77-1.64 (m, 2H), 1.43 (br dd, J=2.4, 12.6 Hz, 2H), 1.25 (dd, J=2.0, 6.7 Hz, 6H), 1.13-1.08 (m, 9H). ESI [M+H]=558.1/560.1.

b) Synthesis of isopropyl (trans-4-(5-(2-(N-(tert-butyl)sulfamoyl)-4-(pyrazolo[1,5-a]pyridin-3-yl)phenyl)thiazol-2-yl)cyclohexyl)carbamate (Compound 3; General Method D)

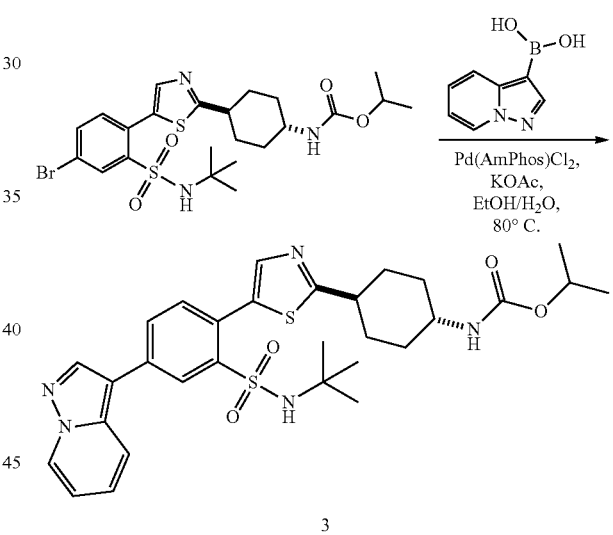

A mixture of isopropyl (trans-4-(5-(4-bromo-2-(N-(tert-butyl)sulfamoyl)phenyl) thiazol-2-yl)cyclohexyl)carbamate (40 mg, 71.6 umol, 1.0 eq.), 3-(4,4,5,5-tetramethyl-1,3,2-dioxaborolan-2-yl)pyrazolo[1,5-a]pyridine (21 mg, 86 umol, 1.2 eq.), KOAc (21.08 mg, 214.84 umol, 3.0 eq.) and Pd(AmPhos)Cl$_2$ (5.07 mg, 7.16 umol, 0.1 eq.) in EtOH (1 mL)/H$_2$O (0.25 mL) was degassed and purged with N$_2$ for 3 times, and then stirred at 80° C. for 12 h. The reaction mixture was concentrated and the residue was purified by prep-HPLC (column: Welch Ultimate AQ-C18 150*30 mm*5 um; mobile phase: [water(0.1% TFA)-ACN]; B %: 50%-80%,12 min) to give isopropyl (trans-4-(5-(2-(N-(tert-butyl)sulfamoyl)-4-(pyrazolo[1,5-a]pyridin-3-yl)phenyl) thiazol-2-yl)cyclohexyl)carbamate (22.64 mg, 37.62 umol, 52.53% yield, 99% purity) as a white solid. $^1$H NMR (400 MHz, DMSO-d$_6$) δ=8.82 (d, J=7.0 Hz, 1H), 8.52 (s, 1H), 8.34 (d, J=1.8 Hz, 1H), 8.03 (d, J=9.0 Hz, 1H), 7.98-7.94 (m, 1H), 7.77 (s, 1H), 7.56 (d, J=7.9 Hz, 1H), 7.50-7.43 (m, 1H), 7.17 (s, 1H), 7.09-7.00 (m, 2H), 4.76 (td, J=6.2, 12.5 Hz, 1H), 2.95 (tt, J=3.6, 11.9 Hz, 1H), 2.16 (br d, J=11.6 Hz, 2H), 1.94 (br d, J=10.4 Hz, 2H), 1.68-1.55 (m, 2H), 1.43-1.31 (m, 2H), 1.18 (d, J=6.2 Hz, 6H), 1.08 (s, 9H). ESI [M+H]=596.2.

Example 4

Preparation of isopropyl (trans-4-(5-(2-(N-(tert-butyl)sulfamoyl)-4-(1-(2,2,2-trifluoroethyl)-1H-pyrazol-4-yl)phenyl)thiazol-2-yl)cyclohexyl)carbamate (Compound 4)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-d$_6$) δ=8.43 (s, 1H), 8.19 (d, J=1.8 Hz, 1H), 8.12 (s, 1H), 7.84 (dd, J=1.8, 7.9 Hz, 1H), 7.70 (s, 1H), 7.45 (d, J=7.9 Hz, 1H), 7.07-6.89 (m, 2H), 5.17 (q, J=9.0 Hz, 2H), 4.71 (td, J=6.2, 12.3 Hz, 1H), 3.36-3.21 (m, 1H), 2.89 (ddd, J=3.3, 8.5, 11.7 Hz, 1H), 2.11 (br d, J=11.7 Hz, 2H), 1.89 (br d, J=10.4 Hz, 2H), 1.55 (dq, J=2.5, 12.7 Hz, 2H), 1.37-1.25 (m, 2H), 1.13 (d, J=6.2 Hz, 6H), 1.01 (s, 9H). ESI [M+H]=628.2.

Example 5

Preparation of isopropyl (trans-4-(5-(2-(N-(tert-butyl)sulfamoyl)-4-(pyridin-3-yl)phenyl)thiazol-2-yl)cyclohexyl)carbamate (Compound 5)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-d$_6$) δ=9.21 (s, 1H), 8.84 (br d, J=5.1 Hz, 1H), 8.67 (br d, J=7.9 Hz, 1H), 8.41 (s, 1H), 8.07 (br d, J=7.9 Hz, 1H), 8.00-7.89 (m, 1H), 7.77 (s, 1H), 7.65 (d, J=7.9 Hz, 1H), 7.10 (s, 1H), 6.98 (br d, J=7.1 Hz, 1H), 4.71 (td, J=6.0, 12.2 Hz, 1H), 3.37-3.23 (m, 1H), 2.92 (br t, J=11.8 Hz, 1H), 2.12 (br d, J=12.1 Hz, 2H), 1.90 (br d, J=11.0 Hz, 2H), 1.63-1.49 (m, 2H), 1.38-1.27 (m, 2H), 1.13 (d, J=6.2 Hz, 6H), 1.00 (s, 9H). ESI [M+H]=557.2.

Example 6

Preparation of isopropyl (trans-4-(5-(2-(N-(tert-butyl)sulfamoyl)-4-(1H-pyrazol-3-yl)phenyl)thiazol-2-yl)cyclohexyl)carbamate (Compound 6)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-d$_6$) δ=8.52 (d, J=1.54 Hz, 1H), 7.99 (dd, J=1.76, 7.94 Hz, 1H), 7.81 (d, J=1.98 Hz, 1H), 7.73 (s, 1H), 7.49 (d, J=7.94 Hz, 1H), 7.07 (s, 1H), 7.00 (br d, J=7.50 Hz, 1H), 6.81 (d, J=2.21 Hz, 1H), 4.73 (td, J=6.17, 12.35 Hz, 1H), 3.31 (br d, J=7.94 Hz, 1H), 2.85-2.98 (m, 1H), 2.13 (br d, J=12.35 Hz, 2H), 1.91 (br d, J=9.92 Hz, 2H), 1.50-1.67 (m, 2H), 1.25-1.43 (m, 2H), 1.15 (d, J=6.39 Hz, 6H), 1.04 (s, 9H). ESI [M+H]=546.2.

Example 7

Preparation of isopropyl (trans-4-(5-(2-(N-(tert-butyl)sulfamoyl)-4-(6-hydroxy pyridin-3-yl)phenyl) thiazol-2-yl)cyclohexyl)carbamate (Compound 7)

From isopropyl (trans-4-(5-(4-bromo-2-(N-(tert-butyl)sulfamoyl)phenyl)thiazol-2-yl)cyclohexyl)carbamate, using the corresponding boric acid or boronate and under the same reaction conditions as for Compound 3. $^1$H NMR (400 MHz, DMSO-d$_6$) δ=8.17 (d, J=1.8 Hz, 1H), 7.93-7.81 (m, 3H), 7.74 (br s, 1H), 7.50 (d, J=8.1 Hz, 1H), 7.11 (br s, 1H), 7.03 (br d, J=7.6 Hz, 1H), 6.50 (d, J=9.4 Hz, 1H), 4.75 (td, J=6.1, 12.4 Hz, 1H), 3.40-3.24 (m, 1H), 2.95 (br d, J=9.9 Hz, 1H), 2.15 (br d, J=12.2 Hz, 2H), 1.93 (br d, J=10.0 Hz, 2H), 1.68-1.52 (m, 2H), 1.41-1.30 (m, 2H), 1.17 (d, J=6.2 Hz, 6H), 1.05 (s, 9H). ESI [M+H]=573.2.

Example 8

Preparation of isopropyl (trans-4-(5-(2-(N-(tert-butyl)sulfamoyl)-4-(2,4-dimethoxy pyrimidin-5-yl) phenyl)thiazol-2-yl)cyclohexyl)carbamate (Compound 8)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-d$_6$) δ=8.50 (s, 1H), 8.25 (d, J=1.8 Hz, 1H), 7.86-7.72 (m, 2H), 7.56 (d, J=8.1 Hz, 1H), 7.21 (s, 1H), 7.05 (br d, J=7.8 Hz, 1H), 4.75 (td, J=6.1, 12.4 Hz, 1H), 3.98 (d, J=4.0 Hz, 6H), 3.42-3.26 (m, 1H), 2.94 (tt, J=3.5, 11.9 Hz, 1H), 2.16 (br d, J=12.0 Hz, 2H), 1.93 (br d, J=10.0 Hz, 2H), 1.67-1.52 (m, 2H), 1.44-1.27 (m, 2H), 1.17 (d, J=6.2 Hz, 6H), 1.13-1.03 (m, 9H). ESI [M+H]=618.3.

Example 9

Preparation of isopropyl (trans-4-(5-(2-(N-(tert-butyl)sulfamoyl)-4-(2H-indazol-6-yl)phenyl)thiazol-2-yl)cyclohexyl)carbamate (Compound 9)

From isopropyl (trans-4-(5-(4-bromo-2-(N-(tert-butyl)sulfamoyl)phenyl)thiazol-2-yl)cyclohexyl)carbamate, using the corresponding boric acid or boronate and under the same reaction conditions as for Compound 3. $^1$H NMR (400 MHz, DMSO-d$_6$) δ=8.39 (d, J=1.7 Hz, 1H), 8.15 (s, 1H), 8.02 (dd, J=1.8, 8.0 Hz, 1H), 7.93 (d, J=8.3 Hz, 1H), 7.84 (s, 1H), 7.79 (s, 1H), 7.60 (d, J=7.9 Hz, 1H), 7.49 (d, J=8.4 Hz, 1H), 7.21 (s, 1H), 7.03 (br d, J=7.6 Hz, 1H), 4.76 (td, J=6.2, 12.4 Hz, 1H), 3.34 (br d, J=7.3 Hz, 1H), 3.01-2.90 (m, 1H), 2.17 (br d, J=12.1 Hz, 2H), 1.94 (br d, J=10.4 Hz, 2H), 1.67-1.53 (m, 2H), 1.43-1.30 (m, 2H), 1.18 (d, J=6.2 Hz, 6H), 1.09 (s, 9H). ESI [M+H]=596.3.

Example 10

Preparation of isopropyl (trans-4-(5-(4-(2-aminopyrimidin-5-yl)-2-(N-(tert-butyl)sulfamoyl)phenyl) thiazol-2-yl)cyclohexyl)carbamate (Compound 10)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-d$_6$) δ=8.66 (s, 2H), 8.23 (d, J=1.7 Hz, 1H), 7.90 (dd, J=1.8, 8.0 Hz, 1H), 7.78-7.69 (m, 1H), 7.53 (d, J=7.9 Hz, 1H), 7.10 (s, 1H), 7.05-6.97 (m, 3H), 4.75 (td, J=6.2, 12.4 Hz, 1H), 3.42-3.26 (br s, 1H), 2.94 (tt, J=3.5, 11.8 Hz, 1H), 2.15 (br d, J=12.0 Hz, 2H), 1.93 (br d, J=10.3 Hz, 2H), 1.67-1.51 (m, 2H), 1.43-1.27 (m, 2H), 1.17 (d, J=6.2 Hz, 6H), 1.06 (s, 9H). ESI [M+H]=573.2.

Example 11

Preparation of isopropyl (trans-4-(5-(4-(benzofuran-5-yl)-2-(N-(tert-butyl)sulfamoyl)phenyl)thiazol-2-yl)cyclohexyl)carbamate (Compound 11)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-d$_6$) δ=8.32 (d, J=2.0 Hz, 1H), 8.06 (d, J=2.2 Hz, 1H), 8.01 (d, J=1.5 Hz, 1H), 7.95 (dd, J=2.0, 7.9 Hz, 1H), 7.77-7.71 (m, 2H), 7.68-7.64 (m, 1H), 7.56 (d, J=7.9 Hz, 1H), 7.12 (s, 1H), 7.07-7.04 (m, 1H), 7.03-6.98 (m, 1H), 4.78-4.68 (m, 1H), 3.27 (br s, 1H), 2.98-2.86 (m, 1H), 2.21-2.09 (m, 2H), 1.91 (br dd, J=2.0, 12.3 Hz, 2H), 1.56 (br d, J=2.2 Hz, 2H), 1.40-1.27 (m, 2H), 1.15 (d, J=6.2 Hz, 6H), 1.05 (s, 9H). ESI [M+H]=596.2.

Example 12

Preparation of isopropyl (trans-4-(5-(2-(N-(tert-butyl)sulfamoyl)-4-(pyrimidin-5-yl)phenyl)thiazol-2-yl)cyclohexyl)carbamate (Compound 12)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-d$_6$) δ=9.23 (s, 1H), 9.18 (s, 2H), 8.37 (d, J=2.0 Hz, 1H), 8.05 (dd, J=1.9, 8.0 Hz, 1H), 7.75 (s, 1H), 7.63 (d, J=7.9 Hz, 1H), 7.13 (s, 1H), 7.01 (br d, J=7.7 Hz, 1H), 4.71 (s, 1H), 3.31 (br d, J=7.72 Hz, 1H), 2.97-2.86 (m, 1H), 2.12 (br d, J=11.7 Hz, 2H), 1.89 (br d, J=10.1 Hz, 2H), 1.56 (dq, J=2.9, 12.8 Hz, 2H), 1.36-1.25 (m, 2H), 1.13 (d, J=6.4 Hz, 6H), 1.02 (s, 9H). ESI [M+H]=558.2.

Example 13

Preparation of isopropyl (trans-4-(5-(2-(N-(tert-butyl)sulfamoyl)-4-(3,6-dimethoxypyridazin-4-yl)phenyl)thiazol-2-yl)cyclohexyl)carbamate (Compound 13)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-d$_6$) δ 8.33 (d, J=1.76 Hz, 1H), 7.87 (dd, J=1.76, 7.94 Hz, 1H), 7.76 (s, 1H), 7.59 (d, J=7.94 Hz, 1H), 7.35 (s, 1H), 7.22 (s, 1H), 6.93-7.05 (m, 1H), 4.73 (td, J=6.17, 12.35 Hz, 1H), 3.99 (d, J=2.20 Hz, 6H), 3.31 (br d, J=7.72 Hz, 1H), 2.81-3.01 (m, 1H), 2.13 (br d, J=12.57 Hz, 2H), 1.84-1.99 (m, 2H), 1.49-1.64 (m, 2H), 1.24-1.43 (m, 2H), 1.15 (d, J=6.17 Hz, 6H), 1.08 (s, 9H). ESI [M+H]=618.2.

Example 14

Preparation of isopropyl (trans-4-(5-(2-(N-(tert-butyl)sulfamoyl)-4-(2-methylthiazol-5-yl)phenyl)thiazol-2-yl)cyclohexyl)carbamate (Compound 14)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-d$_6$) δ=8.24-8.15 (m, 2H), 7.93 (dd, J=2.0, 8.1 Hz, 1H), 7.77 (s, 1H), 7.55 (d, J=8.1 Hz, 1H), 7.27 (s, 1H), 7.03 (br d, J=7.7 Hz, 1H), 4.75 (td, J=6.2, 12.4 Hz, 1H), 3.39-3.25 (m, 1H), 2.94 (tt, J=3.4, 11.8 Hz, 1H), 2.72 (s, 3H), 2.15 (br d, J=11.9 Hz, 2H), 1.93 (br d, J=10.5 Hz, 2H), 1.59 (dq, J=2.9, 12.7 Hz, 2H), 1.41-1.29 (m, 2H), 1.17 (d, J=6.2 Hz, 6H), 1.07 (s, 9H). ESI [M+H]=577.2.

Example 15

Preparation of isopropyl (trans-4-(5-(4-(benzo[d]thiazol-6-yl)-2-(N-(tert-butyl)sulfamoyl)phenyl)thiazol-2-yl)cyclohexyl)carbamate (Compound 15)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-d$_6$) δ=9.47 (s, 1H), 8.63 (d, J=1.6 Hz, 1H), 8.42 (d, J=2.0 Hz, 1H), 8.24 (d, J=8.6 Hz, 1H), 8.05 (dd, J=2.0, 8.1 Hz, 1H), 7.92 (dd, J=1.8, 8.6 Hz, 1H), 7.79 (s, 1H), 7.63 (d, J=8.1 Hz, 1H), 7.14 (s, 1H), 7.09-6.95 (m, 1H), 4.76 (td, J=6.3, 12.4 Hz, 1H), 3.34 (br d, J=4.6 Hz, 1H), 3.02-2.89 (m, 1H), 2.17 (br d, J=11.9 Hz, 2H), 1.94 (br d, J=10.4 Hz, 2H), 1.68-1.54 (m, 2H), 1.42-1.30 (m, 2H), 1.18 (d, J=6.2 Hz, 6H), 1.07 (s, 9H). ESI [M+H]=613.2.

Example 16

Preparation of isopropyl (trans-4-(5-(2-(N-(tert-butyl)sulfamoyl)-4-(5-((dimethylamino)methyl)pyridin-3-yl)phenyl)thiazol-2-yl)cyclohexyl)carbamate (Compound 16)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-d$_6$) δ=9.08 (d, J=2.1 Hz, 1H), 8.75 (d, J=1.7 Hz, 1H), 8.42 (d, J=1.8 Hz, 1H), 8.36 (s, 1H), 8.07 (dd, J=2.0, 7.9 Hz, 1H), 7.80 (s, 1H), 7.68 (d, J=7.9 Hz, 1H), 7.14-6.96 (m, 2H), 4.75 (td, J=6.1, 12.4 Hz, 1H), 4.46 (br s, 2H), 3.45-3.25 (m, 1H), 3.07-2.89 (m, 1H), 2.83 (br s, 6H), 2.17 (br d, J=11.7 Hz, 2H), 1.94 (br d, J=10.3 Hz, 2H), 1.69-1.52 (m, 2H), 1.46-1.27 (m, 2H), 1.17 (d, J=6.2 Hz, 6H), 1.03 (s, 9H). ESI [M+H]=614.3.

Example 17

Preparation of isopropyl (trans-4-(5-(2-(N-(tert-butyl)sulfamoyl)-4-(5-methyl-1H-pyrazol-4-yl)phenyl)thiazol-2-yl)cyclohexyl)carbamate (Compound 17)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-$d_6$) δ=8.12 (d, J=1.8 Hz, 1H), 7.93 (s, 1H), 7.76-7.69 (m, 2H), 7.48 (d, J=7.9 Hz, 1H), 7.15-7.00 (m, 2H), 4.75 (td, J=6.2, 12.5 Hz, 1H), 3.40-3.26 (m, 1H), 2.93 (tt, J=3.4, 11.8 Hz, 1H), 2.43 (s, 3H), 2.15 (br d, J=12.0 Hz, 2H), 1.93 (br d, J=10.4 Hz, 2H), 1.59 (dq, J=2.8, 12.7 Hz, 2H), 1.41-1.29 (m, 2H), 1.17 (d, J=6.2 Hz, 6H), 1.07 (s, 9H). ESI [M+H]=560.2.

Example 18

Preparation of isopropyl (trans-4-(5-(2-(N-(tert-butyl)sulfamoyl)-4-(6-cyano pyridin-3-yl)phenyl)thiazol-2-yl)cyclohexyl)carbamate (Compound 18)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, methanol-$d_4$) δ=9.08 (d, J=1.5 Hz, 1H), 8.49 (d, J=2.2 Hz, 1H), 8.36-8.32 (m, 1H), 8.04-7.99 (m, 2H), 7.85-7.83 (m, 1H), 7.67 (d, J=7.9 Hz, 1H), 4.81-4.75 (m, 1H), 3.48-3.44 (m, 1H), 3.07-3.03 (m, 1H), 2.27-2.23 (m, 2H), 2.10-2.05 (m, 2H), 1.75-1.69 (m, 2H), 1.46-1.40 (m, 2H), 1.25-1.19 (m, 6H), 1.10 (s, 9H). ESI [M+H]=582.2.

Example 19

Preparation of isopropyl (trans-4-(5-(4-(1H-benzo[d][1,2,3]triazol-6-yl)-2-(N-(tert-butyl)sulfamoyl)phenyl)thiazol-2-yl)cyclohexyl)carbamate (Compound 19)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-$d_6$) δ=8.38 (d, J=2.0 Hz, 1H), 8.23 (br s, 1H), 8.08-8.01 (m, 2H), 7.82-7.74 (m, 2H), 7.59 (d, J=7.9 Hz, 1H), 7.18 (s, 1H), 7.00 (br d, J=7.5 Hz, 1H), 4.73 (td, J=6.2, 12.3 Hz, 1H), 3.31 (td, J=3.7, 7.3 Hz, 1H), 2.96-2.89 (m, 1H), 2.14 (br d, J=11.9 Hz, 2H), 1.91 (br d, J=9.9 Hz, 2H), 1.58 (dq, J=2.8, 12.8 Hz, 2H), 1.39-1.29 (m, 2H), 1.15 (d, J=6.2 Hz, 6H), 1.06 (s, 9H). ESI [M+H]=597.2.

Example 20

Preparation of isopropyl (trans-4-(5-(2-(N-(tert-butyl)sulfamoyl)-4-(6-(hydroxymethyl)pyridin-3-yl)phenyl)thiazol-2-yl)cyclohexyl)carbamate (Compound 20)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-$d_6$) δ=8.92 (s, 1H), 8.36 (d, J=1.6 Hz, 2H), 8.08-8.01 (m, 1H), 7.79 (s, 1H), 7.72 (d, J=7.8 Hz, 1H), 7.64 (d, J=8.1 Hz, 1H), 7.19 (s, 1H), 7.04 (br d, J=8.2 Hz, 1H), 4.78-4.73 (m, 1H), 4.70 (s, 2H), 3.39-3.29 (m, 1H), 3.01-2.89 (m, 1H), 2.16 (br d, J=12.7 Hz, 2H), 1.97-1.90 (m, 2H), 1.60 (dd, J=2.6, 12.4 Hz, 2H), 1.42-1.31 (m, 2H), 1.18 (d, J=6.2 Hz, 6H), 1.06 (s, 9H). ESI [M+H]=587.2.

Example 21

Preparation of isopropyl (trans-4-(5-(2-(N-(tert-butyl)sulfamoyl)-4-(3-methyl-1H-indol-6-yl)phenyl)thiazol-2-yl)cyclohexyl)carbamate (Compound 21)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-$d_6$) δ=8.35 (d, J=2.0 Hz, 1H), 7.95 (dd, J=2.0, 8.1 Hz, 1H), 7.77 (s, 1H), 7.68 (d, J=0.9 Hz, 1H), 7.63 (d, J=8.3 Hz, 1H), 7.55 (d, J=8.1 Hz, 1H), 7.38 (dd, J=1.5, 8.3 Hz, 1H), 7.22 (d, J=0.9 Hz, 1H), 7.17 (s, 1H), 7.04 (br d, J=7.8 Hz, 1H), 4.76 (s, 1H), 3.39-3.28 (m, 1H), 2.99-2.90 (m, 1H), 2.30 (d, J=0.6 Hz, 3H), 2.17 (br d, J=11.5 Hz, 2H), 1.94 (br d, J=10.1 Hz, 2H), 1.60 (dq, J=2.8, 12.7 Hz, 2H), 1.42-1.28 (m, 2H), 1.18 (d, J=6.2 Hz, 6H), 1.09 (s, 9H). ESI [M+H]=609.3.

Example 22

Preparation of isopropyl (trans-4-(5-(2-(N-(tert-butyl)sulfamoyl)-4-(2-(trifluoromethyl)pyridin-4-yl)phenyl)thiazol-2-yl)cyclohexyl)carbamate (Compound 22)

From isopropyl (trans-4-(5-(4-bromo-2-(N-(tert-butyl)sulfamoyl)phenyl) thiazol-2-yl)cyclohexyl)carbamate, using the corresponding boric acid or boronate and under the same reaction conditions as for Compound 3. $^1$H NMR (400 MHz, DMSO-$d_6$) δ=8.91 (d, J=5.0 Hz, 1H), 8.49 (d, J=1.8 Hz, 1H), 8.27 (s, 1H), 8.21 (dd, J=1.8, 8.1 Hz, 1H), 8.13 (d, J=4.9 Hz, 1H), 7.81 (s, 1H), 7.69 (d, J=8.1 Hz, 1H), 7.24 (s, 1H), 7.03 (br d, J=7.8 Hz, 1H), 4.80-4.71 (m, 1H), 3.40-3.27 (m, 1H), 2.90 (s, 1H), 2.17 (br d, J=11.7 Hz, 2H), 1.98-1.88 (m, 2H), 1.67-1.54 (m, 2H), 1.41-1.29 (m, 2H), 1.17 (d, J=6.2 Hz, 6H), 1.06 (s, 9H). ESI [M+H]=625.2.

Example 23

Preparation of isopropyl (trans-4-(5-(2-(N-(tert-butyl)sulfamoyl)-4-hydroxy phenyl)thiazol-2-yl)cyclohexyl)carbamate (Compound 23) and isopropyl (trans-4-(5-(4-hydroxy-2-sulfamoylphenyl)thiazol-2-yl)cyclohexyl)carbamate (Compound 24)

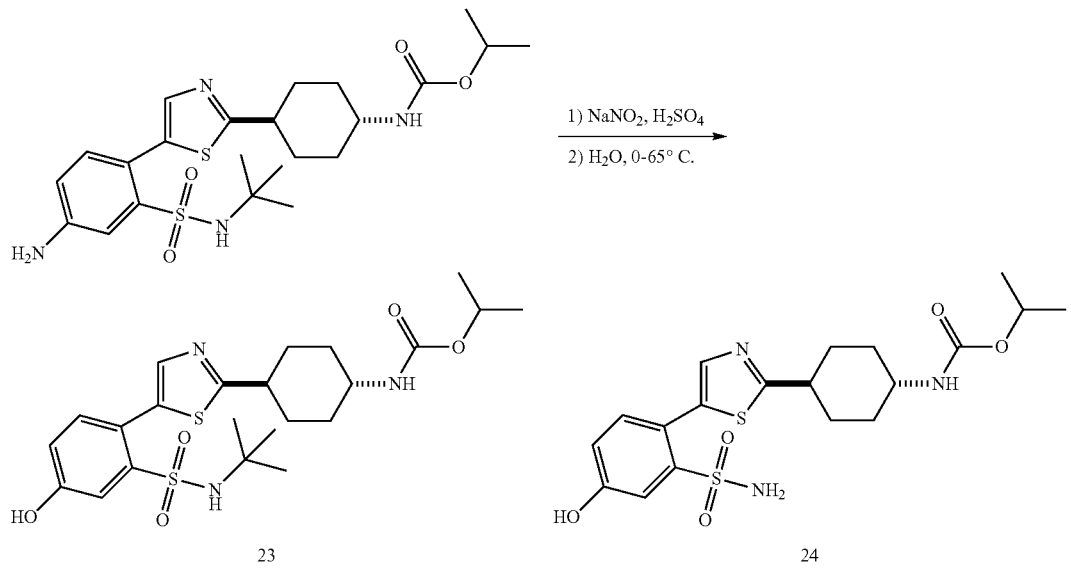

Isopropyl (trans-4-(5-(4-amino-2-(N-(tert-butypsulfamoyl)phenyl)thiazol-2-yl)cyclohexyl)carbamate (1 g, 2.02 mmol, 1.0 eq.) was dissolved in $H_2SO_4$ (30%, aq., 12 mL), cooled to 0° C. and added a solution of $NaNO_2$ (279 mg, 4.04 mmol, 2.0 eq.) in $H_2O$ (2 mL). The mixture was stirred at 0° C. for 1 hr, then added $H_2O$ (28 mL) and the mixture was stirred at 65° C. for 11 h. The reaction mixture was concentrated and the residue was purified by prep-HPLC (column: Xtimate C18 10μ 250 mm*50 mm; mobile phase: [water(0.1% TFA)-ACN]; B %: 30%-60%,20 min) to give isopropyl (trans-4-(5-(2-(N-(tert-butyl)sulfamoyl)-4-hydroxyphenyl)thiazol-2-yl)cyclohexyl)carbamate (Compound 23) (0.3 g, 581 umol, 28.74% yield, 96% purity) as a yellow solid and isopropyl (trans-4-(5-(4-hydroxy-2-sulfamoylphenyl)thiazol-2-yl)cyclohexyl)carbamate (Compound 24) (0.3 g, 669 umol, 33% yield, 98% purity) as a yellow solid.

$^1$H NMR (400 MHz, methanol-$d_4$) δ=7.75 (s, 1H), 7.60 (d, J=2.6 Hz, 1H), 7.32 (d, J=8.4 Hz, 1H), 7.03 (dd, J=2.6, 8.4 Hz, 1H), 4.87-4.81 (m, 1H), 3.47 (tt, J=3.8, 11.6 Hz, 1H), 3.06 (tt, J=3.5, 12.1 Hz, 1H), 2.30-2.21 (m, 2H), 2.14-2.03 (m, 2H), 1.72 (dq, J=3.1, 12.8 Hz, 2H), 1.43 (dq, J=3.2, 12.6 Hz, 2H), 1.24 (br d, J=6.1 Hz, 6H), 1.13 (s, 9H). ESI [M+H]=496.2.

$^1$H NMR (400 MHz, methanol-$d_4$) δ=7.77 (s, 1H), 7.58 (d, J=2.6 Hz, 1H), 7.33 (d, J=8.3 Hz, 1H), 7.03 (dd, J=2.6, 8.3 Hz, 1H), 4.87-4.82 (m, 1H), 3.47 (tt, J=4.0, 11.6 Hz, 1H), 3.06 (tt, J=3.3, 12.0 Hz, 1H), 2.29-2.18 (m, 2H), 2.15-2.00 (m, 2H), 1.72 (dq, J=2.9, 12.8 Hz, 2H), 1.43 (dq, J=3.4, 12.6 Hz, 2H), 1.24 (br d, J=6.1 Hz, 6H). ESI [M+H]=440.1.

Example 24

Preparation of isopropyl N-[trans-4-[5-[4-[2-(tert-butoxycarbonylamino)ethoxy]-2-(tert-butylsulfamoyl)phenyl]thiazol-2-yl]cyclohexyl]carbamate (Compound 25)

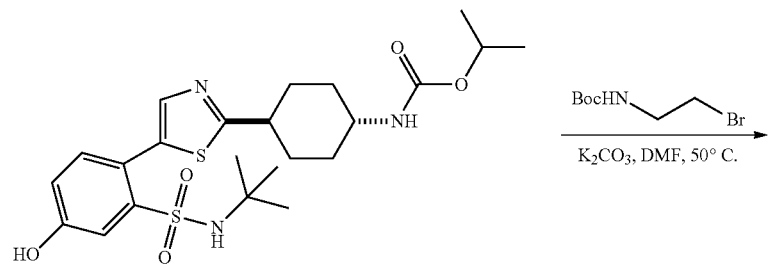

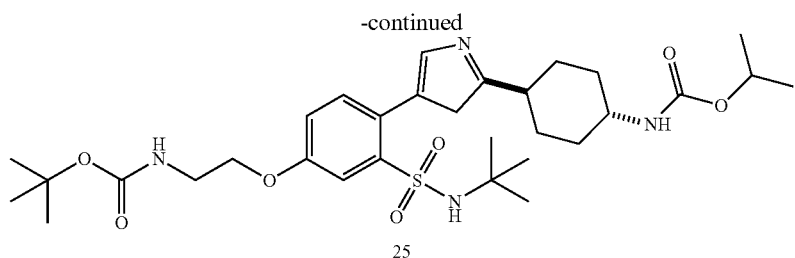

25

To a solution of isopropyl (trans-4-(5-(2-(N-(tert-butyl)sulfamoyl)-4-hydroxyphenyl)thiazol-2-yl)cyclohexyl)carbamate (50 mg, 101 umol, 1.0 eq.) in DMF (1 mL) was added K$_2$CO$_3$ (42 mg, 303 umol, 3.0 eq.) and tert-butyl N-(2-bromoethyl) carbamate (27 mg, 121 umol, 1.2 eq.). The mixture was stirred at 50° C. for 12 h, then diluted with sat.aq.LiCl (10 mL) and extracted with EtOAc (20 mL×2). The combined organic layers were washed with sat.aq.LiCl (10 mL×2), dried over Na$_2$SO$_4$, filtered and concentrated. The residue was purified by prep-HPLC (column: Xtimate C18 150*25 mm*5 um; mobile phase: [water(10 mM NH$_4$HCO$_3$)-ACN]; B %: 50%-80%,8 min) to give isopropyl N-[trans-4-[5-[4-[2-(tert-butoxycarbonylamino)ethoxy]-2-(tert-butylsulfamoyl)phenyl]thiazol-2-yl]cyclohexyl]carbamate (4.98 mg, 7.72 umol, 8% yield, 99% purity) as a white solid. $^1$H NMR (400 MHz, methanol-d$_4$) δ=7.76-7.68 (m, 2H), 7.41 (d, J=8.6 Hz, 1H), 7.21 (dd, J=2.7, 8.6 Hz, 1H), 4.86-4.81 (m, 1H), 4.13 (t, J=5.4 Hz, 2H), 3.49 (t, J=5.4 Hz, 2H), 3.44 (br s, 1H), 3.09-2.95 (m, 1H), 2.25 (br d, J=12.5 Hz, 2H), 2.09 (br d, J=10.9 Hz, 2H), 1.79-1.62 (m, 2H), 1.47 (s, 9H), 1.45-1.36 (m, 2H), 1.25 (br d, J=6.1 Hz, 6H), 1.12 (s, 9H). ESI [M+H]=639.3.

Example 25

Preparation of isopropyl (trans-4-(5-(4-(2-aminoethoxy)-2-(N-(tert-butyl)sulfamoyl)phenyl)thiazol-2-yl)cyclohexyl)carbamate (Compound 26)

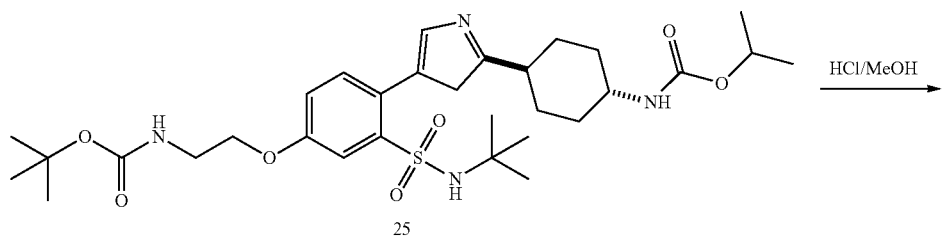

25

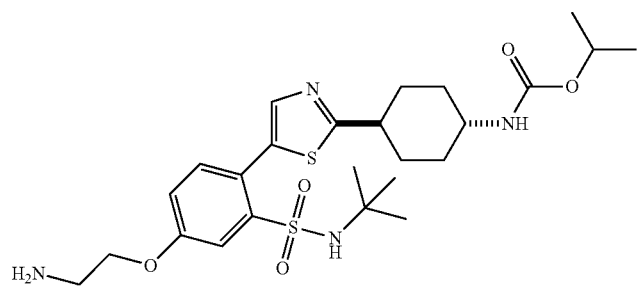

26

A solution of isopropyl N-[trans-4-[5-[4-[2-(tert-butoxycarbonylamino)ethoxy]-2-(tert-butylsulfamoyl)phenyl]thiazol-2-yl]cyclohexyl]carbamate (75 mg, 117.4 umol) in HCl/MeOH (4 M, 1 mL) was stirred at 25° C. for 0.5 hr. The mixture was then concentrated and purified by prep-HPLC (column: Nano-Micro UniSil 5-100 C18 ULTRA 100×250 mm 5 um; mobile phase: [water(0.1% TFA)-ACN]; B %: 25%-45%,10 min) to give isopropyl (trans-4-(5-(4-(2-aminoethoxy)-2-(N-(tert-butyl)sulfamoyl)phenyl)thiazol-2-yl)cyclohexyl)carbamate (10.21 mg, 15.64 umol, 13% yield, 100% purity, TFA salt) as a yellow solid. $^1$H NMR (400 MHz, methanol-$d_4$) δ=7.69 (d, J=2.7 Hz, 1H), 7.60 (s, 1H), 7.35 (d, J=8.4 Hz, 1H), 7.17 (dd, J=2.7, 8.6 Hz, 1H), 4.74-4.68 (m, 1H), 4.24 (t, J=5.0 Hz, 2H), 3.40-3.35 (m, 1H), 3.32 (br t, J=4.8 Hz, 2H), 2.91 (tt, J=3.5, 12.0 Hz, 1H), 2.13 (br d, J=12.0 Hz, 2H), 1.97 (br d, J=9.9 Hz, 2H), 1.59 (dq, J=2.8, 12.8 Hz, 2H), 1.31 (dq, J=3.2, 12.6 Hz, 2H), 1.13 (br d, J=6.1 Hz, 6H), 0.98 (s, 9H). ESI [M+H]=539.2.

Example 26

Preparation of isopropyl (trans-4-(5-(2-(N-(tert-butyl)sulfamoyl)-4-isopropoxy phenyl)thiazol-2-yl)cyclohexyl)carbamate (Compound 27)

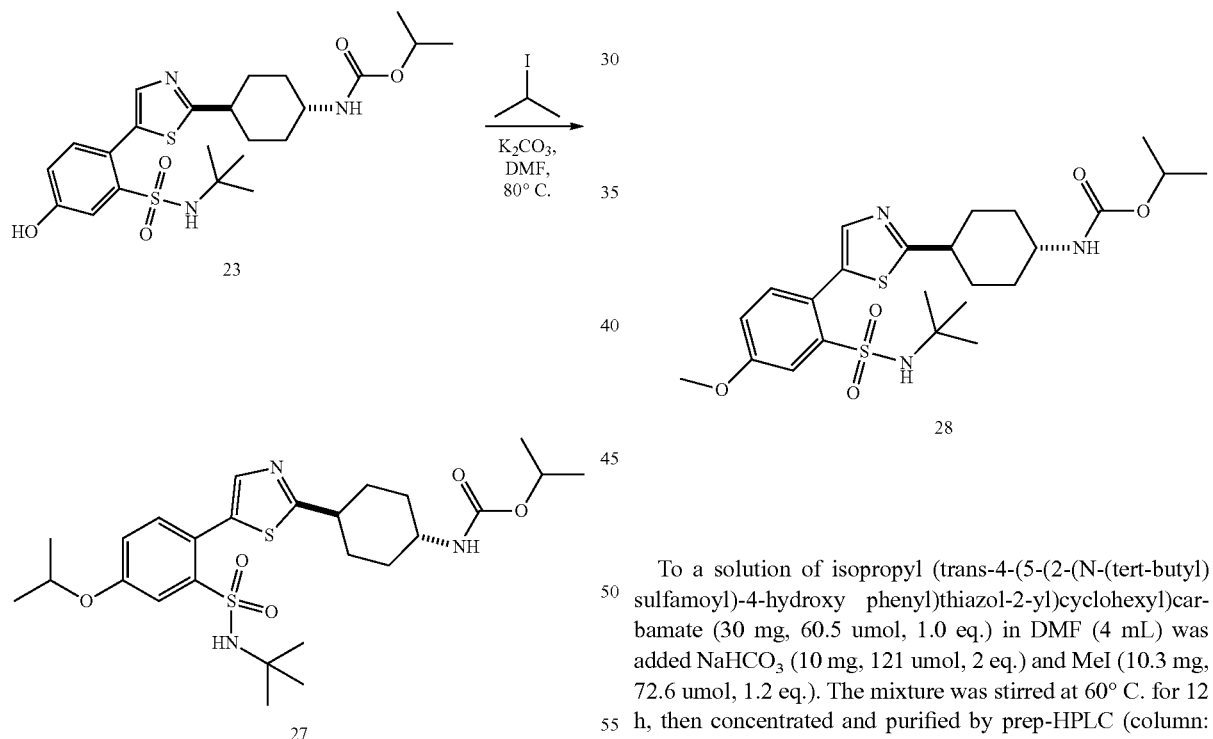

To a solution of isopropyl (trans-4-(5-(2-(N-(tert-butyl)sulfamoyl)-4-hydroxyphenyl)thiazol-2-yl)cyclohexyl)carbamate (30 mg, 60.5 umol, 1.0 eq.) in DMF (5 mL) was added K$_2$CO$_3$ (16.7 mg, 121 umol, 2 eq.) and 2-iodopropane (20.6 mg, 121 umol, 2 eq.). The mixture was stirred at 80° C. for 12 h, then concentrated and purified by prep-HPLC to give isopropyl (trans-4-(5-(2-(N-(tert-butypsulfamoyl)-4-isopropoxyphenyl)thiazol-2-yl)cyclohexyl)carbamate (18 mg, 33.19 umol, 55% yield, 99% purity) as a white solid. $^1$H NMR (400 MHz, methanol-$d_4$) δ=7.69 (s, 1H), 7.62 (d, J=2.6 Hz, 1H), 7.38-7.35 (m, 1H), 7.14 (dd, J=2.6, 8.6 Hz, 1H), 4.84-4.78 (m, 1H), 4.70 (td, J=6.0, 12.1 Hz, 1H), 3.45 (tt, J=3.9, 11.6 Hz, 1H), 3.04-2.97 (m, 1H), 2.26-2.18 (m, 2H), 2.10-2.03 (m, 2H), 1.69 (dq, J=3.0, 12.8 Hz, 2H), 1.46-1.38 (m, 2H), 1.36 (d, J=6.0 Hz, 6H), 1.22 (br d, J=6.2 Hz, 6H), 1.09 (s, 9H). ESI [M+H]=538.2.

Example 27

Preparation of isopropyl (trans-4-(5-(2-(N-(tert-butyl)sulfamoyl)-4-methoxyphenyl)thiazol-2-yl)cyclohexyl)carbamate (Compound 28)

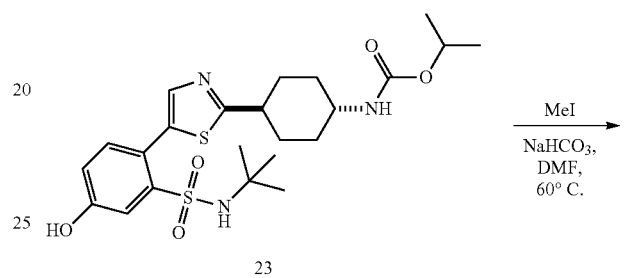

To a solution of isopropyl (trans-4-(5-(2-(N-(tert-butyl)sulfamoyl)-4-hydroxy phenyl)thiazol-2-yl)cyclohexyl)carbamate (30 mg, 60.5 umol, 1.0 eq.) in DMF (4 mL) was added NaHCO$_3$ (10 mg, 121 umol, 2 eq.) and MeI (10.3 mg, 72.6 umol, 1.2 eq.). The mixture was stirred at 60° C. for 12 h, then concentrated and purified by prep-HPLC (column: Welch Ultimate AQ-C18 150*30 mm*5 um; mobile phase: [water(0.1% TFA)-ACN]; B %: 40%-70%,12 min) to give isopropyl (trans-4-(5-(2-(N-(tert-butyl)sulfamoyl)-4-methoxyphenyl)thiazol-2-yl)cyclohexyl)carbamate (2.34 mg, 4.26 umol, 7% yield, 93% purity) as a pale yellow solid. $^1$H NMR (400 MHz, methanol-$d_4$) δ=7.75-7.62 (m, 2H), 7.42 (d, J=8.4 Hz, 1H), 7.20 (dd, J=2.8, 8.5 Hz, 1H), 4.84 (br d, J=5.5 Hz, 1H), 3.92 (s, 3H), 3.53-3.38 (m, 1H), 3.11-2.97 (m, 1H), 2.25 (br d, J=13.1 Hz, 2H), 2.09 (br d, J=10.4 Hz, 2H), 1.78-1.64 (m, 2H), 1.49-1.37 (m, 2H), 1.31-1.21 (m, 6H), 1.11 (s, 9H). ESI [M+H]=510.2.

Example 28

Preparation of tert-butyl (2-(3-(N-(tert-butyl)sulfamoyl)-4-(2-(trans-4-((isopropoxycarbonyl)amino)cyclohexyl)thiazol-5-yl)phenoxy)ethyl)(methyl) carbamate (Compound 29)

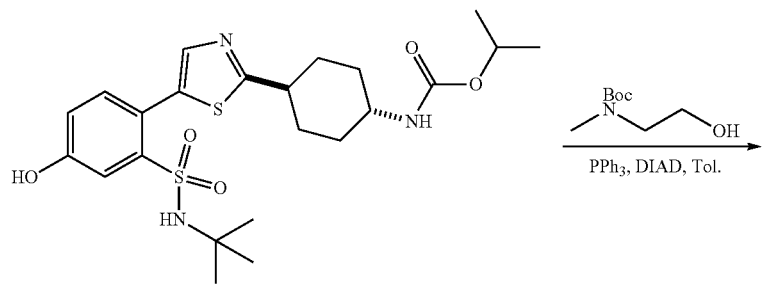

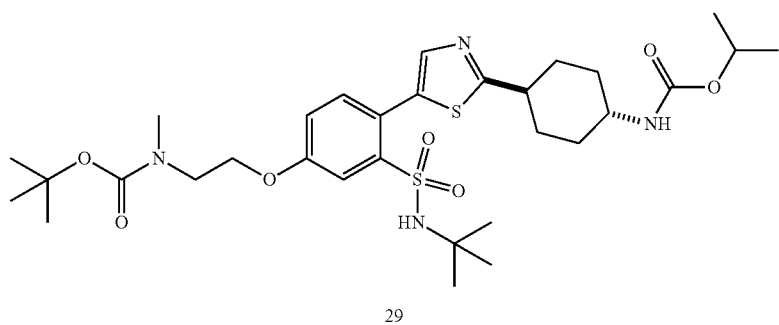

A mixture of isopropyl (trans-4-(5-(2-(N-(tert-butyl)sulfamoyl)-4-hydroxy phenyl)thiazol-2-yl)cyclohexyl)carbamate (140 mg, 282 umol, 1.0 eq.), tert-butyl N-(2-hydroxyethyl)-N-methyl-carbamate (74 mg, 424 umol, 1.5 eq.) and PPh3 (148 mg, 565 umol, 2.0 eq.) in anhydrous THF (2 mL) was degassed and purged with $N_2$ for 3 times, then DIAD (86 mg, 424 umol, 1.5 eq.) was added and the mixture was stirred at 30° C. for 12 h under $N_2$ atmosphere. The reaction mixture was concentrated and the residue was purified prep-HPLC (column: Waters Xbridge 150*25 5 u; mobile phase: [water(10 mM $NH_4HCO_3$)-ACN]; B %: 40%-70%, 10 min) to give tert-butyl (2-(3-(N-(tert-butyl)sulfamoyl)-4-(2-(trans-4-((isopropoxycarbonyl)amino)cyclohexyl)thiazol-5-yl)phenoxy)ethyl)(methyl)carbamate (7.58 mg, 98% purity) as a pale yellow solid. $^1$H NMR (400 MHz, methanol-$d_4$) δ=7.70 (br s, 2H), 7.42 (br d, J=7.9 Hz, 1H), 7.23 (br s, 1H), 4.87-4.77 (m, 1H), 4.25 (br s, 2H), 3.69 (br s, 2H), 3.47 (br s, 1H), 3.00 (br s, 4H), 2.25 (br d, J=11.0 Hz, 2H), 2.09 (br d, J=10.5 Hz, 2H), 1.71 (br d, J=12.1 Hz, 2H), 1.54-1.35 (m, 11H), 1.25 (br d, J=5.0 Hz, 6H), 1.11 (br s, 9H). ESI [M+H]=653.3.

Example 29

Preparation of isopropyl (trans-4-(5-(2-(N-(tert-butyl)sulfamoyl)-4-(2-(dimethyl amino)ethoxy)phenyl)thiazol-2-yl)cyclohexyl)carbamate (Compound 30)

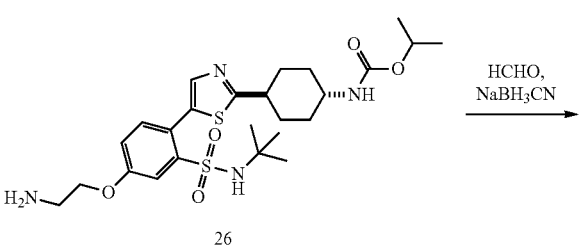

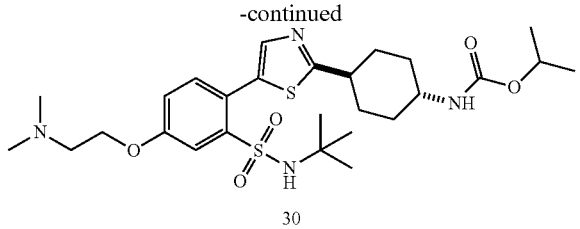

30

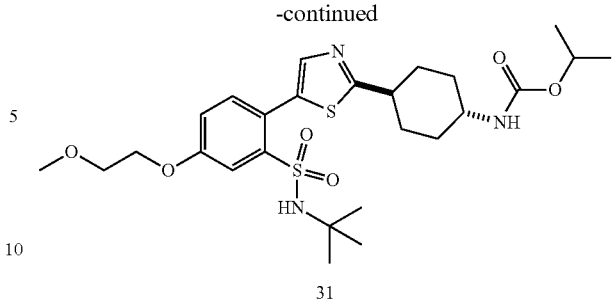

31

To a solution of isopropyl (trans-4-(5-(4-(2-aminoethoxy)-2-(N-(tert-butyl) sulfamoyl)phenyl)thiazol-2-yl)cyclohexyl)carbamate (13 mg, 24.1 umol, 1.0 eq.) in MeOH (1 mL) was added AcOH (one drop), HCHO (3.6 mg, 120.7 umol, 5.0 eq.) followed by NaBH$_3$CN (4.5 mg, 72.4 umol, 3.0 eq.) after 0.5 hr. The mixture was stirred at 25° C. for 12 h and then concentrated. The residue was purified by prep-HPLC (column: Welch Ultimate AQ-C18 150*30 mm*5 um; mobile phase: [water(0.1% TFA)-ACN]; B %: 25%-55%,12 min) to give isopropyl (trans-4-(5-(2-(N-(tert-butyl)sulfamoyl)-4-(2-(dimethylamino)ethoxy)phenyl) thiazol-2-yl)cyclohexyl) carbamate (20.6 mg, 99% purity, TFA salt) as a white solid. $^1$H NMR (400 MHz, methanol-d$_4$) δ=7.81 (br s, 1H), 7.73 (s, 1H), 7.49 (br d, J=8.3 Hz, 1H), 7.31 (br d, J=7.0 Hz, 1H), 4.86 (br d, J=5.7 Hz, 1H), 4.49 (br s, 2H), 3.68 (br s, 2H), 3.55-3.41 (m, 1H), 3.03 (s, 7H), 2.25 (br d, J=11.6 Hz, 2H), 2.09 (br d, J=10.9 Hz, 2H), 1.71 (q, J=12.0 Hz, 2H), 1.50-1.36 (m, 2H), 1.24 (br d, J=5.4 Hz, 6H), 1.10 (s, 9H). ESI [M+H]=567.2.

Example 30

Preparation of isopropyl (trans-4-(5-(2-(N-(tert-butyl)sulfamoyl)-4-(2-methoxy ethoxy)phenyl)thiazol-2-yl)cyclohexyl)carbamate (Compound 31)

A mixture of isopropyl (trans-4-(5-(2-(N-(tert-butyl)sulfamoyl)-4-hydroxyphenyl) thiazol-2-yl)cyclohexyl)carbamate (30 mg, 60.5 umol, 1.0 eq.), 1-bromo-2-methoxy-ethane (6.7 mg, 48.4 umol, 0.8 eq.) and K$_2$CO$_3$ (16.73 mg, 121.05 umol, 2 eq.) in DMF (2 mL) was stirred at 30° C. for 12 h under N$_2$ atmosphere. The mixture was concentrated and purified by prep-HPLC (column: Welch Ultimate AQ-C18 150×30 mm×5 um; mobile phase: [water(0.1% TFA)-ACN]; B %: 40%-70%,12 min) to give isopropyl (trans-4-(5-(2-(N-(tert-butyl)sulfamoyl)-4-(2-methoxyethoxy)phenyl) thiazol-2-yl)cyclohexyl)carbamate (19.84 mg, 35.70 umol, 59% yield, 99% purity) as pale yellow solid. $^1$H NMR (400 MHz, methanol-d$_4$) δ=7.79 (s, 1H), 7.72 (d, J=2.7 Hz, 1H), 7.42 (s, 1H), 7.26-7.20 (m, 1H), 4.87-4.74 (m, 1H), 4.25 (dd, J=3.7, 5.3 Hz, 2H), 3.81 (dd, J=3.7, 5.3 Hz, 2H), 3.54-3.43 (m, 4H), 33.12-3.02 (m, 1H), 2.31-2.19 (m, 2H), 2.13-2.07 (m, 2H), 1.73 (br dd, J=2.8, 12.7 Hz, 2H), 1.50-1.36 (m, 2H), 1.24 (br d, J=6.2 Hz, 6H), 1.13 (s, 9H). ESI [M+H]=554.3.

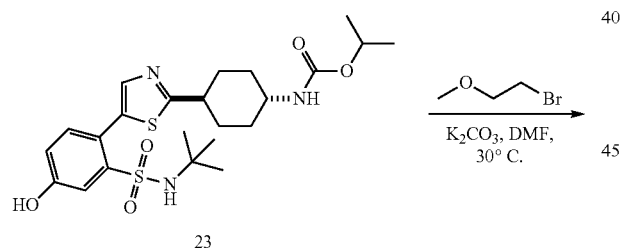

23

Example 31

Preparation of isopropyl (trans-4-(5-(2-(N-(tert-butyl)sulfamoyl)-4-(2-(methyl amino)ethoxy)phenyl)thiazol-2-yl)cyclohexyl)carbamate (Compound 32)

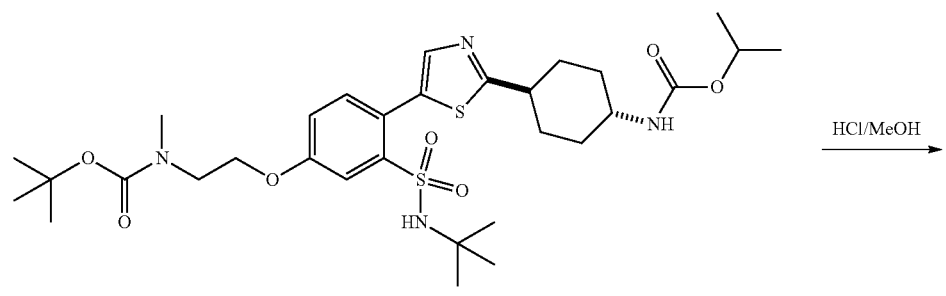

29

-continued

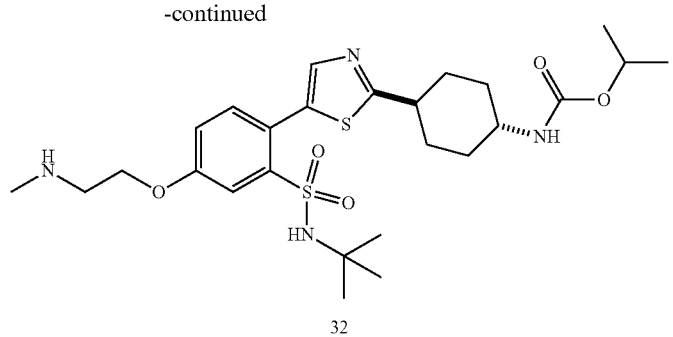

32

A solution of tert-butyl (2-(3-(N-(tert-butyl)sulfamoyl)-4-(2-(trans-4-((isopropoxy carbonyl)amino)cyclohexyl)thiazol-5-yl)phenoxy)ethyl)(methyl)carbamate (0.1 g, 153 umol, 1.0 eq.) in HCl/MeOH (4 M, 5 mL) was stirred at 20° C. for 30 mins. The reaction mixture was concentrated and purified by prep-HPLC (column: Waters Xbridge 150*25 5 u; mobile phase: [water(10 mM $NH_4HCO_3$)-ACN]; B %: 20%-50%,10 min) to give isopropyl (trans-4-(5-(2-(N-(tert-butyl)sulfamoyl)-4-(2-(methylamino)ethoxy)phenyl) thiazol-2-yl)cyclohexyl)carbamate (6.84 mg, 12.25 umol, 8% yield, 99% purity) as a yellow solid. $^1$H NMR (400 MHz, methanol-$d_4$) δ=7.78-7.69 (m, 2H), 7.43 (d, J=8.4 Hz, 1H), 7.23 (dd, J=2.5, 8.5 Hz, 1H), 4.86-4.80 (m, 1H), 4.22 (br t, J=4.8 Hz, 2H), 3.55-3.41 (m, 1H), 3.11-2.95 (m, 3H), 2.50 (br s, 3H), 2.25 (br d, J=12.2 Hz, 2H), 2.09 (br d, J=10.8 Hz, 2H), 1.79-1.63 (m, 2H), 1.49-1.35 (m, 2H), 1.24 (br d, J=6.1 Hz, 6H), 1.11 (s, 9H). ESI [M+H]=553.2.

Example 32

Separation of oxetan-3-yl trans-N-[4-[5-[2-(tert-butylsulfamoyl)-4-(isobutoxymethyl)phenyl]thiazol-2-yl]cyclohexyl]carbamate (Compound 34)

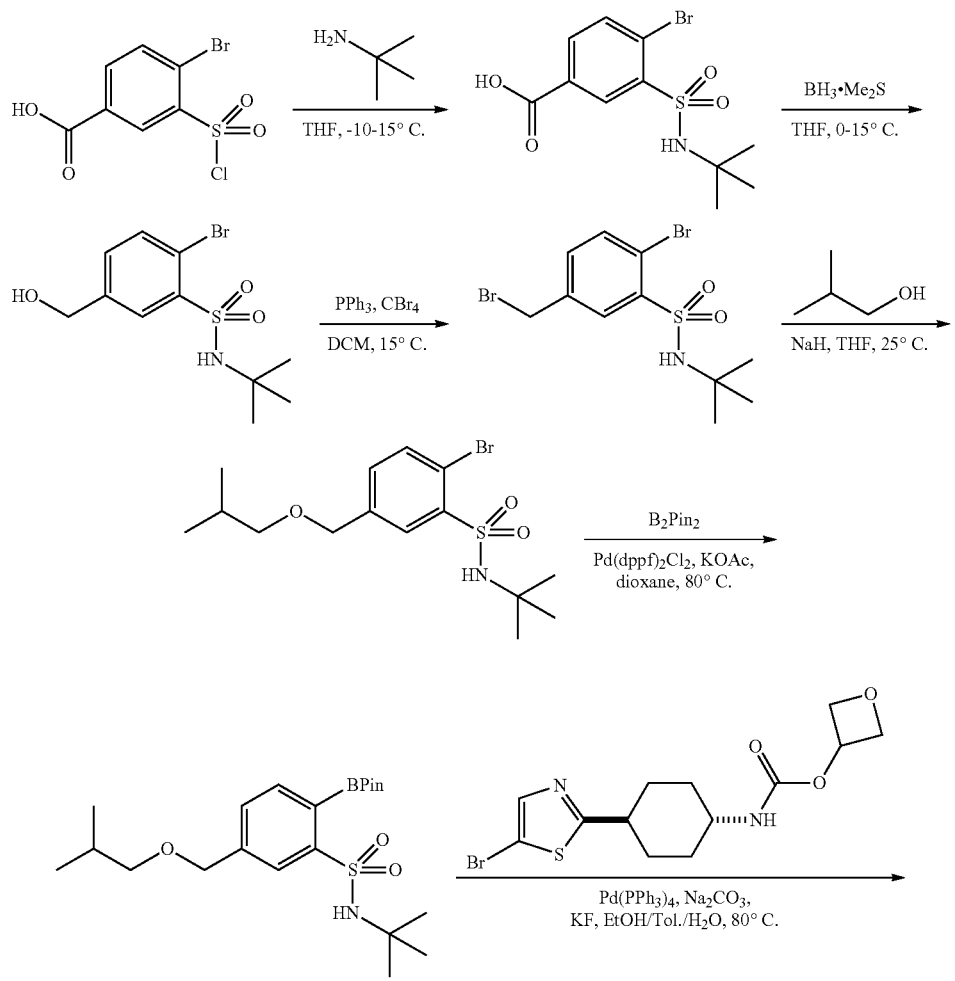

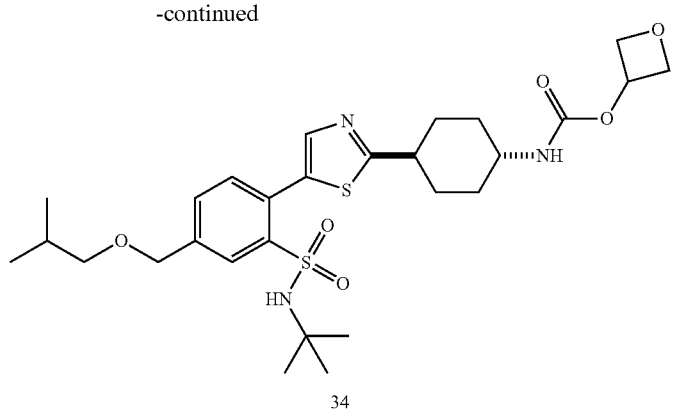

34 a) Synthesis of 4-bromo-3-(tert-butylsulfamoyl)benzoic acid

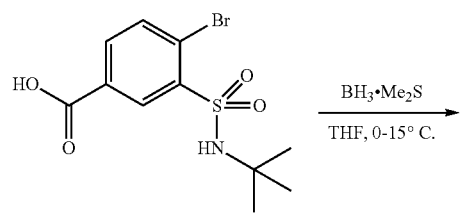

To a solution of 2-methylpropan-2-amine (2.9 g, 40.1 mmol, 3.0 eq.) in DCM (80 mL) was added 4-bromo-3-chlorosulfonyl-benzoic acid (4.0 g, 13.4 mmol, 1 eq.) with THF (20 mL) at −10° C., then the mixture was stirred at 15° C. for 2 h. The reaction mixture was concentrated under reduced pressure, the residue was diluted with HCl (20 mL) and extracted with EtOAc 150 mL (50 mL×3). The combined organic layers were dried over $Na_2SO_4$, filtered and concentrated under reduced pressure to give a residue which was triturated with petroleum ether yielding 4-bromo-3-(tert-butylsulfamoyl)benzoic acid (4.5 g, 13.4 mmol, 100% yield) as a white solid. $^1$H NMR (400 MHz, methanol-$d_4$) δ=8.70 (d, J=1.98 Hz, 1H), 8.03 (dd, J=8.16, 1.98 Hz, 1H) 7.63 (d, J=8.38 Hz, 1H) 1.19 (s, 9H).

b) Synthesis of 2-bromo-N-tert-butyl-5-(hydroxymethyl)benzenesulfonamide

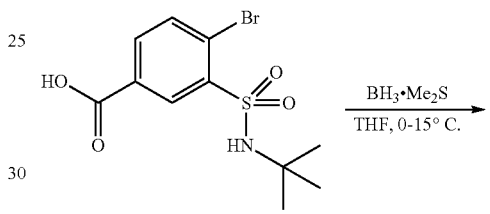

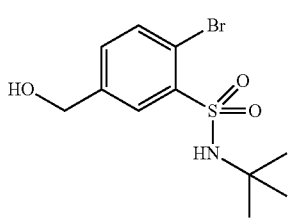

To a solution of 4-bromo-3-(tert-butylsulfamoyl)benzoic acid (3.5 g, 10.4 mmol, 1 eq.) in THF (20 mL) was added $BH_3$-$Me_2S$ (10 M, 12.49 mL, 12 eq.) at 0° C. and stirred at 15° C. for 12 h. The reaction mixture was quenched by addition MeOH (15 mL) at 15° C., then the reaction mixture was concentrated under reduced pressure. The crude product was purified by reversed-phase HPLC (TFA condition) to yield 2-bromo-N-tert-butyl-5-(hydroxymethyl)benzenesulfonamide (3g) as a white solid. $^1$H NMR (400 MHz, methanol-$d_4$) δ=8.17 (d, J=2.08 Hz, 1H), 7.76 (d, J=8.07 Hz, 1H), 7.42-7.52 (m, 1H), 4.65 (s, 2H), 1.21 (s, 9H). ESI[M−H]=319.9/321.9.

c) Synthesis of 2-bromo-5-(bromomethyl)-N-tert-butyl-benzenesulfonamide

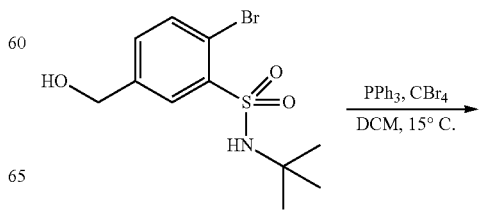

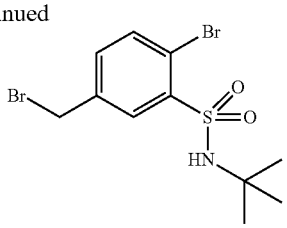

To a solution of 2-bromo-N-tert-butyl-5-(hydroxymethyl)benzenesulfonamide (2.9 g, 9 mmol, 1 eq.) in DCM (50 mL) was added CBr$_4$ (4.6 g, 13.0 mmol, 1.5 eq.) and PPh$_3$ (3.6 g, 13.0 mmol, 1.5 eq.) and stirred at 15° C. for 2 h. The reaction mixture was diluted with H$_2$O (15 mL) and extracted with DCM 150 mL (50 mL×3). The combined organic layers were dried over Na$_2$SO$_4$, filtered and concentrated under reduced pressure. The residue was purified by column chromatography (SiO$_2$, petroleum ether:ethyl acetate=1:0 to 8:1 to 5:1 to 2:1 to 1:1) to yield 2-bromo-5-(bromomethyl)-N-tert-butyl-benzenesulfonamide (5.1 g, 13.0 mmol, quantitative yield) as a white solid. ESI[M−H]=383.8.

d) Synthesis of 2-bromo-N-tert-butyl-5-(isobutoxymethyl)benzene sulfonamide

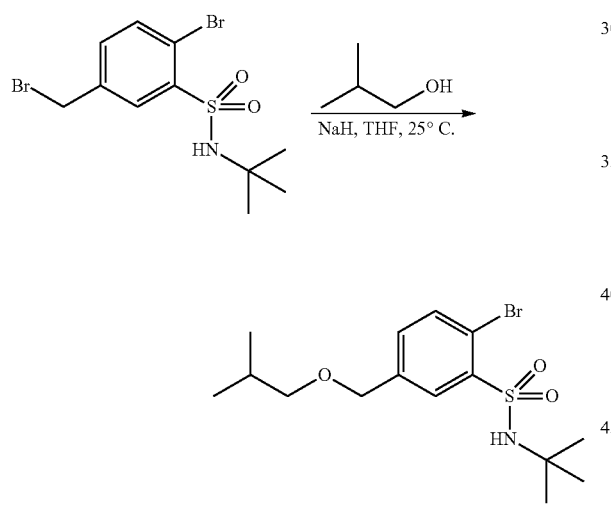

To a solution of 2-methylpropan-1-ol (3.3 g, 45.0 mmol, 5 eq.) in DMF (15 mL) was added NaH (1.1 g, 27.0 mmol, 60% purity, 3.0 eq.) and 2-bromo-5-(bromomethyl)-N-tert-butyl-benzenesulfonamide (3.5 g, 9.0 mmol, 1.0 eq.). The mixture was stirred at 25° C. for 2 h.

The reaction mixture was poured into NaCl (sat.aq.) (15 mL) at 25° C., extracted with EtOAc (30 mL), The combined organic layers were washed with NaCl 60 mL (20 mL×3), dried over Na$_2$SO$_4$, filtered and concentrated under reduced pressure. The residue was purified by prep-HPLC (column: Welch Xtimate C18 250*50 mm*10 um; mobile phase: [water(0.1% TFA)-ACN]; B %: 45%-75%,20 min) to yield 2-bromo-N-tert-butyl-5-(isobutoxymethyl)benzenesulfonamide (820 mg, 2.2 mmol, 24% yield) as a white solid. $^1$H NMR (400 MHz, methanol-d$_4$) δ=8.12 (d, J=1.98 Hz, 1H), 7.74 (d, J=8.16 Hz, 1H), 7.41 (dd, J=8.16, 2.21 Hz, 1H), 3.25-3.33 (m, 4H), 1.85-1.95 (m, 1H), 1.18 (s, 9H), 0.93 (d, J=6.84 Hz, 6H).

e) Synthesis of N-tert-butyl-5-(isobutoxymethyl)-2-(4,4,5,5-tetramethyl-1,3,2-dioxaborolan-2-yl)benzenesulfonamide

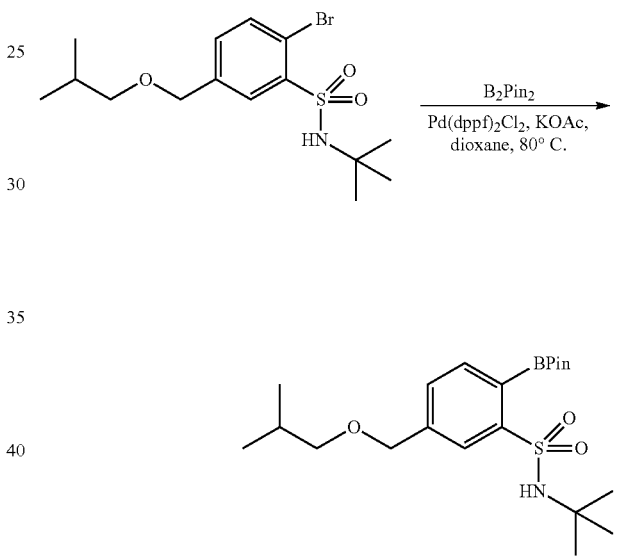

From 2-bromo-N-tert-butyl-5-(isobutoxymethyl)benzenesulfonamide, using General Method B. ESI[M+H]=426.2.

f) Synthesis of oxetan-3-yl trans-N-[4-[5-[2-(tert-butylsulfamoyl)-4-(isobutoxymethyl)phenyl]thiazol-2-yl]cyclohexyl]carbamate (Compound 34)

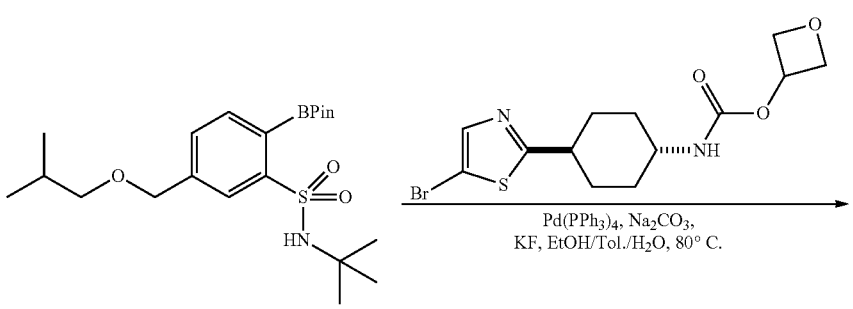

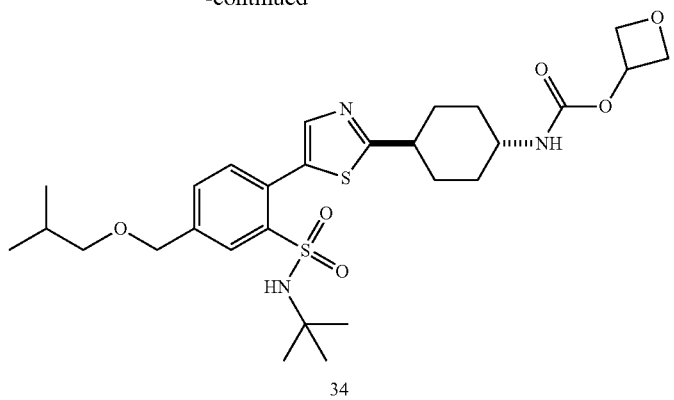

34

From N-tert-butyl-5-(isobutoxymethyl)-2-(4,4,5,5-tetramethyl-1,3,2-dioxaborolan-2-yl)benzenesulfonamide, using General Method C. $^1$H NMR (400 MHz, methanol-$d_4$) δ=8.15 (d, J=1.32 Hz, 1H), 7.75 (s, 1H), 7.57 (dd, J=7.72, 1.32 Hz, 1H), 7.45 (d, J=7.72 Hz, 1H), 5.31-5.40 (m, 1H), 4.87 (s, 1H), 4.84 (br s, 1H), 4.60 (s, 4H), 3.39-3.50 (m, 1H), 3.29 (d, J=1.98 Hz, 2H), 2.98-3.06 (m, 1H), 2.24 (br d, J=12.57 Hz, 2H), 2.02-2.11 (m, 2H), 1.92 (dt, J=13.40, 6.64 Hz, 1H), 1.64-1.76 (m, 2H), 1.38-1.49 (m, 2H), 1.08 (s, 9H), 0.95 (d, J=6.84 Hz, 6H). ESI [M+H]=580.3.

Example 33

Preparation of isopropyl (trans-4-(5-(2-(N-(tert-butyl)sulfamoyl)-4-(isobutoxymethyl)phenyl)thiazol-2-yl)cyclohexyl)carbamate (Compound 33)

Following the same protocol and under the same reaction conditions as for Compound 34, Compound 33 was prepared. $^1$H NMR (400 MHz, methanol-$d_4$) δ=8.06 (s, 1H), 7.67 (s, 1H), 7.48 (br d, J=7.58 Hz, 1H), 7.36 (d, J=7.70 Hz, 1H), 4.51 (s, 2H), 3.30-3.39 (m, 1H) 3.20 (br s, 3H), 2.92 (tt, J=11.83, 3.03 Hz, 1H), 2.14 (br d, J=12.47 Hz, 2H), 1.98 (br d, J=11.00 Hz, 2H), 1.75-1.89 (m, 1H), 1.55-1.67 (m, 2H), 1.32 (qd, J=12.59, 2.69 Hz, 2H), 1.13 (br d, J=5.99 Hz, 6H), 1.00 (s, 9H), 0.86 (d, J=6.72 Hz, 6H). ESI [M+H]=566.3.

Example 34

Preparation of isopropyl trans-N-[4-[5-[4-cyano-2-(ethylsulfamoyl)phenyl]thiazol-2-yl]cyclohexyl]carbamate (Compound 36)

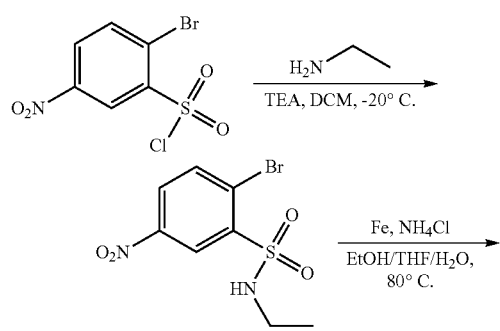

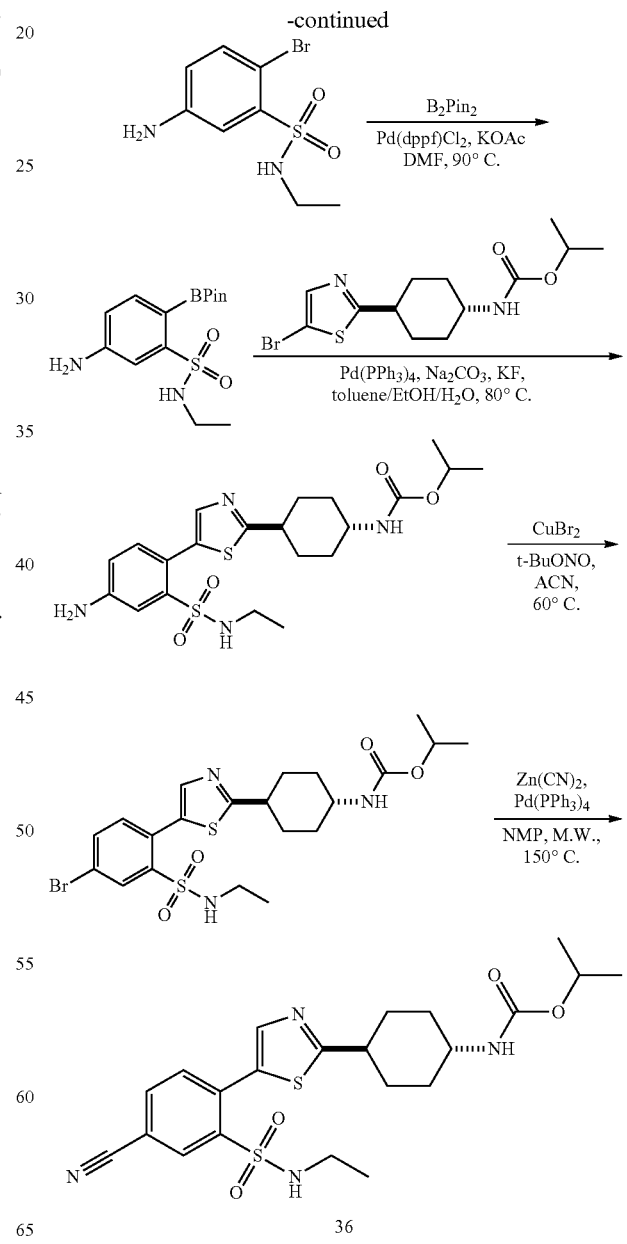

36 a) Synthesis of 2-bromo-N-ethyl-5-nitro-benzenesulfonamide

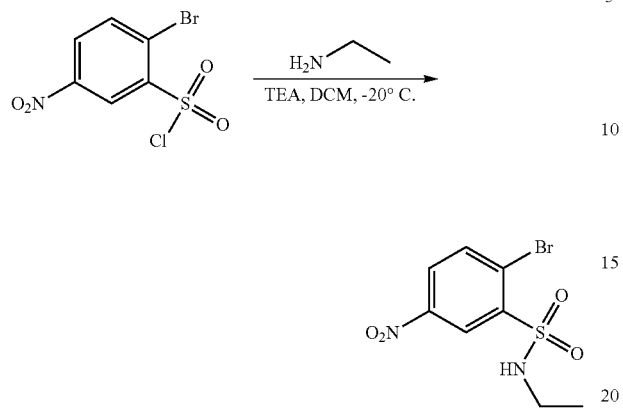

From 1-(2-bromo-5-nitro-phenyl)sulfonyl chloride and ethylamine, using General Method G. $^1$H NMR (400 MHz, methanol-$d_4$) δ=8.82 (d, J=2.9 Hz, 1H), 8.30 (dd, J=2.6, 8.6 Hz, 1H), 8.07 (d, J=8.6 Hz, 1H), 3.01 (q, J=7.3 Hz, 2H), 1.08 (t, J=7.3 Hz, 3H).

b) Synthesis of 5-amino-2-bromo-N-ethyl-benzenesulfonamide

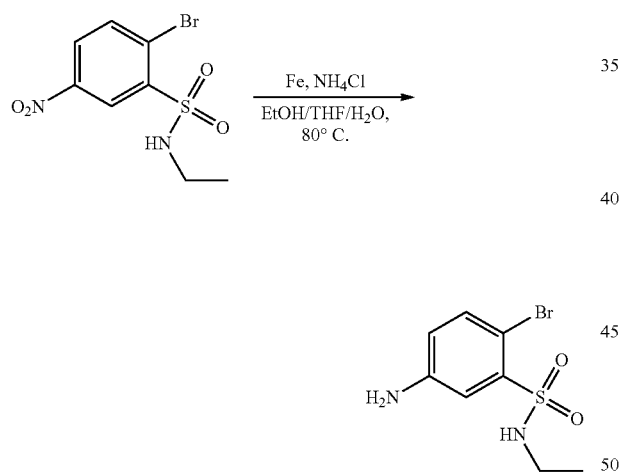

To a solution of 2-bromo-N-ethyl-5-nitro-benzenesulfonamide (100.0 g, 323.5 mmol, 1.0 eq.) in EtOH (600 mL), H$_2$O (200 mL) and THF (600 mL) was added Fe (90.3 g, 1.6 mol, 5.0 eq.) and NH$_4$Cl (51.9 g, 970.4 mmol, 3.0 eq.). The mixture was stirred at 80° C. for 2 h and filtered. Then concentrated under reduced pressure, the residue diluted with H$_2$O (60 mL) and extracted with EtOAc 1200 mL (400 mL×3). The combined organic layers were dried over Na$_2$SO$_4$, filtered and concentrated under reduced pressure. The residue was purified by column chromatography (SiO$_2$, petroleum ether:ethyl acetate=10:1 to 0:1) to yield 5-amino-2-bromo-N-ethyl-benzenesulfonamide (82.0 g, 293.7 mmol, 91% yield) as a yellow solid. $^1$H NMR (400 MHz, methanol-$d_4$) δ=7.44-7.37 (m, 2H), 6.74 (dd, J=2.9, 8.5 Hz, 1H), 2.95 (q, J=7.2 Hz, 2H), 1.08 (t, J=7.3 Hz, 3H). ESI [M+H]=279.0/281.0.

c) Synthesis of 5-amino-N-ethyl-2-(4,4,5,5-tetramethyl-1,3,2-dioxaborolan-2-yl)benzenesulfonamide

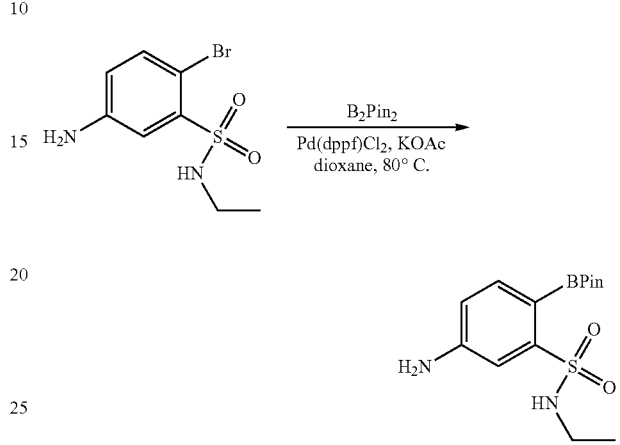

From 5-amino-2-bromo-N-ethyl-benzenesulfonamide, using General Method B. $^1$H NMR (400 MHz, methanol-$d_4$) δ=7.97 (s, 1H), 7.49 (br d, J=7.94 Hz, 2H), 2.98 (s, 2H), 1.35 (s, 12H), 1.00-1.08 (m, 3H). ESI [M+H]=327.3.

d) Synthesis of isopropyl trans-N-[4-[5-[4-amino-2-(ethylsulfamoyl)phenyl]thiazol-2-yl]cyclohexyl]carbamate

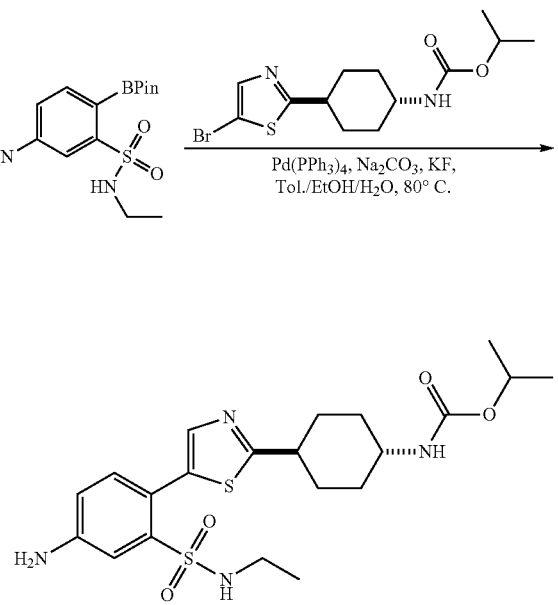

From 5-amino-N-ethyl-2-(4,4,5,5-tetramethyl-1,3,2-dioxaborolan-2-yl)benzene sulfonamide, using General Method C. ESI [M+H]=467.3.

e) Synthesis of isopropyl trans-N-[4-[5-[4-bromo-2-(ethylsulfamoyl)phenyl]thiazol-2-yl]cyclohexyl] carbamate

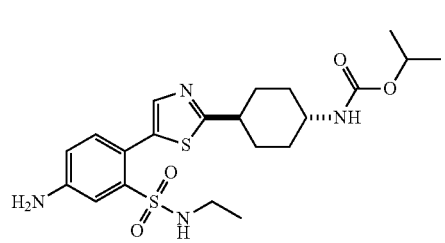
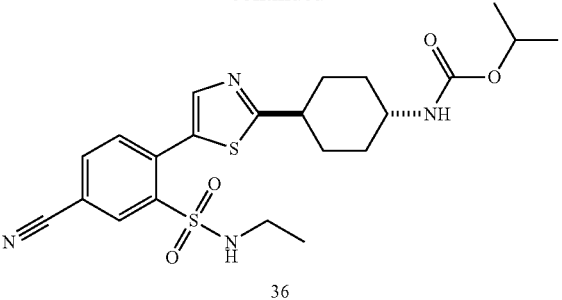

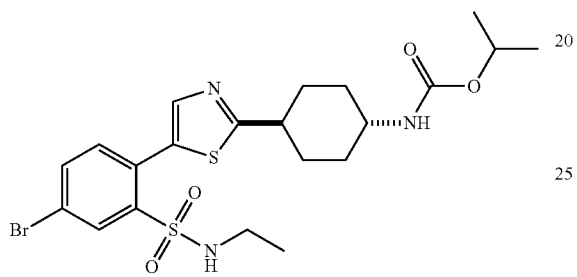

From isopropyl trans-N-[4-[5-[4-amino-2-(ethylsulfamoyl)phenyl] thiazol-2-yl]cyclohexyl]carbamate, using General Method L. $^1$H NMR (400 MHz, methanol-d$_4$) δ=8.21 (d, J=1.47 Hz, 1H), 7.78-7.86 (m, 2H), 7.44 (d, J=8.19 Hz, 1H), 4.85 (br d, J=5.87 Hz, 1H), 3.48 (ddd, J=11.43, 7.70, 3.97 Hz, 1H), 3.00-3.10 (m, 1H), 2.89 (q, J=7.21 Hz, 2H), 2.22-2.30 (m, 2H), 2.10 (br d, J=10.64 Hz, 2H), 1.72 (qd, J=12.76, 2.57 Hz, 2H), 1.43 (qd, J=12.55, 2.93 Hz, 2H), 1.25 (br d, J=5.99 Hz, 6H), 1.04 (t, J=7.21 Hz, 3H). ESI [M+H]=530.1/532.1.

f) Synthesis of isopropyl trans-N-[4-[5-[4-cyano-2-(ethylsulfamoyl)phenyl]thiazol-2-yl]cyclohexyl] carbamate (Compound 36)

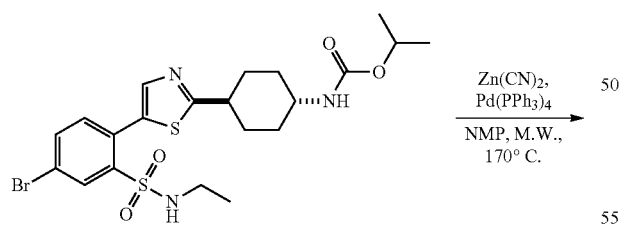

A solution of isopropyl trans-N-[4-[5-[4-bromo-2-(ethylsulfamoyl)phenyl]thiazol-2-yl]cyclohexyl]carbamate (60 mg, 113 umol, 1 eq.), Zn(CN)$_2$ (27 mg, 226 umol, 2 eq.), Pd(PPh$_3$)$_4$ (13 mg, 11 umol, 0.1 eq.) in NMP (2 mL) was stirred for 1 h under microwave at 170° C. Then diluted with H$_2$O (10 mL), extracted with EtOAc 40 mL (20 mL×2). The combined organic layers were dried over Na$_2$SO$_4$, filtered and concentrated to give a residue. The residue was purified by prep-TLC (SiO$_2$, petroleum ether:ethyl acetate=0:1) and prep-HPLC (column: Waters Xbridge BEH C18 100*25 mm*5 um; mobile phase: [water(10 mM NH$_4$HCO$_3$)-ACN]; B %: 20%-50%,10 min.) to yield isopropyl trans-N-[4-[5-[4-cyano-2-(ethylsulfamoyl)phenyl]thiazol-2-yl]cyclohexyl]carbamate (810 ug, 1 umol, 1.3% yield, 86% purity) as a yellow solid. $^1$H NMR (400 MHz, methanol-d$_4$) δ=8.40 (s, 1H), 8.01 (d, J=8.1 Hz, 1H), 7.87 (s, 1H), 7.76-7.65 (m, 1H), 4.83 (br s, 1H), 3.55-3.39 (m, 1H), 3.14-2.99 (m, 1H), 2.95-2.85 (m, 2H), 2.27 (br d, J=12.6 Hz, 2H), 2.10 (br d, J=11.7 Hz, 2H), 1.79-1.67 (m, 2H), 1.50-1.37 (m, 2H), 1.25 (br d, J=6.1 Hz, 6H), 1.11-0.98 (m, 3H). ESI [M+H]=477.1.

Example 35

Preparation of isopropyl trans-N-[4-[5-[2-(tert-butylsulfamoyl)-4-[2-(isopropylamino)-2-oxo-ethyl]phenyl]thiazol-2-yl]cyclohexyl]carbamate (Compound 40)

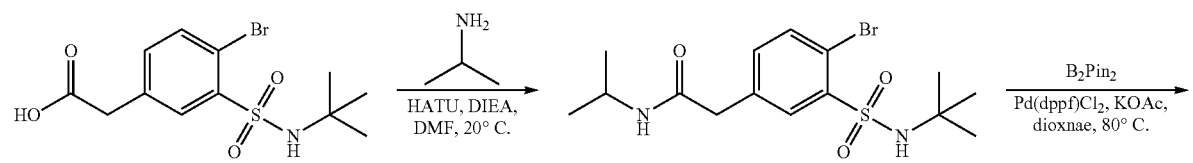

-continued

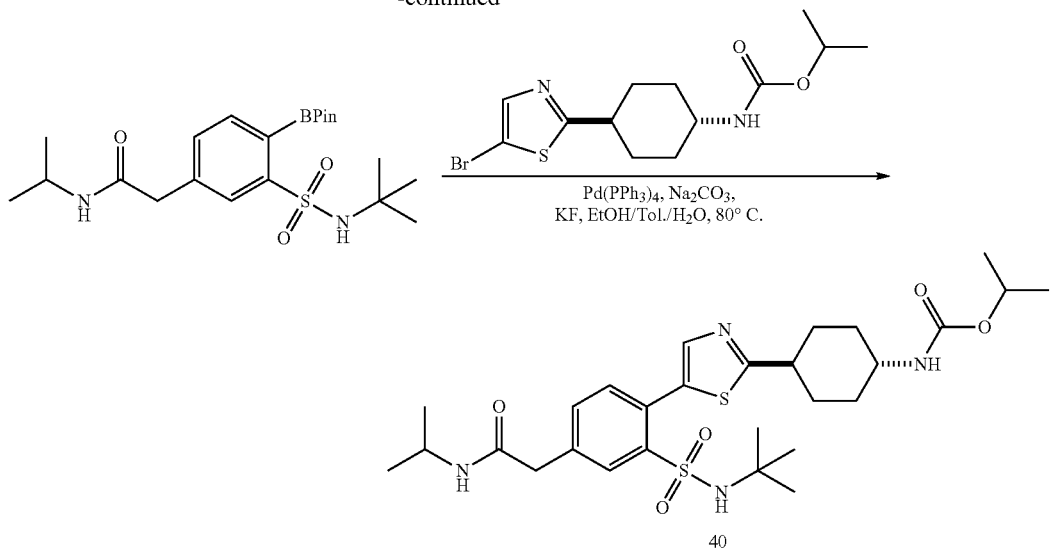

40 a) Synthesis of 2-[4-bromo-3-(tert-butylsulfamoyl)phenyl]-N-isopropyl-acetamide b) Synthesis of 2-[3-(tert-butylsulfamoyl)-4-(4,4,5,5-tetramethyl-1,3,2-dioxaborolan-2-yl)phenyl]-N-isopropyl-acetamide

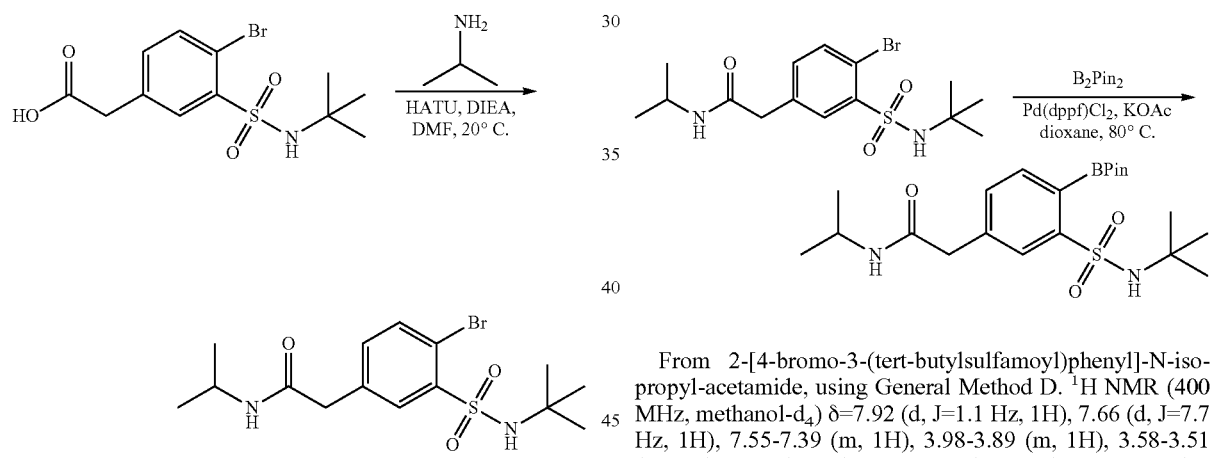

From 2-[4-bromo-3-(tert-butylsulfamoyl)phenyl]-N-isopropyl-acetic acid and isopropylamine, using General Method A. $^1$H NMR (400 MHz, methanol-$d_4$) δ=7.97 (s, 1H), 7.71 (d, J=7.9 Hz, 1H), 7.37 (dd, J=2.1, 8.0 Hz, 1H), 4.00-3.86 (m, 1H), 3.50 (s, 2H), 1.18 (s, 9H), 1.13 (d, J=6.6 Hz, 6H). ESI[M+H]=391.0/393.0.

From 2-[4-bromo-3-(tert-butylsulfamoyl)phenyl]-N-isopropyl-acetamide, using General Method D. $^1$H NMR (400 MHz, methanol-$d_4$) δ=7.92 (d, J=1.1 Hz, 1H), 7.66 (d, J=7.7 Hz, 1H), 7.55-7.39 (m, 1H), 3.98-3.89 (m, 1H), 3.58-3.51 (m, 2H), 1.40 (s, 9H), 1.25-1.16 (m, 12H), 1.15-1.10 (m, 6H). ESI[M+H]=439.2.

c) Synthesis of isopropyl trans-N-[4-[5-[2-(tert-butylsulfamoyl)-4-[2-(isopropylamino)-2-oxo-ethyl]phenyl]thiazol-2-yl]cyclohexyl]carbamate (Compound 40)

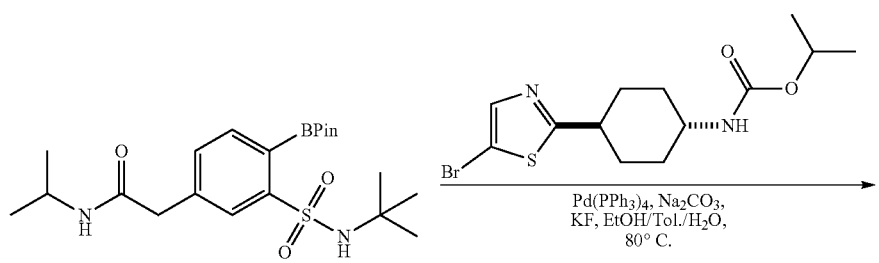

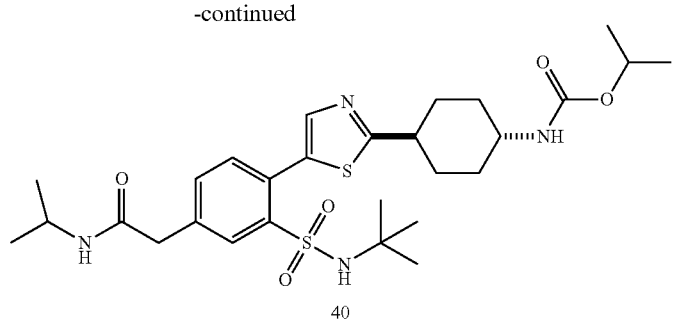

From 2-[3-(tert-butylsulfamoyl)-4-(4,4,5,5-tetramethyl-1,3,2-dioxaborolan-2-yl) phenyl]-N-isopropyl-acetamide, using General Method C. $^1$H NMR (400 MHz, methanol-d$_4$) δ=8.11 (br s, 1H), 7.77 (s, 1H), 7.54 (br d, J=7.3 Hz, 1H), 7.42 (br d, J=7.5 Hz, 1H), 4.82-4.74 (m, 1H), 4.01-3.87 (m, 1H), 3.57 (br s, 2H), 3.45 (br s, 1H), 3.08-2.95 (m, 1H), 2.23 (br d, J=12.3 Hz, 2H), 2.06 (br d, J=10.8 Hz, 2H), 1.78-1.61 (m, 2H), 1.49-1.33 (m, 2H), 1.21 (br d, J=4.9 Hz, 6H), 1.14 (br d, J=6.4 Hz, 6H), 1.08 (s, 9H). ESI [M+H]=579.3.

Example 36

Preparation of oxetan-3-yl (trans-4-(5-(2-(N-(tert-butyl)sulfamoyl)-4-(2-(isopropylamino)-2-oxoethyl) phenyl)thiazol-2-yl)cyclohexyl)carbamate (Compound 41)

Following the same protocol and under the same reaction conditions as for Compound 40, Compound 41 was prepared. $^1$H NMR (400 MHz, DMSO-d$_6$) δ=8.05 (br d, J=7.5 Hz, 1H), 7.97 (s, 1H), 7.67 (s, 1H), 7.49-7.41 (m, 2H), 7.40-7.34 (m, 1H), 6.96 (s, 1H), 5.26 (quin, J=5.7 Hz, 1H), 4.73 (t, J=6.8 Hz, 2H), 4.53-4.37 (m, 2H), 3.78 (qd, J=6.8, 13.6 Hz, 1H), 3.47 (s, 2H), 3.29 (s, 1H), 2.98-2.84 (m, 1H), 2.13 (br d, J=12.1 Hz, 2H), 1.91 (br d, J=10.1 Hz, 2H), 1.66-1.46 (m, 2H), 1.42-1.23 (m, 2H), 1.03 (d, J=6.6 Hz, 6H), 1.01 (s, 9H). ESI [M+H]=593.3.

Example 37

Preparation of isopropyl trans-N-[4-[5-(2-sulfamoylphenyl)thiazol-2-yl]cyclohexyl]carbamate (Compound 44)

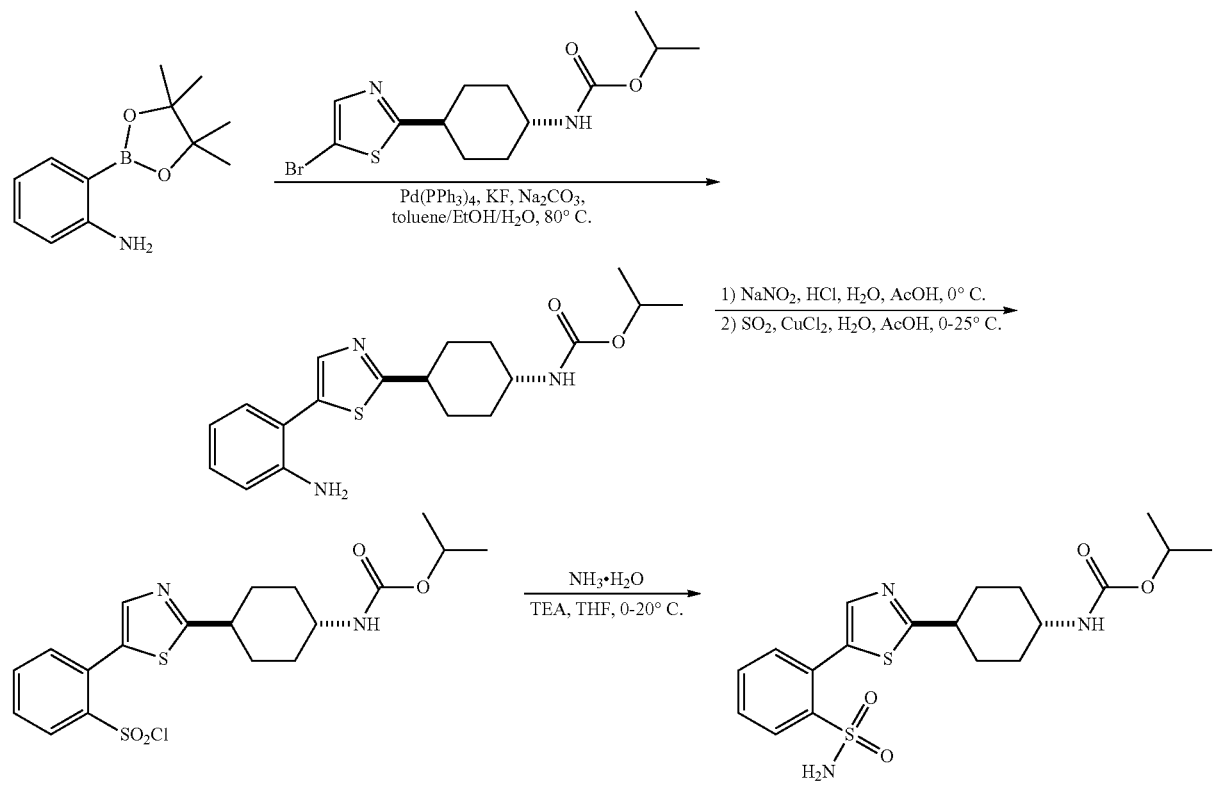

a) Synthesis of isopropyl trans-N-[4-[5-(2-aminophenyl) thiazol-2-yl]cyclohexyl]carbamate

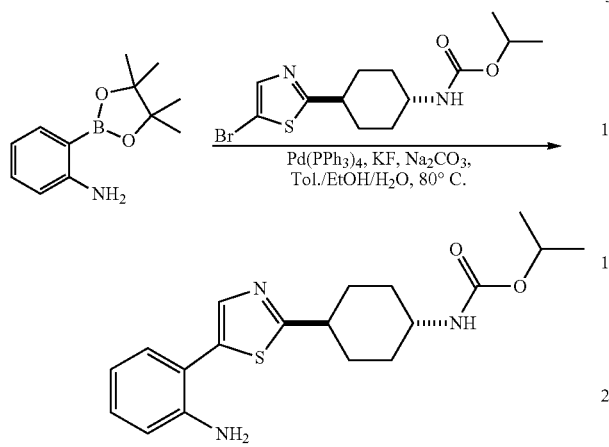

From 2-(4,4,5,5-tetramethyl-1,3,2-dioxaborolan-2-yl)aniline, using General Method C. ¹H NMR (400 MHz, methanol-d₄) δ=7.46-7.27 (m, 1H), 7.21-7.06 (m, 2H), 6.83 (d, J=8.2 Hz, 1H), 6.71 (t, J=7.5 Hz, 1H), 4.82 (br d, J=6.4 Hz, 1H), 3.52-3.38 (m, 1H), 2.98 (tt, J=3.5, 12.1 Hz, 1H), 2.26-2.16 (m, 2H), 2.06 (br d, J=10.6 Hz, 2H), 1.68 (dq, J=2.8, 12.9 Hz, 2H), 1.40 (dq, J=3.3, 12.6 Hz, 2H), 1.24-1.18 (m, 6H). ESI [M+H]=360.1.

b) Synthesis of isopropyl trans-N-[4-[5-(2-chlorosulfonylphenyl)thiazol-2-yl]cyclohexyl]carbamate

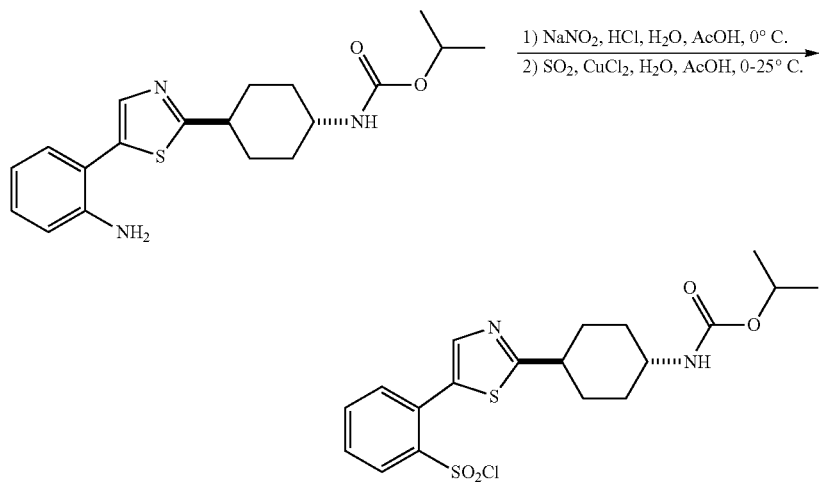

To a solution of isopropyl trans-N-[4-[5-(2-aminophenyl) thiazol-2-yl]cyclohexyl]carbamate (1.0 g, 2.8 mmol, 1.0 eq.) in H₂O (1 mL) and AcOH (5 mL) was added conc. HCl (5 mL) at 0° C. followed by a solution of NaNO₂ (960 mg, 14 mmol, 5 eq.) in H₂O (1 mL), the mixture was stirred at 0° C. for 2.5 h (mixture 1). To another mixture of CuCl₂ (374 mg, 3 mmol, 1 eq.) in H₂O (4 ml) was added a solution of SO₂ in AcOH (20 mL, 2 M) and stirred at 25° C. for 1 h (mixture 2). To the mixture 2 was added the mixture 1 at 0° C. The mixture was stirred at 0° C. for 0.5 h. The reaction mixture was quenched with H₂O (20 mL) at 0° C. and filtered to yield crude product isopropyl trans-N-[4-[5-(2-chlorosulfonylphenyl)thiazol-2-yl]cyclohexyl]carbamate (1.2 g, crude) as a pale yellow solid, without any purification. ESI [M+H]=443.0.

c) Synthesis of isopropyl trans-N-[4-[5-(2-sulfamoylphenyl)thiazol-2-yl]cyclohexyl]carbamate (Compound 44)

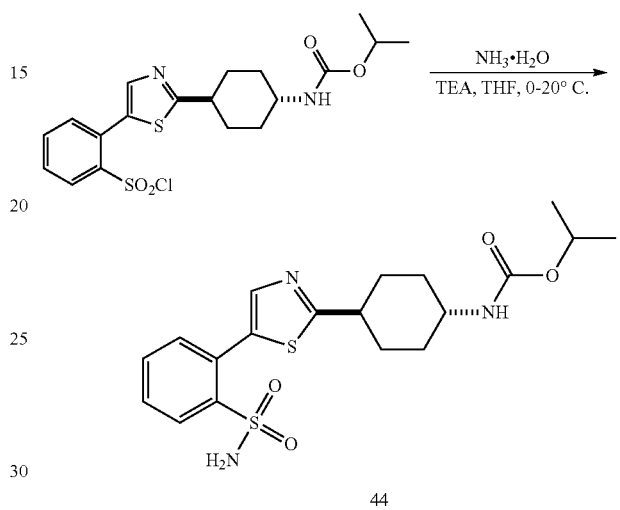

To a solution of TEA (137 mg, 1 mmol, 2 eq.), NH₃·H₂O (395 mg, 3 mmol, 30% purity, 5 eq.) in THF (2 mL) was added a solution of isopropyl trans-N-[4-[5-(2-chlorosulfonylphenyl)thiazol-2-yl]cyclohexyl]carbamate (300 mg, 677 umol, 1 eq.) in THF (2 mL) at 0° C. The mixture was stirred at 20° C. for 1 h and concentrated. The residue was purified by prep-HPLC (column: Welch Ultimate AQ-C18 150*30 mm*5 um; mobile phase: [water(0.1% TFA)-ACN]; B %: 35%-65%,12 min) to yield isopropyl trans-N-[4-[5-(2-sulfamoylphenyl)thiazol-2-yl]cyclohexyl]carbamate (92 mg, 216 umol, 32% yield, 99% purity) as a yellow solid. ¹H NMR (400 MHz, methanol-d₄) δ=8.22-8.12 (m, 1H), 7.87-

7.79 (m, 1H), 7.70-7.58 (m, 2H), 7.56-7.50 (m, 1H), 4.87-4.79 (m, 1H), 3.55-3.40 (m, 1H), 3.12-2.98 (m, 1H), 2.32-2.18 (m, 2H), 2.14-2.01 (m, 2H), 1.79-1.65 (m, 2H), 1.50-1.35 (m, 2H), 1.25 (br d, J=6.2 Hz, 6H). ESI [M+H]=424.1.

Example 38

Preparation of isopropyl (trans-4-(5-(2-(N-ethylsulfamoyl)phenyl)thiazol-2-yl)cyclohexyl)carbamate (Compound 45)

Following the same protocol and under the same reaction conditions as for Compound 44, Compound 45 was prepared. $^1$H NMR (400 MHz, methanol-$d_4$) δ=8.06 (dd, J=1.0, 7.8 Hz, 1H), 7.72 (s, 1H), 7.68-7.55 (m, 2H), 7.49 (dd, J=1.0, 7.4 Hz, 1H), 4.84-4.76 (m, 1H), 3.45 (ddd, J=4.1, 7.6, 11.5 Hz, 1H), 3.00 (tt, J=3.4, 12.1 Hz, 1H), 2.85 (q, J=7.3 Hz, 2H), 2.31-2.17 (m, 2H), 2.12-1.98 (m, 2H), 1.69 (dq, J=2.9, 12.8 Hz, 2H), 1.41 (dq, J=3.1, 12.6 Hz, 2H), 1.22 (br d, J=6.2 Hz, 6H), 1.00 (t, J=7.2 Hz, 3H). ESI [M+H]=452.1.

Example 39

Preparation of isopropyl (trans-4-(5-(2-(N-(tert-butyl)sulfamoyl)phenyl)thiazol-2-yl)cyclohexyl)carbamate (Compound 46)

Following the same protocol and under the same reaction conditions as for Compound 44, Compound 46 was prepared. $^1$H NMR (400 MHz, methanol-$d_4$) δ=8.15 (dd, J=1.3, 7.7 Hz, 1H), 7.76 (s, 1H), 7.68-7.53 (m, 2H), 7.48 (dd, J=1.3, 7.5 Hz, 1H), 4.86-4.76 (m, 1H), 3.45 (tt, J=3.8, 11.5 Hz, 1H), 3.02 (tt, J=3.5, 12.0 Hz, 1H), 2.30-2.17 (m, 2H), 2.12-2.01 (m, 2H), 1.70 (dq, J=2.6, 12.9 Hz, 2H), 1.41 (dq, J=3.1, 12.6 Hz, 2H), 1.22 (br d, J=6.2 Hz, 6H), 1.07 (s, 9H). ESI [M+H]=480.2.

Example 40

Preparation of isopropyl trans-N-[4-[5-(2-methylsulfamoylphenyl)thiazol-2-yl]cyclohexyl]carbamate (Compound 93)

Following the same protocol and under the same reaction conditions as for Compound 44, Compound 93 was prepared. $^1$H NMR (400 MHz, methanol-$d_4$) δ=8.18-7.99 (m, 1H), 7.80-7.77 (m, 1H), 7.71-7.61 (m, 2H), 7.54 (dd, J=1.2, 7.2 Hz, 1H), 4.87-4.80 (m, 1H), 3.54-3.43 (m, 1H), 3.11-2.99 (m, 1H), 2.30-2.23 (m, 2H), 2.13-2.04 (m, 2H), 1.80-1.65 (m, 2H), 1.51-1.37 (m, 2H), 1.25 (br d, J=6.1 Hz, 6H). ESI [M+H]=438.1.

Example 41

Preparation of oxetan-3-yl trans-N-[4-[5-[2-(ethylsulfamoyl)-4-(iso-butoxymethyl)phenyl]thiazol-2-yl]cyclohexyl]carbamate (Compound 52)

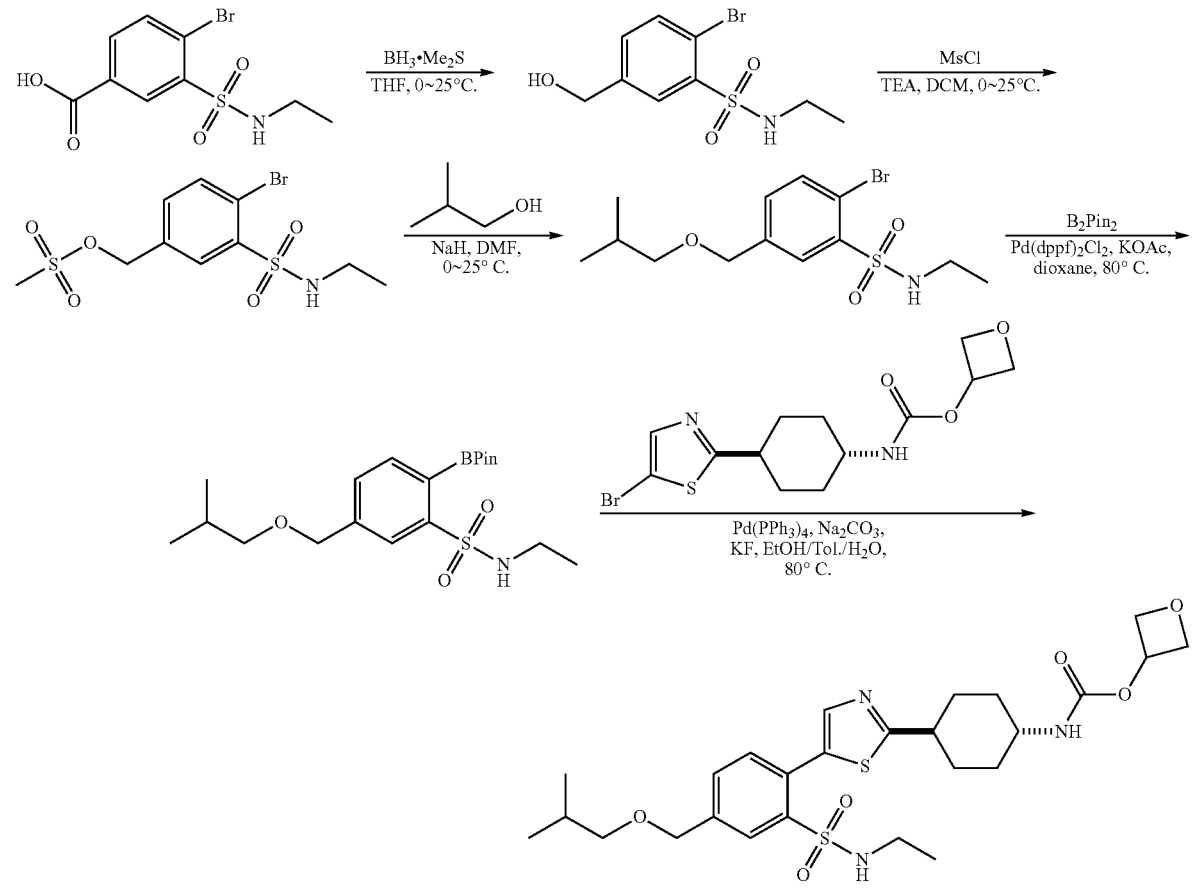

52 a) Synthesis of 2-bromo-N-ethyl-5-(hydroxymethyl)benzenesulfonamide

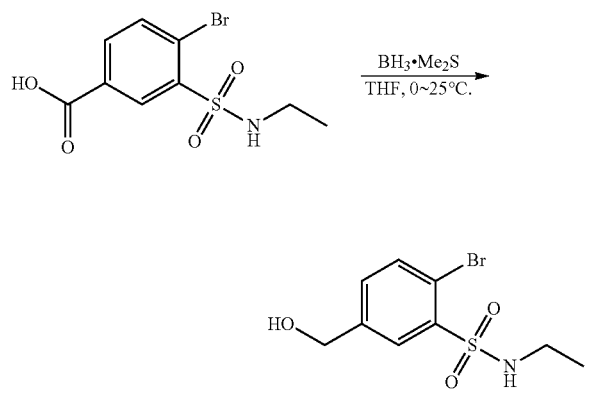

To a solution of 4-bromo-3-(ethylsulfamoyl)benzoic acid (1.8 g, 5.8 mmol, 1.0 eq.) in THF (40 mL) was added BH$_3$·Me$_2$S (10.0 M, 5.8 mL, 10.0 eq.) at 0° C. and stirred at 25° C. for 12 h. The reaction mixture was quenched by MeOH 50 mL at 0° C., and was stirred at 50° C. for 1 h. Then the reaction mixture was concentrated under reduced pressure. The crude product was purified by reversed-phase HPLC (0.1% TFA condition) to yield 2-bromo-N-ethyl-5-(hydroxymethyl)benzenesulfonamide (1.2 g, 4.2 mmol, 71% yield) as a yellow oil. ESI [M−H]=291.8/293.8.

b) Synthesis of [4-bromo-3-(ethylsulfamoyl)phenyl]methyl methanesulfonate

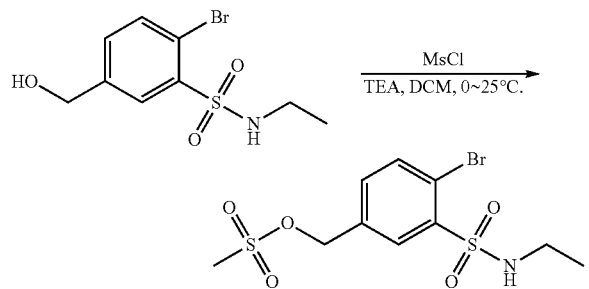

To a solution of 2-bromo-N-ethyl-5-(hydroxymethyl)benzenesulfonamide (1.1 g, 3.8 mmol, 1.0 eq) in DCM (15 mL) was added TEA (770 mg, 8 mmol, 2 eq) and methanesulfonyl chloride (0.15 g, 1.31 mmol, 3.44e-1 eq.) at 0° C. The mixture was stirred at 25° C. for 2 h. The reaction mixture was concentrated under reduced pressure. The residue was diluted with H$_2$O 20 mL and extracted with DCM 60 mL (20 mL×3). The combined organic layers were dried over Na$_2$SO$_4$, filtered and concentrated under reduced pressure to give a residue. The residue was purified by column chromatography (SiO$_2$, petroleum ether:ethyl acetate=1:0 to 0:1) to yield [4-bromo-3-(ethylsulfamoyl)phenyl]methyl methanesulfonate (600 mg, 1 mmol, 42% yield) as a pale yellow solid. ESI [M−H]=369.8/371.8.

c) Synthesis of 2-bromo-N-ethyl-5-(isobutoxymethyl)benzenesulfonamide

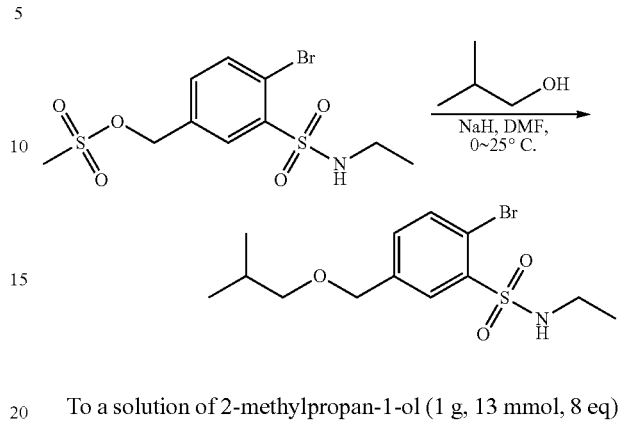

To a solution of 2-methylpropan-1-ol (1 g, 13 mmol, 8 eq) in DMF (10 mL) was added NaH (58 mg, 1.5 mmol, 60% purity, 0.9 eq) at 0° C. The mixture was stirred at 25° C. for 30 min. To the mixture was added a solution of [4-bromo-3-(ethylsulfamoyl)phenyl] methyl methanesulfonate (600 mg, 1.61 mmol, 1 eq) in DMF (10 mL), then stirred at 25° C. for 1 h. The reaction was quenched with sat.aq. NH$_4$Cl 50 mL at 0° C., extracted with EtOAc 150 mL (50 mL×3). The combined organic layers were washed with sat.aq. NaCl 45 mL (15 mL×3), dried over Na$_2$SO$_4$, filtered and concentrated under reduced pressure to give a residue. The residue was purified by column chromatography (SiO$_2$, petroleum ether: ethyl acetate=1:0 to 0:1) to yield 2-bromo-N-ethyl-5-(isobutoxymethyl) benzenesulfonamide (260 mg, 742.28 umol, 46% yield) as a pale yellow oil. $^1$H NMR (400 MHz, methanol-d$_4$) δ=8.07 (d, J=1.8 Hz, 1H), 7.76 (d, J=7.9 Hz, 1H), 7.44 (dd, J=2.0, 8.2 Hz, 1H), 4.53 (s, 2H), 3.29 (br s, 2H), 2.94 (q, J=7.3 Hz, 2H), 1.90 (td, J=6.6, 13.2 Hz, 1H), 1.05 (t, J=7.3 Hz, 3H), 0.94 (d, J=6.8 Hz, 6H). ESI [M−H]=347.9/349.9.

d) Synthesis of N-ethyl-5-(isobutoxymethyl)-2-(4,4,5,5-tetramethyl-1,3,2-dioxaborolan-2-yl)benzenesulfonamide

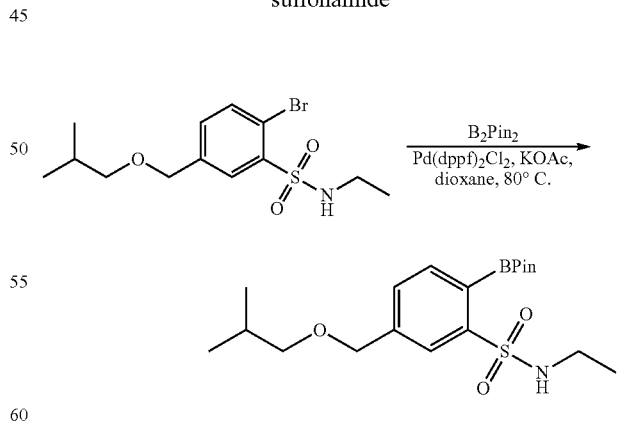

From 2-bromo-N-ethyl-5-(isobutoxymethyl)benzenesulfonamide, using General Method B. $^1$H NMR (400 MHz, methanol-d$_4$) δ=7.76 (d, J=19.6 Hz, 1H), 7.58-7.41 (m, 2H), 4.48 (d, J=3.5 Hz, 2H), 3.18 (s, 2H), 2.89-2.72 (m, 2H), 1.87-1.72 (m, 1H), 1.22-1.05 (m, 12H), 0.94 (td, J=7.3, 9.1 Hz, 3H), 0.84 (d, J=6.7 Hz, 6H). ESI [M+H]=398.2.

e) Synthesis of oxetan-3-yl trans-N-[4-[5-[2-(ethyl-sulfamoyl)-4-(isobutoxy-methyl)phenyl]thiazol-2-yl]cyclohexyl]carbamate (Compound 52)

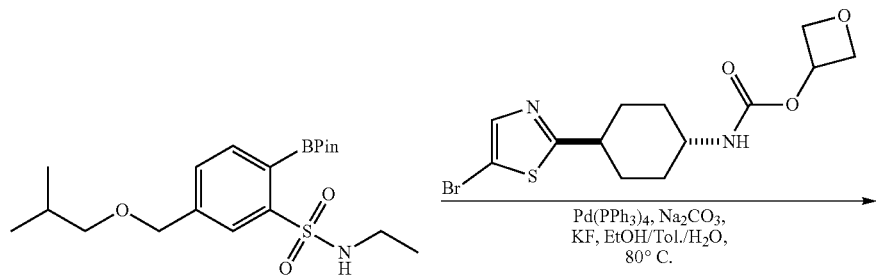

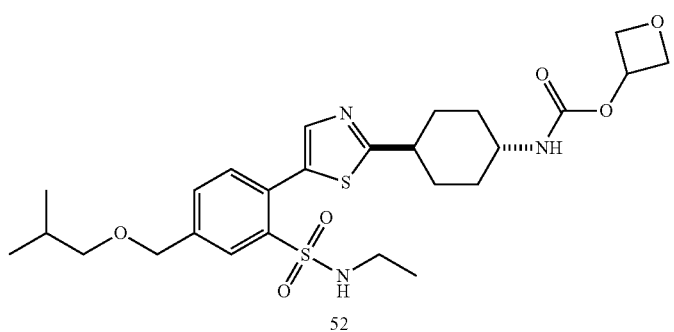

From N-ethyl-5-(isobutoxymethyl)-2-(4,4,5,5-tetramethyl-1,3,2-dioxaborolan-2-yl) benzenesulfonamide, using General Method C. $^1$H NMR (400 MHz, DMSO-d$_6$) δ=7.90 (s, 1H), 7.69 (s, 1H), 7.55 (br d, J=7.9 Hz, 1H), 7.49-7.38 (m, 3H), 5.26 (quin, J=5.7 Hz, 1H), 4.73 (t, J=6.8 Hz, 2H), 4.56 (s, 2H), 4.48-4.39 (m, 2H), 3.29 (br s, 1H), 3.23 (d, J=6.6 Hz, 2H), 2.92 (tt, J=3.3, 11.8 Hz, 1H), 2.77 (br d, J=6.8 Hz, 2H), 2.13 (br d, J=11.9 Hz, 2H), 1.97-1.88 (m, 2H), 1.87-1.78 (m, 1H), 1.63-1.48 (m, 2H), 1.43-1.28 (m, 2H), 0.93 (t, J=7.3 Hz, 3H), 0.88 (d, J=6.8 Hz, 6H). ESI [M+H]=552.2.

Example 42

Preparation of isopropyl (trans-4-(5-(2-(N-ethylsulfamoyl)-4-(isobutoxymethyl)phenyl)thiazol-2-yl)cyclohexyl)carbamate (Compound 51)

Following the same protocol and under the same reaction conditions as for Compound 52, Compound 51 was prepared. $^1$H NMR (400 MHz, methanol-d$_4$) δ=8.08 (s, 1H), 7.77 (s, 1H), 7.62 (d, J=7.8 Hz, 1H), 7.50 (d, J=7.8 Hz, 1H), 4.84 (br s, 1H), 4.63 (s, 2H), 3.47 (tdd, J=3.9, 7.7, 11.4 Hz, 1H), 3.33 (s, 2H), 3.04 (tt, J=3.3, 12.0 Hz, 1H), 2.89 (q, J=7.2 Hz, 2H), 2.26 (br d, J=12.5 Hz, 2H), 2.13-2.05 (m, 2H), 2.01-1.88 (m, 1H), 1.72 (dq, J=2.4, 12.8 Hz, 2H), 1.50-1.37 (m, 2H), 1.24 (br d, J=6.0 Hz, 6H), 1.04 (t, J=7.2 Hz, 3H), 0.98 (d, J=6.7 Hz, 6H). ESI [M+H]=538.3.

Example 43

Preparation of isopropyl trans-N-[4-[5-[2-(azetidin-1-ylsulfonyl)-4-cyano-phenyl]thiazol-2-yl]cyclohexyl]carbamate (Compound 54)

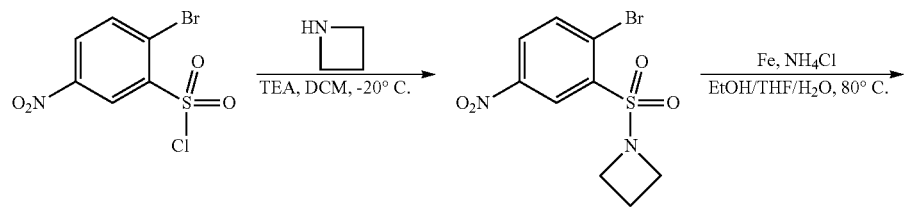

-continued
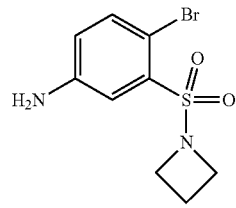 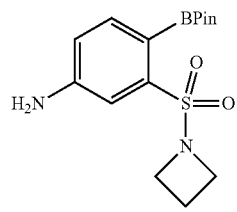
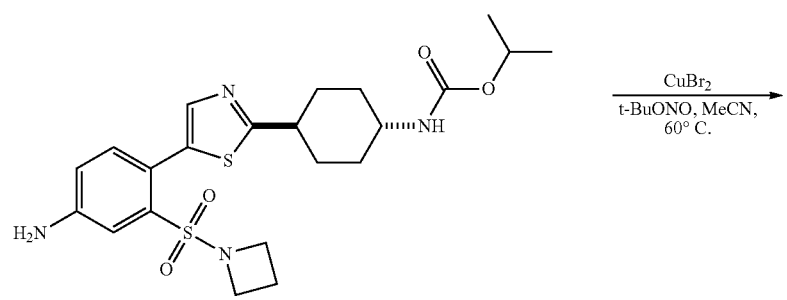
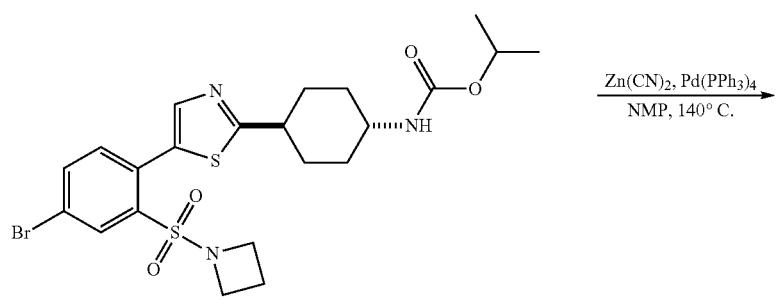
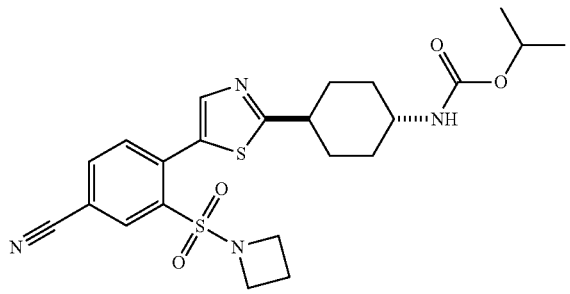

a) Synthesis of 1-(2-bromo-5-nitro-phenyl)sulfonylazetidine

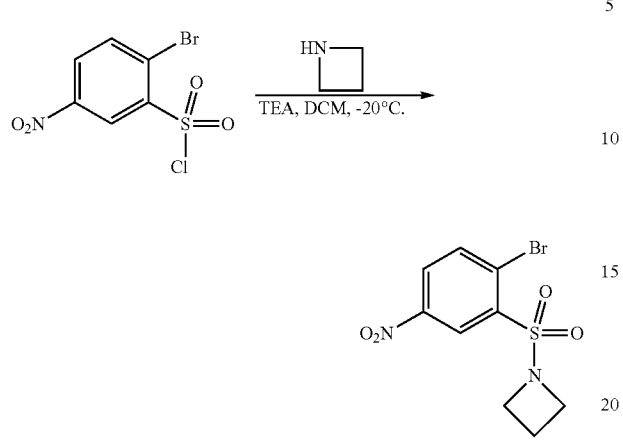

From 1-(2-bromo-5-nitro-phenyl)sulfonyl chloride and azetidine, using General Method G.

b) Synthesis of 3-(azetidin-1-ylsulfonyl)-4-bromo-aniline

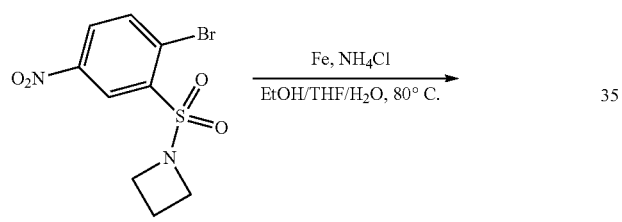

To a solution of 1-(2-bromo-5-nitro-phenyl)sulfonylazetidine (5.2 g, 16.1 mmol, 1.0 eq.) in EtOH (30 mL), H$_2$O (10 mL) and THF (30 mL) was added Fe (4.5 g, 80.8 mmol, 5.0 eq.) and NH$_4$Cl (2.6 g, 48.5 mmol, 3.0 eq.). The mixture was stirred at 80° C. for 12 h. The reaction mixture was filtered. The filtrate was concentrated and the residue was diluted with H$_2$O (30 mL) and extracted with EtOAc 90 mL (30 mL×3). The combined organic layers were dried over Na$_2$SO$_4$, filtered and concentrated. The residue was purified by column chromatography (SiO$_2$, petroleum ether:ethyl acetate=10:1 to 1:10) to yield 3-(azetidin-1-ylsulfonyl)-4-bromo-aniline (2.8 g, 9.6 mmol, 60% yield) as a white solid. ESI [M+H]=291.0/293.0.

c) Synthesis of 3-(azetidin-1-ylsulfonyl)-4-(4,4,5,5-tetramethyl-1,3,2-dioxaborolan-2-yl)aniline

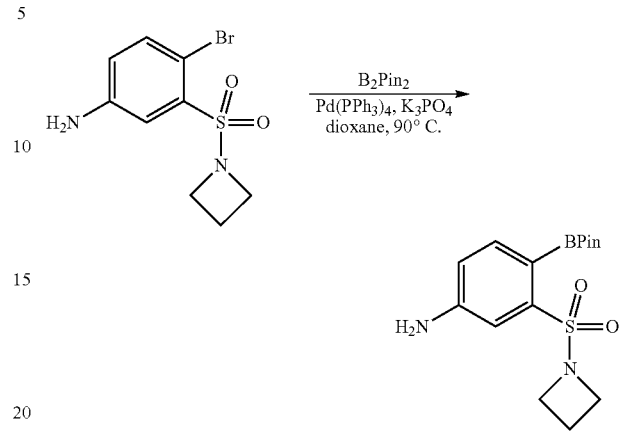

A mixture of 4,4,5,5-tetramethyl-2-(4,4,5,5-tetramethyl-1,3,2-dioxaborolan-2-yl)-1,3,2-dioxaborolane (11.3 g, 44.7 mmol, 5.0 eq.), 3-(azetidin-1-ylsulfonyl)-4-bromo-aniline (2.6 g, 8.9 mmol, 1.0 eq.), K$_3$PO$_4$ (9.5 g, 44.7 mmol, 5.0 eq.), Pd(PPh$_3$)$_4$ (1.0 g, 893.0 umol, 0.1 eq.) in dioxane (120 mL) was stirred at 90° C. for 3 h under N$_2$ atmosphere. The reaction mixture was concentrated and diluted with H$_2$O (30 mL) and extracted with EtOAc 90 mL (30 mL×3). The combined organic layers were dried over Na$_2$SO$_4$, filtered and concentrated. The residue was purified by column chromatography (SiO$_2$, petroleum ether:ethyl acetate=100:1 to 1:100) to yield crude 3-(azetidin-1-ylsulfonyl)-4-(4,4,5,5-tetramethyl-1,3,2-dioxaborolan-2-yl)aniline (3.8 g, crude) as a dark gum. $^1$H NMR (400 MHz, methanol-d$_4$) δ=7.26 (d, J=7.9 Hz, 1H), 7.08 (d, J=2.0 Hz, 1H), 6.91 (dd, J=2.1, 8.0 Hz, 1H), 3.82 (t, J=7.7 Hz, 4H), 2.05 (quin, J=7.8 Hz, 2H), 1.33 (s, 12H). ESI [M+H]=339.2.

d) Synthesis of isopropyl trans-N-[4-[5-[4-amino-2-(azetidin-1-ylsulfonyl)phenyl]thiazol-2-yl]cyclohexyl]carbamate

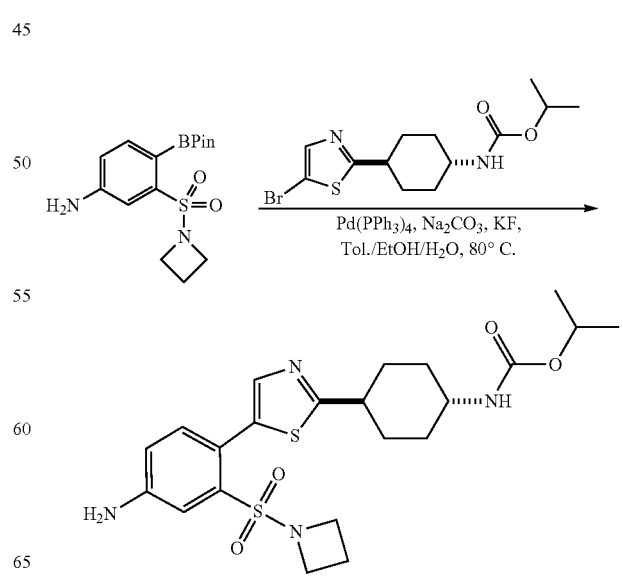

From 3-(azetidin-1-ylsulfonyl)-4-(4,4,5,5-tetramethyl-1,3,2-dioxaborolan-2-yl)aniline, using General Method C. ¹H NMR (400 MHz, methanol-d₄) δ=7.59 (s, 1H), 7.36 (d, J=2.3 Hz, 1H), 7.20 (d, J=8.3 Hz, 1H), 6.89 (dd, J=2.4, 8.3 Hz, 1H), 4.86-4.77 (m, 1H), 3.69 (t, J=7.6 Hz, 4H), 3.53-3.42 (m, 1H), 3.07-2.93 (m, 1H), 2.28-2.17 (m, 2H), 2.16-2.11 (m, 2H), 2.08 (br d, J=7.8 Hz, 2H), 1.79-1.63 (m, 2H), 1.50-1.35 (m, 2H), 1.24 (br d, J=6.1 Hz, 6H). ESI [M+H]=479.2.

e) Synthesis of isopropyl trans-N-[4-[5-[2-(azetidin-1-ylsulfonyl)-4-bromo-phenyl]thiazol-2-yl]cyclohexyl]carbamate (General Method L)

f) Synthesis of isopropyl trans-N-[4-[5-[2-(azetidin-1-ylsulfonyl)-4-cyano-phenyl]thiazol-2-yl]cyclohexyl]carbamate (Compound 54)

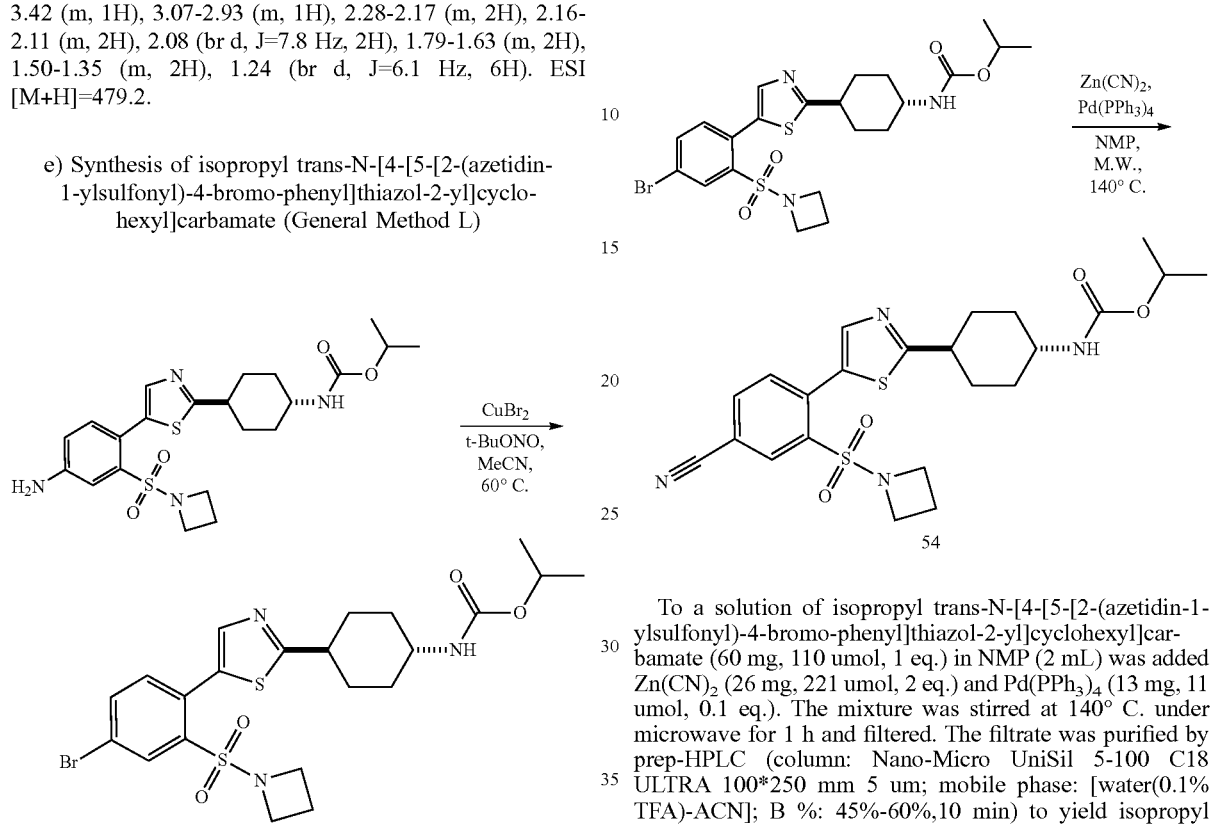

To a solution of isopropyl trans-N-[4-[5-[4-amino-2-(azetidin-1-ylsulfonyl)phenyl]thiazol-2-yl]cyclohexyl]carbamate (200 mg, 418 umol, 1 eq.) in MeCN (6 mL) was added CuBr₂ (37 mg, 167 umol, 0.4 eq.) and tert-butyl nitrite (64 mg, 627 umol, 1.5 eq.). The mixture was stirred at 60° C. for 1 h and concentrated. The residue was diluted with H₂O (5 mL) and extracted with EtOAc 60 mL (20 mL×3). The combined organic layers were dried over Na₂SO₄, filtered and concentrated under reduced pressure to give a residue. The residue was purified by prep-TLC (SiO₂, petroleum ether:ethyl acetate=1:2) to yield isopropyl trans-N-[4-[5-[2-(azetidin-1-ylsulfonyl)-4-bromo-phenyl]thiazol-2-yl]cyclohexyl]carbamate (120 mg, 221 umol, 53% yield) as a white solid. ESI [M+H]=542.0/544.0.

To a solution of isopropyl trans-N-[4-[5-[2-(azetidin-1-ylsulfonyl)-4-bromo-phenyl]thiazol-2-yl]cyclohexyl]carbamate (60 mg, 110 umol, 1 eq.) in NMP (2 mL) was added Zn(CN)₂ (26 mg, 221 umol, 2 eq.) and Pd(PPh₃)₄ (13 mg, 11 umol, 0.1 eq.). The mixture was stirred at 140° C. under microwave for 1 h and filtered. The filtrate was purified by prep-HPLC (column: Nano-Micro UniSil 5-100 C18 ULTRA 100*250 mm 5 um; mobile phase: [water(0.1% TFA)-ACN]; B %: 45%-60%,10 min) to yield isopropyl trans-N-[4-[5-[2-(azetidin-1-ylsulfonyl)-4-cyano-phenyl]thiazol-2-yl]cyclohexyl]carbamate (15 mg, 31 umol, 28% yield, 100% purity) as a yellow solid. ¹H NMR (400 MHz, methanol-d₄) δ=8.42 (s, 1H), 8.04 (br d, J=7.83 Hz, 1H), 7.85 (s, 1H), 7.75 (d, J=7.95 Hz, 1H), 4.77-4.86 (m, 1H), 3.75 (br t, J=7.64 Hz, 4H), 3.44-3.53 (m, 1H), 3.03-3.16 (m, 1H), 2.26 (br d, J=12.59 Hz, 2H), 2.14-2.21 (m, 2H), 2.10 (br d, J=11.98 Hz, 2H), 1.73 (br d, J=12.59 Hz, 2H), 1.38-1.50 (m, 2H), 1.25 (br d, J=5.87 Hz, 6H). ESI [M+H]=489.1.

Example 44

Preparation of isopropyl trans-N-[4-[5-[2-(ethylsulfamoyl)-4-[2-(isopropylamino)-2-oxo-ethyl]phenyl]thiazol-2-yl]cyclohexyl]carbamate (Compound 58)

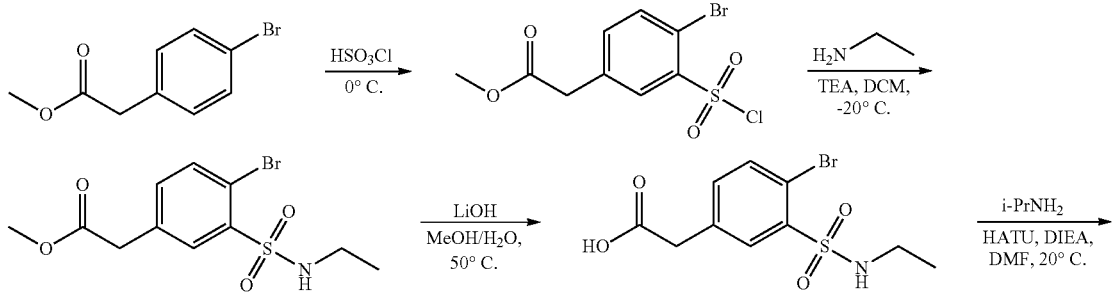

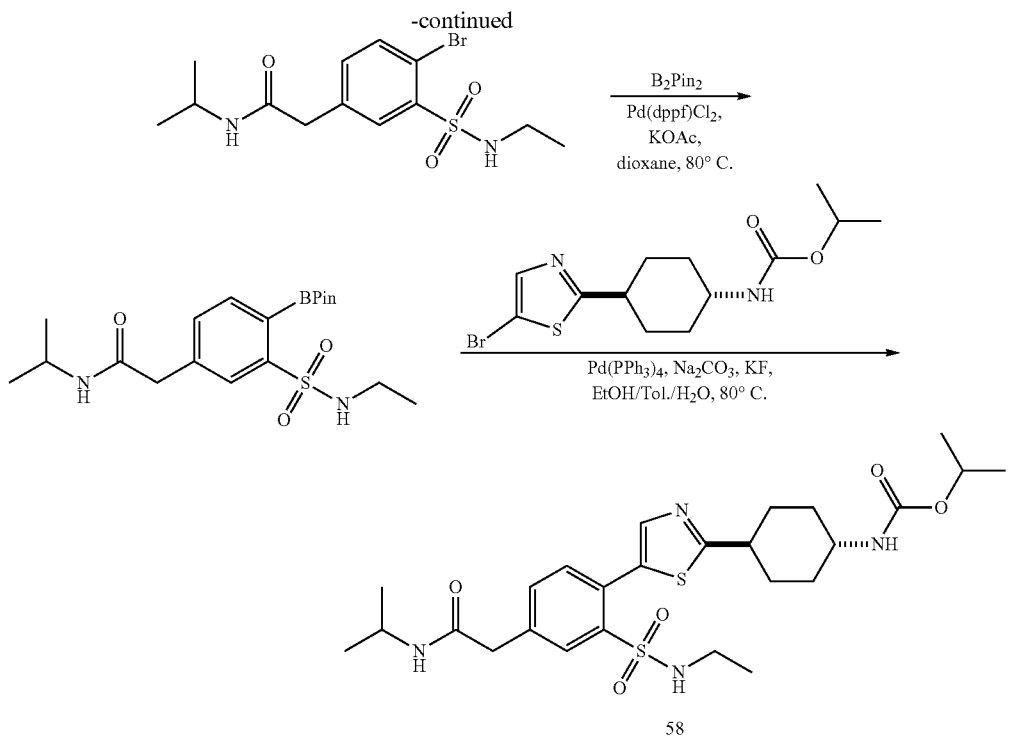

58 a) Synthesis of 2-(4-bromo-3-chlorosulfonyl-phenyl)acetate

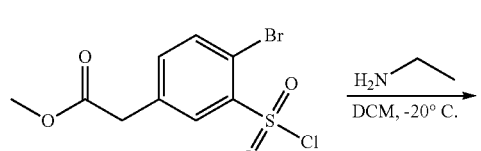

HSO₃Cl (200 mL) was added slowly to a flask containing methyl 2-(4-bromo-phenyl)acetate (20 g, 87 mmol, 1 eq.) was stirred at 0° C. for 5 h. The reaction mixture was quenched with ice-water (1 L) and extracted with DCM 2 L (1 L×2). The combined organic layers were washed with H₂O (500 mL), dried over Na₂SO₄, filtered and concentrated under reduced pressure to yield 2-(4-bromo-3-chlorosulfonyl-phenyl)acetate (30 g, crude) as a yellow oil.

b) Synthesis of methyl 2-[4-bromo-3-(ethylsulfamoyl)phenyl]acetate

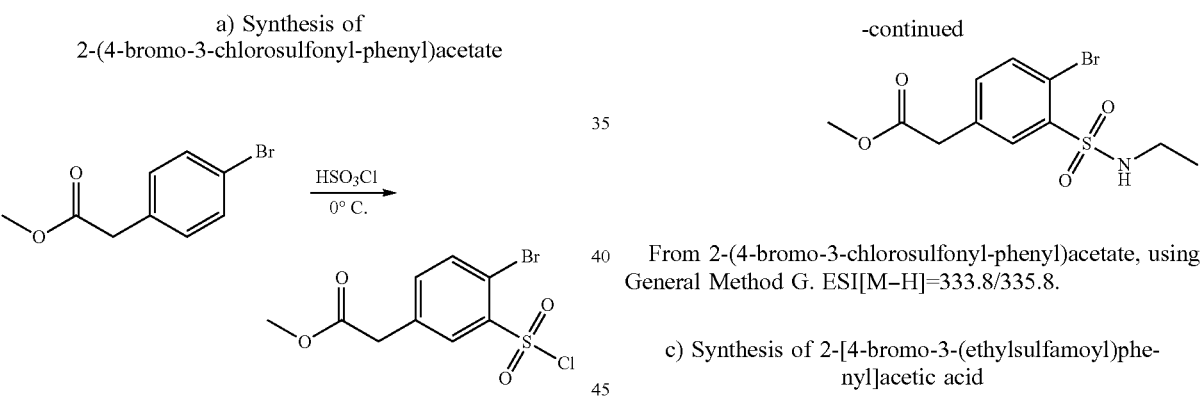

From 2-(4-bromo-3-chlorosulfonyl-phenyl)acetate, using General Method G. ESI[M−H]=333.8/335.8.

c) Synthesis of 2-[4-bromo-3-(ethylsulfamoyl)phenyl]acetic acid

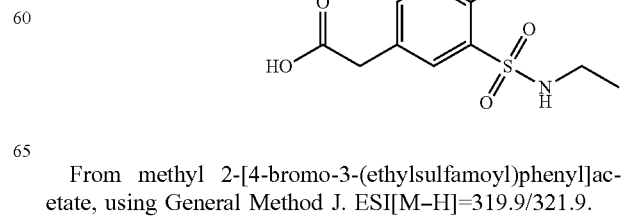

From methyl 2-[4-bromo-3-(ethylsulfamoyl)phenyl]acetate, using General Method J. ESI[M−H]=319.9/321.9.

d) Synthesis of 2-[4-bromo-3-(ethylsulfamoyl)phenyl]-N-isopropyl-acetamide

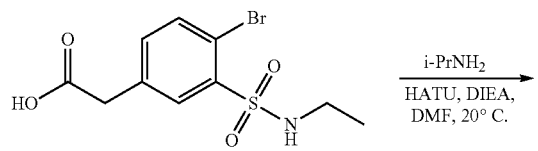

From 2-[4-bromo-3-(ethylsulfamoyl)phenyl]acetic acid and isopropylamine, using General Method A. ¹H NMR (400 MHz, methanol-$d_4$) δ=8.03 (d, J=2.21 Hz, 1H), 7.73 (d, J=8.16 Hz, 1H), 7.39 (dd, J=2.20, 7.94 Hz, 1H), 3.94 (spt, J=6.58 Hz, 1H), 3.51 (s, 2H), 2.88-2.98 (m, 2H), 1.13 (d, J=6.62 Hz, 6H), 1.04 (t, J=7.28 Hz, 3H). ESI [M+H]=363.0/365.0.

e) Synthesis of 2-[3-(ethylsulfamoyl)-4-(4,4,5,5-tetramethyl-1,3,2-dioxa-borolan-2-yl)phenyl]-N-isopropyl-acetamide

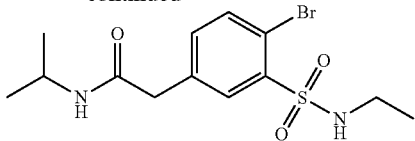

-continued

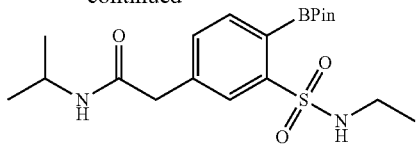

From 2-[4-bromo-3-(ethylsulfamoyl)phenyl]-N-isopropyl-acetamide, using General Method B. ESI [M+H]=411.1.

f) Synthesis of isopropyl trans-N-[4-[5-[2-(ethylsulfamoyl)-4-[2-(isopropyl-amino)-2-oxo-ethyl]phenyl]thiazol-2-yl]cyclohexyl]carbamate (Compound 58)

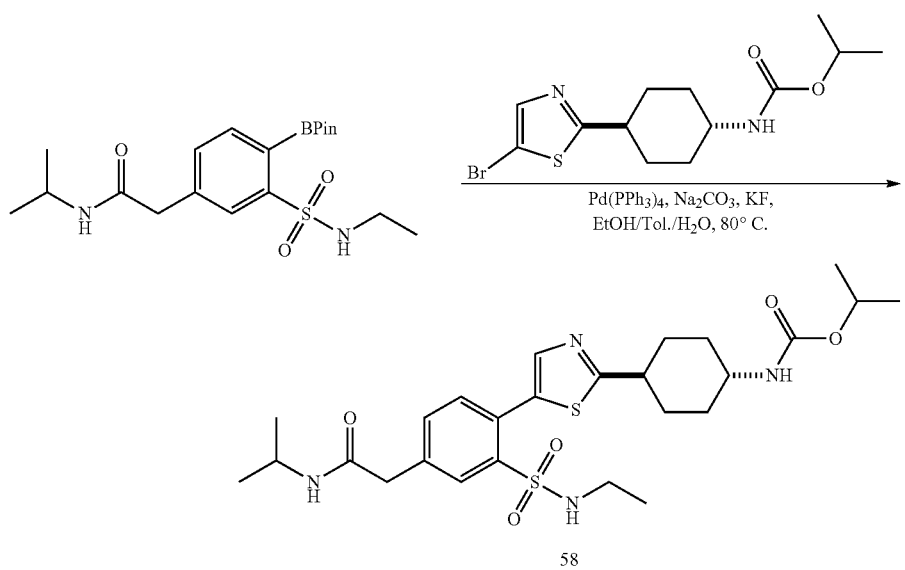

58

From 2-[3-(ethylsulfamoyl)-4-(4,4,5,5-tetramethyl-1,3,2-dioxa-borolan-2-yl)phenyl]-N-isopropyl-acetamide, using General Method C. ¹H NMR (400 MHz, methanol-$d_4$) δ=8.01 (d, J=1.54 Hz, 1H), 7.71 (s, 1H), 7.55 (dd, J=7.72, 1.76 Hz, 1H), 7.43 (d, J=7.94 Hz, 1H), 4.76-4.84 (m, 1H), 3.96 (dt, J=13.12, 6.67 Hz, 1H), 3.59 (s, 2H), 3.38-3.50 (m, 1H), 2.94-3.06 (m, 1H), 2.85 (q, J=7.20 Hz, 2H), 2.19-2.28 (m, 2H), 2.06 (br d, J=10.14 Hz, 2H), 1.63-1.75 (m, 2H), 1.34-1.46 (m, 2H), 1.22 (br d, J=6.17 Hz, 6H), 1.15 (d, J=6.62 Hz, 6H), 1.00 (t, J=7.17 Hz, 3H). ESI [M+H]=551.2.

Example 45

Preparation of oxetan-3-yl (trans-4-(5-(2-(N-ethylsulfamoyl)-4-(2-(isopropylamino)-2-oxoethyl)phenyl)thiazol-2-yl)cyclohexyl)carbamate (Compound 59)

Following the same protocol and under the same reaction conditions as for Compound 58, Compound 59 was prepared. ¹H NMR (400 MHz, methanol-$d_4$) δ=8.01 (s, 1H), 7.71 (s, 1H), 7.55 (br d, J=7.72 Hz, 1H), 7.43 (d, J=7.72 Hz, 1H), 5.29-5.41 (m, 1H), 4.87 (br s, 2H), 4.59 (br t, J=6.06 Hz, 2H), 3.96 (dt, J=13.23, 6.62 Hz, 1H), 3.59 (s, 2H), 3.39-3.51 (m, 1H), 2.96-3.07 (m, 1H), 2.85 (q, J=7.28 Hz, 2H), 2.24 (br d, J=12.35 Hz, 2H), 1.99-2.13 (m, 2H), 1.62-1.75 (m, 2H), 1.36-1.49 (m, 2H), 1.15 (d, J=6.62 Hz, 6H), 1.00 (t, J=7.28 Hz, 3H). ESI [M+H]=564.9.

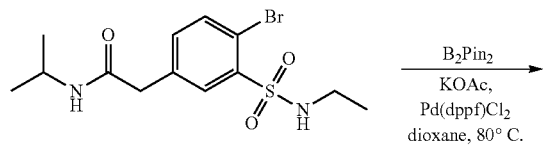

Example 46

Preparation of oxetan-3-yl 4-(5-(2-(N-ethylsulfamoyl)-4-(2-(isopropylamino)-2-oxoethyl)phenyl)thiazol-2-yl)piperazine-1-carboxylate (Compound 96)

Following the same protocol and under the same reaction conditions as for Compound 58, Compound 96 was prepared. $^1$H NMR (400 MHz, methanol-$d_4$) δ=7.99 (d, J=1.54 Hz, 1H), 7.52 (dd, J=7.83, 1.65 Hz, 1H), 7.42-7.46 (m, 1H), 7.28 (s, 1H), 5.36-5.43 (m, 1H), 4.88 (t, J=7.17 Hz, 2H), 4.65 (dd, J=7.83, 5.40 Hz, 2H), 3.95 (dt, J=13.18, 6.53 Hz, 1H), 3.59-3.75 (m, 4H), 3.51-3.58 (m, 6H), 2.86 (q, J=7.28 Hz, 2H), 1.15 (d, J=6.62 Hz, 6H), 1.01 (t, J=7.17 Hz, 3H). ESI [M+H]=551.9.

Example 47

Preparation of trans-3-(ethylsulfamoyl)-4-[2-[4-(oxetan-3-yloxy-carbonylamino)cyclohexyl]thiazol-5-yl]benzoic acid (Compound 66)

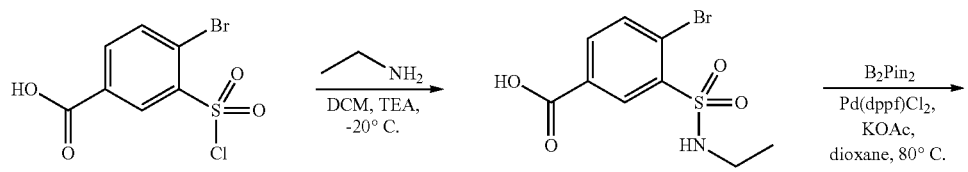

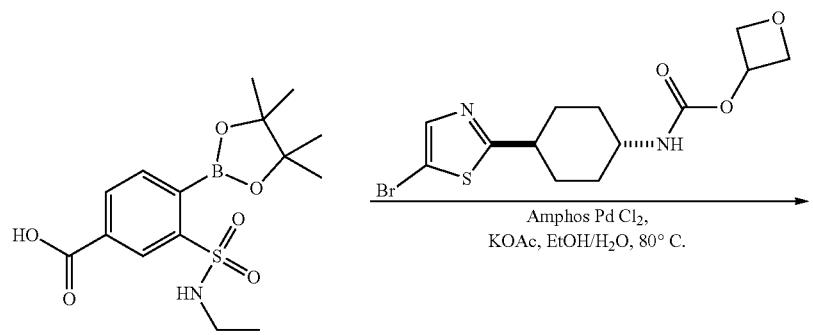

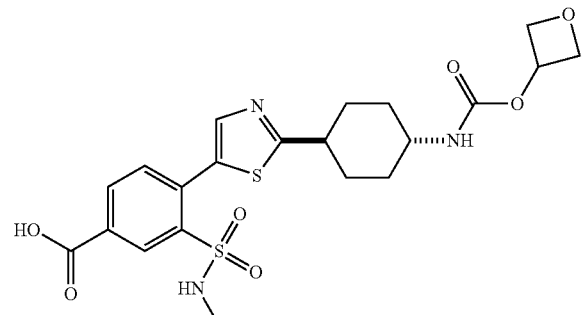

213 a) Synthesis of 4-bromo-3-(ethylsulfamoyl)benzoic acid

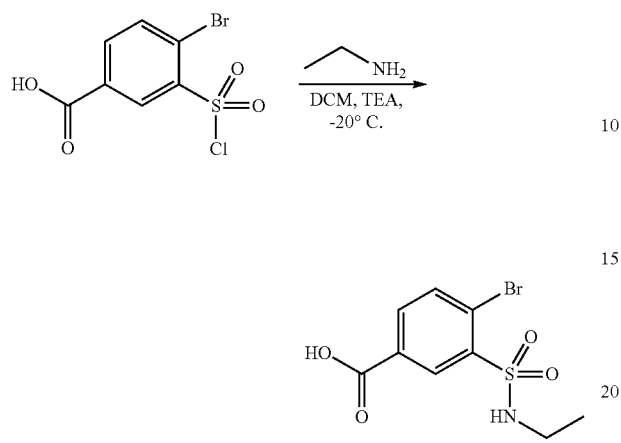

From 4-bromo-3-(chlorosulfonyl)benzoic acid, using General Method G. $^1$H NMR (400 MHz, DMSO-d$_6$) δ=8.48 (s, 1H), 7.87 (d, J=8.2 Hz, 1H), 7.72 (d, J=8.2 Hz, 1H), 2.92 (quin, J=6.8 Hz, 2H), 1.00 (t, J=7.1 Hz, 3H). ESI [M−H]=305.9/307.9.

214 b) Synthesis of 3-(ethylsulfamoyl)-4-(4,4,5,5-tetramethyl-1,3,2-dioxaborolan-2-yl)benzoic acid

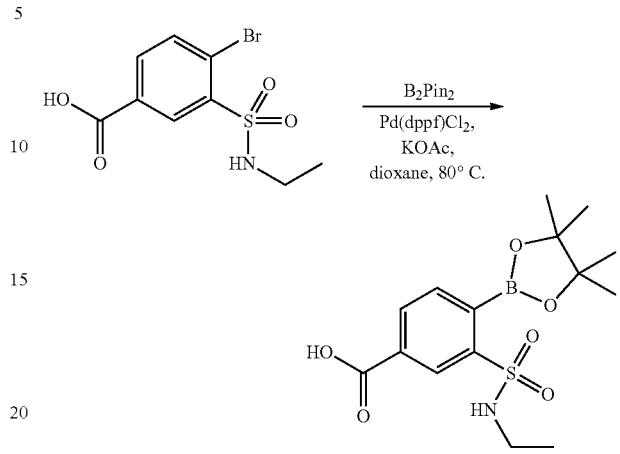

From 4-bromo-3-(ethylsulfamoyl)benzoic acid, using General Method B. ESI [M−H]=354.0.

c) Synthesis of trans-3-(ethylsulfamoyl)-4-[2-[4-(oxetan-3-yloxycarbonyl-amino)cyclohexyl]thiazol-5-yl]benzoic acid (Compound 66)

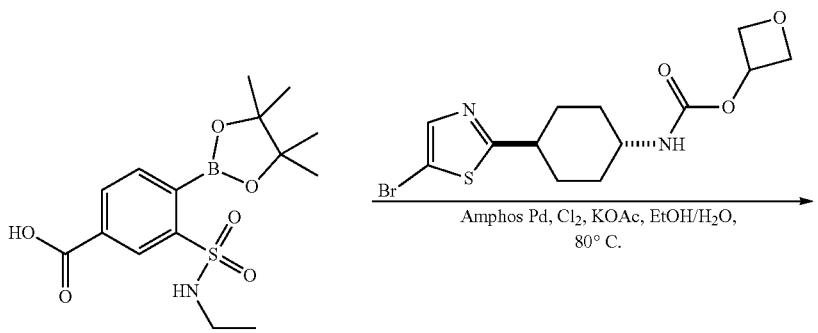

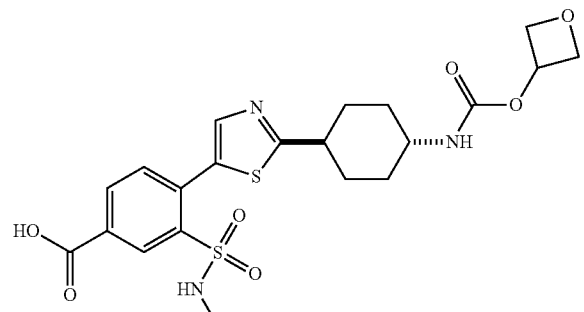

66

From 3-(ethylsulfamoyl)-4-(4,4,5,5-tetramethyl-1,3,2-dioxaborolan-2-yl)benzoic acid and trans-oxetan-3-yl-(-4-(5-bromothiazol-2-yl)cyclohexyl)carbamate, using General Method D. $^1$H NMR (400 MHz, methanol-d$_4$) δ=8.63 (d, J=1.5 Hz, 1H), 8.18 (dd, J=1.5, 7.9 Hz, 1H), 7.80 (s, 1H), 7.55 (d, J=7.7 Hz, 1H), 5.35 (br t, J=5.6 Hz, 1H), 4.86-4.81 (m, 2H), 4.62-4.56 (m, 2H), 3.51-3.38 (m, 1H), 3.10-2.98 (m, 1H), 2.91 (q, J=7.3 Hz, 2H), 2.25 (br d, J=12.6 Hz, 2H), 2.12-2.02 (m, 2H), 1.74-1.63 (m, 2H), 1.47-1.40 (m, 2H), 1.04 (t, J=7.3 Hz, 3H). ESI [M+H]=510.1.

Example 48

Preparation of trans-3-(ethylsulfamoyl)-4-[2-[4-(isopropyloxycarbonyl-amino) cyclohexyl]thiazol-5-yl]benzoic acid (Compound 48)

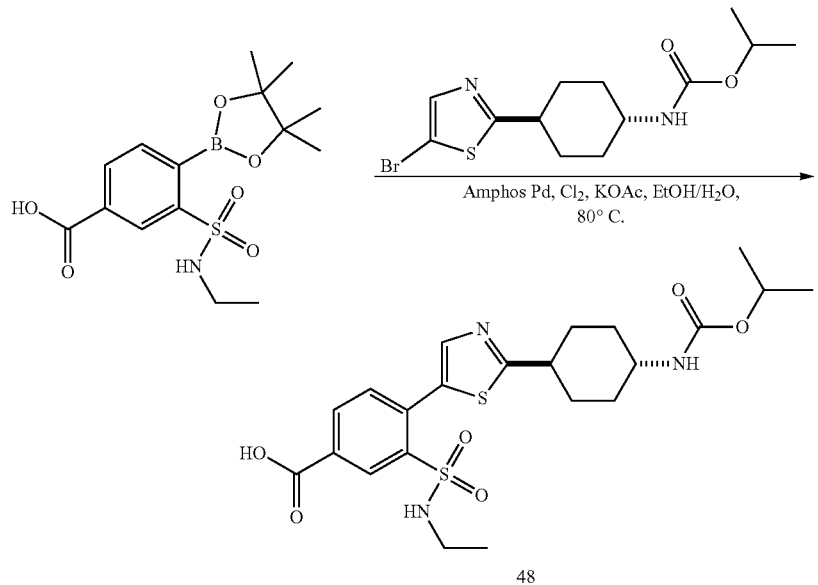

From 3-(ethylsulfamoyl)-4-(4,4,5,5-tetramethyl-1,3,2-dioxaborolan-2-yl)benzoic acid and trans-isopropyl+4-(5-bromothiazol-2-yl)cyclohexyl)carbamate, using General Method D. $^1$H NMR (400 MHz, methanol-d$_4$) δ=8.57 (s, 1H), 8.14 (br d, J=7.9 Hz, 1H), 7.77 (br s, 1H), 7.54 (br d, J=7.7 Hz, 1H), 4.74 (br s, 1H), 3.36 (br t, J=11.5 Hz, 1H), 3.03-2.89 (m, 1H), 2.80 (q, J=7.2 Hz, 2H), 2.16 (br d, J=13.0 Hz, 2H), 1.98 (br d, J=11.0 Hz, 2H), 1.69-1.54 (m, 2H), 1.38-1.28 (m, 2H), 1.22-1.08 (m, 6H), 0.94 (t, J=7.3 Hz, 3H). ESI [M+H]=496.1.

Example 49

Preparation of isopropyl (trans-N-(4-(5-(2-(ethylsulfamoyl)-4-((3-isopropyl-oxetan-3-yl)amino)phenyl)thiazol-2-yl)cyclohexyl))carbamate (Compound 69)

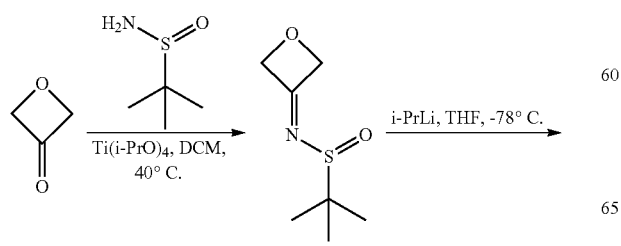

b) Synthesis of N-(3-isopropyloxetan-3-yl-2-methyl-propane-2-sulfinamide

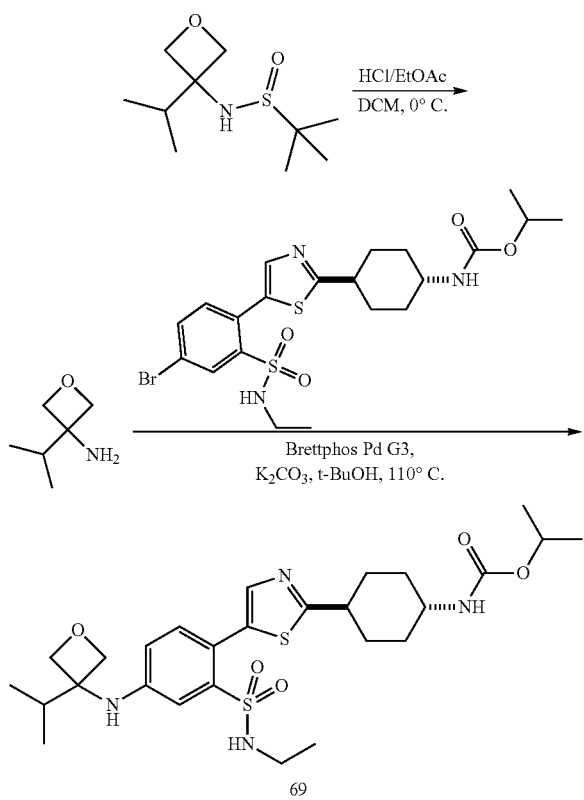

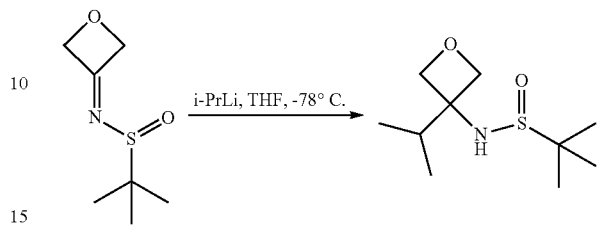

To a solution of 2-methyl-N-(oxetan-3-ylidene)propane-2-sulfinamide (5.7 g, 32.4 mmol, 1.0 eq.) in THF (100 mL) was added isopropyllithium (1.6 M, 40.5 mL, 2.0 eq.) (1.6 M in hexane) under N₂ atmosphere at −78° C. The mixture was stirred at −78° C. for 45 min. The reaction mixture was quenched with THF:AcOH=4:1 (50 mL) at −78° C., then was diluted with H₂O 20 mL and extracted with EtOAc 150 mL (50 mL×3). The combined organic layers were washed with sat.aq. NaCl 30 mL and dried over Na₂SO₄, filtered and concentrated under reduced pressure. The residue was purified by prep-HPLC (column: Welch Xtimate C18 250*50 mm*10 um; mobile phase: [water (0.05% ammonia hydroxide v/v)-ACN]; B %: 2%-40%,20 min) to yield N-(3-isopropyloxetan-3-yl)-2-methyl-propane-2-sulfinamide (300 mg, 1.4 mmol, 4.2% yield) as a white solid. $^1$H NMR (400 MHz, CDCl$_3$) δ=4.86 (d, J=6.8 Hz, 1H), 4.77 (d, J=6.8 Hz, 1H), 4.55 (dd, J=6.8, 11.9 Hz, 2H), 3.40 (s, 1H), 2.32 (td, J=6.8, 13.7 Hz, 1H), 1.26 (s, 9H), 1.09-0.91 (m, 6H)). ESI [M+H]=220.2.

c) Synthesis of 3-isopropyloxetan-3-amine (General Method E)

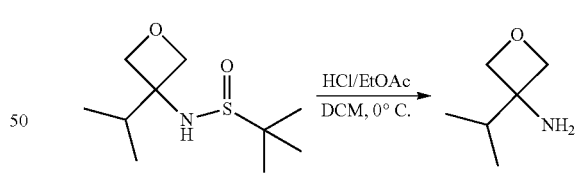

To a solution of N-(3-isopropyloxetan-3-yl)-2-methyl-propane-2-sulfinamide (100 mg, 456 umol, 1 eq.) in DCM (1 mL) was added HCl/EtOAc (4 M, 500 uL, 4.4 eq.). The mixture was stirred at 0° C. for 5 min, then the reaction mixture was diluted with MTBE 3 mL then the solid was formed. The residue was concentrated under reduced pressure to remove solvent at 0° C. Then the residue was triturated with MTBE:Petroleum ether=1:1 (3 mL) and filtered, the filter cake was collected to yield 3-isopropyloxetan-3-amine (20 mg, crude) which was used into the next step without further purification. $^1$H NMR (400 MHz, DMSO-d$_6$) δ=8.61 (br s, 2H), 4.58-4.46 (m, 4H), 2.20-2.10 (m, 1H), 0.94 (d, J=6.8 Hz, 6H). ESI [M+H]=116.1.

a) Synthesis of 2-methyl-N-(oxetan-3-ylidene)propane-2-sulfinamide

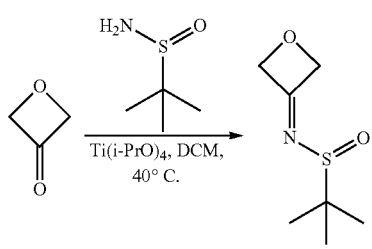

To a solution of oxetan-3-one (5.0 g, 69.4 mmol, 1.0 eq.) and 2-methylpropane-2-sulfinamide (10.1 g, 83.3 mmol, 1.2 eq.) in DCM (60 mL) was added tetraisopropoxy-titanium (39.4 g, 138.8 mmol, 2.0 eq.). The mixture was stirred at 40° C. for 12 h. Then the reaction was quenched with sat.aq. NaHCO$_3$ (30 mL) and filtered. The filtrate was diluted with H$_2$O 30 mL and extracted with DCM 60 mL (20 mL×3). The combined organic layers were dried over Na$_2$SO$_4$, filtered and concentrated under reduced pressure. The residue was purified by column chromatography (SiO$_2$, petroleum ether:ethyl acetate=10:1 to 0:1) to yield 2-methyl-N-(oxetan-3-ylidene)propane-2-sulfinamide (6.0 g, 34.2 mmol, 49.3% yield) as yellow oil. $^1$H NMR (400 MHz, CDCl$_3$) δ=5.81-5.66 (m, 1H), 5.64-5.53 (m, 1H), 5.46-5.30 (m, 2H), 1.20 (s, 9H).

219 d) Synthesis of isopropyl trans-N-[4-[5-[2-(ethylsulfamoyl)-4-[(3-isopropyloxetan-3-yl)amino]phenyl]thiazol-2-yl]cyclohexyl]carbamate (Compound 69; General Method F)

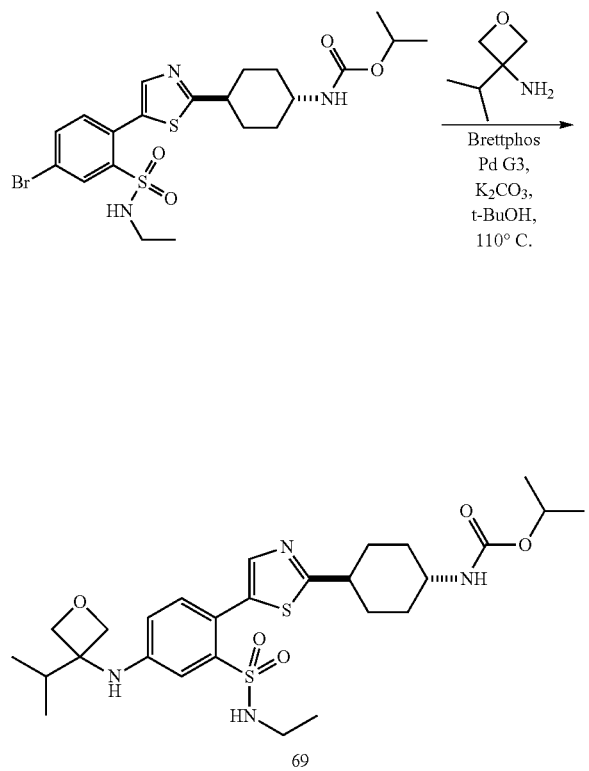

69

A mixture of 3-isopropyloxetan-3-amine (13 mg, 113 umol, 2 eq.), isopropyl N-[4-[5-[4-bromo-2-(ethylsulfamoyl)phenyl]thiazol-2-yl]cyclohexyl]carbamate (30 mg, 56 umol, 1 eq.), $K_2CO_3$ (23 mg, 169 umol, 3 eq.) and BrettPhos Pd G3 (5 mg, 5 umol, 0.1 eq.) in t-BuOH (2 mL) was stirred at 110° C. for 12 h under Ar atmosphere. The reaction mixture was concentrated under reduced pressure, then the residue was purified by prep-TLC(SiO$_2$, petroleum ether: ethyl acetate=2:1) and purified by prep-HPLC (column: YMC-Actus Triart C18 100*30 mm*5 um; mobile phase: [water(0.1% TFA)-ACN]; B %:25%-60%,10 min) to yield isopropyl trans-N-[4-[5-[2-(ethylsulfamoyl)-4-[(3-isopropyloxetan-3-yl)amino]phenyl]thiazol-2-yl]cyclohexyl]carbamate (1 mg, 1.9 umol, 3.3% yield, 89.8% purity) as a yellow gum. $^1$H NMR (400 MHz, DMSO-d$_6$) δ=7.53 (s, 1H), 7.34-7.22 (m, 1H), 7.11 (d, J=8.4 Hz, 1H), 7.05-6.90 (m, 3H), 6.48 (dd, J=1.8, 7.9 Hz, 1H), 4.77-4.69 (m, 1H), 4.64 (d, J=6.0 Hz, 2H), 4.49 (d, J=6.6 Hz, 2H), 3.26-3.23 (m, 1H), 2.86-2.79 (m, 1H), 2.79-2.70 (m, 2H), 2.28-2.20 (m, 1H), 2.13-2.06 (m, 2H), 1.93-1.86 (m, 2H), 1.57-1.45 (m, 2H), 1.37-1.28 (m, 2H), 1.13 (d, J=6.2 Hz, 6H), 1.01-0.90 (m, 9H). ESI [M+H]=565.1.

220

Example 50

Preparation of isopropyl trans-N-[4-[5-[2-(ethylsulfamoyl)-4-[(3-isobutyloxetan-3-yl)amino]phenyl]thiazol-2-yl]cyclohexyl]carbamate (Compound 70)

70 a) Synthesis of N-(3-isobutyloxetan-3-yl)-2-methylpropane-2-sulfinamide

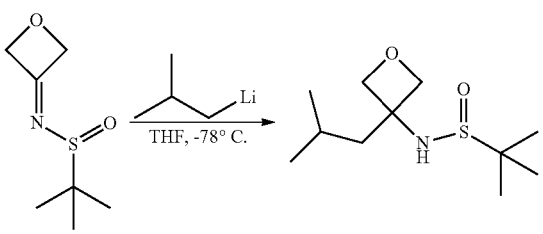

To a solution of 2-methyl-N-(oxetan-3-ylidene)propane-2-sulfinamide (7.0 g, 40.0 mmol, 1.0 eq.) in THF (4 mL) was added isobutyllithium (1.6 M, 50.0 mL, 2.0 eq.) (1M in THF) dropwise at −78° C. under N$_2$ atmosphere. The mixture was stirred at −78° C. for 45 min. Then the reaction mixture was quenched by additional THF:AcOH=4:1 (50 mL) at −78° C. and the reaction was diluted with H$_2$O 20 mL and extracted with EtOAc 150 mL (50 mL×3). The combined organic layers were washed with sat.aq. NaCl (3 mL), and dried over Na$_2$SO$_4$, filtered and concentrated under reduced pressure. Then the residue was purified by prep-HPLC (column: Welch Xtimate C18 250*50 mm*10 um; mobile phase: [water (0.05% ammonia hydroxide v/v)-ACN]; B %:5%-48%,20 min) to yield N-(3-isobutyloxetan-3-yl)-2-methyl-propane-2-sulfinamide (130 mg, 557 umol, 1.4% yield) was obtained as a white solid. $^1$H NMR (400 MHz, CDCl$_3$) δ=4.69 (t, J=7.0 Hz, 2H), 4.57 (d, J=6.9 Hz, 1H), 4.51 (d, J=6.6 Hz, 1H), 3.56 (s, 1H), 1.95 (t, J=6.9 Hz, 1H), 1.86-1.73 (m, 2H), 1.19 (s, 9H), 0.84 (d, J=6.4 Hz, 6H). ESI [M+H]=234.1.

b) Synthesis of 3-isobutyloxetan-3-amine

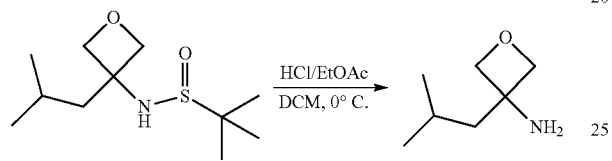

From N-(3-isobutyloxetan-3-yl)-2-methyl-propane-2-sulfinamide, using the conditions of General Method E. $^1$H NMR (400 MHz, DMSO-d$_6$) δ=4.59-4.55 (m, 2H), 4.54-4.50 (m, 2H), 1.84-1.74 (m, 3H), 0.92 (t, J=6.3 Hz, 2H), 0.90-0.86 (m, 6H).

c) Synthesis of isopropyl trans-N-[4-[5-[2-(ethylsulfamoyl)-4-[(3-isobutyloxetan-3-yl)amino]phenyl]thiazol-2-yl]cyclohexyl]carbamate (Compound 70)

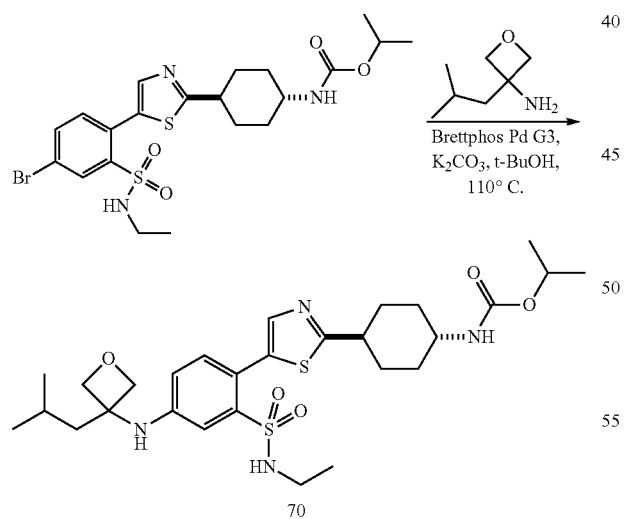

From isopropyl N-[4-[5-[4-bromo-2-(ethylsulfamoyl)phenyl]thiazol-2-yl]cyclohexyl]carbamate and 3-isobutyloxetan-3-amine, using General Method F. $^1$H NMR (400 MHz, DMSO-d$_6$) δ=7.69-7.54 (m, 1H), 7.37 (t, J=5.6 Hz, 1H), 7.22 (d, J=8.4 Hz, 1H), 7.17-7.11 (m, 1H), 7.08 (br d, J=7.3 Hz, 1H), 7.03 (d, J=1.8 Hz, 1H), 6.58 (dd, J=2.1, 8.7 Hz, 1H), 4.87-4.73 (m, 1H), 4.63 (s, 4H), 3.41-3.35 (m, 1H), 3.01-2.90 (m, 1H), 2.88-2.79 (m, 2H), 2.24-2.12 (m, 2H), 2.06 (br d, J=7.1 Hz, 2H), 2.01-1.90 (m, 2H), 1.67-1.52 (m, 3H), 1.46-1.32 (m, 2H), 1.23 (d, J=6.2 Hz, 6H), 1.03 (t, J=7.2 Hz, 3H), 0.89 (d, J=6.6 Hz, 6H). ESI [M+H]=579.3.

Example 51

Preparation of isopropyl trans-N-[4-[5-[2-(ethylsulfamoyl)-4-[(1H-imidazol-2-ylamino)methyl]phenyl]thiazol-2-yl]cyclohexyl]carbamate (Compound 73)

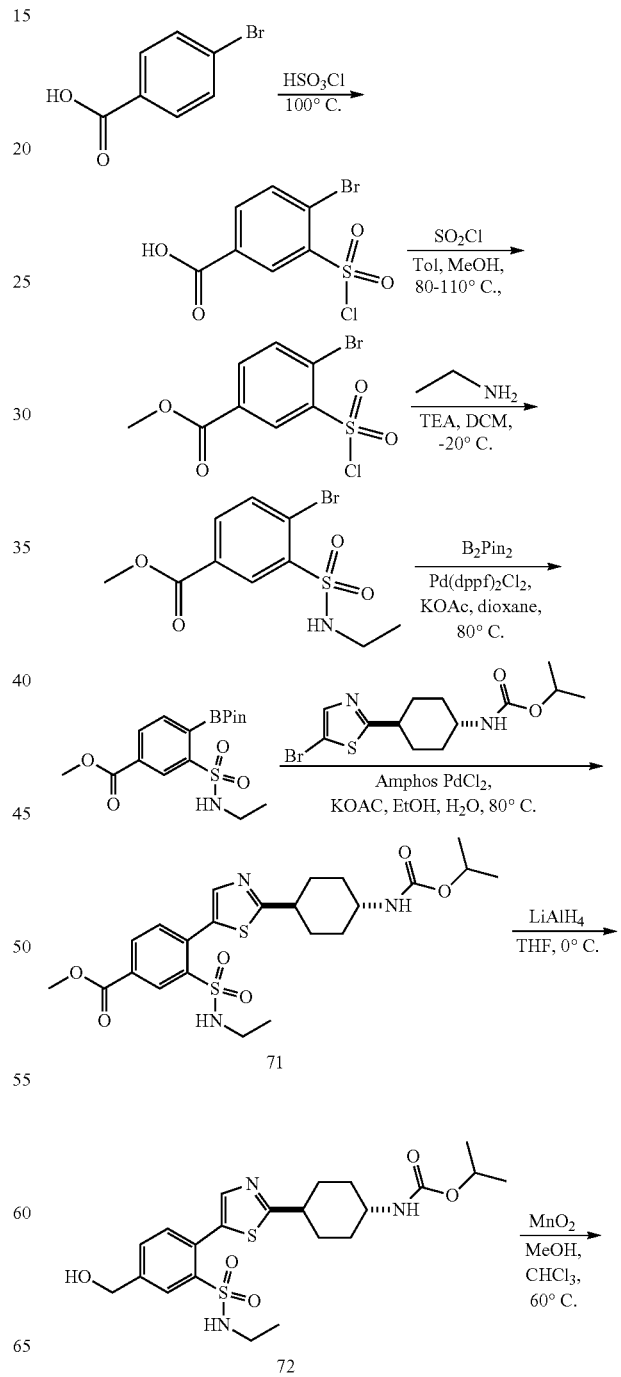

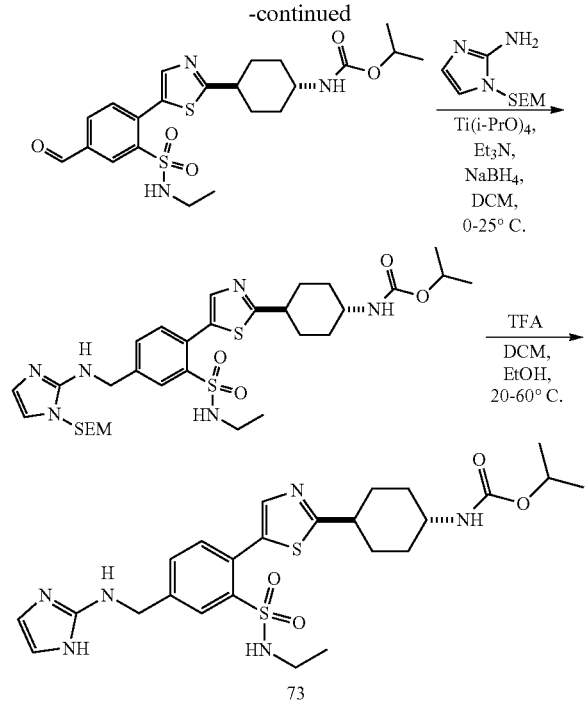

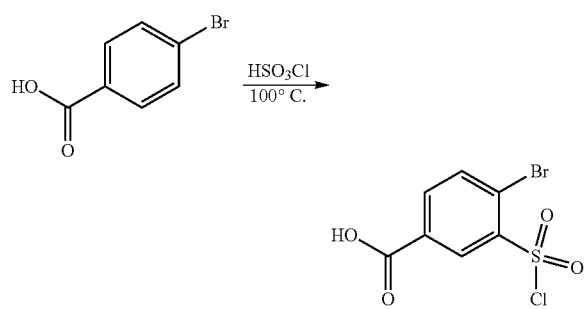

a) Synthesis of 4-bromo-3-(chlorosulfonyl)benzoic acid

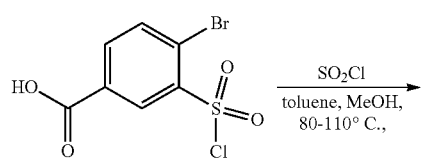

A solution of 4-bromobenzoic acid (20.0 g, 99.5 mmol, 1.0 eq.) in HSO₃Cl (120 mL) was stirred at 100° C. for 12 h, then the reaction mixture was poured into ice water (600 mL) slowly. The mixture was stirred for 0.5 h, then filtrated to yield 4-bromo-3-chlorosulfonyl-benzoic acid (23.4 g, crude) as a pale-yellow solid used directly without any purification.

b) Synthesis of methyl 4-bromo-3-chlorosulfonyl-benzoate

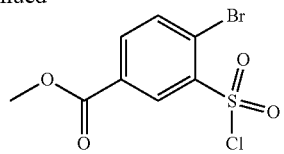

A solution of 4-bromo-3-chlorosulfonyl-benzoic acid (23.4 g, 78.0 mmol, 1.0 eq.) in SOCl₂ (92.7 g, 780.0 mmol, 10.0 eq.) was stirred at 80° C. for 3 h. Then the mixture was concentrated under reduced pressure. The residue was diluted in Tol (50 mL) and MeOH (3.3 g, 101.4 mmol, 1.3 eq.). The mixture was stirred at 110° C. for 2 h. Then concentrated under reduced pressure. The residue was purified by column chromatography (SiO₂, petroleum ether: ethyl acetate=1:0 to 0:1) to yield methyl 4-bromo-3-chlorosulfonyl-benzoate (10.5 g, 33.2 mmol, 42.5% yield) as a white solid. ¹H NMR (400 MHz, methanol-d₄) δ=8.75 (d, J=2.0 Hz, 1H), 8.27 (dd, J=2.1, 8.3 Hz, 1H), 8.16 (d, J=8.3 Hz, 1H), 4.02-3.98 (m, 3H).

c) Synthesis of methyl 4-bromo-3-(ethylsulfamoyl)benzoate (General Method G)

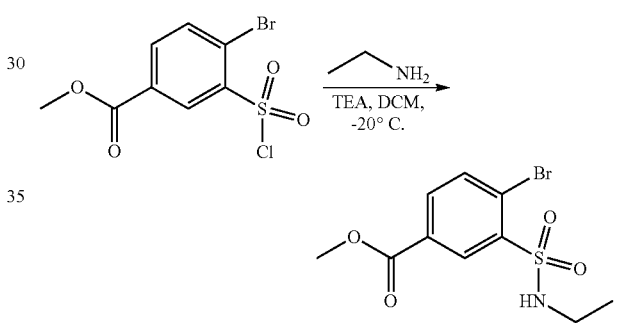

To a solution of TEA (7.8 g, 76.5 mmol, 3 eq.) in DCM (140 mL) was added ethylamine (1.3 g, 28.1 mmol, 1.1 eq.) at −20° C. Then the methyl 4-bromo-3-chlorosulfonyl-benzoate (8.0 g, 25.5 mmol, 1.0 eq.) was added batchwise. The mixture was stirred at −20° C. for 5 min, then the reaction mixture was quenched with HCl (1M, 50 mL, pH=2) and extracted with DCM 150 mL, the organic layers were dried over Na₂SO₄, filtered and concentrated under reduced pressure to yield methyl 4-bromo-3-(ethylsulfamoyl) benzoate (8.0 g, 24.8 mmol, 97.3% yield) as a pale-yellow solid. ¹H NMR (400 MHz, methanol-d₄) δ=8.63 (d, J=1.8 Hz, 1H), 8.10-8.00 (m, 1H), 7.93 (d, J=8.2 Hz, 1H), 3.94 (s, 3H), 2.96 (q, J=7.3 Hz, 2H), 1.05 (t, J=7.2 Hz, 3H).

d) Synthesis of methyl 3-(ethylsulfamoyl)-4-(4,4,5,5-tetramethyl-1,3,2-dioxaborolan-2-yl)benzoate

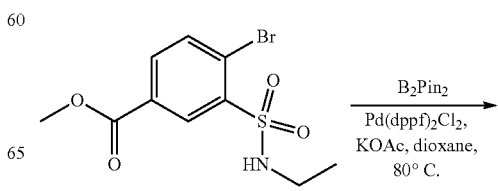

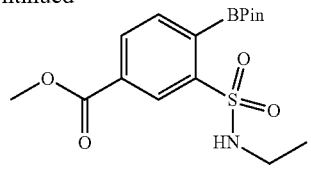

From methyl 4-bromo-3-(ethylsulfamoyl)benzoate, using General Method B. $^1$H NMR (400 MHz, methanol-$d_4$) δ=8.51-8.39 (m, 1H), 8.20 (dd, J=1.5, 7.7 Hz, 1H), 7.74 (d, J=7.7 Hz, 1H), 3.95 (s, 3H), 2.96-2.88 (m, 2H), 1.40 (s, 12H), 1.05-1.00 (m, 3H). ESI [M+H]=370.1.

e) Synthesis of methyl trans-3-(ethylsulfamoyl)-4-[2-[4-(isopropoxycarbonyl-amino)cyclohexyl]thiazol-5-yl]benzoate (Compound 71)

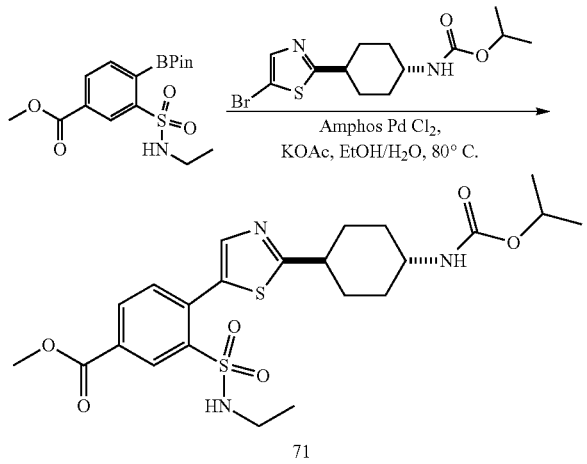

From methyl 3-(ethylsulfamoyl)-4-(4,4,5,5-tetramethyl-1,3,2-dioxaborolan-2-yl)-benzoate, using General Method D. $^1$H NMR (400 MHz, methanol-$d_4$) δ=8.68 (d, J=1.6 Hz, 1H), 8.24 (dd, J=1.8, 8.0 Hz, 1H), 7.85 (s, 1H), 7.66 (d, J=8.0 Hz, 1H), 4.84 (br s, 1H), 3.99 (s, 3H), 3.48 (tt, J=3.8, 11.6 Hz, 1H), 3.05 (ddd, J=3.4, 8.7, 11.9 Hz, 1H), 2.91 (q, J=7.2 Hz, 2H), 2.27 (br d, J=12.1 Hz, 2H), 2.14-2.05 (m, 2H), 1.73 (dq, J=3.0, 12.8 Hz, 2H), 1.44 (dq, J=3.2, 12.6 Hz, 2H), 1.25 (br d, J=6.1 Hz, 6H), 1.05 (t, J=7.3 Hz, 3H). ESI [M+H]=510.2.

f) Synthesis of isopropyl trans-N-[4-[5-[2-(ethylsulfamoyl)-4-(hydroxy-methyl)phenyl]thiazol-2-yl]cyclohexyl]carbamate (Compound 72)

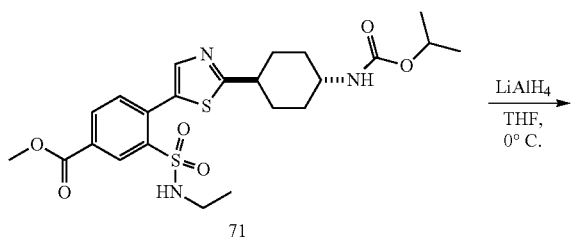

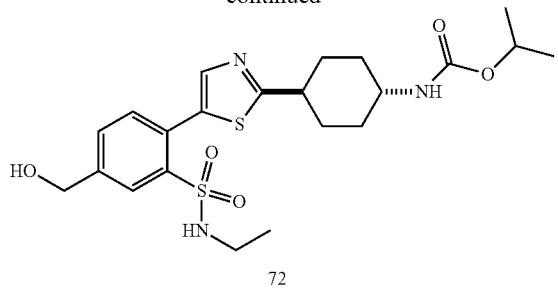

To a solution of trans-methyl 3-(ethylsulfamoyl)-4-[2-[4-(isopropoxycarbonylamino)-cyclohexyl]thiazol-5-yl]benzoate (500 mg, 981 umol, 1 eq.) in THF (6 mL) was added LiAlH$_4$ (74 mg, 2 mmol, 2 eq.), then stirred at 0° C. for 2 h. The reaction was quenched with H$_2$O 10 mL and extracted with EtOAc 30 mL (10 mL×3). The combined organic layers were dried over Na$_2$SO$_4$, filtered and concentrated under reduced pressure. The residue was purified by column chromatography (SiO$_2$, Petroleum ether:Ethyl acetate=1:0 to 0:1) to yield isopropyl trans-N-[4-[5-[2-(ethylsulfamoyl)-4-(hydroxymethyl)phenyl]thiazol-2-yl]cyclohexyl]carbamate (210 mg, 436 umol, 44.4% yield, 98.6% purity) as a white solid. $^1$H NMR (400 MHz, methanol-$d_4$) δ=8.11 (s, 1H), 7.81 (s, 1H), 7.65 (d, J=7.1 Hz, 1H), 7.51 (d, J=7.8 Hz, 1H), 4.85-4.80 (m, 1H), 4.75 (s, 2H), 3.48 (ddd, J=3.6, 7.7, 11.6 Hz, 1H), 3.14-3.01 (m, 1H), 2.90 (q, J=7.3 Hz, 2H), 2.28 (br d, J=12.0 Hz, 2H), 2.15-2.07 (m, 2H), 1.80-1.66 (m, 2H), 1.52-1.38 (m, 2H), 1.25 (br d, J=6.0 Hz, 6H), 1.04 (t, J=7.2 Hz, 3H). ESI [M+H]=482.1.

g) Synthesis of isopropyl trans-N-[4-[5-[2-(ethylsulfamoyl)-4-formyl-phenyl]thiazol-2-yl]cyclohexyl]carbamate

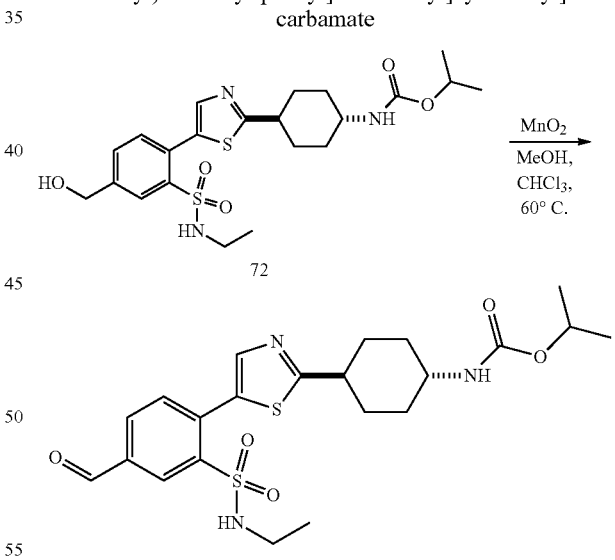

To a solution of isopropyl trans-N-[4-[5-[2-(ethylsulfamoyl)-4-(hydroxymethyl)-phenyl]thiazol-2-yl]cyclohexyl]carbamate (100 mg, 207 umol, 1 eq.) in CHCl$_3$ (1 mL)/MeOH (1 mL) was added MnO$_2$ (361 mg, 4 mmol, 20 eq.). The mixture was stirred at 60° C. for 2 h. The reaction mixture was filtered, and the filtrate was concentrated under reduced pressure. The residue was purified by prep-TLC (SiO$_2$, petroleum ether:ethyl acetate=1:2) to yield isopropyl trans-N-[4-[5-[2-(ethyl-sulfamoyl)-4-formyl-phenyl]thiazol-2-yl]cyclohexyl]carbamate (30 mg, 62.55 umol, 30.13% yield) as a white solid. ESI [M+H]=480.2.

h) Synthesis of isopropyl-trans-N-[4-[5-[2-(ethylsulfamoyl)-4-[[[1-(2-trimethylsilylethoxymethyl)imidazol-2-yl]amino]methyl]phenyl]thiazol-2-yl]cyclohexyl]carbamate (General Method H)

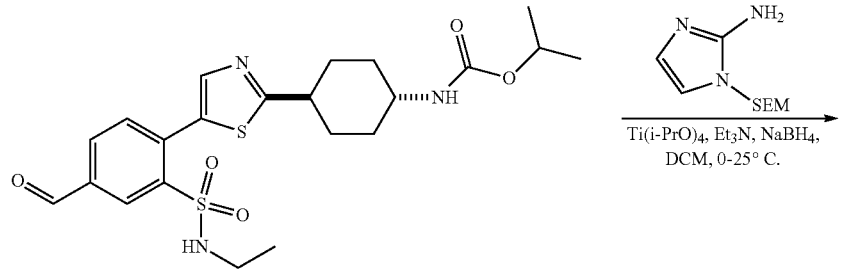

72

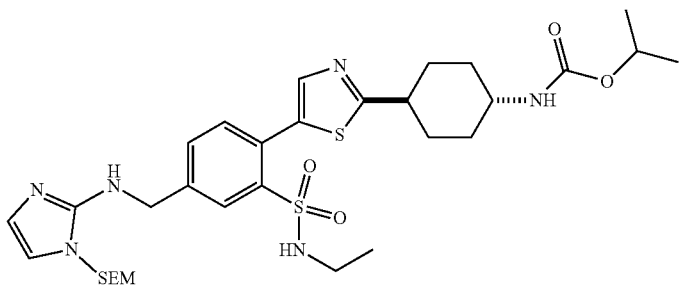

To a mixture of 1-(2-trimethylsilylethoxymethyl)imidazol-2-amine (20 mg, 94 umol, 1.5 eq.) and isopropyl trans-N-[4-[5-[2-(ethylsulfamoyl)-4-formyl-phenyl]thiazol-2-yl]cyclohexyl]carbamate (30 mg, 62 umol, 1 eq.) in DCM (1 mL) was added Ti(i-PrO)₄ (35 mg, 125 umol, 37 uL, 2 eq.) and Et₃N (633 ug, 6 umol, 0.1 eq.), then the mixture was stirred at 25° C. for 16 h under N₂ atmosphere. The mixture was added NaBH₄ (3.6 mg, 93.9 umol, 1.5 eq.) at 0° C., and stirred at 25° C. for 2 h. The reaction mixture was quenched with H₂O 10 mL at 25° C. and concentrated under reduced pressure. The residue was purified by prep-TLC (SiO₂, petroleum ether:ethyl acetate=0:1) to yield isopropyl trans-N-[4-[5-[2-(ethylsulfamoyl)-4-[[[1-(2-trimethylsilylethoxymethyl)imidazol-2-yl]amino]methyl]phenyl]thiazol-2-yl]cyclohexyl]carbamate (50 mg, crude) as a yellow oil. ESI [M+H]=677.3.

i) Synthesis of isopropyl trans-N-[4-[5-[2-(ethylsulfamoyl)-4-[(1H-imidazol-2-ylamino)methyl]phenyl]thiazol-2-yl]cyclohexyl]carbamate (Compound 73; General Method I)

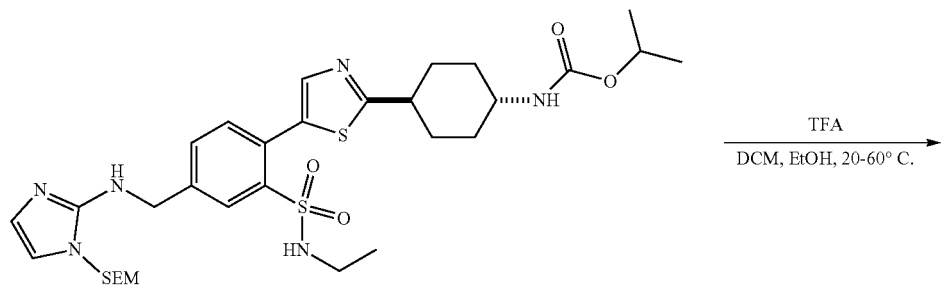

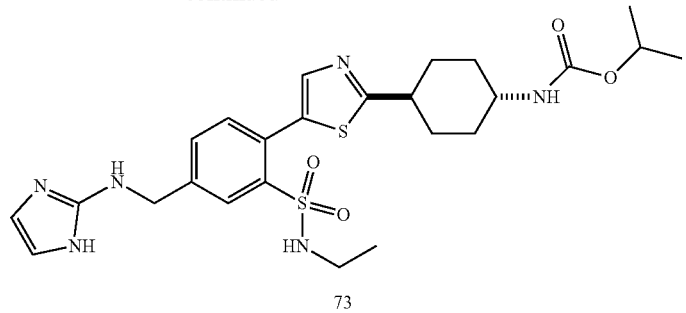

73

A mixture of isopropyl trans-N-[4-[5-[2-(ethylsulfamoyl)-4-[[[1-(2-trimethylsilyl-ethoxymethyl)imidazol-2-yl]amino]methyl]phenyl]thiazol-2-yl]cyclohexyl]carbamate (50 mg, 74 umol, 1 eq.) in TFA (1 mL) and DCM (1 mL) was stirred at 20° C. for 1 h. The reaction mixture was concentrated under reduced pressure to remove DCM at 25° C. The residue was diluted with EtOH (1 mL) and stirred at 60° C. for 3 h. The mixture was concentrated under reduced pressure. The residue was purified by prep-HPLC (TFA condition). (column: Welch Ultimate AQ-C18 150*30 mm*5 um; mobile phase: [water(0.1% TFA)-ACN]; B %: 18%-48%,12 min) to yield isopropyl trans-N-[4-[5-[2-(ethylsulfamoyl)-4-[(1H-imidazol-2-ylamino)methyl]phenyl]thiazol-2-yl]cyclohexyl]carbamate (9 mg, 13 umol, 18% yield, 100% purity, TFA) as a pale yellow solid. $^1$H NMR (400 MHz, methanol-d$_4$) δ=8.08 (d, J=1.1 Hz, 1H), 7.74 (s, 1H), 7.64 (dd, J=1.4, 7.8 Hz, 1H), 7.52 (d, J=7.9 Hz, 1H), 6.88 (s, 2H), 4.85-4.74 (m, 1H), 4.65 (s, 2H), 3.51-3.37 (m, 1H), 3.08-2.96 (m, 1H), 2.81 (q, J=7.3 Hz, 2H), 2.33-2.18 (m, 2H), 2.07 (br d, J=10.4 Hz, 2H), 1.69 (dq, J=3.0, 12.8 Hz, 2H), 1.41 (dq, J=3.1, 12.6 Hz, 2H), 1.22 (br d, J=6.2 Hz, 6H), 0.97 (t, J=7.3 Hz, 3H). ESI [M+H]=547.1.

Example 52

Preparation of isopropyl trans-N-[4-[5-[2-(ethylsulfamoyl)-4-[(oxazol-2-ylamino)methyl]phenyl]thiazol-2-yl]cyclohexyl]carbamate (Compound 74)

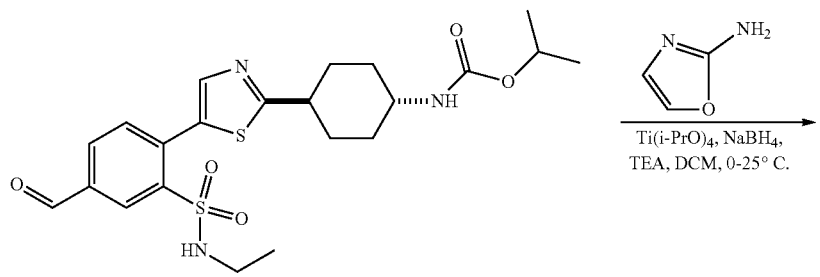

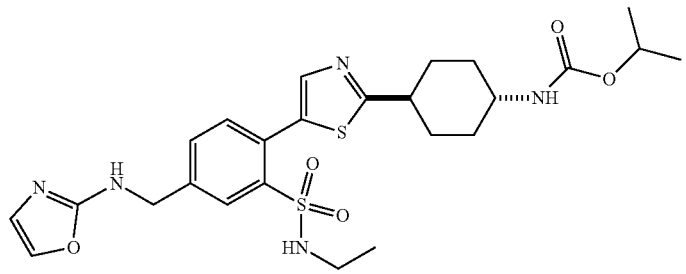

74

From isopropyl trans-N-[4-[5-[2-(ethylsulfamoyl)-4-formyl-phenyl]thiazol-2-yl]cyclohexyl]carbamate and 2-amino oxazole, using General Method H. $^1$H NMR (400 MHz, methanol-d$_4$) δ=8.04 (s, 1H), 7.72 (s, 1H), 7.64-7.55 (m, 1H), 7.46 (d, J=7.7 Hz, 1H), 7.32 (d, J=1.1 Hz, 1H), 6.76 (d, J=0.9 Hz, 1H), 4.60 (br s, 1H), 4.56 (s, 2H), 3.53-3.39 (m, 1H), 3.06-2.94 (m, 1H), 2.84 (q, J=7.3 Hz, 2H), 2.29-2.18 (m, 2H), 2.07 (br d, J=9.9 Hz, 2H), 1.77-1.60 (m, 2H), 1.50-1.36 (m, 2H), 1.23 (br d, J=6.2 Hz, 6H), 1.00 (t, J=7.2 Hz, 3H). ESI [M+H]=548.3.

Example 53

Preparation of isopropyl trans-N-[4-[5-[2-(ethylsulfamoyl)-4-(1H-imidazol-2-yl)phenyl]thiazol-2-yl]cyclohexyl]carbamate (Compound 75)

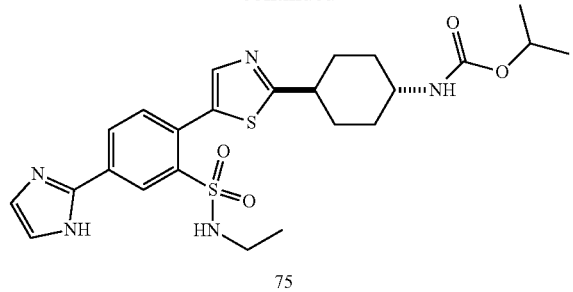

75

To a solution of isopropyl trans-N-[4-[5-[2-(ethylsulfamoyl)-4-formyl-phenyl]thiazol-2-yl]cyclohexyl]carbamate (30 mg, 62 umol, 1 eq.) in EtOH (1 mL) was added oxaldehyde (27 mg, 187 umol, 24 uL, 3 eq.) (40% aq.) and NH$_3$.H$_2$O (146 mg, 1.3 mmol, 30% purity, 20 eq.) at 0° C. The mixture was stirred at 25° C. for 2 h, and concentrated under reduced pressure. The residue was purified by prep-HPLC (column: Welch Ultimate AQ-C18 150*30 mm*5 um; mobile phase: [water(0.1% TFA)-ACN]; B %: 30%-60%,12 min) to yield isopropyl trans-N-[4-[5-[2-(ethylsulfamoyl)-4-(1H-imidazol-2-yl)phenyl]thiazol-2-yl]cyclohexyl]carbamate (16 mg, 25 umol, 40% yield, 99.3% purity, TFA) as a yellow solid. $^1$H NMR (400 MHz, methanol-d$_4$) δ=8.70 (d, J=2.0 Hz, 1H), 8.15 (dd, J=2.0, 8.2 Hz, 1H), 7.86 (s, 1H), 7.78 (d, J=8.2 Hz, 1H), 7.72 (s, 2H), 4.83-4.78 (m, 1H), 3.45 (tdd, J=4.0, 7.6, 11.7 Hz, 1H), 3.04 (tt, J=3.5, 12.0 Hz, 1H), 2.87 (q, J=7.3 Hz, 2H), 2.26 (br d, J=12.1 Hz, 2H), 2.12-2.03 (m, 2H), 1.77-1.65 (m, 2H), 1.48-1.36 (m, 2H), 1.22 (br d, J=6.2 Hz, 6H), 1.05-0.92 (m, 3H). ESI [M+H]=518.0.

Example 54

Preparation of isopropyl trans-N-[4-[5-[2-(ethylsulfamoyl)-4-(1H-imidazol-2-ylmethyl)phenyl]thiazol-2-yl]cyclohexyl]carbamate (Compound 78)

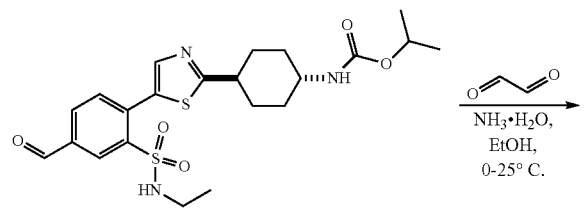

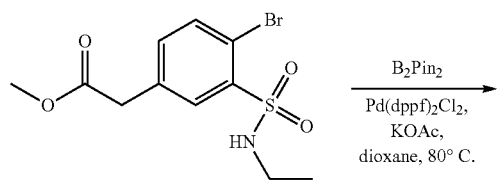

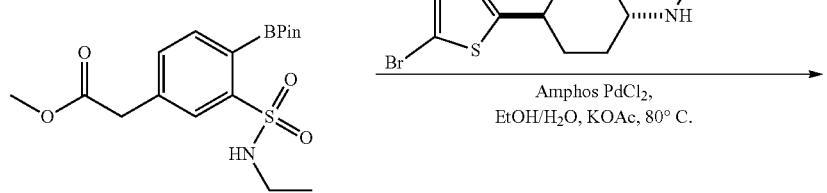

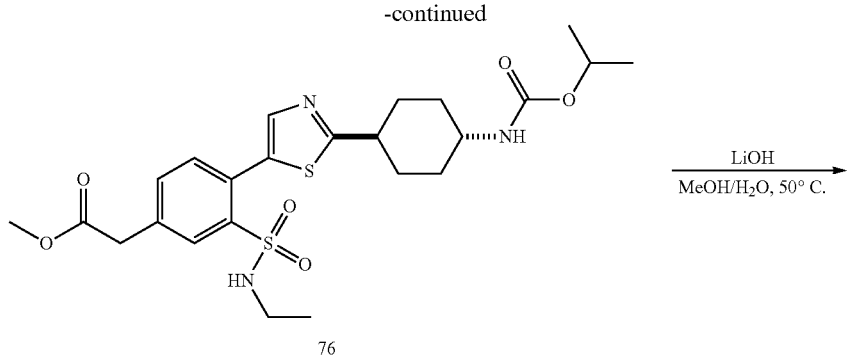
76
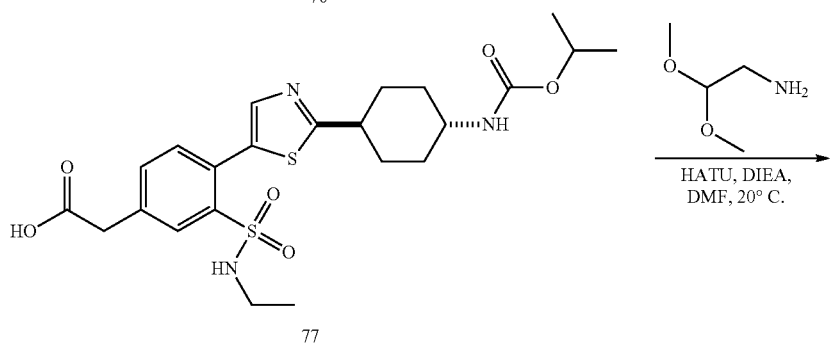
77
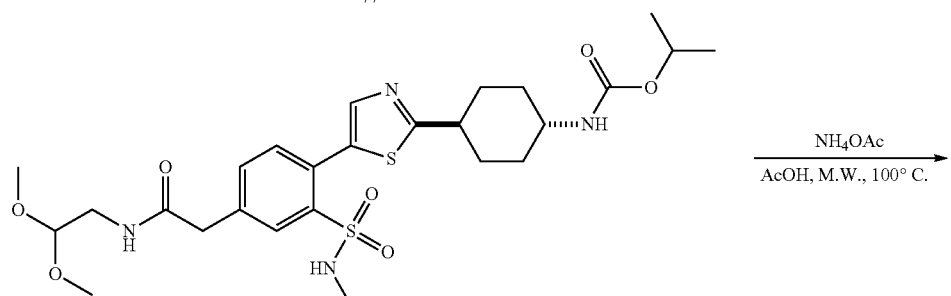
78
a) Synthesis of methyl 2-[3-(ethylsulfamoyl)-4-(4,4,5,5-tetramethyl-1,3,2-dioxaborolan-2-yl)phenyl]acetate
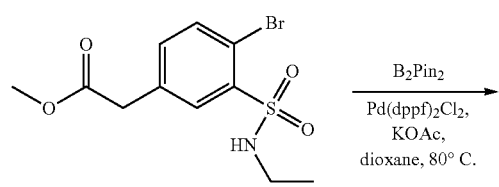
-continued
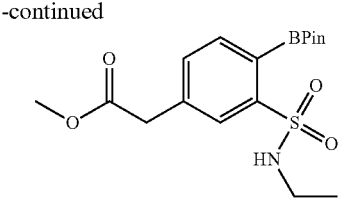
From methyl 2-(4-bromo-3-(N-ethylsulfamoyl)phenyl) acetate, using General Method B. $^1$H NMR (400 MHz, DMSO-$d_6$) δ=7.97-7.83 (m, 1H), 7.70 (s, 1H), 7.51-7.44 (m, 2H), 3.81 (s, 2H), 3.64-3.58 (m, 3H), 2.88-2.75 (m, 2H), 1.29 (s, 12H), 0.93 (t, J=7.2 Hz, 3H). ESI [M+H]=384.1.

b) Synthesis of methyl trans-2-[3-(ethylsulfamoyl)-4-[2-[4-(isopropoxycarbonylamino)cyclohexyl]thiazol-5-yl]phenyl]acetate (Compound 76)

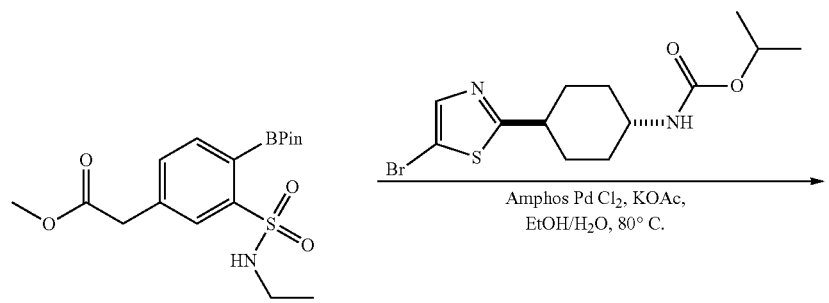

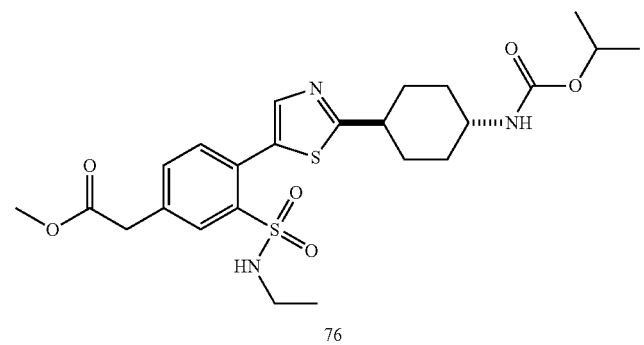

From methyl 2-[3-(ethylsulfamoyl)-4-(4,4,5,5-tetramethyl-1,3,2-dioxaborolan-2-yl)phenyl]acetate and isopropyl (trans-4-(5-bromothiazol-2-yl)cyclohexyl)carbamate, using General Method D. $^1$H NMR (400 MHz, methanol-$d_4$) δ=8.02 (d, J=1.4 Hz, 1H), 7.75 (s, 1H), 7.58 (dd, J=1.6, 7.9 Hz, 1H), 7.47 (d, J=7.9 Hz, 1H), 4.82 (br s, 1H), 3.84 (s, 2H), 3.74 (s, 3H), 3.47 (tt, J=3.8, 11.5 Hz, 1H), 3.35-3.35 (m, 1H), 2.89 (q, J=7.3 Hz, 2H), 2.31-2.21 (m, 2H), 2.14-2.03 (m, 2H), 1.72 (dq, J=2.8, 12.9 Hz, 2H), 1.43 (dq, J=3.1, 12.5 Hz, 2H), 1.24 (br d, J=6.1 Hz, 6H), 1.04 (t, J=7.3 Hz, 3H). ESI [M+H]=524.2.

c) Synthesis of trans-2-[3-(ethylsulfamoyl)-4-[2-[4-(isopropoxycarbonyl-amino)cyclohexyl]thiazol-5-yl]phenyl]acetic acid (Compound 77; General Method J)

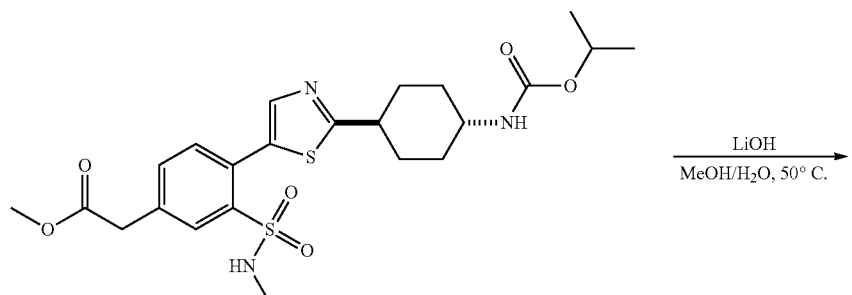

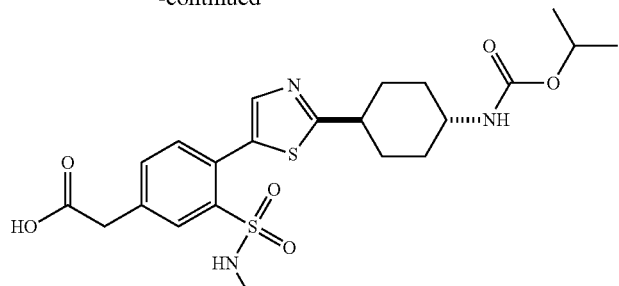

77

To a solution of methyl trans-2-[3-(ethylsulfamoyl)-4-[2-[4-(isopropoxy-carbonylamino)cyclohexyl]thiazol-5-yl]phenyl]acetate (800 mg, 1.5 mmol, 1 eq.) in MeOH (8 mL), H₂O (4 mL) was added LiOH (110 mg, 4.5 mmol, 3 eq.). The mixture was stirred at 50° C. for 2 h. The mixture was concentrated under reduced pressure. The residue was adjusted pH=2 with HCl (6M) and extracted with EtOAc 40 mL (20 mL×2). The combined organic layers were dried over Na₂SO₄, filtered and concentrated under reduced pressure to yield trans-2-[3-(ethylsulfamoyl)-4-[2-[4-(isopropoxycarbonyl-amino) cyclohexyl]thiazol-5-yl]phenyl] acetic acid (750 mg, crude) as a yellow oil. ¹H NMR (400 MHz, methanol-d₄) δ=8.00 (s, 1H), 7.74 (s, 1H), 7.56 (br d, J=7.9 Hz, 1H), 7.45 (d, J=7.7 Hz, 1H), 4.89-4.88 (m, 1H), 3.76 (s, 2H), 3.45 (br t, J=11.0 Hz, 1H), 3.01 (br t, J=12.2 Hz, 1H), 2.87 (q, J=7.2 Hz, 2H), 2.24 (br d, J=12.1 Hz, 2H), 2.07 (br d, J=10.4 Hz, 2H), 1.77-1.62 (m, 2H), 1.48-1.33 (m, 2H), 1.22 (br d, J=6.0 Hz, 6H), 1.01 (t, J=7.3 Hz, 3H). ESI [M+H]=510.2.

d) Synthesis of isopropyl trans-N-[4-[5-[4-[2-(2,2-dimethoxyethylamino)-2-oxo-ethyl]-2-(ethylsulfamoyl)phenyl]thiazol-2-yl]cyclohexyl]carbamate

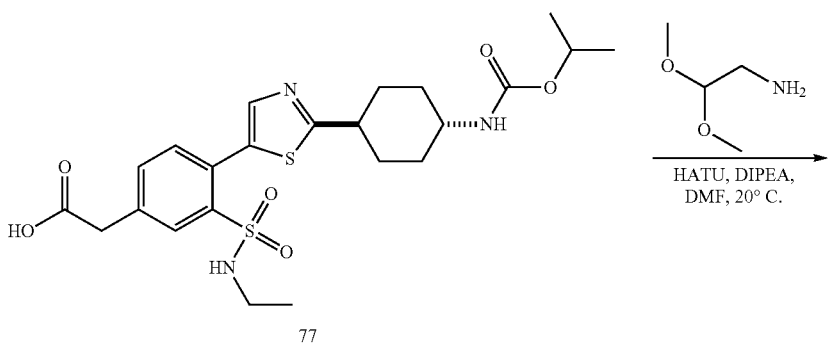

77

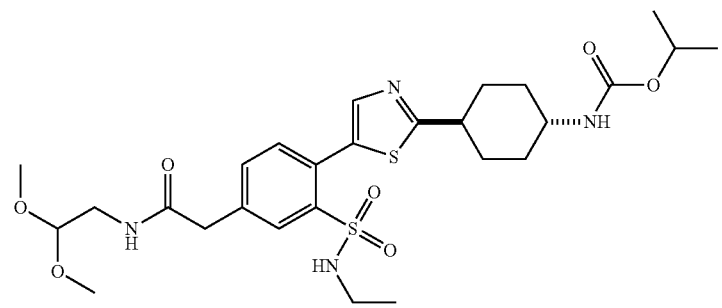

From trans-2-[3-(ethylsulfamoyl)-4-[2-[4-(isopropoxycarbonylamino)cyclohexyl]thiazol-5-yl]phenyl]acetic acid and 2,2-dimethoxyethanamine, using General Method A. ESI [M+H]=597.3.

e) Synthesis of isopropyl trans-N-[4-[5-[2-(ethylsulfamoyl)-4-(1H-imidazol-2-ylmethyl)phenyl]thiazol-2-yl]cyclohexyl]carbamate (Compound 78)

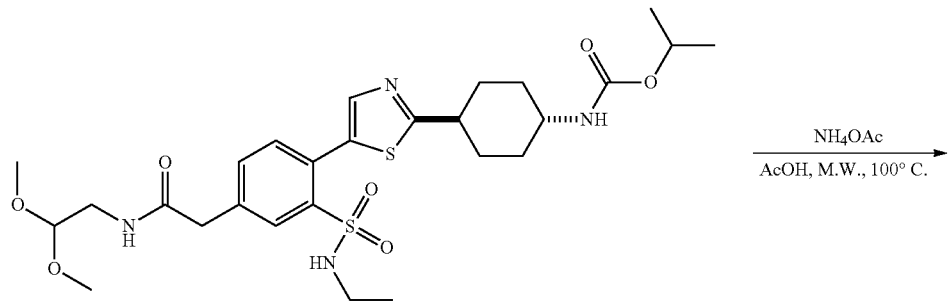

A solution of isopropyl trans-N-[4-[5-[4-[2-(2,2-dimethoxyethylamino)-2-oxo-ethyl]-2-(ethylsulfamoyl)phenyl]thiazol-2-yl]cyclohexyl]carbamate (60 mg, 100 umol, 1 eq.) and NH$_4$OAc (16 mg, 201 umol, 2 eq.) in AcOH (2 mL) was heated at 100° C. for 30 min under microwave. The mixture was concentrated, then the residue was purification by prep-TLC (petroleum ether:ethyl acetate=0:1) to yield isopropyl trans-N-[4-[5-[2-(ethylsulfamoyl)-4-(1H-imidazol-2-ylmethyl)phenyl]thiazol-2-yl]cyclohexyl]carbamate (2 mg, 3.4 umol, 3.4% yield, 91.2% purity) as pale yellow solid. $^1$H NMR (400 MHz, methanol-d$_4$) δ=8.02 (s, 1H), 7.73 (s, 1H), 7.47-7.61 (m, 4H), 4.67-4.77 (m, 1H), 4.51 (s, 2H), 3.44 (br s, 1H), 3.01 (s, 1H), 2.75-2.88 (m, 2H), 2.24 (br d, J=14.99 Hz, 2H), 2.02 (br d, J=18.52 Hz, 2H), 1.60-1.82 (m, 2H), 1.33-1.51 (m, 2H), 1.22 (br d, J=6.17 Hz, 6H), 0.92-1.05 (m, 3H). ESI [M+H]=532.2.

Example 55

Preparation of isopropyl trans-N-[4-[5-[4-[2-(benzylamino)-2-oxo-ethyl]-2-(ethyl-sulfamoyl)phenyl]thiazol-2-yl]cyclohexyl]carbamate (Compound 79)

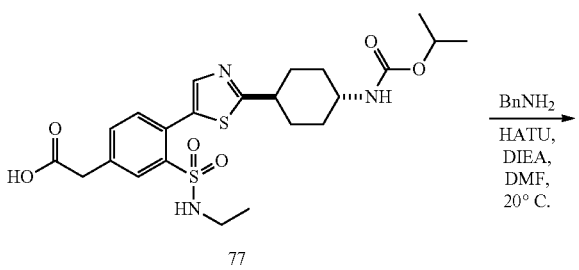

-continued

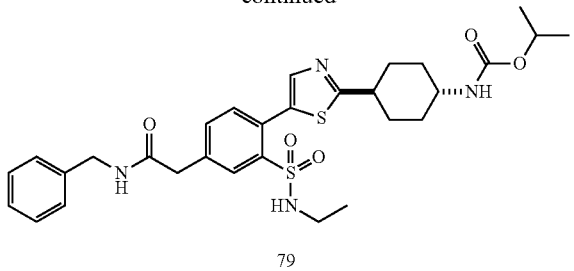

79

From trans-2-[3-(ethylsulfamoyl)-4-[2-[4-(isopropoxy-carbonylamino)cyclohexyl]thiazol-5-yl]phenyl]acetic acid and benzylamine, using General Method A. $^1$H NMR (400 MHz, methanol-d$_4$) δ=8.04 (s, 1H), 7.79 (s, 1H), 7.58 (br d, J=7.5 Hz, 1H), 7.45 (d, J=7.7 Hz, 1H), 7.34-7.18 (m, 5H), 4.87-4.77 (m, 1H), 4.38 (s, 2H), 3.69 (s, 2H), 3.45 (br t, J=11.8 Hz, 1H), 3.11-2.97 (m, 1H), 2.84 (q, J=7.3 Hz, 2H), 2.24 (br d, J=12.8 Hz, 2H), 2.07 (br d, J=10.4 Hz, 2H), 1.78-1.62 (m, 2H), 1.50-1.32 (m, 2H), 1.22 (br d, J=6.2 Hz, 6H), 1.00 (t, J=7.3 Hz, 3H). ESI [M+H]=599.2

Example 56

Preparation of isopropyl trans-N-[4-[5-[4-[2-(isopropyl(methyl)amino)-2-oxo-ethyl]-2-(ethyl-sulfamoyl)phenyl]thiazol-2-yl]cyclohexyl]carbamate (Compound 80)

Following the same General Method A, Compound 80 was prepared. $^1$H NMR (400 MHz, methanol-d$_4$) δ=7.96 (br d, J=3.1 Hz, 1H), 7.80 (s, 1H), 7.57-7.50 (m, 1H), 7.49-7.44 (m, 1H), 4.84-4.75 (m, 1H), 4.27 (td, J=6.7, 13.1 Hz, 1H), 3.95 (s, 1H), 3.89 (s, 1H), 3.45 (br t, J=11.7 Hz, 1H), 3.05 (br t, J=12.0 Hz, 1H), 2.93 (s, 2H), 2.86 (q, J=7.3 Hz, 2H), 2.81 (s, 1H), 2.25 (br d, J=12.6 Hz, 2H), 2.07 (br d, J=11.2 Hz, 2H), 1.78-1.63 (m, 2H), 1.48-1.34 (m, 2H), 1.22 (br d, J=6.2 Hz, 6H), 1.17 (d, J=6.6 Hz, 3H), 1.13 (d, J=6.8 Hz, 3H), 1.01 (t, J=7.2 Hz, 3H). ESI [M+H]=565.3.

Example 57

Preparation of isopropyl trans-N-[4-[5-[4-[2-(benzyl(methyl)amino)-2-oxo-ethyl]-2-(ethyl-sulfamoyl)phenyl]thiazol-2-yl]cyclohexyl]carbamate (Compound 81)

Following the same General Method A, Compound 81 was prepared. $^1$H NMR (400 MHz, methanol-d$_4$) δ=8.01 (s, 0.5H), 7.93 (s, 0.5H), 7.82-7.76 (m, 1H), 7.59-7.53 (m, 1H), 7.47 (br d, J=7.3 Hz, 1H), 7.37-7.29 (m, 2H), 7.28-7.22 (m, 2H), 7.15 (br d, J=7.3 Hz, 1H), 4.83-4.77 (m, 1H), 4.72 (s, 1H), 4.62 (s, 1H), 4.03-3.93 (m, 2H), 3.45 (br t, J=11.6 Hz, 1H), 3.10-3.00 (m, 3H), 2.96 (s, 1H), 2.90-2.77 (m, 2H), 2.24 (br d, J=12.3 Hz, 2H), 2.07 (br d, J=11.7 Hz, 2H), 1.71 (q, J=12.3 Hz, 2H), 1.41 (q, J=11.8 Hz, 2H), 1.22 (br d, J=5.7 Hz, 6H), 1.00 (t, J=7.1 Hz, 3H). ESI [M+H]=613.2.

Example 58

Preparation of isopropyl trans-N-[4-[5-[4-[2-oxo-2-(pyrrolidin-1-yl)ethyl]-2-(ethyl-sulfamoyl)phenyl]thiazol-2-yl]cyclohexyl]carbamate (Compound 82)

Following the same General Method A, Compound 82 was prepared. $^1$H NMR (400 MHz, methanol-d$_4$) δ=7.97 (s, 1H), 7.79 (s, 1H), 7.56-7.52 (m, 1H), 7.48-7.44 (m, 1H), 4.83 (br s, 1H), 3.85 (s, 2H), 3.58 (t, J=6.7 Hz, 2H), 3.45 (br t, J=6.8 Hz, 3H), 3.05 (br t, J=12.1 Hz, 1H), 2.87 (q, J=7.3 Hz, 2H), 2.24 (br d, J=12.6 Hz, 2H), 2.12-2.03 (m, 2H), 2.03-1.96 (m, 2H), 1.94-1.86 (m, 2H), 1.80-1.63 (m, 2H), 1.49-1.33 (m, 2H), 1.22 (br d, J=6.0 Hz, 6H), 1.02 (t, J=7.3 Hz, 3H). ESI [M+H]=563.2.

Example 59

Preparation of isopropyl trans-N-[4-[5-[4-[2-oxo-2-(piperidin-1-yl)ethyl]-2-(ethyl-sulfamoyl)phenyl]thiazol-2-yl]cyclohexyl]carbamate (Compound 83)

Following the same General Method A, Compound 83 was prepared. $^1$H NMR (400 MHz, methanol-d$_4$) δ=7.96 (s, 1H), 7.73 (s, 1H), 7.50-7.56 (m, 1H), 7.41-7.47 (m, 1H), 4.76-4.84 (m, 1H), 3.91 (s, 2H), 3.56 (dt, J=14.17, 5.49 Hz, 4H), 3.40-3.49 (m, 1H), 2.97-3.06 (m, 1H), 2.85 (q, J=7.28 Hz, 2H), 2.24 (br d, J=12.57 Hz, 2H), 2.02-2.11 (m, 2H), 1.61-1.75 (m, 4H), 1.46-1.59 (m, 4H), 1.35-1.45 (m, 2H), 1.22 (br d, J=5.95 Hz, 6H), 1.01 (t, J=7.28 Hz, 3H). ESI [M+H]=577.3.

Example 60

Preparation of isopropyl trans-N-[4-[5-[4-[2-oxo-2-(morpholin-4-yl)ethyl]-2-(ethyl-sulfamoyl)phenyl]thiazol-2-yl]cyclohexyl]carbamate (Compound 84)

Following the same General Method A, Compound 84 was prepared. $^1$H NMR (400 MHz, methanol-d$_4$) δ=7.96 (s, 1H), 7.79 (s, 1H), 7.51-7.57 (m, 1H), 7.43-7.49 (m, 1H), 4.80-4.86 (m, 1H), 3.93 (s, 2H), 3.57-3.70 (m, 8H), 3.40-3.51 (m, 1H), 2.98-3.09 (m, 1H), 2.86 (q, J=7.13 Hz, 2H), 2.21-2.29 (m, 2H), 2.07 (br d, J=11.69 Hz, 2H), 1.65-1.77 (m, 2H), 1.35-1.48 (m, 2H), 1.17-1.26 (m, 6H), 1.01 (t, J=7.17 Hz, 3H). ESI [M+H]=579.3.

Example 61

Preparation of isopropyl trans-N-[4-[5-[4-[2-oxo-2-(3-hydroxyazetidin-1-yl)ethyl]-2-(ethyl-sulfamoyl)phenyl]thiazol-2-yl]cyclohexyl]carbamate (Compound 85)

Following the same General Method A, Compound 85 was prepared. $^1$H NMR (400 MHz, methanol-d$_4$) δ=8.00 (d, J=1.5 Hz, 1H), 7.90 (s, 1H), 7.62-7.56 (m, 1H), 7.54-7.48 (m, 1H), 4.79-4.75 (m, 1H), 4.62 (tt, J=4.3, 6.7 Hz, 1H), 4.57-4.48 (m, 1H), 4.25 (dd, J=7.9, 10.6 Hz, 1H), 4.10-4.04 (m, 1H), 3.80 (dd, J=4.2, 10.6 Hz, 1H), 3.73-3.64 (m, 2H), 3.49 (tt, J=3.9, 11.6 Hz, 1H), 3.19-3.09 (m, 1H), 2.92 (q, J=7.2 Hz, 2H), 2.29 (br d, J=12.5 Hz, 2H), 2.11 (br d, J=10.0 Hz, 2H), 1.75 (dq, J=3.1, 12.8 Hz, 2H), 1.52-1.38 (m, 2H), 1.25 (br d, J=6.1 Hz, 6H), 1.06 (t, J=7.3 Hz, 3H). ESI [M+H]=565.2.

Example 62

Preparation of isopropyl trans-N-[4-[5-[4-[2-amino-2-oxo-ethyl]-2-(ethyl-sulfamoyl)phenyl]thiazol-2-yl]cyclohexyl]carbamate (Compound 86)

Following the same General Method A, Compound 86 was prepared. $^1$H NMR (400 MHz, methanol-d$_4$) δ=8.05 (d, J=1.6 Hz, 1H), 7.80 (s, 1H), 7.64-7.58 (m, 1H), 7.48 (d, J=7.9 Hz, 1H), 4.88-4.87 (m, 1H), 3.68 (s, 2H), 3.52-3.42 (m, 1H), 3.17-3.00 (m, 1H), 2.90 (q, J=7.3 Hz, 2H), 2.27 (br d, J=12.1 Hz, 2H), 2.10 (br d, J=10.3 Hz, 2H), 1.80-1.66 (m, 2H), 1.50-1.38 (m, 2H), 1.25 (br d, J=6.1 Hz, 6H), 1.04 (t, J=7.2 Hz, 3H). ESI [M+H]=509.2.

Example 63

Preparation of isopropyl trans-N-[4-[5-[4-[2-oxo-2-(azetidin-1-yl)ethyl]-2-(ethyl-sulfamoyl)phenyl]thiazol-2-yl]cyclohexyl]carbamate (Compound 87)

Following the same General Method A, Compound 87 was prepared. ¹H NMR (400 MHz, methanol-d₄) δ=7.99 (d, J=1.6 Hz, 1H), 7.81 (s, 1H), 7.57 (dd, J=1.8, 7.9 Hz, 1H), 7.52-7.45 (m, 1H), 4.89-4.88 (m, 1H), 4.34 (t, J=7.7 Hz, 2H), 4.06 (t, J=7.8 Hz, 2H), 3.65 (s, 2H), 3.48 (tt, J=3.9, 11.6 Hz, 1H), 3.08 (tt, J=3.4, 12.0 Hz, 1H), 2.90 (q, J=7.3 Hz, 2H), 2.41-2.32 (m, 2H), 2.30-2.23 (m, 2H), 2.15-2.06 (m, 2H), 1.73 (dq, J=2.9, 12.9 Hz, 2H), 1.51-1.37 (m, 2H), 1.25 (br d, J=6.1 Hz, 6H), 1.05 (t, J=7.2 Hz, 3H). ESI [M+H]=549.2.

Example 64

Preparation of isopropyl trans-N-[4-[5-(4-(methyl-amino)-2-pyrrolidin-1-ylsulfonyl-phenyl)thiazol-2-yl]cyclohexyl]carbamate (Compound 89)

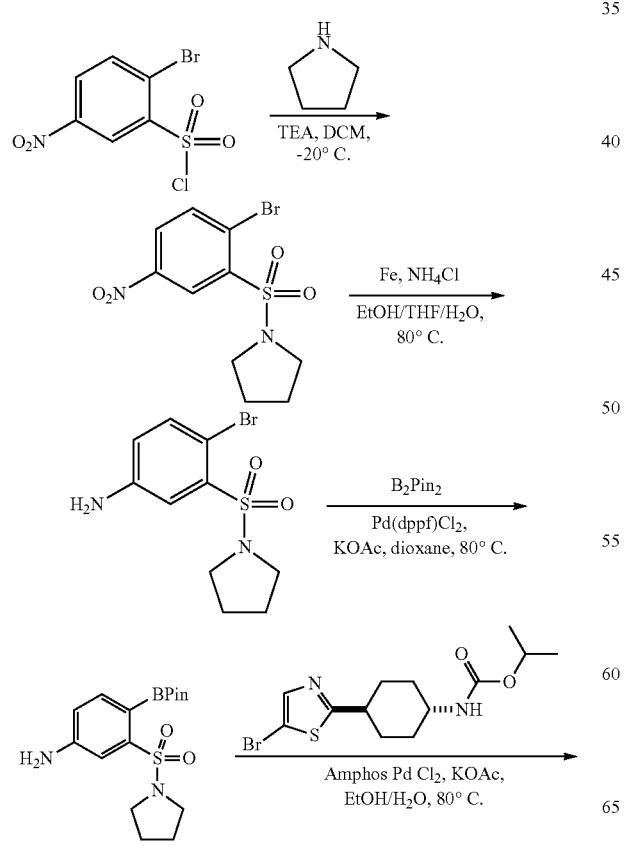

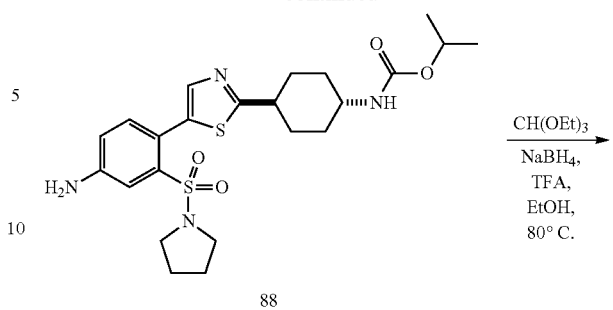

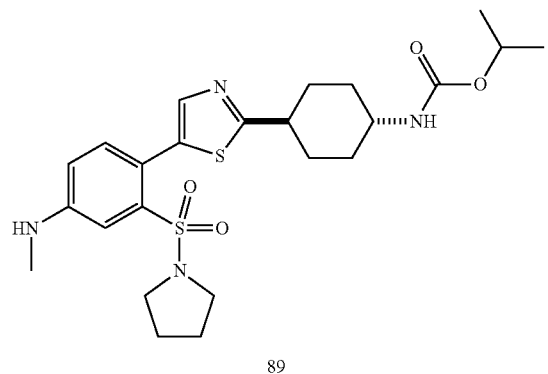

a) Synthesis of 1-(2-bromo-5-nitro-phenyl)sulfonylpyrrolidine

From 2-bromo-5-nitrobenzenesulfonyl chloride General Method G. ¹H NMR (400 MHz, methanol-d₄) δ=8.81 (d, J=2.69 Hz, 1H), 8.33 (dd, J=8.68, 2.69 Hz, 1H), 8.13 (d, J=8.68 Hz, 1H), 3.44-3.49 (m, 4H), 1.97 (dt, J=6.48, 3.48 Hz, 4H).

245 b) Synthesis of 4-bromo-3-pyrrolidin-1-ylsulfonyl-aniline

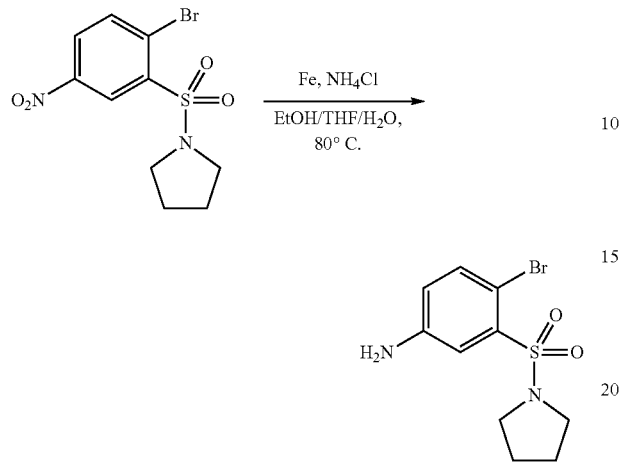

A mixture of 1-(2-bromo-5-nitro-phenyl)sulfonylpyrrolidine (3.0 g, 9.0 mmol, 1.0 eq.), NH₄Cl (1.4 g, 27.0 mmol, 3.0 eq.), Fe (2.5 g, 45.0 mmol, 5.0 eq.) in THF (30 mL), EtOH (30 mL) and H₂O (10 mL) was stirred at 80° C. for 4 h. The reaction mixture was filtered, and the filtrate was concentrated. The residue was diluted with H₂O (10 mL) and extracted with EtOAc 150 mL (50 mL×3). The combined organic layers dried over Na₂SO₄, filtered and concentrated under reduced pressure. The residue was purified by column chromatography (SiO₂, Petroleum ether:Ethyl acetate=10:1 to 1:1 to 0:1) to yield 4-bromo-3-pyrrolidin-1-ylsulfonyl-aniline (2.3 g, 7.5 mmol, 84% yield) as a white solid. ESI [M+H]=304.9/306.9.

c) Synthesis of 3-pyrrolidin-1-ylsulfonyl-4-(4,4,5,5-tetramethyl-1,3,2-dioxaborolan-2-yl)aniline From 4-bromo-3-pyrrolidin-1-ylsulfonyl-aniline, using General Method B. ¹H NMR (400 MHz, DMSO-d₆) δ=7.13-7.04 (m, 1H), 6.96 (s, 1H), 6.80-6.70 (m, 1H), 3.16 (br t, J=6.3 Hz, 4H), 1.67-1.62 (m, 4H), 1.25 (s, 12H). ESI [M+H]=353.1.

246 d) Synthesis of isopropyl trans-N-[4-[5-(4-amino-2-pyrrolidin-1-ylsulfonyl-phenyl)thiazol-2-yl]cyclohexyl]carbamate (Compound 88)

From 3-pyrrolidin-1-ylsulfonyl-4-(4,4,5,5-tetramethyl-1,3,2-dioxaborolan-2-yl)aniline, using General Method D. ¹H NMR (400 MHz, methanol-d₄) δ=7.78-7.66 (m, 1H), 7.41 (br s, 1H), 7.24 (br d, J=8.2 Hz, 1H), 7.00-6.90 (m, 1H), 4.87-4.77 (m, 1H), 3.45 (br t, J=11.7 Hz, 1H), 3.12-3.05 (m, 1H), 3.01 (br t, J=6.1 Hz, 4H), 2.20 (br d, J=12.1 Hz, 2H), 2.07 (br d, J=10.6 Hz, 2H), 1.86-1.75 (m, 4H), 1.74-1.61 (m, 2H), 1.48-1.34 (m, 2H), 1.22 (br d, J=6.0 Hz, 6H). ESI [M+H]=493.2.

e) Synthesis of isopropyl trans-N-[4-[5-(4-(methylamino)-2-pyrrolidin-1-ylsulfonyl-phenynthiazol-2-yl]cyclohexyl]carbamate (Compound 89)

89

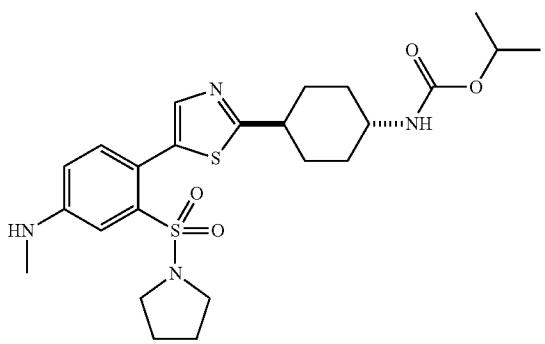

A mixture of isopropyl trans-N-[4-[5-(4-amino-2-pyrrolidin-1-ylsulfonyl-phenyl) thiazol-2-yl]cyclohexyl]carbamate (170 mg, 345 umol, 1 eq.), TFA (4 mg, 35 umol, 0.1 eq.) in diethoxymethoxyethane (2 mL) was stirred at 100° C. for 12 h. The mixture was concentrated followed by addition of EtOH (1 mL) and NaBH$_4$ (39 mg, 1 mmol, 3 eq.) at 0° C. The mixture was stirred at 80° C. for 2 h and quenched by H$_2$O (2 mL) and extracted with EtOAc 10 mL (5 mL×2). The combined organic layers were washed with H$_2$O (5 mL), dried over Na$_2$SO$_4$, filtered and concentrated under reduced pressure to give a residue. The residue was purified by prep-HPLC (column: Welch Ultimate AQ-C18 150*30 mm*5 um; mobile phase: [water(0.1% TFA)-ACN]; B %: 40%-70%,12 min) to yield isopropyl trans-N-[4-[5-(4-(methylamino)-2-pyrrolidin-1-ylsulfonyl-phenyl)thiazol-2-yl]cyclohexyl]carbamate (34 mg, 64 umol, 19% yield, 92% purity) as a yellow solid. $^1$H NMR (400 MHz, methanol-d$_4$) δ=7.67 (s, 1H), 7.29-7.19 (m, 2H), 6.80 (dd, J=2.2, 8.4 Hz, 1H), 4.83 (br s, 1H), 3.45 (br t, J=11.6 Hz, 1H), 3.09-3.02 (m, 1H), 2.99 (br t, J=6.4 Hz, 4H), 2.83 (s, 3H), 2.20 (br d, J=12.1 Hz, 2H), 2.07 (br d, J=11.2 Hz, 2H), 1.78 (br t, J=6.5 Hz, 4H), 1.75-1.61 (m, 2H), 1.47-1.34 (m, 2H), 1.22 (br d, J=6.0 Hz, 6H). ESI [M+H]=507.2.

Example 65

Preparation of isopropyl trans-N-[4-[5-[4-(1H-imidazol-2-ylamino)-2-sulfamoyl-phenyl]thiazol-2-yl]cyclohexyl]carbamate (Compound 90; General Method K)

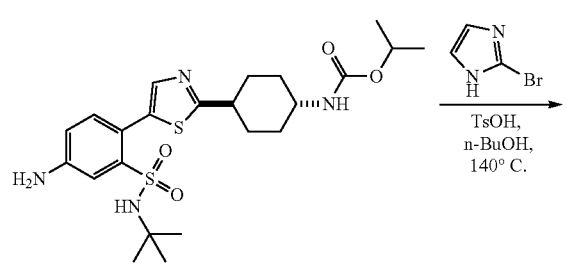

90

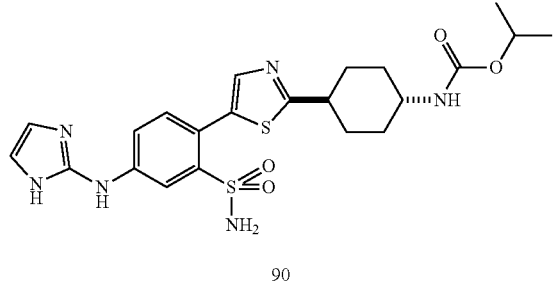

To a solution of isopropyl trans-N-[4-[5-[4-amino-2-(tert-butylsulfamoyl) phenyl]thiazol-2-yl]cyclohexyl]carbamate (200 mg, 404 umol, 1 eq.) in n-BuOH (4 mL) was added TsOH (209 mg, 1 mmol, 3 eq.) and 2-bromo-1H-imidazole (297 mg, 2 mmol, 5 eq.). The mixture was stirred at 140° C. for 12 h. The reaction mixture was concentrated under reduced pressure and purified by prep-HPLC (column: Waters Xbridge BEH C18 100*30 mm*10 um; mobile phase: [water(0.1% TFA)-ACN]; B %: 30%-90%, 10 min) to yield isopropyl trans-N-[4-[5-[4-(1H-imidazol-2-ylamino)-2-sulfamoyl-phenyl]thiazol-2-yl]cyclohexyl]carbamate (12 mg, 20 umol, 40% yield, 100% purity, TFA) as a yellow solid. $^1$H NMR (400 MHz, methanol-d$_4$) δ=7.97 (d, J=2.0 Hz, 1H), 7.80-7.74 (m, 1H), 7.58-7.52 (m, 1H), 7.51-7.45 (m, 1H), 7.10 (s, 2H), 4.83-4.76 (m, 1H), 3.45 (br t, J=11.6 Hz, 1H), 3.09-2.96 (m, 1H), 2.24 (br d, J=12.8 Hz, 2H), 2.11-1.96 (m, 2H), 1.83-1.64 (m, 2H), 1.47-1.32 (m, 2H), 1.22 (br d, J=6.0 Hz, 6H). ESI [M+H]=505.1.

Example 66

Preparation of isopropyl trans-N-[4-[5-[2-(dimethylsulfamoyl)-4-(1H-imidazol-2-ylamino)phenyl]thiazol-2-yl]cyclohexyl]carbamate (Compound 91)

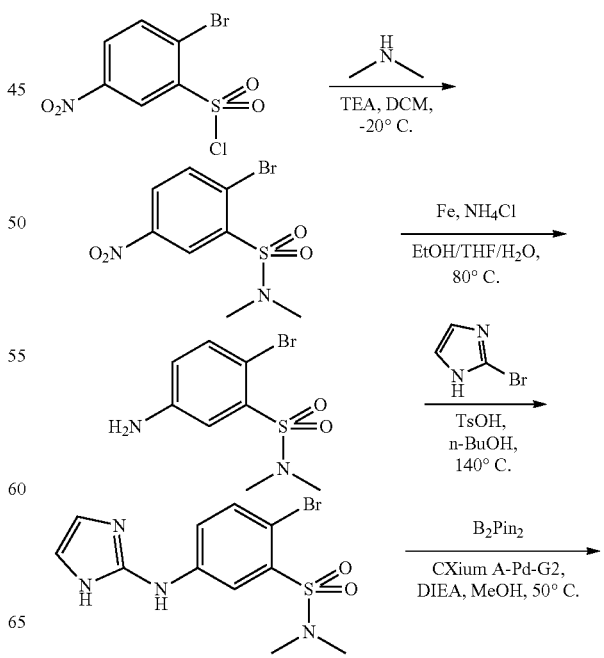

mixture was stirred at 80° C. for 2 h then filtered, and the filtrate was concentrated under reduced pressure. The residue was diluted with H₂O (20 mL) and extracted with EtOAc 90 mL (30 mL×3). The combined organic layers were dried over Na₂SO₄, filtered and concentrated under reduced pressure. The residue was purified by column chromatography (SiO₂, Petroleum ether:Ethyl acetate=1:0 to 0:1) to yield 5-amino-2-bromo-N,N-dimethyl-benzenesulfonamide (3.9 g, 14.0 mmol, 94% yield) as a pale yellow solid. ¹H NMR (400 MHz, methanol-d₄) δ=7.43 (d, J=8.6 Hz, 1H), 7.35 (d, J=2.8 Hz, 1H), 6.75 (dd, J=2.8, 8.6 Hz, 1H), 2.86 (s, 6H). ESI [M+H]=278.9/281.0.

c) Synthesis of 2-bromo-5-(1H-imidazol-2-ylamino)-N,N-dimethyl-benzene sulfonamide

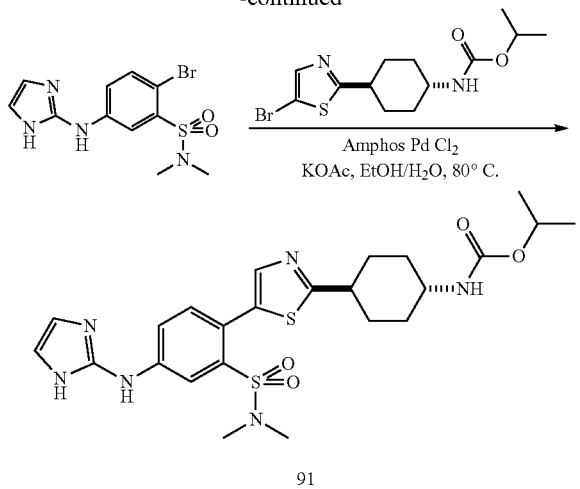

a) Synthesis of 2-bromo-N,N-dimethyl-5-nitro-benzenesulfonamide

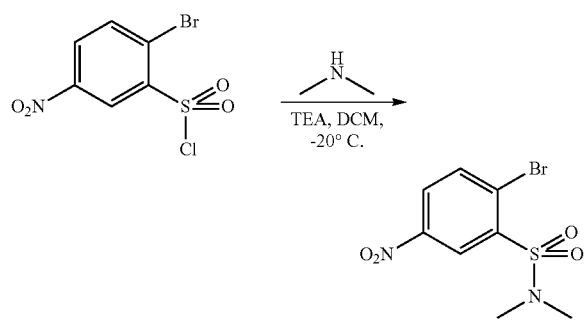

From 2-bromo-5-nitrobenzenesulfonyl chloride and dimethylamine, using General Method G. ESI [M+H]=308.9/310.9.

b) Synthesis of 5-amino-2-bromo-N,N-dimethyl-benzenesulfonamide

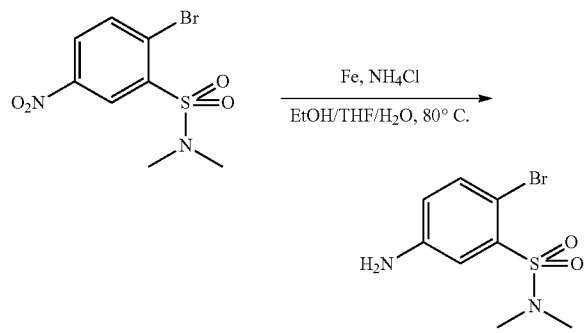

To a solution of 2-bromo-N,N-dimethyl-5-nitro-benzenesulfonamide (4.6 g, 14.8 mmol, 1.0 eq.) in H₂O (20 mL), EtOH (60 mL) and THF (60 mL) was added Fe (4.1 g, 74.1 mmol, 5.0 eq.) and NH₄Cl (2.4 g, 44.5 mmol, 3.0 eq.). The

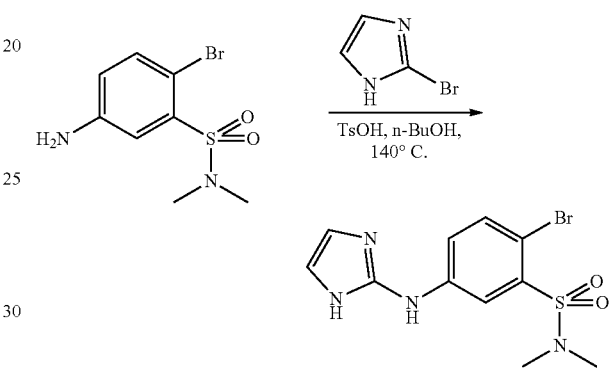

From 5-amino-2-bromo-N,N-dimethyl-benzenesulfonamide, using General Method K. ¹H NMR (400 MHz, methanol-d₄) δ=7.97-7.84 (m, 2H), 7.41 (dd, J=2.8, 8.5 Hz, 1H), 7.12 (s, 2H), 2.93 (s, 6H). ESI [M+H]=345.0/347.0.

d) Synthesis of 5-(1H-imidazol-2-ylamino)-N,N-dimethyl-2-(4,4,5,5-tetra methyl-1,3,2-dioxaborolan-2-yl)benzenesulfonamide

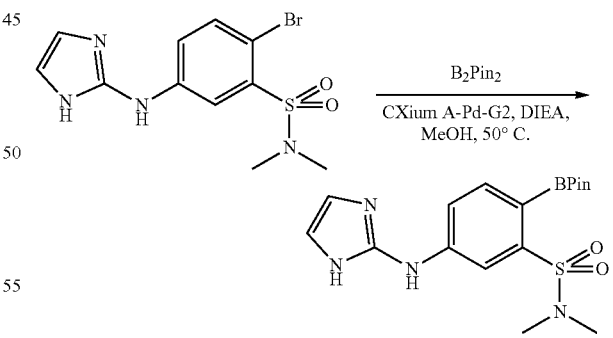

A solution of 2-bromo-5-(1H-imidazol-2-ylamino)-N,N-dimethyl-benzenesulfonamide (380 mg, 1 mmol, 1 eq.), 4,4,5,5-tetramethyl-2-(4,4,5,5-tetramethyl-1,3,2-dioxaborolan-2-yl)-1,3,2-dioxaborolane (1.4 g, 5.5 mmol, 5.0 eq.), [2-(2-aminophenyl)phenyl]-chloro-palladium; bis(1-adamantyl)-butyl-phosphane (74 mg, 110 umol, 0.1 eq.), DIEA (711 mg, 6 mmol, 5 eq.) in MeOH (10 mL) was stirred at 50° C. for 12 h under N₂ atmosphere. The reaction mixture was concentrated and purified by column chromatography (SiO₂, petroleum ether:ethyl acetate=1:0 to THF) to yield 5-(1H-imidazol-2-ylamino)-N,N-dimethyl-2-(4,4,5,5-tetramethyl-1,3,2-dioxa-borolan-2-yl)benzenesulfonamide (300 mg, crude) as a brown oil. $^1$H NMR (400 MHz, methanol-$d_4$) δ=7.53-7.40 (m, 1H), 7.39-7.31 (m, 1H), 7.29-7.14 (m, 1H), 6.92 (s, 1H), 6.82 (d, J=2.4 Hz, 1H), 3.72 (td, J=6.6, 13.2 Hz, 3H), 3.22 (q, J=7.5 Hz, 3H), 1.38-1.36 (m, 12H). ESI [M+H]=393.1.

e) Synthesis of isopropyl trans-N-[4-[5-[2-(dimethylsulfamoyl)-4-(1H-imidazol-2-ylamino)phenyl]thiazol-2-yl]cyclohexyl]carbamate (Compound 91)

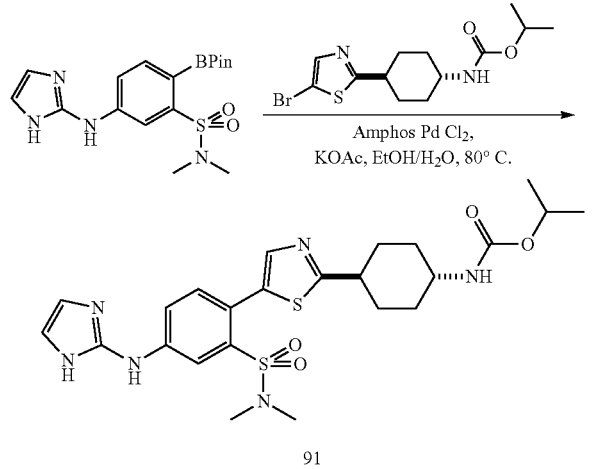

91

From 5-(1H-imidazol-2-ylamino)-N,N-dimethyl-2-(4,4,5,5-tetramethyl-1,3,2-dioxa-borolan-2-yl)benzenesulfonamide, using General Method D. $^1$H NMR (400 MHz, methanol-$d_4$) δ=7.90 (d, J=2.3 Hz, 1H), 7.72 (s, 1H), 7.62-7.51 (m, 2H), 7.14 (s, 2H), 4.84-4.78 (m, 1H), 3.47 (tt, J=3.9, 11.6 Hz, 1H), 3.05 (tt, J=3.5, 12.0 Hz, 1H), 2.65-2.55 (m, 6H), 2.32-2.18 (m, 2H), 2.14-2.03 (m, 2H), 1.71 (dq, J=2.9, 12.8 Hz, 2H), 1.44 (dq, J=3.3, 12.5 Hz, 2H), 1.25 (br d, J=6.3 Hz, 6H). ESI [M+H]=533.2.

Example 67

Preparation of isopropyl trans-N-[4-[5-[4-(1H-imidazol-2-ylamino)-2-pyrrolidin-1-ylsulfonyl-phenyl]thiazol-2-yl]cyclohexyl]carbamate (Compound 92)

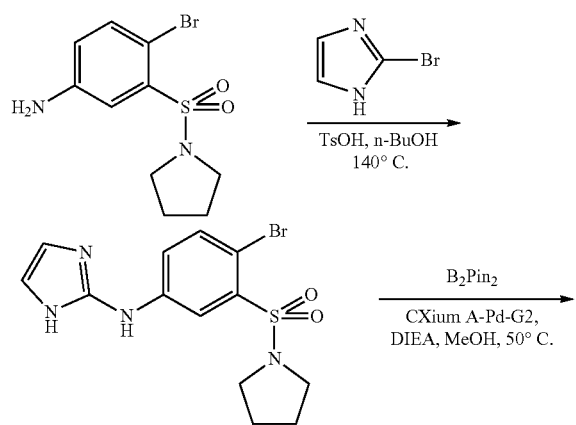

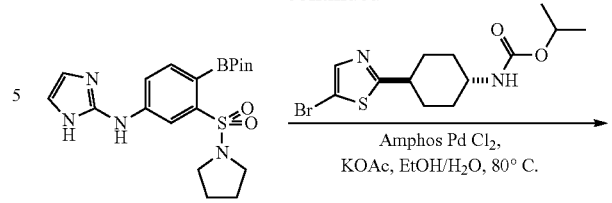

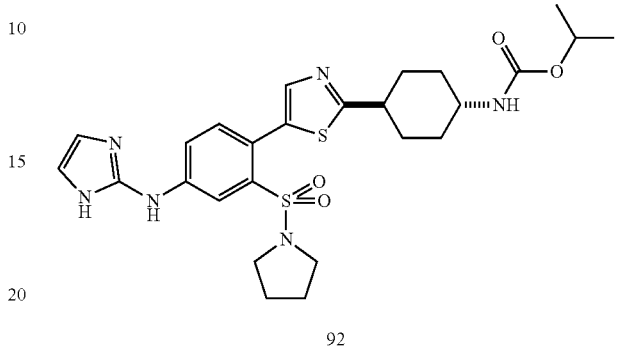

92 a) Synthesis of N-(4-bromo-3-pyrrolidin-1-ylsulfonyl-phenyl)-1H-imidazol-2-amine

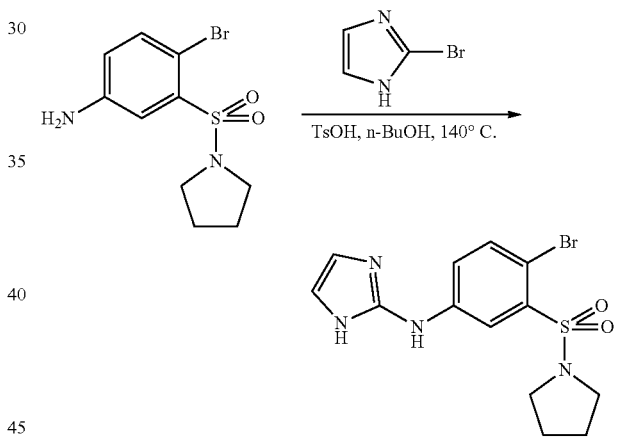

From 4-bromo-3-(pyrrolidin-1-ylsulfonyl)aniline, using General Method K. $^1$H NMR (400 MHz, methanol-$d_4$) δ=7.82-7.92 (m, 2H), 7.38 (dd, J=8.49, 2.76 Hz, 1H), 7.06-7.11 (m, 2H), 3.36-3.48 (m, 4H), 1.93 (dt, J=6.45, 3.50 Hz, 4H). ESI [M+H]=370.9/372.9.

b) Synthesis of N-[3-pyrrolidin-1-ylsulfonyl-4-(4,4,5,5-tetramethyl-1,3,2-dioxaborolan-2-yl)phenyl]-1H-imidazol-2-amine

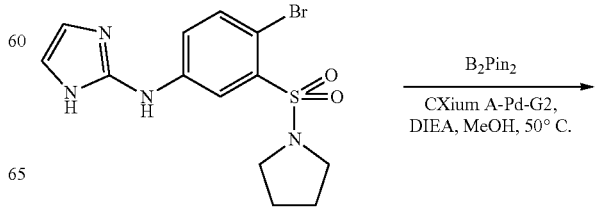

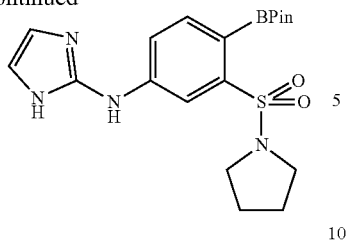

A mixture of 4,4,5,5-tetramethyl-2-(4,4,5,5-tetramethyl-1,3,2-dioxaborolan-2-yl)-1,3,2-dioxaborolane (654 mg, 3 mmol, 5 eq.), N-(4-bromo-3-pyrrolidin-1-ylsulfonyl-phenyl)-1H-imidazol-2-amine (250 mg, 515 umol, 1 eq., TFA), [2-(2-amino-phenyl)phenyl]-chloro-palladium; bis(1-adamantyl)-butyl-phosphane (34 mg, 52 umol, 0.1 eq.), DIEA (333 mg, 3 mmol, 5 eq.) in MeOH (15 mL) was degassed and purged with $N_2$ for 3 times, and then the mixture was stirred at 50° C. for 12 h under $N_2$ atmosphere. The reaction mixture was concentrated and purified by column chromatography ($SiO_2$, petroleum ether:ethyl acetate=1:0 to 5:1 to 1:1 to 0:1) to yield N-[3-pyrrolidin-1-ylsulfonyl-4-(4,4,5,5-tetramethyl-1,3,2-dioxaborolan-2-yl)phenyl]-1H-imidazol-2-amine (190 mg, 454 umol, 88% yield) as a white solid. ESI [M+H]=419.2.

c) Synthesis of isopropyl trans-N-[4-[5-[4-(1H-imidazol-2-ylamino)-2-pyrrolidin-1-ylsulfonyl-phenyl]thiazol-2-yl]cyclohexyl]carbamate (Compound 92)

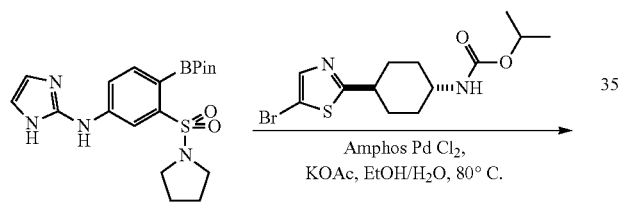

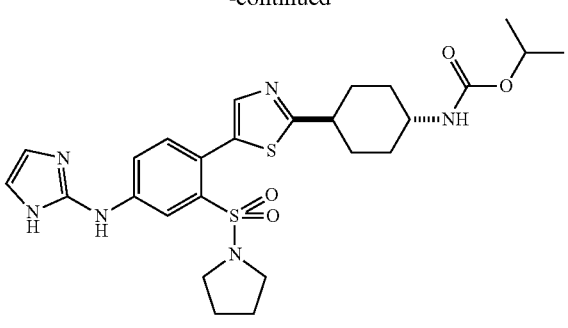

92

From N-[3-pyrrolidin-1-ylsulfonyl-4-(4,4,5,5-tetramethyl-1,3,2-dioxaborolan-2-yl) phenyl]-1H-imidazol-2-amine, using General Method D. $^1$H NMR (400 MHz, methanol-$d_4$) δ=7.91 (d, J=1.75 Hz, 1H), 7.76 (br s, 1H), 7.50-7.59 (m, 2H), 7.13 (s, 2H), 4.82 (br d, J=6.00 Hz, 1H), 3.46 (br t, J=11.57 Hz, 1H), 3.04 (br s, 1H), 2.97 (br t, J=6.25 Hz, 4H), 2.21 (br d, J=12.63 Hz, 2H), 2.07 (br d, J=10.88 Hz, 2H), 1.78 (br t, J=6.25 Hz, 4H), 1.69 (br d, J=12.01 Hz, 2H), 1.38-1.48 (m, 2H), 1.23 (br d, J=6.13 Hz, 6H). ESI [M+H]=559.2.

Example 68

Preparation of isopropyl trans-N-[4-[5-[2-(ethylsulfamoyl)-4-(1H-imidazol-2-ylcarbamoyl)phenyl]thiazol-2-yl]cyclohexyl]carbamate (Compound 94)

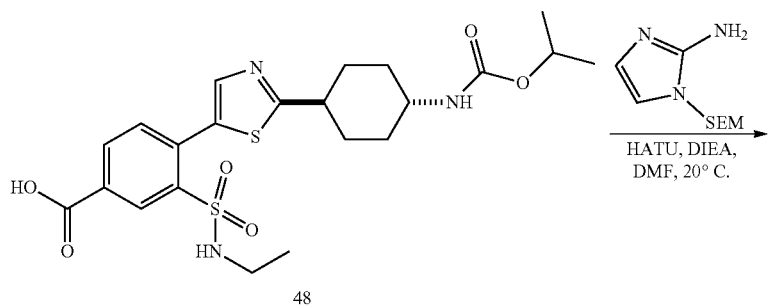

48

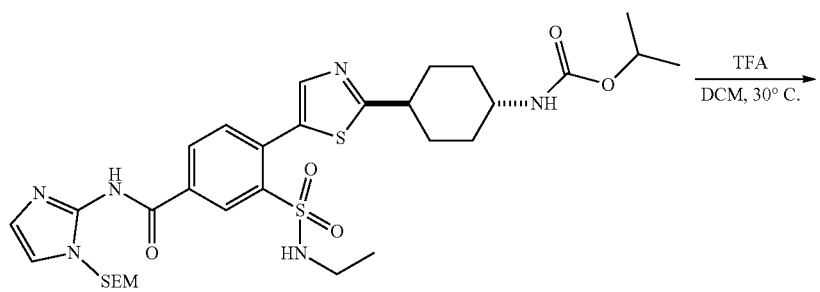

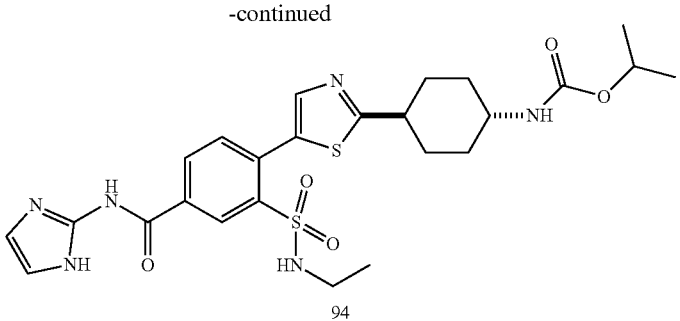

a) Synthesis of isopropyl trans-N-[4-[5-[2-(ethylsul-famoyl)-4-[[1-(2-trimethyl-silylethoxymethyl)-1H-imidazol-2-yl]carbamoyl]phenyl]thiazol-2-yl]cyclohexyl]carbamate

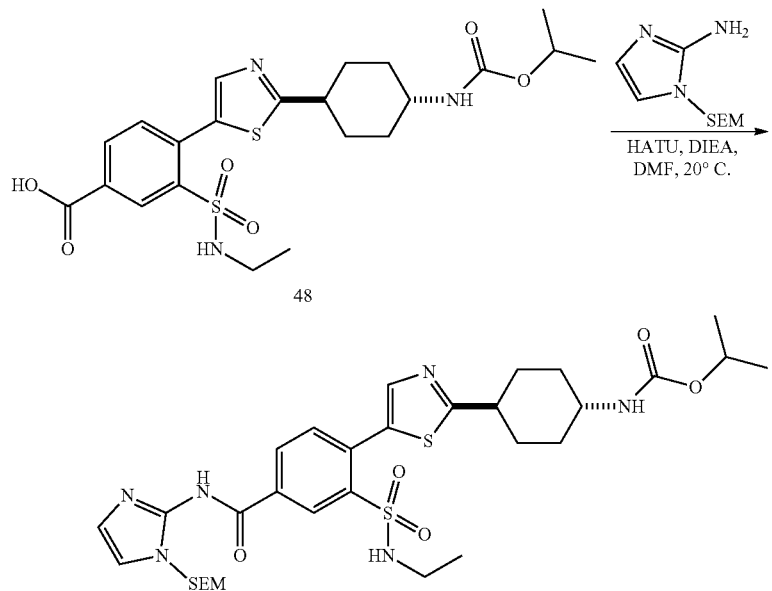

From trans-3-(ethylsulfamoyl)-4-[2-[4-(isopropyloxycarbonyl-amino) cyclohexyl]thiazol-5-yl]benzoic acid (Compound 48) and 1-((2-(trimethylsilyl)ethoxy)methyl)-1H-imidazol-2-amine, using General Method A. ESI [M−H]=691.3.

b) Synthesis of isopropyl trans-N-[4-[5-[2-(ethylsul-famoyl)-4-(1H-imidazol-2-ylcarbamoyl)phenyl]thiazol-2-yl]cyclohexyl]carbamate (Compound 94)

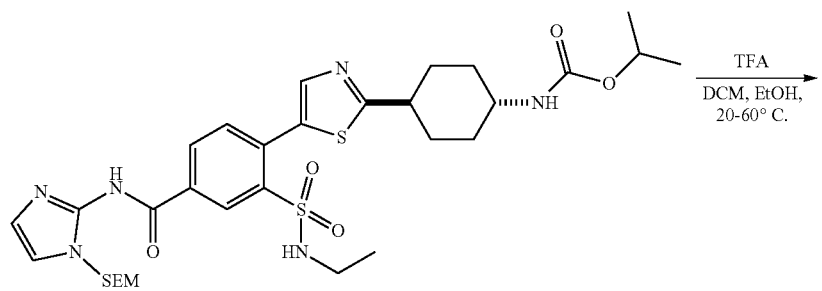

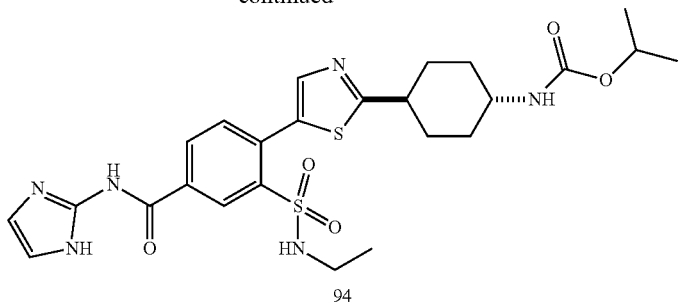

94

From isopropyl trans-N-[4-[5-[2-(ethylsulfamoyl)-4-[[1-(2-trimethyl-silylethoxymethyl)-1H-imidazol-2-yl]carbamoyl]phenyl]thiazol-2-yl]cyclohexyl]carbamate, using General Method I. $^1$H NMR (400 MHz, methanol-$d_4$) δ=8.78 (d, J=1.63 Hz, 1H), 8.28 (dd, J=8.00, 1.63 Hz, 1H), 7.89 (s, 1H), 7.75 (d, J=7.88 Hz, 1H), 7.29 (s, 2H), 4.77-4.84 (m, 1H), 3.42-3.53 (m, 1H), 3.07 (tt, J=11.99, 3.39 Hz, 1H), 2.90 (q, J=7.21 Hz, 2H), 2.29 (br d, J=12.76 Hz, 2H), 2.05-2.14 (m, 2H), 1.74 (qd, J=12.88, 3.00 Hz, 2H), 1.45 (qd, J=12.51, 3.00 Hz, 2H), 1.20-1.31 (m, 6H), 1.03 (t, J=7.19 Hz, 3H). ESI [M+H]=561.2.

Example 69

Preparation of isopropyl trans-N-[4-[5-[4-carbamoyl-2-(ethylsulfamoyl)phenyl]thiazol-2-yl]cyclohexyl]carbamate (Compound 49)

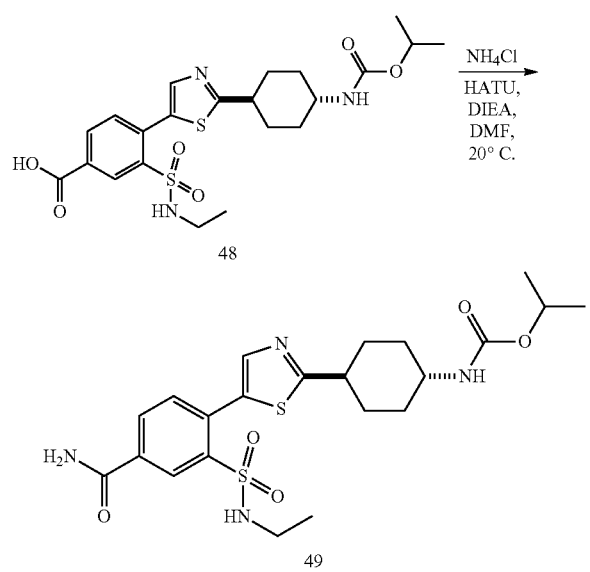

From trans-3-(ethylsulfamoyl)-4-[2-[4-(isopropyloxycarbonyl-amino)cyclohexyl]thiazol-5-yl]benzoic acid (Compound 48) and ammonium chloride, using General Method A. $^1$H NMR (400 MHz, methanol-$d_4$) δ=8.56 (d, J=1.5 Hz, 1H), 8.09 (dd, J=1.8, 7.9 Hz, 1H), 7.85 (s, 1H), 7.61 (d, J=7.9 Hz, 1H), 4.85-4.74 (m, 1H), 3.52-3.40 (m, 1H), 3.05 (tt, J=3.5, 11.9 Hz, 1H), 2.89 (q, J=7.2 Hz, 2H), 2.32-2.20 (m, 2H), 2.11-2.04 (m, 2H), 1.71 (dq, J=2.8, 13.0 Hz, 2H), 1.48-1.36 (m, 2H), 1.22 (br d, J=6.2 Hz, 6H), 1.02 (t, J=7.3 Hz, 3H). ESI [M+H]=495.1.

Example 70

Preparation of isopropyl (trans-4-(5-(2-(N-ethylsulfamoyl)-4-(isopropylcarbamoyl)phenyl)thiazol-2-yl)cyclohexyl)carbamate (Compound 50)

Following the same protocol and under the same reaction conditions as for Compound 94, Compound 50 was prepared. $^1$H NMR (400 MHz, methanol-$d_4$) δ=8.52 (s, 1H), 8.05 (br d, J=7.5 Hz, 1H), 7.83 (s, 1H), 7.61 (d, J=7.9 Hz, 1H), 4.88-4.80 (m, 1H), 4.25 (quin, J=6.6 Hz, 1H), 3.48 (ddd, J=4.2, 7.7, 11.4 Hz, 1H), 3.12-2.99 (m, 1H), 2.91 (q, J=7.1 Hz, 2H), 2.27 (br d, J=12.5 Hz, 2H), 2.17-2.02 (m, 2H), 1.84-1.64 (m, 2H), 1.49-1.40 (m, 2H), 1.30 (d, J=6.6 Hz, 6H), 1.27-1.16 (m, 6H), 1.04 (t, J=7.2 Hz, 3H). ESI [M+H]=537.2.

Example 71

Preparation of isopropyl trans-N-[4-[5-[4-pyrrolidin-1-ylcarbonyl-2-(ethylsulfamoyl)phenyl]thiazol-2-yl]cyclohexyl]carbamate (Compound 95)

Following the same protocol and under the same reaction conditions as for Compound 94, Compound 95 was prepared. $^1$H NMR (400 MHz, methanol-$d_4$) δ=8.20 (d, J=1.5 Hz, 1H), 7.85-7.76 (m, 2H), 7.60 (d, J=7.9 Hz, 1H), 4.84-4.76 (m, 1H), 3.63 (t, J=6.8 Hz, 2H), 3.51 (t, J=6.5 Hz, 2H), 3.48-3.40 (m, 1H), 3.03 (tt, J=3.5, 12.0 Hz, 1H), 2.88 (q, J=7.3 Hz, 2H), 2.30-2.19 (m, 2H), 2.07 (br dd, J=3.2, 13.3 Hz, 2H), 2.03-1.90 (m, 4H), 1.71 (dq, J=2.9, 12.9 Hz, 2H), 1.47-1.36 (m, 2H), 1.22 (br d, J=6.2 Hz, 6H), 1.02 (t, J=7.3 Hz, 3H). ESI [M+H]=549.3.

Example 72

Preparation of oxetan-3-yl trans-N-[4-[5-[4-carbamoyl-2-(ethylsulfamoyl)phenyl]thiazol-2-yl]cyclohexyl]carbamate (Compound 67)

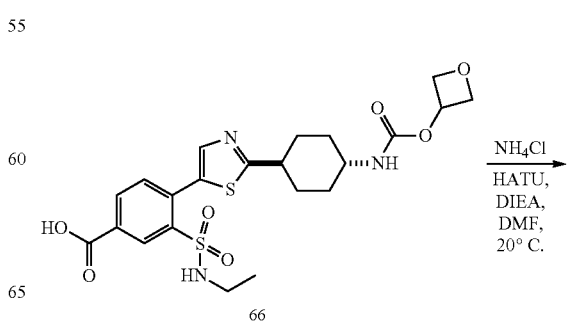

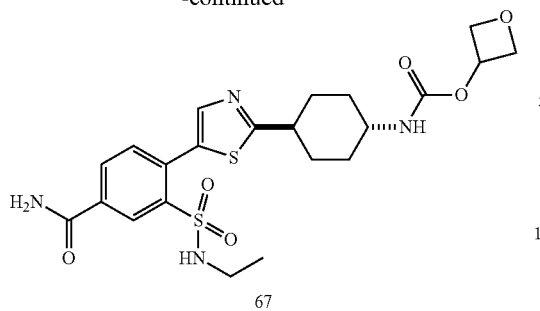

From trans-3-(ethylsulfamoyl)-4-[2-[4-(oxetan-3-yloxycarbonyl-amino)cyclohexyl]thiazol-5-yl]benzoic acid (Compound 66) and ammonium chloride, using General Method A. ¹H NMR (400 MHz, methanol-d₄) δ=8.56 (d, J=1.8 Hz, 1H), 8.08 (dd, J=1.8, 7.9 Hz, 1H), 7.81 (s, 1H), 7.60 (d, J=7.9 Hz, 1H), 5.35 (quin, J=5.7 Hz, 1H), 4.84 (br s, 2H), 4.65-4.54 (m, 2H), 3.45 (ddd, J=3.7, 7.7, 11.5 Hz, 1H), 3.09-2.97 (m, 1H), 2.89 (q, J=7.3 Hz, 2H), 2.29-2.19 (m, 2H), 2.08 (br d, J=10.4 Hz, 2H), 1.71 (dq, J=3.0, 12.8 Hz, 2H), 1.50-1.36 (m, 2H), 1.02 (t, J=7.2 Hz, 3H). ESI [M+H]=509.2.

Example 73

Preparation of oxetan-3-yl (trans-4-(5-(2-(N-ethylsulfamoyl)-4-(isopropylcarbamoyl)phenyl)thiazol-2-yl)cyclohexyl)carbamate (Compound 68)

Following the same protocol and under the same reaction conditions as for Compound 67, Compound 68 was prepared. ¹H NMR (400 MHz, DMSO-d₆) δ=8.53 (d, J=7.7 Hz, 1H), 8.39 (d, J=1.8 Hz, 1H), 8.07 (dd, J=1.7, 8.0 Hz, 1H), 7.76 (s, 1H), 7.59 (d, J=7.9 Hz, 1H), 7.53 (br s, 1H), 7.43 (d, J=7.5 Hz, 1H), 5.26 (quin, J=5.7 Hz, 1H), 4.73 (t, J=6.9 Hz, 2H), 4.46-4.40 (m, 2H), 4.15-4.03 (m, 1H), 3.29 (s, 1H), 2.94 (tt, J=3.6, 11.9 Hz, 1H), 2.77 (q, J=7.1 Hz, 2H), 2.14 (br d, J=11.7 Hz, 2H), 1.91 (br d, J=9.7 Hz, 2H), 1.62-1.51 (m, 2H), 1.41-1.30 (m, 2H), 1.16 (d, J=6.6 Hz, 6H), 0.93 (t, J=7.3 Hz, 3H). ESI [M+H]=551.2.

Example 74

Preparation of isopropyl trans-N-[4-[5-[4-[2-(benzylamino)-2-oxo-ethyl]-2-(tert-butylsulfamoyl)phenyl]thiazol-2-yl]cyclohexyl]carbamate (Compound 97)

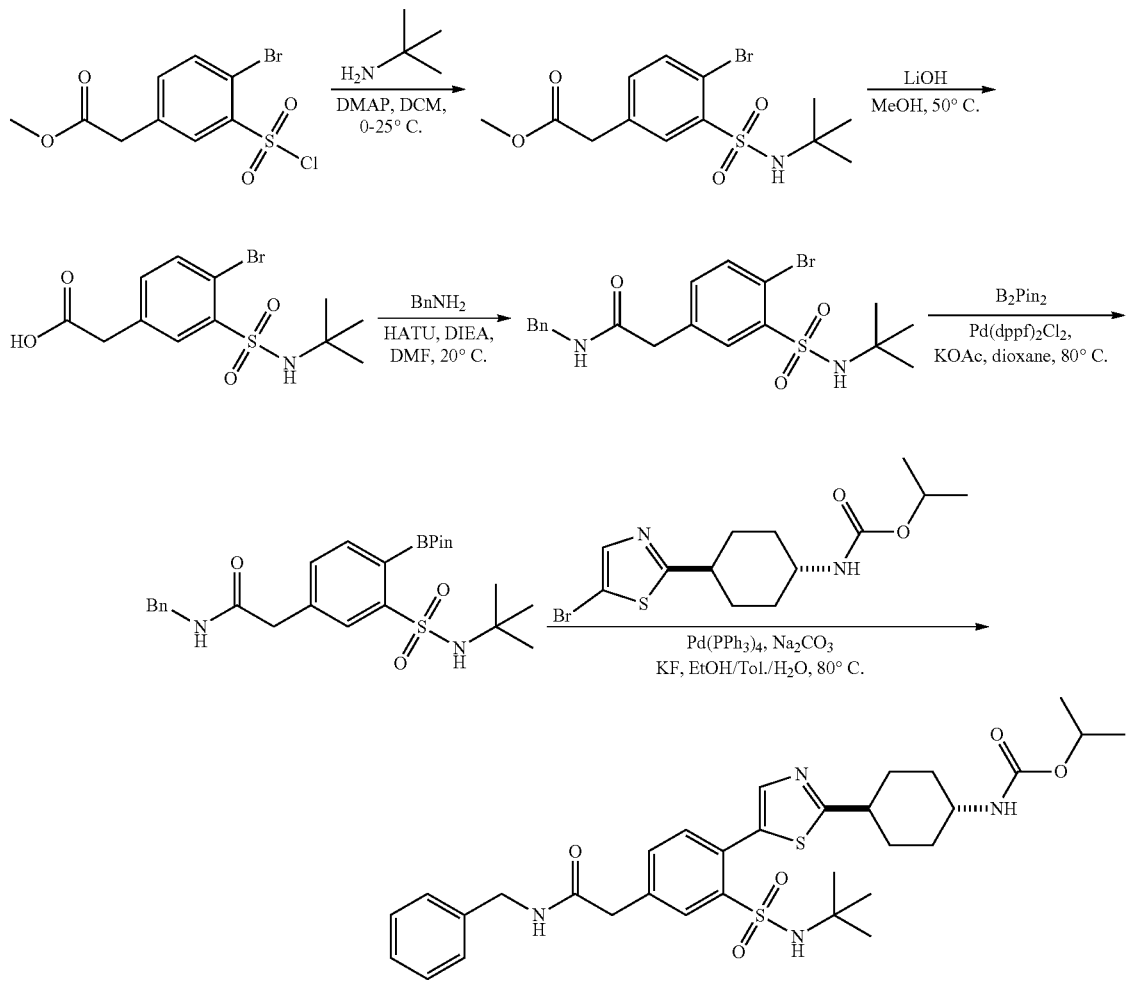

a) Synthesis of methyl 2-[4-bromo-3-(tert-butylsulfamoyl)phenyl]acetate

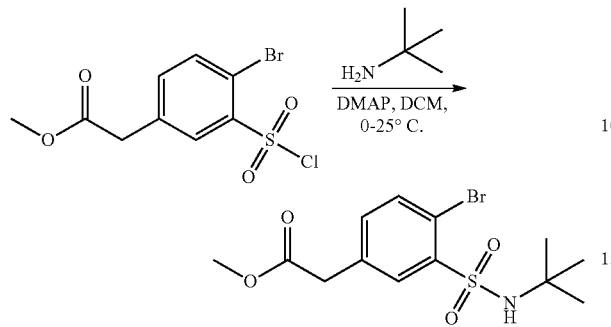

To a solution of 2-methylpropan-2-amine (2.6 g, 36.6 mmol, 3 eq.) in DCM (60 mL) was added DMAP (149 mg, 1 mmol, 0.1 eq.), and methyl 2-(4-bromo-3-chlorosulfonylphenyl)acetate (4.0 g, 12.2 mmol, 1 eq.) at 0° C. The mixture was stirred at 25° C. for 2 h, then diluted with H$_2$O (100 mL) and extracted with DCM 400 mL (200 mL×2). The combined organic layers were dried over Na$_2$SO$_4$, filtered and concentrated under reduced pressure. The residue was slurried in the solution (petroleum ether:ethyl acetate=20:1, 10 mL) for 1 h. Then it was filtered to yield methyl 2-[4-bromo-3-(tert-butylsulfamoyl)phenyl]acetate (2.2 g, 6.0 mmol, 49.4% yield) as a yellow solid. $^1$H NMR (400 MHz, methanol-d$_4$) δ=8.16-8.00 (m, 1H), 7.80-7.62 (m, 1H), 7.36 (dd, J=2.0, 8.2 Hz, 1H), 3.73 (s, 2H), 3.69-3.64 (m, 3H), 1.21-1.15 (m, 9H). ESI[M−H]=361.9/363.9.

b) Synthesis of 2-[4-bromo-3-(tert-butylsulfamoyl)phenyl]acetic acid

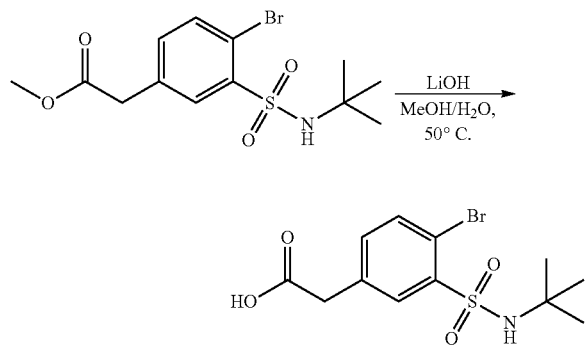

From methyl 2-[4-bromo-3-(tert-butylsulfamoyl)phenyl]acetate, using General Method J.

c) Synthesis of N-benzyl-2-[4-bromo-3-(tert-butylsulfamoyl)phenyl]acetamide

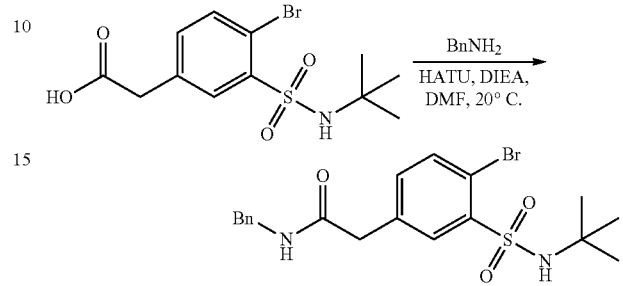

From 2-[4-bromo-3-(tert-butylsulfamoyl)phenyl]acetic acid and benzylamine, using General Method A. $^1$H NMR (400 MHz, methanol-d$_4$) δ=8.11 (d, J=2.0 Hz, 1H), 7.76-7.65 (m, 1H), 7.44-7.33 (m, 2H), 7.32-7.18 (m, 4H), 4.36 (s, 2H), 3.59 (s, 2H), 1.21-1.10 (m, 9H). ESI [M+H]=439.0/441.0.

d) Synthesis of N-benzyl-2-[3-(tert-butylsulfamoyl)-4-(4,4,5,5-tetramethyl-1,3,2-dioxaborolan-2-yl)phenyl]acetamide

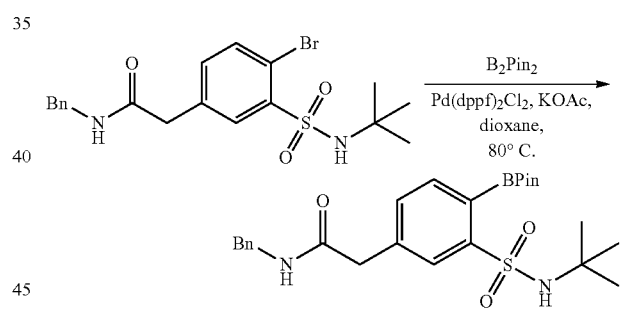

From N-benzyl-2-[4-bromo-3-(tert-butylsulfamoyl)phenyl]acetamide, using General Method B. ESI[M+H]=487.2.

e) Synthesis of isopropyl trans-N-[4-[5-[4-[2-(benzylamino)-2-oxo-ethyl]-2-(tert-butylsulfamoyl)phenyl]thiazol-2-yl]cyclohexyl]carbamate (Compound 97)

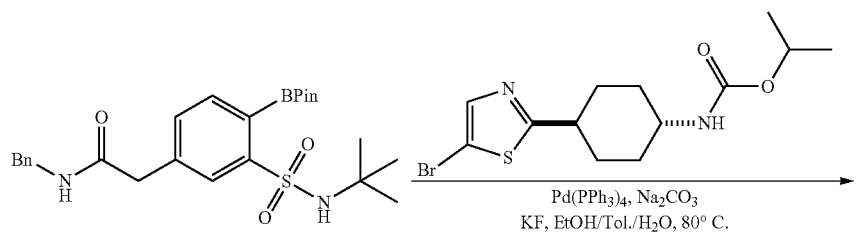

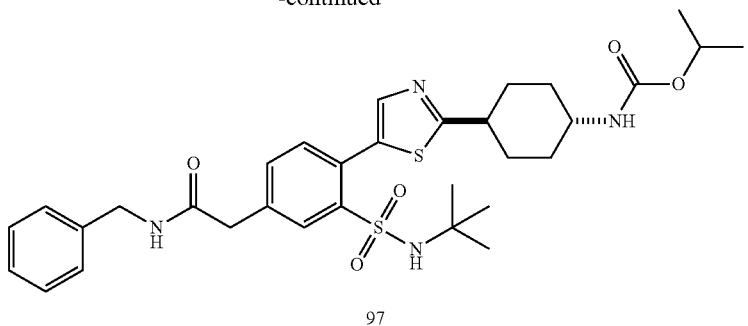

97

From N-benzyl-2-[3-(tert-butylsulfamoyl)-4-(4,4,5,5-tetramethyl-1,3,2-dioxaborolan-2-yl)phenyl]acetamide, using General Method C. $^1$H NMR (400 MHz, methanol-d$_4$) δ=8.14 (d, J=1.5 Hz, 1H), 7.79 (s, 1H), 7.56 (dd, J=1.7, 7.8 Hz, 1H), 7.43 (d, J=7.7 Hz, 1H), 7.34-7.19 (m, 5H), 4.84 (br s, 1H), 4.38 (s, 2H), 3.67 (s, 2H), 3.51-3.39 (m, 1H), 3.03 (tt, J=3.4, 12.0 Hz, 1H), 2.23 (br d, J=12.6 Hz, 2H), 2.07 (br d, J=10.6 Hz, 2H), 1.76-1.60 (m, 2H), 1.41 (dq, J=3.2, 12.5 Hz, 2H), 1.22 (br d, J=6.2 Hz, 6H), 1.13-0.99 (m, 9H). ESI [M+H]=627.3.

Example 75

Preparation of oxetan-3-yl trans-N-[4-[5-[4-[2-(benzylamino)-2-oxo-ethyl]-2-(tert-butylsulfamoyl)phenyl]thiazol-2-yl]cyclohexyl]carbamate (Compound 98)

Following the same protocol and under the same reaction conditions as for Compound 97, Compound 98 was prepared. $^1$H NMR (400 MHz, DMSO-d$_6$) δ=8.66 (t, J=6.0 Hz, 1H), 8.01 (s, 1H), 7.68 (s, 1H), 7.50 (br d, J=7.9 Hz, 1H), 7.45-7.36 (m, 2H), 7.33-7.26 (m, 2H), 7.25-7.18 (m, 3H), 6.94 (s, 1H), 5.26 (quin, J=5.7 Hz, 1H), 4.73 (t, J=6.9 Hz, 2H), 4.52-4.39 (m, 2H), 4.26 (d, J=5.7 Hz, 2H), 3.60 (s, 2H), 3.30-3.20 (m, 1H), 2.99-2.82 (m, 1H), 2.12 (br d, J=11.5 Hz, 2H), 1.90 (br d, J=10.4 Hz, 2H), 1.65-1.48 (m, 2H), 1.42-1.27 (m, 2H), 1.00 (s, 9H). ESI [M+H]=641.3.

Example 76

Preparation of isopropyl trans-N-[4-[5-[2-(ethylsulfamoyl)-4-isopentyloxy-phenyl]thiazol-2-yl]cyclohexyl]carbamate (Compound 99)

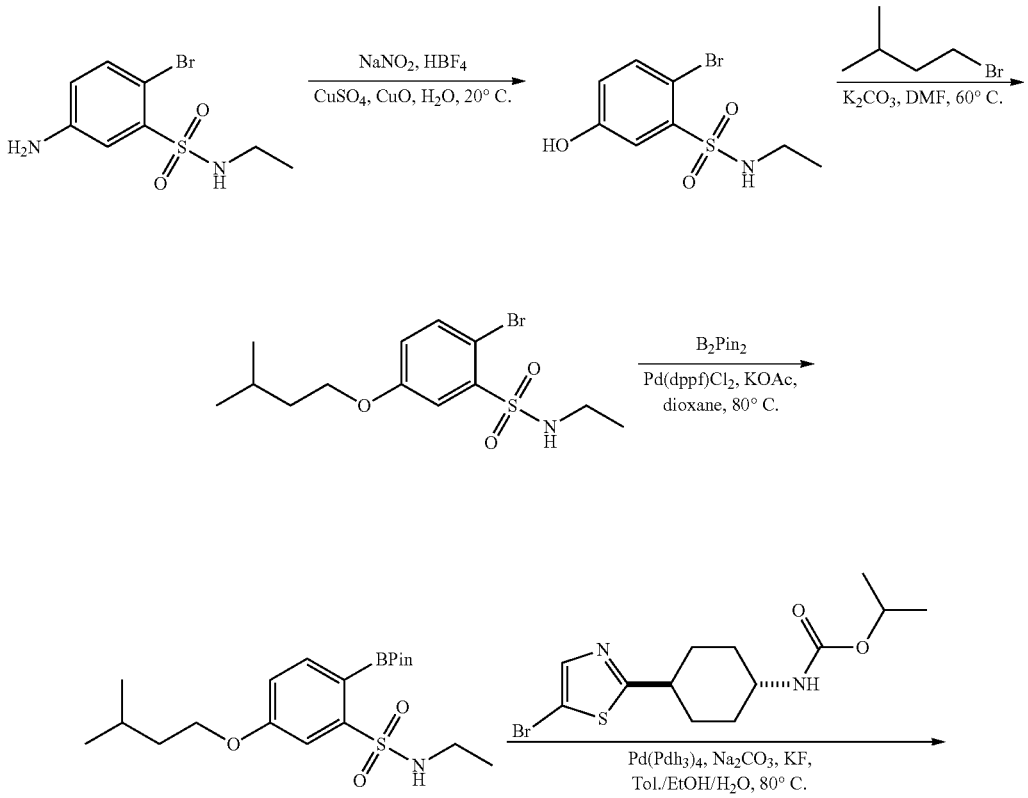

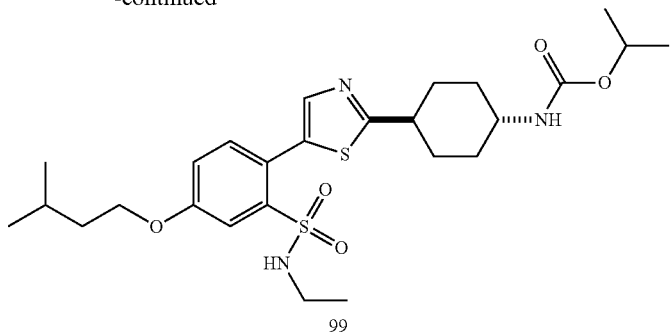

99 a) Synthesis of 2-bromo-N-ethyl-5-hydroxy-benzenesulfonamide

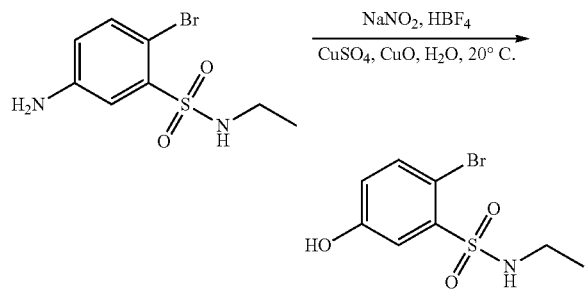

To a solution of 5-amino-2-bromo-N-ethyl-benzenesulfonamide (5 g, 17.91 mmol, 1 eq) in H$_2$O (200 mL) was added trifluoroborane; hydrofluoride (7.8 g, 35.8 mmol, 200 mL, 40% purity). Then NaNO$_2$ (1.4 g, 19.7 mmol, 1.1 eq) in H$_2$O (140 mL) was added batch at 0° C. for 30 mins. Then, sat.aq. CuSO$_4$ (416.0 g, 2.6 mol, 145.52 eq) and CuO (1.42 g, 17.91 mmol, 225.44 uL, 1 eq) was added batchwise. The mixture was stirred at 20° C. for 2 h. The reaction mixture was extracted with DCM 150 mL (50 mL×3). The combined organic layers were dried over Na$_2$SO$_4$, filtered and concentrated under reduced pressure. The crude product was purified by reversed-phase HPLC (0.1% TFA condition) to yield 2-bromo-N-ethyl-5-hydroxy-benzenesulfonamide (2.2 g) as a yellow gum. ESI [M+H]=279.9/281.9.

b) Synthesis of 2-bromo-N-ethyl-5-isopentyloxy-benzenesulfonamide

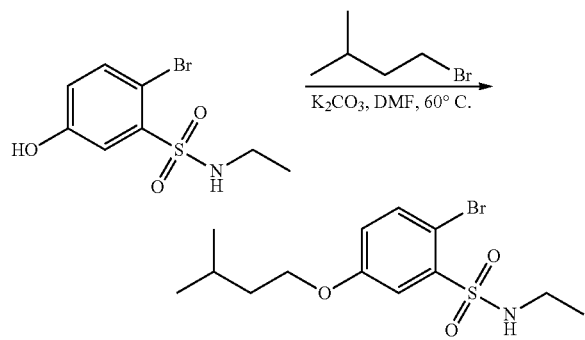

A mixture of 2-bromo-N-ethyl-5-hydroxy-benzenesulfonamide (700 mg, 2.5 mmol, 1 eq), 1-bromo-3-methyl-butane (1.1 g, 7.5 mol, 3.0 eq), K$_2$CO$_3$ (1.0 g, 7.5 mmol, 3.0 eq) in DMF (7 mL) was stirred at 60° C. for 2 h under N$_2$ atmosphere. The reaction mixture was quenched by H$_2$O 70 mL and extracted with EtOAc 120 mL (40 mL×3). The combined organic layers were dried over Na$_2$SO$_4$, filtered and concentrated under reduced pressure. The residue was purified by column chromatography (SiO$_2$, petroleum ether: ethyl acetate=50:1 to 0:1) to yield 2-bromo-N-ethyl-5-isopentyloxy-benzenesulfonamide (920 mg) as colorless oil. $^1$H NMR (400 MHz, methanol-d$_4$) δ=7.65 (d, J=8.8 Hz, 1H), 7.59 (d, J=2.9 Hz, 1H), 7.16-7.15 (m, 1H), 4.06 (t, J=6.5 Hz, 2H), 2.94 (q, J=7.2 Hz, 2H), 1.84 (td, J=6.7, 13.5 Hz, 1H), 1.74-1.61 (m, 2H), 1.06 (t, J=7.2 Hz, 3H), 0.98 (d, J=6.6 Hz, 6H). ESI [M+H]=349.9/352.0.

c) Synthesis of N-ethyl-5-isopentyloxy-2-(4,4,5,5-tetramethyl-1,3,2-dioxa-borolan-2-yl)benzenesulfonamide

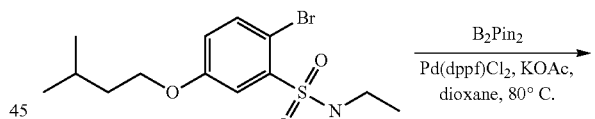

From 2-bromo-N-ethyl-5-isopentyloxy-benzenesulfonamide, using General Method B. $^1$H NMR (400 MHz, methanol-d$_4$) δ=7.64 (d, J=8.2 Hz, 1H), 7.42 (d, J=2.4 Hz, 1H), 7.14 (dd, J=2.5, 8.3 Hz, 1H), 4.09 (t, J=6.5 Hz, 2H), 2.90 (q, J=7.3 Hz, 2H), 1.70 (q, J=6.6 Hz, 2H), 1.39 (s, 1H), 1.38 (s, 12H), 1.03 (t, J=7.2 Hz, 3H), 0.98 (d, J=6.6 Hz, 6H). ESI [M+H]=398.1.

d) Synthesis of isopropyl trans-N-[4-[5-[2-(ethylsulfamoyl)-4-isopentyloxy-phenyl]thiazol-2-yl]cyclohexyl]carbamate (Compound 99)

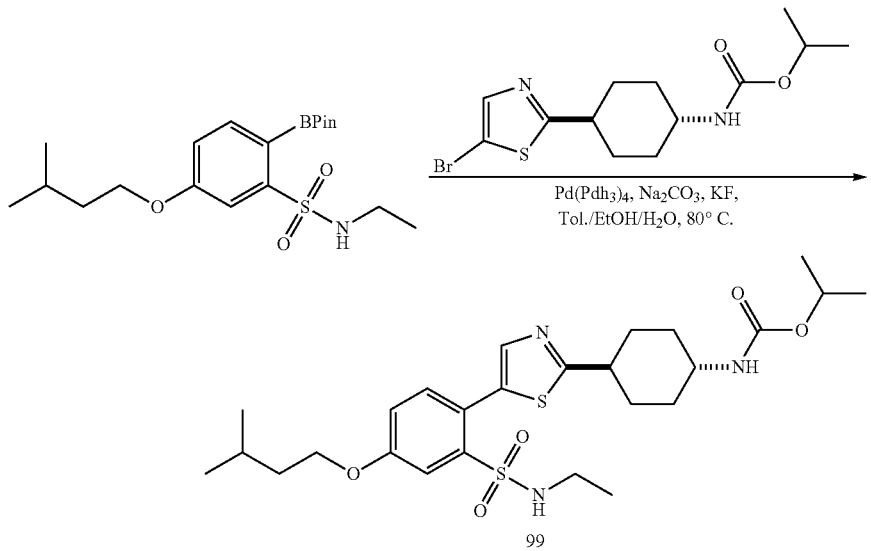

From N-ethyl-5-isopentyloxy-2-(4,4,5,5-tetramethyl-1,3,2-dioxaborolan-2-yl)benzene sulfonamide, using General Method C. $^1$H NMR (400 MHz, DMSO-d$_6$) δ=7.60 (s, 1H), 7.46 (t, J=5.6 Hz, 1H), 7.43-7.36 (m, 2H), 7.19 (dd, J=2.6, 8.6 Hz, 1H), 7.01 (br d, J=7.7 Hz, 1H), 4.72 (td, J=6.3, 12.4 Hz, 1H), 4.08 (t, J=6.5 Hz, 2H), 3.36-3.22 (m, 1H), 2.93-2.84 (m, 1H), 2.82-2.72 (m, 2H), 2.11 (br d, J=11.9 Hz, 2H), 1.89 (br d, J=10.4 Hz, 2H), 1.82-1.71 (m, 1H), 1.63 (q, J=6.5 Hz, 2H), 1.54 (dq, J=2.8, 12.8 Hz, 2H), 1.38-1.25 (m, 2H), 1.14 (d, J=6.2 Hz, 6H), 0.98-0.93 (m, 3H), 0.92 (d, J=6.6 Hz, 6H). ESI [M+H]=538.2.

Example 77

Preparation of oxetan-3-yl trans-N-[4-[5-[2-(ethylsulfamoyl)-4-isopentyloxy-phenyl]thiazol-2-yl]cyclohexyl]carbamate (Compound 100)

Following the same protocol and under the same reaction conditions as for Compound 99, Compound 100 was prepared. $^1$H NMR (400 MHz, DMSO-d$_6$) δ=7.60 (s, 1H), 7.55-7.29 (m, 4H), 7.19 (dd, J=2.5, 8.5 Hz, 1H), 5.25 (quin, J=5.7 Hz, 1H), 4.73 (t, J=6.8 Hz, 2H), 4.49-4.37 (m, 2H), 4.08 (t, J=6.5 Hz, 2H), 3.30-3.25 (m, 1H), 2.90 (tt, J=3.3, 11.8 Hz, 1H), 2.78 (q, J=7.3 Hz, 2H), 2.12 (br d, J=11.9 Hz, 2H), 1.90 (br d, J=10.6 Hz, 2H), 1.83-1.70 (m, 1H), 1.67-1.59 (m, 2H), 1.59-1.46 (m, 2H), 1.39-1.29 (m, 2H), 0.98-0.93 (m, 3H), 0.92 (d, J=6.4 Hz, 6H). ESI [M+H]=552.2.

Example 78

Preparation of isopropyl trans-N-[4-[5-[2-(tert-butylsulfamoyl)-4-isopentyloxy-phenyl]thiazol-2-yl]cyclohexyl]carbamate (Compound 101)

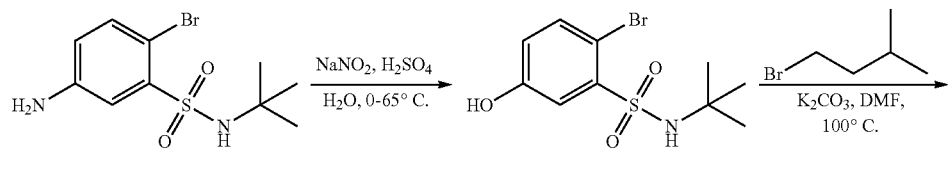

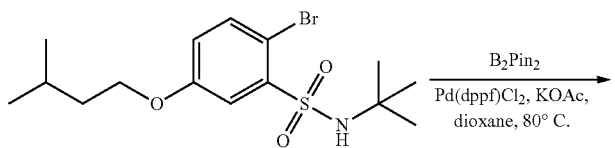

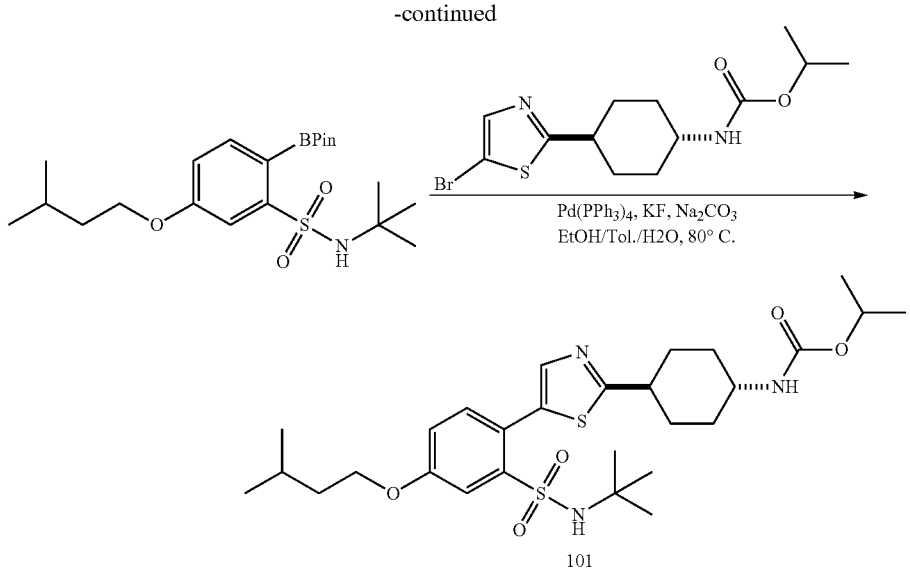

101 a) Synthesis of 2-bromo-N-tert-butyl-5-hydroxy-benzenesulfonamide

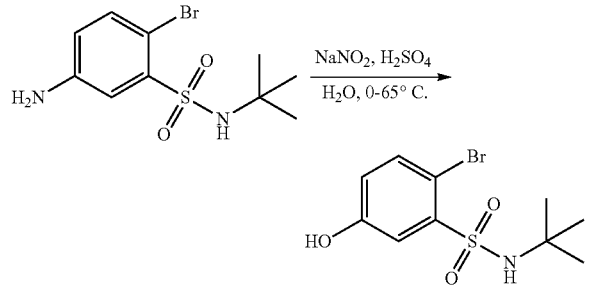

To isopropyl 5-amino-2-bromo-N-tert-butyl-benzenesulfonamide (10.0 g, 32.6 mmol, 1.0 eq.) dissolved in H$_2$SO$_4$ (120 mL, 30% aq.) was added a solution of NaNO$_2$ (2.3 g, 1.1 mol, 34.5 eq.) in H$_2$O (20 mL) at 0° C. and the mixture was stirred at 0° C. for 30 min. Then was added H$_2$O (280 mL) to the mixture and stirred at 65° C. for 11 h. The mixture was extracted with EtOAc (300 mL×3). The combined organic layers were dried over Na$_2$SO$_4$, filtered and concentrated under reduced pressure. The residue was purified by reversed-phase chromatography to yield 2-bromo-N-tert-butyl-5-hydroxy-benzene sulfonamide (1.4 g, 4.5 mmol, 14% yield) was obtained as a red solid. ESI [M−H]=305.8/307.8.

b) Synthesis of 2-bromo-N-tert-butyl-5-isopentyloxy-benzenesulfonamide

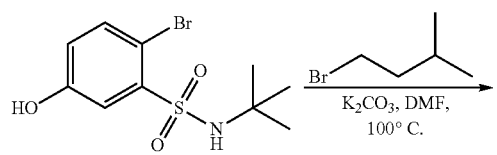

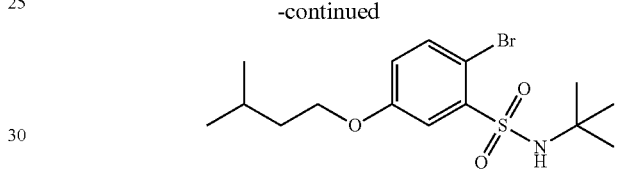

To a solution of 2-bromo-N-tert-butyl-5-hydroxy-benzenesulfonamide (1.5 g, 4.7 mmol, 1.0 eq.) in DMF (30 mL) was added K$_2$CO$_3$ (2.0 g, 14.1 mmol, 3.0 eq.) and 1-bromo-3-methyl-butane (1.1 g, 7.1 mmol, 1.5 eq.). The reaction mixture was stirred at 100° C. for 12 h. The mixture was poured into water (100 mL) and the solid filtrated, yielding 2-bromo-N-tert-butyl-5-isopentyloxy-benzenesulfonamide (1.4 g, crude) as a yellow solid. $^1$H NMR (400 MHz, methanol-d$_4$) δ=7.61-7.70 (m, 2H), 7.04 (dd, J=8.68, 2.69 Hz, 1H), 4.08 (t, J=6.54 Hz, 2H), 1.80-1.92 (m, 1H), 1.71 (q, J=6.48 Hz, 2H), 1.14-1.26 (m, 9H), 0.99 (s, 6H).

c) Synthesis of N-tert-butyl-5-isopentyloxy-2-(4,4,5,5-tetramethyl-1,3,2-dioxaborolan-2-yl)benzenesulfonamide

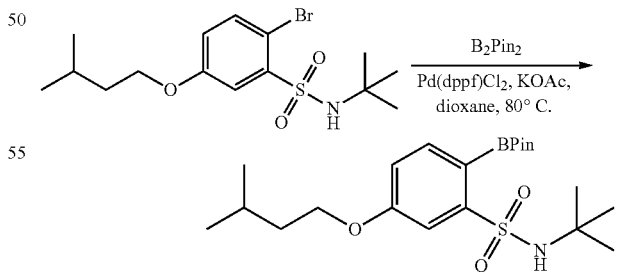

From 2-bromo-N-tert-butyl-5-isopentyloxy-benzenesulfonamide, using General Method B. $^1$H NMR (400 MHz, CDCl$_3$) δ=7.66 (d, J=8.2 Hz, 1H), 7.50 (d, J=2.4 Hz, 1H), 6.92-6.89 (m, 1H), 3.98-3.94 (m, 2H), 1.64-1.59 (m, 3H), 1.32 (s, 12H), 1.14 (s, 9H), 0.91-0.88 (m, 6H). ESI [M+H]=426.2.

d) Synthesis of isopropyl trans-N-[4-[5-[2-(tert-butylsulfamoyl)-4-isopentyloxy-phenyl]thiazol-2-yl]cyclohexyl]carbamate (Compound 101)

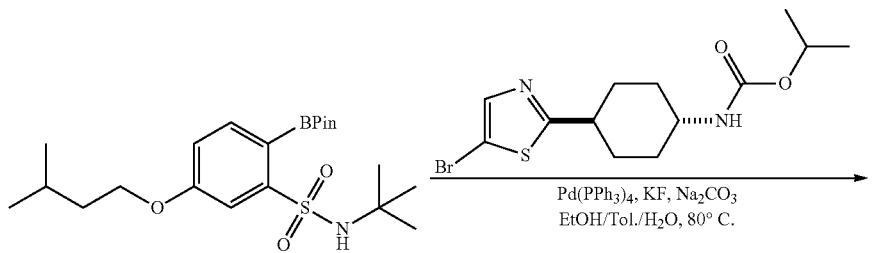

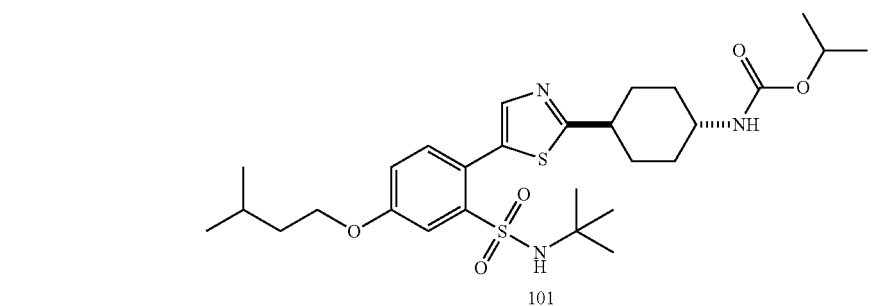

From N-tert-butyl-5-isopentyloxy-2-(4,4,5,5-tetramethyl-1,3,2-dioxaborolan-2-yl)benzenesulfonamide, using General Method C. $^1$H NMR (400 MHz, methanol-$d_4$) δ=7.68-7.53 (m, 2H), 7.30 (d, J=8.4 Hz, 1H), 7.08 (dd, J=2.6, 8.4 Hz, 1H), 4.77-4.69 (m, 1H), 4.03 (t, J=6.5 Hz, 2H), 3.36 (ddd, J=3.9, 7.8, 11.5 Hz, 1H), 2.92 (br t, J=12.1 Hz, 1H), 2.14 (br d, J=12.2 Hz, 2H), 1.98 (br d, J=10.6 Hz, 2H), 1.83-1.71 (m, 1H), 1.67-1.54 (m, 4H), 1.38-1.24 (m, 2H), 1.14 (br d, J=6.1 Hz, 6H), 1.01 (s, 9H), 0.91 (d, J=6.6 Hz, 6H). ESI [M+H]=566.2.

Example 79

Preparation of oxetan-3-yl trans-N-[4-[5-[2-(tert-butylsulfamoyl)-4-isopentyloxy-phenyl]thiazol-2-yl]cyclohexyl]carbamate (Compound 102)

Following the same protocol and under the same reaction conditions as for Compound 101, Compound 102 was prepared. $^1$H NMR (400 MHz, methanol-$d_4$) δ=7.73-7.65 (m, 2H), 7.40 (d, J=8.4 Hz, 1H), 7.18 (dd, J=2.6, 8.5 Hz, 1H), 5.45-5.32 (m, 1H), 4.87 (br s, 2H), 4.66-4.59 (m, 2H), 4.14 (t, J=6.5 Hz, 2H), 3.52-3.40 (m, 1H), 3.03 (br t, J=12.0 Hz, 1H), 2.25 (br d, J=12.3 Hz, 2H), 2.09 (br d, J=11.6 Hz, 2H), 1.89 (quind, J=6.7, 13.4 Hz, 1H), 1.79-1.64 (m, 4H), 1.52-1.39 (m, 2H), 1.11 (s, 9H), 1.02 (d, J=6.6 Hz, 6H). ESI [M+H]=580.2.

Example 80

Preparation of isopropyl trans-N-[4-[5-[2-(ethylsulfamoyl)-4-(oxazol-2-ylmethyl)phenyl]thiazol-2-yl]cyclohexyl]carbamate (Compound 103)

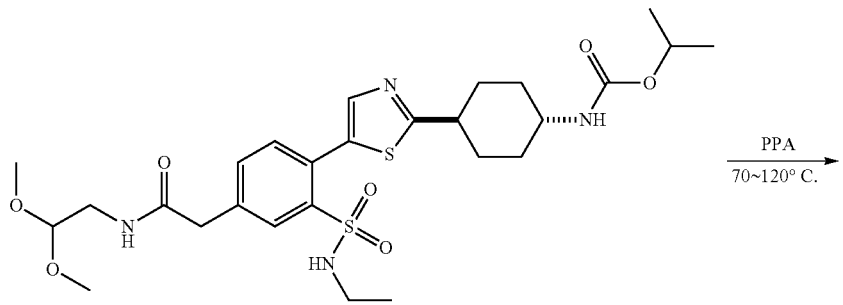

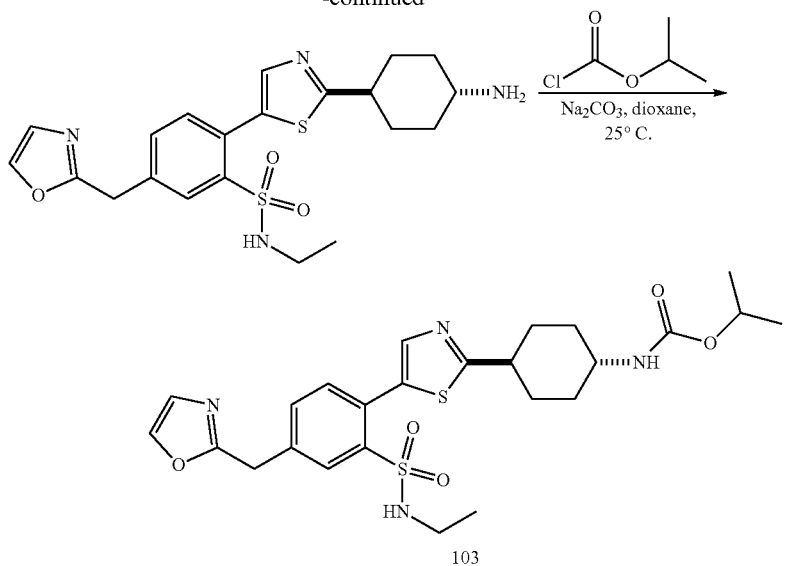

a) Synthesis of trans-2-[2-(4-aminocyclohexyl)thiazol-5-yl]-N-ethyl-5-(oxazol-2-ylmethyl)benzenesulfonamide

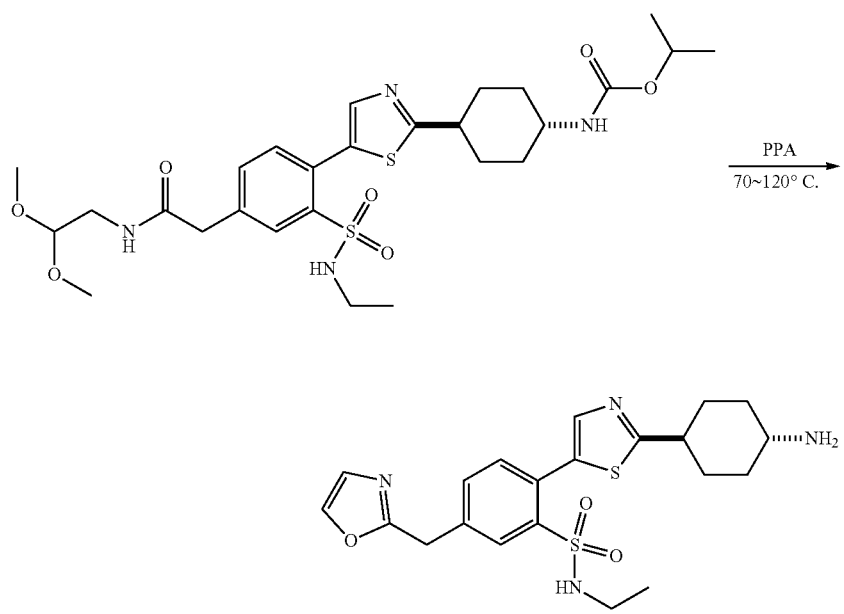

A mixture of isopropyl trans-N-[4-[5-[4-[2-(2,2-dimethoxyethylamino)-2-oxo-ethyl]-2-(ethylsulfamoyl)phenyl]thiazol-2-yl]cyclohexyl]carbamate (50 mg, 83 umol, 1 eq.) in PPA (1 mL) was stirred at 70° C. for 1 h then the mixture warmed to 120° C. for 3 h. The reaction mixture was diluted with MeOH (1 mL). The residue was purified by prep-HPLC (column: Phenomenex Luna C18 100*30 mm*5 um; mobile phase: [water(0.1% TFA)-ACN]; B %: 10%-35%,12 min) to yield trans-2-[2-(4-amino-cyclohexyl)thiazol-5-yl]-N-ethyl-5-(oxazol-2-ylmethyl)benzenesulfonamide (5 mg, 9 umol, 11% yield, TFA) as a white solid. ESI [M+H]=447.2.

b) Synthesis of isopropyl trans-N-[4-[5-[2-(ethylsulfamoyl)-4-(oxazol-2-yl-methyl)phenyl]thiazol-2-yl]cyclohexyl]carbamate (Compound 103)

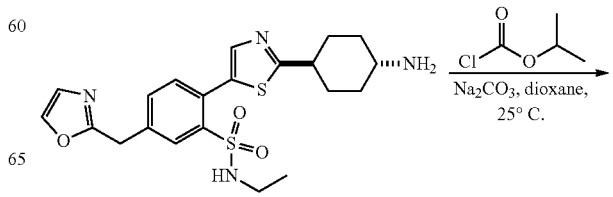

-continued

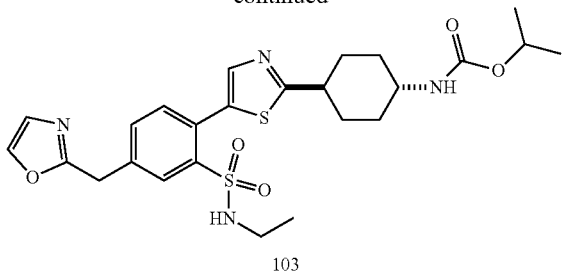

103

To a solution of trans-2-[2-(4-aminocyclohexyl)thiazol-5-yl]-N-ethyl-5-(oxazol-2-ylmethyl)benzenesulfonamide (5 mg, 9 umol, 1 eq., TFA) in dioxane (1 mL) was added sat.aq. Na$_2$CO$_3$ (0.3 mL) and isopropyl chloroformate (2 mg, 17 umol, 2 eq.). The mixture was stirred at 25° C. for 2 h. The reaction mixture was concentrated under reduced pressure and purified by prep-HPLC (column: Welch Ultimate AQ-C18 150*30 mm*5 um; mobile phase: [water(0.1% TFA)-ACN]; B %: 33%-63%,12 min) to yield isopropyl trans-N-[4-[5-[2-(ethylsulfamoyl)-4-(oxazol-2-ylmethyl)phenyl]thiazol-2-yl]cyclohexyl]carbamate (720 ug, 1 umol, 14% yield, 95% purity) as a yellow gum. $^1$H NMR (400 MHz, methanol-d$_4$) δ=7.89 (d, J=1.3 Hz, 1H), 7.78 (s, 1H), 7.63 (s, 1H), 7.48 (dd, J=1.4, 7.9 Hz, 1H), 7.38 (d, J=7.9 Hz, 1H), 7.04 (s, 1H), 4.54 (br s, 1H), 4.21 (s, 2H), 3.40-3.34 (m, 1H), 2.97-2.87 (m, 1H), 2.75 (q, J=7.3 Hz, 2H), 2.18-2.08 (m, 2H), 2.02-1.92 (m, 2H), 1.66-1.55 (m, 2H), 1.38-1.28 (m, 2H), 1.13 (br d, J=6.1 Hz, 6H), 0.91 (t, J=7.3 Hz, 3H). ESI [M+H]=533.0.

Example 81

Preparation of isopropyl trans-N-[4-[5-[2-(ethylsulfamoyl)-4-oxazol-2-yl-phenyl]thiazol-2-yl]cyclohexyl]carbamate (Compound 104)

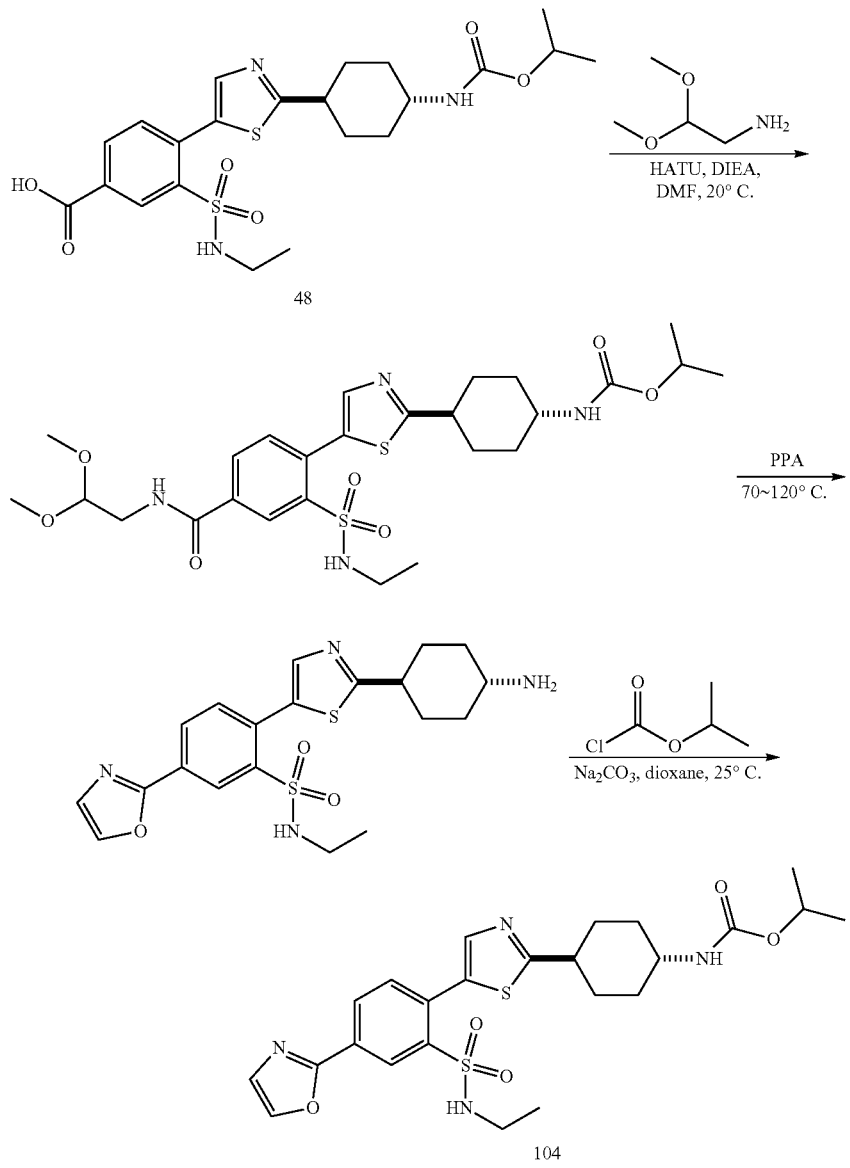

104 a) Synthesis of isopropyl trans-N-[4-[5-[4-(2,2-dimethoxyethylcarbamoyl)-2-(ethylsulfamoyl)phenyl]thiazol-2-yl]cyclohexyl]carbamate

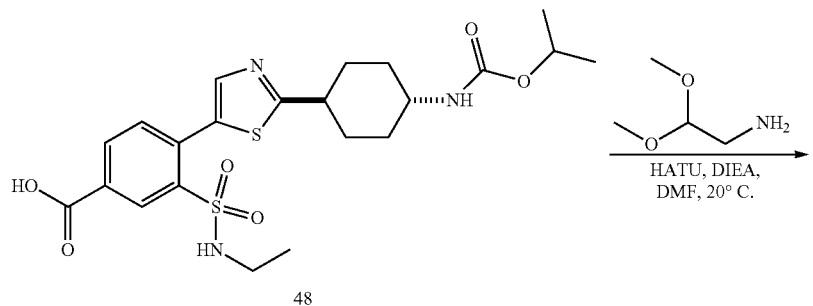

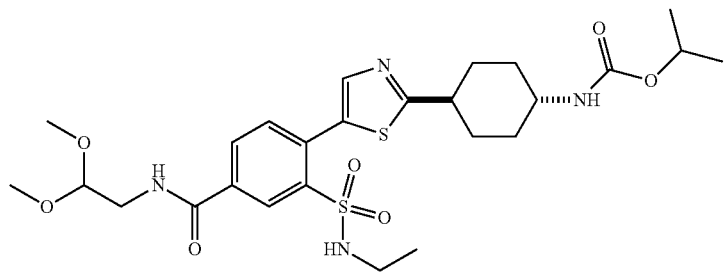

From trans-3-(ethylsulfamoyl)-4-[2-[4-(isopropyloxycarbonyl-amino)cyclohexyl]thiazol-5-yl]benzoic acid (Compound 48), using General Method A. $^1$H NMR (400 MHz, methanol-$d_4$) δ=8.54 (s, 1H), 8.06 (br d, J=7.9 Hz, 1H), 7.84 (s, 1H), 7.63 (br d, J=7.8 Hz, 1H), 5.00-4.96 (m, 1H), 4.61 (br t, J=5.5 Hz, 1H), 3.55 (br d, J=5.3 Hz, 2H), 3.49 (br d, J=11.0 Hz, 1H), 3.44 (s, 6H), 3.37 (br d, J=5.3 Hz, 1H), 2.95-2.89 (m, 2H), 2.35-2.23 (m, 2H), 2.10 (br d, J=10.8 Hz, 2H), 1.79-1.67 (m, 2H), 1.53-1.43 (m, 2H), 1.25 (br d, J=5.9 Hz, 6H), 1.10-0.98 (m, 3H). ESI [M+H]=583.2.

b) Synthesis of trans-2-[2-(4-aminocyclohexyl)thiazol-5-yl]-N-ethyl-5-oxazol-2-yl-benzenesulfonamide

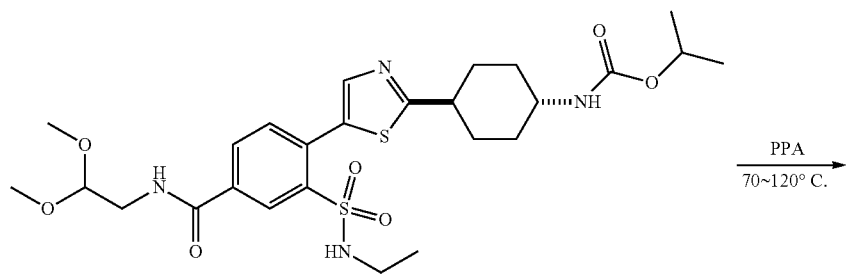

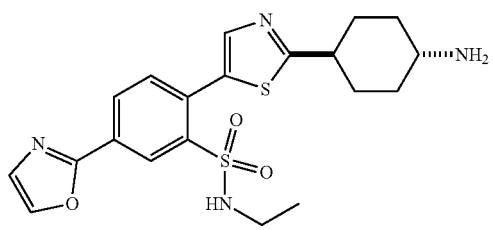

A solution of isopropyl trans-N-[4-[5-[4-(2,2-dimethoxy-ethylcarbamoyl)-2-(ethyl-sulfamoyl)phenyl]thiazol-2-yl]cyclohexyl]carbamate (50 mg, 85 umol, 1 eq.) in PPA (2 mL) was stirred at 70° C. for 1 h then warmed to 120° C. stirred for 2 h. The reaction was concentrated under reduced pressure. The residue was purified by prep-HPLC (column: Nano-micro Kromasil C18 80*25 mm 3 um; mobile phase: [water(0.1% TFA)-ACN]; B %: 15%-45%,7 min) to yield trans-2-[2-(4-aminocyclohexyl)thiazol-5-yl]-N-ethyl-5-oxazol-2-yl-benzenesulfonamide (17 mg, 31 umol, 36% yield, TFA) as brown oil. ESI [M+H]=433.2.

c) Synthesis of isopropyl trans-N-[4-[5-[2-(ethylsulfamoyl)-4-oxazol-2-yl-phenyl]thiazol-2-yl]cyclohexyl]carbamate (Compound 104)

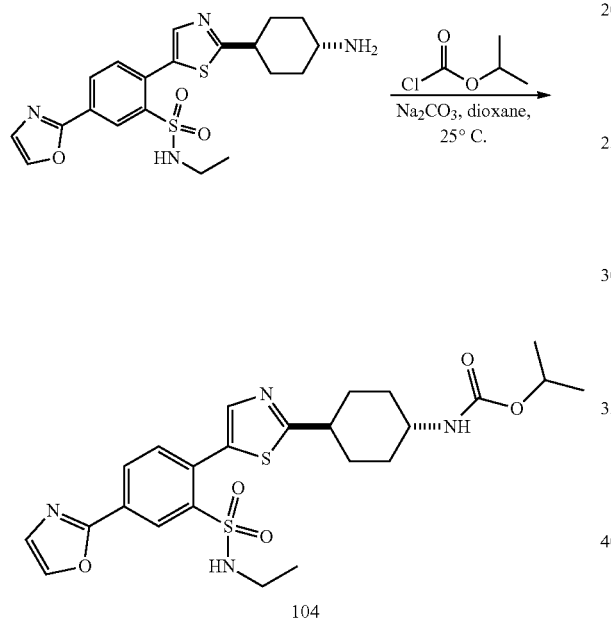

104

To a solution of trans-2-[2-(4-aminocyclohexyl)thiazol-5-yl]-N-ethyl-5-oxazol-2-yl-benzenesulfonamide (15 mg, 27 umol, 1 eq., TFA) in dioxane (2 mL) was added sat.aq. Na$_2$CO$_3$ (0.3 mL) and isopropyl chloroformate (26 mg, 213 umol, 8 eq.). The mixture was stirred at 25° C. for 1 h. The reaction was concentrated and purified by prep-HPLC (column: Nano-micro Kromasil C18 80*25 mm 3 um; mobile phase: [water(0.1% TFA)-ACN]; B %: 45%-62%,7 min) to yield isopropyl trans-N-[4-[5-[2-(ethylsulfamoyl)-4-oxazol-2-yl-phenyl]thiazol-2-yl]cyclohexyl]carbamate (2 mg, 4 umol, 11% yield, 94% purity) as a yellow solid. $^1$H NMR (400 MHz, methanol-d$_4$) δ=8.72 (d, J=1.5 Hz, 1H), 8.27 (dd, J=1.8, 8.0 Hz, 1H), 8.10 (s, 1H), 7.86 (s, 1H), 7.69 (d, J=8.0 Hz, 1H), 7.41 (s, 1H), 4.96-4.91 (m, 1H), 3.53-3.43 (m, 1H), 3.10-3.02 (m, 1H), 2.95 (q, J=7.3 Hz, 2H), 2.28 (br d, J=12.1 Hz, 2H), 2.14-2.04 (m, 2H), 1.80-1.67 (m, 2H), 1.44 (dq, J=2.9, 12.6 Hz, 2H), 1.25 (br d, J=6.1 Hz, 6H), 1.07 (t, J=7.2 Hz, 3H). ESI [M+H]=519.0.

Example 82

Preparation of compound isopropyl trans-N-[4-[5-[2-(ethylsulfamoyl)-4-[(1-methylimidazol-2-yl)amino]phenyl]thiazol-2-yl]cyclohexyl]carbamate (Compound 105) and isopropyl cis-N-[4-[5-[2-(ethylsulfamoyl)-4-[(1-methylimidazol-2-yl)amino]phenyl]thiazol-2-yl]cyclohexyl]carbamate (Compound 106)

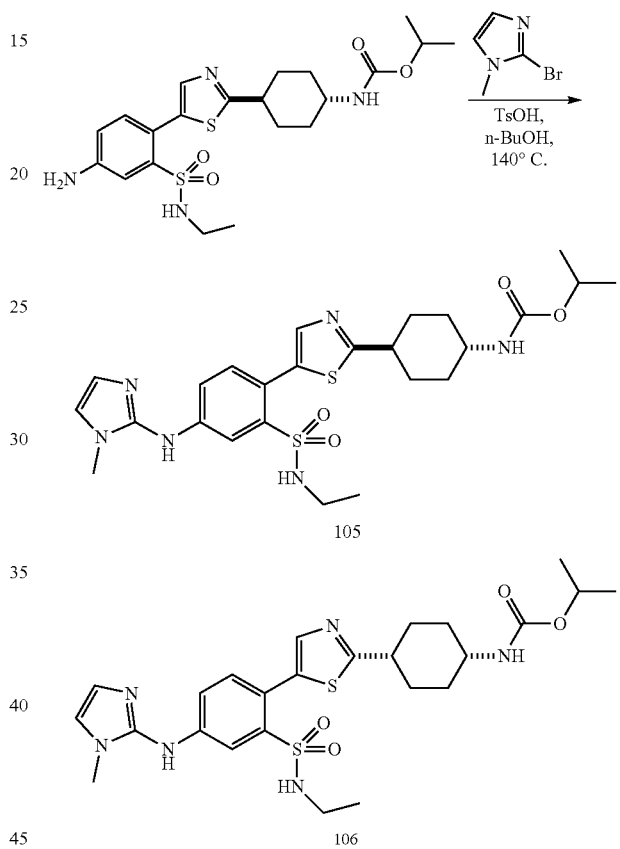

105

106

From isopropyl trans-N-[4-[5-[4-amino-2-(ethylsulfamoyl)phenyl]thiazol-2-yl]cyclohexyl]carbamate and 2-bromo-1-methyl-1H-imidazole, using General Method K. (Compound 105), $^1$H NMR (400 MHz, methanol-d$_4$) δ=7.74 (d, J=2.4 Hz, 1H), 7.63-7.54 (m, 1H), 7.40-7.23 (m, 2H), 7.01 (d, J=2.0 Hz, 1H), 6.92 (d, J=1.8 Hz, 1H), 4.72 (br d, J=6.2 Hz, 1H), 3.61-3.51 (m, 3H), 3.42-3.30 (m, 1H), 2.96-2.87 (m, 1H), 2.77 (q, J=7.2 Hz, 2H), 2.18-2.09 (m, 2H), 1.97 (br d, J=9.9 Hz, 2H), 1.59 (dq, J=2.9, 12.9 Hz, 2H), 1.37-1.24 (m, 2H), 1.13 (br d, J=6.1 Hz, 6H), 0.91 (t, J=7.2 Hz, 3H). ESI [M+H]=547.2. (Compound 106), $^1$H NMR (400 MHz, methanol-d$_4$) δ=7.73 (d, J=2.3 Hz, 1H), 7.69 (s, 1H), 7.37-7.31 (m, 1H), 7.25 (dd, J=2.4, 8.4 Hz, 1H), 6.97 (d, J=1.2 Hz, 1H), 6.86 (d, J=1.3 Hz, 1H), 4.84 (br s, 1H), 3.77 (br d, J=4.9 Hz, 1H), 3.60 (s, 3H), 3.17 (br dd, J=4.2, 8.6 Hz, 1H), 2.91 (q, J=7.2 Hz, 2H), 2.09-1.94 (m, 4H), 1.91-1.71 (m, 4H), 1.25 (d, J=6.2 Hz, 6H), 1.05 (t, J=7.2 Hz, 3H). ESI [M+H]=547.2.

Example 83

Preparation of isopropyl trans-N-[4-[5-[2-(ethylsulfamoyl)-4-[(1-isobutylimidazol-2-yl)amino]phenyl]thiazol-2-yl]cyclohexyl]carbamate (Compound 107)

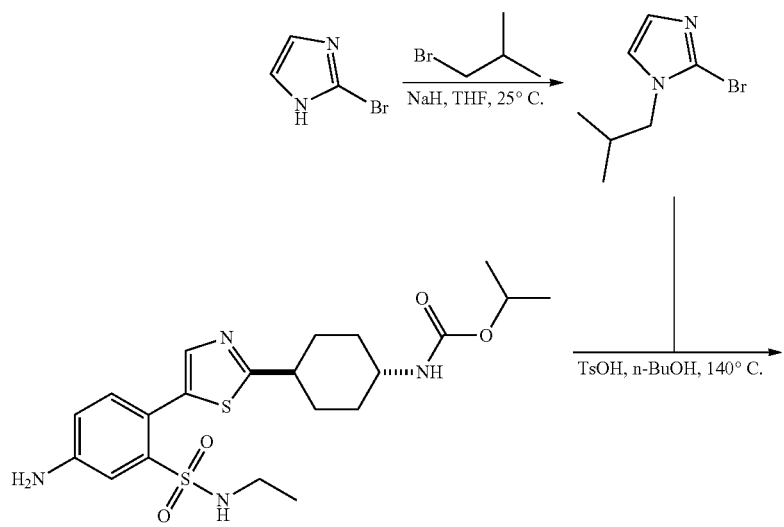

a) Synthesis of 2-bromo-1-isobutyl-1H-imidazole

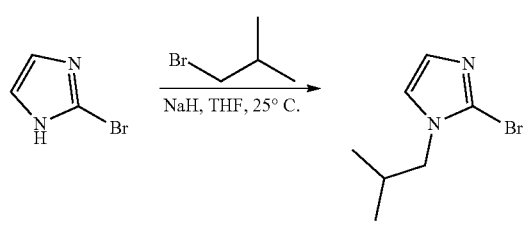

To a mixture of 2-bromo-1H-imidazole (300 mg, 2 mmol, 1 eq.), NaH (245 mg, 6 mmol, 60% purity, 3 eq.) in THF (3 mL) was added 1-bromo-2-methyl-propane (838.55 mg, 6.12 mmol, 665.52 uL, 3 eq.) and stirred at 25° C. for 6 h under $N_2$ atmosphere. The reaction mixture was quenched by addition $H_2O$ 10 mL, extracted with EtOAc 60 mL (20 mL×3). The combined organic layers were washed with sat.aq. NaCl 60 mL (12 mL×5), dried over $Na_2SO_4$, filtered and concentrated under reduced pressure. The residue was purified by prep-HPLC (Nano-micro Kromasil C18 100*30 mm 5 um; mobile phase: [water(0.1% TFA)-ACN]; B %:3%-35%,7 min) to yield 2-bromo-1-isobutyl-1H-imidazole (400 mg, 2 mmol, 97% yield) as yellow oil. $^1$H NMR (400 MHz, $CDCl_3$) δ=7.37 (d, J=1.76 Hz, 1H), 7.10 (d, J=1.76 Hz, 1H), 3.84 (d, J=7.50 Hz, 2H), 2.05-2.27 (m, 1H), 0.98 (d, J=6.84 Hz, 6H). ESI [M+H]=203.0/205.0.

b) Synthesis of isopropyl trans-N-[4-[5-[2-(ethylsulfamoyl)-4-[(1-isobutyl-imidazol-2-yl)amino]phenyl]thiazol-2-yl]cyclohexyl]carbamate (Compound 107)

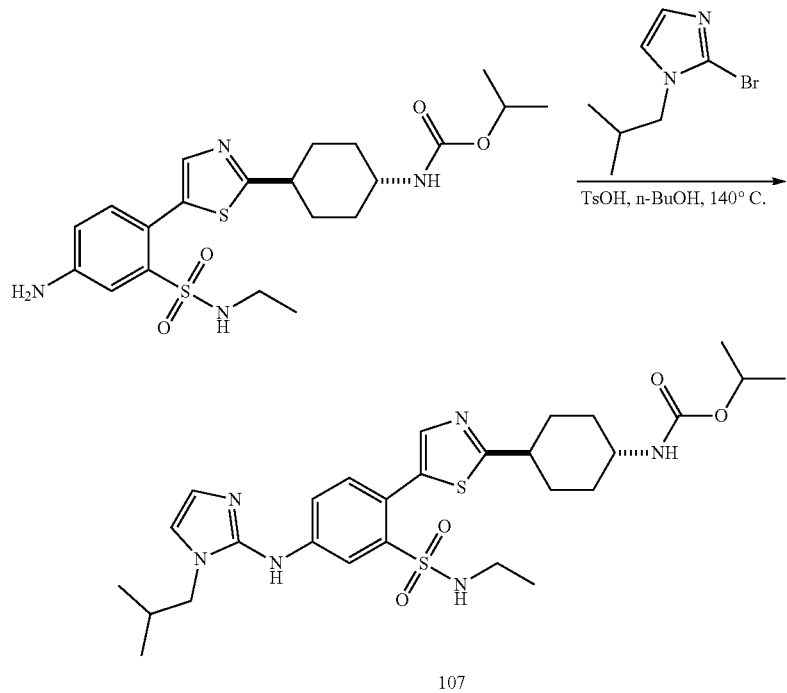

107

From isopropyl trans-N-[4-[5-[4-amino-2-(ethylsulfamoyl)phenyl]thiazol-2-yl]cyclohexyl]carbamate and 2-bromo-1-isobutyl-1H-imidazole, using General Method K. $^1$H NMR (400 MHz, methanol-$d_4$) δ=7.63-7.70 (m, 2H), 7.31 (d, J=8.38 Hz, 1H), 7.18 (dd, J=2.43, 8.38 Hz, 1H), 7.00 (d, J=1.54 Hz, 1H), 6.88 (d, J=1.54 Hz, 1H), 4.83 (br d, J=6.39 Hz, 1H), 3.69-3.79 (m, 2H), 3.45 (br t, J=11.80 Hz, 1H), 2.93-3.05 (m, 1H), 2.86 (q, J=7.28 Hz, 2H), 2.23 (br d, J=12.79 Hz, 2H), 2.01-2.12 (m, 3H), 1.63-1.75 (m, 2H), 1.35-1.47 (m, 2H), 1.23 (br d, J=6.17 Hz, 6H), 1.01 (t, J=7.28 Hz, 3H), 0.90 (d, J=6.62 Hz, 6H). ESI [M+H]=589.3.

Example 84

Preparation of cyclopropyl trans-N-[4-[5-[2-(ethylsulfamoyl)-4-(1H-imidazol-2-ylamino)phenyl]thiazol-2-yl]cyclohexyl]carbamate (Compound 109)

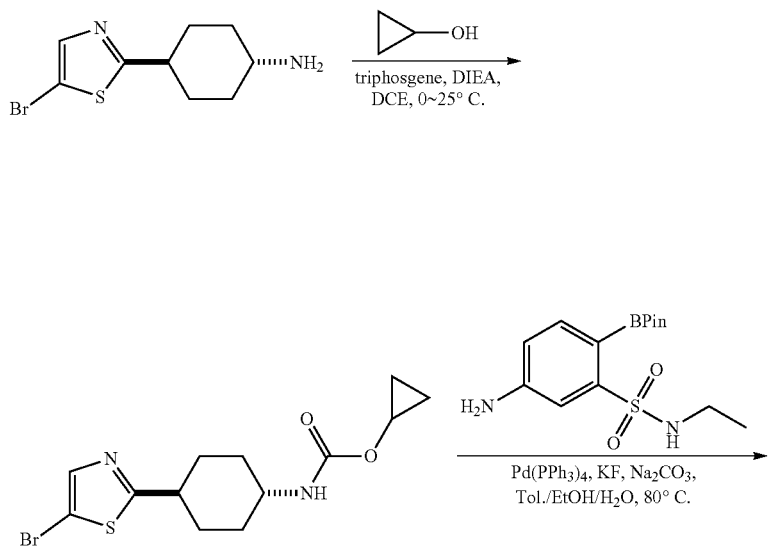

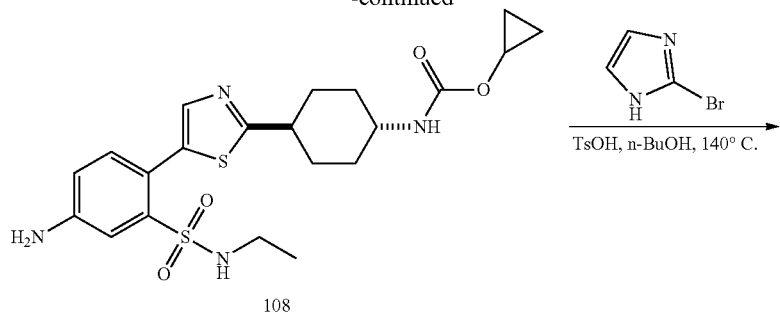

108

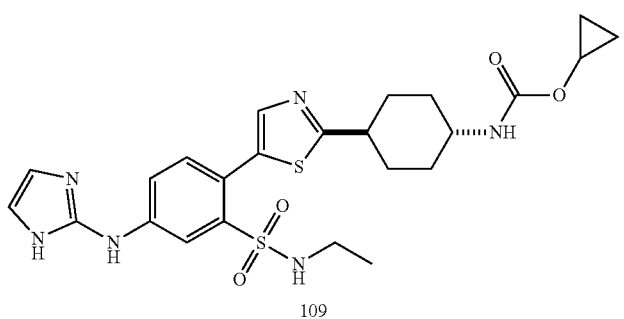

109 a) Synthesis of cyclopropyl trans-N-[4-(5-bromothi-azol-2-yl)cyclohexyl]carbamate

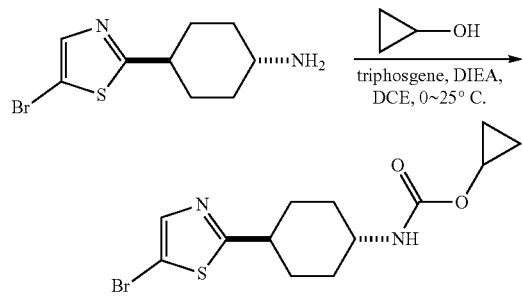

To a solution of cyclopropanol (293 mg, 5 mmol, 5 eq) in DCE (3 mL) was added DIEA (651 mg, 5 mmol, 5 eq) at 0° C. The mixture was stirred at 0° C. for 10 min, followed by the addition of triphosgene (598 mg, 2 mmol, 2 eq) at 0° C. The mixture was stirred at 25° C. for 30 min (mixture 1). To a solution of trans-4-(5-bromothiazol-2-yl)cyclohexanamine (300 mg, 1 mmol, 1 eq, HCl) in DIEA (3 mL) was added mixture 1 and stirred at 25° C. for 2 h. The reaction mixture was quenched by addition sat.aq. $Na_2CO_3$ 5 mL, and extracted with dichloromethane 30 mL (10 mL×3). The combined organic layers were dried over $Na_2SO_4$, filtered and concentrated under reduced pressure. The residue was purified prep-TLC ($SiO_2$, petroleum ether:ethyl acetate=2:1) to yield cyclopropyl trans-N-[4-(5-bromothiazol-2-yl)cyclohexyl]carbamate (140 mg, 406 umol, 40% yield) as a yellow solid. $^1$H NMR (400 MHz, methanol-$d_4$) δ=7.60 (s, 1H), 3.95 (br d, J=3.3 Hz, 1H), 3.43 (br s, 1H), 3.04-2.81 (m, 1H), 2.22-1.89 (m, 4H), 1.72-1.49 (m, 2H), 1.46-1.11 (m, 4H), 0.65-0.61 (m, 2H). ESI [M+H]=345.1/347.0.

b) Synthesis of cyclopropyl trans-N-[4-[5-[4-amino-2-(ethylsulfamoyl) phenyl]thiazol-2-yl]cyclohexyl] carbamate (Compound 108)

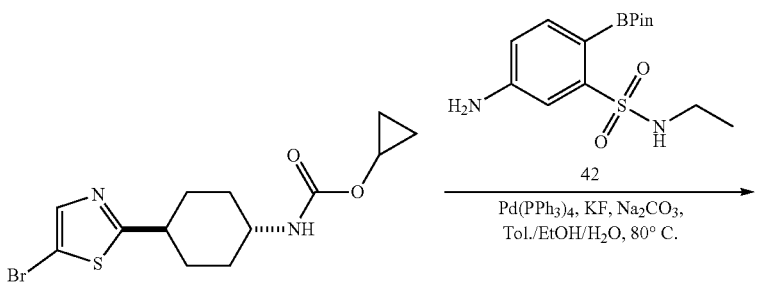

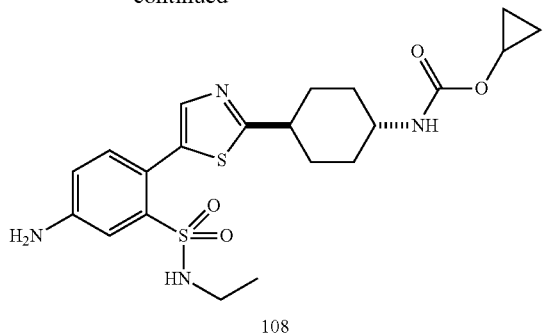

108

From cyclopropyl trans-N-[4-(5-bromothiazol-2-yl)cyclohexyl]carbamate and 5-amino-N-ethyl-2-(4,4,5,5-tetramethyl-1,3,2-dioxaborolan-2-yl)benzenesulfonamide, using General Method C. $^1$H NMR (400 MHz, methanol-$d_4$) δ=7.74 (s, 1H), 7.40 (d, J=2.4 Hz, 1H), 7.21 (d, J=8.2 Hz, 1H), 6.91 (dd, J=2.4, 8.4 Hz, 1H), 3.96 (br d, J=3.3 Hz, 1H), 3.47 (br t, J=11.5 Hz, 1H), 3.06 (br t, J=12.2 Hz, 1H), 2.87 (q, J=7.3 Hz, 2H), 2.23 (br d, J=12.8 Hz, 2H), 2.13-1.95 (m, 2H), 1.83-1.59 (m, 2H), 1.41 (dq, J=3.2, 12.6 Hz, 2H), 1.02 (t, J=7.2 Hz, 3H), 0.63 (br d, J=5.1 Hz, 4H). ESI [M+H]=465.1.

c) Synthesis of cyclopropyl trans-N-[4-[5-[2-(ethylsulfamoyl)-4-(1H-imidazol-2-ylamino)phenyl]thiazol-2-yl]cyclohexyl]carbamate (Compound 109)

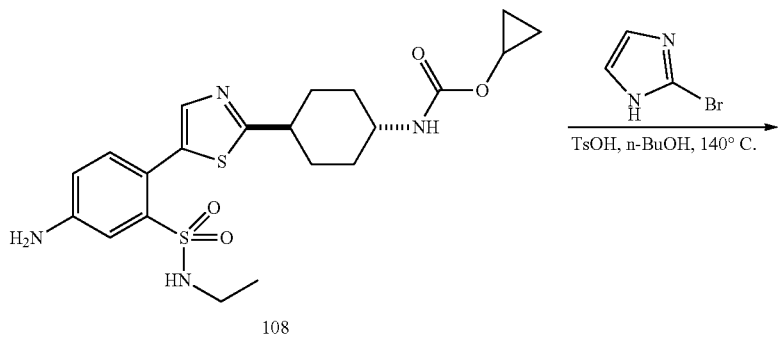

108

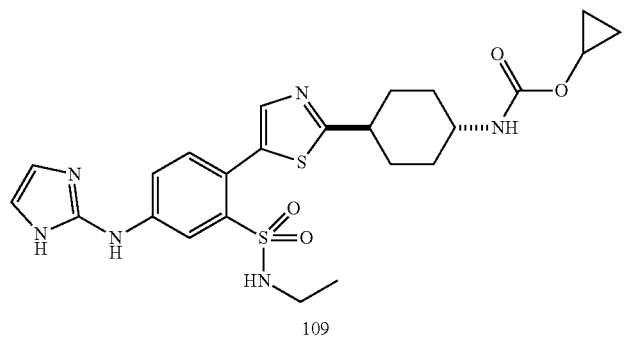

109

From cyclopropyl trans-N-[4-[5-[4-amino-2-(ethylsulfamoyl) phenyl]thiazol-2-yl]cyclohexyl]carbamate (Compound 108) and 2-bromo-1H-imidazole, using General Method K. $^1$H NMR (400 MHz, methanol-$d_4$) δ=7.90 (d, J=1.5 Hz, 1H), 7.72 (s, 1H), 7.53-7.40 (m, 2H), 7.05 (s, 2H), 3.97 (br d, J=3.5 Hz, 1H), 3.47 (br s, 1H), 3.01 (br t, J=11.9 Hz, 1H), 2.87 (q, J=7.3 Hz, 2H), 2.25 (br d, J=12.8 Hz, 2H), 2.08 (br d, J=10.1 Hz, 2H), 1.85-1.63 (m, 2H), 1.50-1.33 (m, 2H), 1.01 (t, J=7.2 Hz, 3H), 0.64 (br d, J=4.6 Hz, 4H). ESI [M+H]=531.1.

Example 85

Preparation of isopropyl trans-N-[4-[5-[2-(tert-butylsulfamoyl)-4-(1H-imidazol-2-ylamino)phenyl] thiazol-2-yl]cyclohexyl]carbamate (Compound 38) and isopropyl cis-N-[4-[5-[2-(tert-butylsulfamoyl)-4-(1H-imidazol-2-ylamino)phenyl]thiazol-2-yl]cyclohexyl]carbamate (Compound 110)

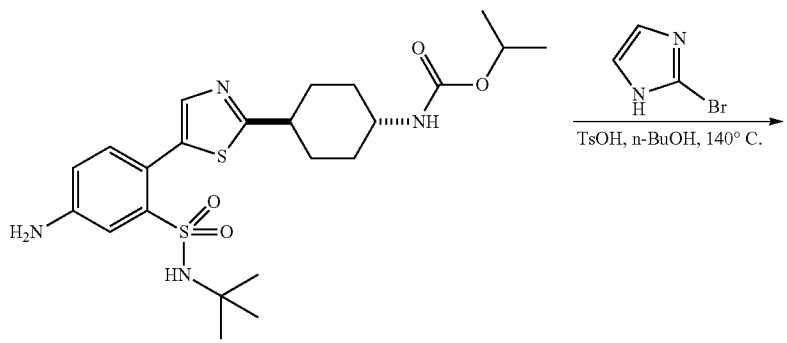

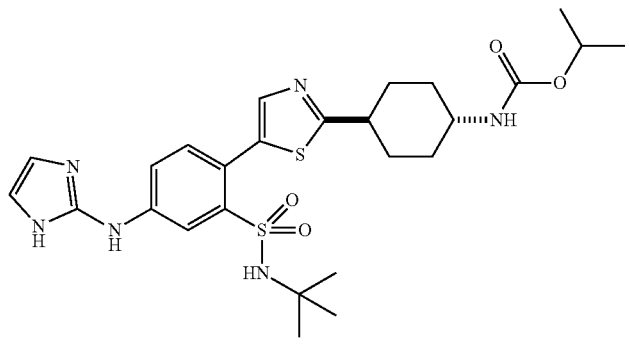

38

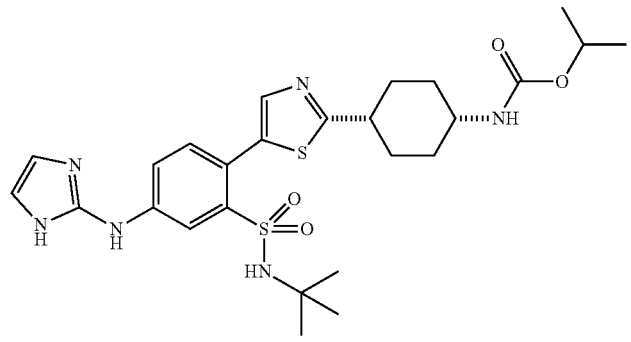

110

From isopropyl trans-N-[4-[5-[4-amino-2-(ethylsulfamoyl)phenyl]thiazol-2-yl]cyclohexyl]carbamate and 2-bromo-1H-imidazole, using General Method K. (Compound 38), ¹H NMR (400 MHz, methanol-d₄) δ=7.95 (t, J=1.3 Hz, 1H), 7.73 (s, 1H), 7.47 (d, J=1.3 Hz, 2H), 7.04 (s, 2H), 4.85-4.79 (m, 1H), 3.55-3.37 (m, 1H), 3.01 (tt, J=3.5, 12.0 Hz, 1H), 2.32-2.16 (m, 2H), 2.13-1.99 (m, 2H), 1.69 (dq, J=3.1, 12.9 Hz, 2H), 1.41 (dq, J=3.2, 12.5 Hz, 2H), 1.22 (br d, J=6.2 Hz, 6H), 1.09 (s, 9H). ESI [M+H]=561.2. (Compound 110), ¹H NMR (400 MHz, methanol-d₄) δ=7.96 (d, J=2.2 Hz, 1H), 7.76 (s, 1H), 7.59-7.42 (m, 2H), 7.08 (s, 2H), 4.83-4.75 (m, 1H), 3.82-3.66 (m, 1H), 3.23-3.08 (m, 1H), 2.08-1.92 (m, 4H), 1.89-1.68 (m, 4H), 1.23 (d, J=6.2 Hz, 6H), 1.10 (s, 9H). ESI [M+H]=561.2.

Example 86

Preparation of isopropyl trans-N-[4-[5-[2-(ethylsulfamoyl)-4-[(4-isopropyl-2-pyridyl)amino]phenyl]thiazol-2-yl]cyclohexyl]carbamate (Compound 111)

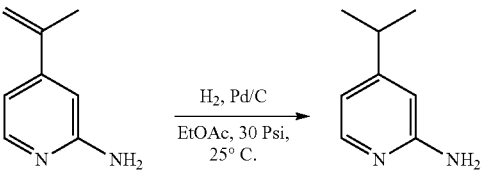

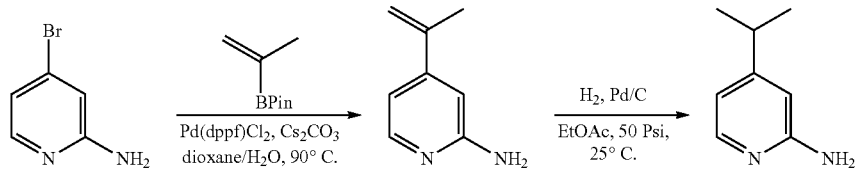

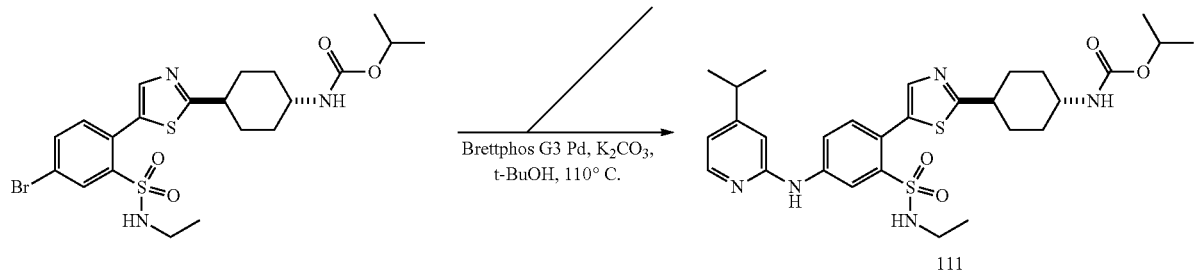

a) Synthesis of 4-isopropenylpyridin-2-amine

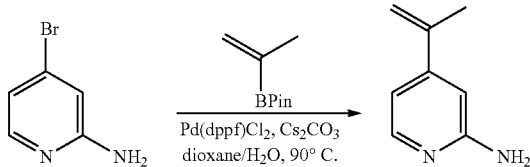

A mixture of 2-isopropenyl-4,4,5,5-tetramethyl-1,3,2-dioxaborolane (2.53 g, 15 mmol, 1.3 eq.), 4-bromopyridin-2-amine (2 g, 12 mmol, 1.0 eq.), Cs₂CO₃ (11.3 g, 35 mmol, 3.0 eq.) and Pd(dppf)Cl₂ (846 mg, 1 mmol, 0.1 eq.) in H₂O (50 mL) and dioxane (100 mL) was stirred at 90° C. for 4 h under N₂ atmosphere. The reaction was concentrated, and then purified by column chromatography (SiO₂, petroleum ether:ethyl acetate=10:1 to 1:1) to yield 4-isopropenylpyridin-2-amine (1.5 g, 11 mmol, 97% yield) as a brown solid. ESI [M+H]=135.1.

b) Synthesis of 4-isopropylpyridin-2-amine

A mixture of 4-isopropenylpyridin-2-amine (1.5 g, 11 mmol, 1 eq.), Pd/C (500 mg, 10% purity) in EtOAc (300 mL) was degassed and purged with H₂ (30 psi) for 3 times, and then the mixture was stirred at 25° C. for 12 h under H₂ atmosphere. The reaction mixture was filtered, and the filtrate was concentrated. The residue was purified by prep-HPLC (Neutral condition: column: Waters Xbridge Prep OBD C18 150*40 mm*10 um; mobile phase: [water(10 mM NH₄HCO₃)-ACN]; B %: 15%-45%,8 min) to yield 4-isopropylpyridin-2-amine (800 mg, 6 mmol, 53% yield) as yellow oil. ¹H NMR (400 MHz, methanol-d₄) δ=7.78 (d, J=5.5 Hz, 1H), 6.56-6.44 (m, 2H), 2.82-2.71 (m, 1H), 1.23 (d, J=6.9 Hz, 6H). ESI [M+H]=137.0.

c) Synthesis of isopropyl trans-N-[4-[5-[2-(ethylsulfamoyl)-4-[(4-isopropyl-2-pyridyl)amino]phenyl]thiazol-2-yl]cyclohexyl]carbamate (Compound 111)

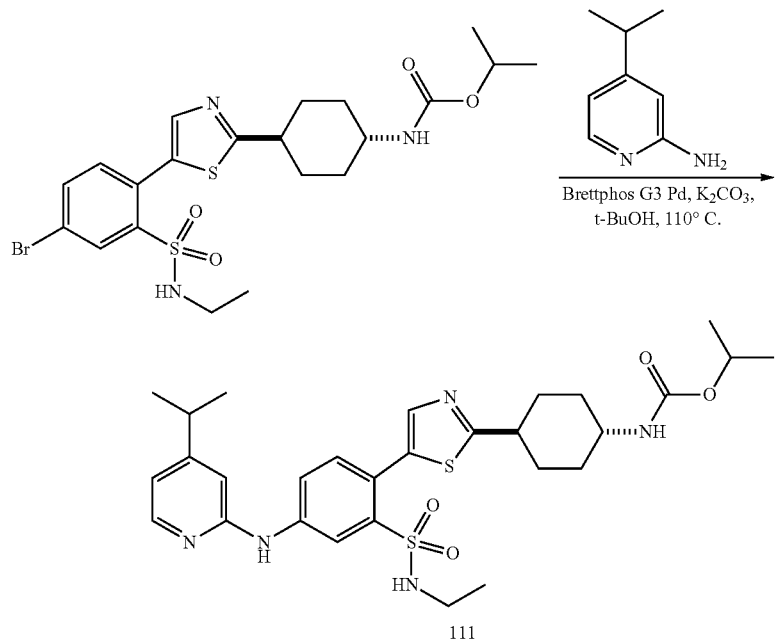

From isopropyl trans-N-[4-[5-[4-bromo-2-(ethylsulfamoyl)phenyl]thiazol-2-yl]cyclohexyl]carbamate and 4-isopropylpyridin-2-amine, using General Method F. $^1$H NMR (400 MHz, methanol-d$_4$) δ=8.16 (d, J=2.3 Hz, 1H), 7.97 (d, J=6.9 Hz, 1H), 7.79 (s, 1H), 7.72 (dd, J=2.2, 8.3 Hz, 1H), 7.60 (d, J=8.1 Hz, 1H), 7.11-7.08 (m, 2H), 4.85-4.85 (m, 1H), 3.48 (br t, J=11.5 Hz, 1H), 3.10-2.98 (m, 2H), 2.91 (q, J=7.2 Hz, 2H), 2.28 (br d, J=12.6 Hz, 2H), 2.10 (br d, J=10.8 Hz, 2H), 1.80-1.67 (m, 2H), 1.51-1.38 (m, 2H), 1.33 (d, J=6.9 Hz, 6H), 1.25 (br d, J=6.1 Hz, 6H), 1.05 (t, J=7.3 Hz, 3H). ESI [M+H]=586.3.

Example 87

Preparation of isopropyl trans-N-[4-[5-[2-(ethylsulfamoyl)-4-[(6-isopropyl-2-pyridyl)amino]phenyl]thiazol-2-yl]cyclohexyl]carbamate (Compound 112)

Following the same protocol and under the same reaction conditions as for Compound 111, Compound 112 was prepared. $^1$H NMR (400 MHz, methanol-d$_4$) δ=8.46 (d, J=2.0 Hz, 1H), 7.85-7.77 (m, 2H), 7.76 (s, 1H), 7.48 (d, J=8.3 Hz, 1H), 6.91 (d, J=7.9 Hz, 2H), 4.82 (br s, 1H), 3.54-3.43 (m, 1H), 3.13-3.00 (m, 2H), 2.91 (q, J=7.2 Hz, 2H), 2.32-2.23 (m, 2H), 2.10 (br dd, J=2.9, 12.8 Hz, 2H), 1.80-1.67 (m, 2H), 1.50-1.41 (m, 2H), 1.38 (d, J=7.0 Hz, 6H), 1.25 (br d, J=6.1 Hz, 6H), 1.04 (t, J=7.2 Hz, 3H). ESI [M+H]=586.1.

Example 88

Preparation of isopropyl trans-N-[4-[5-[2-(ethylsulfamoyl)-4-[(5-isopropyl-2-pyridyl)amino]phenyl]thiazol-2-yl]cyclohexyl]carbamate (Compound 113)

Following the same protocol and under the same reaction conditions as for Compound 111, Compound 113 was prepared. $^1$H NMR (400 MHz, methanol-d$_4$) δ=8.05-7.99 (m, 1H), 7.96-7.89 (m, 1H), 7.79 (s, 1H), 7.67 (s, 1H), 7.62-7.55 (m, 1H), 7.47 (d, J=8.2 Hz, 1H), 7.21-7.07 (m, 1H), 4.74-4.70 (m, 1H), 3.36 (tt, J=3.9, 11.6 Hz, 1H), 2.98-2.84 (m, 2H), 2.80 (q, J=7.2 Hz, 2H), 2.16 (br d, J=12.1 Hz, 2H), 1.98 (br d, J=10.3 Hz, 2H), 1.61 (dq, J=2.3, 12.7 Hz, 2H), 1.38-1.25 (m, 2H), 1.20 (d, J=7.0 Hz, 6H), 1.13 (br d, J=6.2 Hz, 6H), 0.93 (t, J=7.2 Hz, 3H). ESI [M+H]=586.1.

Example 89

Preparation of isopropyl trans-N-[4-[5-[2-(ethylsulfamoyl)-4-[3-isopropoxyazetidin-1-yl]phenyl]thiazol-2-yl]cyclohexyl]carbamate (Compound 114)

Following the same protocol and under the same reaction conditions as for Compound 111, Compound 114 was prepared. $^1$H NMR (400 MHz, methanol-d$_4$) δ=7.62 (s, 1H), 7.28 (d, J=8.38 Hz, 1H), 7.08 (d, J=2.38 Hz, 1H), 6.68 (dd, J=8.32, 2.44 Hz, 1H), 4.72-4.80 (m, 1H), 4.57-4.63 (m, 1H), 4.25 (t, J=7.25 Hz, 2H), 3.71-3.79 (m, 3H), 3.40-3.50 (m, 1H), 2.93-3.05 (m, 1H), 2.87 (q, J=7.21 Hz, 2H), 2.19-2.30 (m, 2H), 2.02-2.14 (m, 2H), 1.62-1.78 (m, 2H), 1.37-1.48 (m, 2H), 1.24 (br d, J=6.13 Hz, 6H), 1.20 (d, J=6.13 Hz, 6H), 1.03 (t, J=7.25 Hz, 3H). ESI [M+H]=565.3.

Example 90

Preparation of isopropyl trans-N-[4-[5-[2-(ethylsulfamoyl)-4-[(5-isopropyl-1,3,4-thiadiazol-2-y)amino]phenyl]thiazol-2-yl]cyclohexyl]carbamate (Compound 115)

Following the same protocol and under the same reaction conditions as for Compound 111, Compound 115 was prepared. ¹H NMR (400 MHz, methanol-d₄) δ=8.46 (d, J=2.25 Hz, 1H), 7.85 (dd, J=8.38, 2.38 Hz, 1H), 7.77 (br s, 1H), 7.47 (d, J=8.38 Hz, 1H), 4.84 (br s, 1H), 3.42-3.53 (m, 1H), 3.35-3.41 (m, 1H), 3.04 (br s, 1H), 2.97 (q, J=7.25 Hz, 2H), 2.26 (br d, J=12.63 Hz, 2H), 2.09 (br d, J=10.51 Hz, 2H), 1.72 (q, J=11.30 Hz, 2H), 1.43 (d, J=6.88 Hz, 8H), 1.25 (br d, J=6.00 Hz, 6H), 1.09 (t, J=7.25 Hz, 3H). ESI [M+H]=593.0.

Example 91

Preparation of isopropyl trans-N-[4-[5-[2-(ethylsulfamoyl)-4-[(3-methyloxetan-3-yl)amino]phenyl]thiazol-2-yl]cyclohexyl]carbamate (Compound 116)

Following the same protocol and under the same reaction conditions as for Compound 111, Compound 116 was prepared. ¹H NMR (400 MHz, DMSO-d₆) δ=7.56 (s, 1H), 7.31 (br s, 1H), 7.23-7.15 (m, 1H), 7.02 (br d, J=7.7 Hz, 1H), 6.98-6.90 (m, 2H), 6.52 (dd, J=2.2, 8.3 Hz, 1H), 4.80-4.70 (m, 1H), 4.63 (br d, J=5.9 Hz, 2H), 4.51 (br d, J=5.7 Hz, 2H), 3.31-3.25 (m, 1H), 2.93-2.82 (m, 1H), 2.81-2.77 (m, 2H), 2.18-2.07 (m, 2H), 1.91 (br d, J=10.6 Hz, 2H), 1.58 (s, 3H), 1.57-1.47 (m, 2H), 1.40-1.26 (m, 2H), 1.17 (br d, J=6.1 Hz, 6H), 0.98 (t, J=7.2 Hz, 3H). ESI [M+H]=537.2.

Example 92

Preparation of isopropyl trans-N-[4-[5-[2-(ethylsulfamoyl)-4-[methyl(1-methyl-1H-imidazol-2-yl)amino]phenyl]thiazol-2-yl]cyclohexyl]carbamate (Compound 117)

Following the same protocol and under the same reaction conditions as for Compound 111, Compound 117 was prepared. ¹H NMR (400 MHz, methanol-d₄) δ=7.78-7.67 (m, 1H), 7.61-7.48 (m, 4H), 7.28-7.13 (m, 1H), 4.86-4.79 (m, 1H), 3.61 (s, 3H), 3.58-3.55 (m, 3H), 3.52-3.40 (m, 1H), 3.08-3.00 (m, 1H), 2.85 (q, J=7.2 Hz, 2H), 2.30-2.22 (m, 2H), 2.14-2.06 (m, 2H), 1.78-1.65 (m, 2H), 1.43 (dq, J=3.2, 12.7 Hz, 2H), 1.25 (br d, J=6.1 Hz, 6H), 1.04-0.99 (m, 3H). ESI [M+H]=561.3.

Example 93

Preparation of isopropyl trans-N-[4-[5-[2-(ethylsulfamoyl)-4-[(1,3,4-oxadiazol-2-yl)amino]phenyl]thiazol-2-yl]cyclohexyl]carbamate (Compound 118)

Following the same protocol and under the same reaction conditions as for Compound 111, Compound 118 was prepared. ¹H NMR (400 MHz, methanol-d₄) δ=8.49 (d, J=2.38 Hz, 1H), 8.31 (s, 1H), 7.93 (dd, J=8.38, 2.38 Hz, 1H), 7.82 (s, 1H), 7.66 (d, J=8.25 Hz, 1H), 4.79-4.84 (m, 1H), 3.42-3.53 (m, 1H), 3.06 (tt, J=12.04, 3.35 Hz, 1H), 2.96 (q, J=7.21 Hz, 2H), 2.20-2.32 (m, 2H), 2.04-2.14 (m, 2H), 1.65-1.80 (m, 2H), 1.34-1.51 (m, 2H), 1.25 (br d, J=6.13 Hz, 6H), 1.02-1.12 (m, 3H). ESI [M+H]=535.2.

Example 94

Preparation of isopropyl trans-N-[4-[5-[2-(ethylsulfamoyl)-4-[(1,3,4-thiadiazol-2-yl)amino]phenyl]thiazol-2-yl]cyclohexyl]carbamate (Compound 119)

Following the same protocol and under the same reaction conditions as for Compound 111, Compound 119 was prepared. ¹H NMR (400 MHz, methanol-d₄) δ=8.90 (s, 1H), 8.51 (d, J=2.5 Hz, 1H), 7.91 (dd, J=2.4, 8.4 Hz, 1H), 7.79 (s, 1H), 7.50 (d, J=8.4 Hz, 1H), 4.84 (br s, 1H), 3.48 (tt, J=3.8, 11.6 Hz, 1H), 3.12-3.03 (m, 1H), 2.99 (q, J=7.2 Hz, 2H), 2.32-2.22 (m, 2H), 2.14-2.05 (m, 2H), 1.73 (dq, J=3.0, 12.9 Hz, 2H), 1.44 (dq, J=3.1, 12.6 Hz, 2H), 1.25 (br d, J=6.1 Hz, 6H), 1.10 (t, J=7.2 Hz, 3H). ESI [M+H]=551.2.

Example 95

Preparation of isopropyl trans-N-[4-[5-[2-(ethylsulfamoyl)-4-[(1H-pyrazol-4-yl)amino]phenyl]thiazol-2-yl]cyclohexyl]carbamate (Compound 120)

Following the same protocol and under the same reaction conditions as for Compound 111, Compound 120 was prepared. ¹H NMR (400 MHz, methanol-d₄) δ=7.68 (s, 1H), 7.61 (s, 2H), 7.45 (d, J=2.4 Hz, 1H), 7.24 (d, J=8.4 Hz, 1H), 6.97 (dd, J=2.4, 8.4 Hz, 1H), 4.84-4.75 (m, 1H), 3.51-3.39 (m, 1H), 3.01 (tt, J=3.4, 12.1 Hz, 1H), 2.86 (q, J=7.2 Hz, 2H), 2.27-2.17 (m, 2H), 2.11-2.03 (m, 2H), 1.68 (dq, J=3.0, 12.8 Hz, 2H), 1.40 (dq, J=3.3, 12.6 Hz, 2H), 1.22 (br d, J=6.2 Hz, 6H), 1.01 (t, J=7.2 Hz, 3H). ESI [M+H]=533.2.

Example 96

Preparation of isopropyl trans-N-[4-[5-[2-(ethylsulfamoyl)-4-[(1H-pyrazol-5-yl)amino]phenyl]thiazol-2-yl]cyclohexyl]carbamate (Compound 121)

Following the same protocol and under the same reaction conditions as for Compound 111, Compound 121 was prepared. ¹H NMR (400 MHz, methanol-d₄) δ=7.97 (d, J=2.4 Hz, 1H), 7.67 (s, 1H), 7.57 (d, J=2.4 Hz, 1H), 7.41 (dd, J=2.4, 8.4 Hz, 1H), 7.28 (d, J=8.4 Hz, 1H), 6.01 (d, J=2.4 Hz, 1H), 4.82-4.74 (m, 1H), 3.45 (tt, J=3.8, 11.5 Hz, 1H), 3.05-2.95 (m, 1H), 2.91 (q, J=7.1 Hz, 2H), 2.27-2.18 (m, 2H), 2.10-2.01 (m, 2H), 1.68 (dq, J=3.0, 12.8 Hz, 2H), 1.40 (dq, J=3.1, 12.6 Hz, 2H), 1.22 (br d, J=6.2 Hz, 6H), 1.04 (t, J=7.3 Hz, 3H). ESI [M+H]=533.2.

Example 97

Preparation of isopropyl trans-N-[4-[5-[2-(ethylsulfamoyl)-4-[(pyrazin-2-yl)amino]phenyl]thiazol-2-yl]cyclohexyl]carbamate (Compound 122)

Following the same protocol and under the same reaction conditions as for Compound 111, Compound 122 was prepared. ¹H NMR (400 MHz, methanol-d₄) δ=8.59 (d, J=2.2 Hz, 1H), 8.26-8.16 (m, 2H), 7.99-7.90 (m, 2H), 7.72 (s, 1H), 7.41 (d, J=8.4 Hz, 1H), 4.82 (br s, 1H), 3.52-3.40 (m, 1H), 3.06-2.98 (m, 1H), 2.95 (q, J=7.1 Hz, 2H), 2.29-2.18 (m, 2H), 2.11-2.01 (m, 2H), 1.70 (dq, J=3.2, 12.8 Hz, 2H), 1.41 (dq, J=3.4, 12.5 Hz, 2H), 1.22 (br d, J=6.2 Hz, 6H), 1.07 (t, J=7.3 Hz, 3H). ESI [M+H]=545.2.

Example 98

Preparation of isopropyl trans-N-[4-[5-[2-(ethylsulfamoyl)-4-[(pyridazin-3-yl)amino]phenyl]thiazol-2-yl]cyclohexyl]carbamate (Compound 123)

Following the same protocol and under the same reaction conditions as for Compound 111, Compound 123 was prepared. ¹H NMR (400 MHz, methanol-d₄) δ=8.95 (d, J=4.25 Hz, 1H) 8.56 (d, J=2.38 Hz, 1H) 7.92-8.04 (m, 2H) 7.72-

7.82 (m, 2H) 7.55 (d, J=8.38 Hz, 1H) 4.76-4.89 (m, 1H) 3.40-3.54 (m, 1H) 3.06 (tt, J=12.10, 3.35 Hz, 1H) 2.92 (q, J=7.25 Hz, 2H) 2.22-2.35 (m, 2H) 2.00-2.13 (m, 2H) 1.73 (qd, J=12.78, 2.94 Hz, 2H) 1.44 (qd, J=12.57, 3.06 Hz, 2H) 1.25 (br d, J=6.13 Hz, 6H) 1.05 (t, J=7.25 Hz, 3H). ESI [M+H]=545.2.

Example 99

Preparation of isopropyl trans-N-[4-[5-[2-(ethylsulfamoyl)-4-[(pyrimidin-4-yl)amino]phenyl]thiazol-2-yl]cyclohexyl]carbamate (Compound 124)

Following the same protocol and under the same reaction conditions as for Compound 111, Compound 124 was prepared. $^1$H NMR (400 MHz, methanol-$d_4$) δ=8.96 (s, 1H), 8.55 (d, J=1.88 Hz, 1H) 8.40 (dd, J=7.13, 1.13 Hz, 1H), 8.02 (dd, J=8.32, 2.19 Hz, 1H), 7.81 (s, 1H) 7.60 (d, J=8.38 Hz, 1H), 7.15 (d, J=7.13 Hz, 1H), 4.76-4.90 (m, 1H), 3.42-3.54 (m, 1H), 3.01-3.12 (m, 1H), 2.92 (q, J=7.25 Hz, 2H), 2.21-2.32 (m, 2H), 2.04-2.14 (m, 2H), 1.73 (qd, J=12.84, 2.88 Hz, 2H), 1.44 (qd, J=12.57, 3.06 Hz, 2H), 1.25 (br d, J=6.13 Hz, 6H), 1.05 (t, J=7.25 Hz, 3H). ESI [M+H]=545.2.

Example 100

Preparation of isopropyl trans-N-[4-[5-[2-(ethylsulfamoyl)-4-[(pyridin-4-yl)amino]phenyl]thiazol-2-yl]cyclohexyl]carbamate (Compound 125)

Following the same protocol and under the same reaction conditions as for Compound 111, Compound 125 was prepared. $^1$H NMR (400 MHz, methanol-$d_4$) δ=8.28 (d, J=7.3 Hz, 2H), 8.02 (d, J=2.0 Hz, 1H), 7.79 (s, 1H), 7.69-7.57 (m, 2H), 7.27 (d, J=7.3 Hz, 2H), 4.85-4.77 (m, 1H), 3.45 (tt, J=3.8, 11.5 Hz, 1H), 3.03 (tt, J=3.3, 12.0 Hz, 1H), 2.88 (q, J=7.1 Hz, 2H), 2.29-2.20 (m, 2H), 2.11-2.01 (m, 2H), 1.70 (dq, J=3.0, 12.8 Hz, 2H), 1.41 (dq, J=3.1, 12.6 Hz, 2H), 1.22 (br d, J=6.2 Hz, 6H), 1.01 (t, J=7.3 Hz, 3H). ESI [M+H]=544.2.

Example 101

Preparation of isopropyl trans-N-[4-[5-[2-(ethylsulfamoyl)-4-[(pyridin-2-yl)amino]phenyl]thiazol-2-yl]cyclohexyl]carbamate (Compound 126)

Following the same protocol and under the same reaction conditions as for Compound 111, Compound 126 was prepared. $^1$H NMR (400 MHz, methanol-$d_4$) δ=8.10 (d, J=2.3 Hz, 1H), 7.98 (dd, J=1.1, 5.9 Hz, 1H), 7.89 (ddd, J=1.8, 7.2, 8.8 Hz, 1H), 7.70-7.60 (m, 2H), 7.46 (d, J=8.3 Hz, 1H), 7.11 (d, J=8.8 Hz, 1H), 7.02-6.93 (m, 1H), 4.74-4.67 (m, 1H), 3.36 (tt, J=3.9, 11.6 Hz, 1H), 2.94 (tt, J=3.5, 12.1 Hz, 1H), 2.81 (q, J=7.2 Hz, 2H), 2.20-2.11 (m, 2H), 2.02-1.94 (m, 2H), 1.61 (dq, J=3.1, 12.9 Hz, 2H), 1.38-1.26 (m, 2H), 1.13 (d, J=6.1 Hz, 6H), 0.94 (t, J=7.2 Hz, 3H). ESI [M+H]=544.2.

Example 102

Preparation of isopropyl trans-N-[4-[5-[2-(ethylsulfamoyl)-4-[(pyrimidin-2-yl)amino]phenyl]thiazol-2-yl]cyclohexyl]carbamate (Compound 127)

Following the same protocol and under the same reaction conditions as for Compound 111, Compound 127 was prepared. $^1$H NMR (400 MHz, methanol-$d_4$) δ=8.66 (d, J=2.3 Hz, 1H), 8.53 (d, J=4.8 Hz, 2H), 7.97 (dd, J=2.3, 8.4 Hz, 1H), 7.79 (s, 1H), 7.43 (d, J=8.4 Hz, 1H), 6.91 (t, J=4.9 Hz, 1H), 4.87-4.80 (m, 1H), 3.48 (tt, J=3.8, 11.5 Hz, 1H), 3.11-3.02 (m, 1H), 2.99 (q, J=7.3 Hz, 2H), 2.31-2.21 (m, 2H), 2.14-2.05 (m, 2H), 1.72 (dq, J=2.9, 12.8 Hz, 2H), 1.43 (dq, J=3.2, 12.6 Hz, 2H), 1.25 (br d, J=6.1 Hz, 6H), 1.10 (t, J=7.3 Hz, 3H). ESI [M+H]=545.2.

Example 103

Preparation of isopropyl trans-N-[4-[5-[2-(ethylsulfamoyl)-4-[(pyridin-3-yl)amino]phenyl]thiazol-2-yl]cyclohexyl]carbamate (Compound 128)

Following the same protocol and under the same reaction conditions as for Compound 111, Compound 128 was prepared. $^1$H NMR (400 MHz, methanol-$d_4$) δ=8.54 (d, J=2.63 Hz, 1H), 8.30 (d, J=5.50 Hz, 1H), 8.22-8.27 (m, 1H), 7.90-7.96 (m, 2H), 7.78 (s, 1H), 7.51-7.59 (m, 2H), 4.82-4.88 (m, 1H), 3.42-3.52 (m, 1H), 3.06 (tt, J=12.04, 3.53 Hz, 1H), 2.90 (q, J=7.17 Hz, 2H), 2.20-2.34 (m, 2H), 2.03-2.17 (m, 2H), 1.74-1.75 (m, 2H) 1.38-1.51 (m, 2H), 1.25 (d, J=6.13 Hz, 6H), 1.04 (t, J=7.25 Hz, 3H). ESI [M+H]=544.2.

Example 104

Preparation of isopropyl trans-N-[4-[5-[2-(ethylsulfamoyl)-4-[(1-isopropyl-1H-pyrazol-5-yl)amino]phenyl]thiazol-2-yl]cyclohexyl]carbamate (Compound 129)

Following the same protocol and under the same reaction conditions as for Compound 111, Compound 129 was prepared. $^1$H NMR (400 MHz, methanol-$d_4$) δ=7.74 (s, 1H), 7.61 (d, J=1.75 Hz, 1H), 7.49 (d, J=2.50 Hz, 1H), 7.34 (d, J=8.38 Hz, 1H), 7.04 (dd, J=8.32, 2.44 Hz, 1H, 6.18 (d, J=2.00 Hz, 1H), 4.77-4.87 (m, 1H), 4.62 (dt, J=13.35, 6.64 Hz, 1H), 3.40-3.53 (m, 1H), 3.06 (tt, J=12.07, 3.38 Hz, 1H), 2.87 (q, J=7.25 Hz, 2H), 2.19-2.31 (m, 2H), 2.02-2.17 (m, 2H), 1.72 (qd, J=12.82, 2.81 Hz, 2H), 1.46 (d, J=6.63 Hz, 8H), 1.24 (br d, J=6.13 Hz, 6H), 1.02 (t, J=7.25 Hz, 3H). ESI [M+H]=575.2.

Example 105

Preparation of isopropyl trans-N-[4-[5-[2-(ethylsulfamoyl)-4-[4-hydroxypiperidin-1-yl]phenyl]thiazol-2-yl]cyclohexyl]carbamate (Compound 130)

Following the same protocol and under the same reaction conditions as for Compound 111, Compound 130 was prepared. $^1$H NMR (400 MHz, methanol-$d_4$) δ=7.79 (s, 1H), 7.61 (d, J=2.4 Hz, 1H), 7.35 (d, J=8.6 Hz, 1H), 7.22 (dd, J=2.4, 8.6 Hz, 1H), 4.81 (br s, 1H), 3.85 (tt, J=4.0, 8.5 Hz, 1H), 3.80-3.65 (m, 2H), 3.45 (tdd, J=3.8, 7.5, 11.2 Hz, 1H), 3.20-3.00 (m, 3H), 2.87 (q, J=7.2 Hz, 2H), 2.24 (br d, J=12.6 Hz, 2H), 2.08 (br d, J=10.4 Hz, 2H), 1.99 (br dd, J=3.6, 9.4 Hz, 2H), 1.79-1.56 (m, 4H), 1.47-1.34 (m, 2H), 1.22 (br d, J=6.2 Hz, 6H), 1.02 (t, J=7.2 Hz, 3H). ESI [M+H]=551.2.

Example 106

Preparation of isopropyl trans-N-[4-[5-[2-(ethylsulfamoyl)-4-[(2-hydroxyethyl)(methyl))amino]phenyl]thiazol-2-yl]cyclohexyl]carbamate (Compound 131)

Following the same protocol and under the same reaction conditions as for Compound 111, Compound 131 was prepared. ¹H NMR (400 MHz, methanol-d₄) δ=7.68 (s, 1H), 7.38 (d, J=2.9 Hz, 1H), 7.27 (d, J=8.6 Hz, 1H), 6.95 (dd, J=2.9, 8.6 Hz, 1H), 4.82-4.78 (m, 1H), 3.80-3.70 (m, 2H), 3.67-3.54 (m, 2H), 3.51-3.40 (m, 1H), 3.09 (s, 3H), 3.02 (tt, J=3.4, 12.0 Hz, 1H), 2.87 (q, J=7.1 Hz, 2H), 2.31-2.15 (m, 2H), 2.10-2.00 (m, 2H), 1.69 (dq, J=2.9, 12.9 Hz, 2H), 1.41 (dq, J=3.2, 12.6 Hz, 2H), 1.22 (br d, J=6.2 Hz, 6H), 1.02 (t, J=7.3 Hz, 3H). ESI [M+H]=525.2.

Example 107

Preparation of isopropyl (trans-4-(5-(2-(N-ethylsulfamoyl)-4-(oxazol-2-ylamino)phenyl)thiazol-2-yl) cyclohexyl)carbamate (Compound 60)

Following the same protocol and under the same reaction conditions as for Compound 111, Compound 60 was prepared. ¹H NMR (400 MHz, methanol-d₄) δ=8.37 (d, J=2.3 Hz, 1H), 7.89-7.73 (m, 2H), 7.54 (d, J=0.9 Hz, 1H), 7.46 (d, J=8.4 Hz, 1H), 7.03 (s, 1H), 4.85 (br s, 1H), 3.54-3.45 (m, 1H), 3.15-3.02 (m, 1H), 2.96 (q, J=7.3 Hz, 2H), 2.27 (br d, J=12.1 Hz, 2H), 2.10 (br d, J=10.6 Hz, 2H), 1.81-1.67 (m, 2H), 1.49-1.36 (m, 2H), 1.25 (br d, J=6.1 Hz, 6H), 1.09 (t, J=7.2 Hz, 3H). ESI [M+H]=534.2.

Example 108

Preparation of isopropyl trans-N-[4-[5-[2-(ethylsulfamoyl)-4-[(2-methoxyethyl) (methyl))amino]phenyl]thiazol-2-yl]cyclohexyl]carbamate (Compound 132)

Following the same protocol and under the same reaction conditions as for Compound 111, Compound 132 was prepared. ¹H NMR (400 MHz, methanol-d₄) δ=7.68 (s, 1H), 7.40 (d, J=2.6 Hz, 1H), 7.29 (d, J=8.6 Hz, 1H), 6.97 (dd, J=2.7, 8.6 Hz, 1H), 3.71-3.57 (m, 4H), 3.47 (br t, J=11.6 Hz, 1H), 3.37 (s, 3H), 3.09 (s, 3H), 3.06-2.97 (m, 1H), 2.94-2.85 (m, 2H), 2.25 (br d, J=12.6 Hz, 2H), 2.14-2.03 (m, 2H), 1.78-1.64 (m, 2H), 1.49-1.35 (m, 2H), 1.25 (br d, J=6.0 Hz, 6H), 1.08-1.01 (m, 3H). ESI [M+H]=539.2.

Example 109

Preparation of isopropyl trans-N-[4-[5-[2-(ethylsulfamoyl)-4-[1,1-dioxidothiomorpholino]phenyl]thiazol-2-yl]cyclohexyl]carbamate (Compound 133)

Following the same protocol and under the same reaction conditions as for Compound 111, Compound 133 was prepared. ¹H NMR (400 MHz, methanol-d₄) δ=7.73 (s, 1H), 7.67-7.63 (m, 1H), 7.41 (d, J=8.4 Hz, 1H), 7.29 (dd, J=2.8, 8.6 Hz, 1H), 4.87-4.81 (m, 1H), 4.02 (br s, 4H), 3.53-3.42 (m, 1H), 3.20 (br s, 4H), 3.05 (ddd, J=3.5, 8.7, 12.1 Hz, 1H), 2.88 (q, J=7.2 Hz, 2H), 2.26 (br d, J=12.5 Hz, 2H), 2.09 (br d, J=11.0 Hz, 2H), 1.79-1.65 (m, 2H), 1.50-1.38 (m, 2H), 1.25 (br d, J=6.1 Hz, 6H), 1.04 (t, J=7.3 Hz, 3H). ESI [M+H]=585.2.

Example 110

Preparation of isopropyl trans-N-[4-[5-[2-(ethylsulfamoyl)-4-[morpholino]phenyl]thiazol-2-yl]cyclohexyl]carbamate (Compound 134)

Following the same protocol and under the same reaction conditions as for Compound 111, Compound 134 was prepared. ¹H NMR (400 MHz, methanol-d₄) δ=7.74 (br s, 1H), 7.57 (br s, 1H), 7.34 (br d, J=7.9 Hz, 1H), 7.17 (br d, J=7.3 Hz, 1H), 4.82-4.74 (m, 1H), 3.85 (br s, 4H), 3.45 (br s, 1H), 3.28 (br s, 4H), 3.01 (br s, 1H), 2.85 (q, J=7.2 Hz, 2H), 2.24 (br d, J=12.6 Hz, 2H), 2.07 (br d, J=10.6 Hz, 2H), 1.68 (br s, 2H), 1.49-1.34 (m, 2H), 1.22 (br d, J=6.0 Hz, 6H), 1.01 (t, J=7.3 Hz, 3H). ESI [M+H]=537.2.

Example 111

Preparation of isopropyl trans-N-[4-[5-[2-(ethylsulfamoyl)-4-[piperidin-1-yl]phenyl]thiazol-2-yl]cyclohexyl]carbamate (Compound 135)

Following the same protocol and under the same reaction conditions as for Compound 111, Compound 135 was prepared. ¹H NMR (400 MHz, methanol-d₄) δ=7.76 (s, 1H), 7.66 (br s, 1H), 7.45-7.33 (m, 1H), 7.26 (br d, J=7.1 Hz, 1H), 4.86-4.79 (m, 1H), 3.53-3.46 (m, 1H), 3.41 (br s, 4H), 3.07 (br t, J=11.4 Hz, 1H), 2.88 (q, J=7.1 Hz, 2H), 2.26 (br d, J=12.7 Hz, 2H), 2.10 (br d, J=11.0 Hz, 2H), 1.86-1.63 (m, 8H), 1.50-1.36 (m, 2H), 1.24 (br d, J=5.7 Hz, 6H), 1.04 (br t, J=7.2 Hz, 3H). ESI [M+H]=535.2.

Example 112

Preparation of isopropyl trans-N-[4-[5-[2-(ethylsulfamoyl)-4-[(2-isopropylpyrimidin-4-yl)amino]phenyl]thiazol-2-yl]cyclohexyl]carbamate (Compound 136)

Following the same protocol and under the same reaction conditions as for Compound 111, Compound 136 was prepared. ¹H NMR (400 MHz, methanol-d₄) δ=8.83 (br s, 1H), 8.30 (d, J=7.21 Hz, 1H), 7.90 (dd, J=2.20, 8.31 Hz, 1H), 7.77-7.83 (m, 1H), 7.60 (d, J=8.31 Hz, 1H), 7.01 (d, J=7.09 Hz, 1H), 4.81-4.85 (m, 1H), 3.48 (tt, J=3.88, 11.58 Hz, 1H), 3.21 (spt, J=6.83 Hz, 1H), 3.05 (tt, J=3.50, 12.03 Hz, 1H), 2.87 (q, J=7.21 Hz, 2H), 2.28 (br d, J=12.35 Hz, 2H), 2.10 (br d, J=9.90 Hz, 2H), 1.73 (dq, J=2.93, 12.92 Hz, 2H), 1.47 (d, J=6.85 Hz, 6H), 1.29-1.45 (m, 2H), 1.25 (br d, J=6.11 Hz, 6H), 1.01 (t, J=7.21 Hz, 3H). ESI [M+H]=587.1.

Example 113

Preparation of isopropyl trans-N-[4-[5-[2-(ethylsulfamoyl)-4-[(oxetan-3-yl)amino]phenyl]thiazol-2-yl] cyclohexyl]carbamate (Compound 137)

Following the same protocol and under the same reaction conditions as for Compound 111, Compound 137 was prepared. ¹H NMR (400 MHz, DMSO-d₆) δ=7.53 (s, 1H), 7.25 (t, J=5.7 Hz, 1H), 7.19-7.11 (m, 2H), 7.04 (d, J=2.4 Hz, 1H), 6.99 (br d, J=7.7 Hz, 1H), 6.62 (dd, J=2.4, 8.4 Hz, 1H), 4.85 (t, J=6.5 Hz, 2H), 4.72 (td, J=6.2, 12.5 Hz, 1H), 4.57 (sxt, J=6.4 Hz, 1H), 4.45-4.38 (m, 2H), 3.30-3.22 (m, 1H), 2.90-2.80 (m, 1H), 2.80-2.72 (m, 2H), 2.10 (br d, J=11.2 Hz, 2H), 1.89 (br d, J=10.1 Hz, 2H), 1.61-1.44 (m, 2H), 1.39-1.21 (m, 2H), 1.14 (d, J=6.4 Hz, 6H), 0.95 (t, J=7.2 Hz, 3H). ESI [M+H]=523.2.

Example 114

Preparation of isopropyl trans-N-[4-[5-[2-(ethylsulfamoyl)-4-[(3-isopropylimidazol-4-yl)amino]phenyl]thiazol-2-yl]cyclohexyl]carbamate (Compound 138)

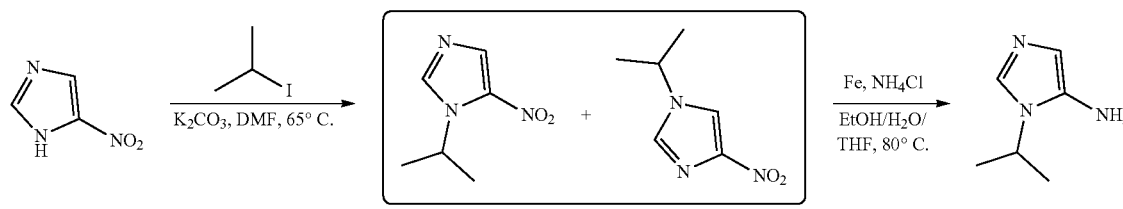

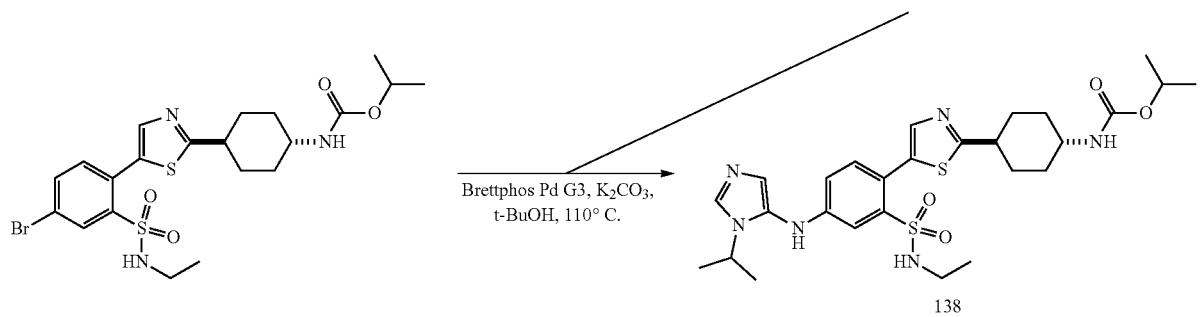

a) Synthesis of 1-isopropyl-5-nitro-1H-imidazole b) Synthesis of 3-isopropylimidazol-4-amine

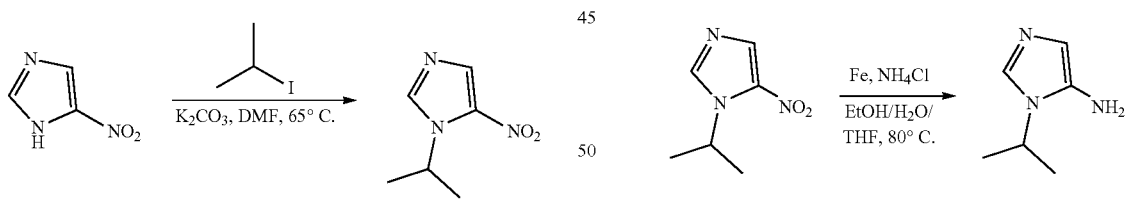

To a solution of 5-nitro-1H-imidazole (15 g, 133 mmol, 1.0 eq.) in DMF (50 mL) was added $K_2CO_3$ (55 g, 398 mmol, 3.0 eq.) and 2-iodopropane (24.81 g, 146 mmol, 1.1 eq.). The mixture was stirred at 65° C. for 12 h. The reaction was filtered and filtrate was concentrated under reduced pressure. The residue was purified by prep-HPLC (neutral condition; column: Phenomenex luna C18 250*80 mm*10 um; mobile phase: [water(0.1% TFA)-ACN]; B %: 5%-30%, 20 min) to yield 1-isopropyl-5-nitro-1H-imidazole (1.7 g, 11 mmol, 8% yield) as a yellow solid. $^1$H NMR (400 MHz, $CDCl_3$) δ=8.19 (s, 1H), 8.11 (s, 1H), 5.33 (br d, J=6.8 Hz, 1H), 1.63 (br d, J=6.6 Hz, 6H). ESI [M+H]=156.1.

A mixture of 1-isopropyl-5-nitro-1H-imidazole (200 mg, 1 mmol, 1.0 eq.), Fe (360 mg, 6 mmol, 5 eq.), $NH_4Cl$ (207 mg, 4 mmol, 3.0 eq.) in THF (10 mL), EtOH (10 mL) and $H_2O$ (3 mL) was stirred at 80° C. for 2 h under $N_2$ atmosphere. The reaction was filtered, then the filter was concentrated under reduced pressure. The residue was diluted with $H_2O$ 20 mL and extracted with EtOAc 90 mL (30 mL×3). The combined organic layers dried over $Na_2SO_4$, filtered and concentrated under reduced pressure to yield 3-isopropylimidazol-4-amine (150 mg, crude) as a black oil. ESI [M+H]=126.1.

c) Synthesis of isopropyl trans-N-[4-[5-[2-(ethylsulfamoyl)-4-[(3-isopropylimidazol-4-yl)amino]phenyl]thiazol-2-yl]cyclohexyl]carbamate (Compound 138)

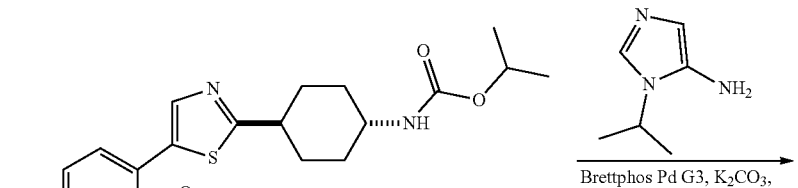

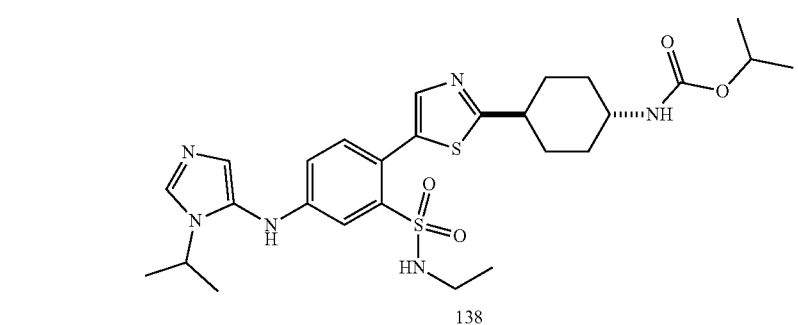

From isopropyl trans-N-[4-[5-[4-bromo-2-(ethylsulfamoyl)phenyl]thiazol-2-yl]cyclohexyl]carbamate, using General Method F. $^1$H NMR (400 MHz, methanol-$d_4$) δ=9.12 (s, 1H), 7.69 (s, 1H), 7.59 (s, 1H), 7.48 (d, J=2.38 Hz, 1H), 7.38 (d, J=8.38 Hz, 1H), 7.05 (dd, J=8.25, 2.38 Hz, 1H), 4.78-4.83 (m, 1H), 4.61 (dt, J=13.41, 6.61 Hz, 1H), 3.46 (qd, J=7.61, 3.56 Hz, 1H), 3.02 (ddd, J=11.88, 8.69, 3.44 Hz, 1H), 2.84 (q, J=7.21 Hz, 2H), 2.25 (br d, J=12.26 Hz, 2H), 2.09 (br d, J=10.38 Hz, 2H), 1.65-1.77 (m, 2H), 1.58 (d, J=6.63 Hz, 6H), 1.39-1.48 (m, 2H), 1.24 (br d, J=6.00 Hz, 6H), 1.01 (t, J=7.19 Hz, 3H). ESI [M+H]=575.1.

Example 115

Preparation of isopropyl trans-N-[4-[5-[2-(ethylsulfamoyl)-4-[(1-isopropyl-1H-imidazol-4-yl)amino]phenyl]thiazol-2-yl]cyclohexyl]carbamate (Compound 139)

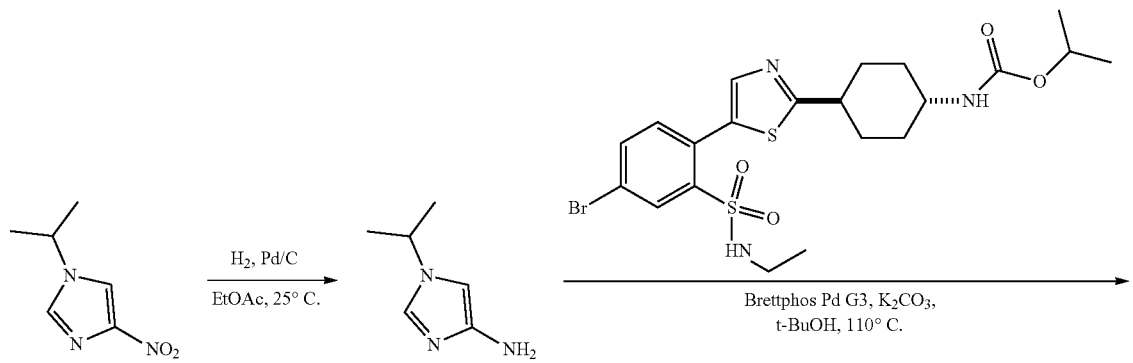

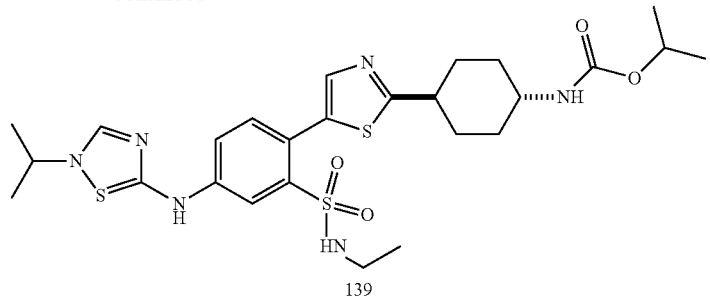

139 a) Synthesis of 1-isopropylimidazol-4-amine

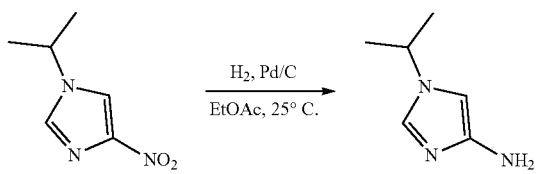

To a solution of 1-isopropyl-4-nitro-imidazole (1.0 g, 6.5 mmol, 1.0 eq.) in EtOAc (50 mL) was added Pd/C (0.1 g, 10% purity) and the mixture was stirred under H₂ (15 psi) at 25° C. for 3 h, and then filtered and concentrated under reduced pressure. The residue was purified by prep-HPLC (TFA condition). column: Phenomenex luna C18 250*50 mm*10 um; mobile phase: [water(0.1% TFA)-ACN]; B %: 1%-10%,10 min to yield 1-isopropylimidazol-4-amine (390 mg, 3.12 mmol, 48% yield) as a yellow oil. $^1$H NMR (400 MHz, CDCl$_3$) δ=7.91-7.77 (m, 1H), 6.34-6.23 (m, 1H), 4.42-4.30 (m, 1H), 1.53 (d, J=6.7 Hz, 6H). ESI [M+H]=126.1.

b) Synthesis of isopropyl trans-N-[4-[5-[2-(ethylsulfamoyl)-4-[(1-isopropyl-1H-imidazol-4-yl)amino]phenyl]thiazol-2-yl]cyclohexyl]carbamate (Compound 139)

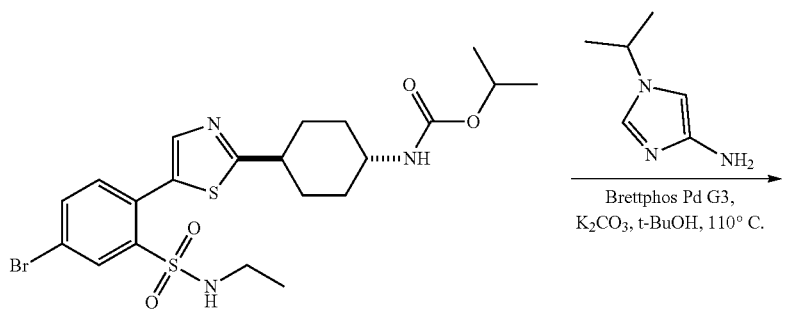

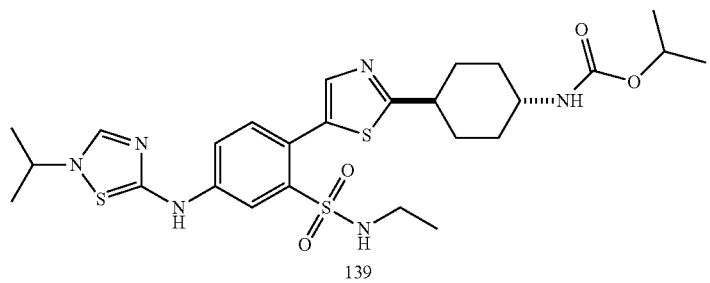

139

From isopropyl trans-N-[4-[5-[4-bromo-2-(ethylsulfamoyl)phenyl]thiazol-2-yl]cyclohexyl]carbamate and 1-isopropylimidazol-4-amine, using General Method F. $^1$H NMR (400 MHz, methanol-$d_4$) δ=8.91-8.86 (m, 1H), 7.70 (s, 1H), 7.63-7.59 (m, 2H), 7.42-7.37 (m, 1H), 7.18-7.12 (m, 1H), 4.87-4.81 (m, 1H), 4.73-4.62 (m, 1H), 3.54-3.43 (m, 1H), 3.03 (tt, J=3.5, 12.0 Hz, 1H), 2.86 (q, J=7.2 Hz, 2H), 2.31-2.21 (m, 2H), 2.13-2.04 (m, 2H), 1.77-1.67 (m, 2H), 1.65-1.61 (m, 6H), 1.49-1.39 (m, 2H), 1.25 (br d, J=6.1 Hz, 6H), 1.07-0.98 (m, 3H). ESI [M+H]=575.3.

Example 116

Preparation of isopropyl trans-N-[4-[5-[2-(ethylsulfamoyl)-4-[(6-isopropylpyrazin-2-yl)amino]phenyl]thiazol-2-yl]cyclohexyl]carbamate (Compound 140)

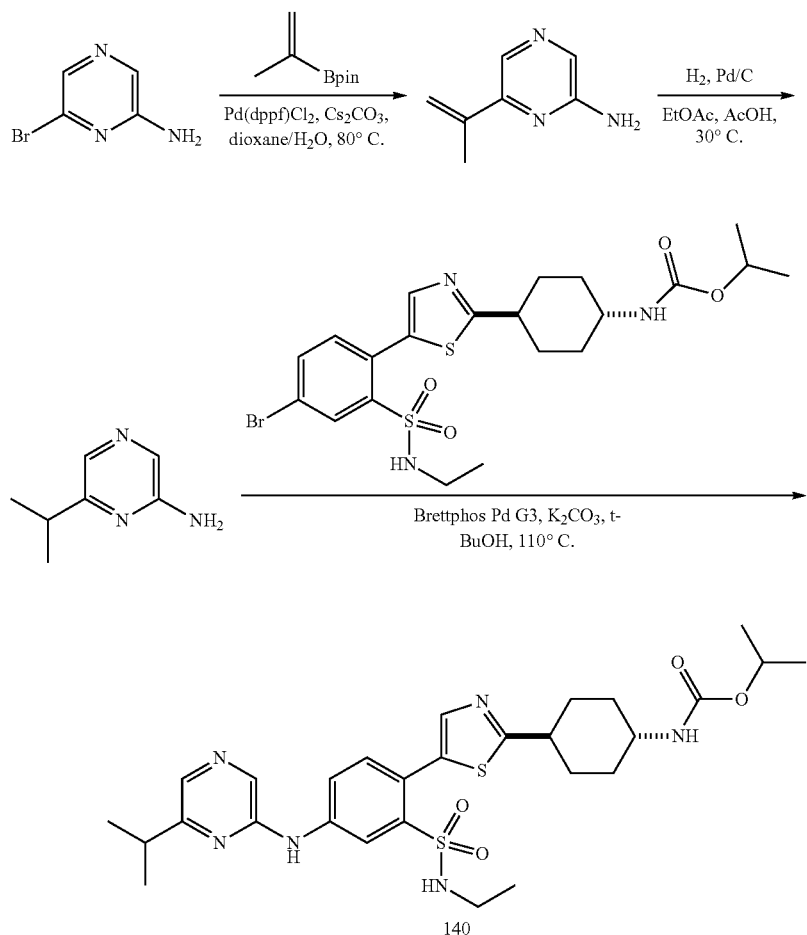

a) Synthesis of 6-isopropenylpyrazin-2-amine

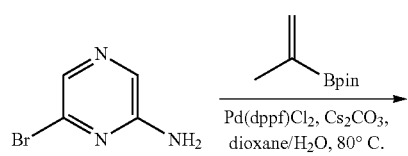

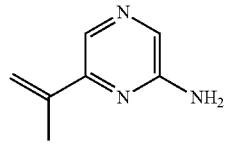

A mixture of 2-isopropenyl-4,4,5,5-tetramethyl-1,3,2-dioxaborolane (1.0 g, 6.0 mmol, 1.3 eq.), 6-bromopyrazin-2-amine (820 mg, 5 mmol, 1.0 eq.), $Cs_2CO_3$ (4.6 g, 14 mmol, 3.0 eq.) and Pd(dppf)$Cl_2$ (345 mg, 471 umol, 0.1 eq.) in dioxane (20 mL) and $H_2O$ (10 mL) was stirred at 80° C. for 12 h under $N_2$ atmosphere. The reaction mixture was concentrated under reduced pressure. The residue was diluted with $H_2O$ 20 mL and extracted with EtOAc 90 mL (30 mL×3). The combined organic layers dried over $Na_2SO_4$, filtered and concentrated under reduced pressure. The residue was purified by column chromatography (SiO$_2$, petroleum ether:ethyl acetate=10:1 to 5:1 to 3:1 to 1:1 to 0:1) to yield 6-isopropenylpyrazin-2-amine (730 mg, crude) as a white solid. $^1$H NMR (400 MHz, methanol-$d_4$) δ=7.91 (s, 1H), 7.79 (s, 1H), 5.87 (s, 1H), 5.29 (s, 1H), 2.14 (s, 3H). ESI [M+H]=136.1.

b) Synthesis of 6-isopropylpyrazin-2-amine

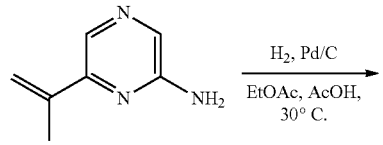

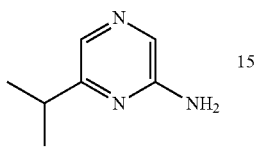

To a solution of 6-isopropenylpyrazin-2-amine (700 mg, 5 mmol, 1 eq.) in EtOAc (20 mL) was added AcOH (31 mg, 518 umol, 0.1 eq.) and Pd/C (100 mg, 10% purity). The mixture was stirred under H$_2$ (15 psi) at 30° C. for 12 h. The mixture was filtered, the filter liquor was concentrated under reduced pressure. The residue was purified by prep-HPLC (column: Phenomenex Luna C18 200*40 mm*10 um; mobile phase: [water(10 mM NH$_4$HCO$_3$)-ACN]; B %: 1%-30%,10 min) to yield 6-isopropylpyrazin-2-amine (300 mg) as a white solid. $^1$H NMR (400 MHz, methanol-d$_4$) δ=7.73 (s, 1H) 7.63 (s, 1H) 2.82-2.92 (m, 1H) 1.27 (d, J=6.88 Hz, 6H). ESI [M+H]=138.2.

c) Synthesis of isopropyl trans-N-[4-[5-[2-(ethylsulfamoyl)-4-[(6-isopropylpyrazin-2-yl)amino]phenyl]thiazol-2-yl]cyclohexyl]carbamate (Compound 140)

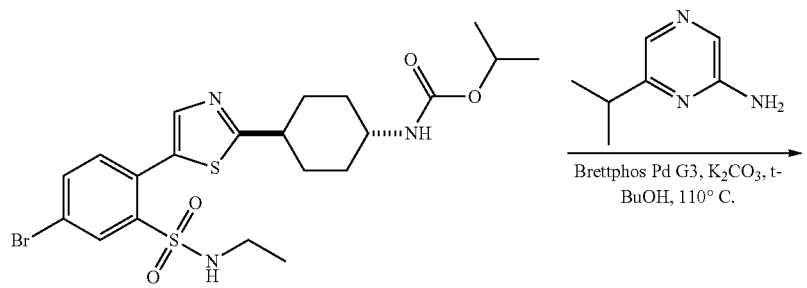

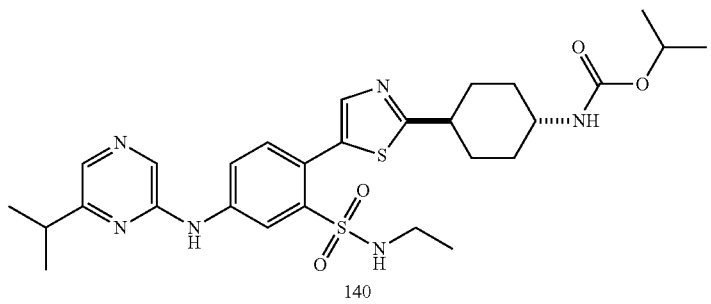

140

From isopropyl trans-N-[4-[5-[4-bromo-2-(ethylsulfamoyl)phenyl]thiazol-2-yl]cyclohexyl]carbamate and 6-isopropylpyrazin-2-amine, using General Method F. ¹H NMR (400 MHz, methanol-d₄) δ=8.84 (d, J=2.25 Hz, 1H), 8.03 (s, 1H), 7.94 (dd, J=8.38, 2.25 Hz, 1H), 7.90 (s, 1H), 7.72 (s, 1H) 7.43 (d, J=8.38 Hz, 1H), 4.81-4.85 (m, 1H), 3.41-3.55 (m, 1H), 2.99-3.13 (m, 2H), 2.90 (q, J=7.13 Hz, 2H), 2.27 (br d, J=12.26 Hz, 2H), 2.10 (br d, J=10.51 Hz, 2H), 1.66-1.77 (m, 2H), 1.42-1.51 (m, 2H), 1.39 (d, J=6.88 Hz, 6H), 1.25 (br d, J=6.13 Hz, 6H), 1.03 (t, J=7.19 Hz, 3H). ESI [M+H]=587.1.

Example 117

Preparation of isopropyl trans-N-[4-[5-[2-(ethylsulfamoyl)-4-[(5-methyl-1H-imidazol-2-yl)amino]phenyl]thiazol-2-yl]cyclohexyl]carbamate (Compound 141)

a) Synthesis of isopropyl trans-N-[4-[5-[2-(ethylsulfamoyl)-4-guanidino-phenyl]thiazol-2-yl]cyclohexyl]carbamate

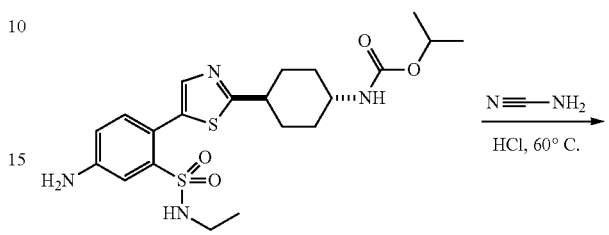

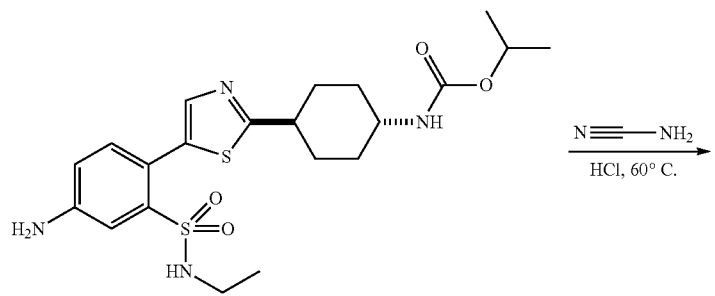

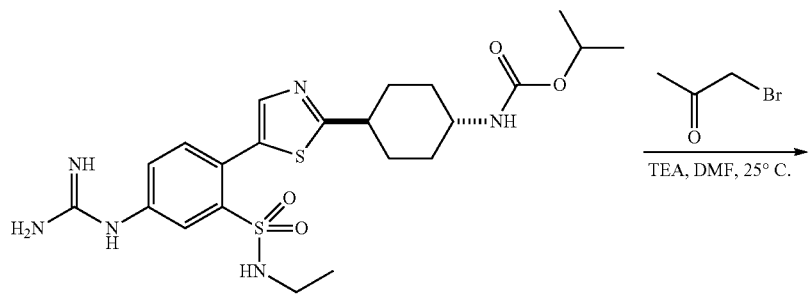

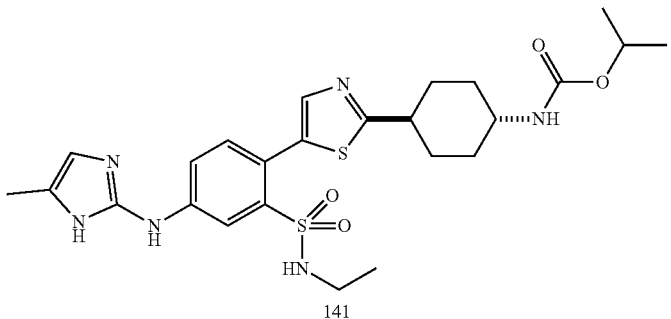

141

-continued

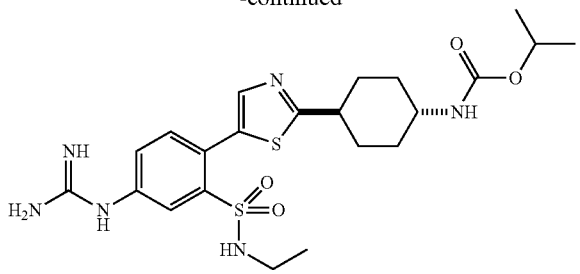

To a solution of isopropyl trans-N-[4-[5-[4-amino-2-(ethylsulfamoyl)phenyl]thiazol-2-yl]cyclohexyl]carbamate (0.5 g, 1 mmol, 1 eq.) in HCl (10 mL) was added cyanamide (180 mg, 2 mmol, 2 eq.). The mixture was stirred at 60° C. for 6 h, and then filtered. The residue was purified by prep-HPLC (TFA condition). column: Phenomenex luna C18 250*50 mm*10 um; mobile phase: [water(0.1% TFA)-ACN]; B %: 20%-50%,10 min to yield isopropyl trans-N-[4-[5-[2-(ethylsulfamoyl)-4-guanidino-phenyl]thiazol-2-yl]cyclohexyl] carbamate (0.31 g, 497.85 umol, 46% yield, TFA salt) as a white solid. 1H NMR (400 MHz, methanol-$d_4$) δ=8.04-7.94 (m, 1H), 7.82-7.74 (m, 1H), 7.64-7.55 (m, 2H), 4.84-4.75 (m, 1H), 3.55-3.40 (m, 1H), 3.14-3.02 (m, 1H), 2.94-2.83 (m, 2H), 2.33-2.23 (m, 2H), 2.12-2.04 (m, 2H), 1.80-1.64 (m, 2H), 1.56-1.38 (m, 2H), 1.25 (br d, J=6.1 Hz, 6H), 1.08-0.98 (m, 3H). ESI [M+H]=509.1.

b) Synthesis of isopropyl trans-N-[4-[5-[2-(ethylsulfamoyl)-4-[(5-methyl-1H-imidazol-2-yl)amino]phenyl]thiazol-2-yl]cyclohexyl]carbamate (Compound 141)

To a solution of isopropyl trans-N-[4-[5-[2-(ethylsulfamoyl)-4-guanidino-phenyl]thiazol-2-yl]cyclohexyl]carbamate (136 mg, 219 umol, 1.5 eq., TFA), TEA (44 mg, 438 umol, 3 eq.) in DMF (3 mL) was added 1-bromopropan-2-one (20 mg, 146 umol, 1 eq.). The mixture was stirred at 25° C. for 5 h. The residue was purified by prep-HPLC (TFA condition). column: Phenomenex Luna C18 100*30 mm*5 um; mobile phase: [water(0.1% TFA)-ACN]; B %: 10%-40%,12 min to yield isopropyl trans-N-[4-[5-[2-(ethylsulfamoyl)-4-[(5-methyl-1H-imidazol-2-yl)amino]phenyl]thiazol-2-yl]cyclohexyl]carbamate (98% purity, TFA salt) (15 mg) as a pale yellow solid. $^1$H NMR (400 MHz, methanol-$d_4$) δ=8.22-8.08 (m, 1H), 7.86-7.70 (m, 3H), 6.89-6.75 (m, 1H), 5.01-4.90 (m, 1H), 3.53-3.41 (m, 1H), 3.11-3.01 (m, 1H), 2.92 (q, J=7.1 Hz, 2H), 2.34-2.20 (m, 5H), 2.10 (br d, J=10.6 Hz, 2H), 1.80-1.64 (m, 2H), 1.51-1.36 (m, 2H), 1.25 (br d, J=6.0 Hz, 6H), 1.13-0.97 (m, 3H). ESI [M+H]=547.1.

Example 118

Preparation of isopropyl trans-N-[4-[5-[2-(ethylsulfamoyl)-4-[(5-isopropyl-1H-imidazol-2-yl)amino]phenyl]thiazol-2-yl]cyclohexyl]carbamate (Compound 142)

Following the same protocol and under the same reaction conditions as for Compound 141, Compound 142 was prepared. $^1$H NMR (400 MHz, methanol-$d_4$) δ=8.26-8.14 (m, 1H), 7.85-7.80 (m, 2H), 7.77-7.73 (m, 1H), 6.93-6.85 (m, 1H), 4.85-4.81 (m, 1H), 3.53-3.39 (m, 1H), 3.14-2.98 (m, 1H), 2.97-2.85 (m, 3H), 2.33-2.24 (m, 2H), 2.13-2.05 (m, 2H), 1.80-1.63 (m, 2H), 1.51-1.37 (m, 2H), 1.33 (d, J=6.8 Hz, 6H), 1.25 (br d, J=6.1 Hz, 6H), 1.10-0.99 (m, 3H). ESI [M+H]=575.1.

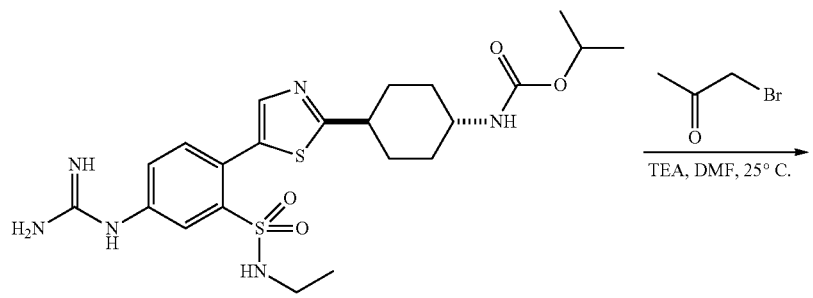

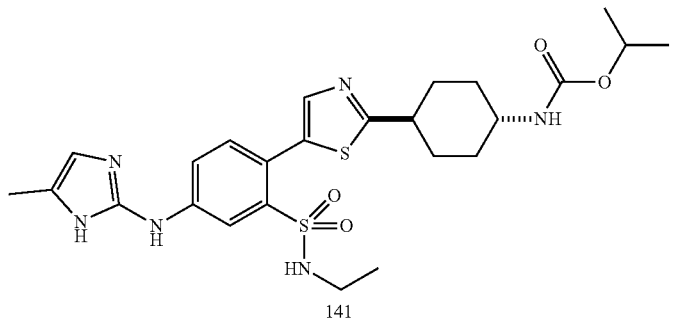

141

Example 119

Preparation of isopropyl trans-N-[4-[5-[2-(ethylsulfamoyl)-4-[(6-isopropylpyridazin-3-yl)amino]phenyl]thiazol-2-yl]cyclohexyl]carbamate (Compound 143)

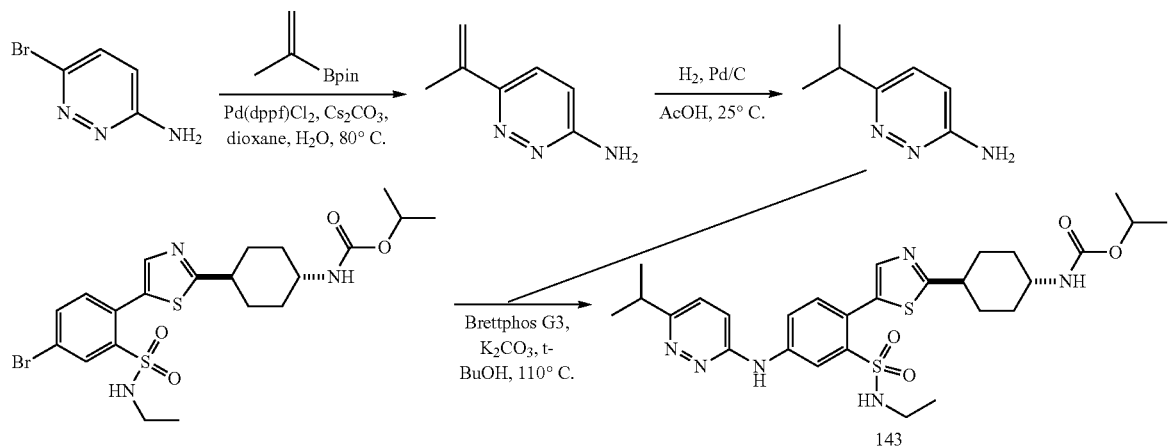

a) Synthesis of 6-isopropenylpyridazin-3-amine

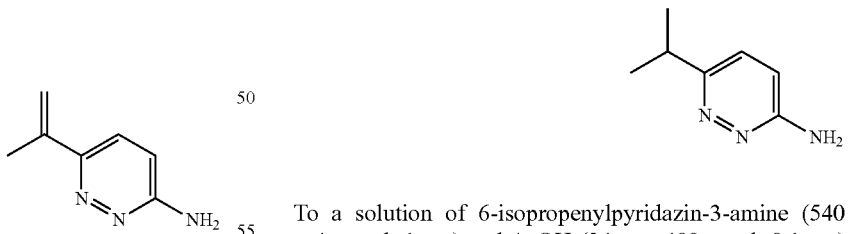

A mixture of 2-isopropenyl-4,4,5,5-tetramethyl-1,3,2-dioxaborolane (1.16 g, 7 mmol, 1.2 eq.), 6-bromopyridazin-3-amine (1 g, 6 mmol, 1 eq.), Cs₂CO₃ (5.6 g, 17 mmol, 3 eq.), Pd(dppf)Cl₂ (421 mg, 575 umol, 0.1 eq.) in dioxane (20 mL)/H₂O (10 mL) was stirred at 80° C. for 12 h under N₂ atmosphere, and then concentrated under reduced pressure to give a residue which was purified by column chromatography (SiO₂, petroleum ether:ethyl acetate=10:1 to 0:1) to yield 6-isopropenylpyridazin-3-amine (550 mg, 4 mmol, 71% yield) as a pale yellow solid. ESI [M+H]=136.1.

b) Synthesis of 6-isopropylpyridazin-3-amine

To a solution of 6-isopropenylpyridazin-3-amine (540 mg, 4 mmol, 1 eq.) and AcOH (24 mg, 400 umol, 0.1 eq.) in EtOAc (30 mL) was added Pd/C (50 mg, 10% purity) and the mixture was stirred under H₂ (15 psi) at 25° C. for 12 h. The reaction mixture was filtered and concentrated under reduced pressure to give a residue which was purified by prep-HPLC (neutral condition). column: Waters Xbridge Prep OBD C18 150*40 mm*10 um: mobile phase: [water (10 mM NH₄HCO₃)-ACN]; B %: 1%-15%,8 min to yield 6-isopropylpyridazin-3-amine (300 mg, 2 mmol, 55% yield) as a white solid. ¹H NMR (400 MHz, CDCl₃) δ=7.18-7.09 (m, 1H), 6.78-6.69 (m, 1H), 4.91-4.66 (m, 2H), 3.27-3.10 (m, 1H), 1.30 (d, J=7.0 Hz, 6H). ESI [M+H]=138.2.

c) Synthesis of isopropyl trans-N-[4-[5-[2-(ethylsulfamoyl)-4-[(6-isopropylpyridazin-3-yl)amino]phenyl]thiazol-2-yl]cyclohexyl]carbamate (Compound 143)

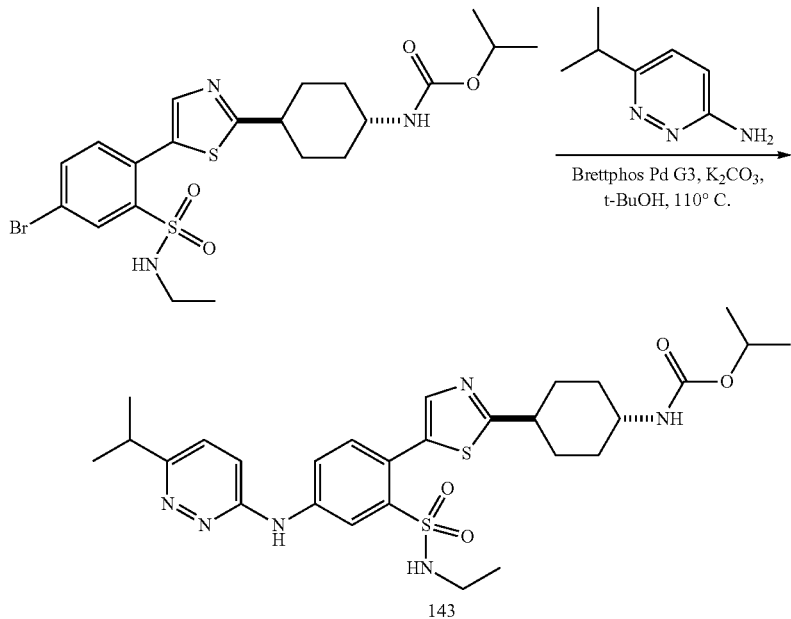

From isopropyl trans-N-[4-[5-[4-bromo-2-(ethylsulfamoyl)phenyl]thiazol-2-yl]cyclo-hexyl]carbamate and 6-isopropylpyridazin-3-amine, using General Method F. $^1$H NMR (400 MHz, methanol-$d_4$) δ=8.63-8.49 (m, 1H), 7.99-7.94 (m, 1H), 7.93-7.88 (m, 1H), 7.75 (s, 1H), 7.62-7.55 (m, 1H), 7.50 (d, J=8.3 Hz, 1H), 4.86-4.82 (m, 1H), 3.48 (tt, J=3.8, 11.5 Hz, 1H), 3.31-3.25 (m, 1H), 3.10-2.98 (m, 1H), 2.91 (q, J=7.2 Hz, 2H), 2.31-2.23 (m, 2H), 2.14-2.06 (m, 2H), 1.79-1.66 (m, 2H), 1.50-1.43 (m, 2H), 1.42 (d, J=7.0 Hz, 6H), 1.25 (br d, J=6.2 Hz, 6H), 1.07-0.98 (m, 3H). ESI [M+H]=587.1.

Example 120

Preparation of isopropyl trans-N-[4-[5-[2-(ethylsulfamoyl)-4-[[1-(2-methylpropanoyl)azetidin-3-yl]amino]phenyl]thiazol-2-yl]cyclohexyl]carbamate (Compound 146)

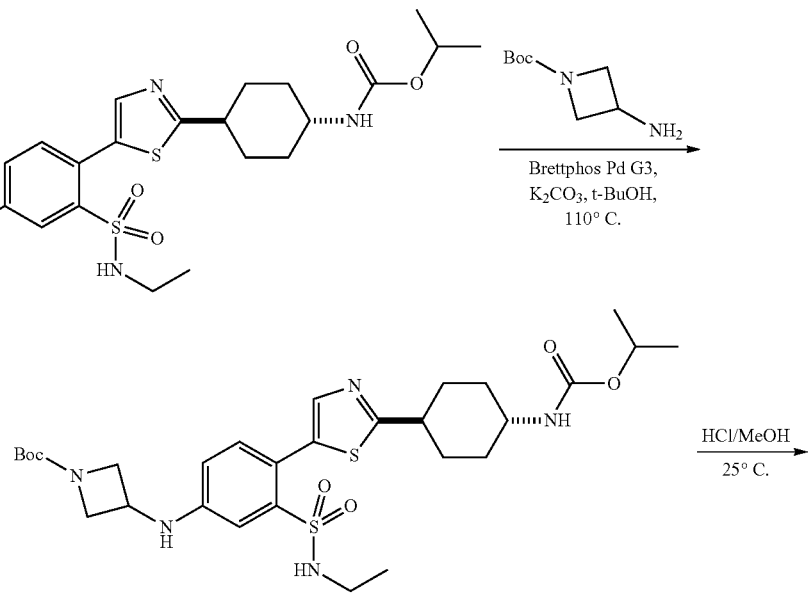

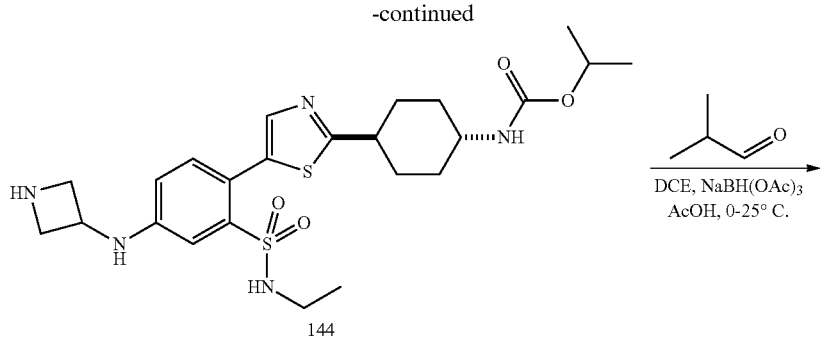
144
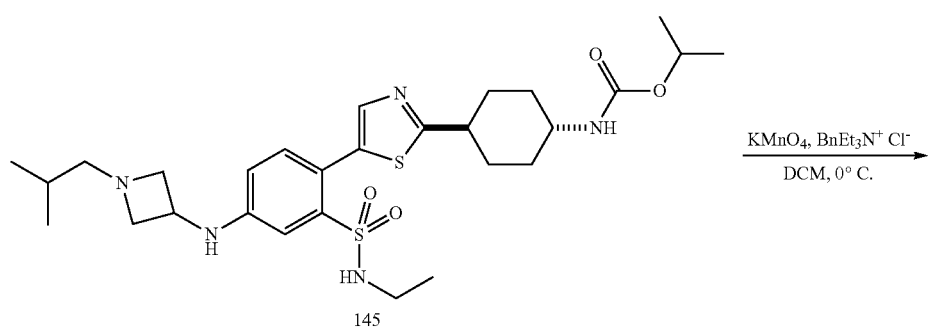
145
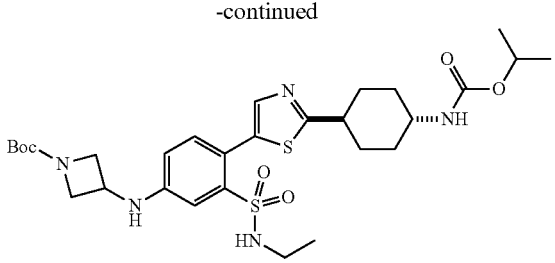
146
a) Synthesis of tert-butyl trans-3-[3-(ethylsulfamoyl)-4-[2-[4-(isopropoxy-carbonylamino)cyclohexyl]thiazol-5-yl]anilino]azetidine-1-carboxylate
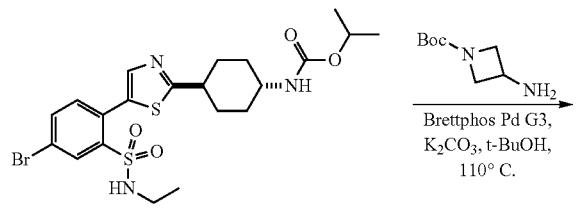
From isopropyl trans-N-[4-[5-[4-bromo-2-(ethylsulfamoyl)phenyl]thiazol-2-yl]cyclo-hexyl]carbamate and tert-butyl 3-aminoazetidine-1-carboxylate, using General Method F. ESI [M+H]=622.2.

b) Synthesis of isopropyl trans-N-[4-[5-[4-(azetidin-3-ylamino)-2-(ethyl-sulfamoyl)phenyl]thiazol-2-yl]cyclohexyl]carbamate (Compound 144)

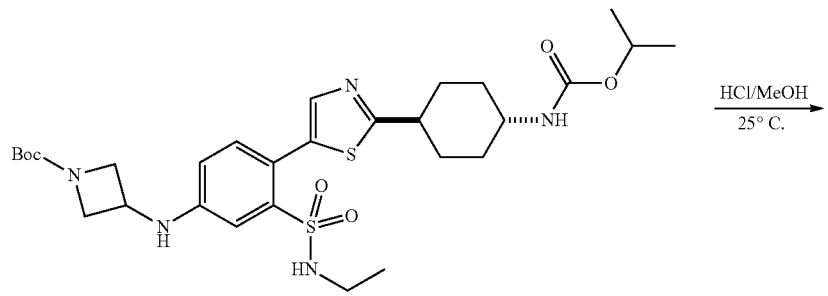

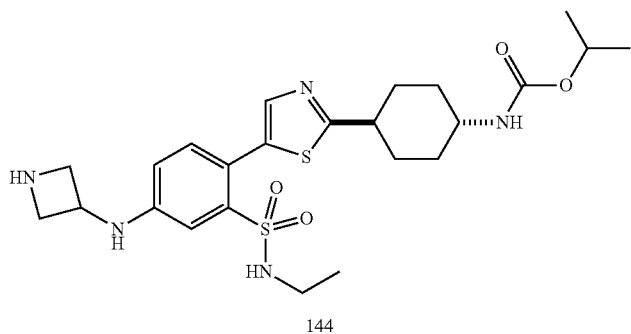

144

A mixture of tert-butyltrans-3-[3-(ethylsulfamoyl)-4-[2-[4-(isopropoxycarbonyl-amino)cyclohexyl]thiazol-5-yl]anilino]azetidine-1-carboxylate (100 mg, 161 umol, 1 eq.) in HCl/MeOH (2 mL) (4 M) was stirred at 25° C. for 30 min under $N_2$ atmosphere. The reaction mixture was concentrated under reduced pressure to yield isopropyl trans-N-[4-[5-[4-(azetidin-3-ylamino)-2-(ethylsulfamoyl)phenyl]thiazol-2-yl]cyclohexyl]carbamate (89.76 mg, crude, HCl salt) as a yellow oil. $^1$H NMR (400 MHz, methanol-$d_4$) δ=7.73 (s, 1H), 7.30 (dd, J=2.8, 5.0 Hz, 2H), 6.90-6.71 (m, 1H), 4.88-4.77 (m, 1H), 4.71-4.56 (m, 1H), 4.46 (br t, J=8.9 Hz, 2H), 4.15-3.97 (m, 2H), 3.47 (br t, J=11.6 Hz, 1H), 3.07 (br t, J=12.0 Hz, 1H), 2.87 (q, J=7.2 Hz, 2H), 2.25 (br d, J=12.2 Hz, 2H), 2.09 (br d, J=10.9 Hz, 2H), 1.78-1.59 (m, 2H), 1.52-1.35 (m, 2H), 1.24 (br d, J=5.9 Hz, 6H), 1.03 (br t, J=7.2 Hz, 3H). ESI [M+H]=522.2.

c) Synthesis of isopropyl trans-N-[4-[5-[2-(ethylsulfamoyl)-4-[(1-isobutyl-azetidin-3-yl)amino]phenyl]thiazol-2-yl]cyclohexyl]carbamate (Compound 145)

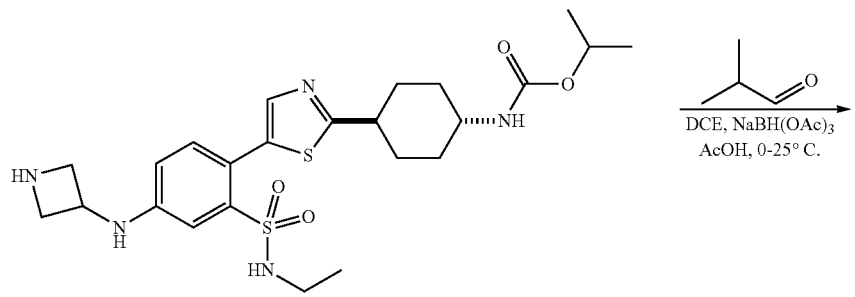

144

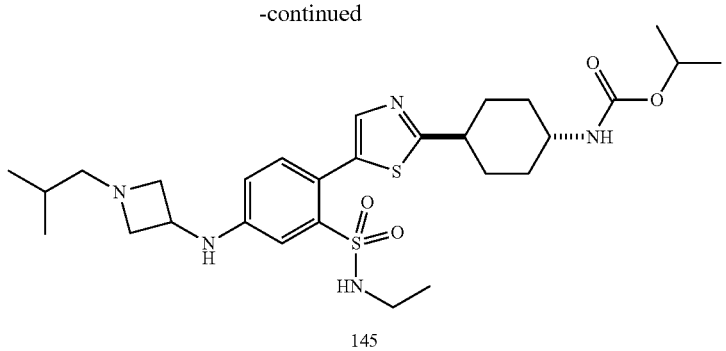

145

To a solution of isopropyl trans-N-[4-[5-[4-(azetidin-3-ylamino)-2-(ethylsulfamoyl) phenyl]thiazol-2-yl]cyclohexyl]carbamate (89 mg, 159 umol, 1.0 eq., HCl salt) in DCE (2 mL) was added AcOH (1 mg, 16 umol, 0.1 eq.), 2-methylpropanal (11.50 mg, 159 umol, 1.0 eq.), NaBH(OAc)$_3$ (101 mg, 478 umol, 3.0 eq.) at 0° C. The mixture was stirred at 25° C. for 2 h. The reaction mixture was concentrated under reduced pressure. The residue was purified by prep-HPLC (neutral condition; column: Waters Xbridge BEH C18 100*30 mm*10 um; mobile phase: [water(10 mM NH$_4$HCO$_3$)-ACN]; B %: 45%-75%,10 min) to yield isopropyl trans-N-[4-[5-[2-(ethylsulfamoyl)-4-[(1-isobutylazetidin-3-yl)amino]phenyl]thiazol-2-yl]cyclohexyl]carbamate (80 mg, 138 umol, 86.8% yield) as a yellow solid. $^1$H NMR (400 MHz, methanol-d$_4$) δ=7.62 (s, 1H), 7.33-7.22 (m, 2H), 6.86-6.71 (m, 1H), 4.80 (br d, J=6.0 Hz, 1H), 4.77-4.65 (m, 1H), 4.55 (br d, J=7.1 Hz, 1H), 4.44 (br s, 1H), 4.25 (br s, 1H), 3.99 (br d, J=9.5 Hz, 1H), 3.51-3.35 (m, 1H), 3.24-3.09 (m, 2H), 3.06-2.92 (m, 1H), 2.82 (q, J=7.1 Hz, 2H), 2.22 (br d, J=11.9 Hz, 2H), 2.06 (br d, J=10.4 Hz, 2H), 2.02-1.91 (m, 1H), 1.78-1.59 (m, 2H), 1.49-1.31 (m, 2H), 1.22 (d, J=6.2 Hz, 6H), 1.02 (d, J=6.6 Hz, 6H), 0.99 (t, J=7.3 Hz, 3H). ESI [M+H]=578.2.

d) Synthesis of isopropyl trans-N-[4-[5-[2-(ethylsulfamoyl)-[[1-(2-methylpropanoyl)azetidin-3-yl]amino]phenyl]thiazol-2-yl]cyclohexyl]carbamate (Compound 146)

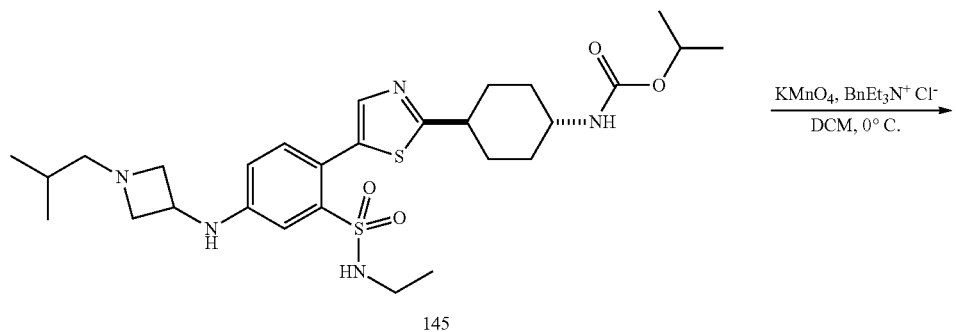

145

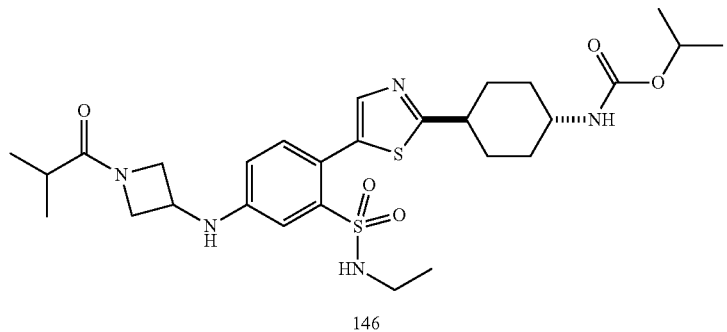

146

To a solution of isopropyl trans-N-[4-[5-[2-(ethylsulfamoyl)-4-[(1-isobutylazetidin-3-yl)amino]phenyl]thiazol-2-yl]cyclohexyl]carbamate (30 mg, 52 umol, 1.0 eq.) in DCM (2 mL) was added KMnO₄ (25 mg, 156 umol, 3.0 eq.) and benzyltriethylammonium chloride (35 mg, 156 umol, 3 eq.). The mixture was stirred at 0° C. for 0.5 h. The reaction was quenched with sat.aq. Na₂SO₃ 20 mL and extracted with DCM 20 mL (10 mL×2). The combined organic layers were dried with Na₂SO₄ and concentrated under reduced pressure. The residue was purified by prep-HPLC (TFA condition; column: Phenomenex Luna C18 150*30 mm*5 um; mobile phase: [water(0.1% TFA)-ACN]; B %: 45%-75%,10 min) to yield isopropyl trans-N-[4-[5-[2-(ethylsulfamoyl)-4-[[1-(2-methylpropanoyl)azetidin-3-yl]amino]phenyl]thiazol-2-yl]cyclohexyl]carbamate (6.1 mg, 9.6 umol, 18% yield, 92.8% purity) as a pale yellow solid. ¹H NMR (400 MHz, methanol-d₄) δ=7.64 (s, 1H), 7.24 (dd, J=2.9, 5.3 Hz, 2H), 6.76 (dd, J=2.4, 8.4 Hz, 1H), 4.83-4.75 (m, 1H), 4.70-4.59 (m, 1H), 4.42-4.29 (m, 2H), 4.10-3.96 (m, 1H), 3.88-3.73 (m, 1H), 3.51-3.35 (m, 1H), 2.99 (br t, J=12.0 Hz, 1H), 2.85 (q, J=7.3 Hz, 2H), 2.57 (td, J=6.6, 13.5 Hz, 1H), 2.22 (br d, J=12.8 Hz, 2H), 2.06 (br d, J=10.8 Hz, 2H), 1.76-1.60 (m, 2H), 1.47-1.33 (m, 2H), 1.22 (br d, J=6.0 Hz, 6H), 1.08 (dd, J=5.1, 6.6 Hz, 6H), 1.01 (t, J=7.3 Hz, 3H). ESI [M+H]=592.1.

Example 121

Preparation of isopropyl trans-N-[4-[5-[2-(ethylsulfamoyl)-4-[(3-methylazetidin-3-yl)amino]phenyl]thiazol-2-yl]cyclohexyl]carbamate (Compound 147)

a) Synthesis of tert-butyl trans-3-[3-(ethylsulfamoyl)-4-[4-(isopropoxy-carbonylamino)cyclohexyl]thiazol-5-yl]anilino]-3-methyl-azetidine-1-carboxylate

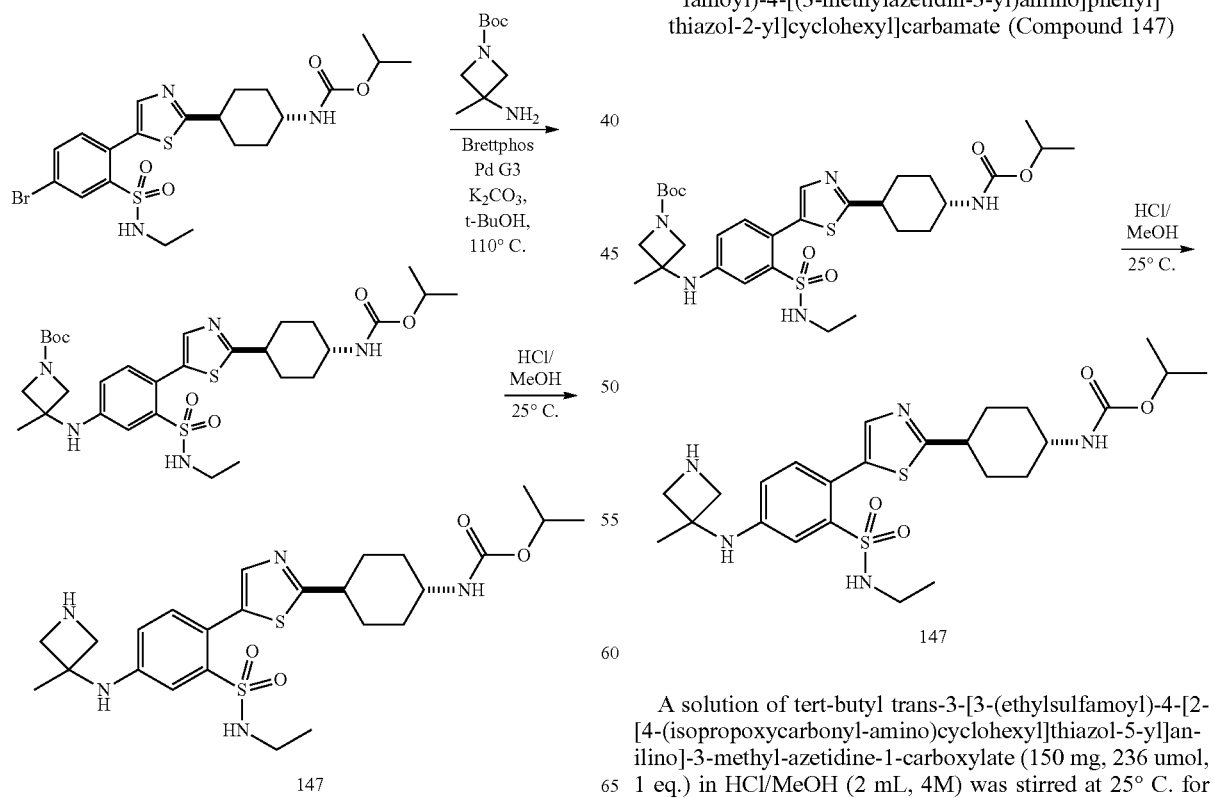

From isopropyl trans-N-[4-[5-[4-bromo-2-(ethylsulfamoyl)phenyl]thiazol-2-yl]cyclo-hexyl]carbamate and tert-butyl 3-amino-3-methylazetidine-1-carboxylate, using General Method F. ESI [M+H]=636.2.

b) Synthesis of isopropyl trans-N-[4-[5-[2-(ethylsulfamoyl)-4-[(3-methylazetidin-3-yl)amino]phenyl]thiazol-2-yl]cyclohexyl]carbamate (Compound 147)

A solution of tert-butyl trans-3-[3-(ethylsulfamoyl)-4-[2-[4-(isopropoxycarbonyl-amino)cyclohexyl]thiazol-5-yl]anilino]-3-methyl-azetidine-1-carboxylate (150 mg, 236 umol, 1 eq.) in HCl/MeOH (2 mL, 4M) was stirred at 25° C. for 2 h. The reaction was concentrated. The residue was purified by prep-HPLC (TFA condition: column: Phenomenex luna C18 250*50 mm*10 um; mobile phase: [water(0.1% TFA)-ACN]; B %: 15%-45%,10 min) to yield isopropyl trans-N-[4-[5-[2-(ethylsulfamoyl)-4-[(3-methylazetidin-3-yl)amino]phenyl]thiazol-2-yl]cyclohexyl]carbamate (6.7 mg, 10 umol, 4.3% yield, 99.4% purity, TFA) as a pale yellow solid. $^1$H NMR (400 MHz, methanol-d$_4$) δ=7.70-7.66 (m, 1H), 7.30 (d, J=8.4 Hz, 1H), 7.22 (d, J=2.5 Hz, 1H), 6.71 (dd, J=2.4, 8.3 Hz, 1H), 4.85 (br s, 1H), 4.25-4.14 (m, 4H), 3.47 (ddd, J=4.1, 7.7, 11.5 Hz, 1H), 3.04 (br t, J=12.0 Hz, 1H), 2.86 (q, J=7.1 Hz, 2H), 2.25 (br d, J=12.3 Hz, 2H), 2.13-2.03 (m, 2H), 1.76-1.66 (m, 5H), 1.43 (dq, J=3.0, 12.5 Hz, 2H), 1.28-1.20 (m, 6H), 1.03 (t, J=7.2 Hz, 3H). ESI [M+H]=536.2.

Example 122

Preparation of isopropyl trans-N-[4-[5-[2-(azetidin-1-ylsulfonyl)-4-(1H-imidazol-2-ylamino)phenyl]thiazol-2-yl]cyclohexyl]carbamate (Compound 148)

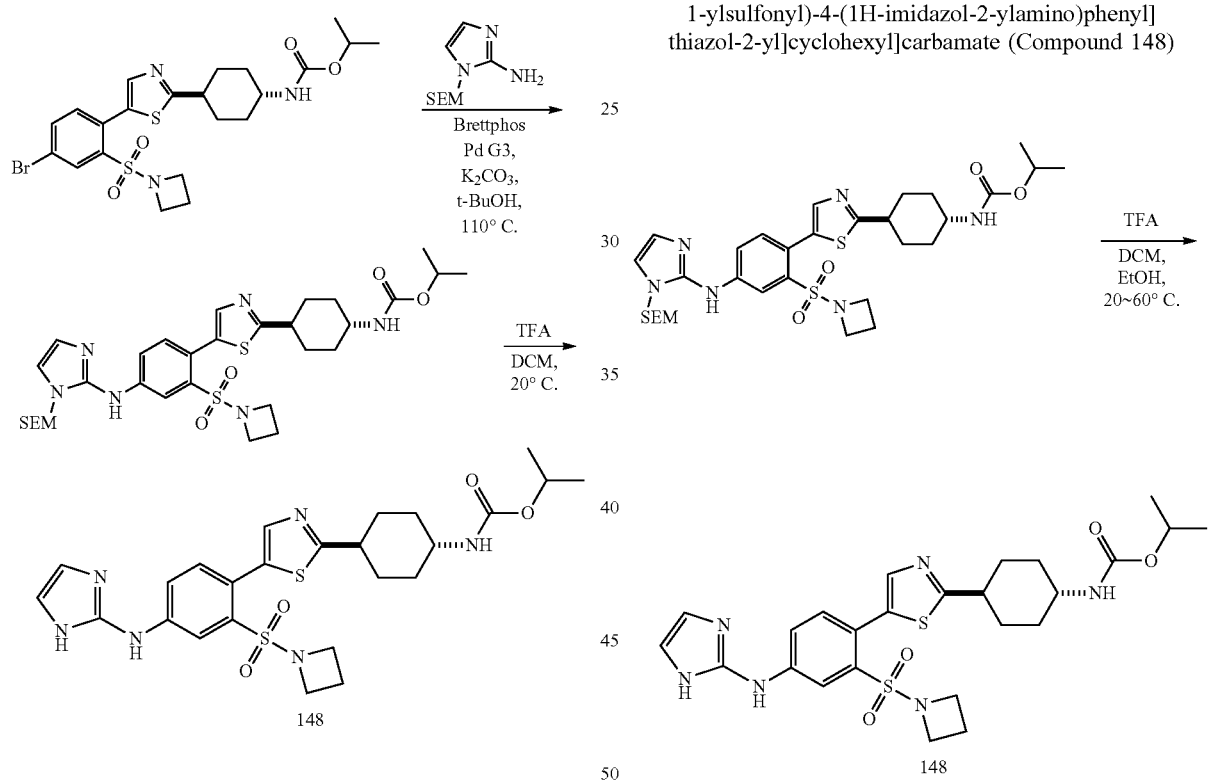

a) Synthesis of isopropyl trans-N-[4-[5-[2-(azetidin-1-ylsulfonyl)-4-[[1-(2-trimethylsilylethoxymethyl)-1H-imidazol-2-yl]amino]phenyl]thiazol-2-yl]cyclohexyl]carbamate

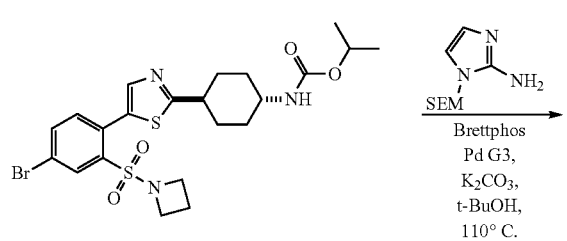

From isopropyl trans-N-[4-[5-[2-(azetidin-1-ylsulfonyl)-4-bromo-phenyl]thiazol-2-yl]cyclohexyl]carbamate and 1-((2-(trimethylsilyl)ethoxy)methyl)-1H-imidazol-2-amine, using General Method F. ESI [M+H]=675.3.

b) Synthesis of isopropyl trans-N-[4-[5-[2-(azetidin-1-ylsulfonyl)-4-(1H-imidazol-2-ylamino)phenyl]thiazol-2-yl]cyclohexyl]carbamate (Compound 148)

From isopropyl trans-N-[4-[5-[2-(azetidin-1-ylsulfonyl)-4-[[1-(2-trimethylsilylethoxy-methyl)-1H-imidazol-2-yl]amino]phenyl]thiazol-2-yl]cyclohexyl]carbamate, using General Method I. $^1$H NMR (400 MHz, methanol-d$_4$) δ=7.89 (d, J=2.2 Hz, 1H), 7.71 (s, 1H), 7.62-7.48 (m, 2H), 7.11 (s, 2H), 4.84-4.76 (m, 1H), 3.68 (t, J=7.7 Hz, 4H), 3.54-3.38 (m, 1H), 3.04 (tt, J=3.5, 12.1 Hz, 1H), 2.27-2.17 (m, 2H), 2.17-2.09 (m, 2H), 2.07 (br d, J=10.8 Hz, 2H), 1.70 (dq, J=2.9, 12.8 Hz, 2H), 1.41 (dq, J=3.1, 12.6 Hz, 2H), 1.22 (br d, J=6.2 Hz, 6H). ESI [M+H]=545.2.

Example 123

Preparation of isopropyl trans-N-[4-[5-[2-(ethylsulfamoyl)-4-(2H-triazol-4-ylamino)phenyl]thiazol-2-yl]cyclohexyl]carbamate (Compound 149)

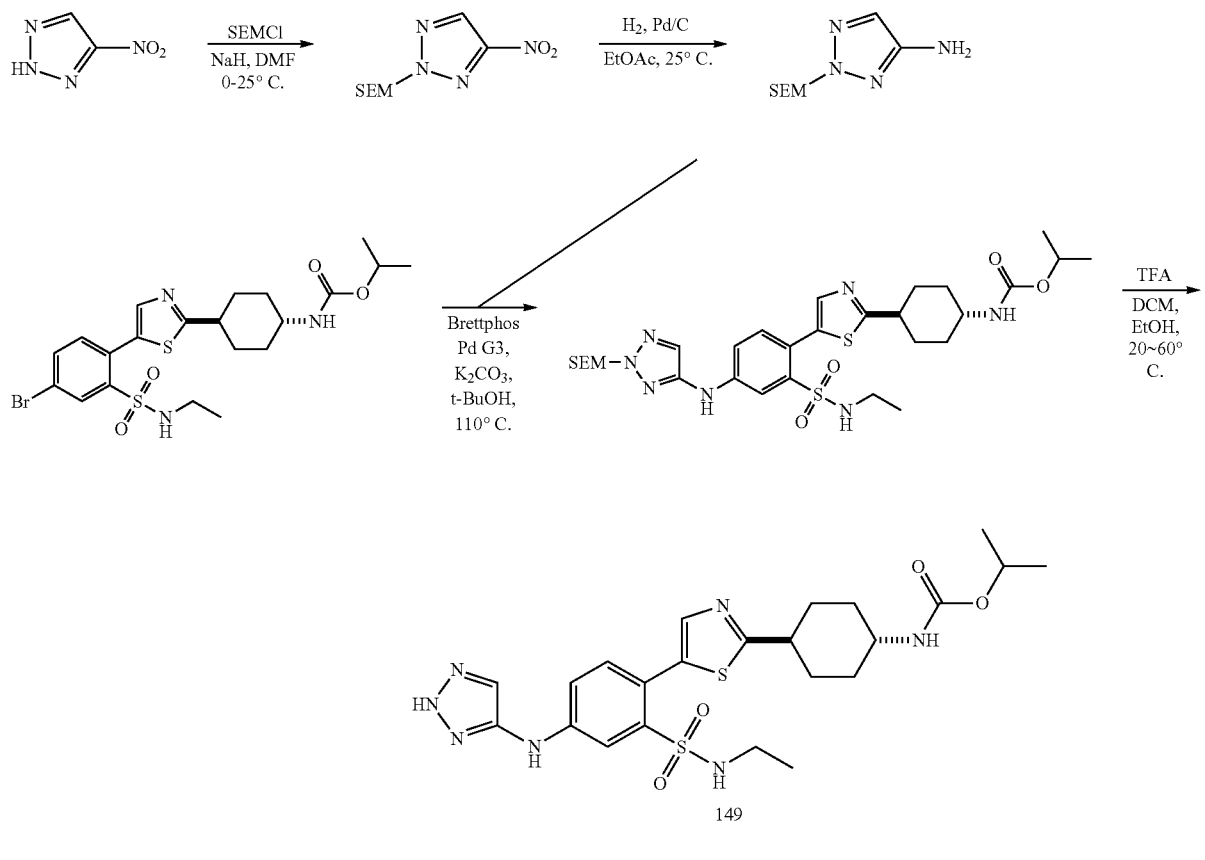

a) Synthesis of trimethyl-[2-[(4-nitrotriazol-2-yl)methoxy]ethyl]silane b) Synthesis of 2-(2-trimethylsilylethoxymethyl)triazol-4-amine

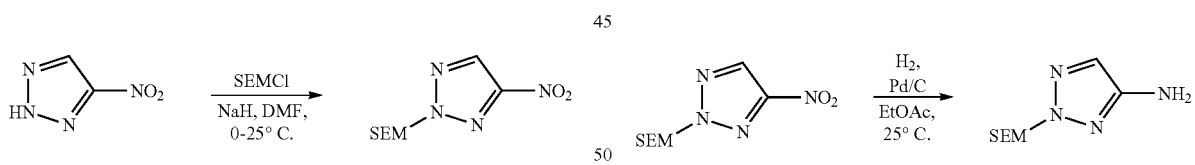

To a solution of 4-nitro-2H-triazole (1 g, 8.7 mmol, 1 eq.) in THF (20 mL) was added SEM-Cl (1.75 g, 10.5 mmol, 1.2 eq.) and NaH (385 mg, 9.6 mmol, 60% in oil, 1.1 eq.) at 0° C. The mixture was stirred at 25° C. for 12 h. The reaction mixture was quenched by sat.aq. NH$_4$Cl (10 mL) at 0° C., and then extracted with ethyl acetate (60 mL) (20 mL×3). The combined organic layers were dried over Na$_2$SO$_4$, filtered and concentrated under reduced pressure to give a residue, which was purified by MPLC (SiO$_2$, petroleum ether:ethyl acetate=50:1 to 10:1) to yield trimethyl-[2-[(4-nitrotriazol-2-yl)methoxy]ethyl]silane (0.76 g, 3.1 mmol, 35% yield) as colorless oil. $^1$H NMR (400 MHz, CDCl$_3$) δ=8.30-8.21 (m, 1H), 5.67-5.56 (m, 2H), 3.79-3.68 (m, 2H), 1.01-0.92 (m, 2H), 0.05-0.05 (m, 9H).

To a solution of trimethyl-[2-[(4-nitrotriazol-2-yl)methoxy]ethyl]silane (0.76 g, 3.1 mmol, 1 eq.) in ethyl acetate (20 mL) was added Pd/C (0.05 g, 10% purity). The mixture was stirred under H$_2$ (15 psi) at 25° C. for 12 h. The reaction mixture was filtered and concentrated under reduced pressure to give a residue, which was purified by prep-HPLC (neutral condition: column: Welch Xtimate C18 150*30 mm*5 um; mobile phase: [water(10 mM NH$_4$HCO$_3$)-ACN]; B %: 20%-50%,8 min) to yield 2-(2-trimethylsilyl-ethoxymethyl)triazol-4-amine (0.3 g, 1.4 mmol, 45% yield) as a white solid. $^1$H NMR (400 MHz, CDCl$_3$) δ=7.17-7.03 (m, 1H), 5.55-5.43 (m, 2H), 3.86-3.73 (m, 2H), 3.68-3.54 (m, 2H), 1.00-0.82 (m, 2H), 0.00 (s, 9H). ESI [M+H]=215.1.

c) Synthesis of isopropyl trans-N-[4-[5-[2-(ethylsulfamoyl)-4-[[2-(2-trimethyl-silylethoxymethyl)triazol-4-yl]amino]phenyl]thiazol-2-yl]cyclohexyl]carbamate

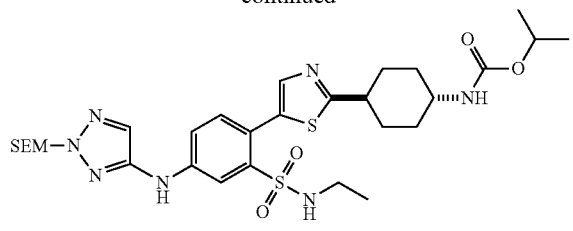

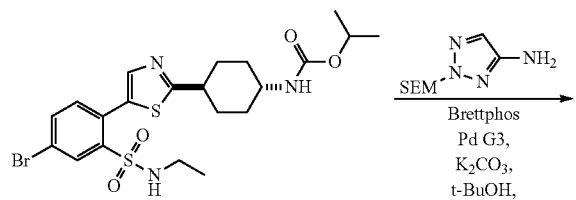

From isopropyl trans-N-[4-[5-[4-bromo-2-(ethylsulfamoyl)phenyl]thiazol-2-yl]cyclo-hexyl]carbamate and 2-(2-trimethylsilyl-ethoxymethyl)triazol-4-amine, using General Method F. ESI [M+H]=664.3.

d) Synthesis of isopropyl trans-N-[4-[5-[2-(ethylsulfamoyl)-4-(2H-triazol-4-ylamino)phenyl]thiazol-2-yl]cyclohexyl]carbamate (Compound 149)

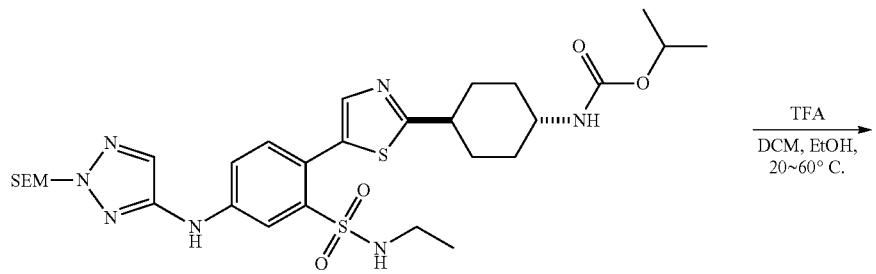

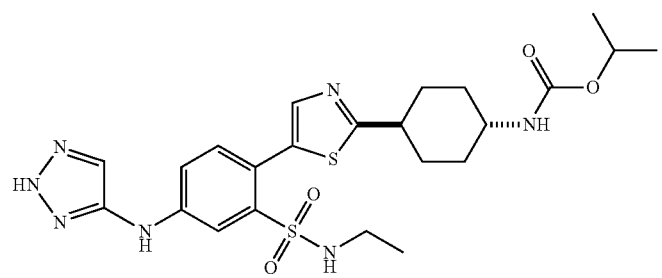

149

From isopropyl trans-N-[4-[5-[2-(ethylsulfamoyl)-4-[[2-(2-trimethyl-silylethoxy-methyl)triazol-4-yl]amino]phenyl]thiazol-2-yl]cyclohexyl]carbamate, using General Method I. $^1$H NMR (400 MHz, methanol-$d_4$) δ=8.15-8.03 (m, 1H), 7.80-7.71 (m, 1H), 7.58-7.50 (m, 1H), 7.49-7.44 (m, 1H), 7.41-7.33 (m, 1H), 4.80-4.71 (m, 1H), 3.54-3.42 (m, 1H), 3.12-3.03 (m, 1H), 2.99-2.90 (m, 2H), 2.33-2.23 (m, 2H), 2.16-2.03 (m, 2H), 1.81-1.66 (m, 2H), 1.52-1.36 (m, 2H), 1.34-1.20 (m, 6H), 1.12-1.05 (m, 3H). ESI [M+H]=534.2.

Example 124

Preparation of isopropyl trans-N-[4-[5-[2-(ethylsulfamoyl)-4-[1H-imidazol-2-yl(methyl)amino]phenyl]thiazol-2-yl]cyclohexyl]carbamate (Compound 150)

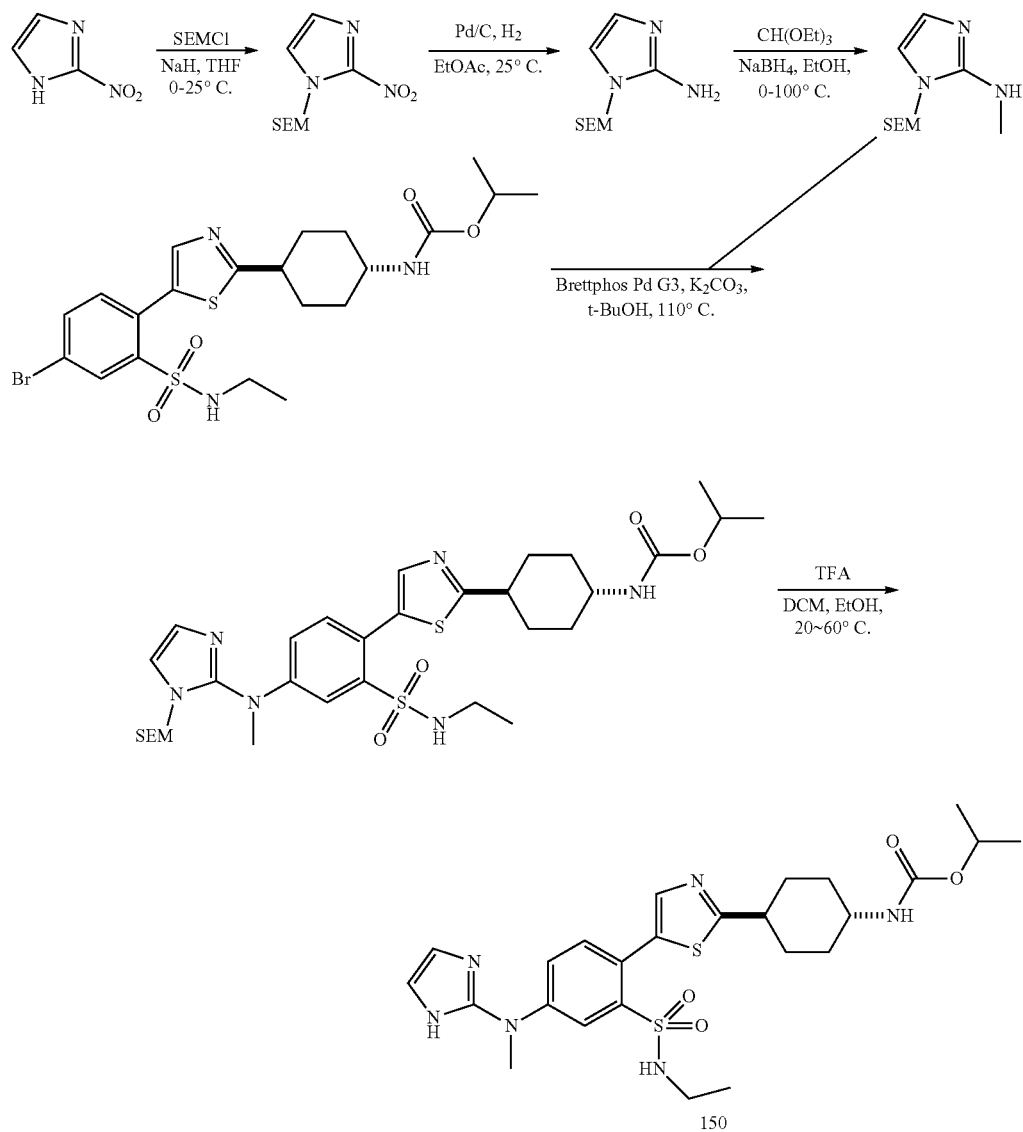

a) Synthesis of trimethyl-[2-[(2-nitroimidazol-1-yl)methoxy]ethyl]silane

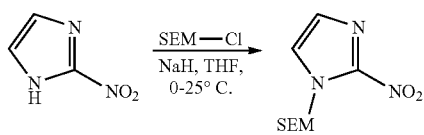 [SMILES: O=[N+]([O-])c1ncc[nH]1 ; C[Si](C)(C)CCOCCl ; C[Si](C)(C)CCOCn1ccnc1[N+](=O)[O-]]

A mixture of 2-nitro-1H-imidazole (9 g, 79.5 mmol, 1 eq.), NaH (9.55 g, 238.7 mmol, 60% purity, 3 eq.) in THF (150 mL) was degassed and purged with $N_2$ for 3 times, and then the mixture was stirred at 0° C. for 30 min under $N_2$ atmosphere, then to the mixture was added 2-(chloromethoxy)ethyl-trimethyl-silane (15.92 g, 95.5 mmol, 16.9 mL, 1.2 eq.) at 0° C. The mixture was stirred at 25° C. for 2 h. The reaction mixture was quenched by pouring into sat.aq. $NH_4Cl$ 50 mL at 0° C. and then diluted with $H_2O$ (50 mL) and extracted with ethyl acetate 450 mL (150 mL×3). The combined organic layers were dried over $Na_2SO_4$, filtered and concentrated under reduced pressure to give a residue, which was purified by column chromatography ($SiO_2$, petroleum ether:ethyl acetate=10:1 to 2:1) to yield trimethyl-[2-[(2-nitroimidazol-1-yl)methoxy]ethyl]silane (13 g, 53.4 mmol, 67% yield) as a white solid. $^1H$ NMR (400 MHz, $CDCl_3$) δ=7.34 (d, J=0.88 Hz, 1H), 7.18 (d, J=0.88 Hz, 1H), 5.78 (s, 2H) 3.59-3.72 (m, 2H), 0.87-1.04 (m, 2H), 0.04-0.02 (m, 9H).

b) Synthesis of 1-(2-trimethylsilylethoxymethyl)imidazol-2-amine

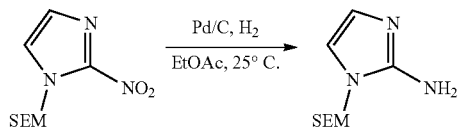 [SMILES: C[Si](C)(C)CCOCn1ccnc1[N+](=O)[O-] ; C[Si](C)(C)CCOCn1ccnc1N]

A mixture of trimethyl-[2-[(2-nitroimidazol-1-yl)methoxy]ethyl]silane (4 g, 16.44 mmol, 1 eq.), Pd/C (200 mg, 10% purity), in ethyl acetate (20 mL) was degassed and purged with N$_2$ for 3 times, and then the mixture was stirred at 25° C. for 3 h under H$_2$ atmosphere. The reaction was filtered and the filtrate was concentrated under reduced pressure to give a residue which was purified by prep-HPLC (column: Welch Xtimate C18 250*50 mm*10 um; mobile phase: [water(10 mM NH$_4$HCO$_3$)-ACN]; B %: 20%-50%, 23 min) to yield 1-(2-trimethylsilylethoxymethyl)imidazol-2-amine (3.1 g, 14.5 mmol, 88% yield) as a white solid. $^1$H NMR (400 MHz, methanol-d$_4$) δ=6.67 (d, J=1.63 Hz, 1H), 6.48 (d, J=1.75 Hz, 1H), 5.13 (s, 2H), 3.46-3.61 (m, 2H), 0.84-0.96 (m, 2H), 0.00 (s, 9H). ESI [M+H]=214.2.

c) Synthesis of N-methyl-1-(2-trimethylsilylethoxymethyl)imidazol-2-amine

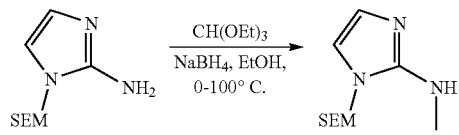

A solution of 1-(2-trimethylsilylethoxymethyl)imidazol-2-amine (2 g, 9.3 mmol, 1 eq.) in diethoxymethoxyethane (20 mL) was stirred at 100° C. for 3 h. The reaction mixture was concentrated under reduced pressure. The residue was dissolved in EtOH (20 mL) and NaBH$_4$ (1.06 g, 28.1 mmol, 3 eq.) was added to the solution in portions at 0° C. and stirred at 80° C. for 2 h. The reaction mixture was quenched with H$_2$O (10 mL) at 30° C., the reaction mixture was concentrated under reduced pressure to remove solvent, and then the mixture was diluted with H$_2$O (20 mL) and extracted with ethyl acetate 90 mL (30 mL×3). The combined organic layers dried over Na$_2$SO$_4$, filtered and concentrated under reduced pressure to give a residue which was purified by prep-HPLC (column: Agela DuraShell C18 250*25 mm*10 um; mobile phase: [water(10 mM NH$_4$HCO$_3$)-ACN]; B %: 5%-33%,22 min) to yield N-methyl-1-(2-trimethylsilylethoxy-methyl)imidazol-2-amine (470 mg, 2.0 mmol, 22% yield) as a pale yellow oil. $^1$H NMR (400 MHz, methanol-d$_4$) δ=6.69 (d, J=1.71 Hz, 1H), 6.44-6.57 (m, 1H), 5.10 (s, 2H), 3.52-3.63 (m, 2H), 2.89 (s, 3H), 0.88-0.95 (m, 2H), 0.00 (s, 9H). ESI [M+H]=228.0 d) Synthesis of isopropyl trans-N-[4-[5-[2-(ethylsulfamoyl)-4-[methyl-[1-(2-trimethylsilylethoxymethyl)imidazol-2-yl]amino]phenyl]thiazol-2-yl]cyclohexyl]carbamate

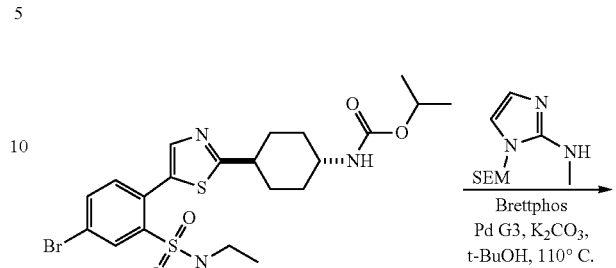

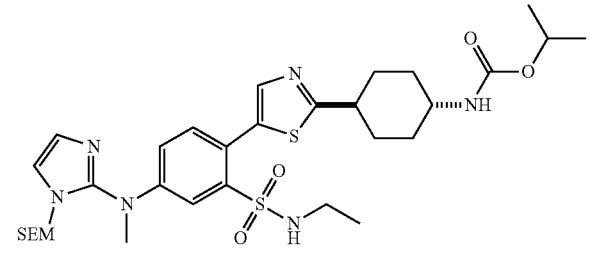

From isopropyl trans-N-[4-[5-[4-bromo-2-(ethylsulfamoyl)phenyl]thiazol-2-yl]cyclo-hexyl]carbamate and N-methyl-1-(2-trimethylsilylethoxy-methyl)imidazol-2-amine, using General Method F. ESI [M+H]=677.3.

e) Synthesis of isopropyl trans-N-[4-[5-[2-(ethylsulfamoyl)-4-[1H-imidazol-2-yl(methyl)amino]phenyl]thiazol-2-yl]cyclohexyl]carbamate (Compound 150)

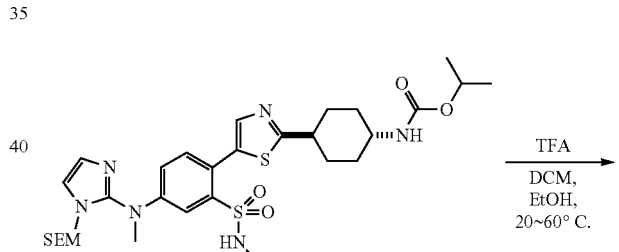

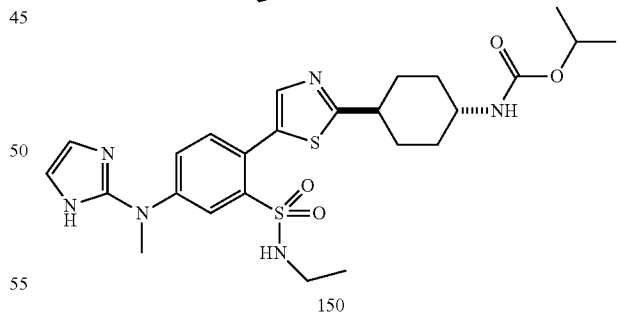

From isopropyl trans-N-[4-[5-[2-(ethylsulfamoyl)-4-[methyl-[1-(2-trimethylsilyl-ethoxymethyl)imidazol-2-yl]amino]phenyl]thiazol-2-yl]cyclohexyl]carbamate, using General Method I. $^1$H NMR (400 MHz, methanol-d$_4$) δ=8.11 (d, J=2.25 Hz, 1H), 7.80 (s, 1H), 7.65-7.76 (m, 2H), 7.06 (s, 2H), 4.75 (br s, 1H), 3.60 (s, 3H), 3.48 (tt, J=11.58, 3.99 Hz, 1H), 3.05 (tt, J=12.05, 3.52 Hz, 1H), 2.90 (q, J=7.25 Hz, 2H), 2.22-2.34 (m, 2H), 2.02-2.15 (m, 2H), 1.73 (qd, J=12.84, 3.00 Hz, 2H), 1.37-1.53 (m, 2H), 1.25 (br d, J=6.25 Hz, 6H), 1.00-1.08 (m, 3H). ESI [M+H]=547.2.

Example 125
Preparation of isopropyl trans-N-[4-[5-[2-(tert-butylsulfamoyl)-4-(4H-1,2,4-triazol-3-ylamino)phenyl]thiazol-2-yl]cyclohexyl]carbamate (Compound 151)
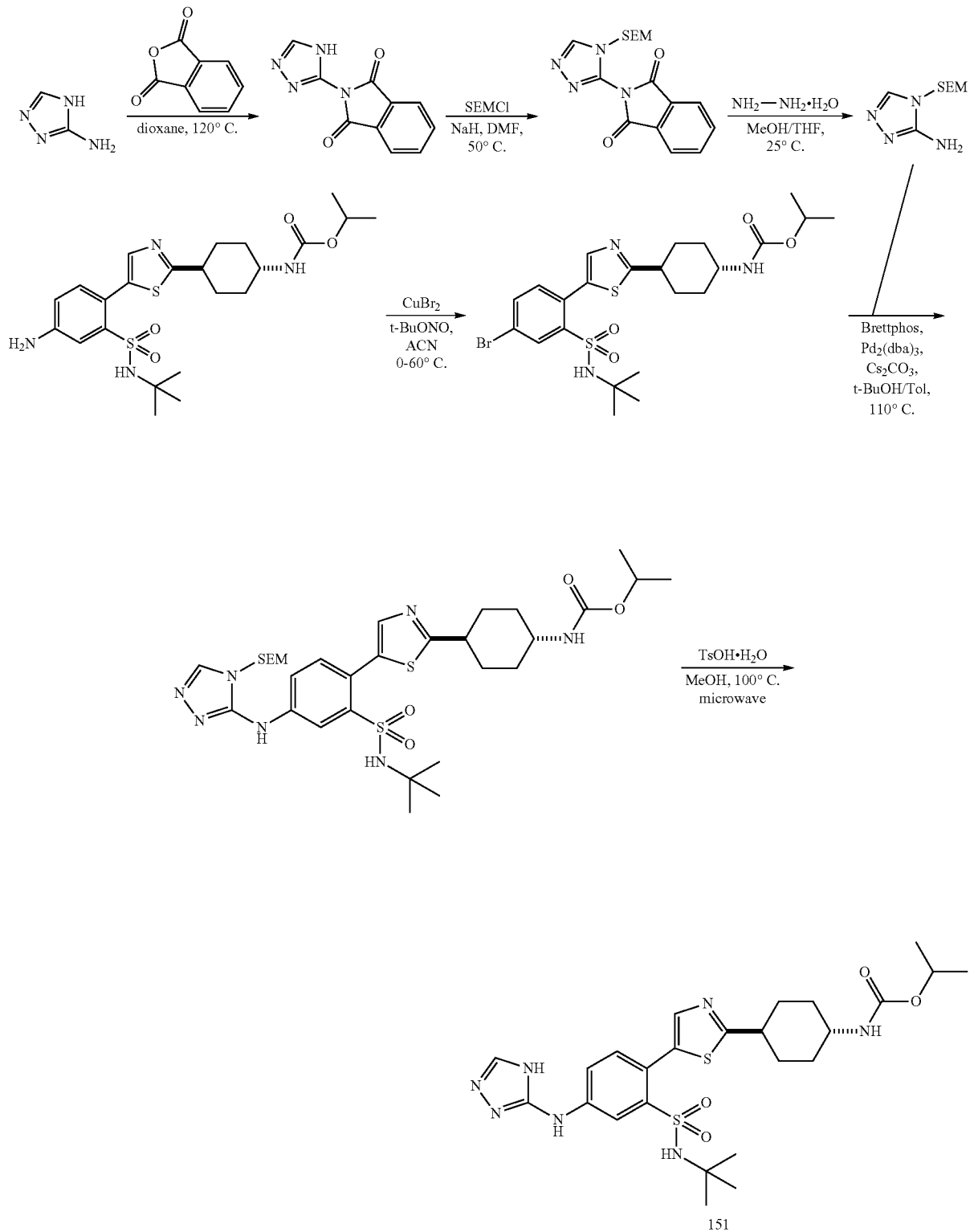

a) Synthesis of 2-(4H-1,2,4-triazol-3-yl)isoindoline-1,3-dione

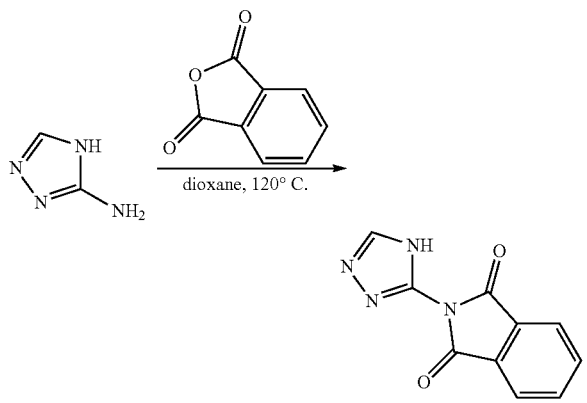

A mixture of 1H-1,2,4-triazol-3-amine (8.4 g, 99.9 mmol, 1 eq) and isobenzofuran-1,3-dione (14.80 g, 99.9 mmol, 1 eq) in dioxane (200 mL) the mixture was stirred at 120° C. for 10 h under N₂ atmosphere. The mixture was cooled to 25° C., and then filtered to yield 2-(4H-1,2,4-triazol-3-yl)isoindoline-1,3-dione (14 g, 65.3 mmol, 65.4% yield) as a white solid. ESI [M−H]=212.9.

b) Synthesis of 2-[4-(2-trimethylsilylethoxymethyl)-1,2,4-triazol-3-yl]isoindoline-1,3-dione

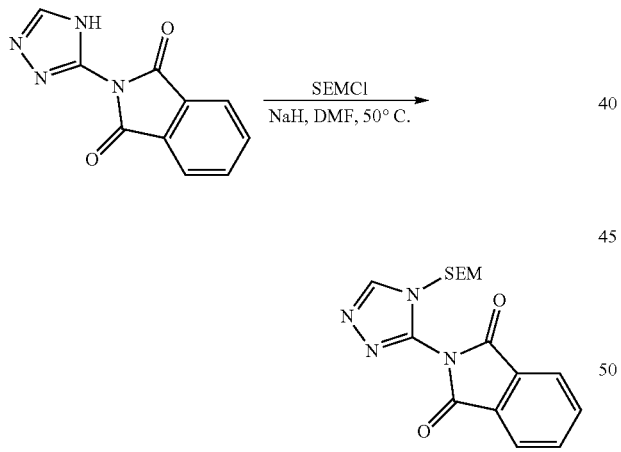

To a mixture of 2-(chloromethoxy)ethyl-trimethyl-silane (5.84 g, 35.0 mmol, 1.5 eq), 2-(4H-1,2,4-triazol-3-yl)isoindoline-1,3-dione (5 g, 23.3 mmol, 1 eq) was added NaH (1.40 g, 35.0 mmol, 60% in oil, 1.5 eq) in DMF (50 mL), and then the mixture was stirred at 50° C. for 5 h under N₂ atmosphere. The reaction mixture was quenched with H₂O (20 mL) and extracted with ethyl acetate 180 mL (60 mL×3). The combined organic layers were washed with sat.aq. NaCl 100 mL (20 mL×5), dried over Na₂SO₄, filtered and concentrated under reduced pressure to yield 2-[4-(2-trimethylsilylethoxymethyl)-1,2,4-triazol-3-yl]isoindoline-1,3-dione (9 g, crude) as yellow oil. ESI [M+H]=345.2.

c) Synthesis of 4-(2-trimethylsilylethoxymethyl)-1,2,4-triazol-3-amine

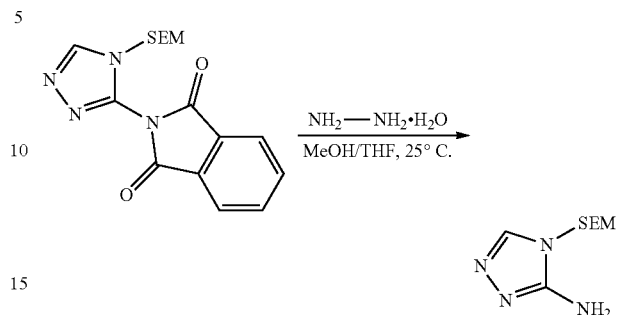

To a solution of 2-[4-(2-trimethylsilylethoxymethyl)-1,2,4-triazol-3-yl]isoindoline-1,3-dione (8 g, 23.2 mmol, 1 eq) in THF (40 mL) and MeOH (40 mL) was added NH₂—NH₂.H₂O (1.74 g, 34.8 mmol, 98% purity, 1.5 eq,), and then the mixture was stirred at 25° C. for 10 h under N₂ atmosphere. The mixture was concentrated, and purified by column chromatography (SiO₂, petroleum ether:ethyl acetate=1:1 to 0:1) to yield 4-(2-trimethylsilylethoxymethyl)-1,2,4-triazol-3-amine (2 g, 9.3 mmol, 40% yield) as white solid. $^1$H NMR (400 MHz, methanol-d₄) δ=8.11-8.25 (m, 1H), 5.25 (br s, 2H), 3.51-3.69 (m, 2H), 0.81-1.00 (m, 2H), −0.10-0.10 (m, 9H). ESI [M+H]=215.1.

d) Synthesis of isopropyl trans-N-[4-[5-[4-bromo-2-(tert-butylsulfamoyl) phenyl]thiazol-2-yl]cyclohexyl]carbamate

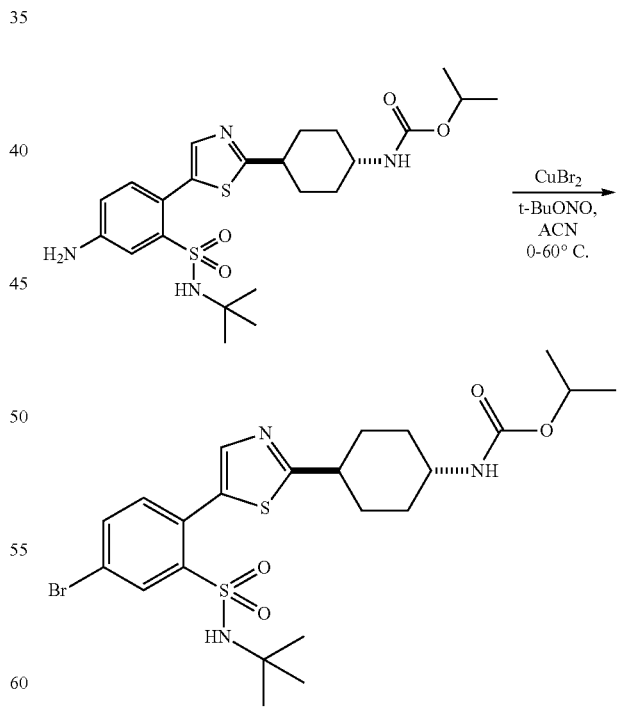

From isopropyl (trans-4-(5-(4-amino-2-(N-(tert-butyl)sulfamoyl)phenyl)thiazol-2-yl)cyclohexyl)carbamate, using General Method L. $^1$H NMR (400 MHz, methanol-d₄) δ=8.26 (d, J=2.2 Hz, 1H), 7.83-7.76 (m, 2H), 7.41 (d, J=8.2 Hz, 1H), 4.85-4.78 (m, 1H), 3.52-3.39 (m, 1H), 3.03 (tt, J=3.6, 12.0 Hz, 1H), 2.28-2.18 (m, 2H), 2.12-2.02 (m, 2H), 1.70 (dq, J=2.6, 12.9 Hz, 2H), 1.46-1.34 (m, 2H), 1.22 (br d, J=6.2 Hz, 6H), 1.09 (s, 9H).

e) Synthesis of isopropyl trans-N-[4-[5-[2-(tert-butylsulfamoyl)-4-[[4-(2-trimethylsilylethoxymethyl)-1,2,4-triazol-3-yl]amino]phenyl]thiazol-2-yl]cyclohexyl]carbamate

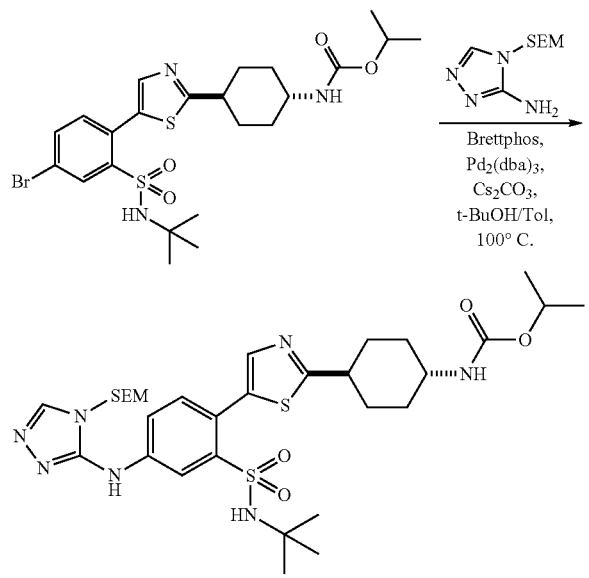

A mixture of isopropyl trans-N-[4-[5-[4-bromo-2-(tert-butylsulfamoyl)phenyl]thiazol-2-yl]cyclohexyl]carbamate (150 mg, 268.5 umol, 1 eq.), 4-(2-trimethylsilyl-ethoxymethyl)-1,2,4-triazol-3-amine (86 mg, 402.8 umol, 1.5 eq.), Cs$_2$CO$_3$ (175 mg, 537.1 umol, 2 eq.), Brettphos (14 mg, 26.8 umol, 0.1 eq.) and Pd$_2$(dba)$_3$ (24 mg, 26.8 umol, 0.1 eq.) in t-BuOH (1.5 mL) and toluene (1.5 mL) was stirred at 100° C. for 12 h under Ar atmosphere. The reaction mixture was concentrated, and purified by prep-TLC (SiO$_2$, petroleum ether:ethyl acetate=1:1) to yield isopropyl trans-N-[4-[5-[2-(tert-butylsulfamoyl)-4-[[4-(2-trimethylsilylethoxymethyl)-1,2,4-triazol-3-yl]amino]phenyl]thiazol-2-yl]cyclohexyl]carbamate (205 mg, crude) as a yellow solid. ESI [M+H]=692.3.

f) Synthesis of isopropyl trans-N-[4-[5-[2-(tert-butylsulfamoyl)-4-(4H-1,2,4-triazol-3-ylamino)phenyl]thiazol-2-yl]cyclohexyl]carbamate (Compound 151)

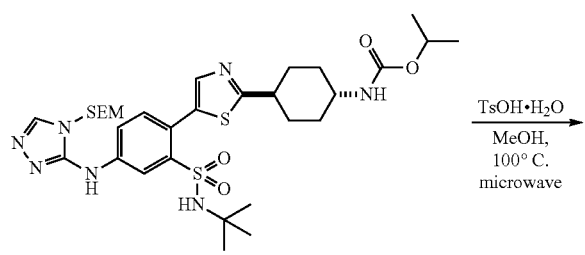

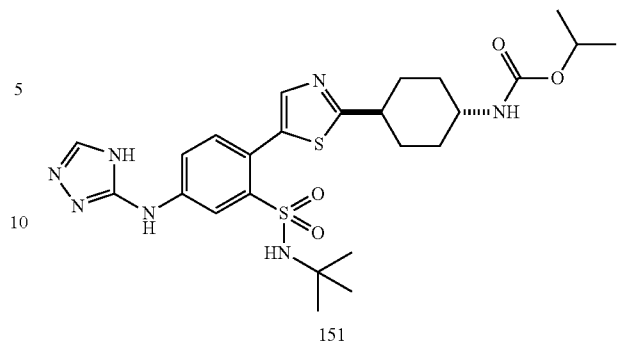

Isopropyl trans-N-[4-[5-[2-(tert-butylsulfamoyl)-4-[[4-(2-trimethylsilylethoxymethyl)-1,2,4-triazol-3-yl]amino]phenyl]thiazol-2-yl]cyclohexyl]carbamate (80 mg, 115.6 umol, 1 eq.) and TsOH.H$_2$O (32 mg, 173.4 umol, 1.5 eq.) were taken up into a microwave tube with MeOH (3 mL). The sealed tube was heated at 100° C. for 0.5 h under microwave. The reaction mixture was concentrated under reduced pressure and purified by prep-HPLC (TFA condition: column: Nano-micro Kromasil C18 80*25 mm 3 um; mobile phase: [water(0.1% TFA)-ACN]; B %: 24%-58%,7 min) to yield isopropyl trans-N-[4-[5-[2-(tert-butylsulfamoyl)-4-(4H-1,2,4-triazol-3-ylamino)phenyl]thiazol-2-yl]cyclohexyl]carbamate (7 mg, 13.3 umol, 12% yield, 100% purity) as a pale yellow solid. $^1$H NMR (400 MHz, DMSO-d$_6$) δ=9.74 (s, 1H), 8.40 (d, J=2.4 Hz, 1H), 8.30 (br s, 1H), 7.68 (dd, J=2.3, 8.5 Hz, 1H), 7.62 (s, 1H), 7.30 (d, J=8.4 Hz, 1H), 7.00 (br d, J=7.7 Hz, 1H), 6.79 (s, 1H), 4.72 (td, J=6.2, 12.5 Hz, 1H), 3.30 (td, J=3.6, 7.4 Hz, 1H), 2.87 (tt, J=3.4, 11.9 Hz, 1H), 2.11 (br d, J=11.7 Hz, 2H), 1.90 (br d, J=10.4 Hz, 2H), 1.55 (dq, J=2.6, 12.7 Hz, 2H), 1.37-1.25 (m, 2H), 1.14 (d, J=6.4 Hz, 6H), 1.07 (s, 9H). ESI [M+H]=562.3.

Example 126

Preparation of isopropyl trans-N-[4-[5-[2-(ethylsulfamoyl)-4-(4H-1,2,4-triazol-3-ylamino)phenyl]thiazol-2-yl]cyclohexyl]carbamate (Compound 152)

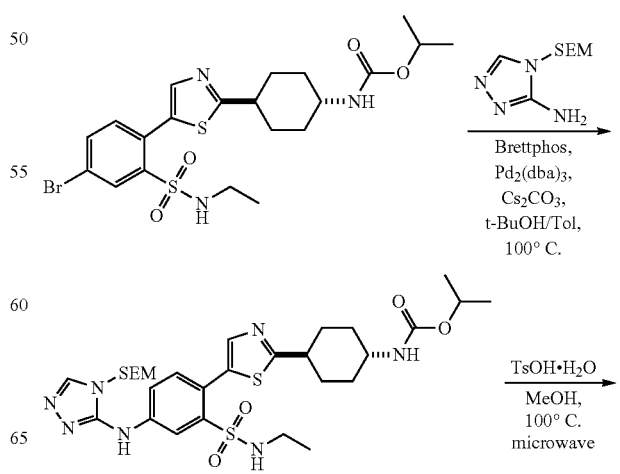

-continued

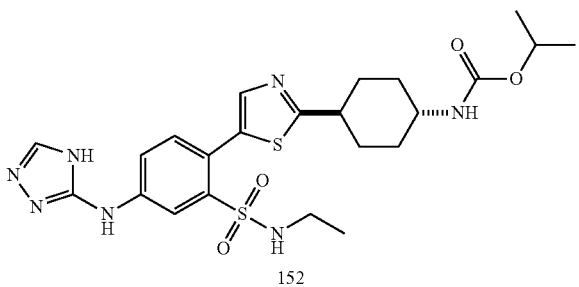

152 a) Synthesis of isopropyl trans-N-[4-[5-[2-(ethylsulfamoyl)-4-[[4-(2-trimethyl-silylethoxymethyl)-1,2,4-triazol-3-yl]amino]phenyl]thiazol-2-yl]cyclohexyl]carbamate

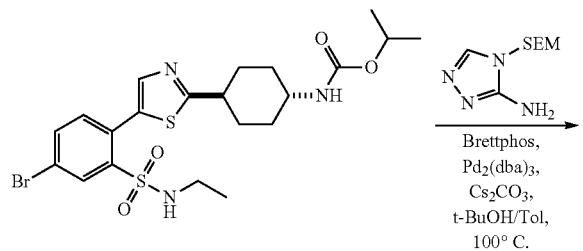

A mixture of isopropyl trans-N-[4-[5-[4-bromo-2-(ethylsulfamoyl)phenyl]thiazol-2-yl]cyclohexyl]carbamate (0.13 g, 245.0 umol, 1 eq.), 4-(2-trimethylsilylethoxy-methyl)-1,2,4-triazol-3-amine (105 mg, 490.1 umol, 2 eq.), Pd₂(dba)₃ (22 mg, 24.5 umol, 0.1 eq.), Cs₂CO₃ (159 mg, 490.1 umol, 2 eq.) and dicyclohexyl-[3,6-dimethoxy-2-(2,4,6-triisopropylphenyl)phenyl]phosphane (13 mg, 24.5 umol, 0.1 eq.) in toluene (2 mL) and t-BuOH (2 mL) was stirred at 100° C. for 12 h under N₂ atmosphere. The reaction mixture was concentrated under reduced pressure to give a residue which was purified by prep-TLC (SiO₂, petroleum ether:ethyl acetate=0:1) to yield isopropyl trans-N-[4-[5-[2-(ethylsulfamoyl)-4-[[4-(2-trimethylsilylethoxymethyl)-1,2,4-triazol-3-yl]amino]phenyl]thiazol-2-yl]cyclohexyl]carbamate (120 mg, 180.7 umol, 74% yield) as a yellow solid. ESI [M+H]=664.3.

b) Synthesis of isopropyl trans-N-[4-[5-[2-(ethylsulfamoyl)-4-(4H-1,2,4-triazol-3-ylamino)phenyl]thiazol-2-yl]cyclohexyl]carbamate (Compound 152)

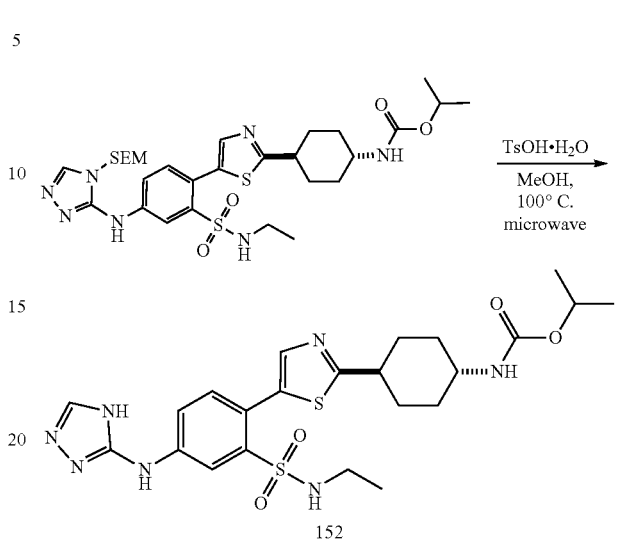

152

A mixture of isopropyl trans-N-[4-[5-[2-(ethylsulfamoyl)-4-[[4-(2-trimethylsilyl-ethoxymethyl)-1,2,4-triazol-3-yl]amino]phenyl]thiazol-2-yl]cyclohexyl]carbamate (95 mg, 143.0 umol, 1 eq.) and TsOH.H₂O (40 mg, 214.6 umol, 1.5 eq.) were taken up into a microwave tube with MeOH (2 mL). The sealed tube was heated at 100° C. for 0.5 h under microwave. The reaction mixture was concentrated under reduced pressure to give a residue, which was purified by prep-HPLC (TFA condition: column: Phenomenex Luna C18 100*30 mm*5 um; mobile phase: [water(0.1% TFA)-ACN]; B %: 15%-50%,12 min) to yield isopropyl trans-N-[4-[5-[2-(ethylsulfamoyl)-4-(4H-1,2,4-triazol-3-ylamino)phenyl]thiazol-2-yl]cyclohexyl]carbamate (38 mg, 72.9 umol, 51% yield) as a yellow gum. $^1$H NMR (400 MHz, DMSO-$d_6$) δ=9.94-9.78 (m, 1H), 8.44-8.33 (m, 2H), 7.85-7.80 (m, 1H), 7.75-7.71 (m, 1H), 7.45-7.40 (m, 1H), 7.38-7.33 (m, 1H), 7.15-7.06 (m, 1H), 4.84 (td, J=6.2, 12.4 Hz, 1H), 3.45-3.35 (m, 1H), 3.04-2.90 (m, 3H), 2.27-2.19 (m, 2H), 2.05-1.97 (m, 2H), 1.71-1.60 (m, 2H), 1.50-1.36 (m, 2H), 1.26 (d, J=6.3 Hz, 6H), 1.12-1.04 (m, 3H). ESI [M+H]=534.3.

Example 127

Preparation of isopropyl trans-[4-[5-[4-(oxazol-2-ylamino)-2-pyrrolidin-1-ylsulfonyl-phenyl]thiazol-2-yl]cyclohexyl]carbamate (153)

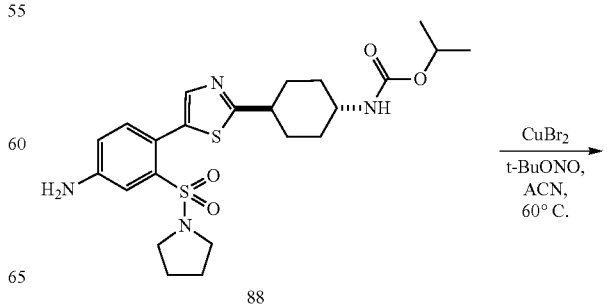

88

-continued

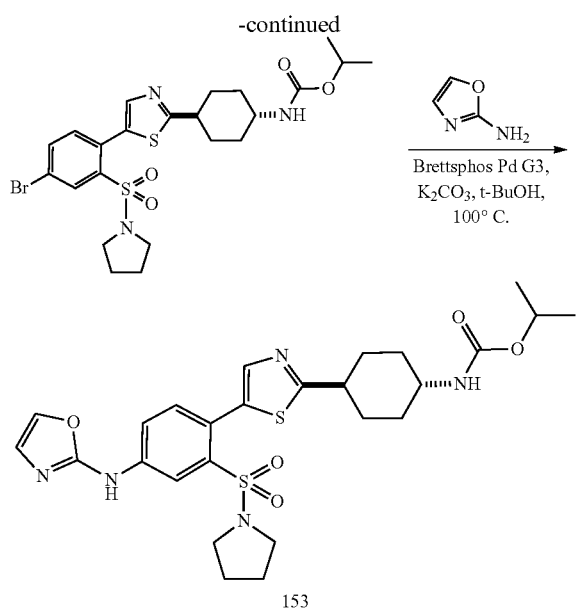

153 a) Synthesis of isopropyl trans-N-[4-[5-(4-bromo-2-pyrrolidin-1-ylsulfonyl-phenyl)thiazol-2-yl]cyclohexyl]carbamate From isopropyl trans-N-[4-[5-(4-amino-2-pyrrolidin-1-ylsulfonyl-phenyl) thiazol-2-yl]cyclohexyl]carbamate, using General Method L. $^1$H NMR (400 MHz, methanol-d$_4$) δ=8.23 (d, J=2.00 Hz, 1H), 7.86 (dd, J=8.19, 2.06 Hz, 1H), 7.76 (s, 1H), 7.46 (d, J=8.13 Hz, 1H), 4.80-4.86 (m, 1H), 3.47 (tt, J=11.44, 3.63 Hz, 1H), 3.02-3.09 (m, 1H), 2.97 (br t, J=6.63 Hz, 4H), 2.19-2.25 (m, 2H), 2.09 (br d, J=10.26 Hz, 2H), 1.77-1.82 (m, 4H), 1.64-1.75 (m, 2H), 1.41-1.46 (m, 2H), 1.24 (br d, J=6.00 Hz, 6H). ESI [M+H]=556.1/558.1.

b) Synthesis of isopropyl trans-[4-[5-[4-(oxazol-2-ylamino)-2-pyrrolidin-1-ylsulfonyl-phenyl]thiazol-2-yl]cyclohexyl]carbamate (Compound 153)

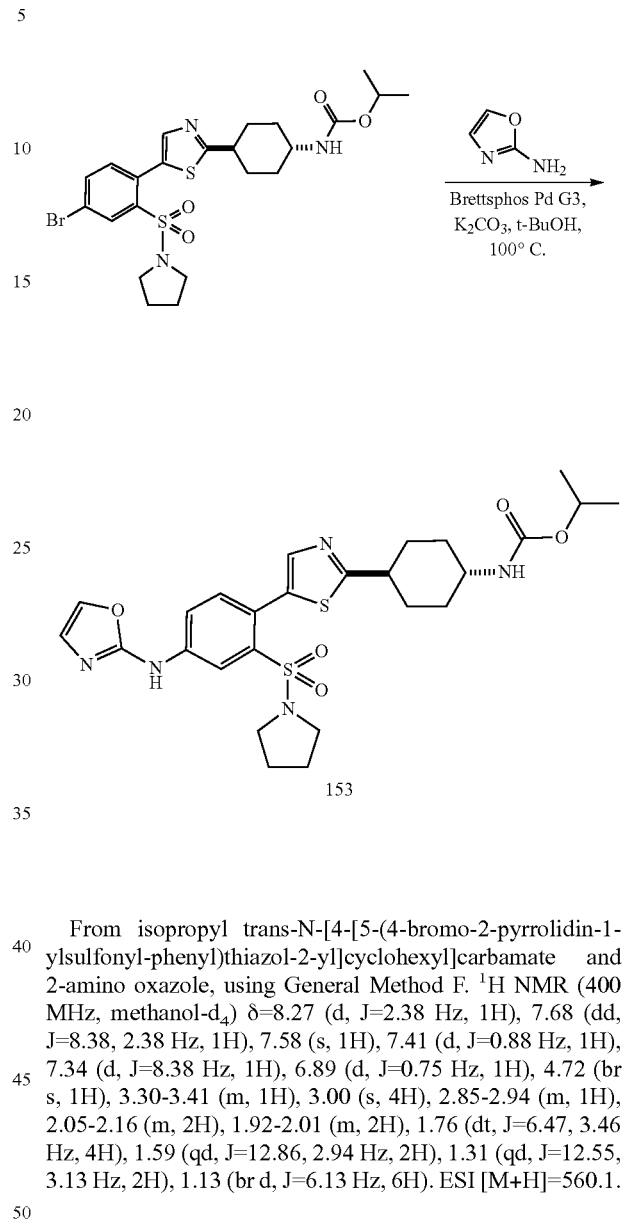

153

From isopropyl trans-N-[4-[5-(4-bromo-2-pyrrolidin-1-ylsulfonyl-phenyl)thiazol-2-yl]cyclohexyl]carbamate and 2-amino oxazole, using General Method F. $^1$H NMR (400 MHz, methanol-d$_4$) δ=8.27 (d, J=2.38 Hz, 1H), 7.68 (dd, J=8.38, 2.38 Hz, 1H), 7.58 (s, 1H), 7.41 (d, J=0.88 Hz, 1H), 7.34 (d, J=8.38 Hz, 1H), 6.89 (d, J=0.75 Hz, 1H), 4.72 (br s, 1H), 3.30-3.41 (m, 1H), 3.00 (s, 4H), 2.85-2.94 (m, 1H), 2.05-2.16 (m, 2H), 1.92-2.01 (m, 2H), 1.76 (dt, J=6.47, 3.46 Hz, 4H), 1.59 (qd, J=12.86, 2.94 Hz, 2H), 1.31 (qd, J=12.55, 3.13 Hz, 2H), 1.13 (br d, J=6.13 Hz, 6H). ESI [M+H]=560.1.

Example 128

Preparation of isopropyl (trans-4-(5-(2-(N-(tert-butyl)sulfamoyl)-4-(oxazol-2-ylamino)phenyl)thiazol-2-yl)cyclohexyl)carbamate (Compound 42)

Following the same protocol and under the same reaction conditions as for Compound 153, Compound 42 was prepared. $^1$H NMR (400 MHz, methanol-d$_4$) δ=8.44 (d, J=2.4 Hz, 1H), 7.81 (dd, J=2.5, 8.4 Hz, 1H), 7.73 (s, 1H), 7.52 (d, J=1.0 Hz, 1H), 7.42 (d, J=8.4 Hz, 1H), 7.00 (d, J=1.0 Hz, 1H), 4.84-4.80 (m, 1H), 3.48 (tt, J=3.8, 11.7 Hz, 1H), 3.02 (tt, J=3.5, 12.1 Hz, 1H), 2.29-2.21 (m, 2H), 2.12-2.05 (m, 2H), 1.72 (dq, J=3.0, 12.9 Hz, 2H), 1.49-1.38 (m, 2H), 1.25 (br d, J=6.1 Hz, 6H), 1.16 (s, 9H). ESI [M+H]=562.2.

Example 129

Preparation of isopropyl trans-N-[4-[5-[2-(ethylsulfamoyl)-4-(1H-imidazol-2-ylamino)phenyl]thiazol-2-yl]cyclohexyl]carbamate (Compound 56)

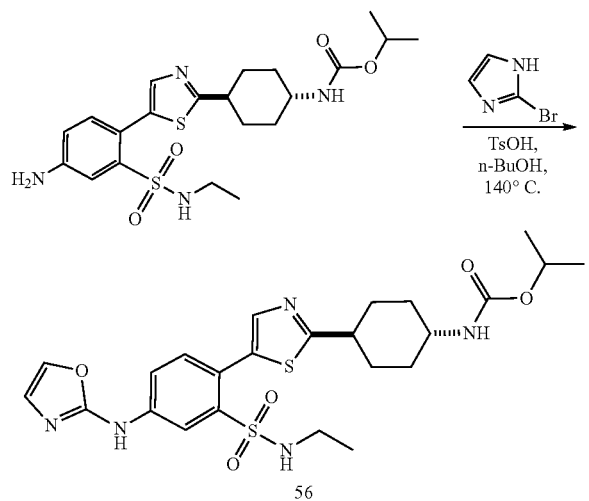

From isopropyl trans-N-[4-[5-[4-amino-2-(ethylsulfamoyl)phenyl]thiazol-2-yl]cyclo-hexyl]carbamate and 2-bromo-1H-imidazole, using General Method K. $^1$H NMR (400 MHz, methanol-$d_4$) δ=7.90 (d, J=2.4 Hz, 1H), 7.78-7.69 (m, 1H), 7.59-7.44 (m, 2H), 7.12 (s, 2H), 4.85-4.76 (m, 1H), 3.52-3.38 (m, 1H), 3.02 (tt, J=3.4, 12.0 Hz, 1H), 2.93-2.80 (m, 2H), 2.34-2.14 (m, 2H), 2.13-2.02 (m, 2H), 1.77-1.63 (m, 2H), 1.41 (dq, J=3.1, 12.6 Hz, 2H), 1.22 (br d, J=6.0 Hz, 6H), 1.05-0.97 (m, 3H). ESI [M+H]=533.2.

Example 130

Preparation of isopropyl trans-N-[4-[5-[2-(ethylsulfamoyl)-4-[(1-isopropylimidazol-2-yl)amino]phenyl]thiazol-2-yl]cyclohexyl]carbamate (Compound 154)

a) Synthesis of 2-bromo-1-isopropyl-imidazole

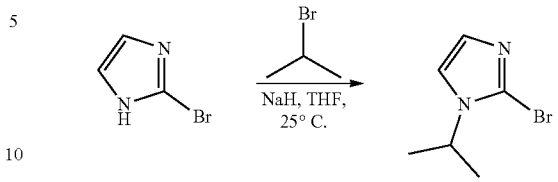

To a mixture of 2-bromo-1H-imidazole (300 mg, 2 mol, 1 eq.), NaH (245 mg, 6 mmol, 60% in oil, 3 eq.) in THF (3 mL) was added 2-bromopropane (753 mg, 6 mmol, 3 eq.). The mixture was stirred at 25° C. for 6 h under $N_2$ atmosphere. The reaction mixture was quenched by $H_2O$ (10 mL) and extracted with EtOAc 60 mL (20 mL×3). The combined organic layers were washed with sat.aq. NaCl 60 mL (12 mL×5), dried over $Na_2SO_4$, filtered and concentrated under reduced pressure. The residue was purified by prep-HPLC (column: Nano-micro Kromasil C18 100*30 mm 5 um; mobile phase: [water(0.1% TFA)-ACN]; B %: 1%-25%,10 min) to yield 2-bromo-1-isopropyl-imidazole (300 mg, 2 mmol, 78% yield) as yellow oil. $^1$H NMR (400 MHz, $CDCl_3$) δ=7.36 (d, J=1.76 Hz, 1H), 7.17 (s, 1H), 4.59 (spt, J=6.73 Hz, 1H), 1.50 (d, J=6.62 Hz, 6H). ESI [M+H]=188.9/190.9.

b) Synthesis of isopropyl trans-N-[4-[5-[2-(ethylsulfamoyl)-4-[(1-isopropylimidazol-2-yl)amino]phenyl]thiazol-2-yl]cyclohexyl]carbamate (Compound 154)

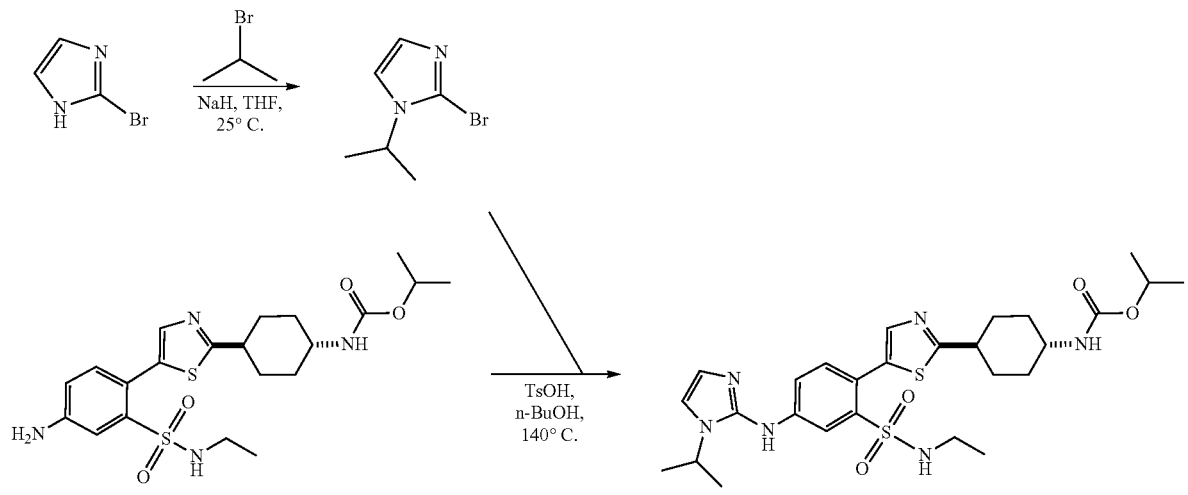

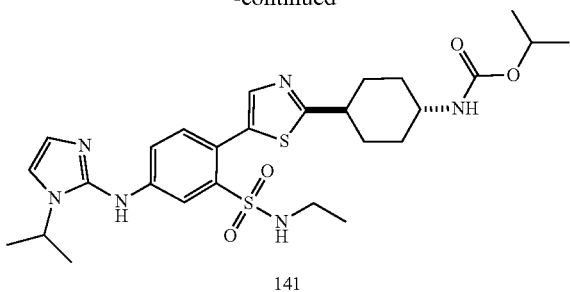

141

From isopropyl trans-N-[4-[5-[4-amino-2-(ethylsulfamoyl)phenyl]thiazol-2-yl]cyclo-hexyl]carbamate and 2-bromo-1-isopropyl-imidazole, using General Method K. $^1$H NMR (methanol-$d_4$, 400 MHz) δ=7.87 (d, 1H, J=2.4 Hz), 7.7-7.8 (m, 1H), 7.5-7.6 (m, 1H), 7.4-7.5 (m, 2H), 7.23 (d, 1H, J=2.4 Hz), 4.63 (quin, 1H, J=6.8 Hz), 3.45 (br t, 1H, J=11.6 Hz), 3.1-3.2 (m, 1H), 3.0-3.1 (m, 1H), 2.8-2.9 (m, 2H), 2.24 (br d, 2H, J=12.6 Hz), 2.0-2.1 (m, 2H), 1.6-1.8 (m, 2H), 1.55 (d, 6H, J=6.6 Hz), 1.3-1.5 (m, 2H), 1.22 (br d, 6H, J=6.0 Hz), 0.9-1.0 (m, 3H). ESI [M+H]=575.2.

Example 131

Preparation of isopropyl trans-N-[4-[5-[12-(ethylsulfamoyl)-4-[(2-hydroxypyrimidin-4-yl)amino]phenyl]thiazol-2-yl]cyclohexyl]carbamate (Compound 156)

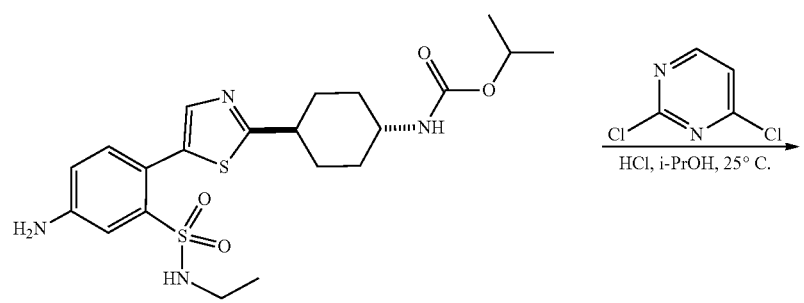

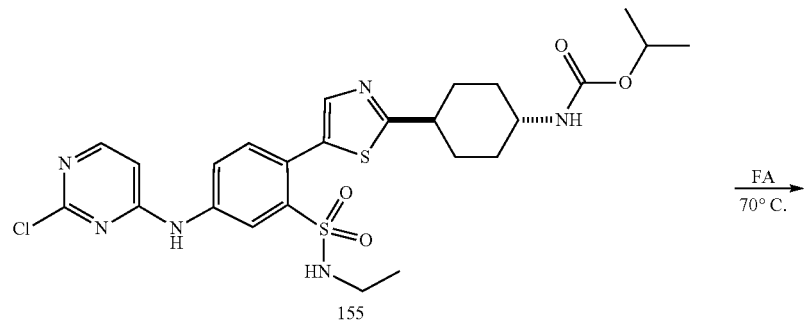

155

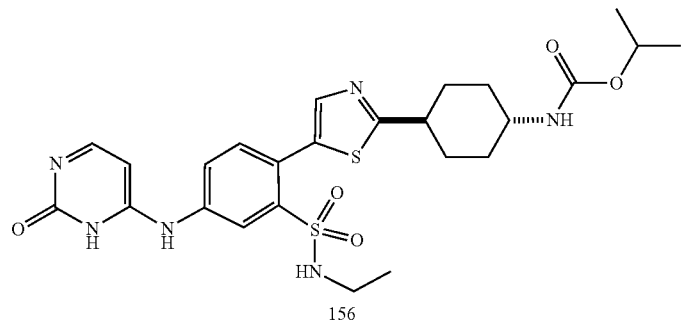

156 a) Synthesis of isopropyl trans-N-[4-[5-[4-[(2-chloropyrimidin-4-yl)amino]-2-(ethylsulfamoyl)phenyl]thiazol-2-yl]cyclohexyl]carbamate (Compound 155)

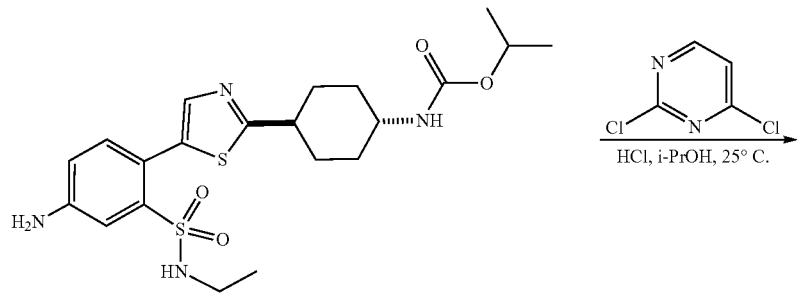

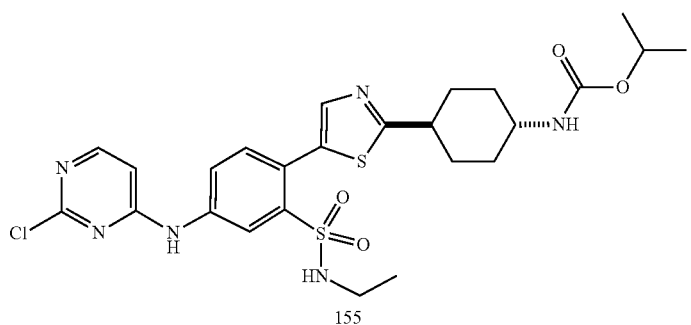

To a solution of isopropyl trans-N-[4-[5-[4-amino-2-(ethylsulfamoyl)phenyl]thiazol-2-yl]cyclohexyl]carbamate (200 mg, 429 umol, 1.0 eq.) in i-PrOH (2 mL) was added 2,4-dichloropyrimidine (127 mg, 857 umol, 2.0 eq.) and HCl (12 M, one drop) and the mixture was stirred at 25° C. for 1 h. The reaction mixture was then concentrated under reduced pressure to yield isopropyl trans-N-[4-[5-[4-[(2-chloropyrimidin-4-yl)amino]-2-(ethylsulfamoyl)phenyl]thiazol-2-yl]cyclohexyl]carbamate (350 mg, crude) as a yellow oil. 40 mg of crude was purified by prep-HPLC (column: Phenomenex Luna C18 150*30 mm*5 um; mobile phase: [water(0.1% TFA)-ACN]; B %: 45%-65%,10 min) to give pure compound CYT-2056 (2.93 mg, 86.4% purity) as a gray solid. $^1$H NMR (400 MHz, methanol-$d_4$) δ=8.50 (d, J=2.20 Hz, 1H), 8.20 (d, J=5.87 Hz, 1H), 7.90-8.00 (m, 1H), 7.77 (s, 1H), 7.48-7.52 (m, 1H), 6.80 (d, J=5.99 Hz, 1H), 4.82-4.84 (m, 1H), 3.48 (ddd, J=3.55, 7.83, 11.74 Hz, 1H), 3.03 (q, J=7.30 Hz, 3H), 2.27 (br d, J=12.23 Hz, 2H), 2.05-2.15 (m, 2H), 1.73 (dq, J=3.12, 12.82 Hz, 2H), 1.44 (dq, J=3.36, 12.53 Hz, 2H), 1.25 (br d, J=6.11 Hz, 6H), 1.10 (t, J=7.21 Hz, 3H). ESI [M+H]=579.2.

b) Synthesis of isopropyl trans-N-[4-[5-[2-(ethylsulfamoyl)-4-[(2-hydroxypyrimidin-4-yl)amino]phenyl]thiazol-2-yl]cyclohexyl]carbamate (Compound 156)

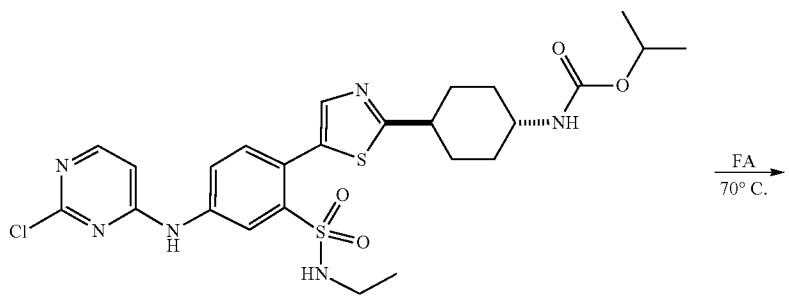

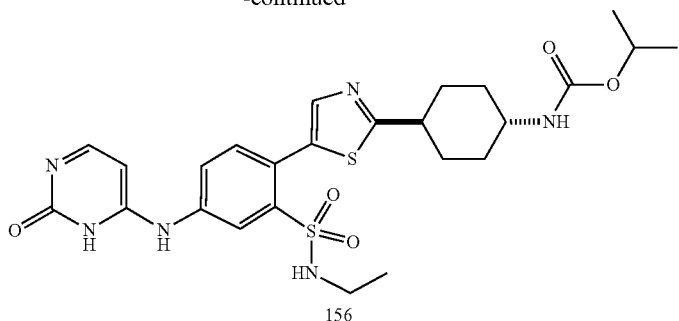

156

A mixture of isopropyl trans-N-[4-[5-[4-[(2-chloropyrimidin-4-yl)amino]-2-(ethylsulfamoyl)phenyl]thiazol-2-yl]cyclohexyl]carbamate (250 mg, 432 umol, 1.0 eq.) in formic acid (2.5 mL) was stirred at 70° C. for 12 h. The reaction mixture was concentrated under reduced pressure and then purified by prep-HPLC (column: Phenomenex Luna C18 200*40 mm*10 um; mobile phase: [water(0.2% FA)-ACN]; B %: 1%-30%,8 min) to yield isopropyl trans-N-[4-[5-[2-(ethylsulfamoyl)-4-[(2-hydroxypyrimidin-4-yl)amino]phenyl]thiazol-2-yl]cyclohexyl]carbamate (7 mg, 13 umol, 3% yield, 97% purity) as a white solid. $^1$H NMR (400 MHz, methanol-d$_4$) δ=8.82 (s, 1H), 7.94 (dd, J=2.14, 8.38 Hz, 1H), 7.74 (s, 1H), 7.59 (d, J=7.09 Hz, 1H), 7.48 (d, J=8.31 Hz, 1H), 6.09 (d, J=7.09 Hz, 1H), 4.76-4.83 (m, 1H), 3.42-3.55 (m, 1H), 2.93-3.08 (m, 3H), 2.26 (br d, J=12.23 Hz, 2H), 2.10 (br d, J=10.39 Hz, 2H), 1.65-1.79 (m, 2H), 1.37-1.51 (m, 2H), 1.25 (br d, J=6.11 Hz, 6H), 1.13 (t, J=7.21 Hz, 3H). ESI [M+H]=561.2.

Example 132

Preparation of isopropyl trans-N-[4-[5-[4-[(6-ethylpyridazin-3-yl) amino]-2-(ethylsulfamoyl)phenyl]thiazol-2-yl]cyclohexyl]carbamate (Compound 157)

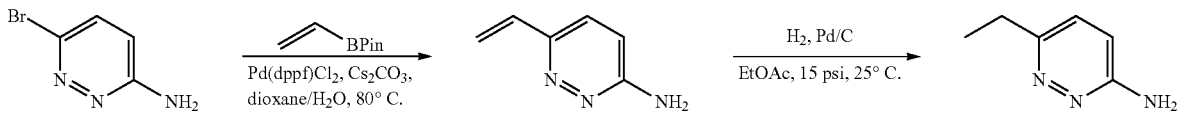

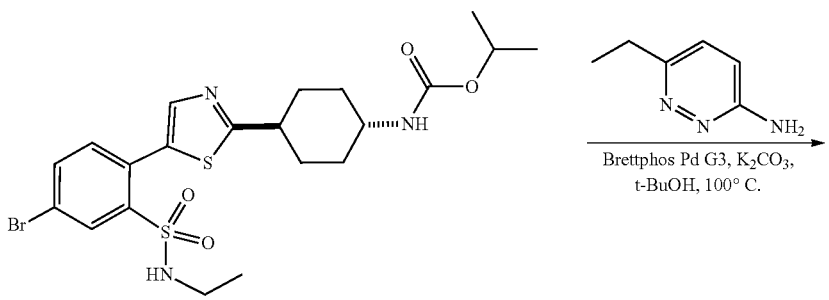

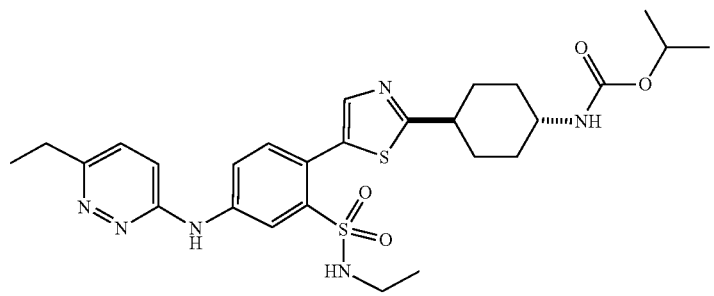

157 a) Synthesis of 6-vinylpyridazin-3-amine

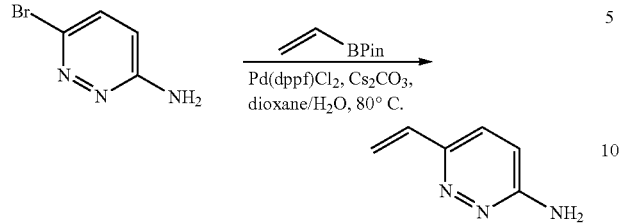

A mixture of 4,4,5,5-tetramethyl-2-vinyl-1,3,2-dioxaborolane (1.1 g, 6.9 mmol, 1.2 eq.), 6-bromopyridazin-3-amine (1 g, 5.8 mmol, 1.0 eq.), Cs$_2$CO$_3$ (5.6 g, 17.3 mmol, 3.0 eq.) and Pd(dppf)Cl$_2$ (420 mg, 575 umol, 0.1 eq.) in dioxane (20 mL)/H$_2$O (10 mL) was stirred at 80° C. for 3 h under N$_2$ atmosphere. The reaction mixture was concentrated under reduced pressure and then purified by column chromatography (SiO$_2$, petroleum ether:ethyl acetate=10:1 to 0:1) to yield 6-vinylpyridazin-3-amine (0.3 g, 2.5 mmol, 43% yield) as a pale yellow solid. ESI [M+H]=122.0.

b) Synthesis of 6-ethylpyridazin-3-amine

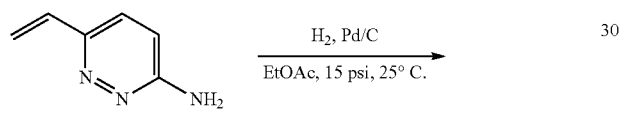

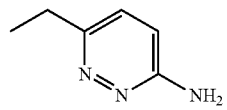

To a solution of 6-vinylpyridazin-3-amine (0.3 g, 2.5 mmol, 1.0 eq.) and AcOH (15 mg, 248 umol, 0.1 eq.) in EtOAc (20 mL) was added Pd/C (100 mg, 10% purity) under N$_2$.

The suspension was degassed under vacuum and purged with H$_2$ for 3 times and then stirred under H$_2$ (15 psi) at 25° C. for 2 h. The reaction mixture was filtered, the filtrate was concentrated under reduced pressure and then purified by prep-HPLC (column: Phenomenex Gemini-NX C18 75*30 mm*3 um; mobile phase: [water(10 mM NH$_4$HCO$_3$)-ACN]; B %: 1%-15%,10 min) to yield 6-ethylpyridazin-3-amine (220 mg, 1.8 mmol, 72% yield) as a white solid. $^1$H NMR (400 MHz, methanol-d$_4$) δ=7.30-7.24 (m, 1H), 6.96-6.86 (m, 1H), 2.80-2.69 (m, 2H), 1.33-1.19 (m, 3H). ESI [M+H]=124.2.

c) Synthesis of isopropyl trans-N-[4-[5-[4-[(6-ethylpyridazin-3-yl)amino]-2-(ethylsulfamoyl)phenyl]thiazol-2-yl]cyclohexyl]carbamate (Compound 157)

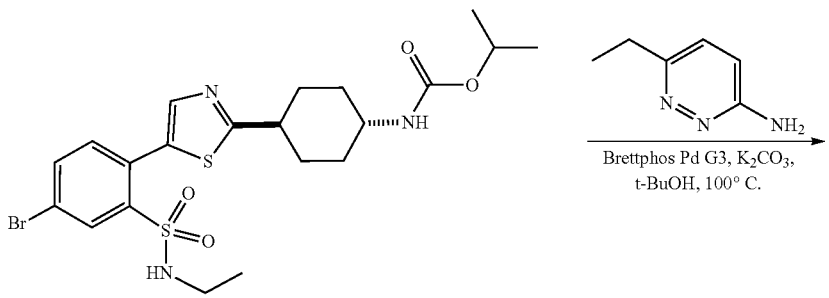

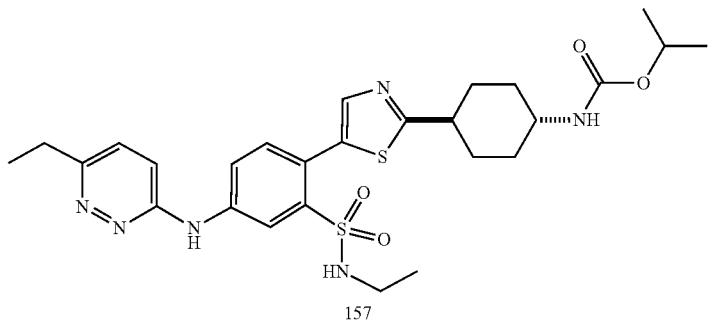

157

From isopropyl trans-N-[4-[5-[4-bromo-2-(ethylsulfamoyl)phenyl]thiazol-2-yl]cyclohexyl]carbamate and 6-ethylpyridazin-3-amine, using General Method F. $^1$H NMR (400 MHz, methanol-d$_4$) δ=8.61-8.53 (m, 1H), 8.11-8.02 (m, 1H), 7.95-7.88 (m, 1H), 7.87-7.79 (m, 1H), 7.79-7.74 (m, 1H), 7.56-7.49 (m, 1H), 4.86 (br d, J=6.8 Hz, 1H), 3.53-3.41 (m, 1H), 3.12-3.00 (m, 3H), 2.94-2.84 (m, 2H), 2.32-2.19 (m, 2H), 2.15-1.94 (m, 2H), 1.78-1.57 (m, 2H), 1.53-1.37 (m, 5H), 1.29-1.18 (m, 6H), 1.09-0.92 (m, 3H). ESI [M+H]=573.2.

Example 133

Preparation of isopropyl trans-N-[4-[5-[4-[(5-ethylpyridazin-3-yl)amino]-2-(ethylsulfamoyl)phenyl]thiazol-2-yl]cyclohexyl]carbamate (Compound 158)

AgNO$_3$ (570 mg, 3.4 mmol, 0.1 eq.), propionic acid (3.0 g, 40.3 mmol, 1.2 eq.) and TFA (0.1 mL) were added in that order into a solution of 3,6-dichloropyridazine (5.0 g, 34.0 mmol, 1.0 eq.) in H$_2$O (50 mL). The reaction solution was heated to 70° C., then slowly added (NH$_4$)$_2$S$_2$O$_8$ (15.3 g, 68 mmol, 2.0 eq.). The reaction was stirred at 70° C. for 12 h, then extracted with dichloromethane (90 mL, 30 mL×3), The combined organic layers was dried over Na$_2$SO$_4$, filtered and concentrated under reduced pressure to give a residue. The residue was purified by column chromatography (SiO$_2$, petroleum ether:ethyl acetate=10:1 to 5:1) to yield 3,6-dichloro-4-ethyl-pyridazine (3.1 g, 17.5 mmol, 52% yield) as a yellow oil which was used directly in the next step.

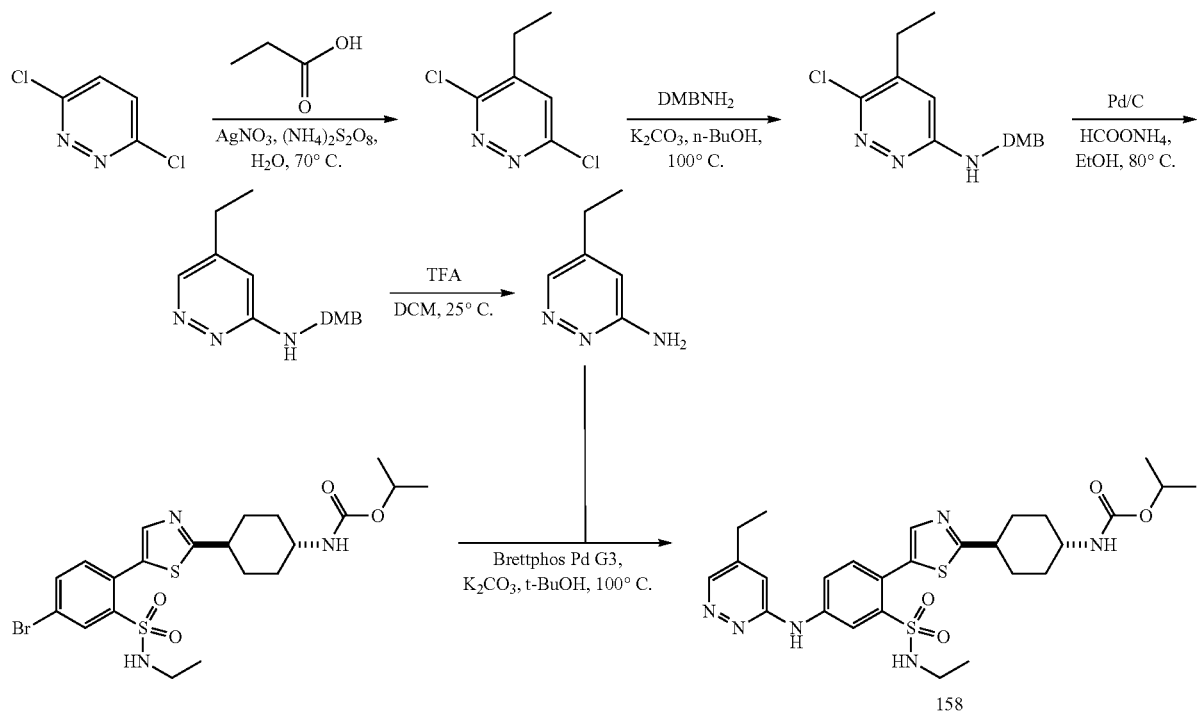

a) Synthesis of 3,6-dichloro-4-ethyl-pyridazine

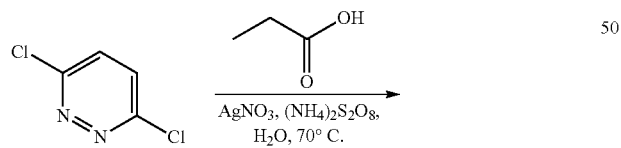

b) Synthesis of 6-chloro-N-[(2,4-dimethoxyphenyl)methyl]-5-ethyl-pyridazin-3-amine

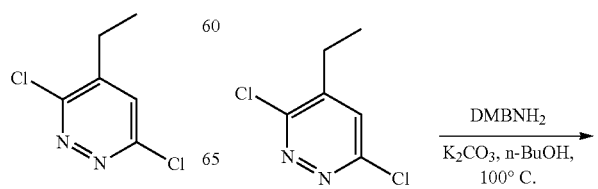

-continued

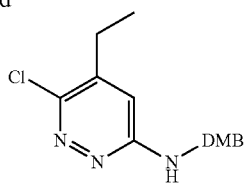

To a solution of 3,6-dichloro-4-ethyl-pyridazine (3.1 g, 17.5 mmol, 1 eq.) in n-BuOH (50 mL) was added (2,4-dimethoxyphenyl)methanamine (4.4 g, 26.3 mmol, 1.5 eq.) and $K_2CO_3$ (4.8 g, 35.0 mmol, 2.0 eq.). The mixture was stirred at 100° C. for 12 h, and then concentrated under reduced pressure and purified by column chromatography ($SiO_2$, petroleum ether:ethyl acetate=3:1 to 1:1) to yield 6-chloro-N-[(2,4-dimethoxyphenyl) methyl]-5-ethyl-pyridazin-3-amine (700 mg, 2 mmol, 13% yield) as a pale yellow oil.

c) Synthesis of N-[(2,4-dimethoxyphenyl)methyl]-5-ethyl-pyridazin-3-amine

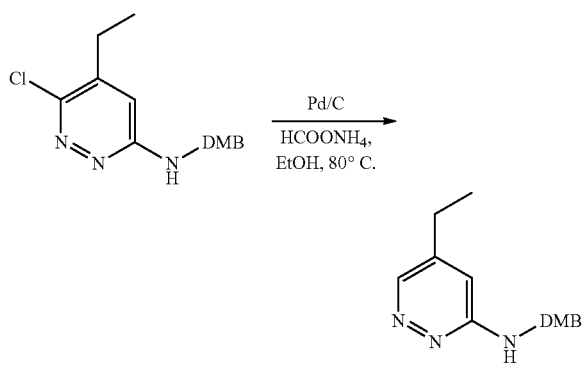

A mixture of 6-chloro-N-[(2,4-dimethoxyphenyl) methyl]-5-ethyl-pyridazin-3-amine (600 mg, 2.0 mmol, 1.0 eq.), Pd/C (10 mg, 10% purity), TEA (20 mg, 195 umol, 0.1 eq.) and $HCOONH_4$ (3.7 g, 58.5 mmol, 30 eq.) in EtOH (40 mL) was stirred at 80° C. for 1 h under $N_2$ atmosphere. The reaction mixture was filtered, and the filtrate was concentrated under reduced pressure to remove solvent. The residue was diluted with $H_2O$ (10 mL), extracted with EtOAc (60 mL, 20 mL×3), dried over $Na_2SO_4$, filtered and concentrated under reduced pressure to yield N-[(2,4-dimethoxy-phenyl) methyl]-5-ethyl-pyridazin-3-amine (700 mg, crude) as a yellow oil. ESI [M+H]=274.1.

d) Synthesis of 5-ethylpyridazin-3-amine

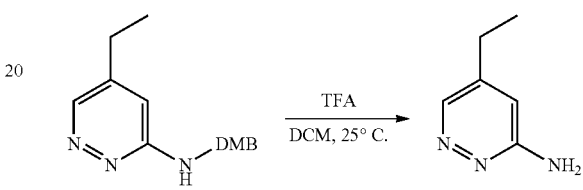

A mixture of N-[(2,4-dimethoxyphenyl)methyl]-5-ethyl-pyridazin-3-amine (600 mg, 2 mmol, 1.0 eq.) in DCM (6 mL)/TFA (2 mL) was stirred at 25° C. for 1 h. The reaction mixture was concentrated under reduced pressure and then purified by prep-HPLC (column: Phenomenex luna C18 250*50 mm*10 um; mobile phase: [water(0.1% TFA)-ACN]; B %: 1%-20%,10 min) to yield 5-ethylpyridazin-3-amine (250 mg, 2 mmol, 92% yield) as a white solid. $^1H$ NMR (400 MHz, methanol-$d_4$) δ=8.34 (d, J=1.4 Hz, 1H), 7.26 (s, 1H), 2.77 (q, J=7.4 Hz, 2H), 1.32 (t, J=7.5 Hz, 3H). ESI [M+H]=124.0.

e) Synthesis of isopropyl trans-N-[4-[5-[4-[(5-ethylpyridazin-3-yl)amino]-2-(ethylsulfamoyl)phenyl]thiazol-2-yl]cyclohexyl]carbamate (Compound 158)

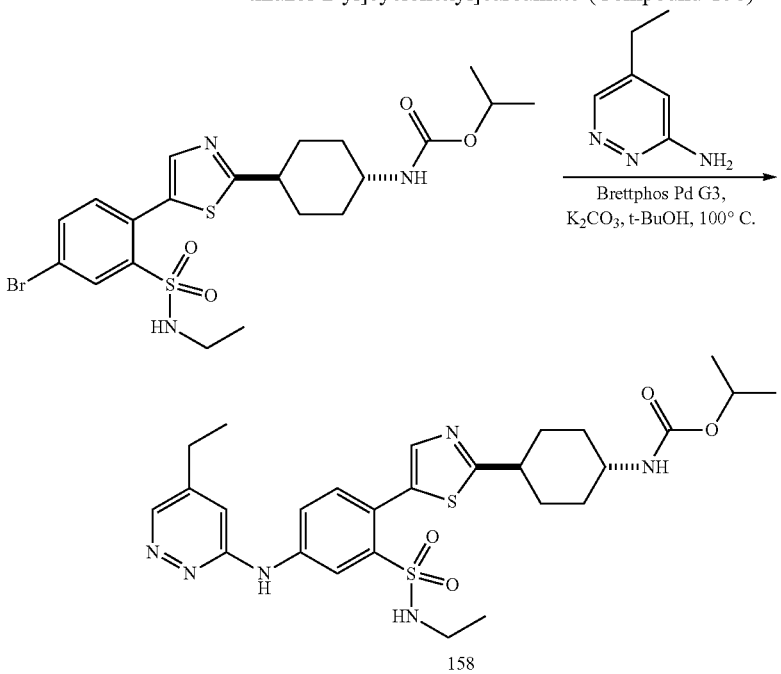

158

From isopropyl trans-N-[4-[5-[4-bromo-2-(ethylsulfamoyl)phenyl]thiazol-2-yl]cyclohexyl]carbamate and 5-ethylpyridazin-3-amine, using General Method F. $^1$H NMR (400 MHz, methanol-$d_4$) δ=8.94 (s, 1H), 8.52 (d, J=2.4 Hz, 1H), 7.95 (dd, J=2.4, 8.4 Hz, 1H), 7.78 (s, 1H), 7.61 (s, 1H), 7.55 (d, J=8.4 Hz, 1H), 4.87-4.82 (m, 1H), 3.48 (tt, J=4.0, 11.6 Hz, 1H), 3.05 (tt, J=3.5, 12.0 Hz, 1H), 2.97-2.83 (m, 4H), 2.27 (br d, J=12.3 Hz, 2H), 2.10 (br d, J=10.3 Hz, 2H), 1.73 (dq, J=3.0, 12.8 Hz, 2H), 1.51-1.34 (m, 5H), 1.25 (br d, J=6.1 Hz, 6H), 1.05 (t, J=7.2 Hz, 3H). ESI [M+H]=573.2.

Example 134

Preparation of isopropyl trans-N-[4-[5-[2-(ethylsulfamoyl)-4-[(6-oxo-1H-pyridazin-3-yl)amino]phenyl]thiazol-2-yl]cyclohexyl]carbamate (Compound 160)

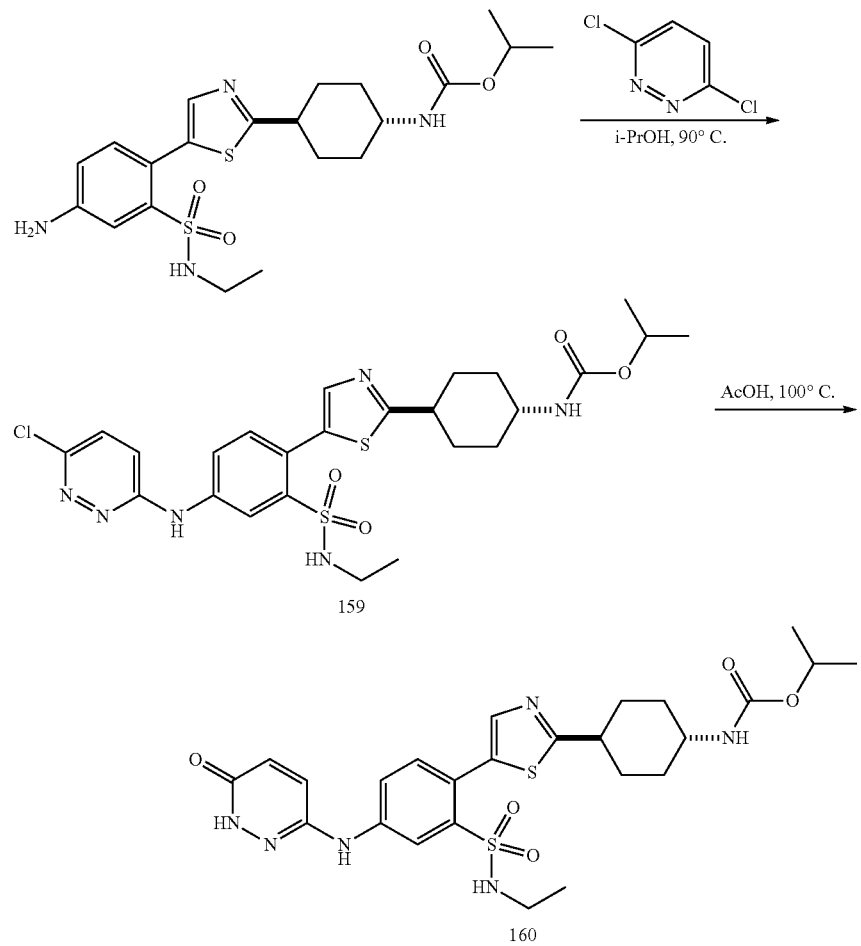

a) Synthesis of isopropyl trans-N-[4-[5-[4-[(6-chloropyridazin-3-yl)amino]-2-(ethylsulfamoyl)phenyl]thiazol-2-yl]cyclohexyl]carbamate (Compound 159)

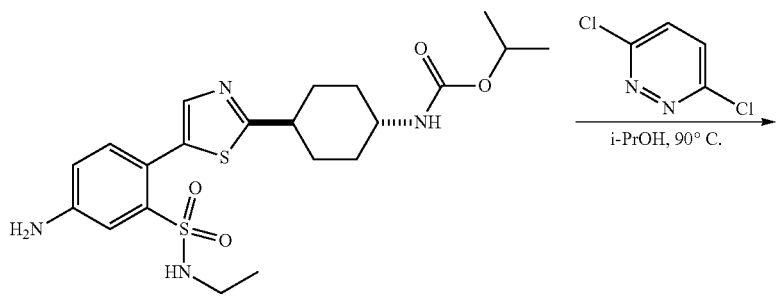

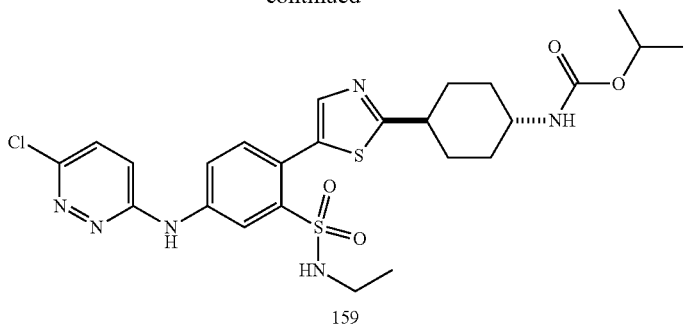

159

A mixture of isopropyl trans-N-[4-[5-[4-amino-2-(ethylsulfamoyl)phenyl]thiazol-2-yl]cyclohexyl]carbamate (500 mg, 1 mmol, 1.0 eq.), 3,6-dichloropyridazine (160 mg, 1 mmol, 1.0 eq.) in i-PrOH (5 mL) was stirred at 90° C. for 12 h. The reaction mixture was concentrated under reduced pressure to remove solvent. The residue was triturated with EtOAc (10 mL) to yield isopropyl trans-N-[4-[5-[4-[(6-chloropyridazin-3-yl)amino]-2-(ethylsulfamoyl)phenyl]thiazol-2-yl]cyclohexyl]carbamate (200 mg, 345 umol, 32% yield) a yellow solid. ¹H NMR (400 MHz, methanol-d₄) δ=8.55 (d, J=2.4 Hz, 1H), 8.04-7.94 (m, 1H), 7.77 (s, 1H), 7.56 (d, J=9.5 Hz, 1H), 7.45 (d, J=8.6 Hz, 1H), 7.23 (d, J=9.3 Hz, 1H), 4.82-4.77 (m, 1H), 3.45 (br t, J=11.7 Hz, 1H), 3.09-3.00 (m, 1H), 2.95 (q, J=7.2 Hz, 2H), 2.24 (br d, J=13.5 Hz, 2H), 2.07 (br d, J=11.2 Hz, 2H), 1.78-1.60 (m, 2H), 1.48-1.35 (m, 2H), 1.22 (br d, J=6.2 Hz, 6H), 1.13-0.99 (m, 3H). ESI [M+H]=579.2.

b) Synthesis of isopropyl trans-N-[4-[5-[2-(ethylsulfamoyl)-4-[(6-oxo-1H-pyridazin-3-yl)amino]phenyl]thiazol-2-yl]cyclohexyl]carbamate (Compound 160)

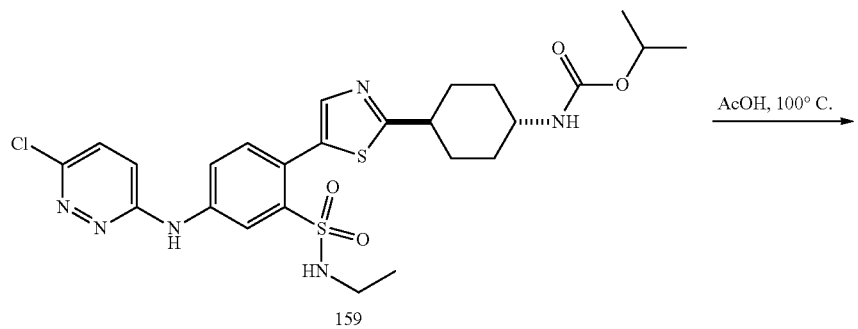

159

AcOH, 100° C.

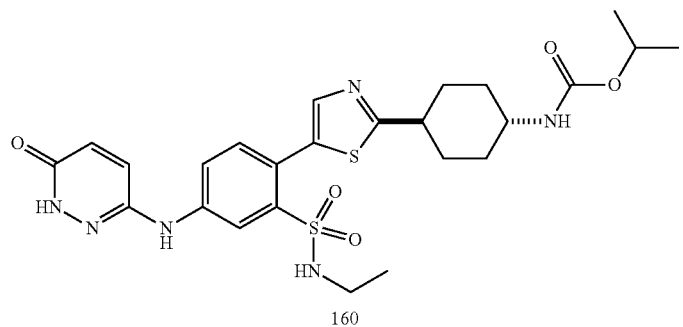

160

A mixture of isopropyl trans-N-[4-[5-[4-[(6-chloro-pyridazin-3-yl)amino]-2-(ethyl-sulfamoyl)phenyl]thiazol-2-yl]cyclohexyl]carbamate (30 mg, 52 umol, 1 eq.) in AcOH (1 mL) was stirred at 100° C. for 2 h and then concentrated under reduced pressure to remove AcOH. The residue was purified by SFC (column: (s,s) WHELK-O1 (250 mm*30 mm, 5 um); mobile phase: [0.1% NH₃H₂O IPA]; B %: 50%-50%, min), then by prep-HPLC (column: Phenomenex Luna C18 150*30 mm*5 um; mobile phase: [water(0.1% TFA)-ACN]; B %: 30%-60%,10 min) to yield isopropyl trans-N-[4-[5-[2-(ethylsulfamoyl)-4-[(6-oxo-1H-pyridazin-3-yl)amino]phenyl]thiazol-2-yl]cyclohexyl]carbamate (1 mg, 2 umol, 3% yield, 97% purity) as a pale yellow solid. ¹H NMR (400 MHz, methanol-d₄) δ=8.38 (d, J=2.4 Hz, 1H), 7.82 (dd, J=2.5, 8.5 Hz, 1H), 7.72-7.65 (m, 1H), 7.37 (d, J=8.6 Hz, 1H), 7.28 (d, J=9.7 Hz, 1H), 6.95 (d, J=9.9 Hz, 1H), 4.83-4.73 (m, 1H), 3.45 (br t, J=11.6 Hz, 1H), 3.05-2.94 (m, 1H), 2.89 (q, J=7.4 Hz, 2H), 2.23 (br d, J=13.2 Hz, 2H), 2.07 (br d, J=10.6 Hz, 2H), 1.76-1.62 (m, 2H), 1.47-1.35 (m, 2H), 1.29-1.20 (m, 6H), 1.06-0.98 (m, 3H). ESI [M+H]=561.2.

Example 135

Preparation of isopropyl trans-N-[4-[5-[2-(ethylsulfamoyl)-4-[(5-methylpyridazin-3-yl)amino]phenyl]thiazol-2-yl]cyclohexyl]carbamate (Compound 161)

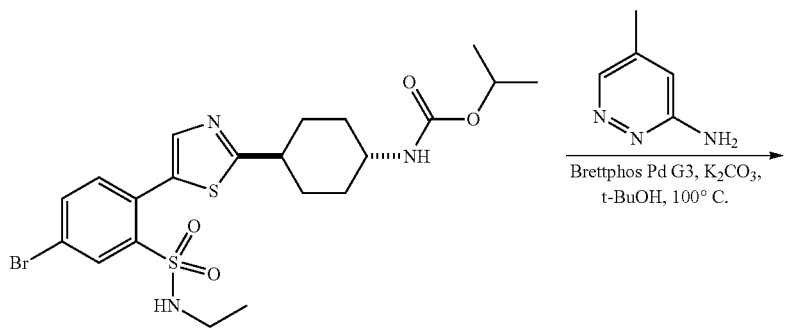

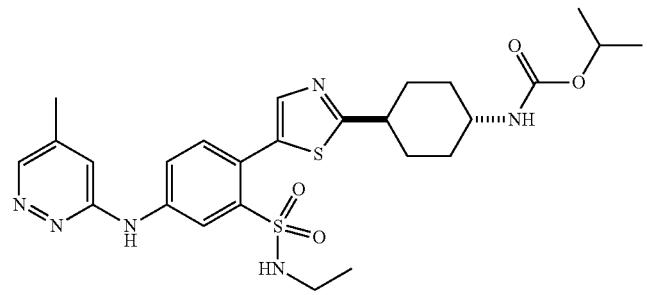

161

From isopropyl trans-N-[4-[5-[4-bromo-2-(ethylsulfamoyl)phenyl]thiazol-2-yl]cyclohexyl]carbamate and 5-methylpyridazin-3-amine, using General Method F. $^1$H NMR (400 MHz, methanol-$d_4$) δ=8.86 (br s, 1H), 8.46 (d, J=2.2 Hz, 1H), 7.89 (dd, J=2.2, 8.4 Hz, 1H), 7.76 (s, 1H), 7.59-7.49 (m, 2H), 4.84-4.78 (m, 1H), 3.45 (tt, J=3.9, 11.6 Hz, 1H), 3.03 (tt, J=3.3, 12.0 Hz, 1H), 2.89 (q, J=7.3 Hz, 2H), 2.51 (s, 3H), 2.29-2.19 (m, 2H), 2.13-2.03 (m, 2H), 1.70 (dq, J=3.0, 12.8 Hz, 2H), 1.47-1.33 (m, 2H), 1.22 (br d, J=6.0 Hz, 6H), 1.02 (t, J=7.3 Hz, 3H). ESI [M+H]=559.3.

Example 136

Preparation of isopropyl trans-N-[4-[5-[2-(ethylsulfamoyl)-4-[(6-methylpyridazin-3-yl)amino]phenyl]thiazol-2-yl]cyclohexyl]carbamate (Compound 162)

Following the same protocol and under the same reaction conditions as for Compound 161, Compound 162 was prepared. $^1$H NMR (400 MHz, DMSO-$d_6$) δ=10.08 (br s, 1H), 8.40 (d, J=2.3 Hz, 1H), 8.00 (dd, J=2.3, 8.5 Hz, 1H), 7.75-7.65 (m, 2H), 7.52-7.29 (m, 3H), 7.02 (br d, J=8.6 Hz, 1H), 3.34-3.30 (m, 1H), 3.34-3.30 (m, 1H), 2.99-2.78 (m, 3H), 2.58 (s, 3H), 2.60-2.56 (m, 2H), 2.22-2.10 (m, 2H), 1.67-1.50 (m, 2H), 1.45-1.27 (m, 2H), 1.17 (d, J=6.3 Hz, 6H), 0.97 (t, J=7.2 Hz, 3H). ESI [M+H]=559.2.

Example 137

Preparation of isopropyl trans-N-[4-[5-[2-(ethylsulfamoyl)-4-[(5-isopropylpyrazin-2-yl)amino]phenyl]thiazol-2-yl]cyclohexyl]carbamate (Compound 163)

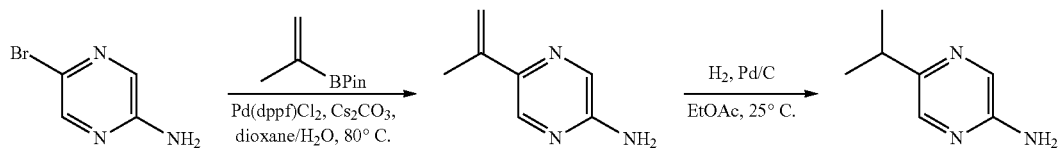

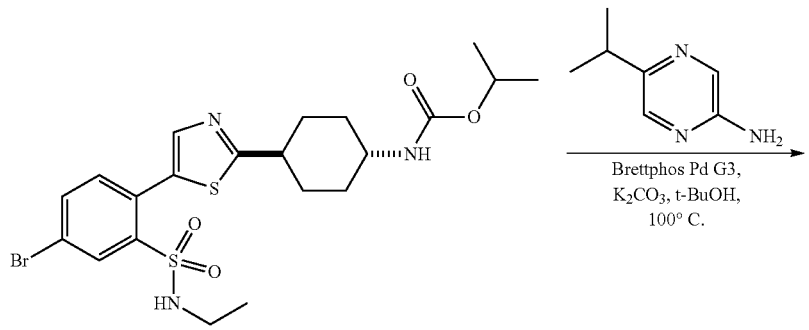

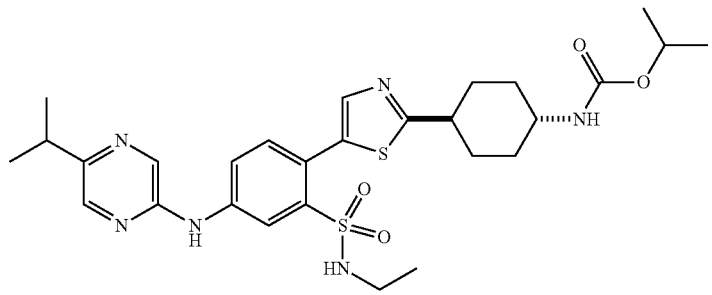

163

369
a) Synthesis of 5-isopropenylpyrazin-2-amine

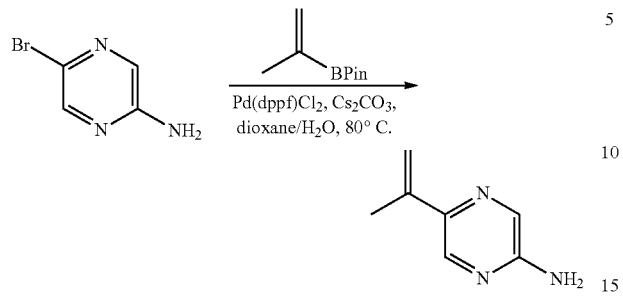

A mixture of 5-bromopyrazin-2-amine (1.0 g, 5.8 mmol, 1.0 eq.), 2-isopropenyl-4,4,5,5-tetramethyl-1,3,2-dioxaborolane (1.3 g, 7.5 mmol, 1.3 eq.), $Cs_2CO_3$ (5.6 g, 17.2 mmol, 3.0 eq.) and $Pd(dppf)Cl_2$ (421 mg, 575 umol, 0.1 eq.) in dioxane (20 mL)/$H_2O$ (10 mL) was stirred at 80° C. for 12 h under $N_2$ atmosphere. The reaction mixture was concentrated under reduced pressure to remove solvent, then the residue was diluted with $H_2O$ (10 mL) and extracted with EtOAc (90 mL, 30 mL×3). The combined organic layer was dried over $Na_2SO_4$, filtered and concentrated. The residue was purified by column chromatography ($SiO_2$, petroleum ether:ethyl acetate=10:1 to 5:1 to 1:1 to 0:1) to yield 5-isopropenylpyrazin-2-amine (750 mg, 97% yield) as a white solid. $^1$H NMR (400 MHz, methanol-$d_4$) δ=8.06 (s, 1H), 7.90 (d, J=1.10 Hz, 1H), 5.63 (d, J=0.66 Hz, 1H), 5.00-5.13 (m, 1H), 2.11 (s, 3H). ESI [M+H]=136.1.

370
b) Synthesis of 5-isopropylpyrazin-2-amine

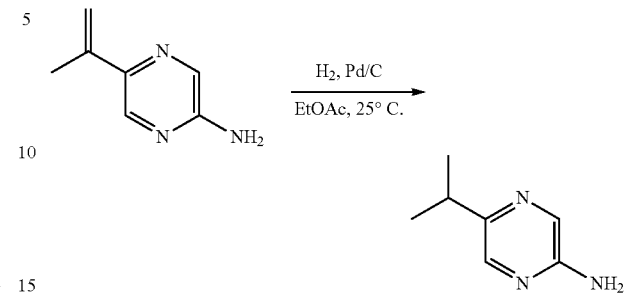

To a solution of 5-isopropenylpyrazin-2-amine (490 mg, 4 mmol, 1.0 eq.) in EtOAc (20 mL) was added AcOH (22 mg, 363 umol, 0.1 eq.) and Pd/C (100 mg, 10% purity). The suspension was degassed under vacuum and purged with $H_2$ for 3 times. The mixture was stirred under $H_2$ (15 psi) at 25° C. for 4 h, then filtered and concentrated under reduced pressure to yield 5-isopropylpyrazin-2-amine (500 mg, crude) as a pale yellow oil. $^1$H NMR (400 MHz, methanol-$d_4$) δ=7.87 (d, J=1.32 Hz, 1H), 7.78 (d, J=1.10 Hz, 1H), 2.91 (dt, J=13.89, 6.95 Hz, 1H), 1.23 (d, J=7.06 Hz, 6H). ESI [M+H]=138.1.

c) Synthesis of isopropyl trans-N-[4-[5-[2-(ethylsulfamoyl)-4-[(5-isopropylpyrazin-2-yl)amino]phenyl]thiazol-2-yl]cyclohexyl]carbamate (Compound 163)

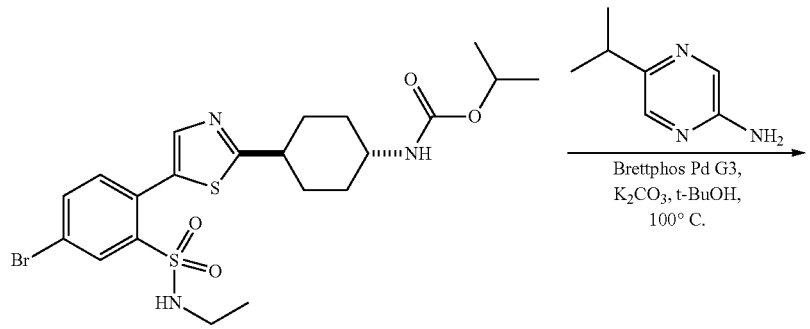

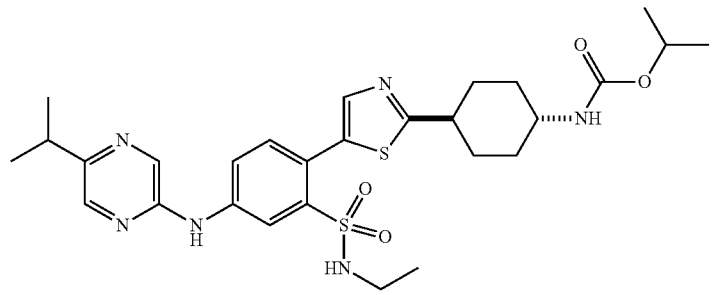

163

From isopropyl trans-N-[4-[5-[4-bromo-2-(ethylsulfamoyl)phenyl]thiazol-2-yl]cyclohexyl]carbamate and 5-isopropylpyrazin-2-amine, using General Method F. ¹H NMR (400 MHz, methanol-d₄) δ=8.58 (d, J=2.38 Hz, 1H), 8.16 (dd, J=8.88, 1.25 Hz, 2H), 7.94 (dd, J=8.38, 2.38 Hz, 1H), 7.74 (s, 1H), 7.42 (d, J=8.38 Hz, 1H), 4.78-4.86 (m, 1H), 3.43-3.52 (m, 1H), 3.00-3.10 (m, 2H), 2.97 (q, J=7.21 Hz, 2H), 2.22-2.30 (m, 2H), 2.06-2.14 (m, 2H), 1.72 (qd, J=12.84, 3.00 Hz, 2H), 1.43 (qd, J=12.57, 3.31 Hz, 2H), 1.33 (d, J=6.88 Hz, 6H), 1.25 (br d, J=6.13 Hz, 6H), 1.09 (t, J=7.25 Hz, 3H). ESI [M+H]=587.2.

Example 138

Preparation of isopropyl trans-N-[4-[5-[2-(ethylsulfamoyl)-4-[(5-isopropylpyridazin-3-yl)amino]phenyl]thiazol-2-yl]cyclohexyl]carbamate (Compound 164)

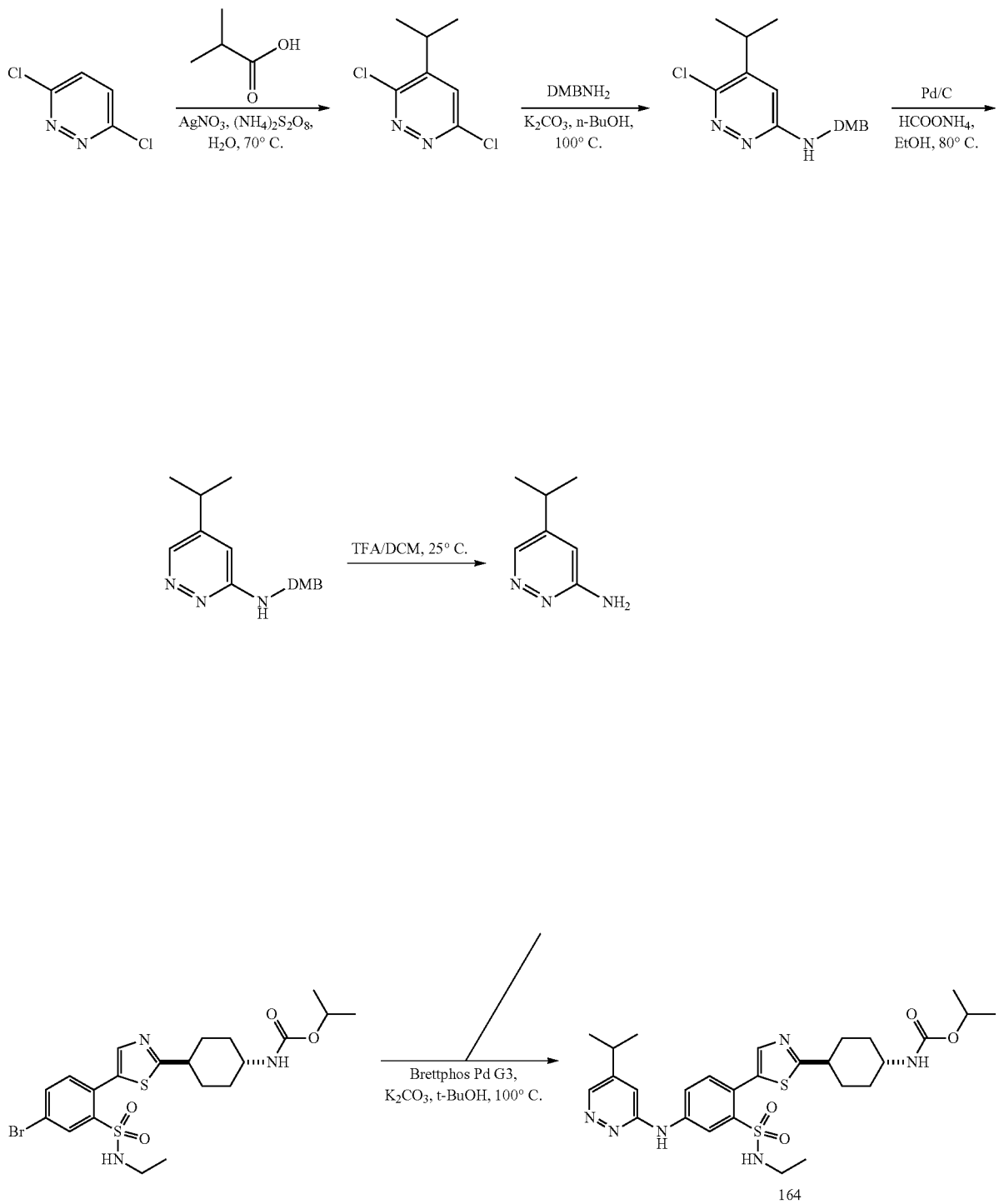

a) Synthesis of 3,6-dichloro-4-isopropyl-pyridazine

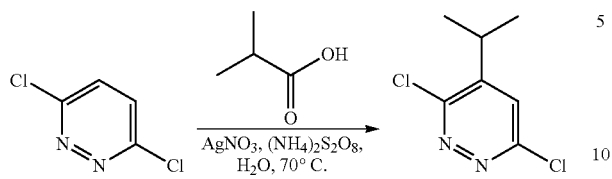

AgNO₃ (57 mg, 336 umol, 0.1 eq.), 2-methylpropanoic acid (355 mg, 4 mmol, 1.2 eq.) and TFA (0.1 mL) were added (in order) to a solution of 3,6-dichloropyridazine (500 mg, 3 mmol, 1.0 eq.) in H₂O (5 mL). The reaction solution was heated to 70° C., then slowly added (NH₄)₂S₂O₈ (1.5 g, 6.7 mmol, 2.0 eq.). The reaction was stirred for 12 h at 70° C., then extracted with dichloromethane (90 mL, 30 mL×3). The combined organic layers were dried over Na₂SO₄, filtered and concentrated under reduced pressure to yield 3,6-dichloro-4-isopropyl-pyridazine (650 mg, crude) as a yellow oil. ESI [M+H]=191.0/193.0.

b) Synthesis of 6-chloro-N-[(2,4-dimethoxyphenyl)methyl]-5-isopropyl-pyridazin-3-amine

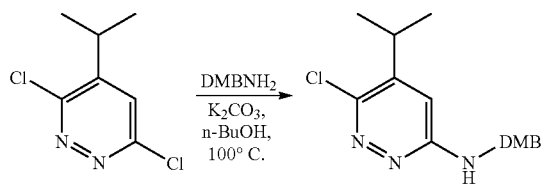

To a solution of (2,4)-dimethoxyphenyl)methanamine (853 mg, 4.5 mmol, 1.5 eq.) and 3,6-dichloro-4-isopropyl-pyridazine (650 mg, 3 mmol, 1.0 eq.) in n-BuOH (30 mL) was added K₂CO₃ (1.4 g, 10.2 mmol, 3.0 eq.) and the mixture was stirred at 100° C. for 12 h. The reaction mixture was concentrated and purified by column chromatography (SiO₂, petroleum ether:ethyl acetate=10:1 to 0:1) to yield 6-chloro-N-[(2,4-dimethoxyphenyl)methyl]-5-isopropyl-pyridazin-3-amine (320 mg, 994 umol, 29% yield) as a light yellow oil which was used directly in the next step.

c) Synthesis of N-[(2,4-dimethoxyphenyl)methyl]-5-isopropyl-pyridazin-3-amine

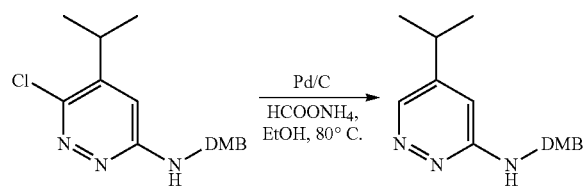

To a solution of 6-chloro-N-[(2,4-dimethoxyphenyl)methyl]-5-isopropyl-pyridazin-3-amine (300 mg, 932 umol, 1.0 eq.) and Pd/C (300 mg, 10% purity) in EtOH (10 mL) was added TEA (573 mg, 6 mmol, 6.0 eq.) and HCOONH₄ (1.8 g, 28.0 mmol, 30.0 eq.). The mixture was stirred at 80° C. for 1 h, then filtered and concentrated. The residue was diluted with H₂O (10 mL) and extracted with EtOAc (45 mL, 15 mL×3). The combined organic layers were dried over Na₂SO₄, filtered and concentrated under reduced pressure to yield N-[(2,4-dimethoxyphenyl)methyl]-5-isopropyl-pyridazin-3-amine (250 mg, crude) as a yellow oil. ESI [M+H]=287.9.

d) Synthesis of 5-isopropylpyridazin-3-amine

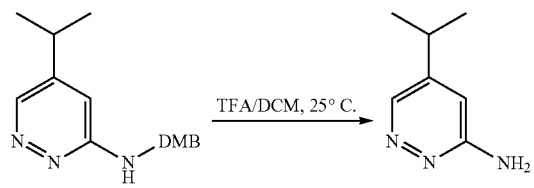

A solution of N-[(2,4-dimethoxyphenyl)methyl]-5-isopropyl-pyridazin-3-amine (230 mg, 800 umol, 1.0 eq.) in DCM (20 mL) and TFA (7 mL) was stirred at 25° C. for 1 h. The mixture was concentrated, diluted with H₂O (20 mL) and extracted with EtOAc (60 mL, 20 mL×3). The combined organic layers were dried over Na₂SO₄, filtered and concentrated under reduced pressure to give a residue. The residue was purified by prep-HPLC (column: Nano-micro Kromasil C18 100*40 mm 10 um; mobile phase: [water(10 mM NH₄HCO₃)-ACN]; B %: 1%-20%,8 min) to yield 5-isopropylpyridazin-3-amine (30 mg, 218 umol, 27% yield) as a white solid. ¹H NMR (400 MHz, methanol-d₄) δ=8.42 (s, 1H), 7.25 (s, 1H), 3.04 (spt, J=6.9 Hz, 1H), 1.33 (d, J=6.8 Hz, 6H). ESI [M+H]=138.0.

e) Synthesis of isopropyl trans-N-[4-[5-[2-(ethylsulfamoyl)-4-[(5-isopropylpyridazin-3-yl)amino]phenyl]thiazol-2-yl]cyclohexyl]carbamate (Compound 164)

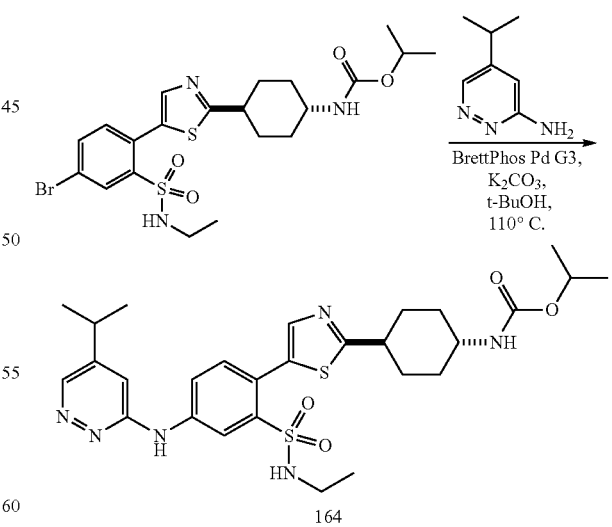

From isopropyl trans-N-[4-[5-[4-bromo-2-(ethylsulfamoyl)phenyl]thiazol-2-yl]cyclohexyl]carbamate and 5-isopropylpyridazin-3-amine, using General Method F. ¹H NMR (400 MHz, DMSO-d₆) δ=9.90 (s, 1H), 8.84 (s, 1H), 8.40 (d, J=2.1 Hz, 1H), 8.07 (dd, J=2.1, 8.4 Hz, 1H), 7.69 (s, 1H), 7.47 (d, J=8.4 Hz, 1H), 7.39 (t, J=5.5 Hz, 1H), 7.11 (s, 1H), 7.02 (br d, J=7.3 Hz, 1H), 4.75 (td, J=6.2, 12.5 Hz, 1H), 3.32 (br s, 1H), 3.00-2.90 (m, 2H), 2.89-2.80 (m, 2H), 2.16 (br d, J=11.6 Hz, 2H), 1.93 (br d, J=10.0 Hz, 2H), 1.67-1.53 (m, 2H), 1.42-1.29 (m, 2H), 1.26 (d, J=6.9 Hz, 6H), 1.18 (d, J=6.3 Hz, 6H), 0.99 (t, J=7.2 Hz, 3H). ESI [M+H]=587.3.

Example 139

Preparation of methyl trans-N-[4-[5-[2-(ethylsulfamoyl)-4-[(3-methyl-oxetan-3-yl)amino]phenyl]thiazol-2-yl]cyclohexyl]carbamate (Compound 165)

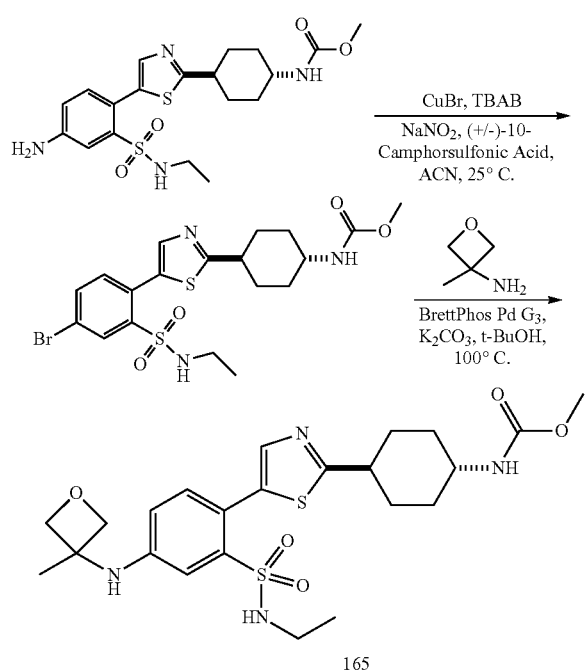

a) Synthesis of methyl trans-N-[4-[5-[4-bromo-2-(ethylsulfamoyl)phenyl]thiazol-2-yl]cyclohexyl]carbamate

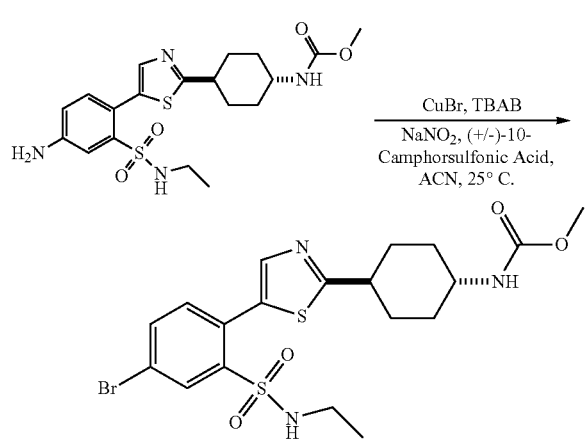

To a solution of methyl trans-N-[4-[5-[4-amino-2-(ethylsulfamoyl)phenyl]thiazol-2-yl]cyclohexyl]carbamate (2.5 g, 5.7 mmol, 1.0 eq.) in MeCN (50 mL) was added CuBr (981 mg, 7 mmol, 1.2 eq.), [(1S,4R)-7,7-dimethyl-2-oxo-norbornan-1-yl]methanesulfonic acid (4.0 g, 17.1 mmol, 3.0 eq.), TBAB (11.0 g, 34.2 mmol, 6.0 eq.) and NaNO$_2$ (1.2 g, 17.1 mmol, 3 eq.). The reaction mixture was stirred at 25° C. for 1 h, then quenched with with Na$_2$CO$_3$ sat.aq. (50 mL), and concentrated under reduced pressure to remove MeCN.

The residue was diluted with H$_2$O (50 mL) and extracted with EtOAc (300 mL, 100 mL×3), dried over Na$_2$SO$_4$, filtered and concentrated under reduced pressure. The residue was purified by reversed-phase HPLC(0.1% TFA condition) to yield methyl trans-N-[4-[5-[4-bromo-2-(ethylsulfamoyl)phenyl]thiazol-2-yl]cyclohexyl]carbamate (1.4 g, 2.8 mmol, 48.9% yield) as a yellow solid. $^1$H NMR (400 MHz, methanol-d$_4$) δ=8.21 (d, J=1.6 Hz, 1H), 7.93-7.71 (m, 2H), 7.43 (d, J=8.1 Hz, 1H), 3.65 (s, 3H), 3.48 (br t, J=11.6 Hz, 1H), 3.04 (br s, 1H), 2.89 (q, J=7.1 Hz, 2H), 2.26 (br d, J=12.5 Hz, 2H), 2.09 (br d, J=11.0 Hz, 2H), 1.72 (q, J=11.9 Hz, 2H), 1.51-1.37 (m, 2H), 1.04 (t, J=7.2 Hz, 3H). ESI [M+H]=502.1/504.1.

b) Synthesis of methyl trans-N-[4-[5-[2-(ethylsulfamoyl)-4-[(3-methyl-oxetan-3-yl)amino]phenyl]thiazol-2-yl]cyclohexyl]carbamate (Compound 165)

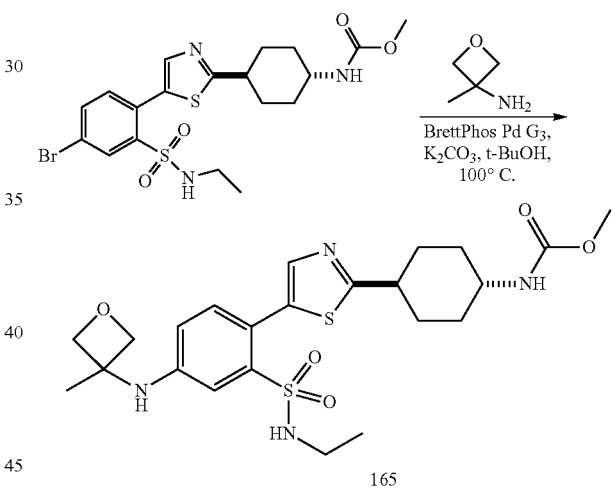

From methyl trans-N-[4-[5-[4-bromo-2-(ethylsulfamoyl)phenyl]thiazol-2-yl]cyclohexyl]carbamate and 3-methyl-oxetan-3-amine, using General Method F. $^1$H NMR (400 MHz, methanol-d$_4$) δ=7.60 (s, 1H), 7.20 (d, J=8.4 Hz, 1H), 7.11 (d, J=2.4 Hz, 1H), 6.60 (dd, J=2.5, 8.3 Hz, 1H), 4.79 (d, J=6.2 Hz, 2H), 4.59 (d, J=6.0 Hz, 2H), 3.62 (s, 3H), 3.50-3.39 (m, 1H), 3.03-2.92 (m, 1H), 2.85 (q, J=7.1 Hz, 2H), 2.21 (br d, J=12.8 Hz, 2H), 2.06 (br d, J=10.8 Hz, 2H), 1.74-1.60 (m, 5H), 1.40 (dq, J=3.1, 12.5 Hz, 2H), 1.01 (t, J=7.3 Hz, 3H). ESI [M+H]=509.2.

Example 140

Preparation of methyl trans-N-[4-[5-[2-(ethylsulfamoyl)-4-[(1H-pyrazol-4-yl)amino]phenyl]thiazol-2-yl]cyclohexyl]carbamate (Compound 166)

Following the same protocol and under the same reaction conditions as for Compound 165, Compound 166 was prepared. $^1$H NMR (400 MHz, methanol-d$_4$) δ=7.71 (s, 1H), 7.64 (s, 2H), 7.47 (d, J=2.4 Hz, 1H), 7.27 (d, J=8.4 Hz, 1H), 7.00 (dd, J=2.5, 8.4 Hz, 1H), 3.65 (s, 3H), 3.48 (ddd, J=4.0, 7.5, 11.5 Hz, 1H), 3.10-2.99 (m, 1H), 2.88 (q, J=7.3 Hz, 2H), 2.25 (br d, J=13.0 Hz, 2H), 2.09 (br d, J=10.5 Hz, 2H), 1.78-1.65 (m, 2H), 1.50-1.37 (m, 2H), 1.03 (t, J=7.3 Hz, 3H). ESI [M+H]=505.2.

Example 141

Preparation of methyl trans-N-[4-[5-[2-(ethylsulfamoyl)-4-[(1H-pyrazol-5-yl)amino]phenyl]thiazol-2-yl]cyclohexyl]carbamate (Compound 167)

Following the same protocol and under the same reaction conditions as for Compound 165, Compound 167 was prepared. ¹H NMR (400 MHz, methanol-d₄) δ=8.00 (d, J=1.5 Hz, 1H), 7.87 (s, 1H), 7.75-7.62 (m, 1H), 7.52-7.42 (m, 1H), 7.36 (d, J=8.3 Hz, 1H), 6.11 (br s, 1H), 3.65 (s, 3H), 3.56-3.42 (m, 1H), 3.13 (br t, J=11.8 Hz, 1H), 2.95 (q, J=7.2 Hz, 2H), 2.27 (br d, J=12.3 Hz, 2H), 2.10 (br d, J=10.8 Hz, 2H), 1.82-1.65 (m, 2H), 1.54-1.36 (m, 2H), 1.07 (t, J=7.2 Hz, 3H). ESI [M+H]=505.2.

Example 142

Preparation of isopropyl trans-N-[4-[5-[2-(ethylsulfamoyl)-4-[[(3R)-1-isobutyl-2-oxo-azetidin-3-yl]amino]phenyl]thiazol-2-yl]cyclohexyl]carbamate (Compound 168)

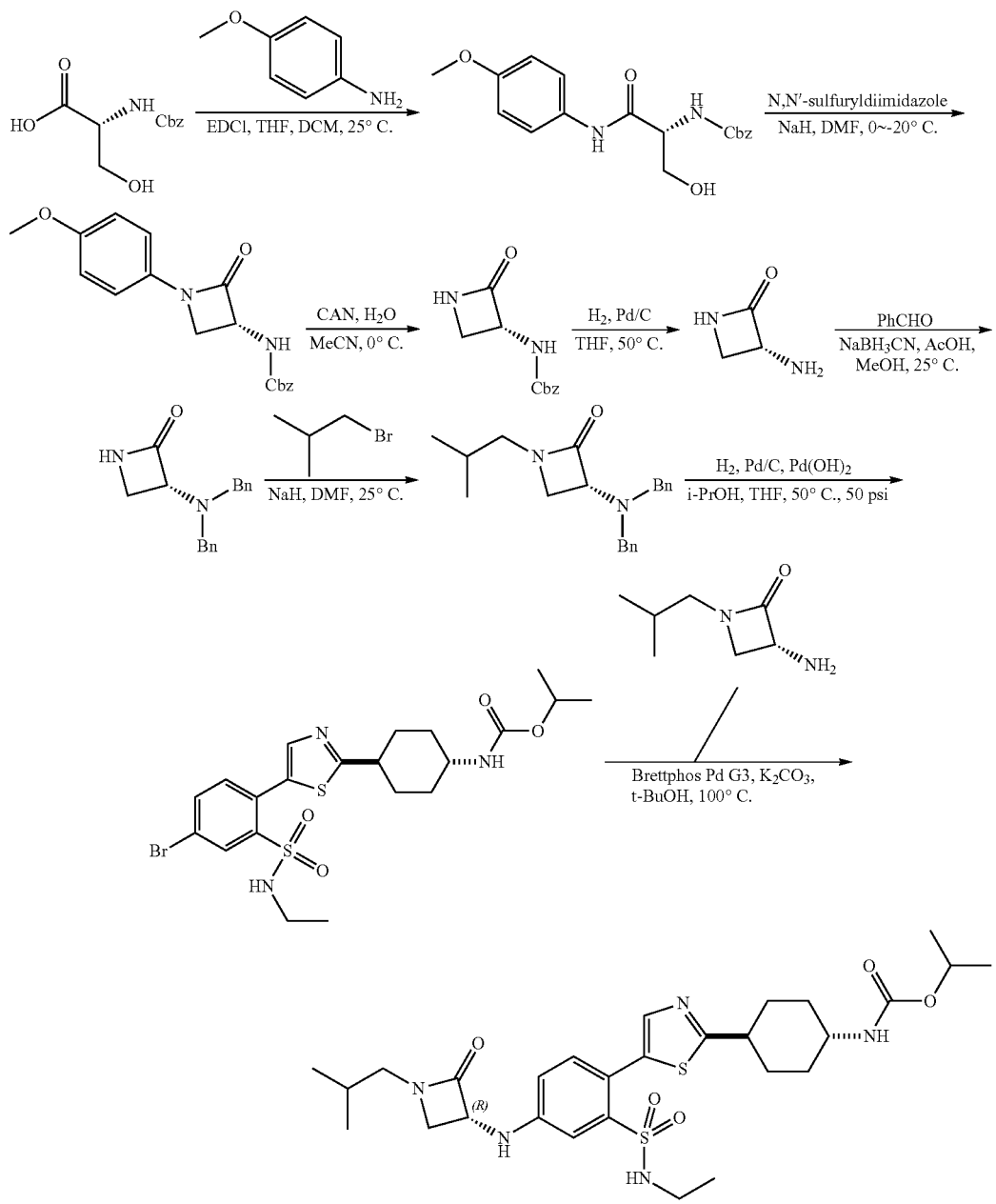

a) Synthesis of benzyl N-[(1R)-1-(hydroxymethyl)-2-(4-methoxyanilino)-2-oxo-ethyl]carbamate

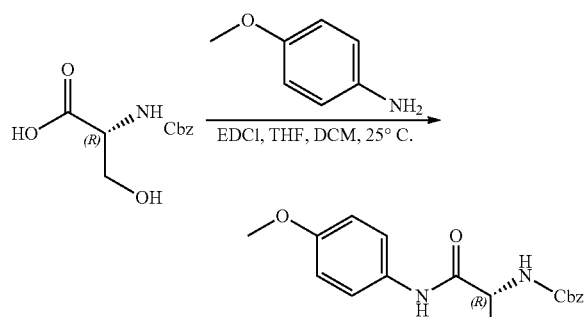

To a solution of 4-methoxyaniline (25.7 g, 208.7 mmol, 1.0 eq.) in THF (300 mL) and DCM (100 mL) was added (2R)-2-(benzyloxycarbonylamino)-3-hydroxy-propanoic acid (10.0 g, 41.7 mmol, 0.2 eq.) and EDCI (8.0 g, 41.7 mmol, 0.2 eq.) at 0° C. for 30 min. The mixture was stirred at 25° C. for 12 h and concentrated under reduced pressure. The residue was purified by column chromatography (SiO$_2$, petroleum ether:ethyl acetate=10:1 to 0:1) to yield benzyl N-[(1R)-1-(hydroxymethyl)-2-(4-methoxy-anilino)-2-oxo-ethyl]carbamate (8.0 g, 23.2 mmol, 11% yield) as a white solid. $^1$H NMR (400 MHz, methanol-d$_4$) δ=6.73 (d, J=1.1 Hz, 9H), 4.86-4.84 (m, 2H), 4.39-4.31 (m, 1H), 3.86 (br d, J=5.4 Hz, 2H), 3.80-3.75 (m, 3H). ESI [M+H]=345.0.

b) Synthesis of benzyl N-[(3R)-1-(4-methoxyphenyl)-2-oxo-azetidin-3-yl]carbamate

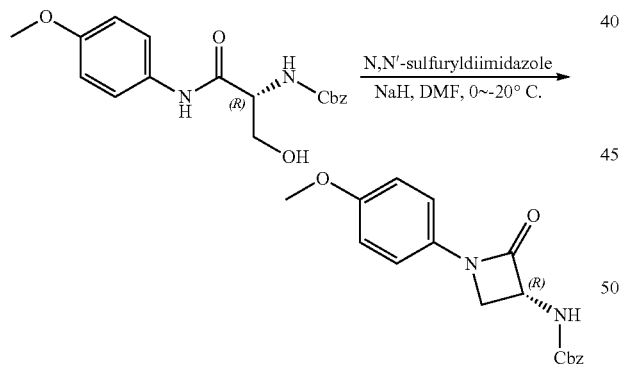

To a solution of benzyl N-[(1R)-1-(hydroxymethyl)-2-(4-methoxyanilino)-2-oxo-ethyl]carbamate (7.0 g, 20.3 mmol, 1.0 eq.) in DMF (200 mL) was added 1-imidazol-1-ylsulfonylimidazole (6.0 g, 30.5 mmol, 1.5 eq.) at 0° C. under under N$_2$ atmosphere. The resulting mixture was stirred at 0° C. for additional 0.5 h and then cooled to −20° C. Under vigorous stirring, NaH (1.2 g, 30.5 mmol, 60% purity, 1.5 eq.) was added portionwise. The resulting suspension was vigorously stirred at −20° C. for additional 1 h. The reaction mixture was quenched with water (200 mL). The collected precipitate was filtered, washed with additional water (100 mL) and then dried under reduced pressure to yield benzyl N-[(3R)-1-(4-methoxyphenyl)-2-oxo-azetidin-3-yl]carbamate (4.5 g, 13.8 mmol, 68% yield) as a pale yellow solid. $^1$H NMR (400 MHz, CDCl$_3$) δ=7.32-7.08 (m, 7H), 6.83-6.72 (m, 2H), 5.70-5.60 (m, 1H), 5.10-5.01 (m, 2H), 4.96-4.87 (m, 1H), 3.89-3.78 (m, 1H), 3.70 (s, 3H), 3.53-3.43 (m, 1H). ESI [M+H]=327.1.

c) Synthesis of benzyl N-[(3R)-2-oxoazetidin-3-yl]carbamate

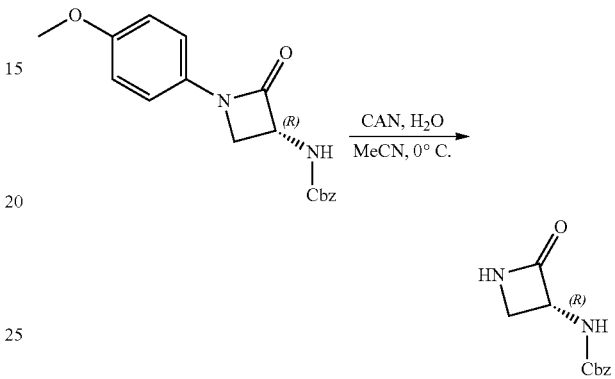

To a solution of benzyl N-[(3R)-1-(4-methoxyphenyl)-2-oxo-azetidin-3-yl]carbamate (2.3 g, 7.1 mmol, 1.0 eq.) in MeCN (110 mL)/H$_2$O (88 mL) was added CAN (11.6 g, 21.0 mmol, 3.0 eq.) at 0° C. The reaction mixture was stirred at 0° C. for 15 min, then quenched by addition of sat.aq. NaHCO$_3$ (110 mL) at 0° C. The mixture was filtered, and the filtrate was extracted with EtOAc (120 mL, 40 mL×3). The combined organic layers dried over Na$_2$SO$_4$, filtered and concentrated under reduced pressure. The residue was purified by prep-HPLC (column: Phenomenex luna C18 250*50 mm*10 um; mobile phase:[water(0.1% TFA)-ACN]; B %: 10%-40%,10 min) to yield benzyl N-[(3R)-2-oxoazetidin-3-yl]carbamate (890 mg, 4 mmol, 57% yield) as a purple solid. $^1$H NMR (400 MHz, CDCl$_3$) δ=7.45-7.33 (m, 5H), 6.08-5.93 (m, 1H), 5.68-5.52 (m, 1H), 5.25-5.08 (m, 2H), 4.97-4.82 (m, 1H), 3.76-3.57 (m, 1H), 3.46-3.34 (m, 1H). ESI [M+H]=221.1.

d) Synthesis of (3R)-3-aminoazetidin-2-one

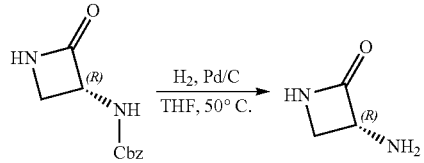

To a solution of benzyl N-[(3R)-2-oxoazetidin-3-yl]carbamate (890 mg, 4 mmol, 1 eq.) in THF (50 mL) was added Pd(OH)$_2$ (50 mg, 10% purity) and Pd/C (50 mg, 10% purity). The suspension was stirred under H$_2$ (50 psi) at 50° C. for 4 h, then filtered and concentrated under reduced pressure to yield (3R)-3-aminoazetidin-2-one (500 mg, crude) as a purple oil. ESI [2M+H]=173.1.

e) Synthesis of (3R)-3-(dibenzylamino)azetidin-2-one

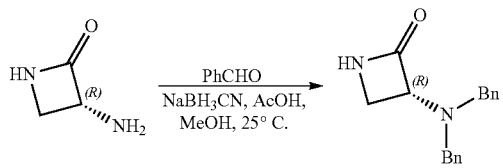

To a solution of (3R)-3-aminoazetidin-2-one (500 mg, 6 mmol, 1.0 eq.), benzaldehyde (555 mg, 5 mmol, 0.9 eq.) in MeOH (20 mL) was added AcOH (34 mg, 580 umol, 0.1 eq.) and NaBH$_3$CN (1.1 g, 17.4 mmol, 3 eq.). The mixture was stirred at 25° C. for 12 h and then quenched with NH$_3$.H$_2$O (5 mL). The mixture was concentrated under reduced pressure and then purified by column chromatography (SiO$_2$, Petroleum ether:Ethyl acetate=10:1 to 1:1) to yield (3R)-3-(dibenzylamino)azetidin-2-one (620 mg, crude) as a yellow oil. $^1$H NMR (400 MHz, CDCl$_3$) δ=7.44-7.29 (m, 10H), 6.58-6.42 (m, 1H), 4.44-4.31 (m, 2H), 4.26 (br d, J=2.5 Hz, 1H), 4.11 (br d, J=13.1 Hz, 2H), 3.28 (br d, J=5.4 Hz, 1H), 3.11-3.04 (m, 1H). ESI [M+H]=267.1.

Synthesis of (R)-3-(dibenzylamino)-1-isobutylazetidin-2-one

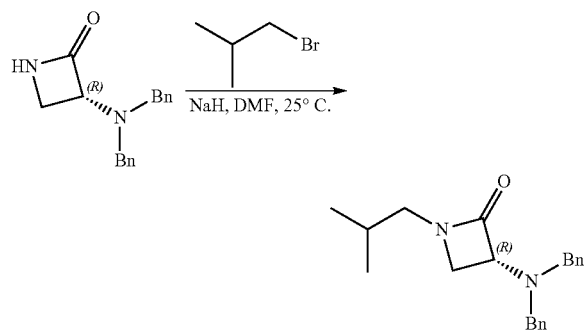

To a solution of (3R)-3-(dibenzylamino)azetidin-2-one (600 mg, 2 mmol, 1 eq.) in DMF (2 mL) was added NaH (135 mg, 3 mmol, 60% in oil, 1.5 eq.) and 1-bromo-2-methyl-propane (926 mg, 7 mmol, 3 eq.). The mixture was stirred at 25° C. for 1 h and then quenched with NH$_4$Cl (10 mL) at 0° C. The mixture was diluted with H$_2$O (20 mL) and extracted with EtOAc (60 mL, 20 mL×3). The combined organic layers were washed with brine (30 mL), dried over Na$_2$SO$_4$, filtered and concentrated under reduced pressure. The residue was purified by prep-HPLC (column: Nano-micro Kromasil C18 100*40 mm 10 um; mobile phase: [water(0.1% TFA)-ACN]; B %: 40%-67%,8 min) to yield (R)-3-(dibenzylamino)-1-isobutylazetidin-2-one (220 mg, 682 umol, 30% yield) as a yellow oil. $^1$H NMR (400 MHz, CDCl$_3$) δ=7.53-7.23 (m, 10H), 4.54-4.37 (m, 2H), 4.34-4.21 (m, 1H), 4.13 (br d, J=13.0 Hz, 2H), 3.39-3.32 (m, 1H), 3.12-3.02 (m, 1H), 2.99-2.87 (m, 2H), 1.79-1.68 (m, 1H), 0.90-0.76 (m, 6H). ESI [M+H]=323.1.

g) Synthesis of (3R)-3-amino-1-isobutyl-azetidin-2-one

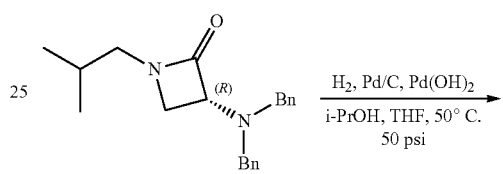

To a solution of (R)-3-(dibenzylamino)-1-isobutylazetidin-2-one (220 mg, 682 umol, 1 eq.) in THF (50 mL) and i-PrOH (50 mL) was added Pd(OH)$_2$ (20 mg, 10%) and Pd/C (20 mg, 10%). The suspension was stirred under H$_2$ (50 psi) at 50° C. for 12 h. The reaction mixture was filtered and concentrated under reduced pressure to yield (3R)-3-amino-1-isobutyl-azetidin-2-one (210 mg, crude) as a black gum. ESI [2M+H]=285.2.

h) Synthesis of isopropyl trans-N-[4-[5-[2-(ethylsulfamoyl)-4-[[(3R)-1-iso-butyl-2-oxo-azetidin-3-yl]amino]phenyl]thiazol-2-yl]cyclohexyl]carbamate (Compound 168)

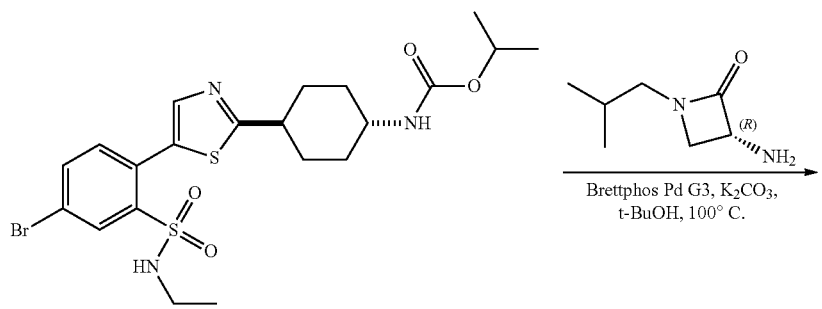

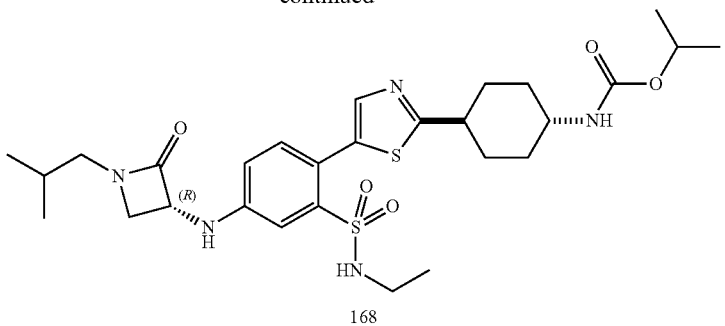

168

From isopropyl trans-N-[4-[5-[4-bromo-2-(ethylsulfamoyl)phenyl]thiazol-2-yl]cyclohexyl]carbamate and (3R)-3-amino-1-isobutyl-azetidin-2-one, using General Method F. $^1$H NMR (400 MHz, methanol-$d_4$) δ=7.75-7.63 (m, 1H), 7.44-7.36 (m, 1H), 7.33-7.23 (m, 1H), 6.98-6.87 (m, 1H), 4.91-4.87 (m, 1H), 3.81-3.75 (m, 1H), 3.53-3.42 (m, 1H), 3.38-3.36 (m, 1H), 3.29 (dd, J=2.0, 5.7 Hz, 1H), 3.18-3.08 (m, 2H), 3.07-2.96 (m, 1H), 2.94-2.83 (m, 2H), 2.25 (br d, J=12.5 Hz, 2H), 2.14-2.05 (m, 2H), 2.01-1.90 (m, 1H), 1.79-1.60 (m, 2H), 1.49-1.36 (m, 2H), 1.25 (br d, J=6.1 Hz, 6H), 1.04 (t, J=7.2 Hz, 3H), 0.99 (dd, J=3.8, 6.7 Hz, 6H). ESI [M+H]=592.2.

Example 143

Preparation of isopropyl trans-N-[4-[5-[2-(ethylsulfamoyl)-4-[[(3S)-1-isobutyl-2-oxo-azetidin-3-yl]amino]phenyl]thiazol-2-yl]cyclohexyl]carbamate (Compound 169)

Following the same protocol and under the same reaction conditions as for Compound 168, Compound 169 was prepared. $^1$H NMR (400 MHz, methanol-$d_4$) δ=7.66 (s, 1H), 7.39 (d, J=2.5 Hz, 1H), 7.26 (d, J=8.4 Hz, 1H), 6.93 (dd, J=2.4, 8.4 Hz, 1H), 4.81 (br s, 1H), 3.79 (t, J=5.2 Hz, 1H), 3.52-3.42 (m, 1H), 3.37 (br s, 1H), 3.29 (dd, J=2.0, 5.6 Hz, 1H), 3.18-3.07 (m, 2H), 3.07-2.97 (m, 1H), 2.89 (q, J=7.2 Hz, 2H), 2.25 (br d, J=12.3 Hz, 2H), 2.09 (br d, J=10.3 Hz, 2H), 2.01-1.91 (m, 1H), 1.76-1.63 (m, 2H), 1.48-1.37 (m, 2H), 1.25 (br d, J=6.0 Hz, 6H), 1.08-0.96 (m, 9H). ESI [M+H]=592.3.

Example 144

Preparation of tert-butyl trans-N-[4-[5-[2-(ethylsulfamoyl)-4-[(2-isopropylpyrazol-3-yl)amino]phenyl]thiazol-2-yl]cyclohexyl]carbamate (Compound 170)

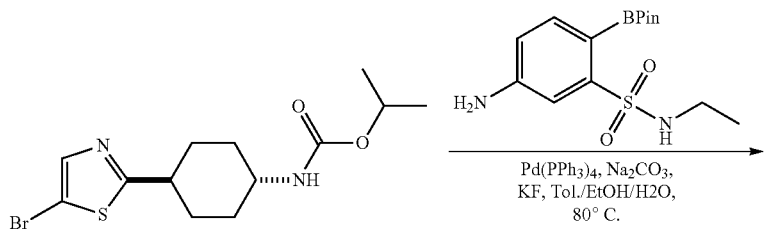

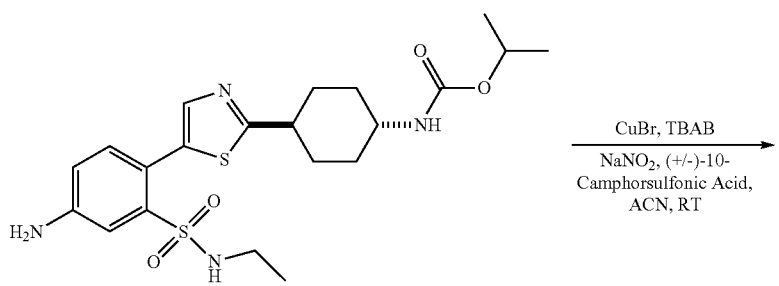

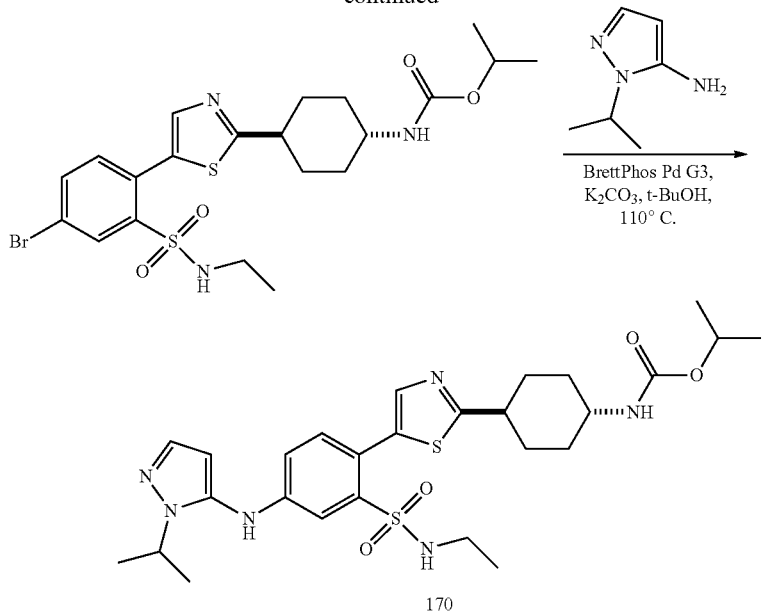

a) Synthesis of tert-butyl trans-N-[4-[5-[4-amino-2-(ethylsulfamoyl)phenyl]thiazol-2-yl]cyclohexyl]carbamate

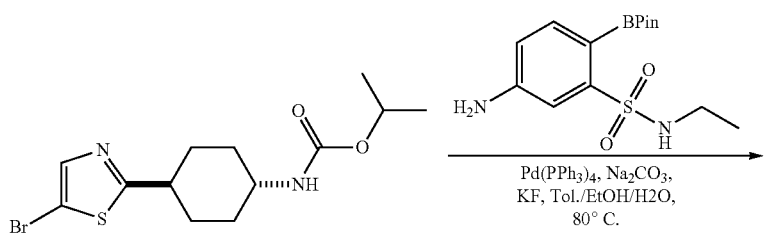

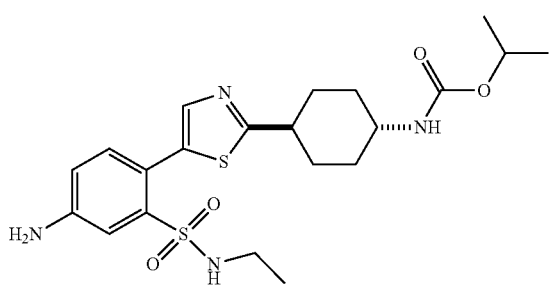

A mixture of 5-amino-N-ethyl-2-(4,4,5,5-tetramethyl-1,3,2-dioxaborolan-2-yl)benzenesulfonamide (2.8 g, 8.5 mmol, 1.4 eq), tert-butyl trans-N-[4-(5-bromo-thiazol-2-yl)cyclohexyl]carbamate (2.2 g, 6.1 mmol, 1 eq), KF (530 mg, 9 mmol, 1.5 eq), Na$_2$CO$_3$ (1.9 g, 18.3 mmol, 3 eq) and Pd(PPh$_3$)$_4$ (703 mg, 609 umol, 0.1 eq) in toluene (30 mL), EtOH (30 mL) and H$_2$O (10 mL) was stirred at 80° C. for 2 h under N$_2$ atmosphere. The reaction mixture was concentrated under reduced pressure, then diluted with H$_2$O (20 mL) and extracted with EtOAc (90 mL, 30 mL×3), dried over Na$_2$SO$_4$, filtered and concentrated under reduced pressure to give a residue which was purified by reversed-phase HPLC (0.1% TFA condition) to yield tert-butyl trans-N-[4-[5-[4-amino-2-(ethylsulfamoyl)phenyl]thiazol-2-yl]cyclohexyl]carbamate (2.9 g, 6.0 mmol, 99% yield) as a brown solid. $^1$H NMR (400 MHz, methanol-d$_4$) δ=7.64 (s, 1H), 7.60 (br s, 1H), 7.56 (d, J=3.0 Hz, 1H), 7.47 (d, J=3.4 Hz, 1H), 3.46-3.39 (m, 1H), 3.37 (s, 2H), 3.02 (tt, J=3.5, 12.1 Hz, 1H), 2.19 (br d, J=13.5 Hz, 2H), 2.05 (br d, J=10.1 Hz, 2H), 1.66 (dt, J=10.1, 12.9 Hz, 2H), 1.46 (s, 9H), 1.45-1.34 (m, 3H), 1.23-0.89 (m, 2H). ESI [M+H]=481.2.

b) Synthesis of tert-butyl trans-N-[4-[5-[4-bromo-2-(ethylsulfamoyl)phenyl]thiazol-2-yl]cyclohexyl]carbamate

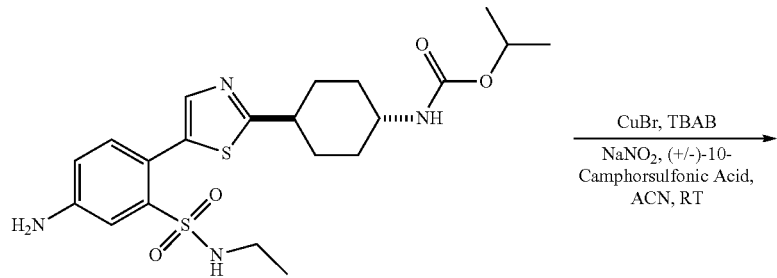

To a solution of tert-butyl trans-N-[4-[5-[4-amino-2-(ethylsulfamoyl)phenyl]thiazol-2-yl]cyclohexyl]carbamate (1.0 g, 2.1 mmol, 1.0 eq.) in MeCN (30 mL) was added TBAB (4.0 g, 12.5 mmol, 6.0 eq.), CuBr (358 mg, 2.5 mmol, 1.2 eq.), [(1S,4R)-7,7-dimethyl-2-oxo-norbornan-1-yl]methanesulfonic acid (1.5 g, 6.0 mmol, 3.0 eq.) and NaNO$_2$ (430 mg, 6 mmol, 3 eq.). The mixture was stirred at 25° C. for 1 h, then quenched with sat.aq.Na$_2$CO$_3$ (20 mL). The mixture was concentrated, diluted with H$_2$O (20 mL) and extracted with EtOAc (150 mL, 50 mL×3), dried over Na$_2$SO$_4$, filtered and concentrated under reduced pressure to give a residue which was purified by column chromatography (SiO$_2$, petroleum ether:ethyl acetate=3:1 to 1:1) to yield tert-butyl trans-N-[4-[5-[4-bromo-2-(ethylsulfamoyl)phenyl]thiazol-2-yl]cyclohexyl]carbamate (500 mg, 918 umol, 44% yield) as a yellow oil. $^1$H NMR (400 MHz, methanol-d$_4$) δ=8.18 (d, J=2.0 Hz, 1H), 7.80 (dd, J=2.0, 8.2 Hz, 1H), 7.74 (s, 1H), 7.40 (d, J=8.2 Hz, 1H), 3.39 (br t, J=11.7 Hz, 1H), 2.99 (tt, J=3.5, 12.0 Hz, 1H), 2.85 (q, J=7.3 Hz, 2H), 2.23 (br d, J=12.8 Hz, 2H), 2.10-1.99 (m, 2H), 1.75-1.58 (m, 2H), 1.44 (s, 9H), 1.41-1.32 (m, 2H), 1.01 (t, J=7.3 Hz, 3H). ESI [M+H]=544.0/546.0.

c) Synthesis of tert-butyl trans-N-[4-[5-[2-(ethylsulfamoyl)-4-[(2-isopropyl-pyrazol-3-yl)amino]phenyl]thiazol-2-yl]cyclohexyl]carbamate (Compound 170)

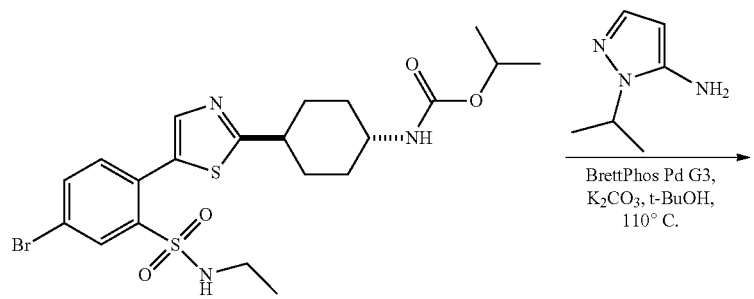

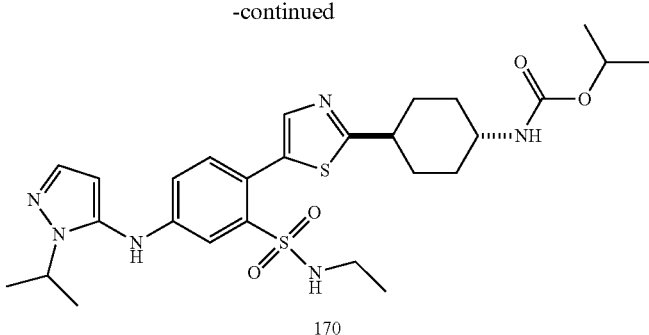

170

From tert-butyl trans-N-[4-[5-[4-bromo-2-(ethylsulfamoyl)phenyl]thiazol-2-yl]cyclohexyl]carbamate and 3-amino-2-isopropylpyrazole, using General Method F. $^1$H NMR (400 MHz, methanol-$d_4$) δ=7.77 (s, 1H), 7.63 (d, J=1.8 Hz, 1H), 7.50 (d, J=2.5 Hz, 1H), 7.35 (d, J=8.4 Hz, 1H), 7.05 (dd, J=2.5, 8.4 Hz, 1H), 6.19 (d, J=2.0 Hz, 1H), 4.63 (spt, J=6.6 Hz, 1H), 3.42 (br t, J=11.4 Hz, 1H), 3.12-3.01 (m, 1H), 2.87 (q, J=7.2 Hz, 2H), 2.26 (br d, J=12.9 Hz, 2H), 2.08 (br d, J=10.5 Hz, 2H), 1.79-1.65 (m, 2H), 1.48-1.44 (m, 15H), 1.44-1.35 (m, 2H), 1.02 (t, J=7.3 Hz, 3H). ESI [M+H]=589.3.

Example 145

Preparation of isopropyl trans-N-[4-[5-[2-(ethylsulfamoyl)-4-[(6-isopropylpyrimidin-4-yl)amino]phenyl]thiazol-2-yl]cyclohexyl]carbamate (Compound 171)

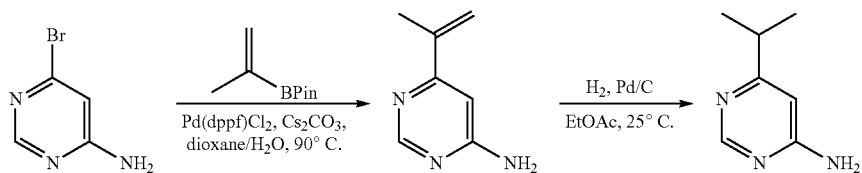

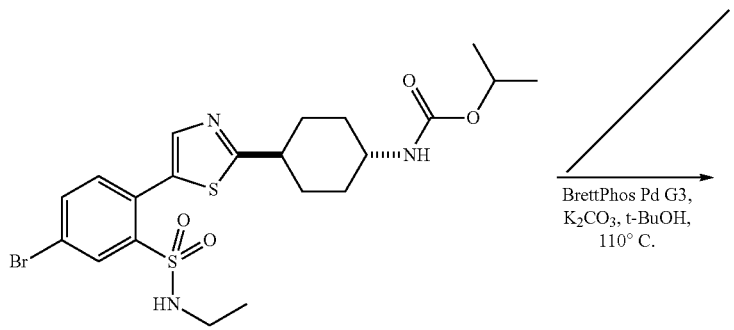

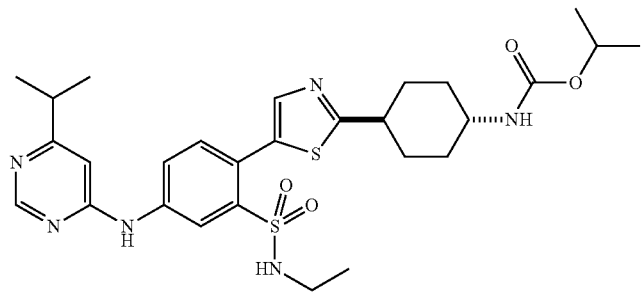

171 a) Synthesis of 6-isopropenylpyrimidin-4-amine

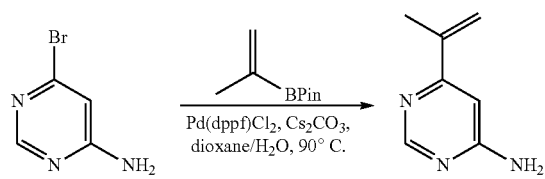

A mixture of 2-isopropenyl-4,4,5,5-tetramethyl-1,3,2-dioxaborolane (1.2 g, 7.1 mmol, 1.3 eq.), 6-bromopyrimidin-4-amine (950 mg, 5 mmol, 1 eq.), $Cs_2CO_3$ (5.3 g, 16.4 mmol, 3 eq.) and Pd(dppf)$Cl_2$ (399 mg, 546 umol, 0.1 eq.) in $H_2O$ (15 mL)/dioxane (30 mL) was stirred at 90° C. for 12 h under $N_2$ atmosphere. The reaction mixture was concentrated under reduced pressure to remove solvent. The residue was diluted with $H_2O$ (20 mL) and extracted with EtOAc (60 mL, 20 mL×3). The combined organic layers were dried over $Na_2SO_4$, filtered and concentrated under reduced pressure to give a residue which was purified by column chromatography ($SiO_2$, petroleum ether:ethyl acetate=1:0 to 0:1) to yield 6-isopropenylpyrimidin-4-amine (330 mg, 2 mmol, 45% yield) as a pale yellow solid. $^1$H NMR (400 MHz, methanol-$d_4$) δ=8.19 (d, J=0.9 Hz, 1H), 6.51 (d, J=1.0 Hz, 1H), 5.84 (d, J=0.8 Hz, 1H), 5.25 (t, J=1.5 Hz, 1H), 2.00 (s, 3H). ESI [M+H]=136.0.

b) Synthesis of 6-isopropylpyrimidin-4-amine

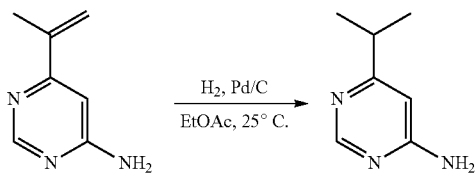

To a solution of 6-isopropenylpyrimidin-4-amine (330 mg, 2 mmol, 1 eq.) in EtOAc (20 mL) was added Pd/C (50 mg, 10% purity) and the suspension was stirred under $H_2$ (15 psi) at 25° C. for 2 h. The reaction mixture was filtered, and the filtrate was concentrated under reduced pressure to yield 6-isopropylpyrimidin-4-amine (320 mg, 2 mmol, 96% yield) as a white solid. $^1$H NMR (400 MHz, methanol-$d_4$) δ=8.15 (d, J=0.8 Hz, 1H), 6.31 (d, J=0.6 Hz, 1H), 2.67 (td, J=6.9, 13.9 Hz, 1H), 1.13 (d, J=7.0 Hz, 6H). ESI [M+H]=138.0.

c) Synthesis of isopropyl trans-N-[4-[5-[2-(ethylsulfamoyl)-4-[(6-isopropylpyrimidin-4-yl)amino]phenyl]thiazol-2-yl]cyclohexyl]carbamate (Compound 171)

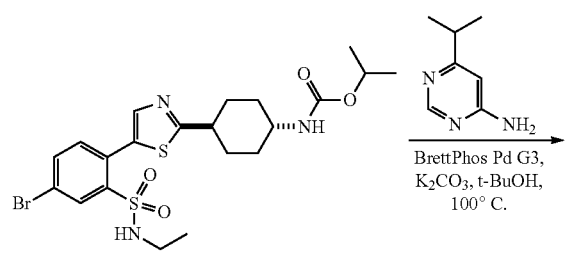

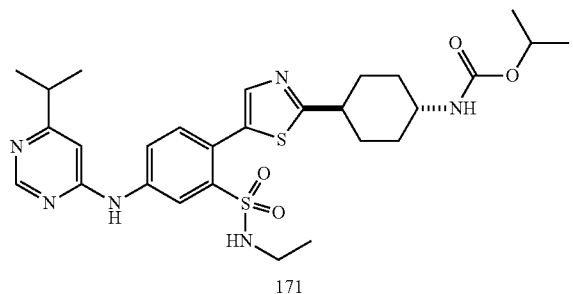

From isopropyl trans-N-[4-[5-[4-bromo-2-(ethylsulfamoyl)phenyl]thiazol-2-yl]cyclohexyl]carbamate and 6-isopropylpyrimidin-4-amine, using General Method F. $^1$H NMR (400 MHz, methanol-$d_4$) δ=8.82 (s, 1H), 8.52 (d, J=2.2 Hz, 1H), 7.97 (dd, J=2.2, 8.4 Hz, 1H), 7.76 (s, 1H), 7.55 (d, J=8.4 Hz, 1H), 6.91 (s, 1H), 4.83-4.77 (m, 1H), 3.50-3.39 (m, 1H), 3.12-2.96 (m, 2H), 2.89 (q, J=7.2 Hz, 2H), 2.31-2.16 (m, 2H), 2.13-2.00 (m, 2H), 1.76-1.63 (m, 2H), 1.38 (d, J=6.8 Hz, 8H), 1.22 (br d, J=6.2 Hz, 6H), 1.02 (t, J=7.3 Hz, 3H). ESI [M+H]=587.3.

Example 146

Preparation of isopropyl trans-N-[4-[5-[2-(ethylsulfamoyl)-4-[(1-methyl-6-oxo-pyridazin-3-yl)amino]phenyl]thiazol-2-yl]cyclohexyl]carbamate (Compound 172)

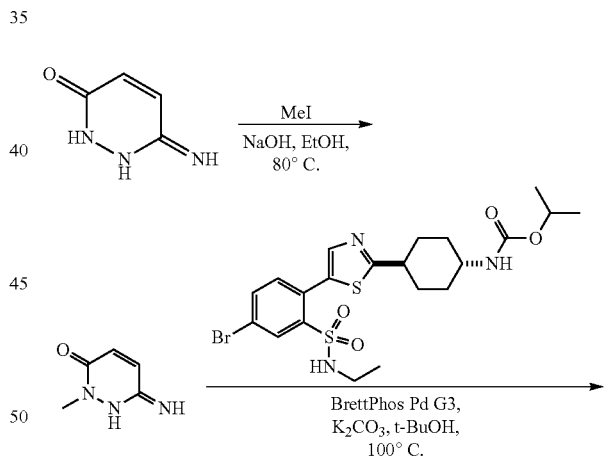

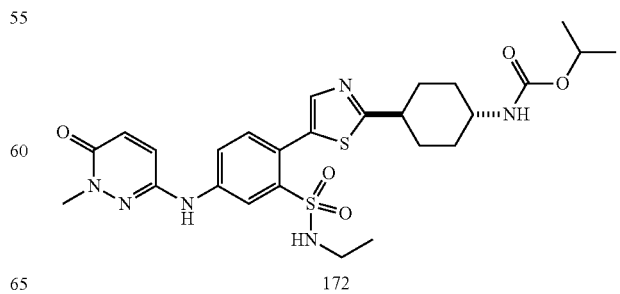

a) Synthesis of 6-imino-2-methyl-1H-pyridazin-3-one

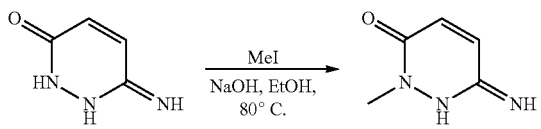

To a solution of 6-imino-1,2-dihydropyridazin-3-one (250 mg, 2 mmol, 1 eq.) in EtOH (5 mL) was added NaOH (180 mg, 5 mmol, 2 eq.) and MeI (351 mg, 2 mmol, 1 eq.). The mixture was stirred at 80° C. for 2 h and then quenched with $NH_3 \cdot H_2O$ (0.1 mL) at 25° C. The mixture was purified by prep-TLC ($SiO_2$, dichloromethane:methanol=8:1) and further purified by prep-HPLC (column: Waters Xbridge BEH C18 100*25 mm*5 um; mobile phase: [water(10 mM $NH_4HCO_3$)-ACN]; B %: 1%-12%,10 min) to yield 6-imino-2-methyl-1H-pyridazin-3-one (120 mg, 959 umol, 43% yield) as a white solid. $^1$H NMR (400 MHz, DMSO-$d_6$) δ=6.91 (d, J=9.7 Hz, 1H), 6.71 (d, J=9.5 Hz, 1H), 5.73 (s, 2H), 3.39 (s, 3H). ESI [2M+H]=251.1.

b) Synthesis of isopropyl trans-N-[4-[5-[2-(ethylsulfamoyl)-4-[(1-methyl-6-oxo-pyridazin-3-yl)amino]phenyl]thiazol-2-yl]cyclohexyl]carbamate (Compound 172)

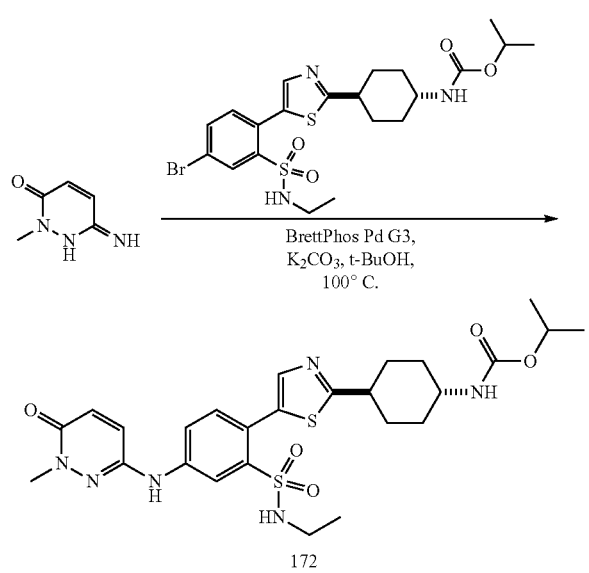

From isopropyl trans-N-[4-[5-[4-bromo-2-(ethylsulfamoyl)phenyl]thiazol-2-yl]cyclohexyl]carbamate and 6-imino-2-methyl-1H-pyridazin-3-one, using General Method F. $^1$H NMR (400 MHz, methanol-$d_4$) δ=8.47 (d, J=2.4 Hz, 1H), 7.80 (dd, J=2.3, 8.3 Hz, 1H), 7.72 (s, 1H), 7.40 (d, J=8.4 Hz, 1H), 7.24 (d, J=9.7 Hz, 1H), 6.95 (d, J=9.7 Hz, 1H), 4.82-4.77 (m, 1H), 3.74 (s, 3H), 3.54-3.38 (m, 1H), 3.09-2.97 (m, 1H), 2.95-2.84 (m, 2H), 2.30-2.18 (m, 2H), 2.11-2.01 (m, 2H), 1.77-1.62 (m, 2H), 1.49-1.34 (m, 2H), 1.22 (br d, J=6.2 Hz, 6H), 1.03 (t, J=7.2 Hz, 3H). ESI [M+H]=575.3.

Example 147

Preparation of isopropyl trans-N-[4-[5-[2-(tert-butylsulfamoyl)-4-[(6-chloro pyridazin-3-yl)amino]phenyl]thiazol-2-yl]cyclohexyl]carbamate (Compound 173)

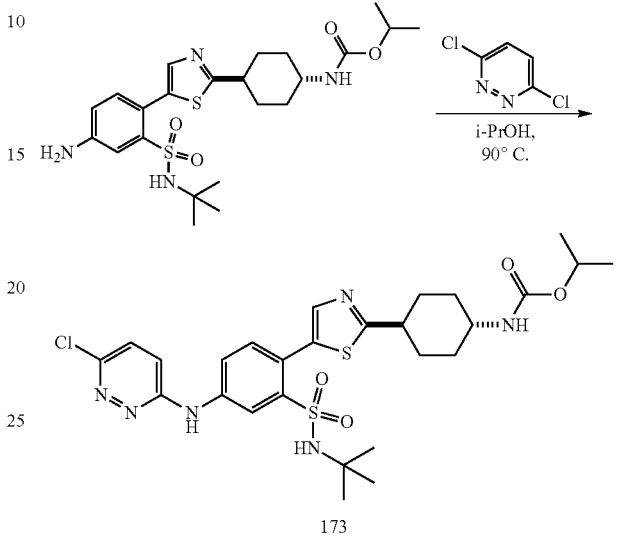

To a solution of isopropyl trans-N-[4-[5-[4-amino-2-(tert-butylsulfamoyl)phenyl]thiazol-2-yl]cyclohexyl]carbamate (20 mg, 40 umol, 1 eq) in i-PrOH (2 mL) was added 3,6-dichloropyridazine (18 mg, 121 umol, 3 eq) and the mixture was stirred at 90° C. for 1 h. The reaction mixture was concentrated under reduced pressure and purified by prep-HPLC (column: Welch Xtimate C18 150*25 mm*5 um; mobile phase: [water(0.04% HCl)-ACN]; B %: 50%-80%,10 min) to yield isopropyl trans-N-[4-[5-[2-(tert-butylsulfamoyl)-4-[(6-chloropyridazin-3-yl)amino]phenyl]thiazol-2-yl]cyclo-hexyl]carbamate (14 mg, 23 umol, 57% yield, 96% purity) as a white solid. $^1$H NMR (400 MHz, methanol-$d_4$) δ=8.65-8.54 (m, 1H), 8.12-8.03 (m, 1H), 7.89-7.81 (m, 1H), 7.60-7.54 (m, 1H), 7.50-7.43 (m, 1H), 7.27-7.18 (m, 1H), 4.84-4.80 (m, 1H), 3.53-3.41 (m, 1H), 3.15-3.05 (m, 1H), 2.30-2.22 (m, 2H), 2.14-2.04 (m, 2H), 1.80-1.65 (m, 2H), 1.50-1.35 (m, 2H), 1.22 (br d, J=6.2 Hz, 6H), 1.17-1.15 (m, 9H). ESI [M+H]=607.2/609.2.

Example 148

Preparation of isopropyl trans-N-[4-[5-[2-(tert-butylsulfamoyl)-4-(pyridazin-3-ylamino)phenyl]thiazol-2-yl]cyclohexyl]carbamate (Compound 174)

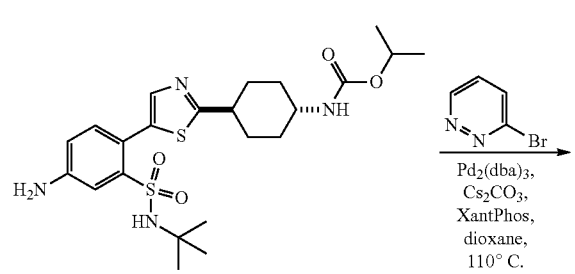

-continued

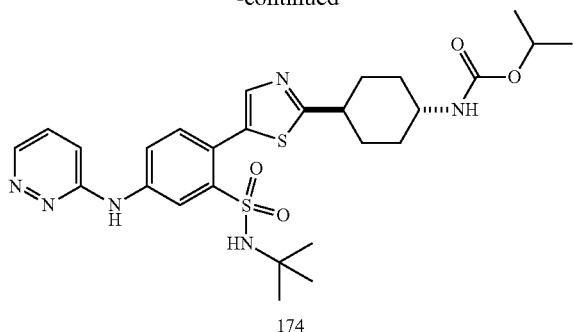

174

A mixture of 3-bromopyridazine (13 mg, 81 umol, 2 eq), isopropyl trans-N-[4-[5-[4-amino-2-(tert-butylsulfamoyl)phenyl]thiazol-2-yl]cyclohexyl]carbamate (20 mg, 40 umol, 1 eq), $Pd_2(dba)_3$ (4 mg, 4 umol, 0.1 eq), $Cs_2CO_3$ (40 mg, 121 umol, 3 eq) and Xantphos (2 mg, 4 umol, 0.1 eq) in dioxane (2 mL) was stirred at 110° C. for 12 h under $N_2$ atmosphere. The reaction mixture was concentrated and purified by prep-HPLC (column: Nano-micro Kromasil C18 100*40 mm 3 um; mobile phase: [water (0.1% TFA)-ACN]; B %: 30%-60%,8 min) to yield isopropyl trans-N-[4-[5-[2-(tert-butylsulfamoyl)-4-(pyridazin-3-ylamino)phenyl]thiazol-2-yl]cyclohexyl]carbamate (4 mg, 6 umol, 15% yield, 100% purity) as a yellow solid. $^1$H NMR (400 MHz, methanol-$d_4$) δ=8.89 (br d, J=4.50 Hz, 1H), 8.61 (d, J=2.13 Hz, 1H), 8.00 (dd, J=8.38, 2.00 Hz, 1H), 7.90 (br dd, J=9.07, 4.82 Hz, 1H), 7.79 (s, 1H), 7.63 (br d, J=9.13 Hz, 1H), 7.51 (d, J=8.38 Hz, 1H), 4.78 (br s, 1H), 3.44-3.52 (m, 1H), 3.05 (ddd, J=11.94, 8.69, 3.50 Hz, 1H), 2.26 (br d, J=11.88 Hz, 2H), 2.10 (br d, J=10.13 Hz, 2H), 1.67-1.79 (m, 2H), 1.38-1.49 (m, 2H), 1.25 (br d, J=6.00 Hz, 6H), 1.13 (s, 9H). ESI [M+H]=573.2

Example 149

Compound Primary Screening

Primary screening was a phenotypic screen that utilized the synthetic lethal interaction between AID and RAD51 to identify compounds that were both potent and on target. AID expressing cells are dependent upon RAD51 for survival; inhibiting RAD51 in AID positive cells results in a cytotoxic effect. Based on such an effect, compounds that were potent in AID positive cells and were significantly less potent in AID negative cells were identified.

Materials and Supplies

Plastic ware and consumables needed for the experiment include: cell culture media; Evaporation Buffer media; 100% DMSO; 96 well U-bottom sterile culture plates; 250 mL bottle; 1.5 mL Opaque amber epi tubes; Epi Tube rack; 300 mL reservoirs; 25 mL reservoir; 25 mL serological pipette tips; 5 mL serological pipette tips P1000 Pipette Tips; and P200 Pipette Tips.

Equipment needed for this experiment include: Viaflo 384 liquid handler; Eppendorf serological pipette; Eppendorf P1000 Pipette; and Eppendorf P200 Pipette.

Daudi Cell Culture is also needed for this experiment. Lastly, compounds (e.g., the compounds of this application) to be tested are needed.

Procedure

All steps were performed in a sterile environment inside the Biosafety cabinet.

A 96 well u-bottom plate was prepared by writing the experiment number, plate number, date and initials in the top right corner of the plate lid. With a sterile 300 ml reservoir, and 25 ml serological pipette, evaporation buffer media was pipetted into reservoir in 25 ml increments. Using the liquid handler, 150 ul of evaporation buffer media was pipetted from reservoir into rows A and H, and Columns 1 and 12 of the 96 well u-bottom plate. Cell cultures were counted to obtain the density of cells per ml, and the culture viability. The cell density information was used to obtain 1,000,000 cells from culture using a 5 mL serological pipette into an epi tube. The cell density information from the culture was used to calculate the number of cells and volume of media needed for the assay to seed 1250 cells in 130 ul of media per available culture well in the 96 well u-bottom plate. Rows B through F were used for cells (50 wells in total), with row G left for an empty media control. The calculation was overestimated by 10 mL to account for the dead volume in the 300 ml reservoir. Once the media volume was calculated, the appropriate volume of media was pipetted in 25 mL increments into the 250 mL bottle using a 25 mL serological pipette. The 250 ml bottle was capped tightly, and placed into a 37° C. water bath for 2 minutes. While the culture media was warming, 10 mL of fresh media was pipetted from the 500 mL culture media bottle into a sterile 25 mL reservoir. Using the Eppendorf multichannel pipette, 130 ul of media was pipetted from the 25 mL reservoir into row G of the 96 well u-bottom plate. Once the 250 mL bottle of media was warmed, the volume of culture needed was pipetted into the bottle, and mixed gently with a 25 mL serological pipette as to not create bubbles, and then the contents of the bottle were pipetted into a new 300 mL reservoir. Using the liquid handler, 130 ul of culture was pipetted from the 300 mL reservoir into rows B through F of the 96 well u-bottom plate. Once the culture was added, the plate was placed into a 37° C. incubator until the compound master plate was prepared for use.

Two 96 well u-bottom plates were prepared by writing the master plate name in the upper right corner of the plate lid. Labeling one DMSO master and the other Media Master. The compounds of interest were obtained from the laboratory freezer, and placed into a 25 well storage box with a lid, and set the box aside. The compounds were vortexed after thawing but before use. Using an automatic multichannel pipette, 20 ul of 100% DMSO was pipetted into wells B3-B11 through G3-G11 of the DMSO master plate. For each compound on the master plate, 50 ul of the compound were pipetted in the appropriate well of row 2 (reference plate map to determine appropriate well). A serial dilution was prepared beginning by aspirating 20 ul from row 2 and mixing with row 3, repeating until row 11 was reached. Using the liquid handler, 194 ul of Daudi media was dispensed into wells B2-B11 through G2-G11 of the Media master plate. Using the liquid handler, 6 ul from the DMSO master plate was aspirated and dispensed into the media master plate, mixing 100 ul twice.

Compounds from master plate were then added to the culture plate. The culture plates were removed from the incubator, and set inside the biosafety cabinet. Using a liquid handler, 20 ul from wells B2 to B11 through G2 to G11 of master plate were aspirated, and dispensed into wells B2 to B11 through G2 to G11 of culture plate. This set was continued with each culture plate. Once the culture plates acquired their 20 ul of compound dilutions, they were placed back into the incubator, until their reads on Day 7 of experiment.

Cell death was measured on Day 7 of the experiment using Cell-Titer Glo and a Promega Plate reader.

Percent cell death and $EC_{50}$ values were calculated by comparing the cell viability of the compound treated wells to the non-treated wells. Normalized RLU values were obtained by subtracting the media well values from each of the wells in the same column, and then dividing that value by the DMSO treated cells values. The percent kill was then calculated by subtracting the normalized RLU value from 1 and multiplying by 100. The average normalized percent kill value and standard error of the mean was then calculated. The kill values were then inputted into Prism with the corresponding standard errors. In Prism a non-linear regression line was plotted with the data points using a semi-log scale, and the $EC_{50}$ value was calculated. For compounds that showed good potency in the Daudi cell line, the assay was repeated using WI-38 cells (AID negative).

The biological activity of the compounds of the present application measured above is listed below.

TABLE 2

| Cmpd No. | Cellular activity in AID + (Daudi) |
| --- | --- |
| 1 | D |
| 2 | D |
| 3 | B |
| 4 | B |
| 5 | C |
| 6 | C |
| 7 | C |
| 8 | B |
| 9 | C |
| 10 | B |
| 11 | C |
| 12 | D |
| 13 | B |
| 14 | C |
| 15 | C |
| 16 | C |
| 17 | C |
| 18 | C |
| 19 | D |
| 20 | C |
| 21 | C |
| 22 | C |
| 23 | B |
| 24 | B |
| 25 | C |
| 26 | C |
| 27 | C |
| 28 | D |
| 29 | C |
| 30 | D |
| 31 | C |
| 32 | D |
| 33 | B |
| 34 | C |
| 36 | C |
| 38 | A |
| 40 | A |
| 41 | B |
| 42 | A |
| 44 | C |
| 45 | C |
| 46 | C |
| 48 | C |
| 49 | B |
| 50 | B |
| 51 | B |
| 52 | B |
| 54 | C |
| 56 | A |
| 58 | B |
| 59 | B |
| 60 | A |
| 66 | C |
| 67 | C |
| 68 | B |
| 69 | A |
| 70 | B |
| 71 | C |
| 72 | C |
| 73 | C |
| 74 | B |
| 75 | C |
| 76 | C |
| 77 | C |
| 78 | C |
| 79 | A |
| 80 | B |
| 81 | B |
| 82 | B |
| 83 | B |
| 84 | B |
| 85 | B |
| 86 | B |
| 87 | B |
| 88 | B |
| 89 | B |
| 90 | B |
| 91 | B |
| 92 | B |
| 93 | C |
| 94 | A |
| 95 | B |
| 96 | D |
| 97 | A |
| 98 | A |
| 99 | B |
| 100 | B |
| 101 | C |
| 102 | C |
| 103 | B |
| 104 | B |
| 105 | A |
| 106 | A |
| 107 | A |
| 108 | A |
| 109 | B |
| 110 | B |
| 111 | B |
| 112 | A |
| 113 | A |
| 114 | B |
| 115 | A |
| 116 | A |
| 117 | B |
| 118 | B |
| 119 | A |
| 120 | A |
| 121 | A |
| 122 | A |
| 123 | A |
| 124 | A |
| 125 | A |
| 126 | A |
| 127 | B |
| 128 | A |
| 129 | A |
| 130 | B |
| 131 | A |
| 132 | B |
| 133 | C |
| 134 | B |
| 135 | B |
| 136 | A |
| 137 | A |
| 138 | B |
| 139 | A |
| 140 | B |
| 141 | C |
| 142 | C |
| 143 | A |
| 144 | B |
| 145 | B |
| 146 | A |

TABLE 2-continued

| Cmpd No. | Cellular activity in AID + (Daudi) |
|---|---|
| 147 | C |
| 148 | A |
| 149 | A |
| 150 | B |
| 151 | A |
| 152 | A |
| 153 | A |
| 154 | A |
| 155 | B |
| 156 | B |
| 157 | A |
| 158 | B |
| 159 | A |
| 160 | B |
| 161 | A |
| 162 | A |
| 163 | B |
| 164 | B |
| 165 | C |
| 166 | C |
| 167 | B |
| 168 | B |
| 169 | A |
| 170 | B |
| 171 | B |
| 172 | B |
| 173 | B |
| 174 | B |

EC$_{50}$: A: ≤0.1 µM, B: 0.1 µM-1 µM, C: 1 µM-10 µM, D: >10 µM

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula I:

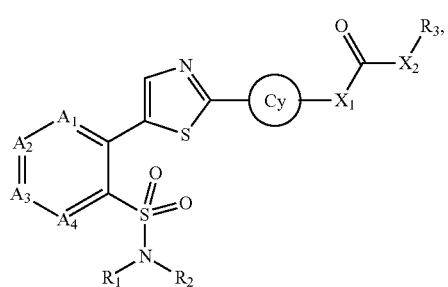

(I)

or a pharmaceutically acceptable salt or solvate thereof, wherein:

the thiazolyl ring

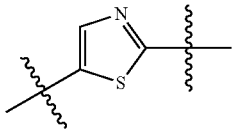 [SMILES: *c1cnc(*)s1]

is optionally substituted with F or Cl;

the ring Cy is $C_3$-$C_7$ cycloalkyl, bridged $C_6$-$C_{12}$ cycloalkyl, or saturated heterocyclyl comprising one or two 3- to 7-membered rings and 1-3 heteroatoms selected from N, O, and S, wherein the cycloalkyl or heterocyclyl moiety is optionally substituted with one or more groups selected from halogen, OH, CN, $NH_2$, $C_1$-$C_4$ alkyl, $C_1$-$C_4$ haloalkyl, $C_1$-$C_4$ alkoxy, and $C_1$-$C_4$ haloalkoxy;

$X_1$ is $NR_8$ or O, or, when $X_1$ is bonded to a nitrogen atom in the ring Cy, $X_1$ is absent;

$X_2$ is $NR_8$ or O;

$R_1$ is H or $C_1$-$C_6$ alkyl optionally substituted with halogen, OH, $C_1$-$C_6$ alkoxy, or $C_6$-$C_{10}$ aryloxy;

$R_2$ is H or $C_1$-$C_6$ alkyl optionally substituted with halogen, OH, $C_1$-$C_6$ alkoxy, or $C_6$-$C_{10}$ aryloxy;

or $R_1$ and $R_2$, together with the nitrogen atom to which they are attached, form a heterocyclyl comprising one or two 3- to 7-membered rings and 1-3 heteroatoms selected from N, O, and S;

$R_3$ is $C_1$-$C_6$ alkyl optionally substituted with one or more groups selected from halogen, OH, and CN, phenyl, $CH_2$-phenyl, $C_3$-$C_7$ cycloalkyl, $CH_2$—($C_3$-$C_7$) cycloalkyl, heterocyclyl, or $CH_2$-heterocyclyl, wherein the heterocyclyl comprises one or two 3- to 7-membered rings and 1-3 heteroatoms selected from N, O, and S, wherein the cycloalkyl, phenyl, or heterocyclyl moiety is optionally substituted with one or more groups selected from halogen, OH, CN, $C_1$-$C_4$ alkyl, $C_1$-$C_4$ haloalkyl, $C_1$-$C_4$ alkoxy, and $C_1$-$C_4$ haloalkoxy;

$A_1$, $A_2$, $A_3$, and $A_4$ are each independently N or $C(R_4)$;

each $R_4$ is independently H, halogen, CN, OH, $N(R_6')_2$, $C_1$-$C_6$ alkoxy, $C(=O)N(R_6)_2$, $C(=O)OR_6$, $C(=O)R_6$, Q-T, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$;

each Q is independently $C_1$-$C_4$ alkylene or O—($C_1$-$C_4$) alkylene wherein the oxygen atom is bonded to the ring

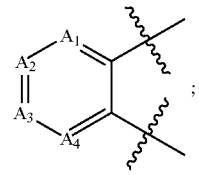

each T is independently $C_1$-$C_4$ alkoxy, OH, $N(R_6)_2$, $N(R_5)C(=O)R_6$, $N(R_5)C(=O)OR_6$, $C(=O)N(R_6)_2$, $C(=O)OR_6$, $C(=O)R_6$, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$;

each $R_5$ is independently H or $C_1$-$C_4$ alkyl;

each $R_6'$ is independently H, $C_1$-$C_6$ alkyl optionally substituted with one or more $R_7$, $C_1$-$C_6$ haloalkyl, $C_3$-$C_7$ cycloalkyl, heterocyclyl comprising one or two 3- to 7-membered rings and 1-3 heteroatoms selected from N, O, and S, $C_6$-$C_{10}$ aryl, or heteroaryl comprising one or two 5- or 6-membered rings and 1-3 heteroatoms selected from N, O, and S, wherein the cycloalkyl, heterocyclyl, aryl, or heteroaryl moiety is optionally substituted with one or more $R_9$, wherein at least one $R_6'$ is not H;

or two $R_6'$ together with the atoms to which they are attached form a 3- to 10-membered heterocyclyl comprising 1-3 heteroatoms selected from N, O, and S, wherein the heterocyclyl is optionally substituted with one or more $R_9$;

each $R_6$ is independently H, $C_1$-$C_6$ alkyl optionally substituted with one or more $R_7$, $C_1$-$C_6$ haloalkyl, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$;

or two $R_6$ together with the atoms to which they are attached form a 3- to 10-membered heterocyclyl comprising 1-3 heteroatoms selected from N, O, and S, wherein the heterocyclyl is optionally substituted with one or more $R_9$;

each $R_7$ is independently $N(R_8)_2$, $OR_8$, $C_6$-$C_{10}$ aryl, or heteroaryl comprising one or two 5- or 6-membered rings and 1-3 heteroatoms selected from N, O, and S;

each $R_5$ is independently H or $C_1$-$C_6$ alkyl; and each $R_9$ is independently oxo, halogen, OH, CN, $NH_2$, $N(C_1$-$C_4$ alkyl$)_2$, $C_1$-$C_6$ alkyl, $C_1$-$C_6$ haloalkyl, $C_1$-$C_6$ alkoxy, or $C_1$-$C_6$ haloalkoxy, wherein the $C_1$-$C_6$ alkyl is optionally substituted with one or more oxo, OH, $O(C_1$-$C_4$ alkyl), CN, $NH_2$, $NH(C_1$-$C_4$ alkyl), or $N(C_1$-$C_4$ alkyl$)_2$.

2. The compound of claim 1, wherein the ring Cy is $C_3$-$C_7$ cycloalkyl or saturated heterocyclyl comprising one or two 3- to 7-membered rings and 1-3 heteroatoms selected from N, O, and S, wherein the cycloalkyl or heterocyclyl is optionally substituted with one or more groups selected from halogen, OH, CN, $NH_2$, $C_1$-$C_4$ alkyl, $C_1$-$C_4$ haloalkyl, $C_1$-$C_4$ alkoxy, and $C_1$-$C_4$ haloalkoxy.

3. The compound of claim 1, wherein $A_1$, $A_2$, $A_3$, and $A_4$ are each $C(R_4)$.

4. The compound of claim 1, wherein one, two, or three of $A_1$, $A_2$, $A_3$, and $A_4$ are N.

5. The compound of claim 1, wherein $X_1$ is $NR_8$ and $X_2$ is $NR_8$.

6. The compound of claim 1, wherein $X_1$ is $NR_8$ and $X_2$ is O.

7. The compound of claim 1, wherein $X_1$ is O and $X_2$ is $NR_8$.

8. The compound of claim 1, wherein $X_1$ is absent and $X_2$ is $NR_8$.

9. The compound of claim 1, wherein $X_1$ is absent and $X_2$ is O.

10. The compound of claim 1, wherein $R_3$ is $C_1$-$C_6$ alkyl optionally substituted with one or more groups selected from halogen, OH, and CN.

11. The compound of claim 1, wherein $R_3$ is phenyl or $CH_2$-phenyl, wherein the phenyl moiety is optionally substituted with one or more groups selected from halogen, OH, CN, $C_1$-$C_4$ alkyl, $C_1$-$C_4$ haloalkyl, $C_1$-$C_4$ alkoxy, and $C_1$-$C_4$ haloalkoxy.

12. The compound of claim 1, wherein $R_3$ is $C_3$-$C_7$ cycloalkyl or $CH_2$—($C_3$-$C_7$) cycloalkyl, wherein the cycloalkyl moiety is optionally substituted with one or more groups selected from halogen, OH, CN, $C_1$-$C_4$ alkyl, $C_1$-$C_4$ haloalkyl, $C_1$-$C_4$ alkoxy, and $C_1$-$C_4$ haloalkoxy.

13. The compound of claim 1, wherein $R_3$ is heterocyclyl or $CH_2$-heterocyclyl, wherein the heterocyclyl moiety is optionally substituted with one or more groups selected from halogen, OH, CN, $C_1$-$C_4$ alkyl, $C_1$-$C_4$ haloalkyl, $C_1$-$C_4$ alkoxy, and $C_1$-$C_4$ haloalkoxy.

14. The compound of claim 1, wherein $R_1$ is H.

15. The compound of claim 1, wherein $R_1$ is $C_1$-$C_6$ alkyl optionally substituted with halogen, OH, $C_1$-$C_6$ alkoxy, or $C_6$-$C_{10}$ aryloxy.

16. The compound of claim 1, wherein $R_2$ is H.

17. The compound of claim 1, wherein $R_2$ is $C_1$-$C_6$ alkyl optionally substituted with halogen, OH, $C_1$-$C_6$ alkoxy, or $C_6$-$C_{10}$ aryloxy.

18. The compound of claim 1, wherein $R_1$ and $R_2$, together with the nitrogen atom to which they are attached, form a heterocyclyl.

19. The compound of claim 1, wherein each $R_4$ is H.

20. The compound of claim 1, wherein at least one $R_4$ is halogen, CN, OH, $N(R_6')_2$, $C_1$-$C_4$ alkoxy, $C(=O)N(R_6)_2$, $C(=O)OR_6$, $C(=O)R_6$, Q-T, $C_6$-$C_{10}$ aryl, or heteroaryl comprising one or two 5- or 6-membered rings and 1-3 heteroatoms selected from N, O, and S, wherein the aryl or heteroaryl moiety is optionally substituted with one or more $R_9$.

21. The compound of claim 1, wherein the compound is of Formula Ia, Ib, Ic, Id, Ie, If, or Ig:

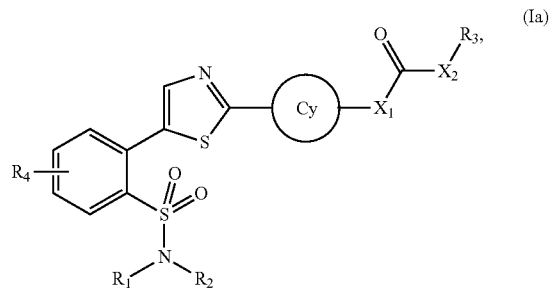

(Ia)

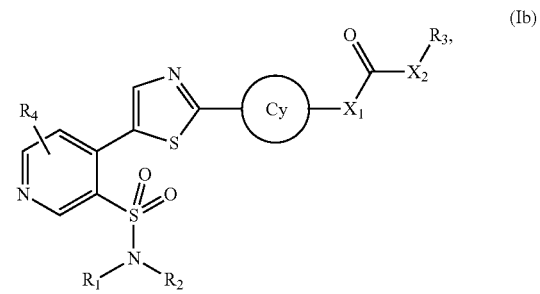

(Ib)

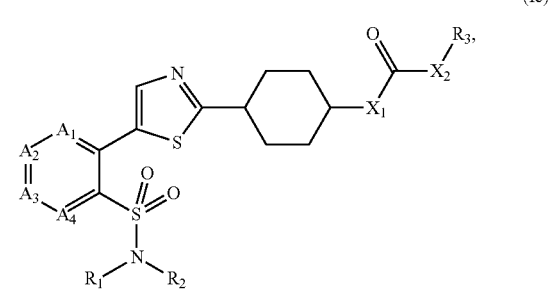

(Ic)

-continued
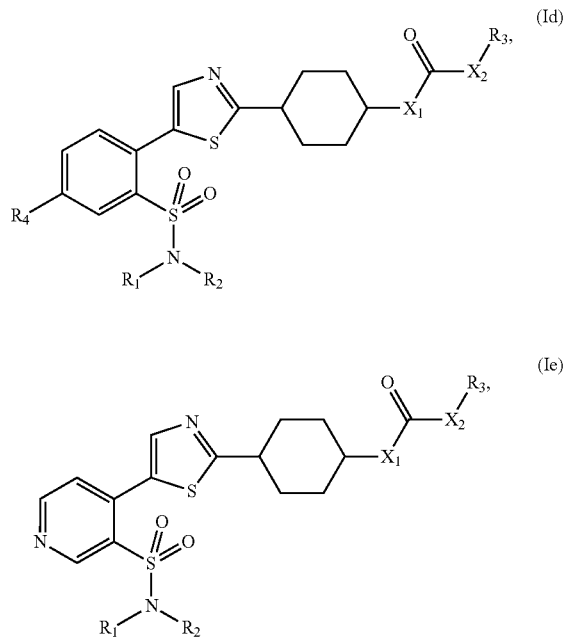
(Id)
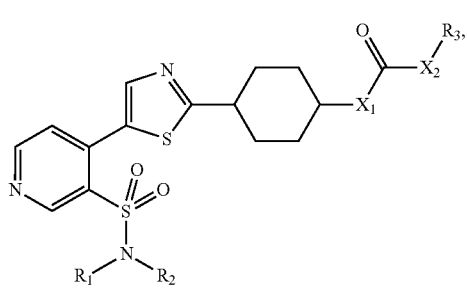
(Ie)
-continued
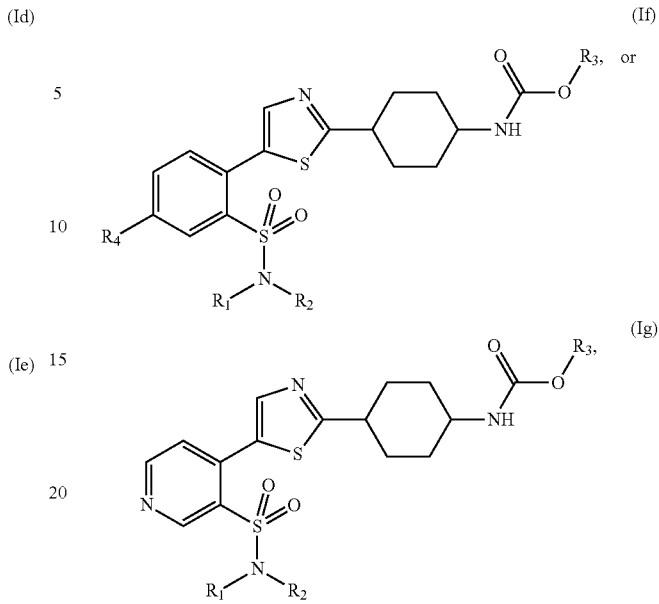
(If)
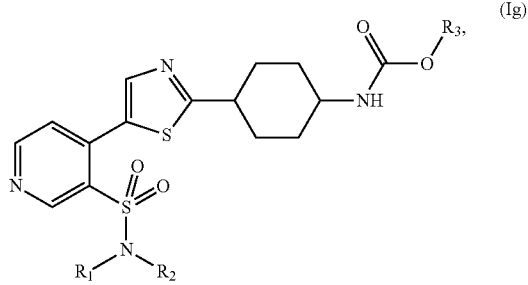
(Ig)
or a pharmaceutically acceptable salt or solvate thereof.
22. A compound selected from:
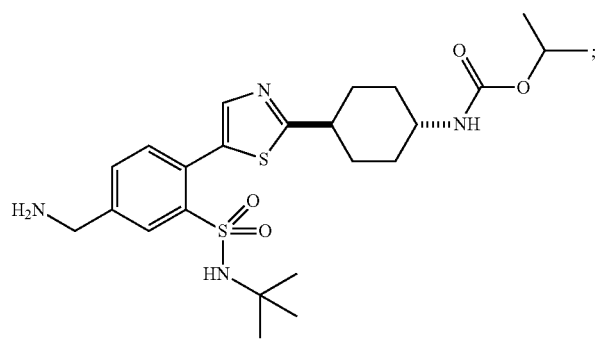
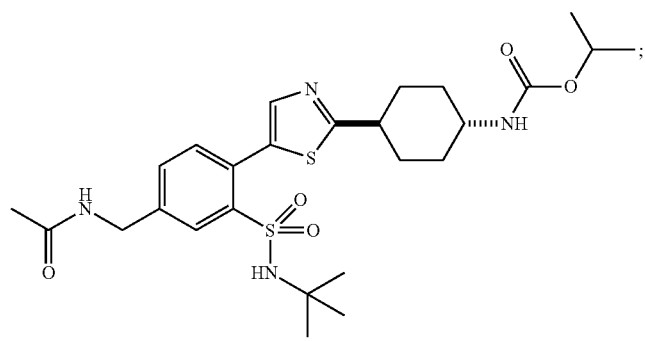

-continued
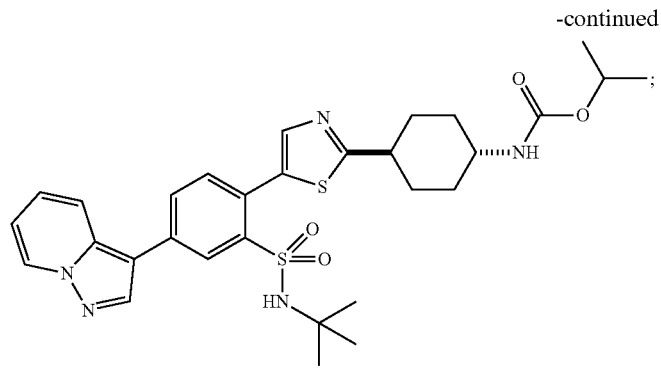
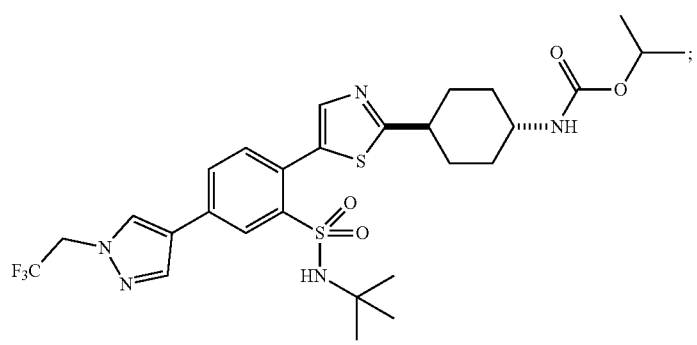
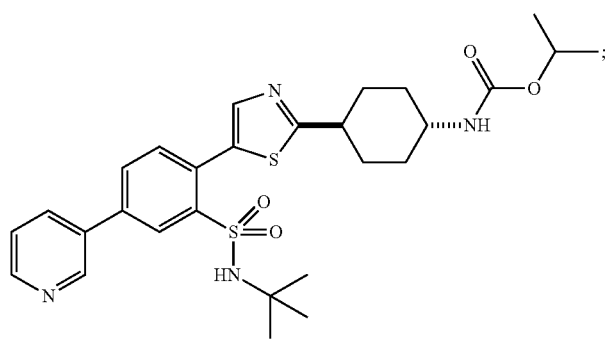
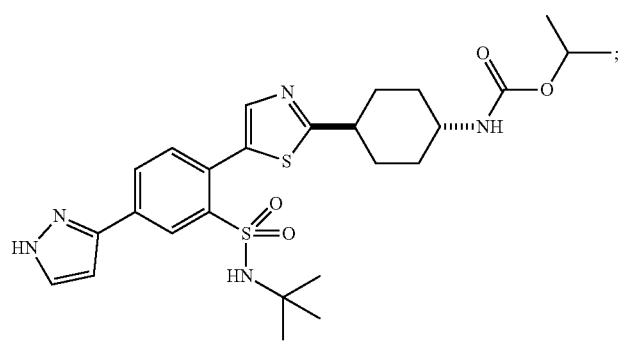
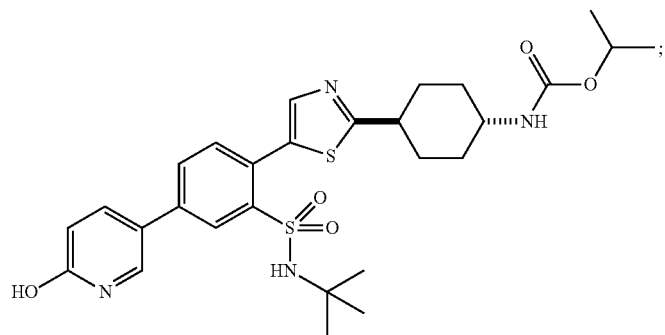

-continued
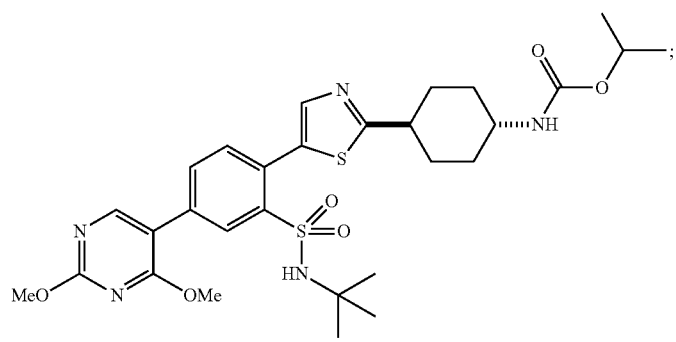
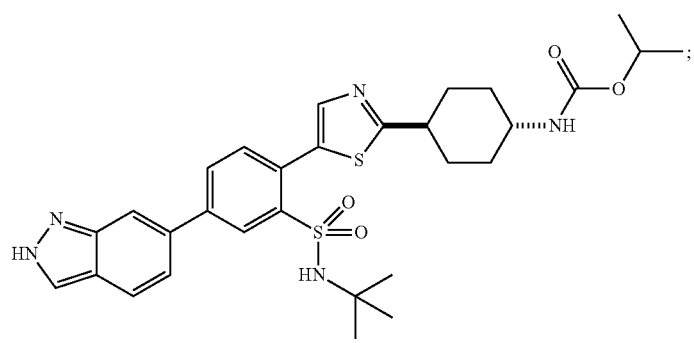
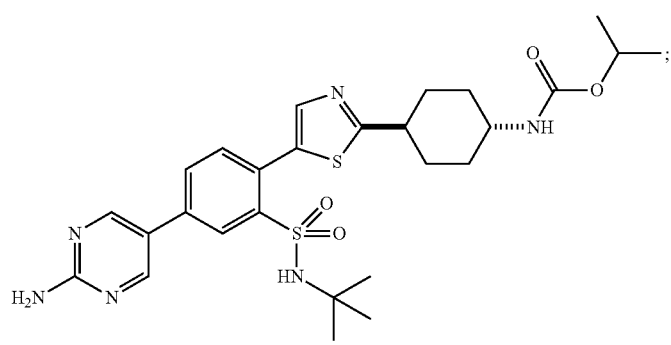
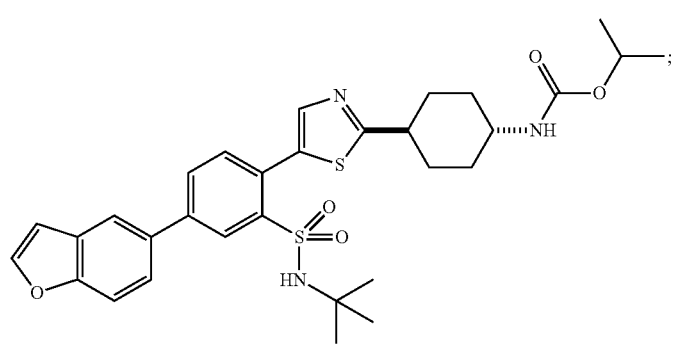
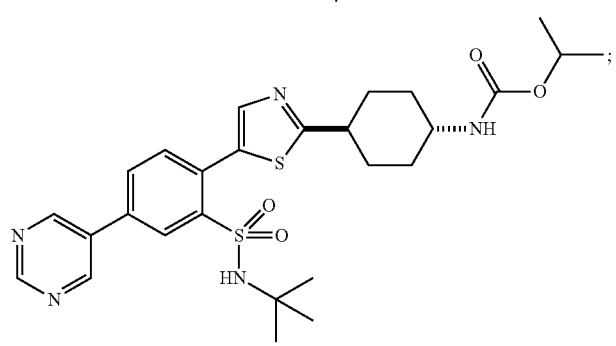

-continued
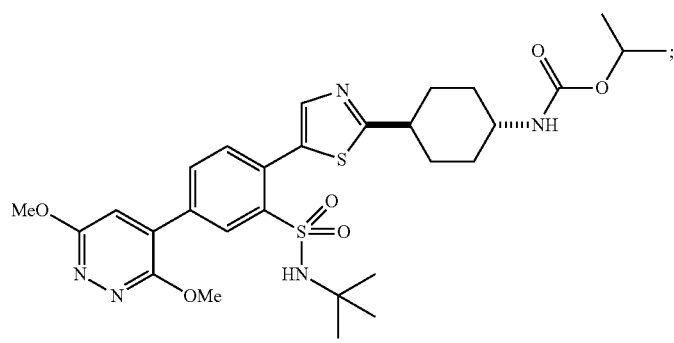
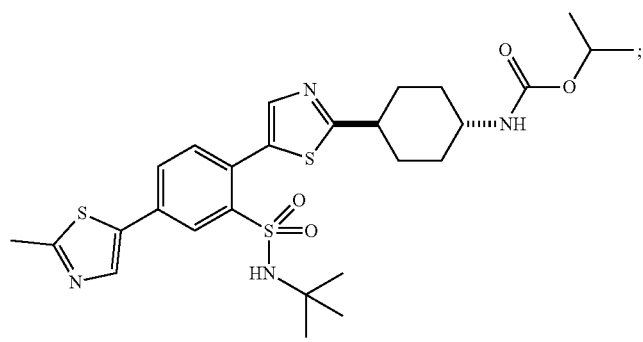
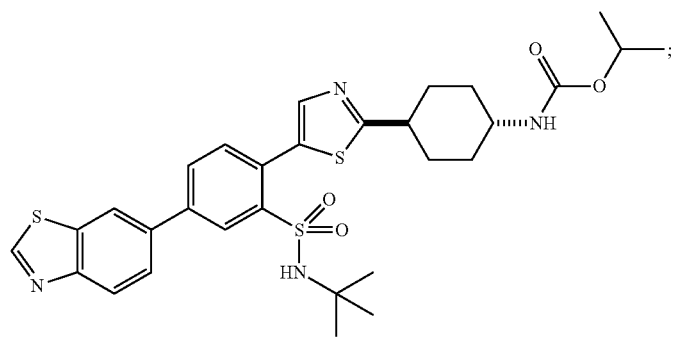
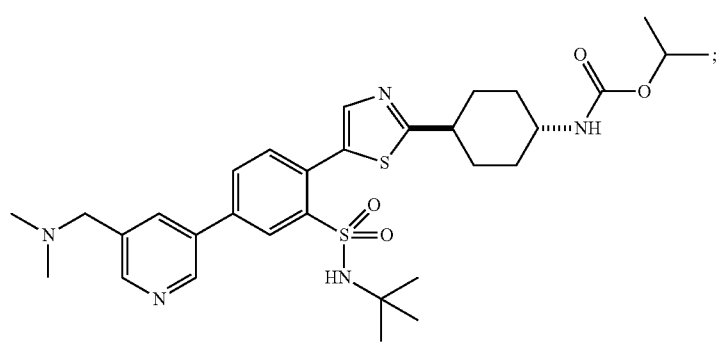
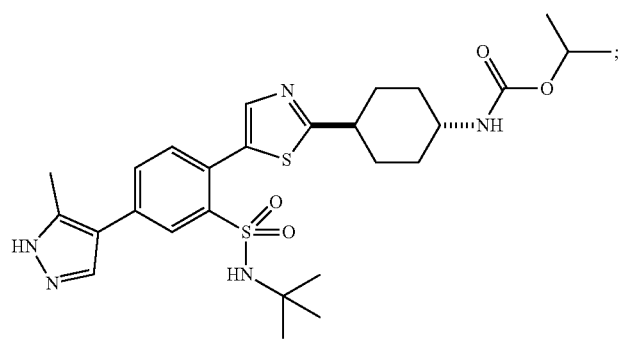

-continued
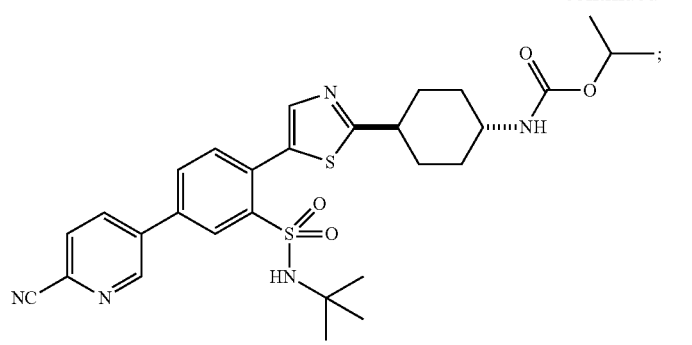
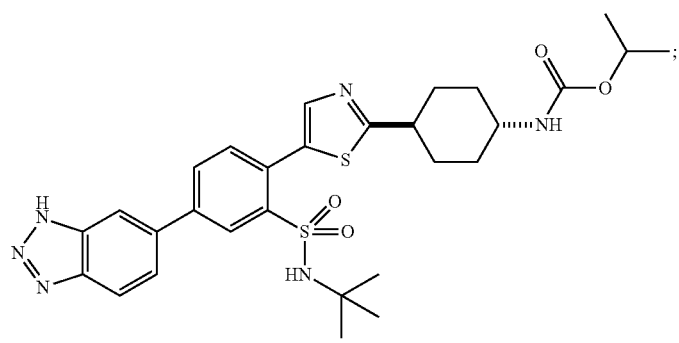
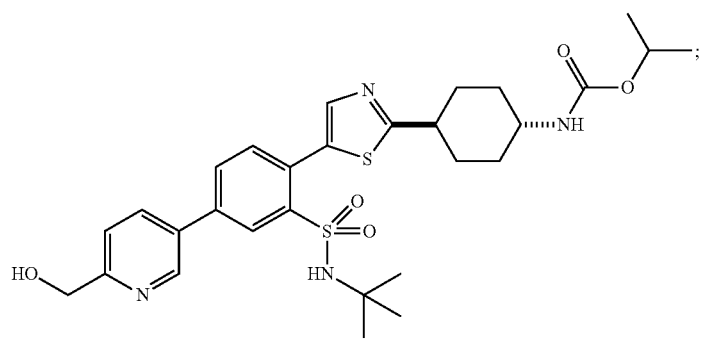
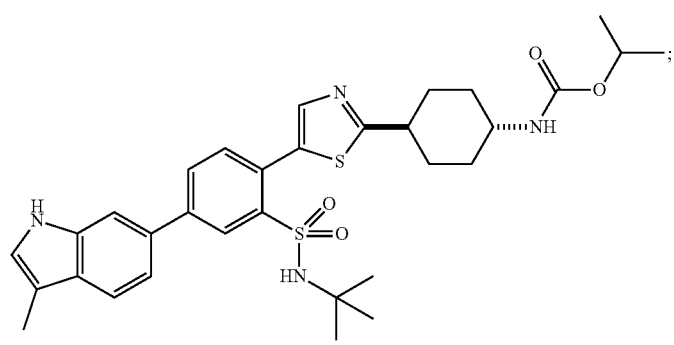
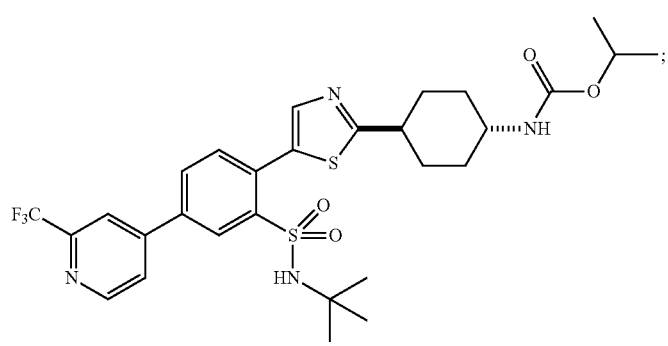

413 414
-continued
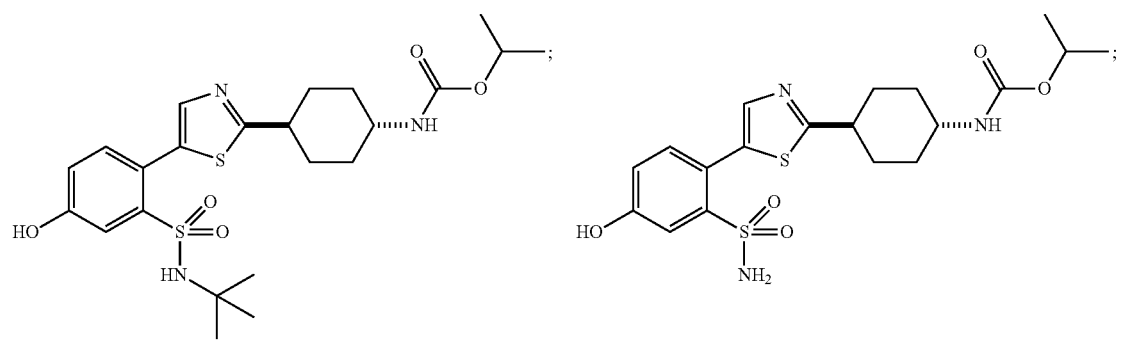
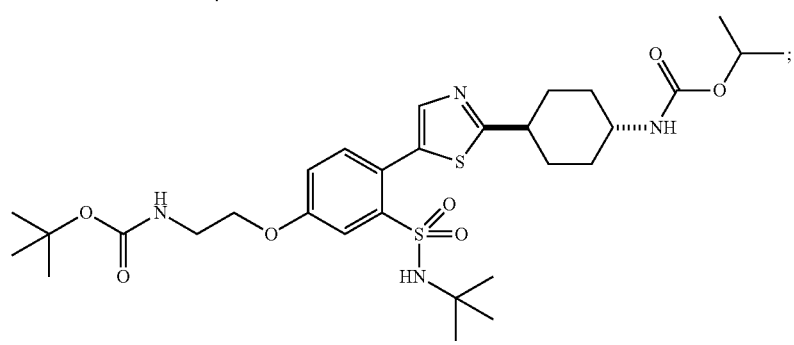
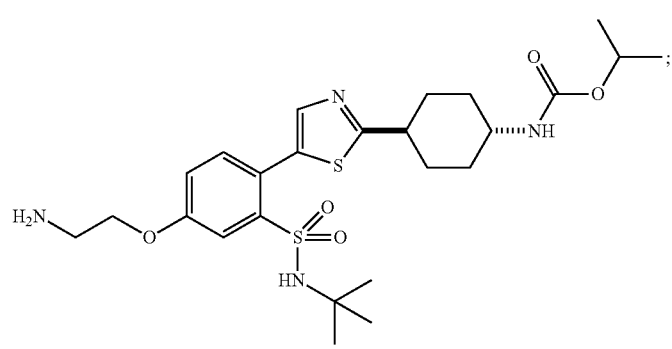
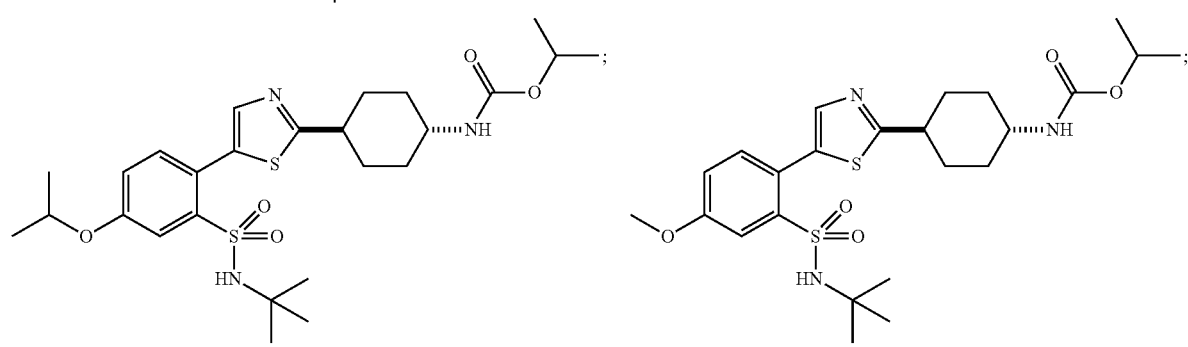
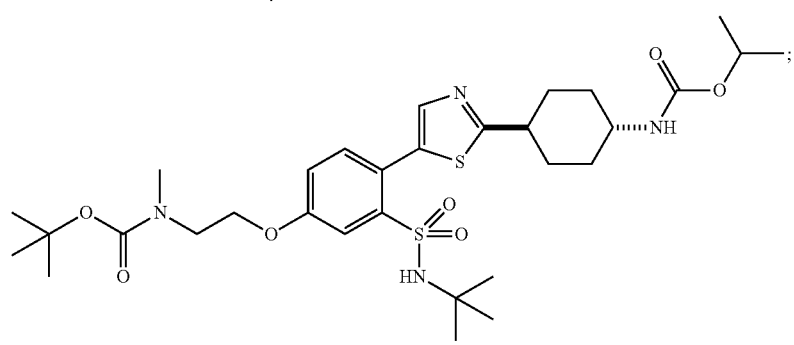

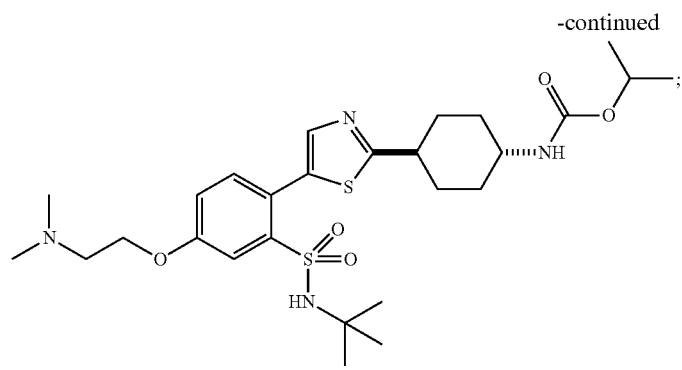
-continued
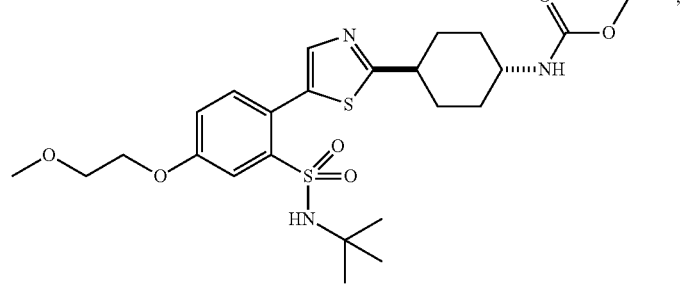
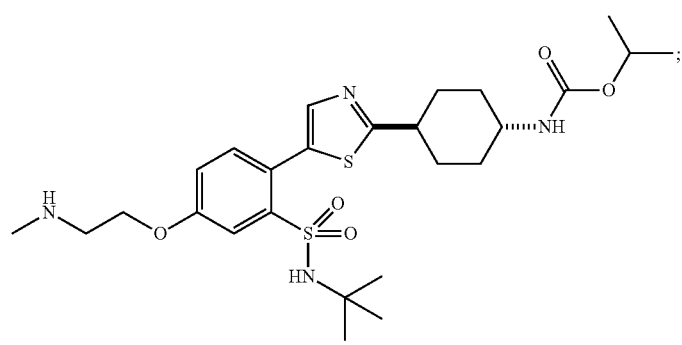
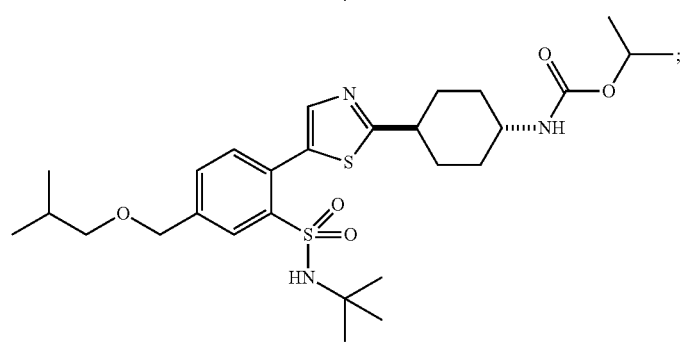
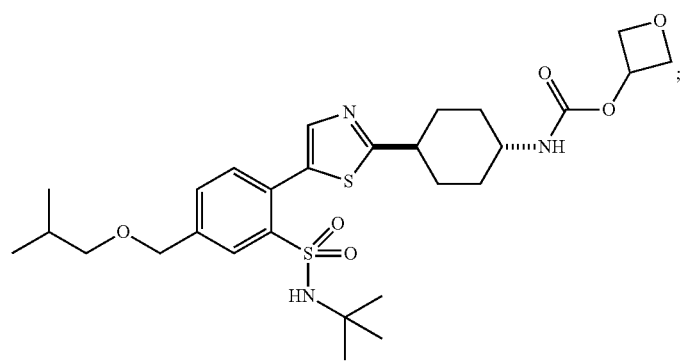

417 418
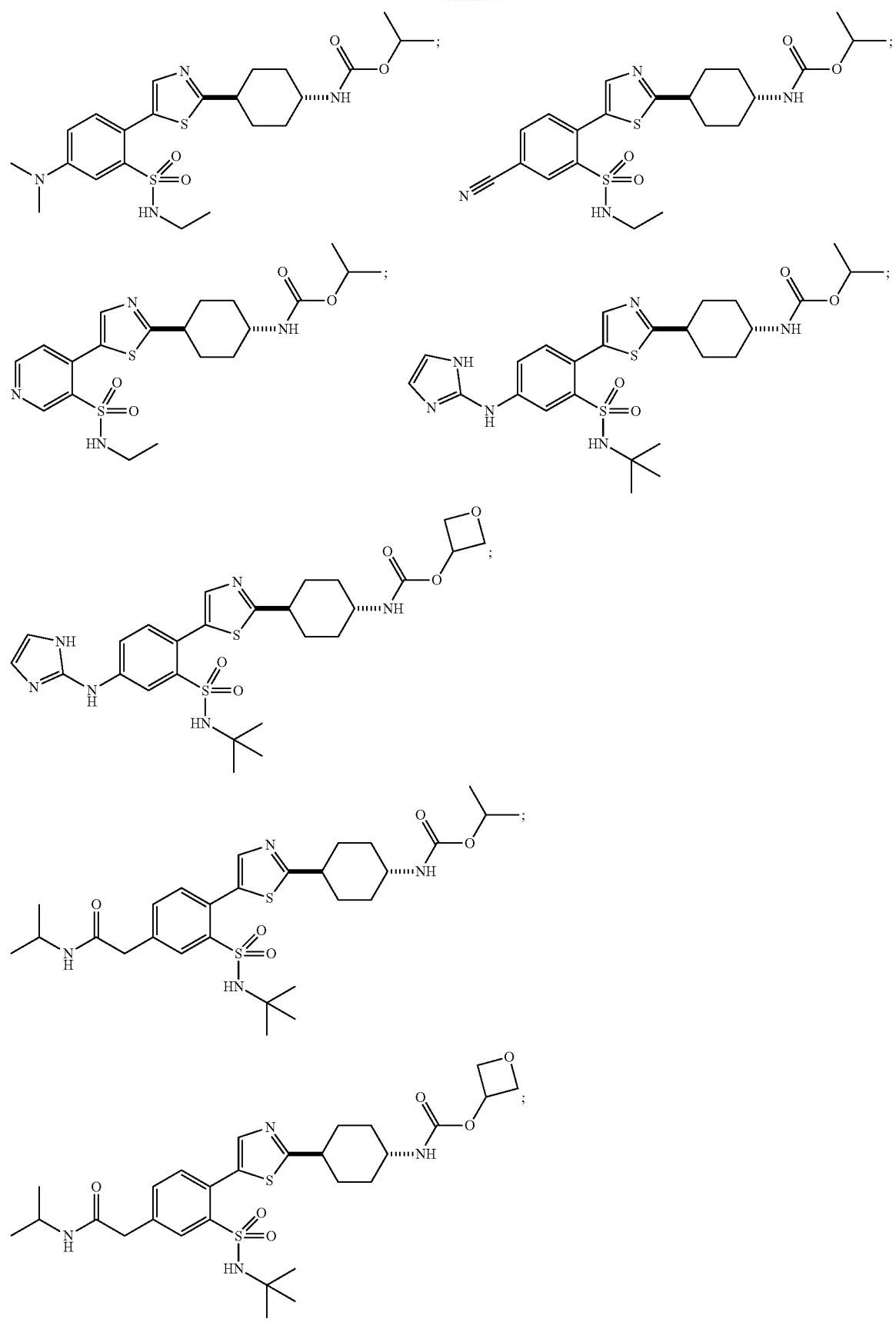
-continued 419                                                420
-continued
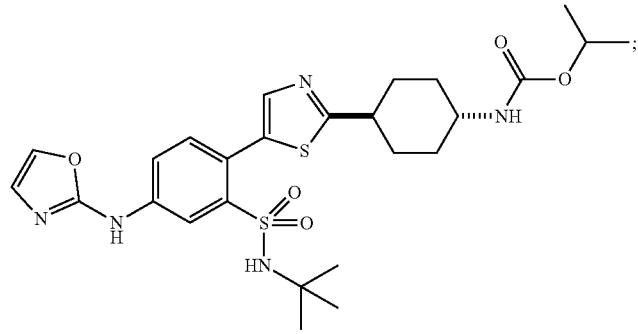
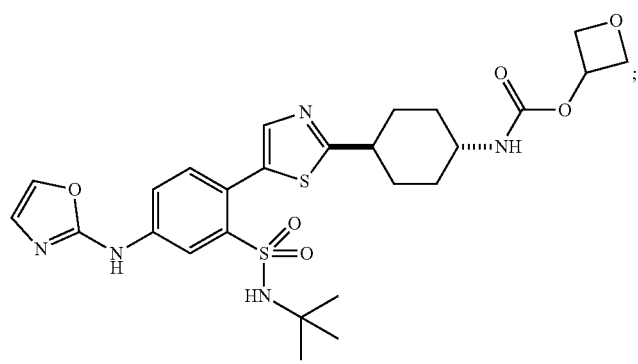
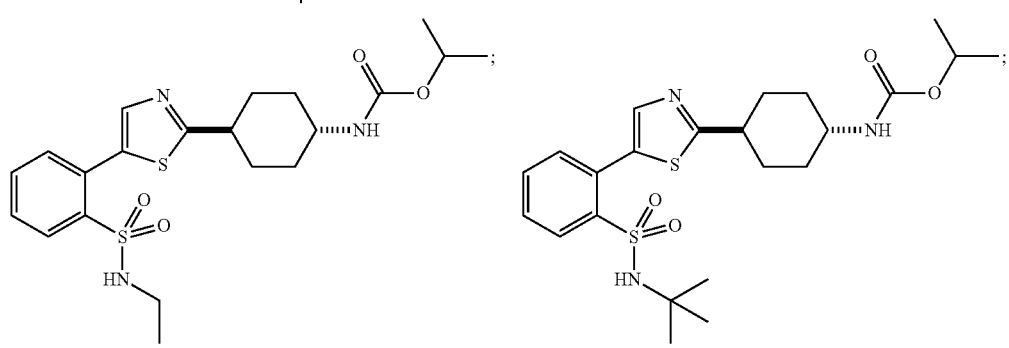
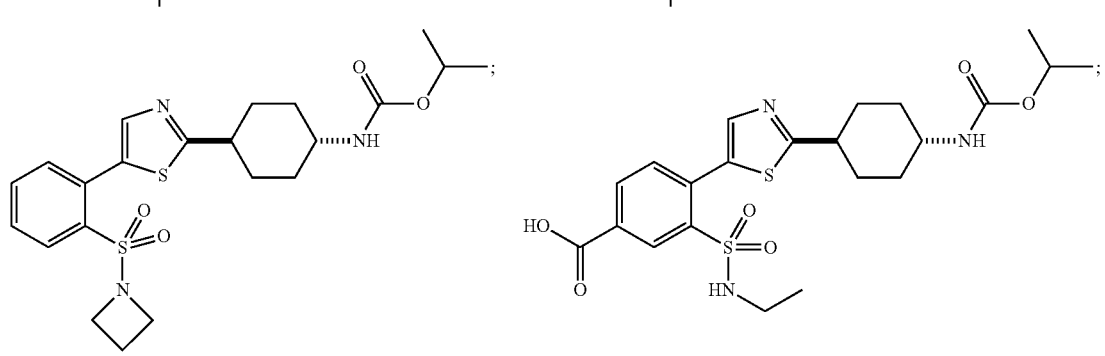
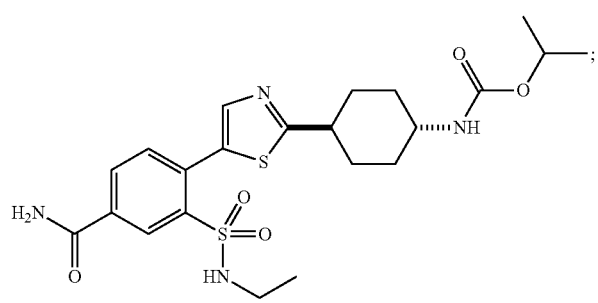

421 422
-continued
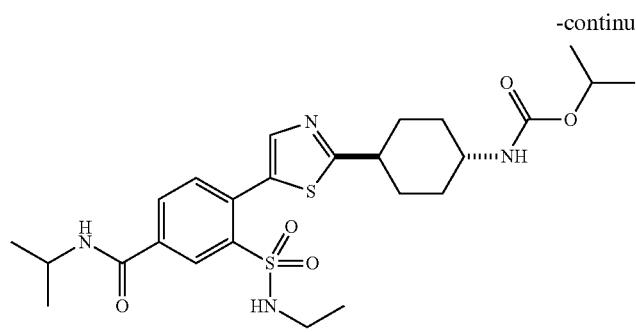
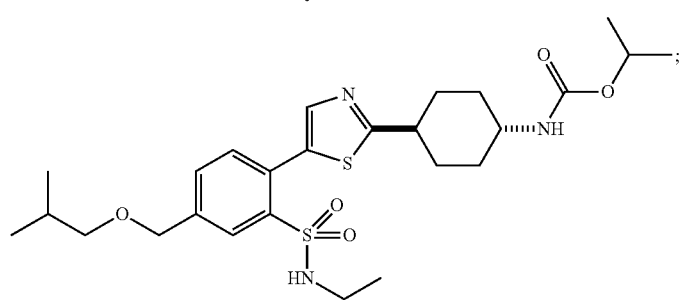
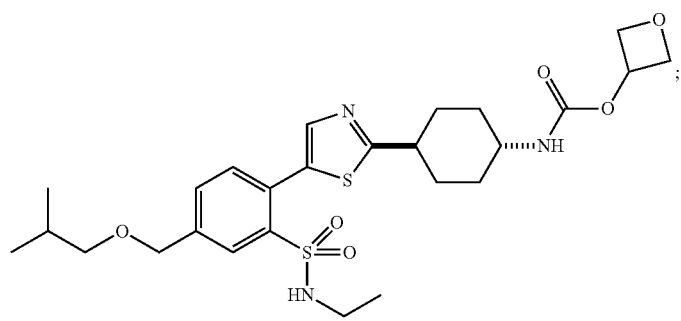
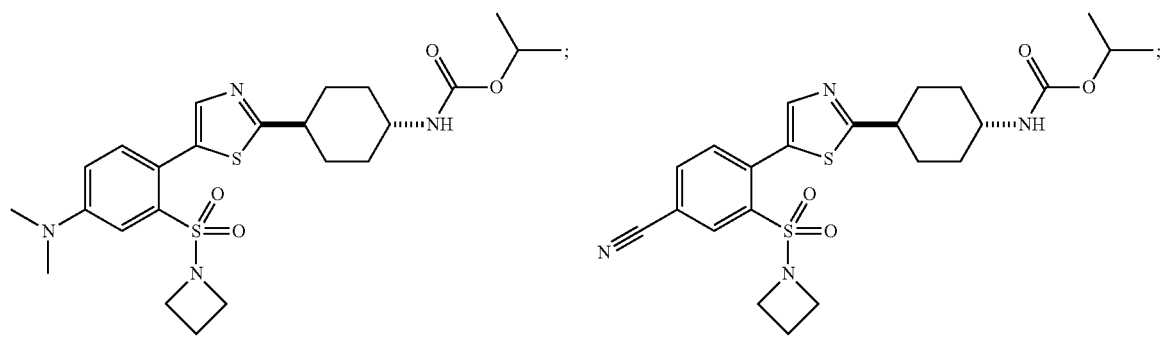
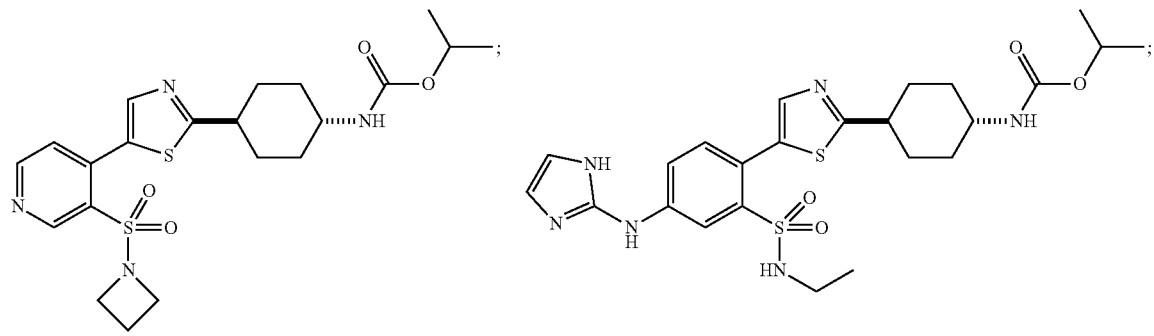

423
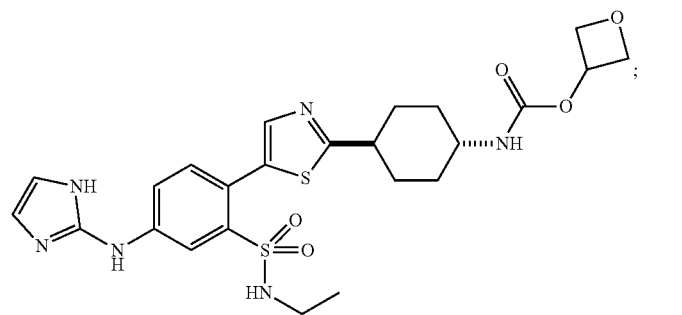
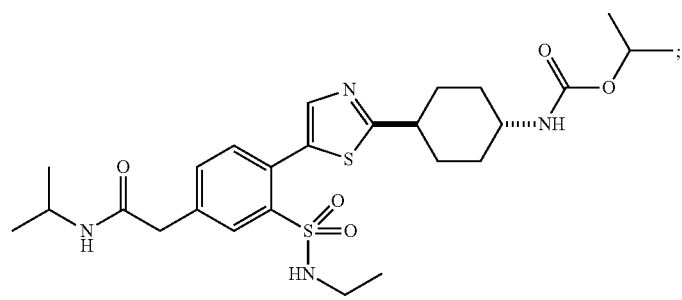
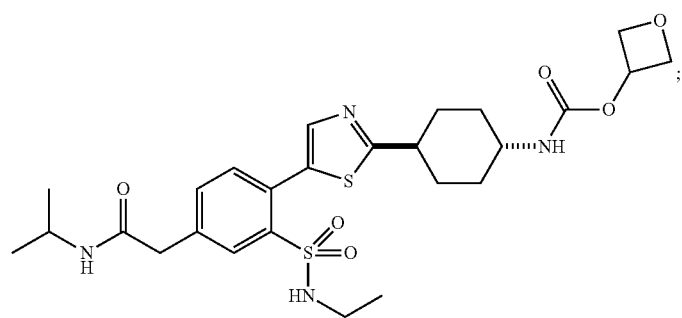
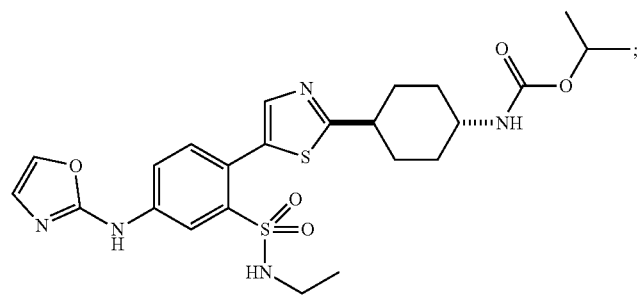
424
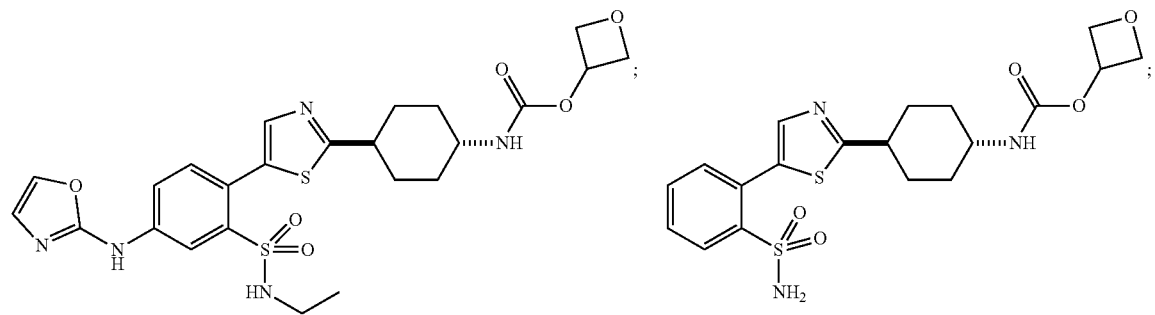

-continued
425
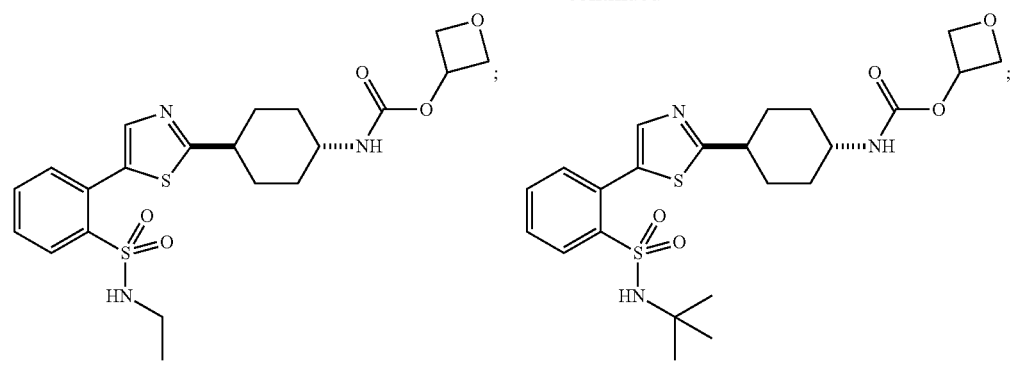
426
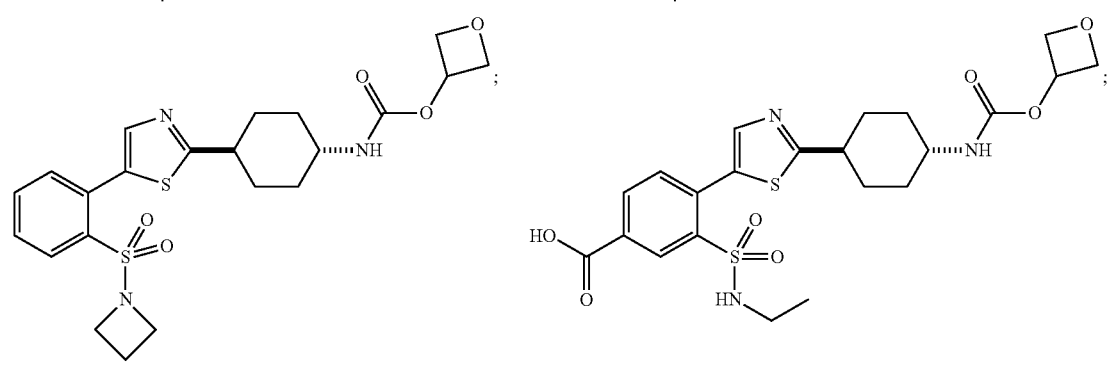
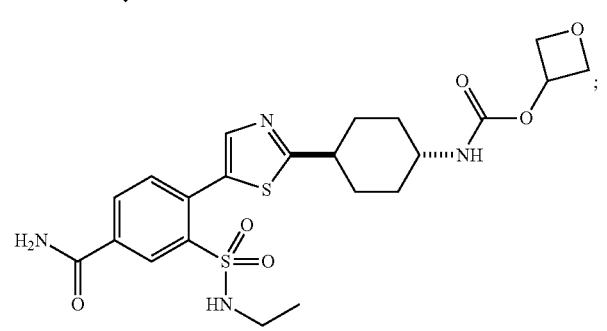
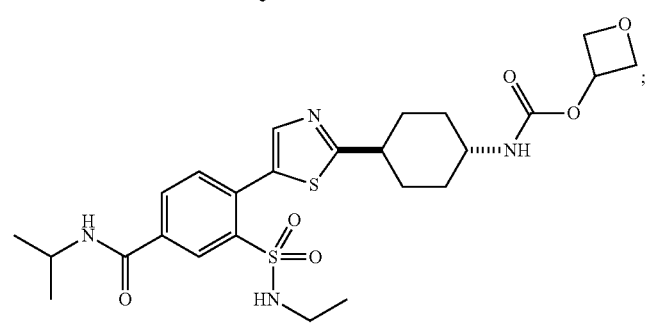
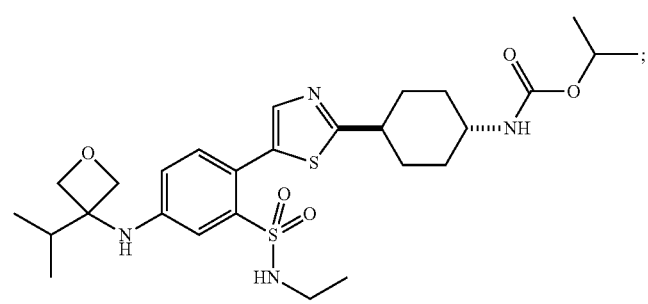

-continued
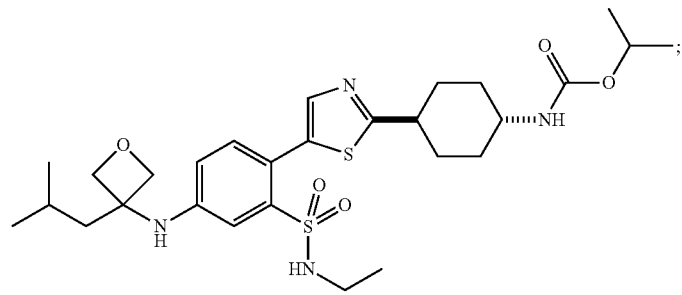
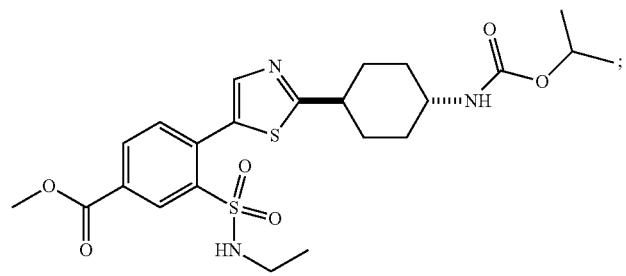
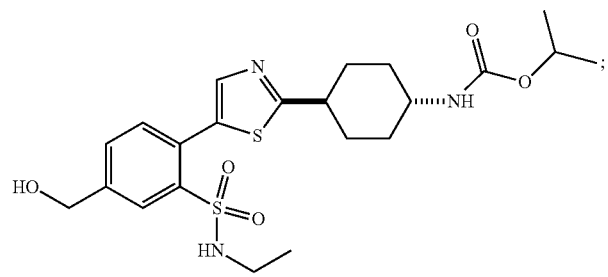
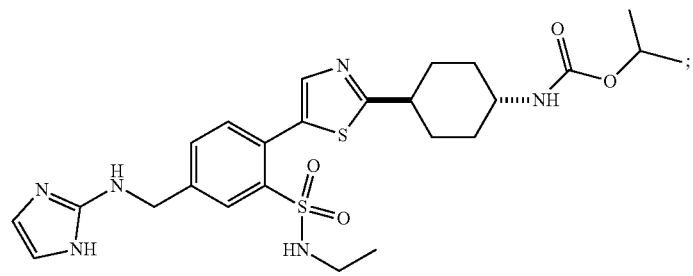
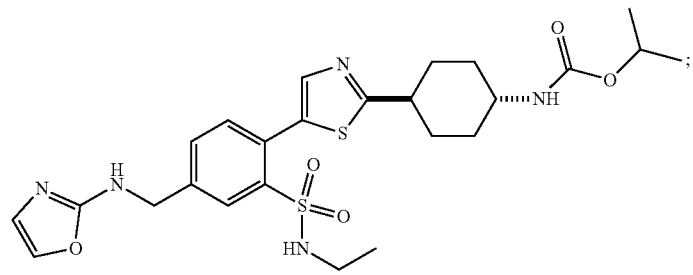
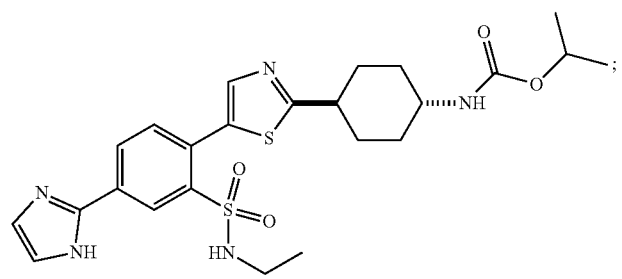

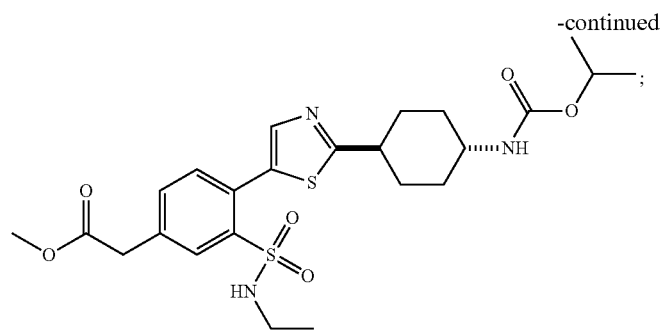
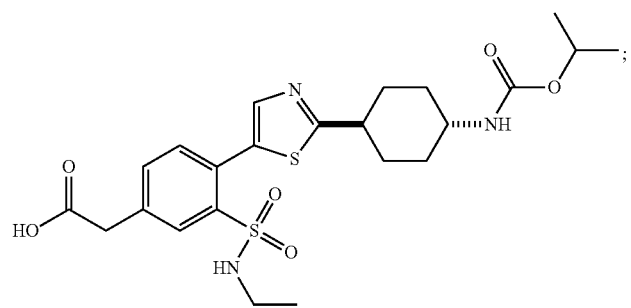
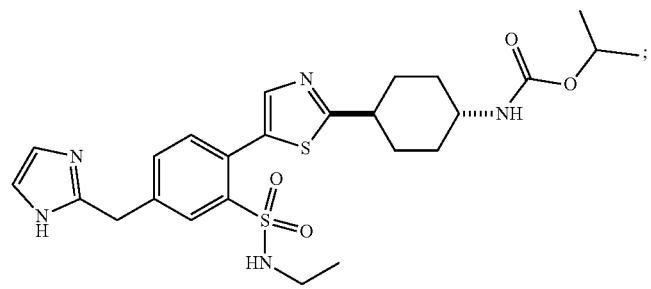
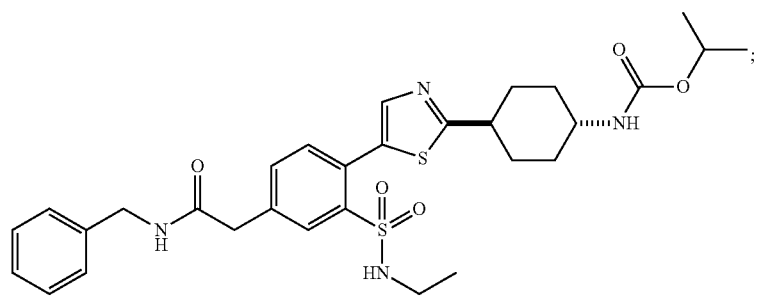
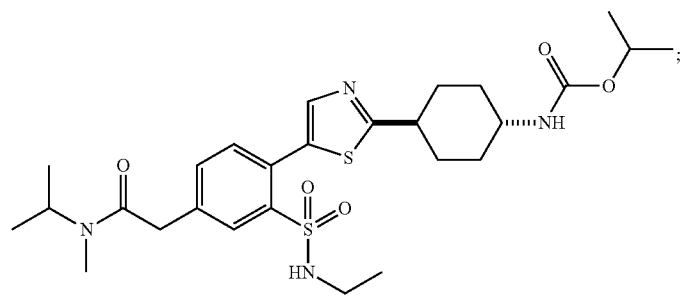

-continued
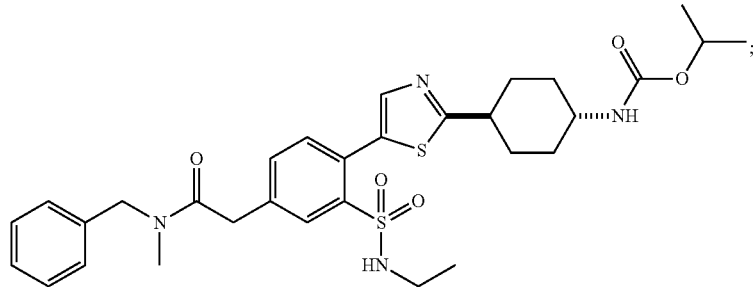
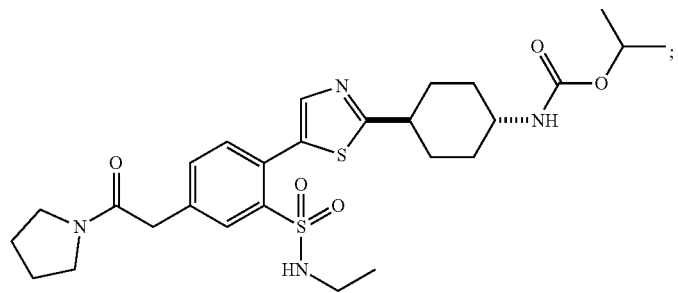
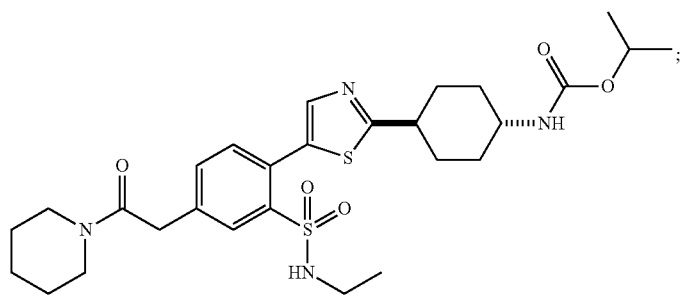
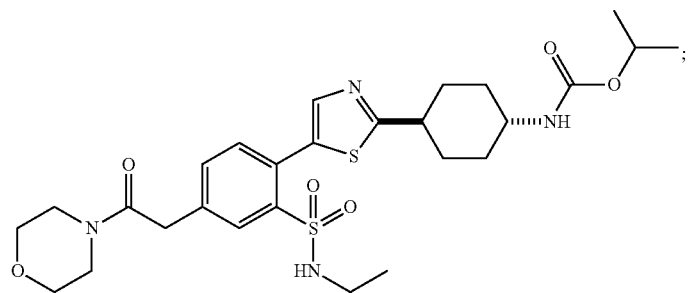
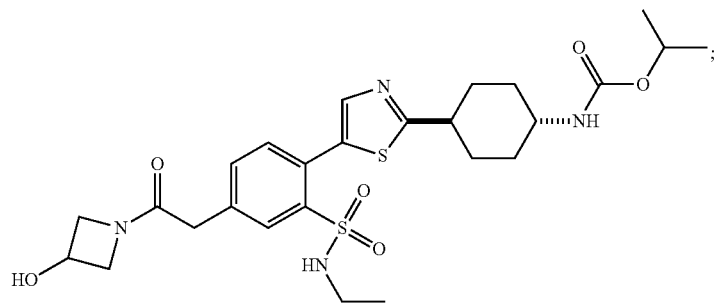

433            434
-continued
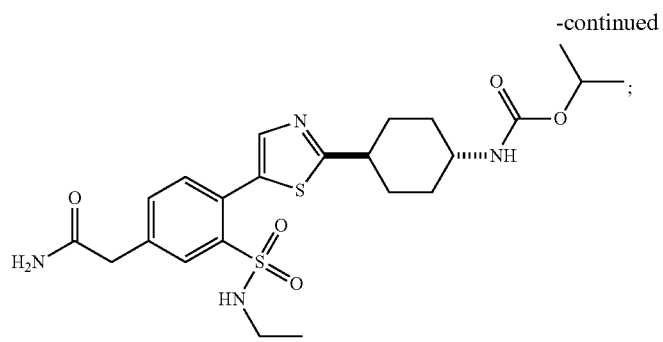
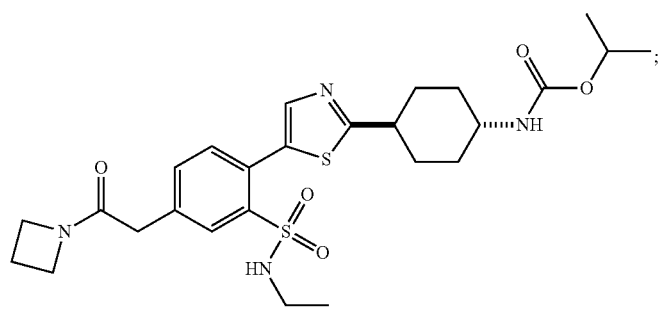
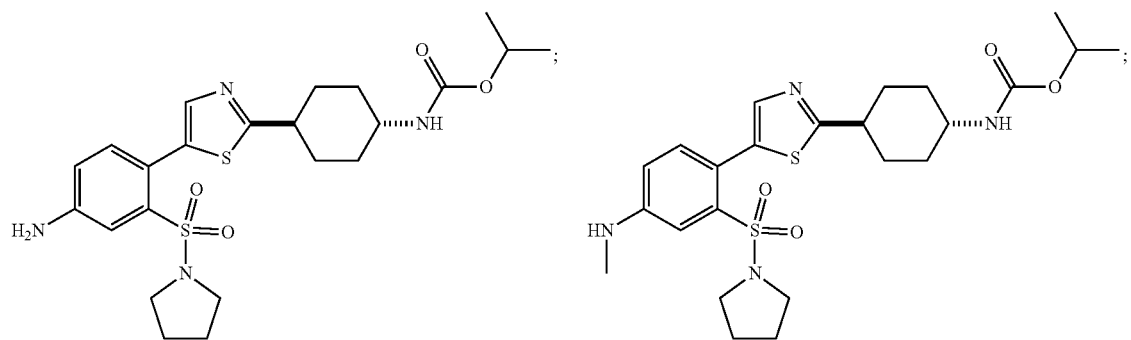
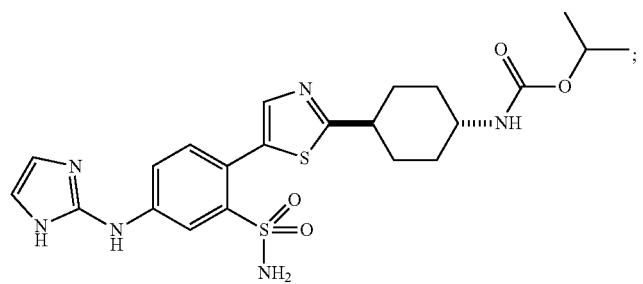
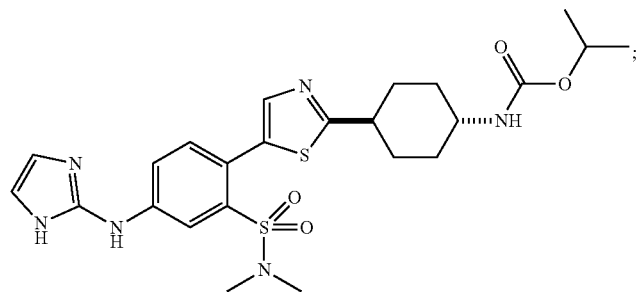

435 436
-continued
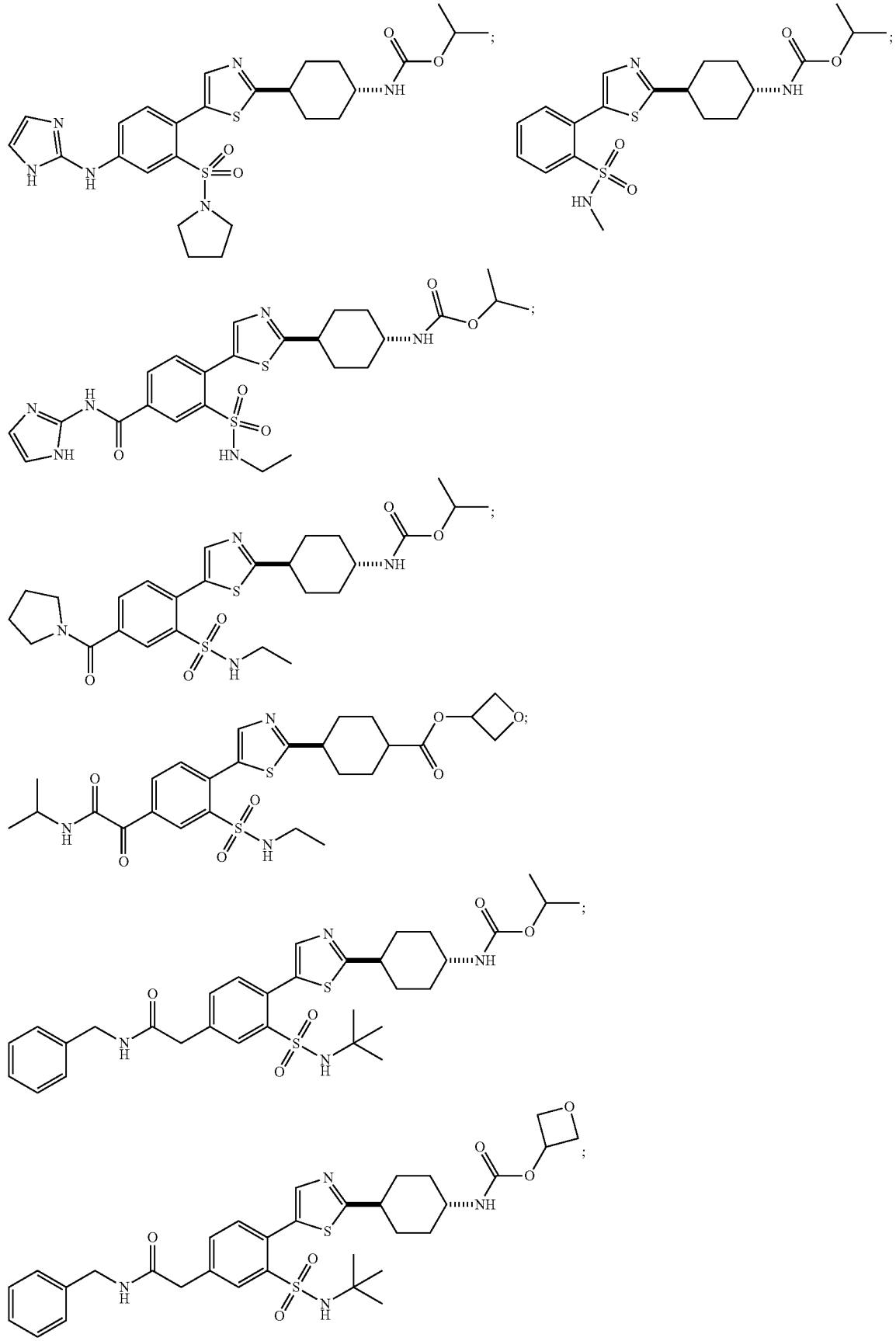

-continued
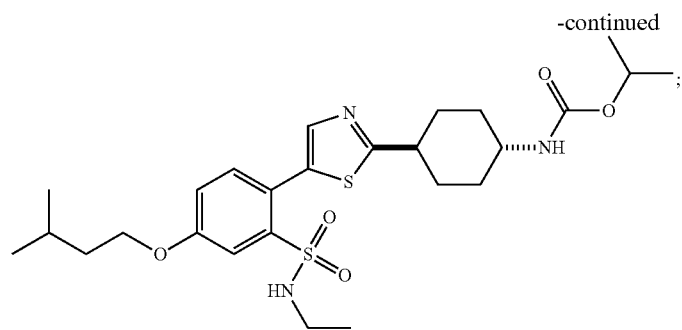
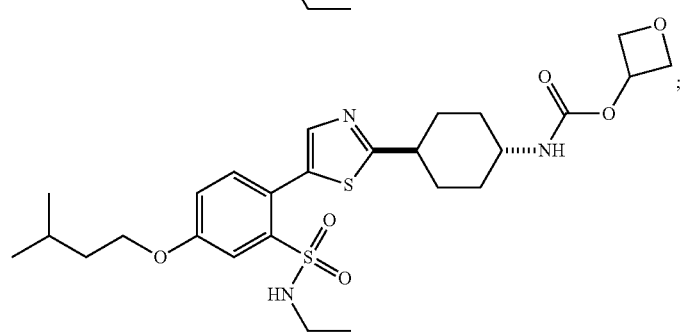
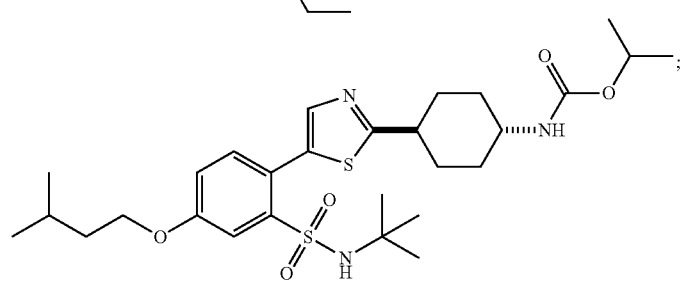
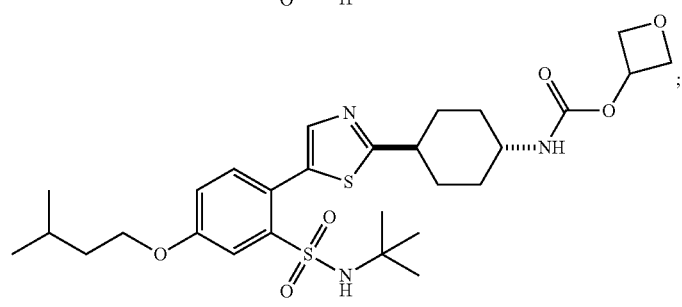
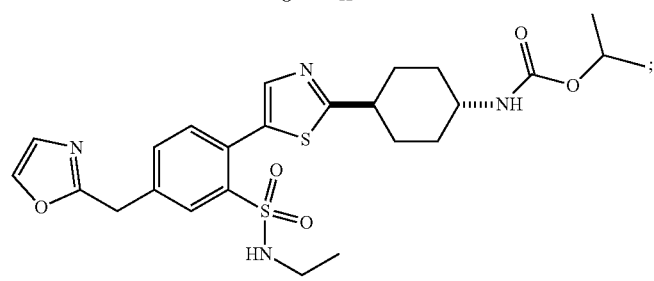
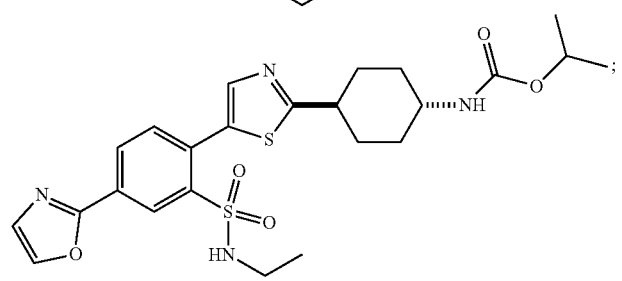

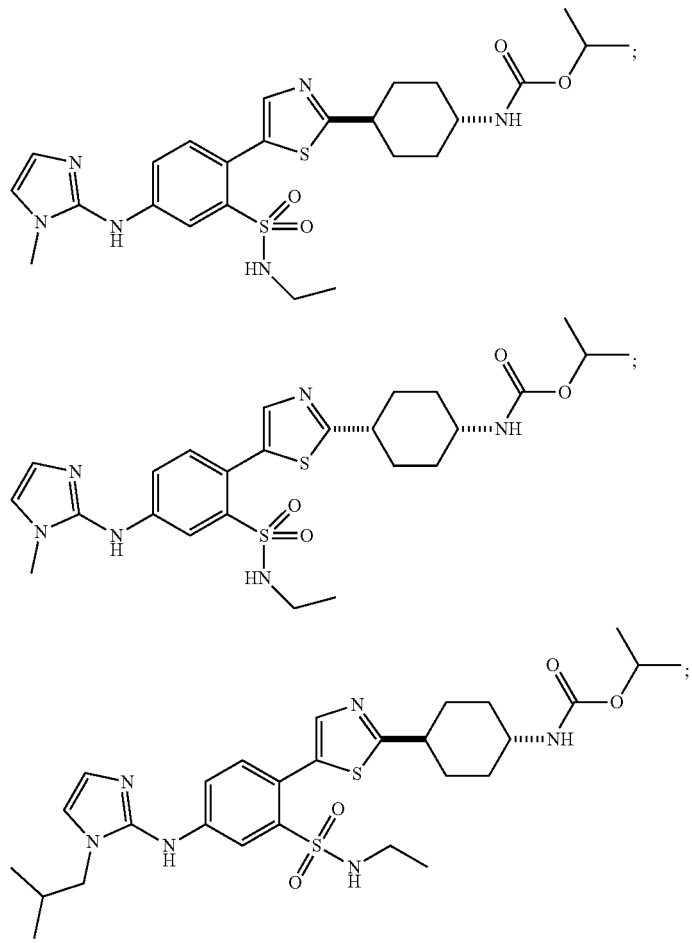
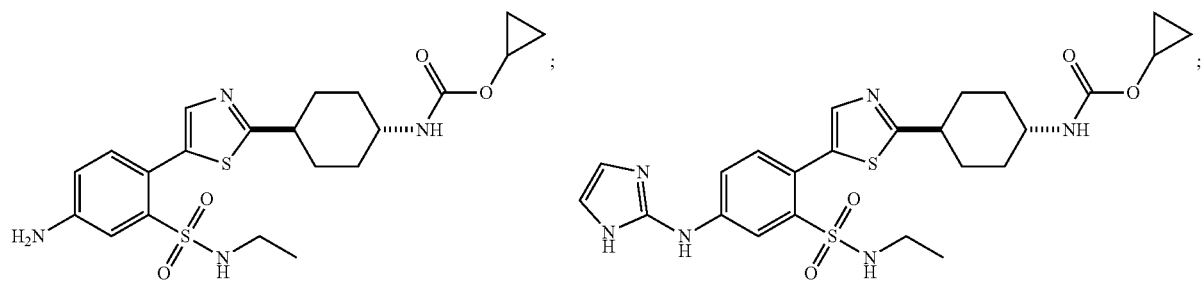
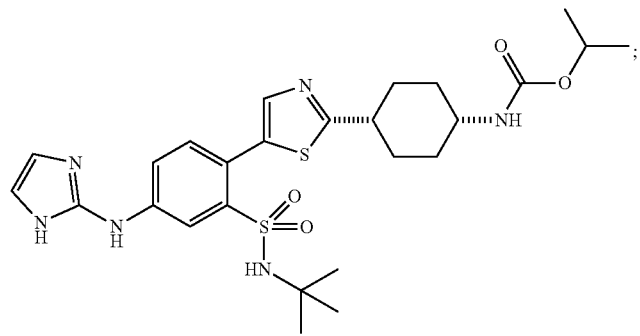

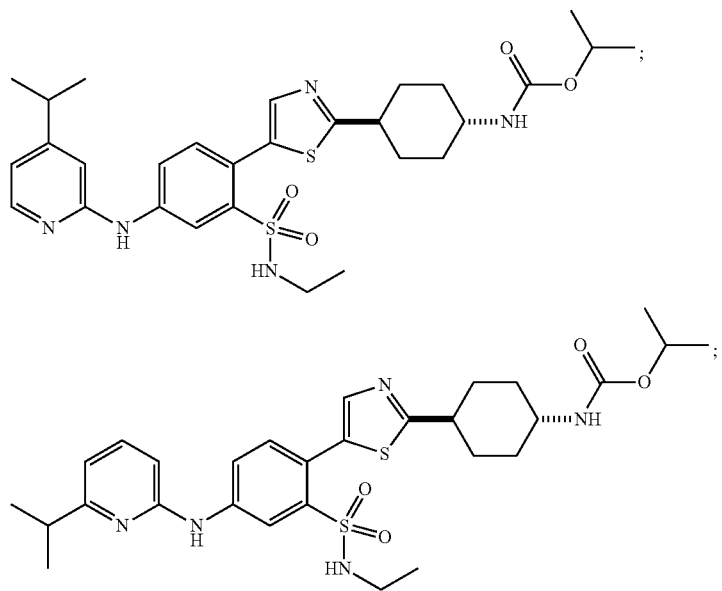
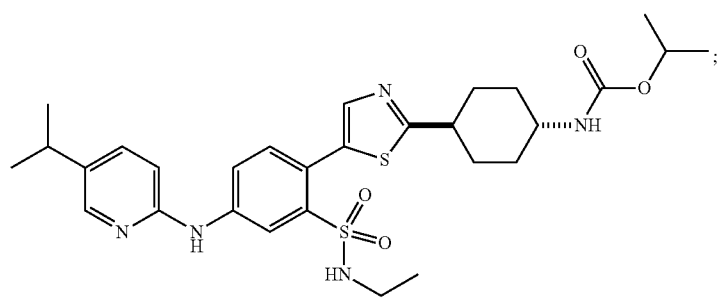
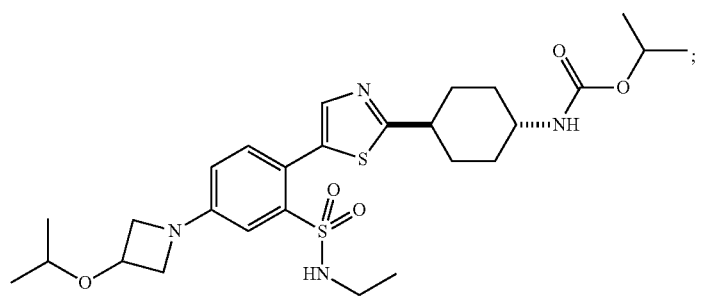
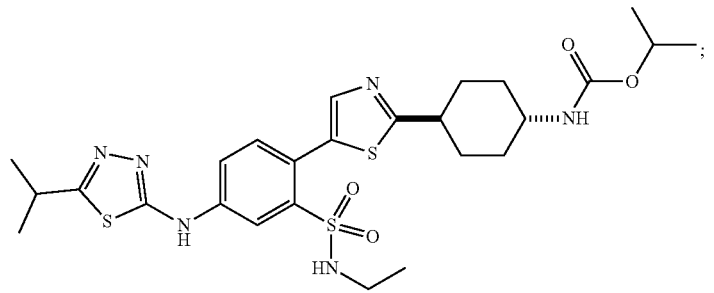

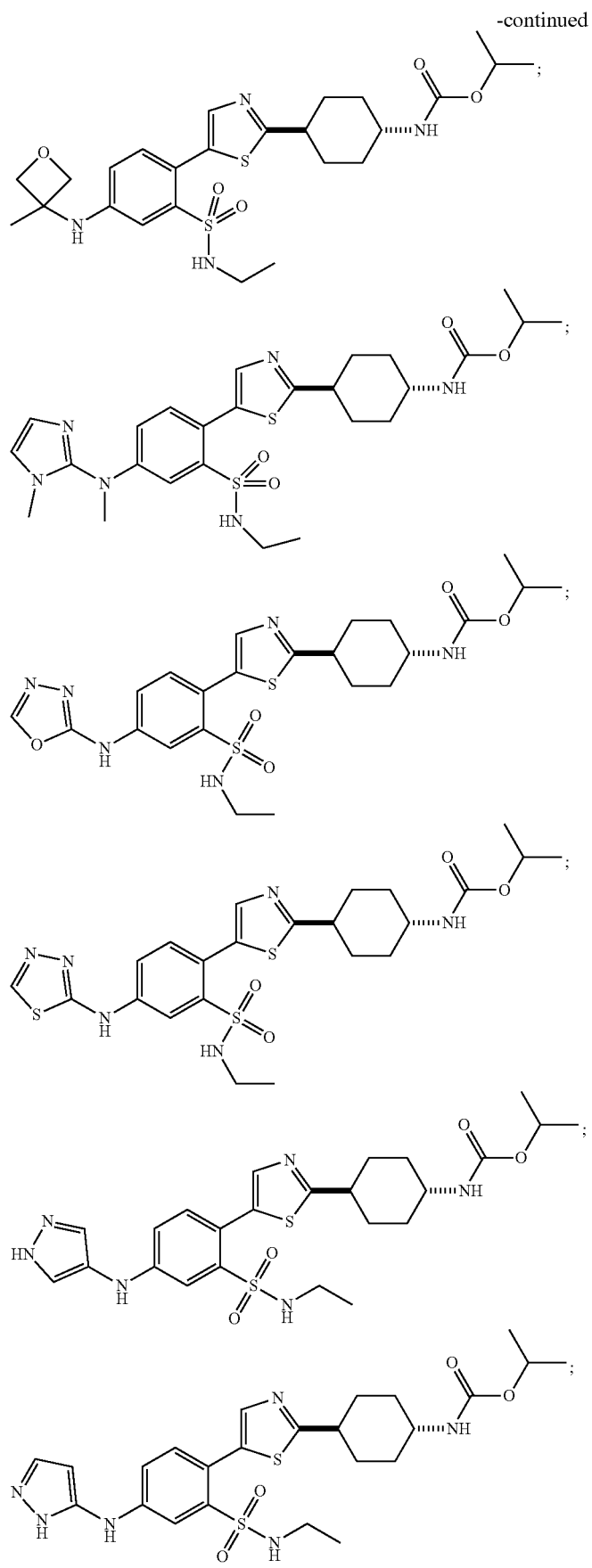

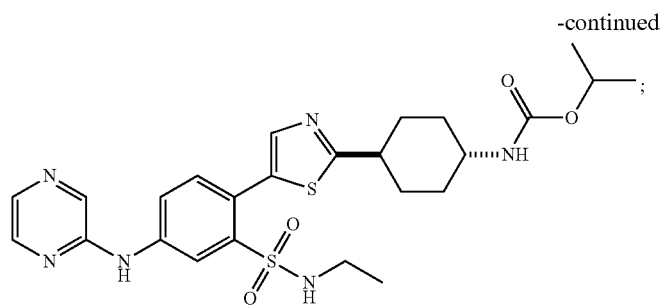
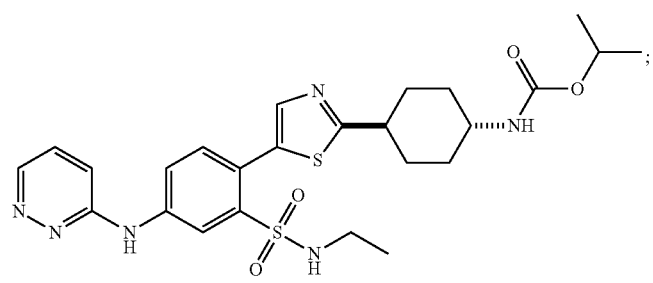
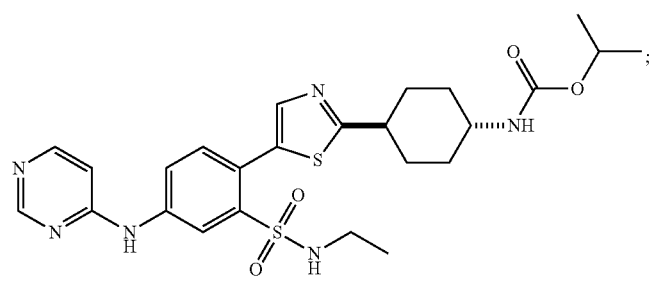
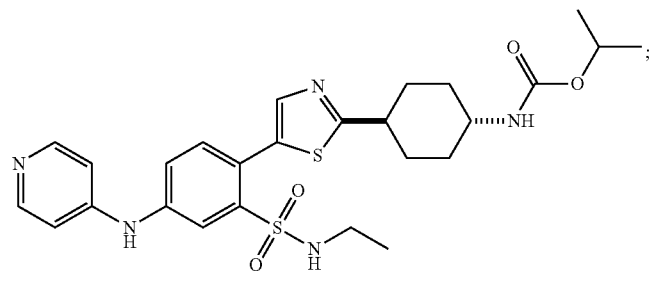
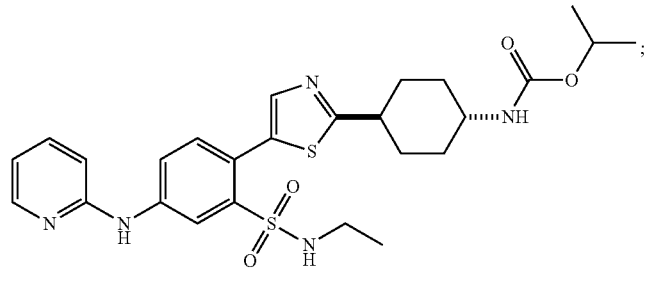
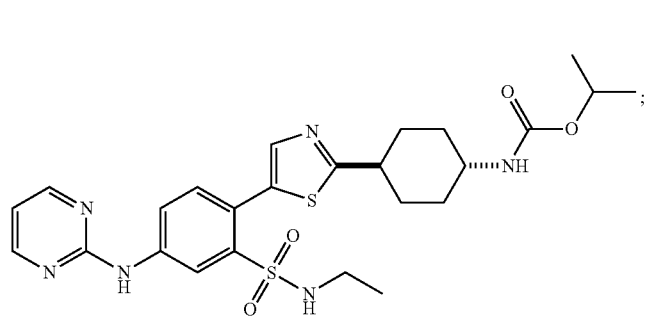

-continued
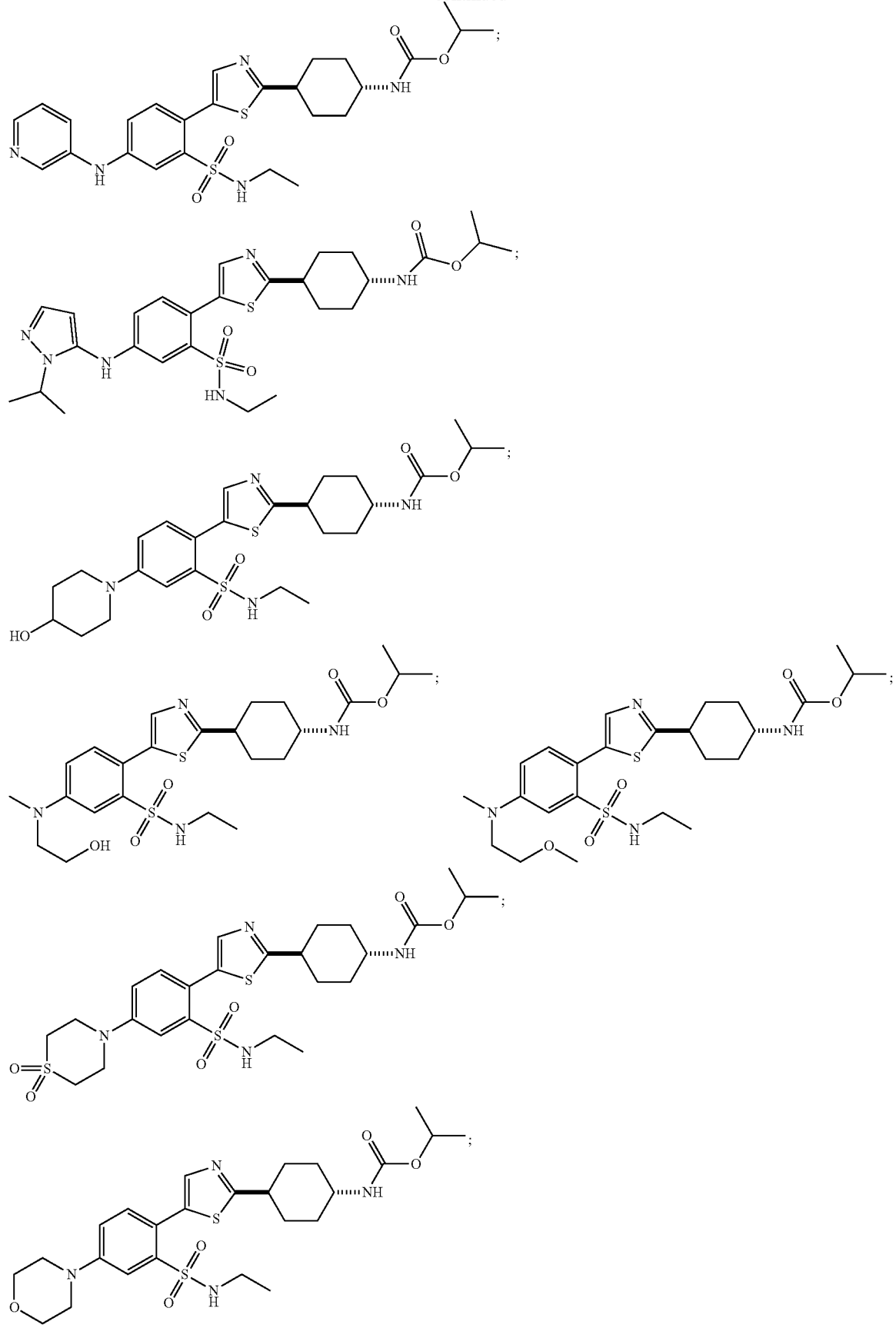

-continued
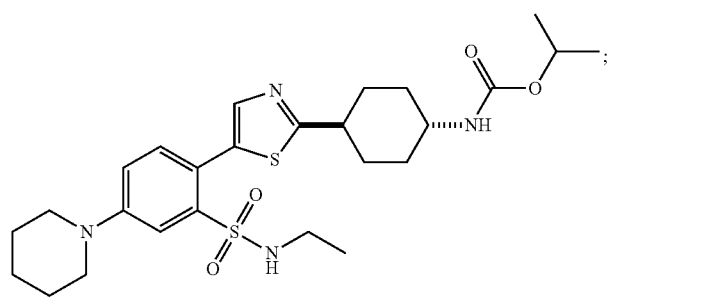
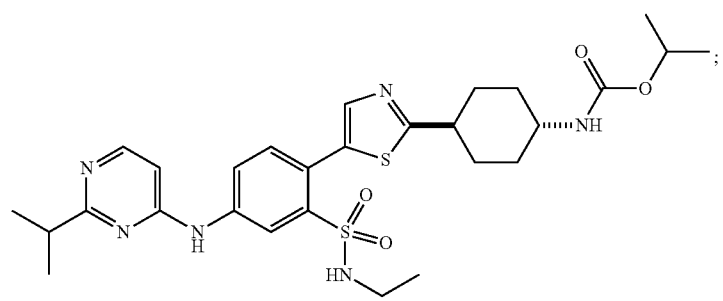
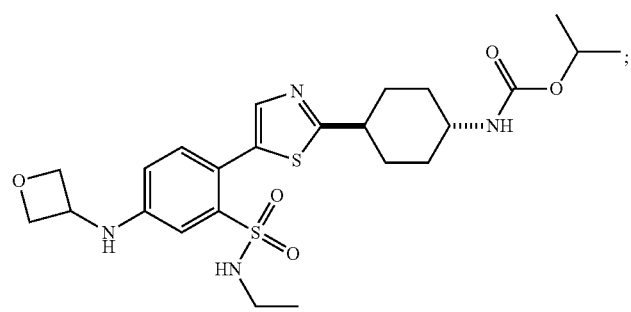
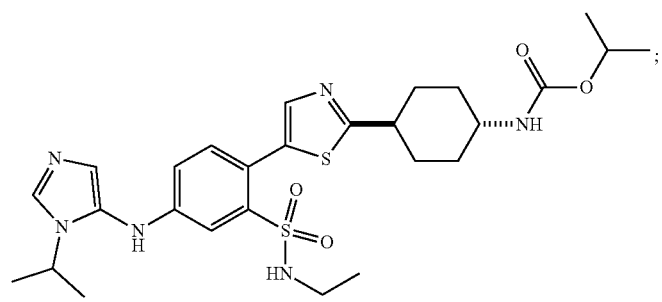
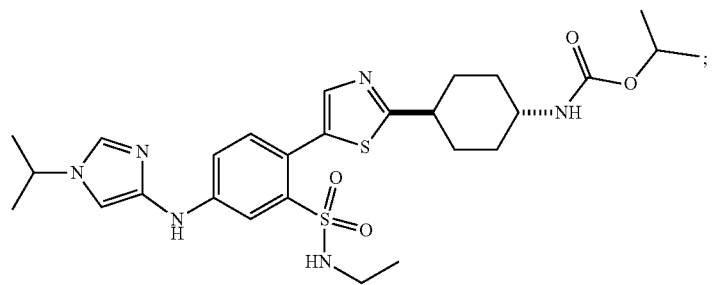

-continued
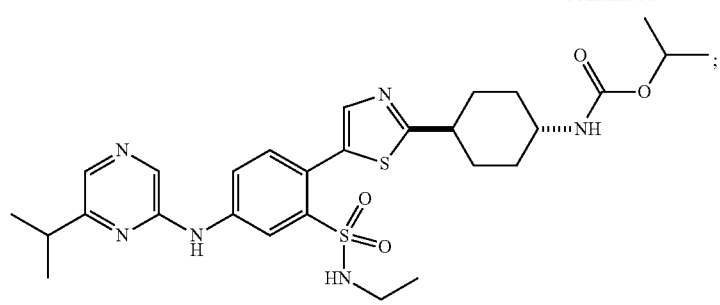
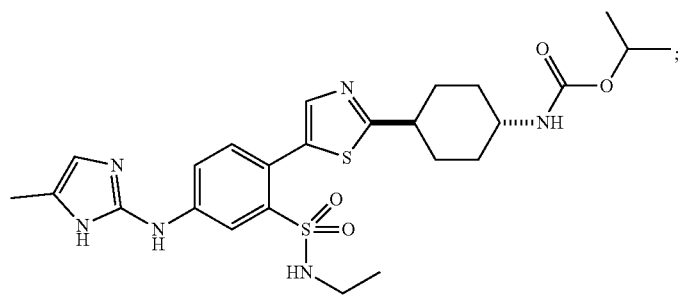
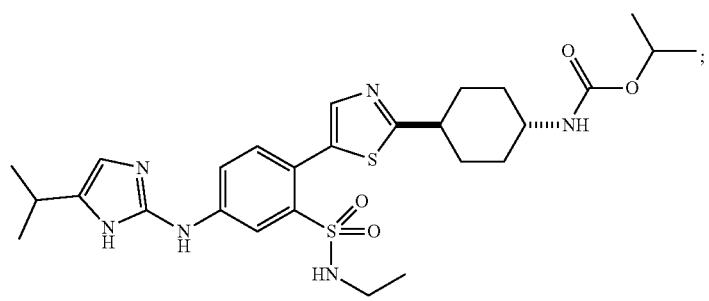
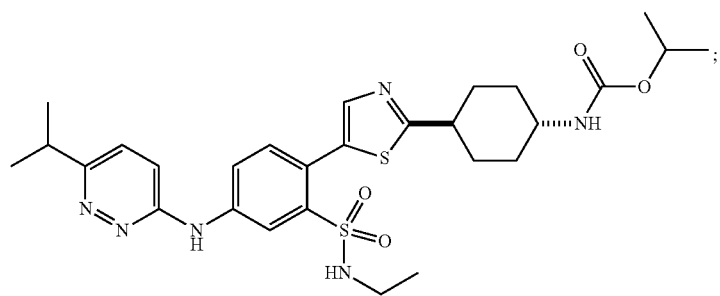
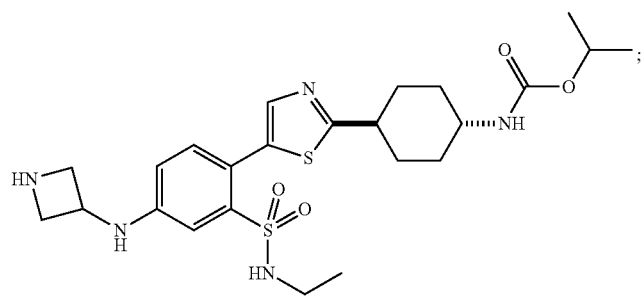

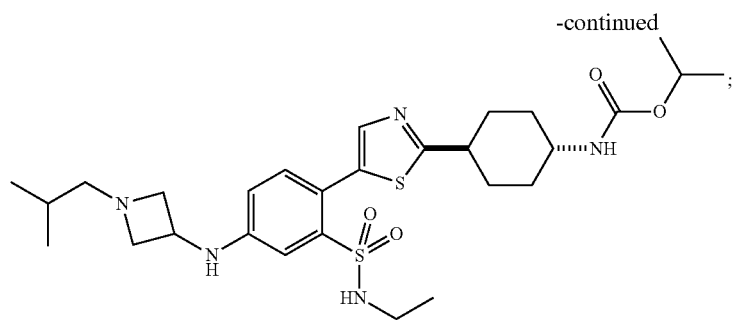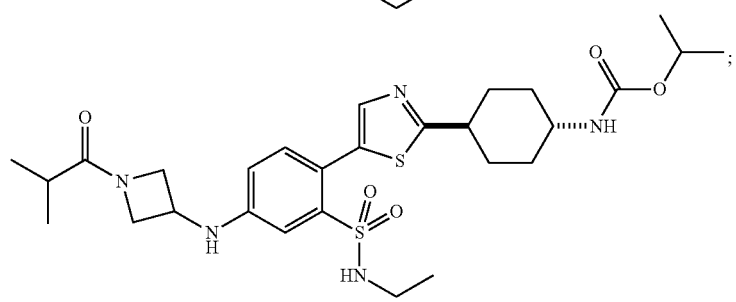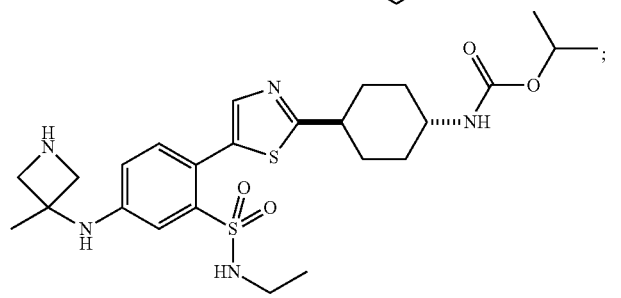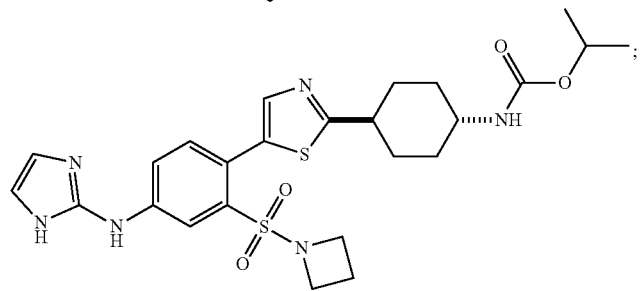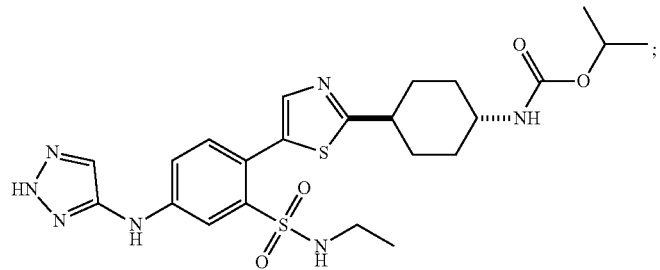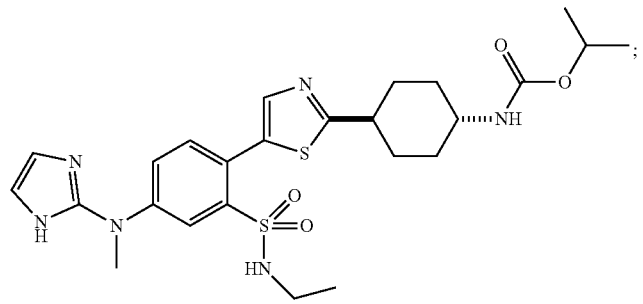

-continued
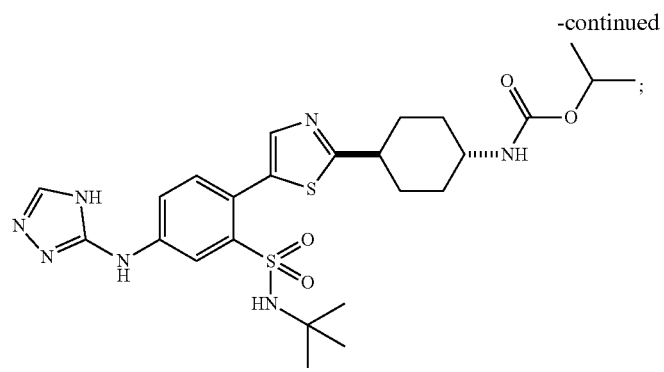
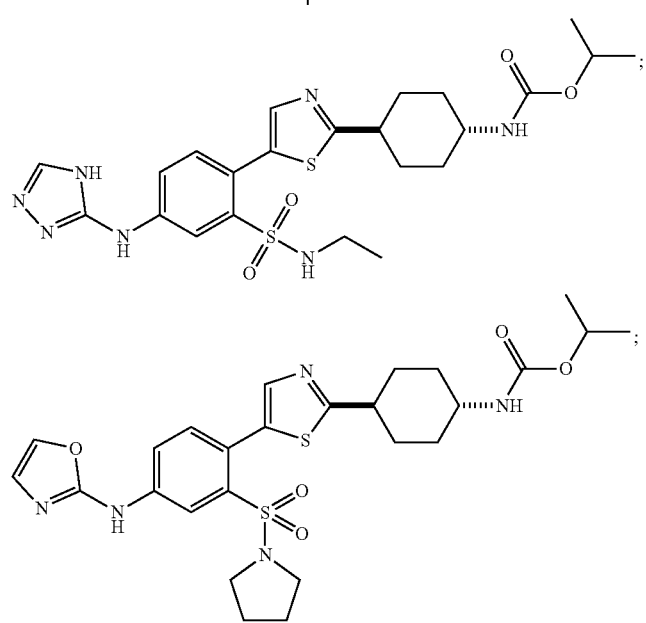
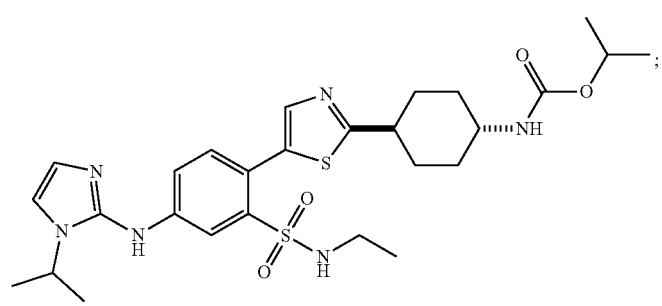
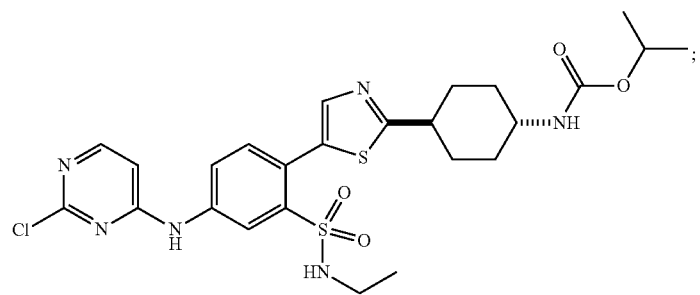

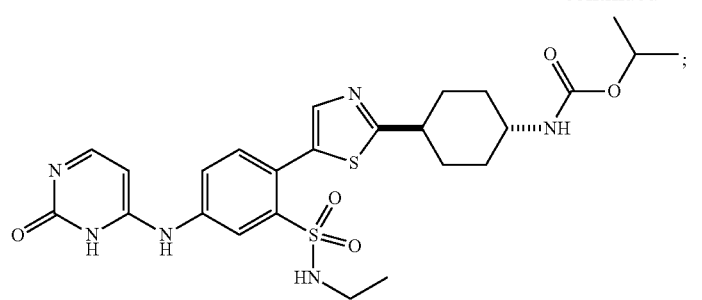
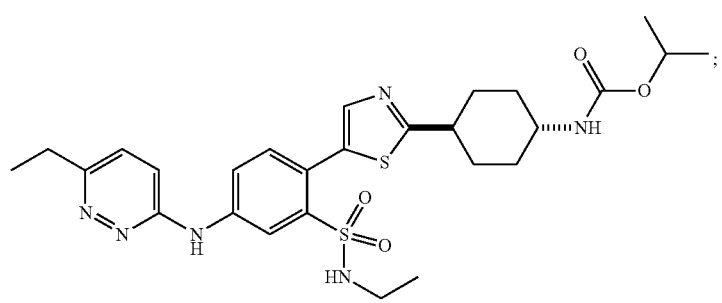
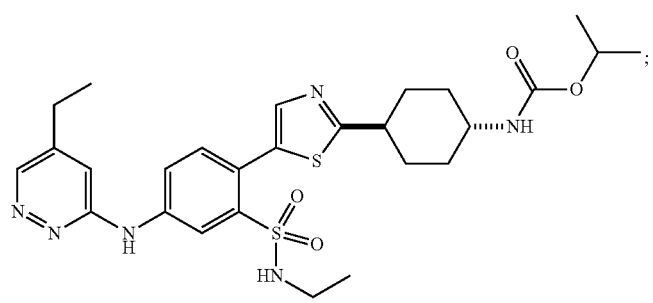
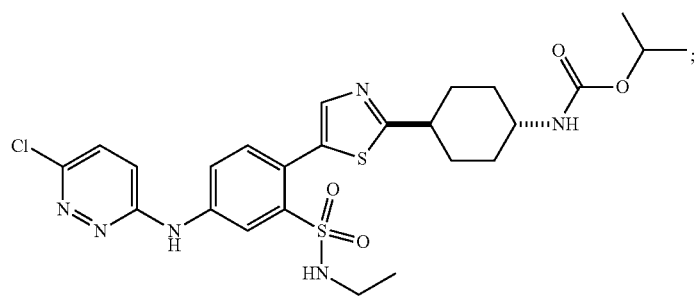
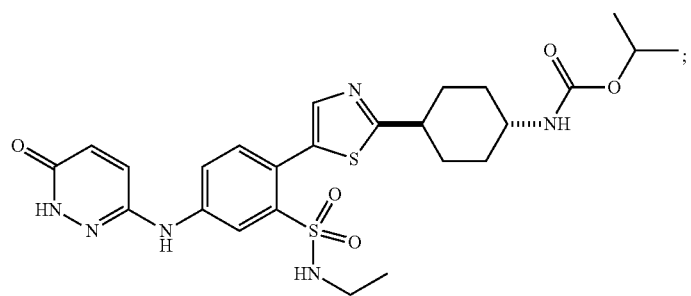

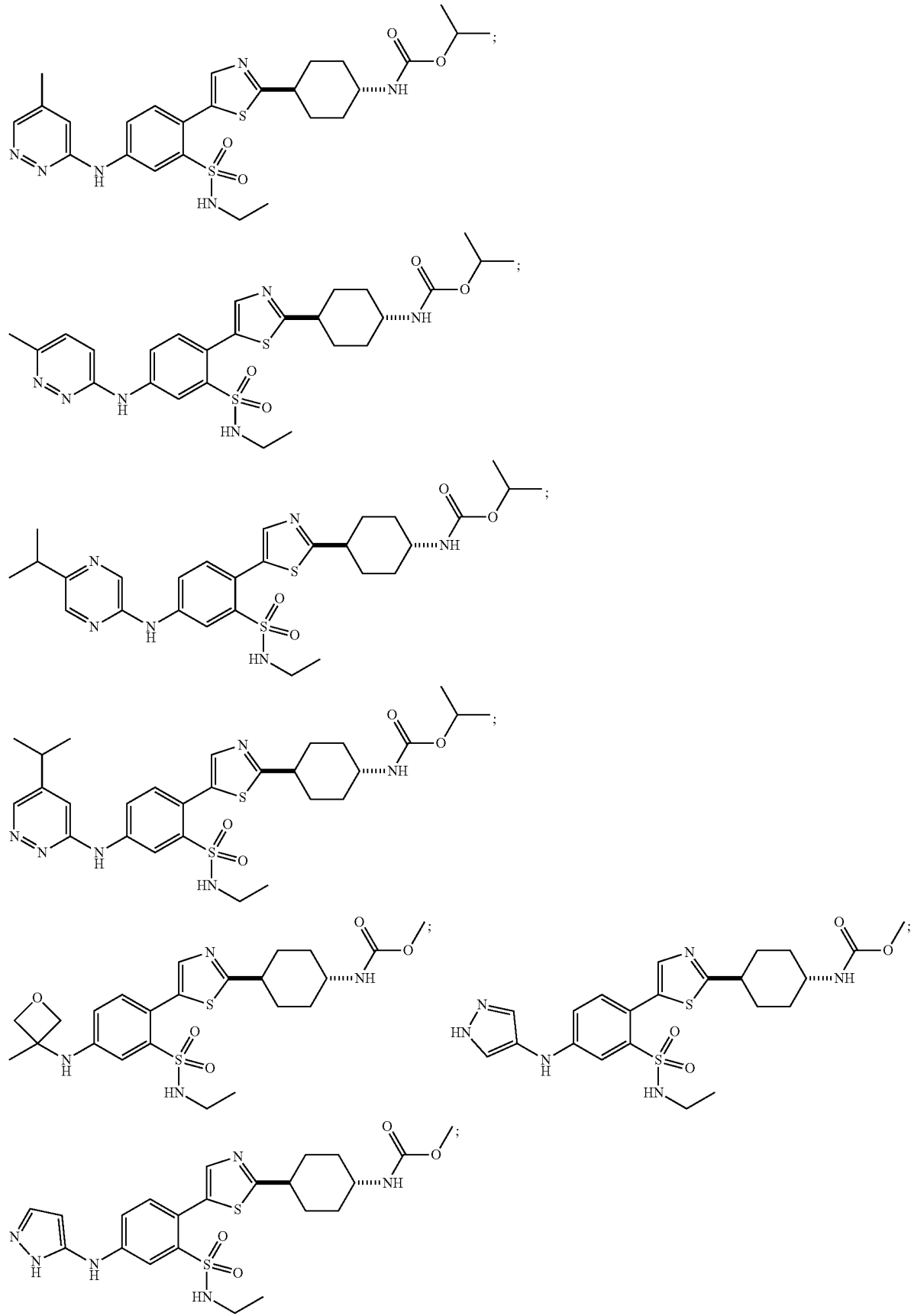

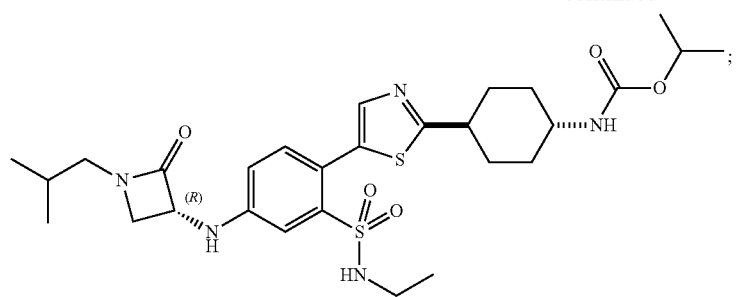
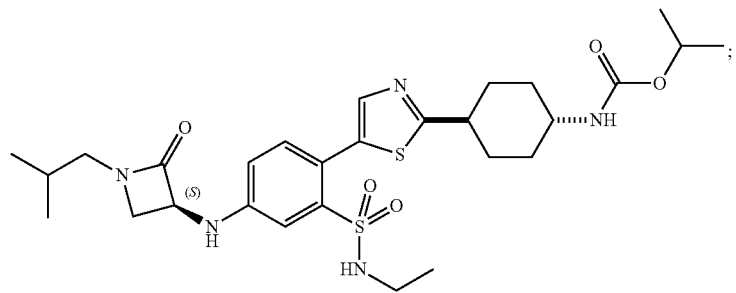
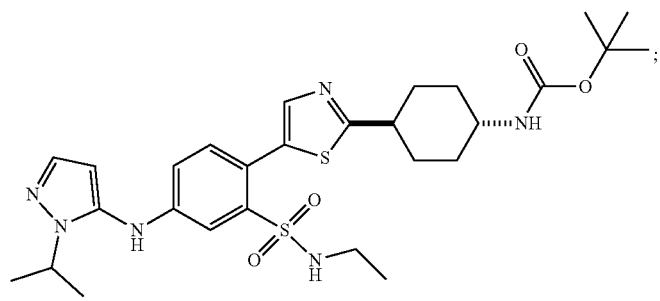
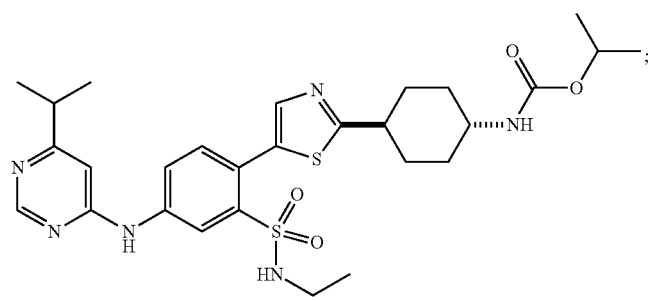
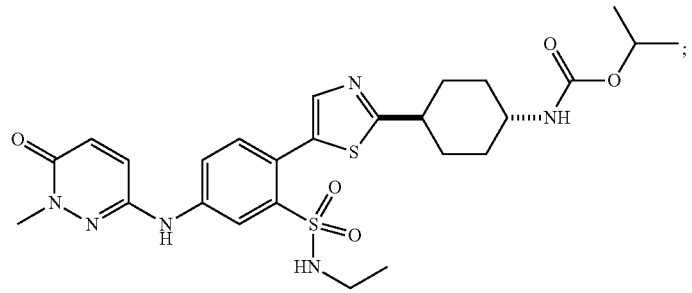

-continued

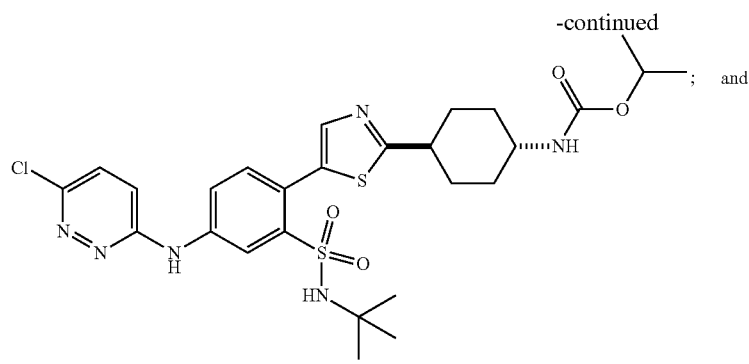

; and

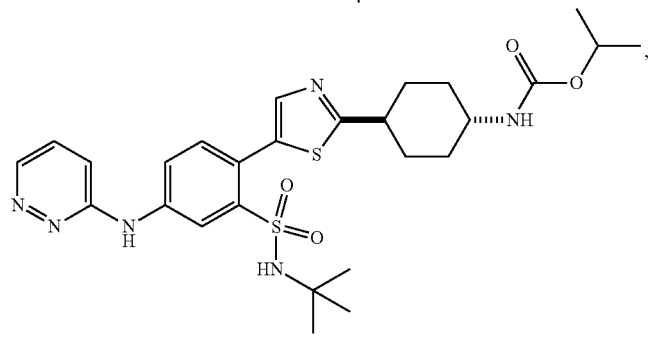

or a pharmaceutically acceptable salt or solvate thereof.

23. The compound of claim 1, wherein the compound is

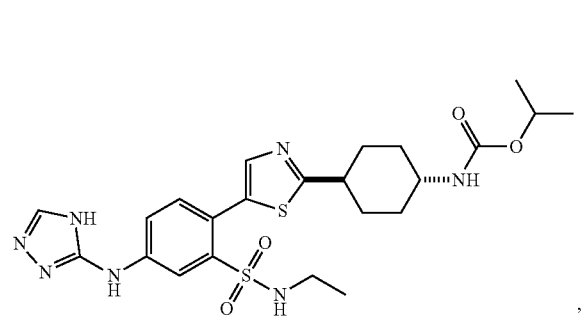 [SMILES: CCNS(=O)(=O)c1cc(Nc2nnc[nH]2)ccc1-c1cnc([C@H]2CC[C@H](NC(=O)OC(C)C)CC2)s1]

or a pharmaceutically acceptable salt or solvate thereof.

24. The compound of claim 1, wherein the compound is

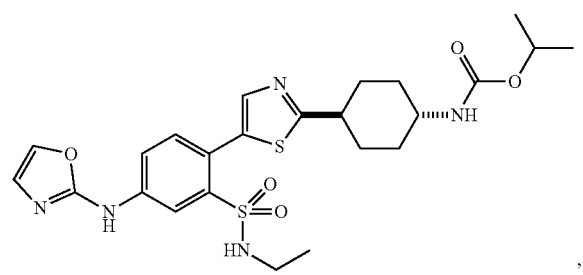 [SMILES: CCNS(=O)(=O)c1cc(Nc2ncco2)ccc1-c1cnc([C@H]2CC[C@H](NC(=O)OC(C)C)CC2)s1]

or a pharmaceutically acceptable salt or solvate thereof.

25. The compound of claim 1, wherein the compound is

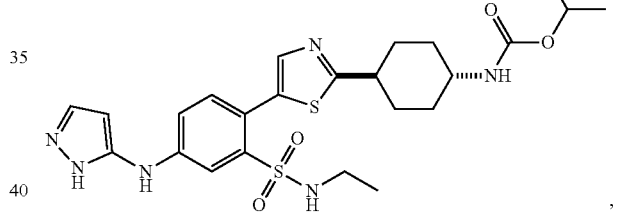

or a pharmaceutically acceptable salt or solvate thereof.

26. A pharmaceutical composition comprising the compound of claim 1 or a pharmaceutically acceptable salt or solvate thereof, and a pharmaceutically acceptable carrier or diluent.

27. A pharmaceutical composition comprising the compound of claim 23 or a pharmaceutically acceptable salt or solvate thereof, and a pharmaceutically acceptable carrier or diluent.

28. A pharmaceutical composition comprising the compound of claim 24 or a pharmaceutically acceptable salt or solvate thereof, and a pharmaceutically acceptable carrier or diluent.

29. A pharmaceutical composition comprising the compound of claim 25 or a pharmaceutically acceptable salt or solvate thereof, and a pharmaceutically acceptable carrier or diluent.

30. A method of treating a disease or disorder selected from cancer, an autoimmune disease, an immune deficiency, and a neurodegenerative disease, comprising administering to a subject in need thereof an effective amount of the compound of claim 1 or a pharmaceutically acceptable salt or solvate thereof, wherein treating is improving at least one symptom of the disease or disorder.

31. A method of treating a disease or disorder selected from cancer, an autoimmune disease, an immune deficiency, and a neurodegenerative disease, comprising administering to a subject in need thereof an effective amount of the compound of claim 23 or a pharmaceutically acceptable salt or solvate thereof, wherein treating is improving at least one symptom of the disease or disorder.

32. A method of treating a disease or disorder selected from cancer, an autoimmune disease, an immune deficiency, and a neurodegenerative disease, comprising administering to a subject in need thereof an effective amount of the compound of claim 24 or a pharmaceutically acceptable salt or solvate thereof, wherein treating is improving at least one symptom of the disease or disorder.

33. A method of treating a disease or disorder selected from cancer, an autoimmune disease, an immune deficiency, and a neurodegenerative disease, comprising administering to a subject in need thereof an effective amount of the compound of claim 25 or a pharmaceutically acceptable salt or solvate thereof, wherein treating is improving at least one symptom of the disease or disorder.

* * * * *

UNITED STATES PATENT AND TRADEMARK OFFICE
CERTIFICATE OF CORRECTION

Page 1 of 1

PATENT NO. : 11,247,988 B2
APPLICATION NO. : 16/816393
DATED : February 15, 2022
INVENTOR(S) : Lapierre et al.

It is certified that error appears in the above-identified patent and that said Letters Patent is hereby corrected as shown below:

In the Claims

At Column 401, Claim number 1, Line number 32, replace:
"each $R_5$ is independently H or $C_1$-$C_6$ alkyl; and"
With:
--each $R_8$ is independently H or $C_1$-$C_6$ alkyl; and--

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*